(12) United States Patent
Gibbens, III et al.

(10) Patent No.: US 7,338,504 B2
(45) Date of Patent: Mar. 4, 2008

(54) CYCLING SUTURING AND KNOT-TYING DEVICE

(75) Inventors: George Hathaway Gibbens, III, deceased, late of Shreveport, LA (US); by Susan Duke Gibbens, legal representative, Shreveport, LA (US); Claude Vidal, Santa Barbara, CA (US); Russell J. Redmond, Goleta, CA (US); Michael Collinson, Goleta, CA (US)

(73) Assignee: Gibbens Group, L.L.C., Santa Barbara, CA (US)

( * ) Notice: Subject to any disclaimer, the term of this patent is extended or adjusted under 35 U.S.C. 154(b) by 69 days.

(21) Appl. No.: 11/223,737

(22) Filed: Sep. 9, 2005

(65) Prior Publication Data

US 2006/0111732 A1 May 25, 2006

Related U.S. Application Data

(63) Continuation-in-part of application No. 10/263,902, filed on Oct. 3, 2002, now Pat. No. 7,004,951.

(51) Int. Cl.
*A61B 17/04* (2006.01)
*A61B 17/06* (2006.01)

(52) U.S. Cl. ........................ 606/144; 606/222
(58) Field of Classification Search ................ 606/144, 606/145, 139, 148, 147, 222
See application file for complete search history.

(56) References Cited

U.S. PATENT DOCUMENTS

| 1,583,271 | A | | 5/1926 | Biro |
| 1,757,129 | A | | 5/1930 | McClure |
| 4,899,746 | A | * | 2/1990 | Brunk ........................ 606/144 |
| 5,437,681 | A | | 8/1995 | Meade et al. |
| 5,540,705 | A | | 7/1996 | Meade et al. |
| 5,728,108 | A | | 3/1998 | Griffiths et al. |
| 5,766,186 | A | * | 6/1998 | Faraz et al. .................. 606/145 |
| 5,911,727 | A | * | 6/1999 | Taylor ........................ 606/145 |
| 6,454,778 | B2 | * | 9/2002 | Kortenbach ................. 606/144 |
| 6,923,819 | B2 | | 8/2005 | Meade et al. |

FOREIGN PATENT DOCUMENTS

WO    WO 94/28801    12/1994

\* cited by examiner

*Primary Examiner*—Michael J. Hayes
*Assistant Examiner*—Christina Gettman
(74) *Attorney, Agent, or Firm*—James E. Brunton, Esq.

(57) ABSTRACT

A cycling suturing and knot-tying device is characterized by an arcuate fixed, grooved or recessed way provided in a correspondingly-shaped support frame for accommodating a curved needle fitted with thread, and frictional needle-engaging devices provided in the way for selectively engaging the needle and driving the needle in one or both rotational directions to suture a wound with the thread. Selective articulation of the frame and the way and driving of the needle in the way by positioning the frictional needle-engaging devices with respect to the needle are typically effected by manipulation of a pistol-grip operating apparatus having a transmission tube that mounts the frame and the way in articulating relationship and rotates and articulates with respect to the pistol grip and carries various operating elements that interface with the frictional needle-engaging devices in the way. In at least one embodiment needle direction-adjusting elements are provided in the frame in cooperation with selected devices in the way for determining the direction of needle rotation responsive to manipulation of an interfacing operating element located on the operating apparatus. Auxiliary thread-handling or incrementing and knot-tying devices are also disclosed.

28 Claims, 215 Drawing Sheets

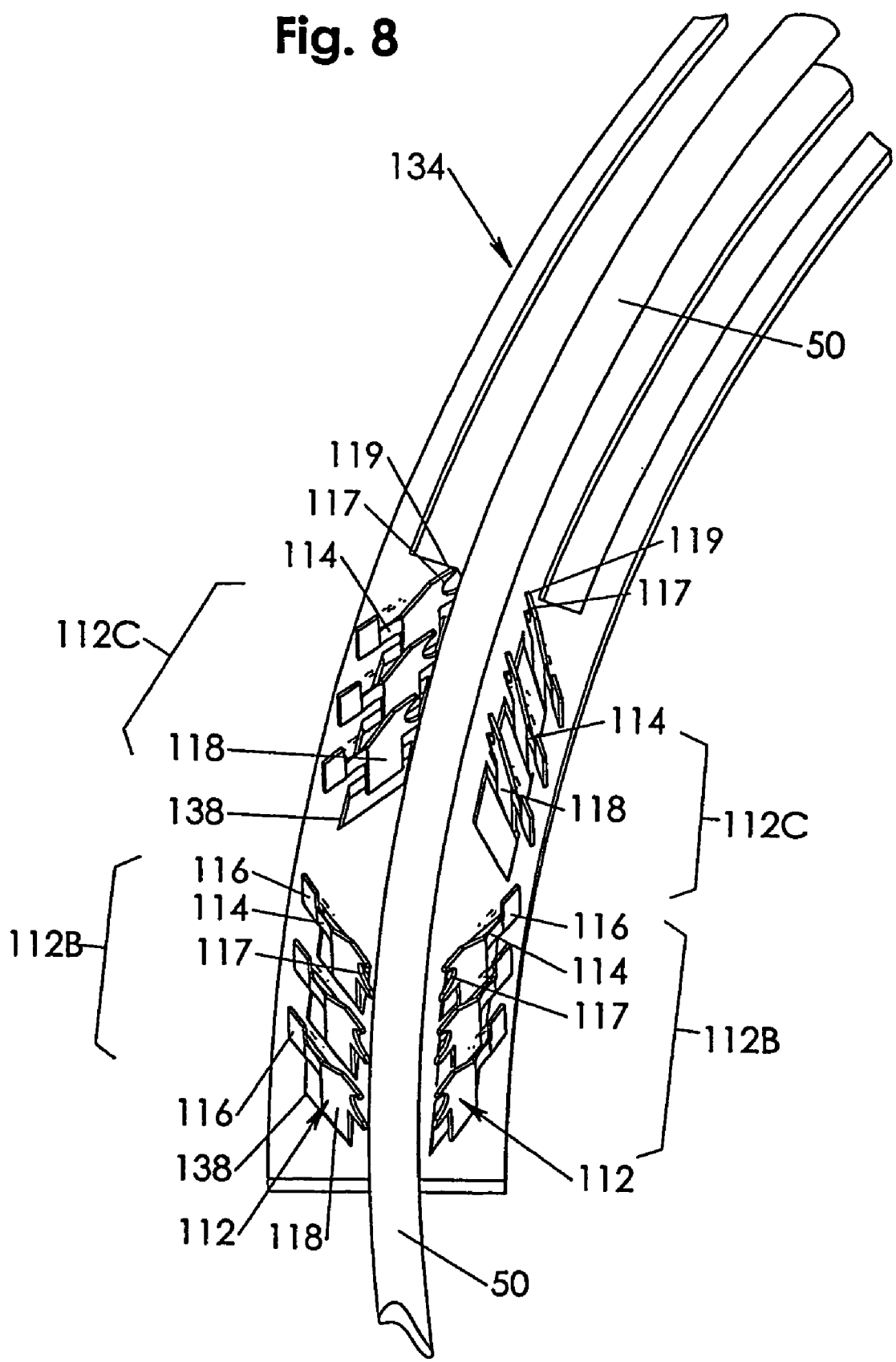

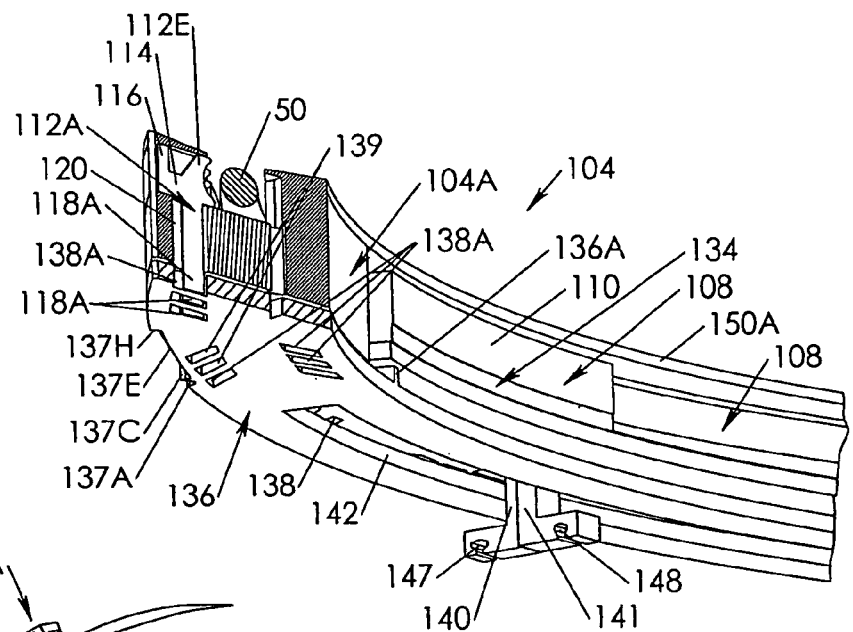
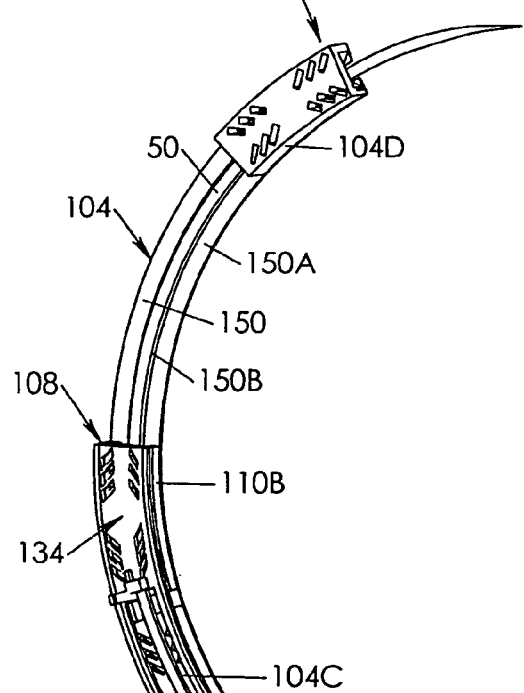
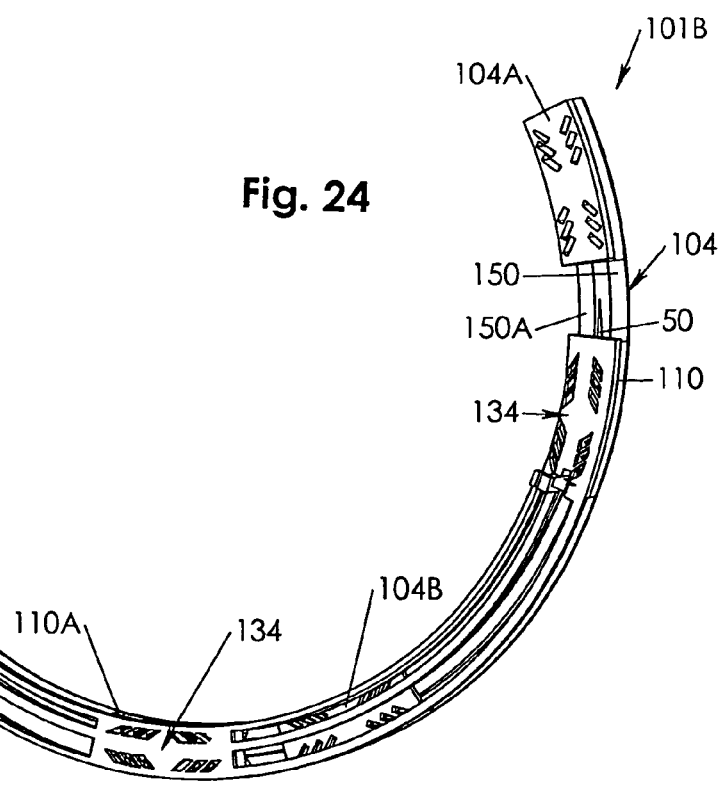

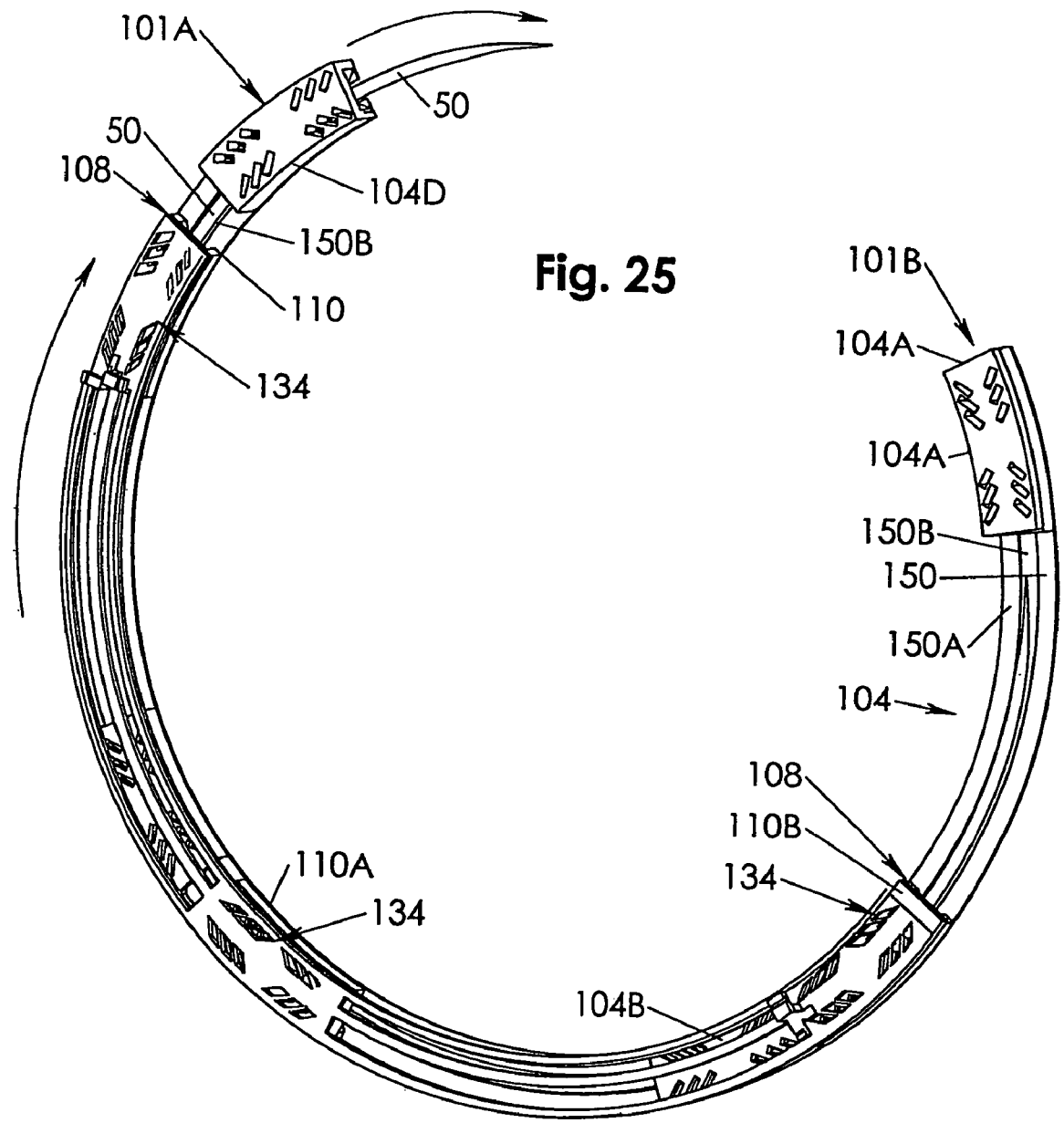

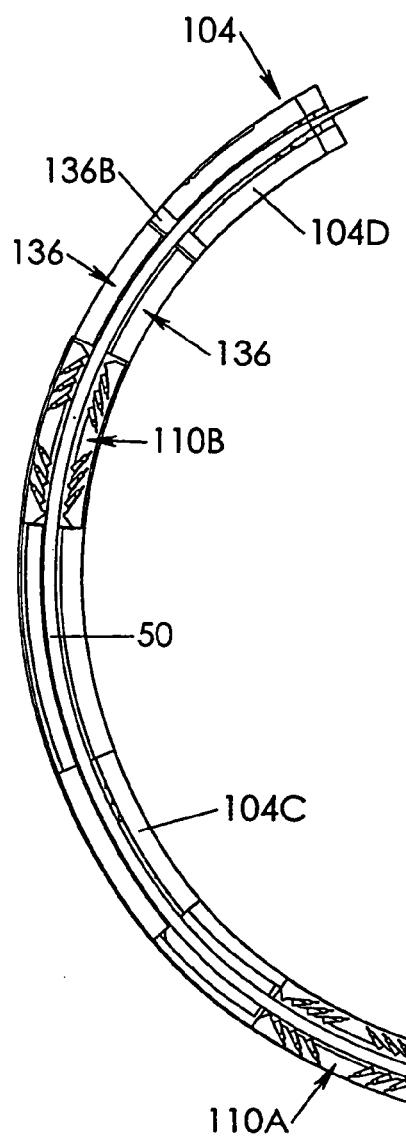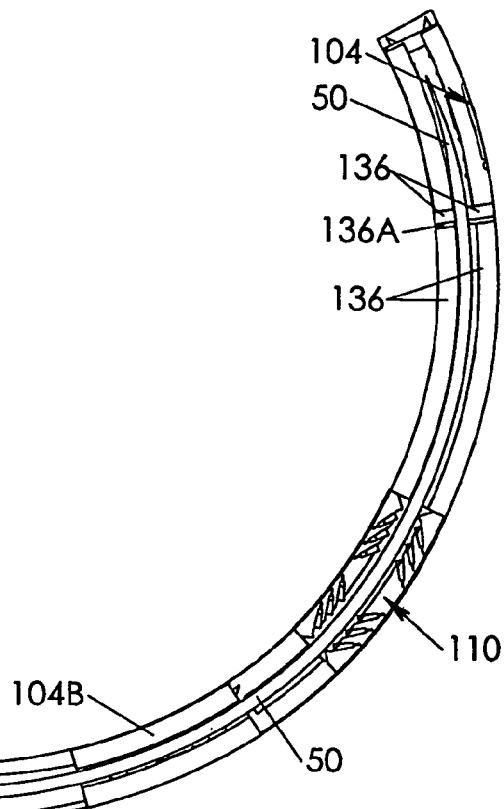
Fig. 30

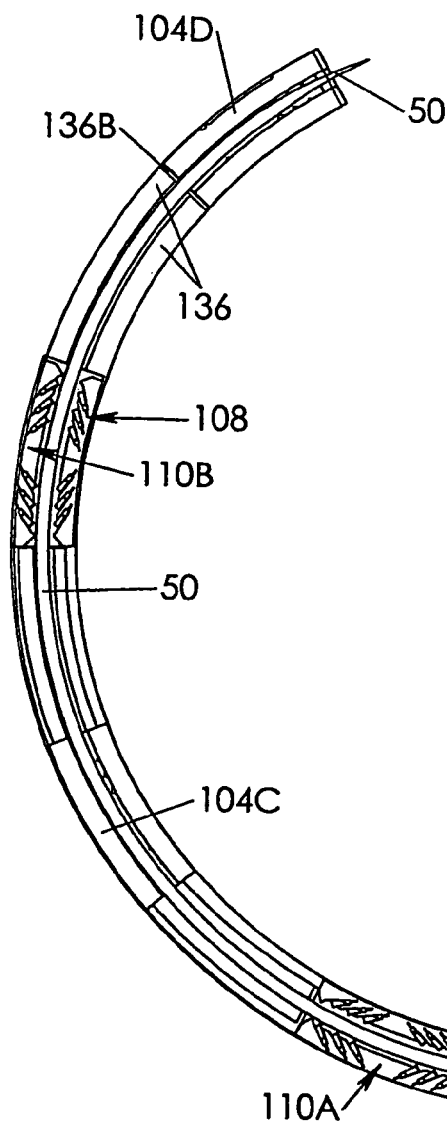
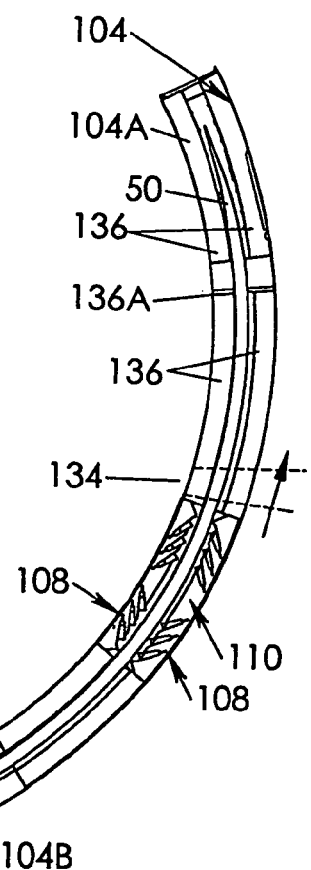
Fig. 31

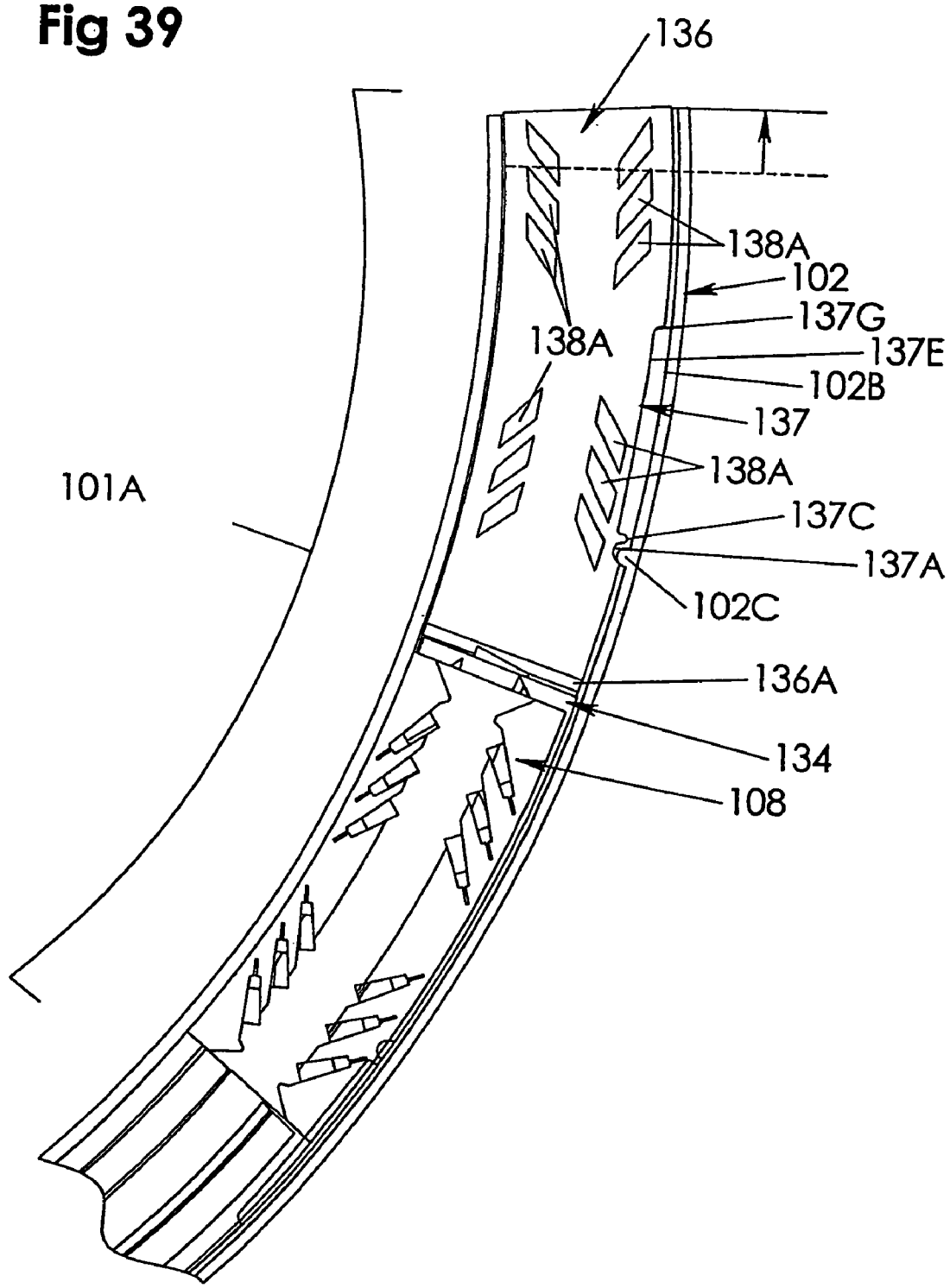

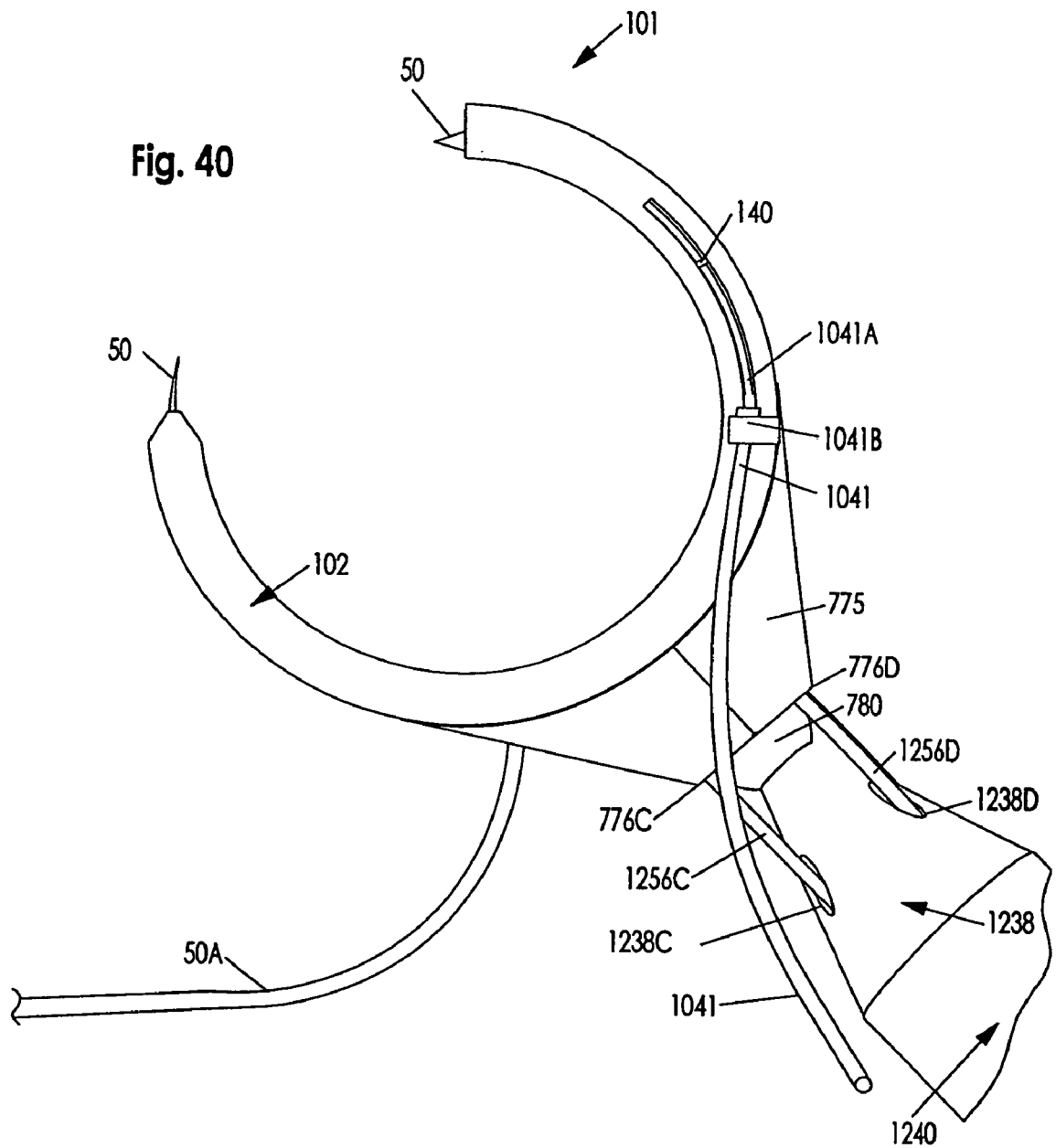

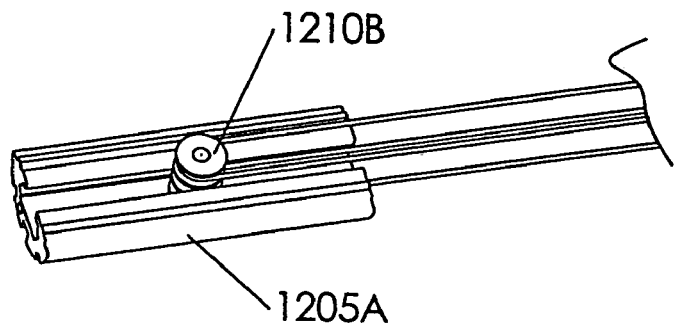
Fig. 75
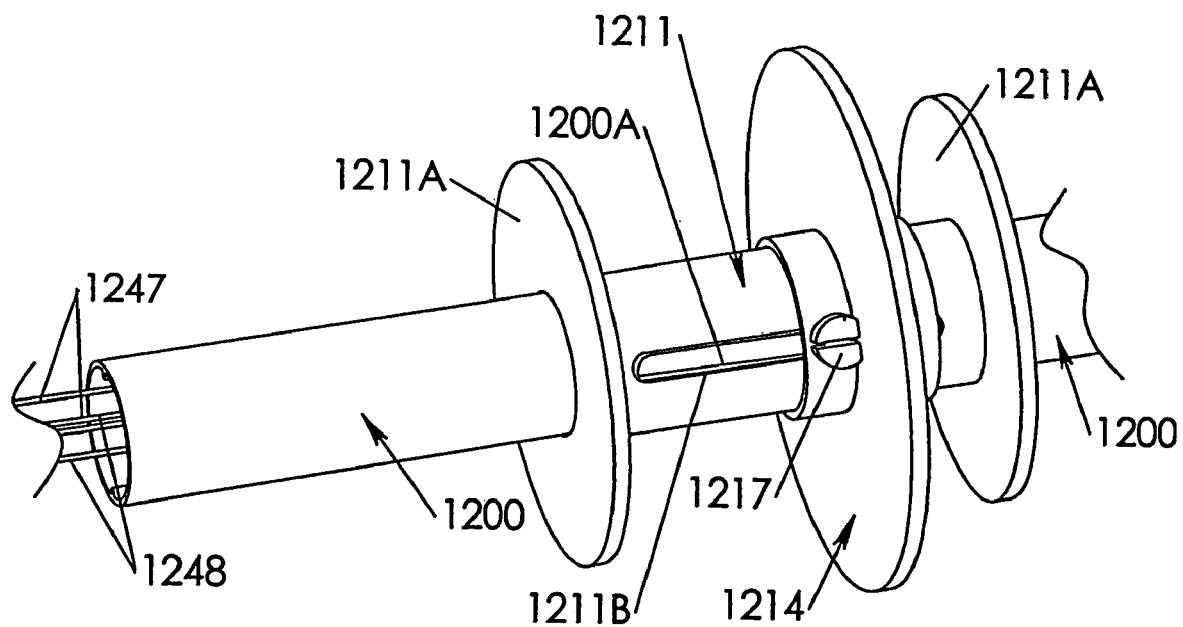

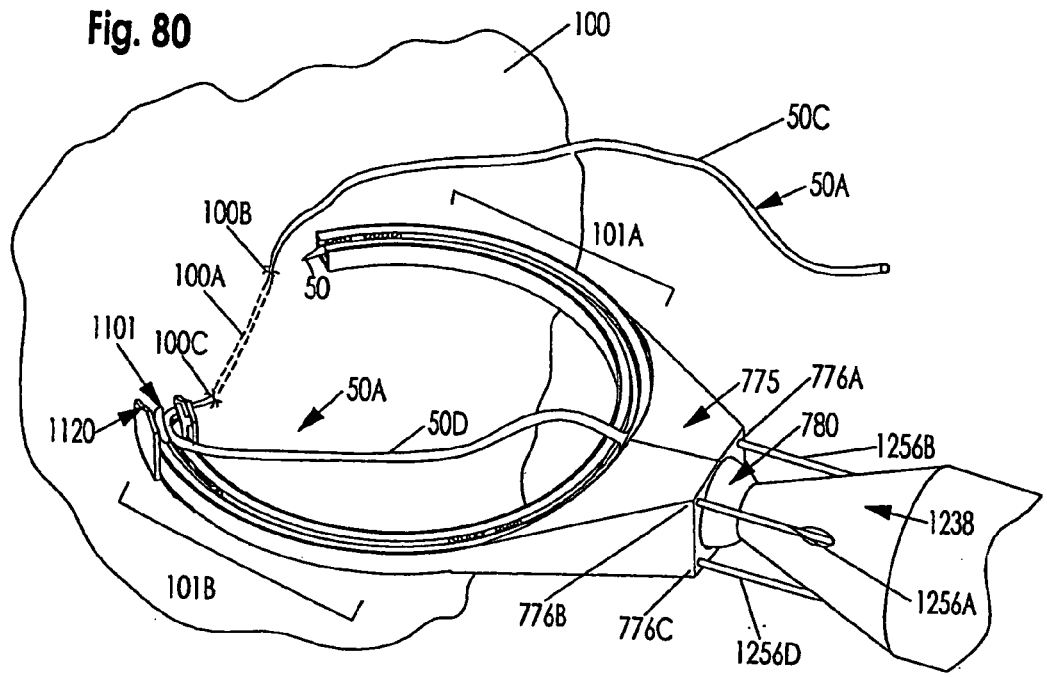
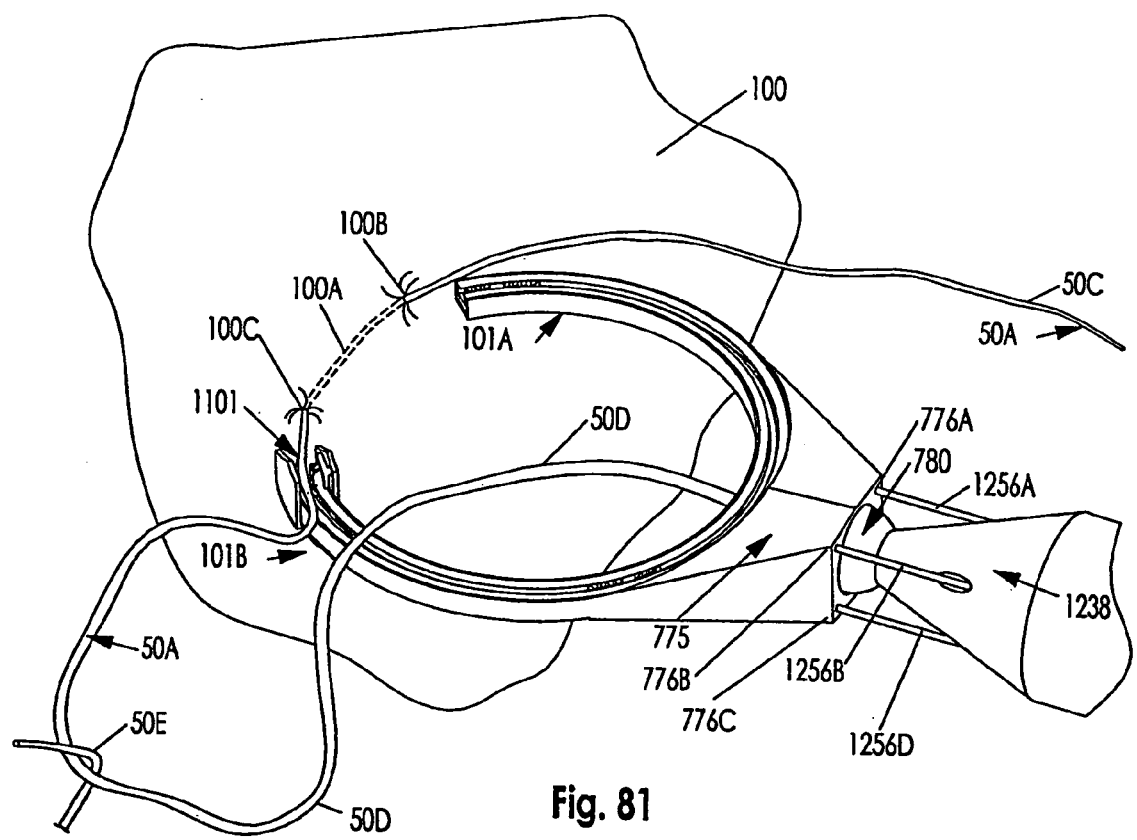

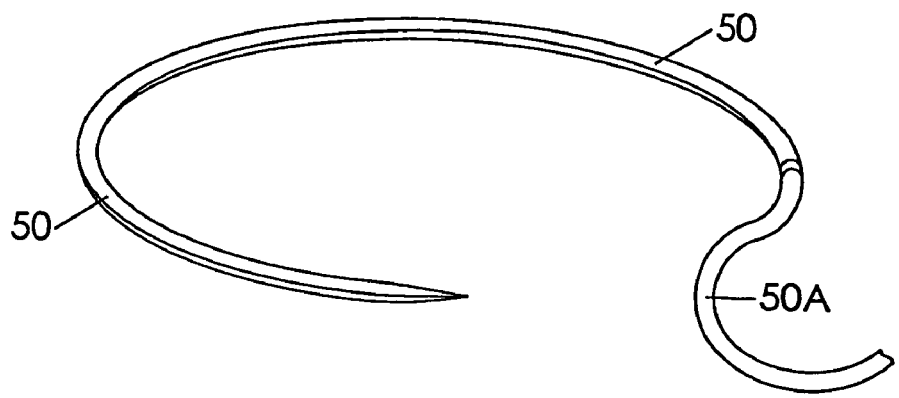
Fig. 109A
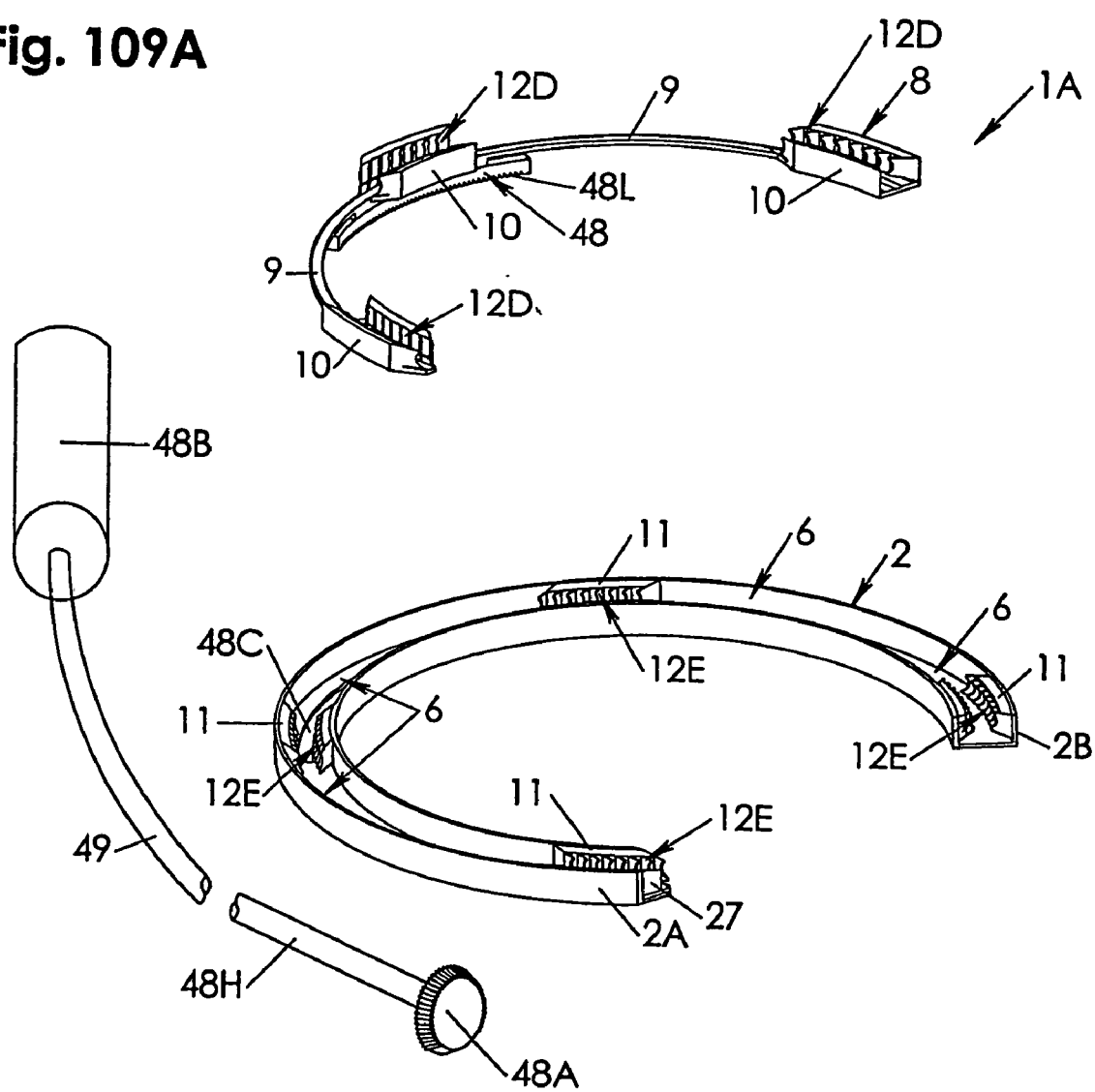

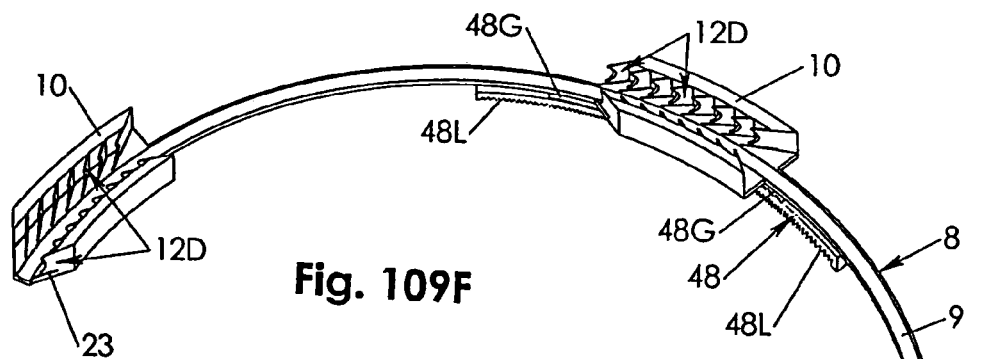
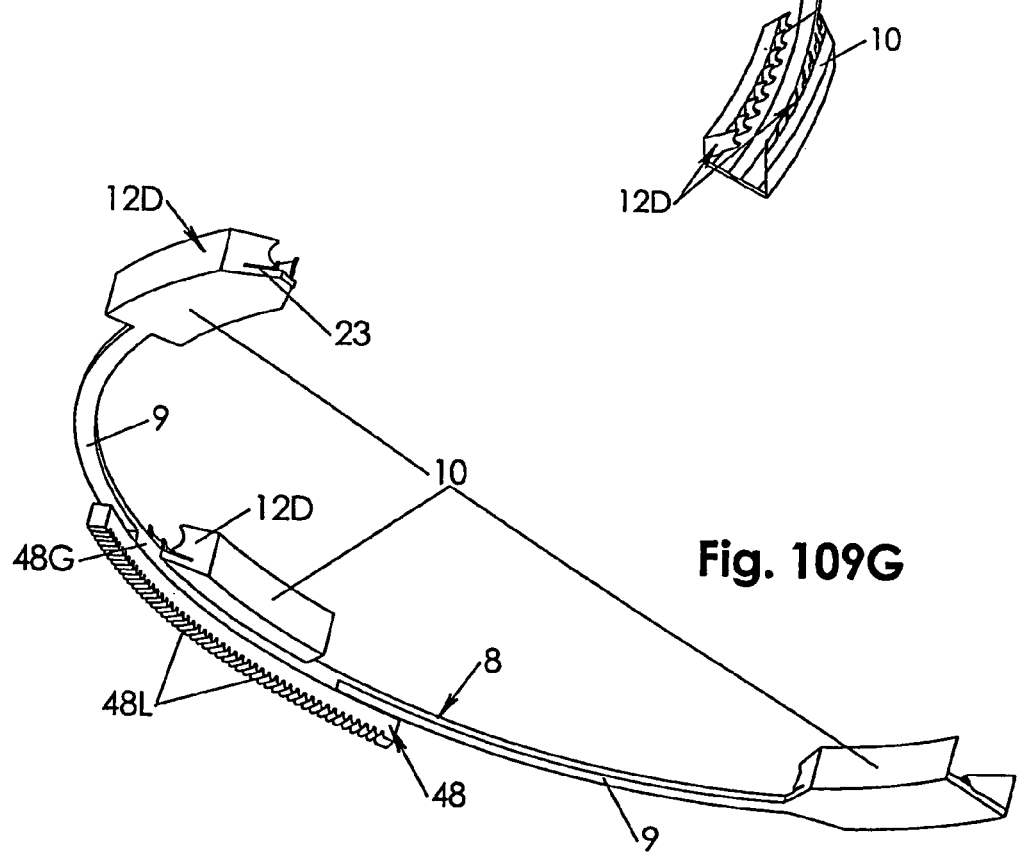

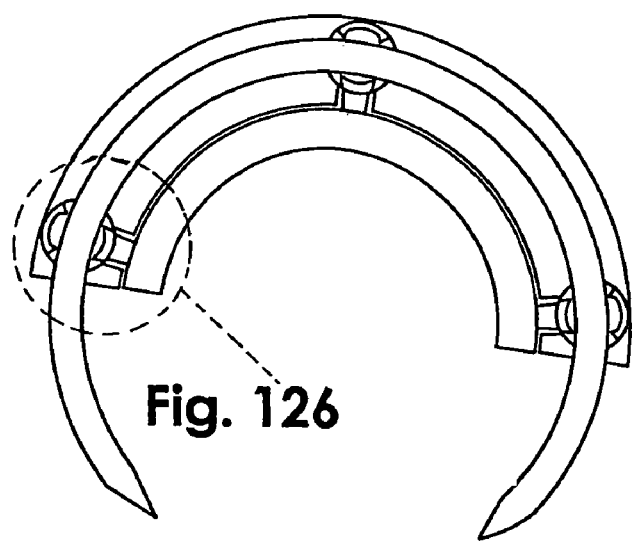
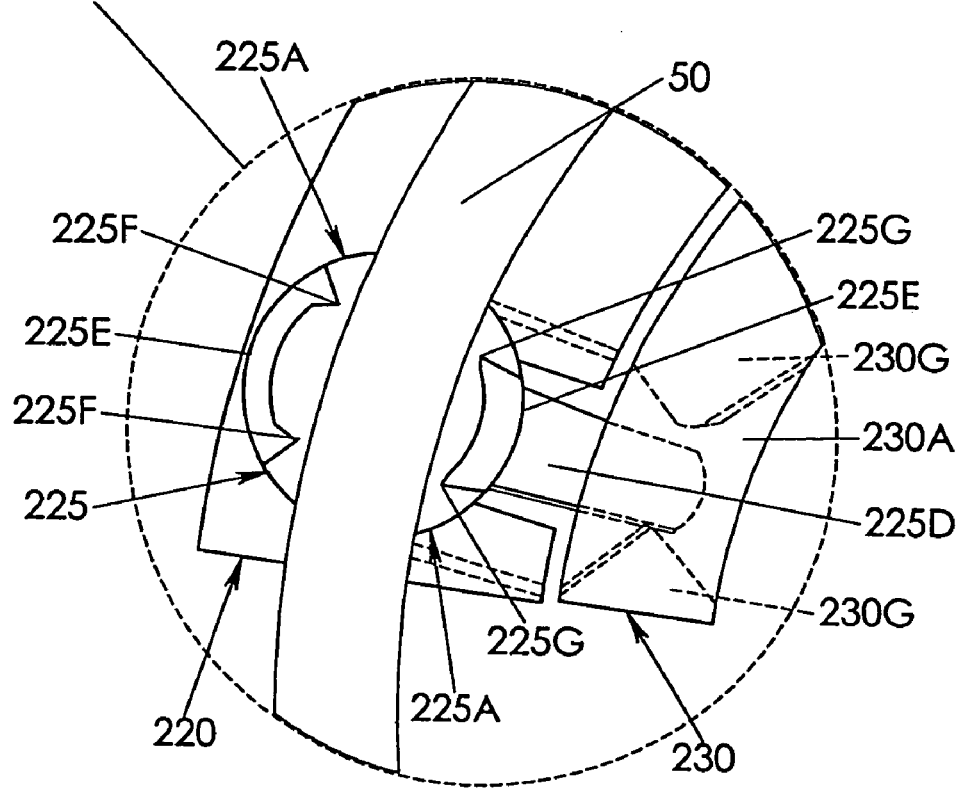
Fig. 126

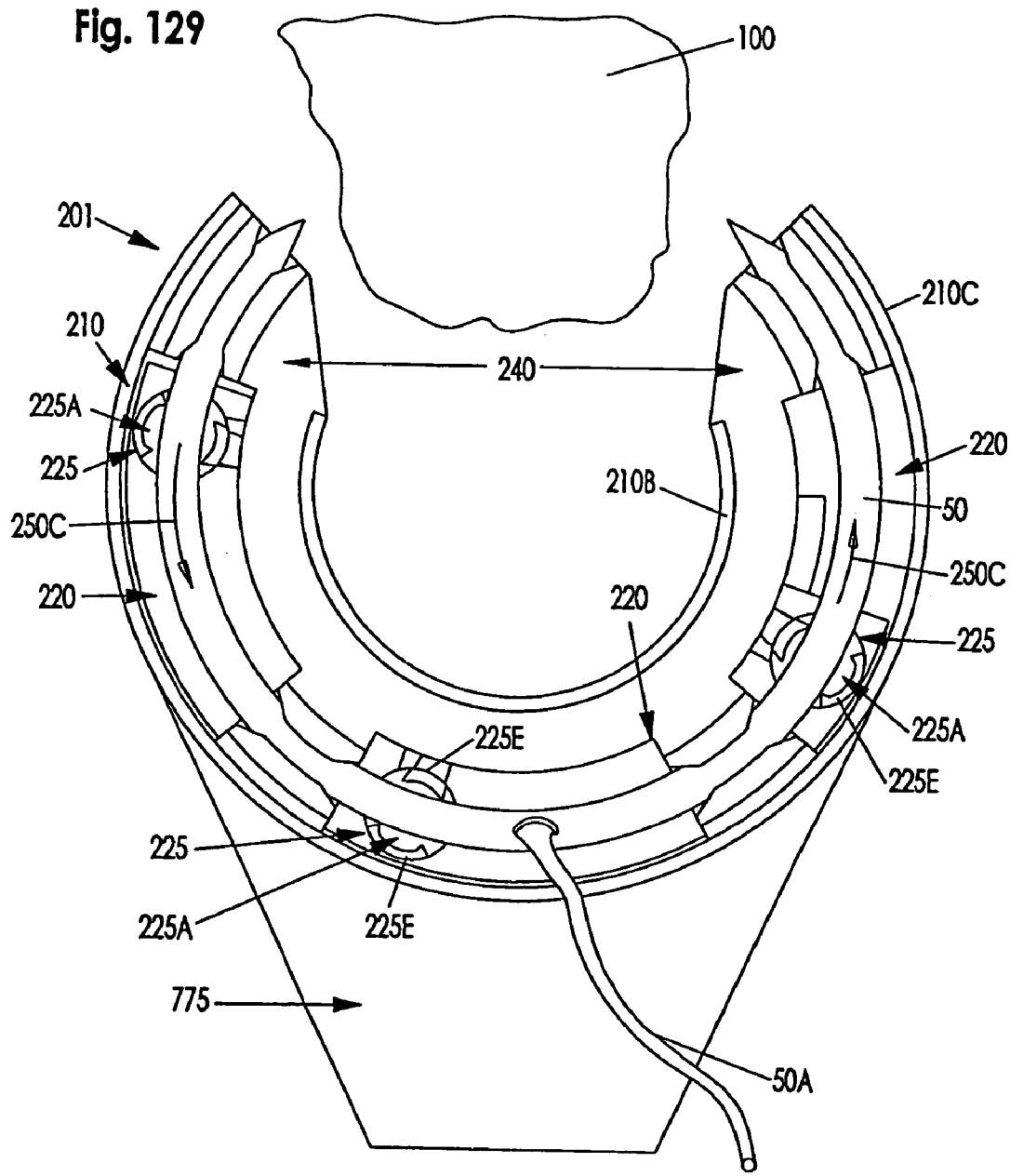

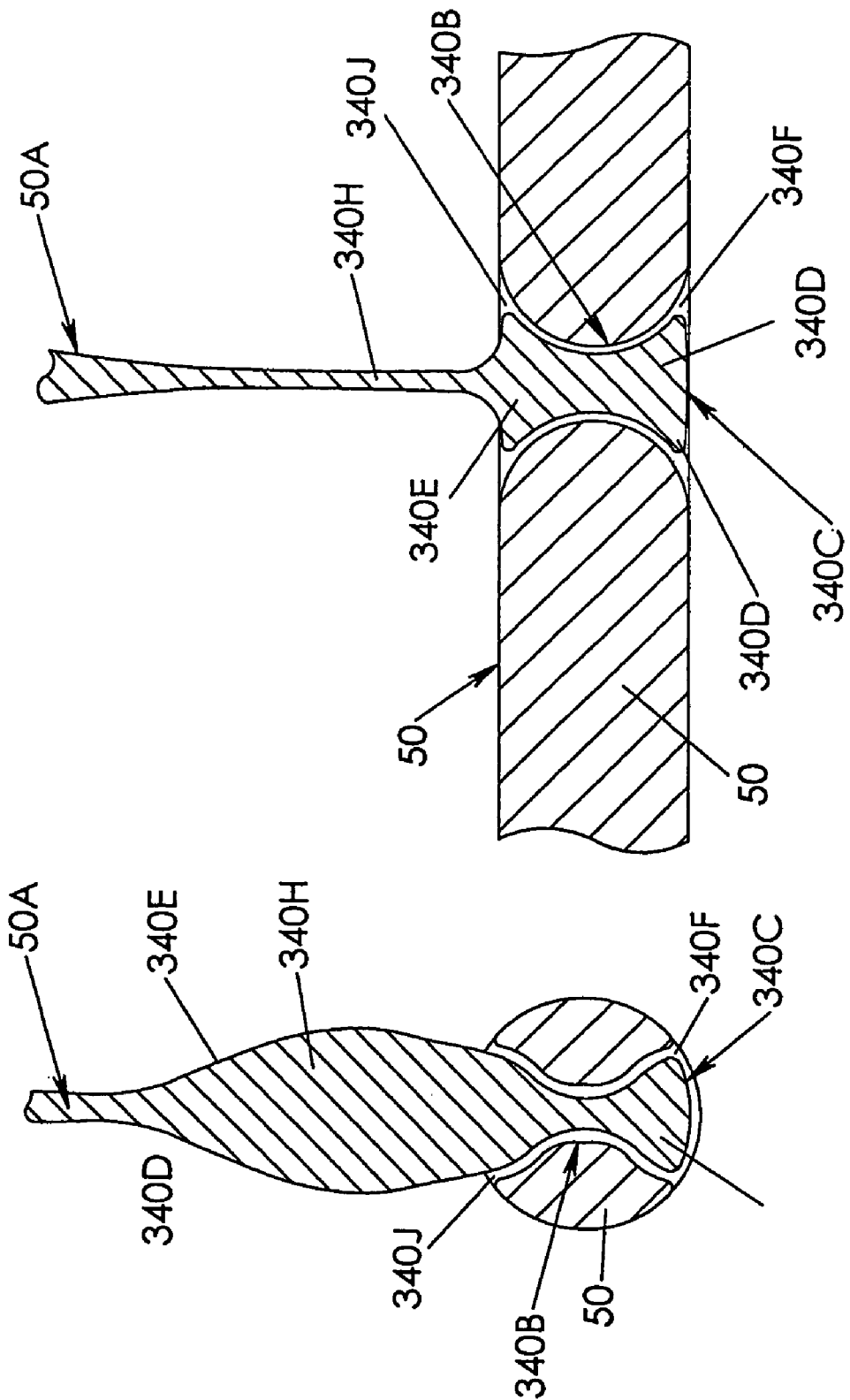

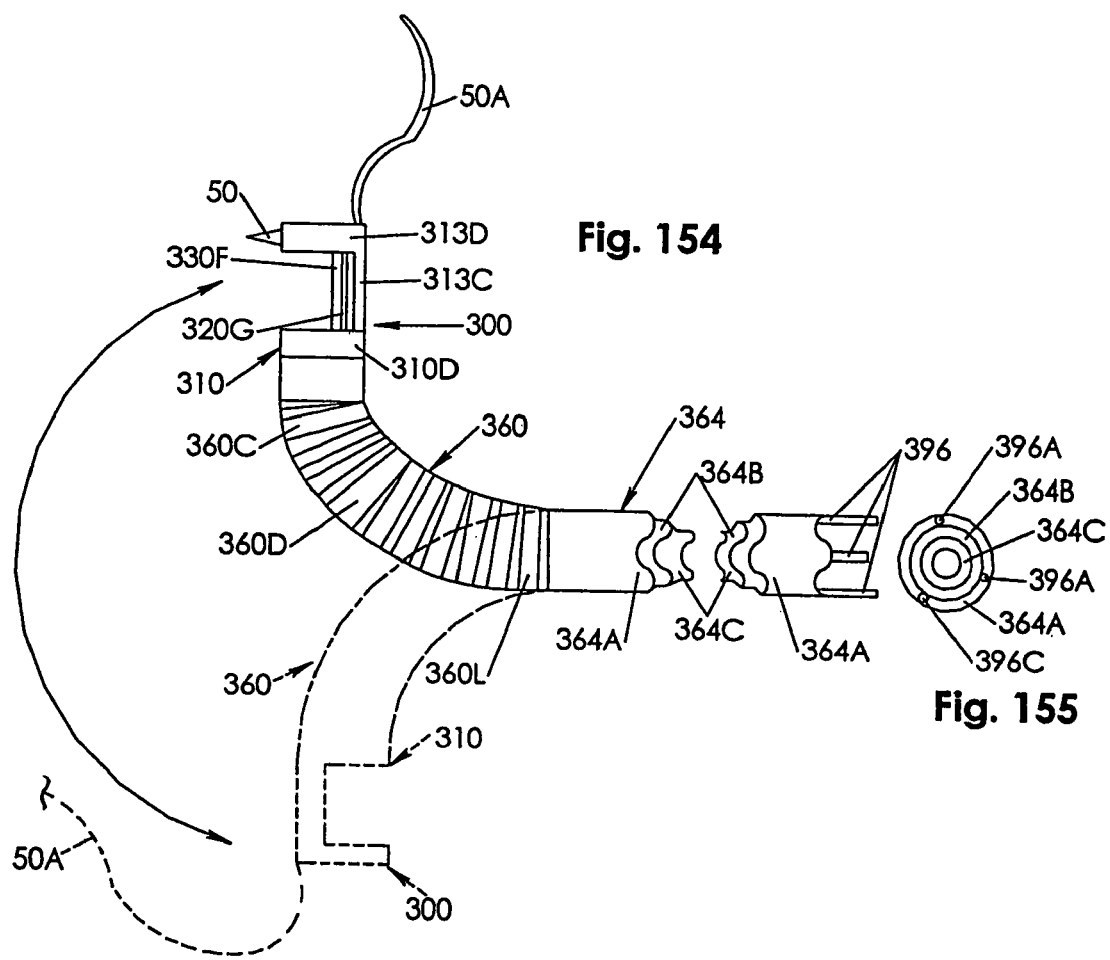

Fig. 165
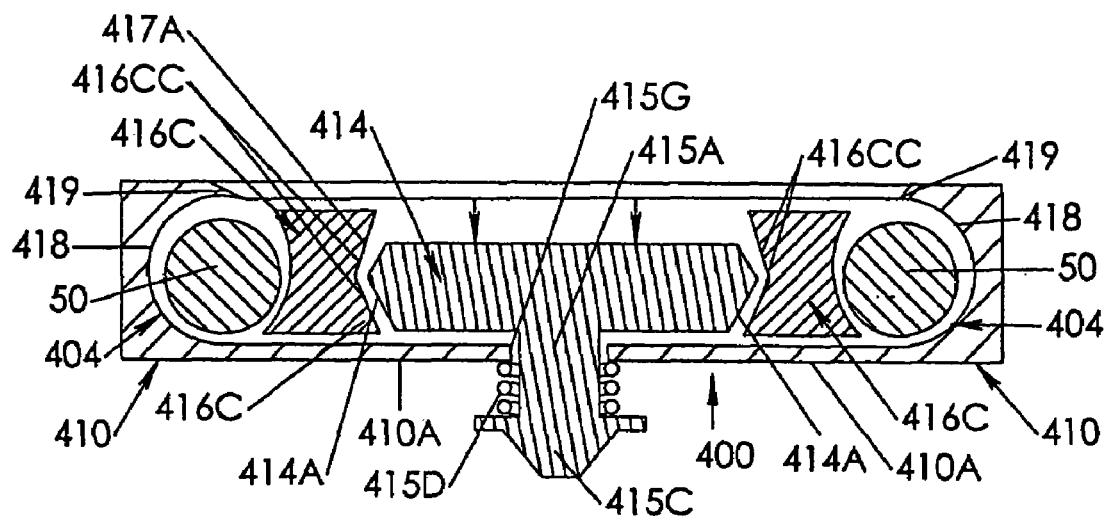
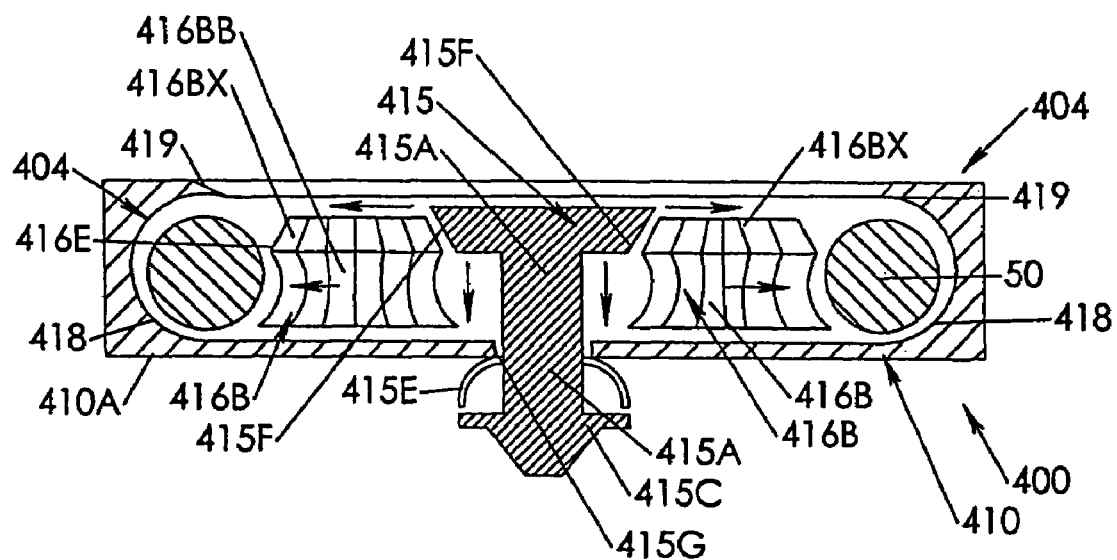
Fig. 166

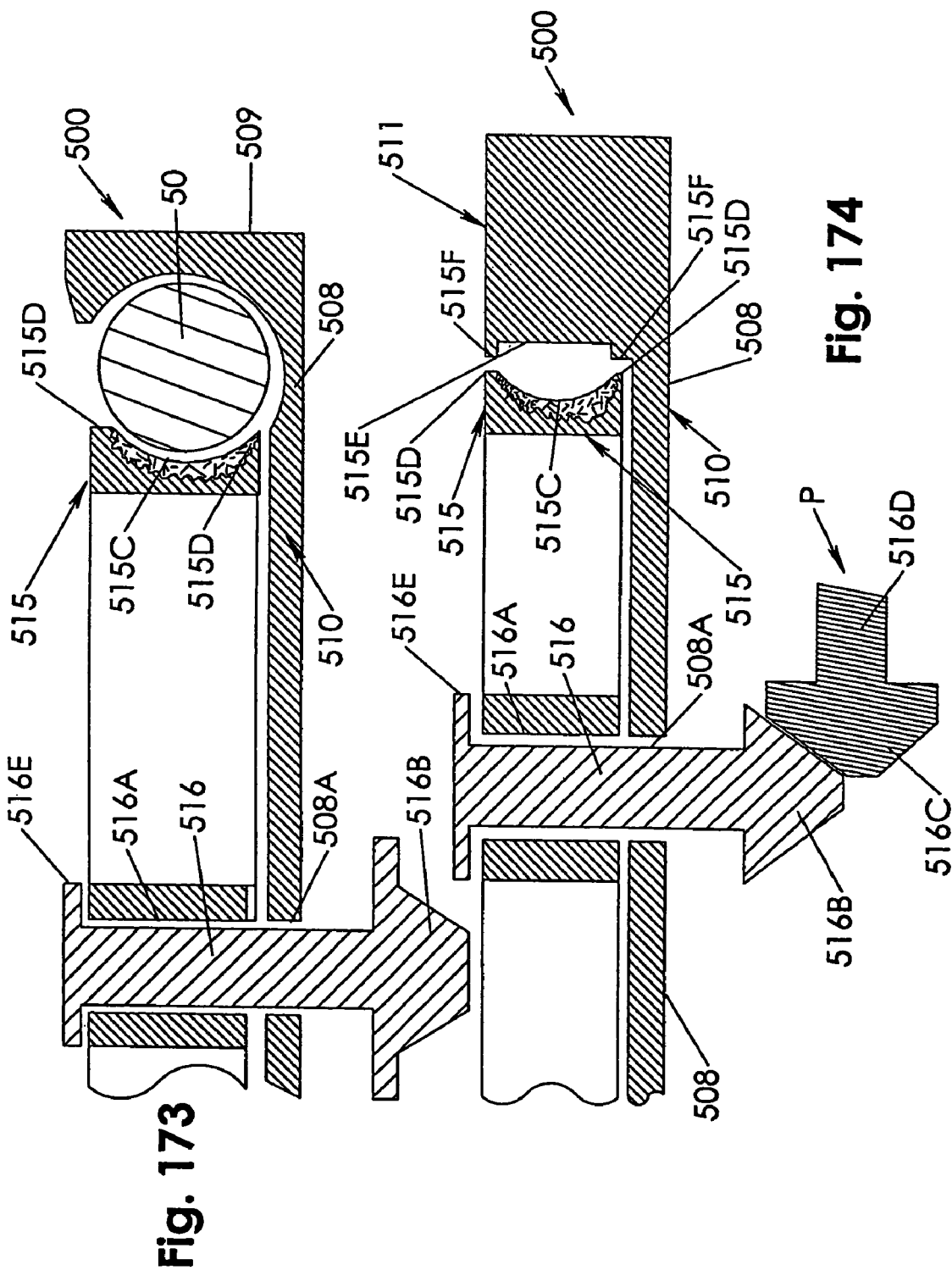

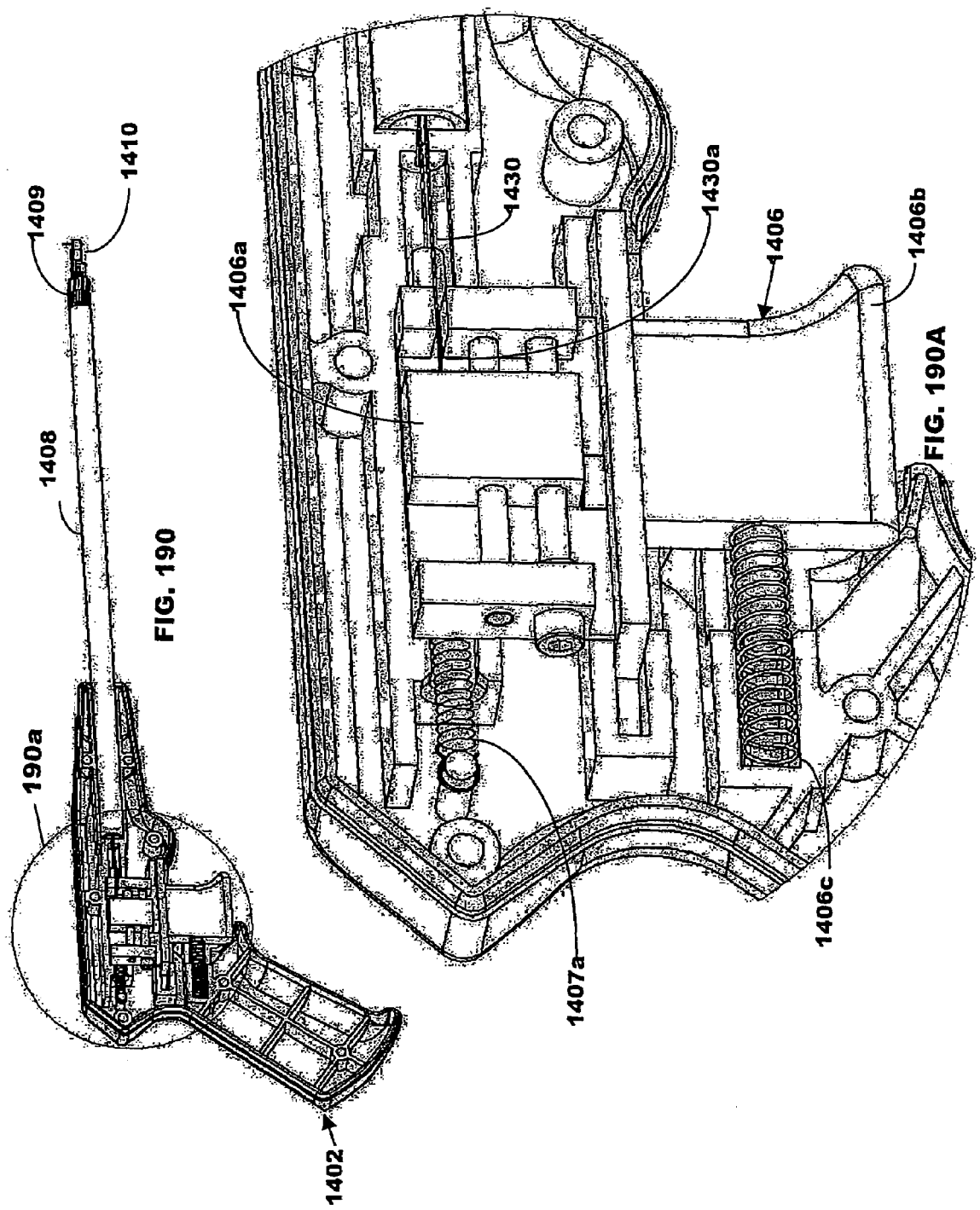

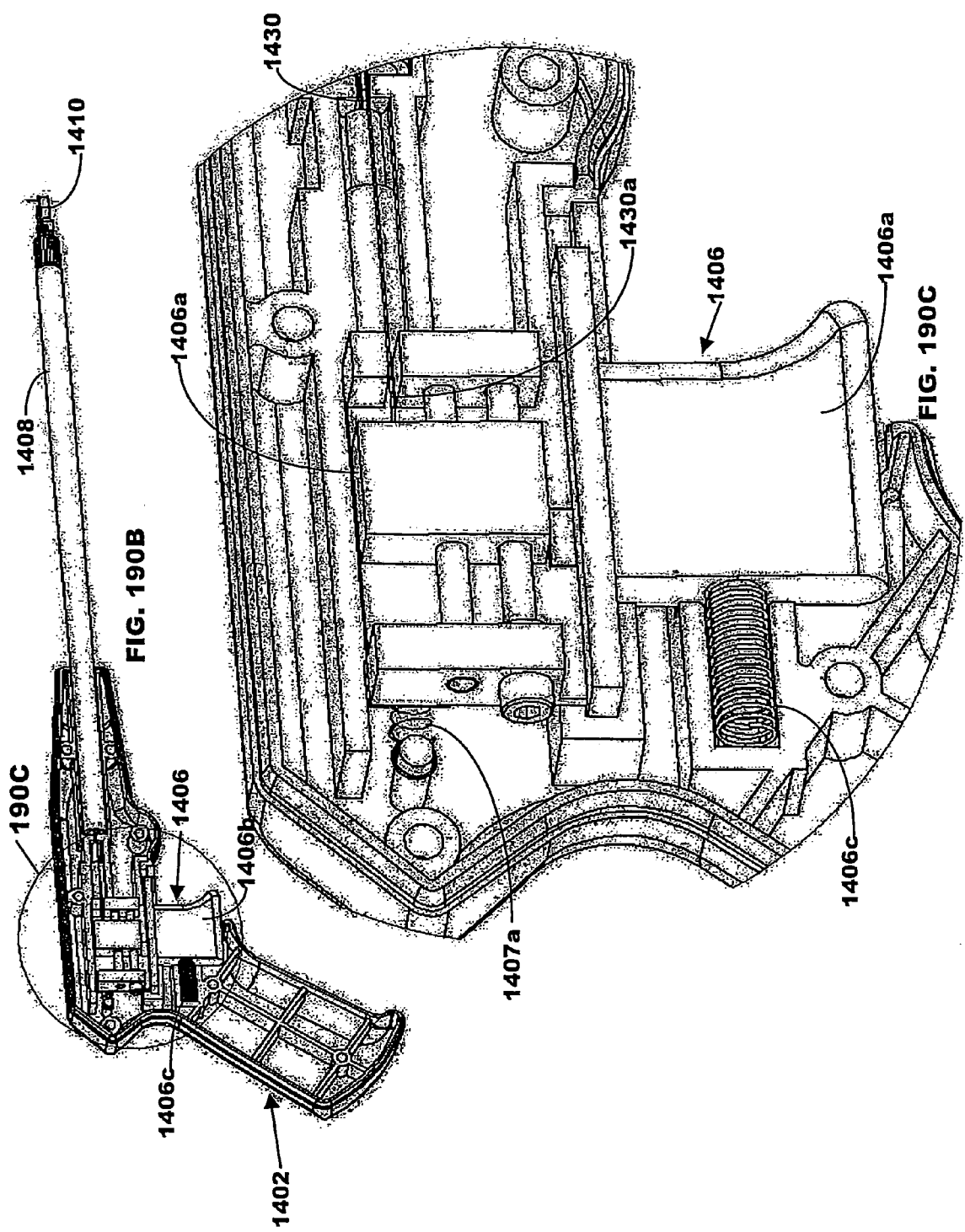

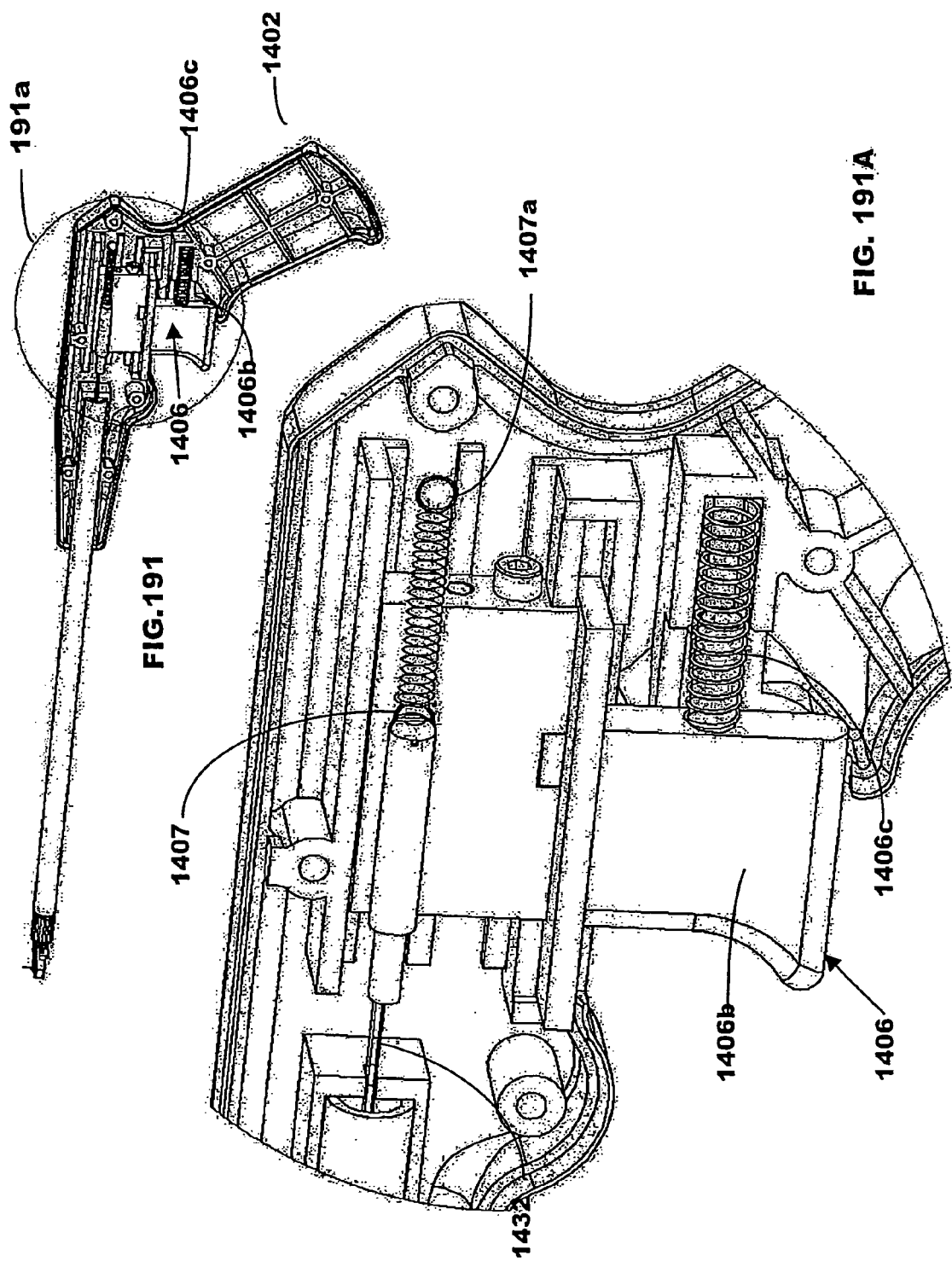

CYCLING SUTURING AND KNOT-TYING DEVICE

This is a Continuation-In-Part of application Ser. No. 10/263,902 filed Oct. 3, 2002 now U.S. Pat. No. 7,004,951.

BACKGROUND OF THE INVENTION

Field of the Invention

This invention relates to the suturing of surgical incisions, wounds and any other joining or fixing of tissue in general surgical procedures and in particular, the suturing, joining or binding of tissue in surgical procedures involving very small, cramped or otherwise inaccessible fields of operation, such as in general laparoscopic and neurological brain surgery. One of the problems which is inherent in many surgical procedures is that of limited access of the surgeon's hands, as well as the needle and suturing implements, into the incision or wound. This problem is amplified under circumstances where delicate surgery such as heart, brain, and spinal surgery, as well as surgery on infants and children is undertaken, since the surgical areas of interest involve minute features. Many surgical procedures that would otherwise be possible on adults and children are impossible due to the tiny operating fields and many conditions that might otherwise be corrected by surgery are therefore considered to be inoperable. The same situation occurs under circumstances such as suturing within interior and normally inaccessible areas of the body, where no known surgical techniques and/or instruments can access these areas and provide the necessary surgical relief.

The micro-sized cyclical suturing and knot-tying device of this invention is designed to optimize surgical suturing and in particular, to facilitate access to very small, normally, but not limited to, inaccessible areas of the body, including the heart, brain and spinal cord, as well as conventional procedures on infants, to allow surgical relief which has heretofore been unavailable by conventional surgical techniques. The device of this invention is characterized by an arcuate, fixed, grooved or recessed way provided in a correspondingly configured support frame mounted for articulation on an operating device and capable of receiving a rotating, curved needle fitted with a length of thread. Frictional devices are provided in the way for selectively engaging the needle and causing the needle to rotate in either direction for suturing a wound, which can be operated with sufficient force in an articulated state. These frictional devices are responsive to manipulation of various operating elements or components in the operating device. Needle direction-adjusting elements can also be provided in the frame for selectively adjusting the direction of needle rotation. Articulation of the support frame that carries the way and the rotating needle with respect to the operating device is typically facilitated by means of cables connecting the ball or universal joint-mounted frame to a "joy stick"-type lever provided on the operating device. Accordingly, rotation of the needle incrementally in one or both directions can be effected by manipulation of the appropriate directional and drive operating elements on the operating device, and articulation of the frame, and thus the way and the needle in concert, by manipulation of the lever on the operating device. Various thread incrementing and handling accessories and hook/unhook knot-tying devices can also be utilized in cooperation with the operating device to facilitate pulling, handling and tying of the thread to define suturing knots as the tissue suturing is effected by the operating device and the rotating needle.

The curved or arcuate frame is constructed to support the needle from end to end when the needle is in the starting position. The arcuate grooved or recessed support way is shaped in such a manner as to provide the correspondingly-shaped needle with adequate support while leaving the top of the groove or recess, located on the top of the disk of rotation open to permit passage of the thread around the way circuit traversed by the needle without trapping the thread in any of the needle support and drive structure. All friction and locking forces are applied by means of the frictional devices to the needle at selected locations on the way. Both the needle and the frame, as well as the way, have a corresponding gap to accommodate tissue to be sewn. Accordingly, when the needle is driven in a circular path by manipulation of the appropriate operating components or elements in the operating device, the needle passes through tissue which protrudes into the gap in the way. Furthermore, since the thread is attached to the needle, either at one end of the needle, in the case of unidirectional needle motion, or in the case of bidirectional needle operation in the center of the needle, the thread is drawn behind the needle, around the open top of the way, across the gap and through the tissue as the needle traverses the tissue. Although the thread cannot be trapped within the way, it is entrapped within the tissue through which the needle and thread is passed. If this penetration and entrapment is followed by successive encirclements of segments of the trailing portion or tail of the thread by the leading portion or head of the thread, where it joins the needle, rather than penetrating the tissue, then a knot is formed, which may be drawn tight and will bind in the same manner as a conventional surgically tied knot. It is significant that all of the knots commonly used in conventional surgery may be tied in this manner by use of the device of this invention in a fraction of the time required by conventional sewing and knotting techniques.

Various elements and components are provided in the operating device in cooperation with the way, the needle and the support frame for effecting rotation of the needle in one or both directions responsive to manipulation of the operating device. Typical of the needle drive devices is a needle driver and a drive direction setting plate combination mounted in the support frame, such that the drive direction setting plate and needle driver may be manipulated in sequence by the corresponding operating elements or components in the operating device to set the direction of rotation of the needle and then drive the needle in that direction. A second drive mechanism includes a rack and pinion mechanical arrangement that typically moves the needle in one direction responsive to operation of the operating device. A third drive mechanism includes multiple forked blades that rotate within the frame by manipulation of the operating device to engage the blade and operate the blade in a selected direction by means of a driver plate. Another driving mechanism for causing the needle to traverse the way in a selected direction is provided by multiple, fork-shaped blades that selectively engage the needle responsive to a drive spur device operated by the operating device. Yet another driving mechanism includes a planetary wheel and gear mechanism operated by a pair of beveled gears that drive toothed rotors for engaging and driving the needle. A universal joint arrangement typically connects the support frame to the operating device in but not limited to this embodiment of the invention. Another embodiment of the needle articulation and drive mechanism includes a flexible rotor that selectively engages the needle and is driven responsive to operation of the operating device. Still another drive mechanism for causing the needle to traverse the way in an articulating, controlled manner is a pawl and crank device which includes a pawl mounted in the frame and a cooperating crank that rides in a V-shaped slot in the pawl to effect selective engagement of the needle by the pawl teeth and rotation of the needle in the way by manipulation of the operating device. Various operating devices may be utilized to interact and interface with the respective drive mechanisms for traversing the needle around the way in the frame in an articulating, controlled manner, as hereinafter described.

SUMMARY OF THE INVENTION

These and other objects of the invention are provided in a suturing device which includes an arcuate frame having an open groove; an arcuate needle disposed within the frame and seated in the groove; engaging means disposed within the frame and selectively extending into the groove for releasably engaging the needle; and drive means engaging the engaging means for driving the needle in the groove.

An object of one form of the invention is to provide a suturing device which comprises a uniquely configured articulating suturing head that includes a plurality of strategically shaped, circumferentially-spaced cavities, a generally semicircular-shaped shuttle track along which a novel needle advancing shuttle is slidably movable and a generally semicircular-shaped needle guide along which a novel suturing needle is sequentially advanced by movement of the needle advancing shuttle.

Another object of one form of the invention is to provide a suturing device of the character described in the preceding paragraph which includes a suturing needle that has a novel rectangular cross section, a circumferentially extending, notched wall and a strategically angled chamfered end that compensates for needle deformation in the suturing process.

Another object of one form of the invention is to provide a suturing device of the aforementioned character, which includes a plurality of uniquely configured needle engaging and advancing members that are disposed within the plurality of strategically shaped, circumferentially-spaced cavities formed in the articulating suturing head portion and are adapted for both transverse and pivotal movement within the cavities in response to movement of the needle advancing shuttle.

Another object of one form of the invention is to provide a suturing device of the character described in the preceding paragraphs which comprises a dual-cable shuttle advancing subsystem that includes a cooperating biasing spring and trigger mechanism for smoothly and positively moving the needle advancing shuttle along the shuttle track of the suture head of the device.

BRIEF DESCRIPTION OF THE DRAWINGS

FIG. 8 is a top perspective view of one end of the drive direction setting plate component of the crescent, more particularly illustrating two sets of spaced-apart, oppositely-disposed, needle-engaging blades for sequentially engaging the needle and determining the direction of rotation of the needle responsive to operation of blade-positioning operating components in the operating device.

FIG. 23 is a bottom perspective view of one end of the assembled fixed way, needle driver, drive direction setting plate and fixed way direction setting plate assembly illustrated in FIG. 6.

FIG. 24 is a bottom perspective view of the assembled fixed way, needle driver and drive direction setting plate underlying the needle driver, which needle driver is seated on the fixed way for selectively driving a curved needle around the crescent in a counterclockwise rotational sequence.

FIG. 25 is a bottom perspective view of the assembled fixed way, drive direction setting plate, needle driver and fixed way, with the needle driver gripping the needle and rotated with the drive direction setting plate on the fixed way for driving one end of the crescent-shaped needle into the crescent slot for suturing tissue.

FIG. 30 is a top view of the needle fixed way direction setting plate and drive direction setting plate (hidden by the fixed way direction setting plate) superimposed on the bottom of the needle driver and the fixed way, with the fixed way overhead connecting members removed for brevity.

FIG. 31 is a top view of the fixed way direction setting plate and drive direction setting plate superimposed on the bottom of the needle driver and the fixed way illustrated in FIG. 30, further illustrating the incremental movement distance of the needle driver and the drive direction setting plate with respect to the fixed way direction setting plate on the fixed way.

FIG. 39 is a top view of the needle driver, the drive direction setting plate, the fixed way direction setting plate and the case illustrated in FIG. 38, more particularly illustrating travel mode of the needle in the counterclockwise direction with respect to the case.

FIG. 40 is a bottom view of the crescent, mounted in articulating ball and socket relationship on a transition guide cone provided on one end of the extension tube extending from the transmission tube, with articulation control cables extending through the extension tube to the crescent at the ball and socket mount between the crescent and the transition guide cone.

FIG. 75 is a perspective view, partially in section, of the needle direction actuator mechanism slidably mounted on the transmission tube and including a set of cables extending through the transmission tube and around pulleys mounted on inserts provided in the transmission tube, for extension to the crescent.

FIG. 80 is a perspective view of the crescent in close proximity to tissue to be sutured, more particularly illustrating operating of the operating device and crescent to suture the tissue.

FIG. 81 is a perspective view of the crescent illustrated in FIG. 80, illustrating a preferred manipulation and incrementing of thread typically centered on the curved needle using the thread incrementing device during a suturing operation.

FIG. 102 is a perspective view, partially in section, of one of the receiving arms illustrated in FIG. 98, attached to a housing enclosing a pair of plunger discs (illustrated in phantom) for manipulating the various elements of the receiving arm.

FIG. 102A is a perspective view of a receiving arm, illustrating alignment of the respective access slots.

FIG. 103 is a side sectional view of the receiving arm and operating elements, more particularly illustrating the relationship between the grip/eject/cut blade element and the inner housing tube elements, of the hook/unhook device.

FIG. 104 is a perspective view of the pair of receiving arms in the hook/unhook device, with the receiving arms located in close proximity to tissue being sutured and the suturing thread, for manipulating the thread into suturing knots.

FIG. 105 is a perspective view of the receiving arms of the hook/unhook device illustrated in FIG. 104, more particularly illustrating engagement of respective thread segments by the arms and further manipulating the thread segments to tie a knot in the suturing thread.

FIG. 106 is a perspective view of the receiving arms illustrated in FIGS. 104 and 105, more particularly illustrating additional manipulation of the receiving arms to tighten the knot in the thread during the suturing operation.

FIG. 107 is a perspective view of a preferred embodiment of the housing tube of the hook/unhook device, with a receiving arm extending from one end of the housing tube in engagement with the length of the thread for manipulating the thread.

FIG. 108 is a perspective view, partially in section, of the housing tube illustrated in FIG. 107, more particularly illustrating the internal components of the housing tube and the receiving arm manipulating elements attached to the housing tube for manipulating the receiving arms.

FIG. 109 is a perspective view of a unidirectional device of the cycling suturing and knot-tying device.

FIG. 109A is an exploded view of a unidirectional device illustrated in FIG. 109, more particularly illustrating the fixed way/case, the driver blades and connection member mount and the crescent needle.

FIG. 109B is a perspective view of a preferred discontinuous-tooth beveled pinion gear for driving the unidirectional device illustrated in FIG. 109A.

FIG. 109C is a perspective view of the unidirectional device, with the needle in place and ready for incrementation around the fixed way/case.

Figure 109:
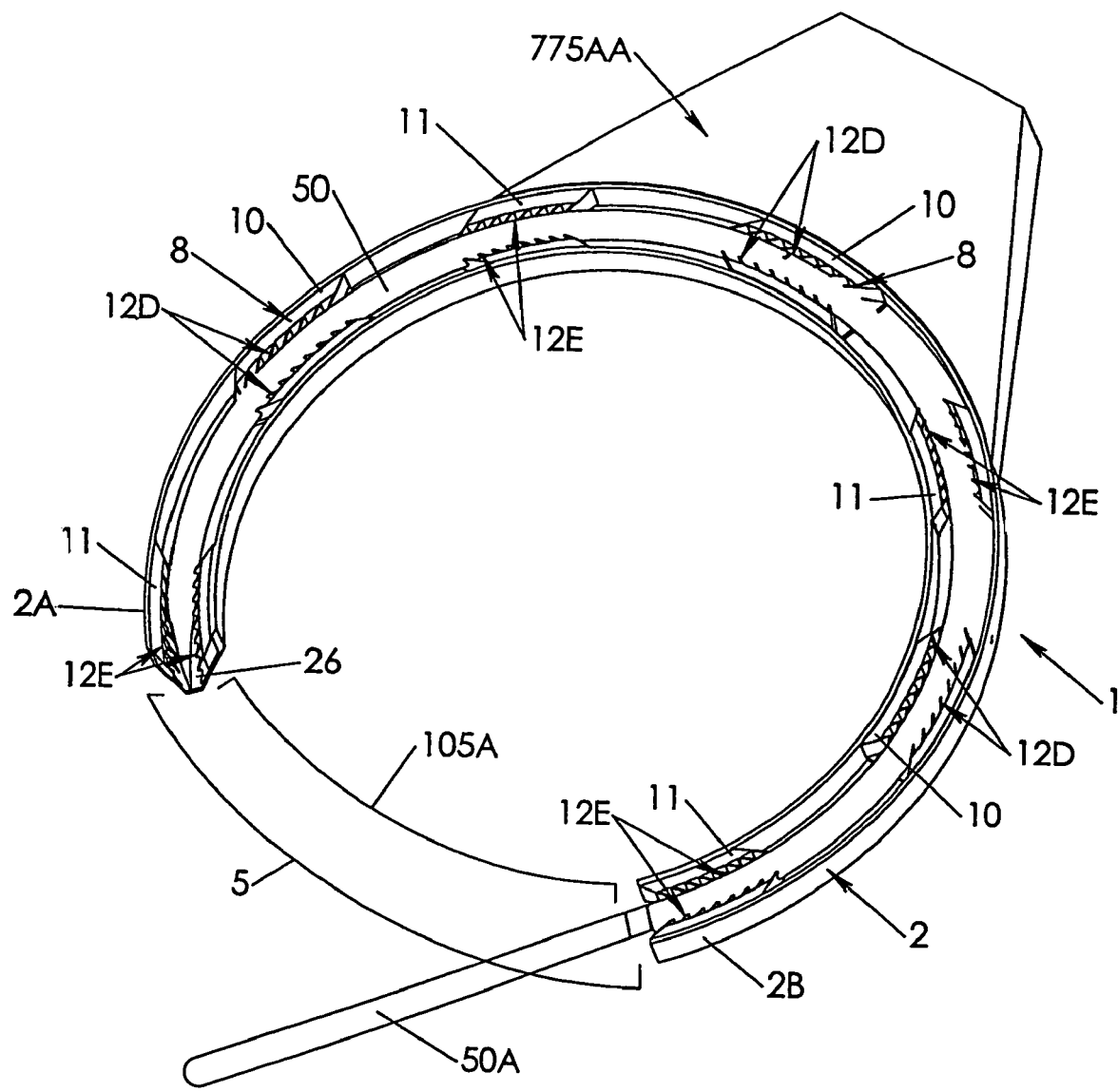
Figure 109B:
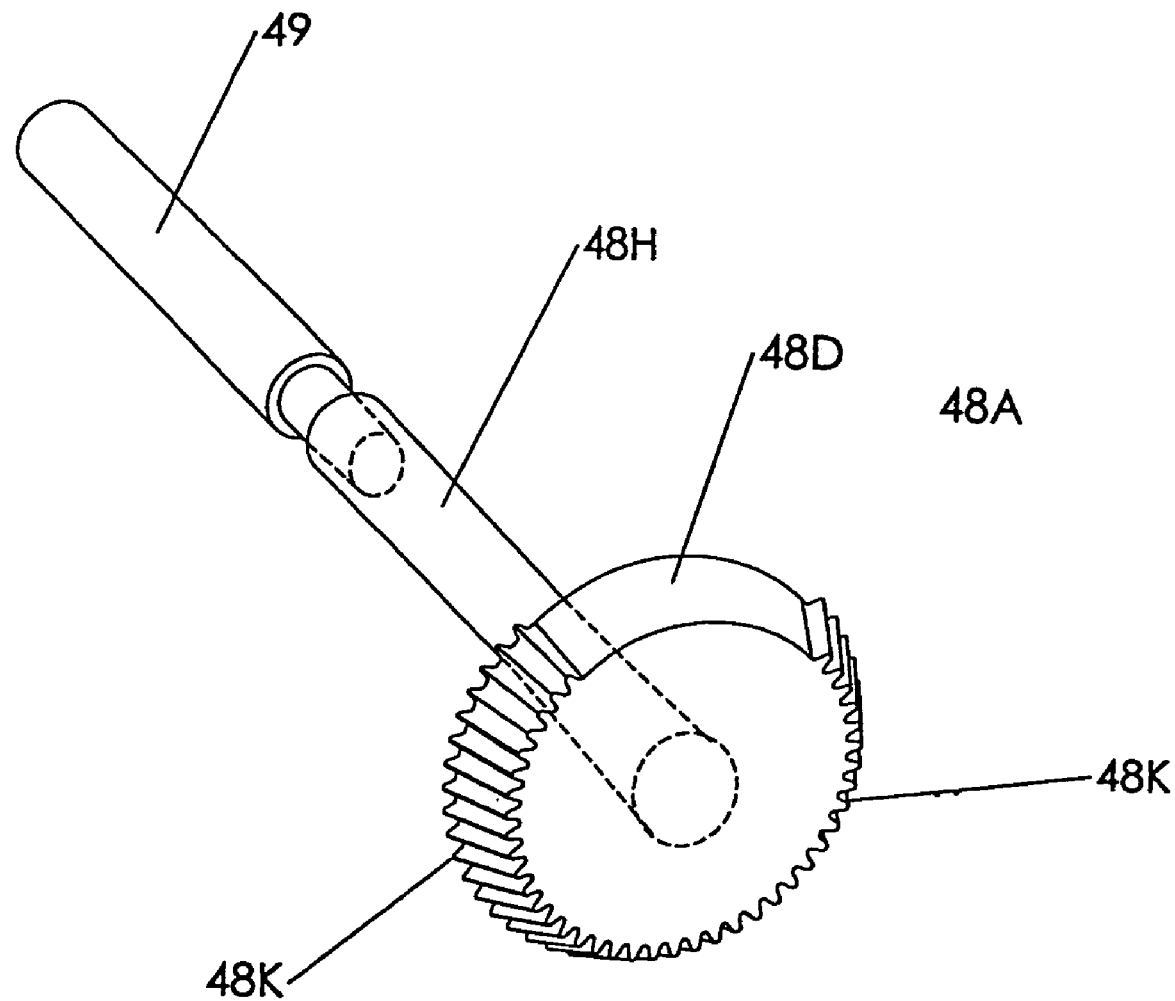
Figure 109C:
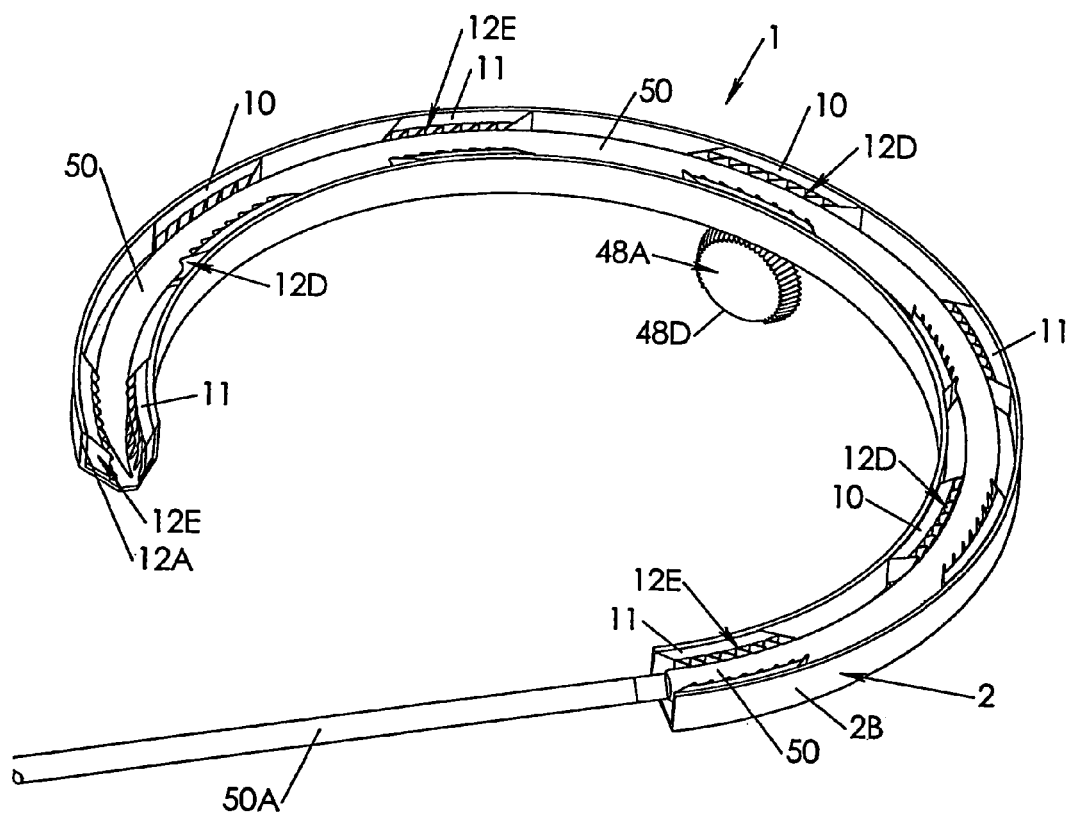
Figure 109D:
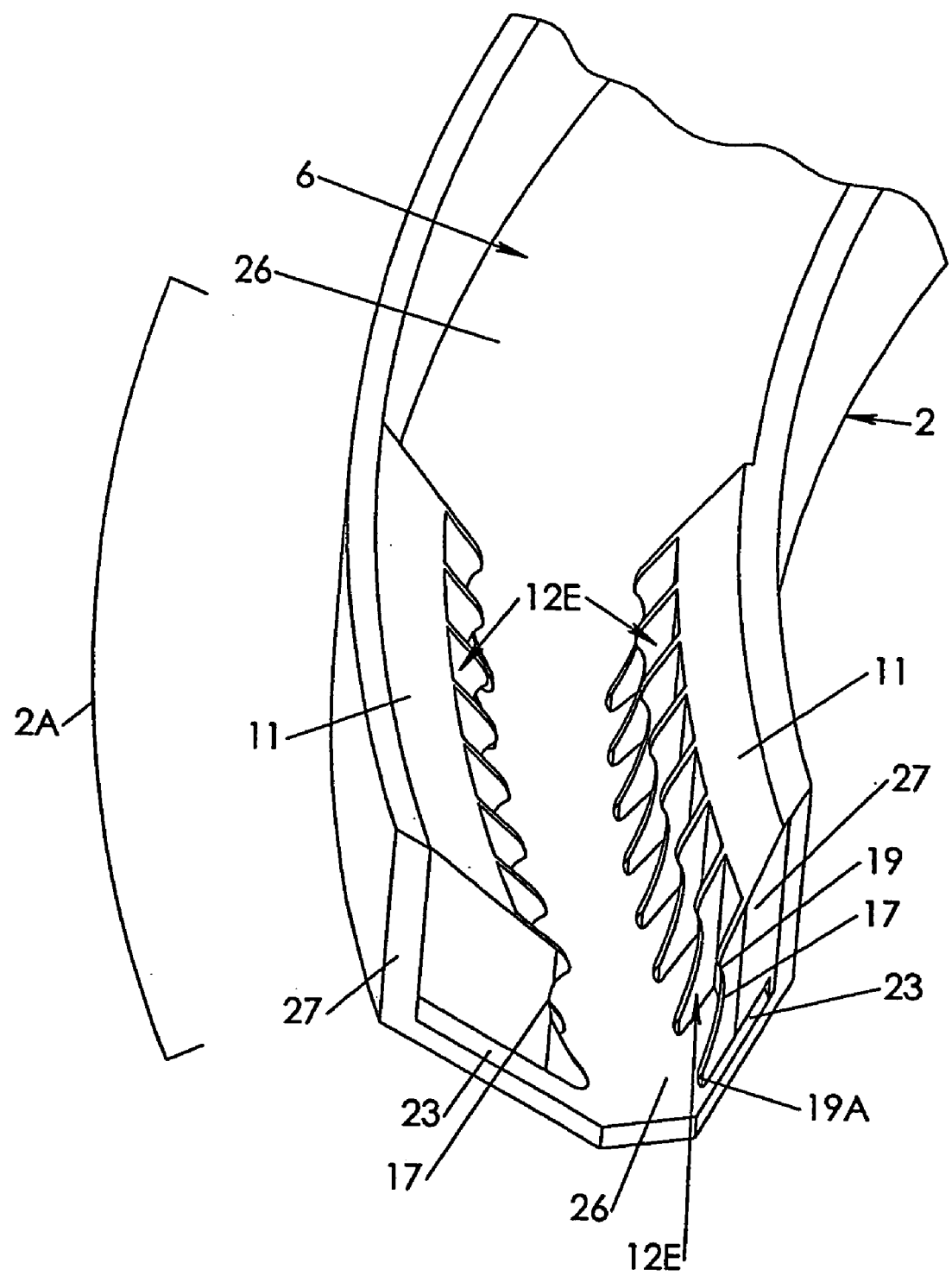

FIG. 109D is a perspective view of one end of the fixed way/case, illustrating an array of the fixed way blades.

Figure 109E:
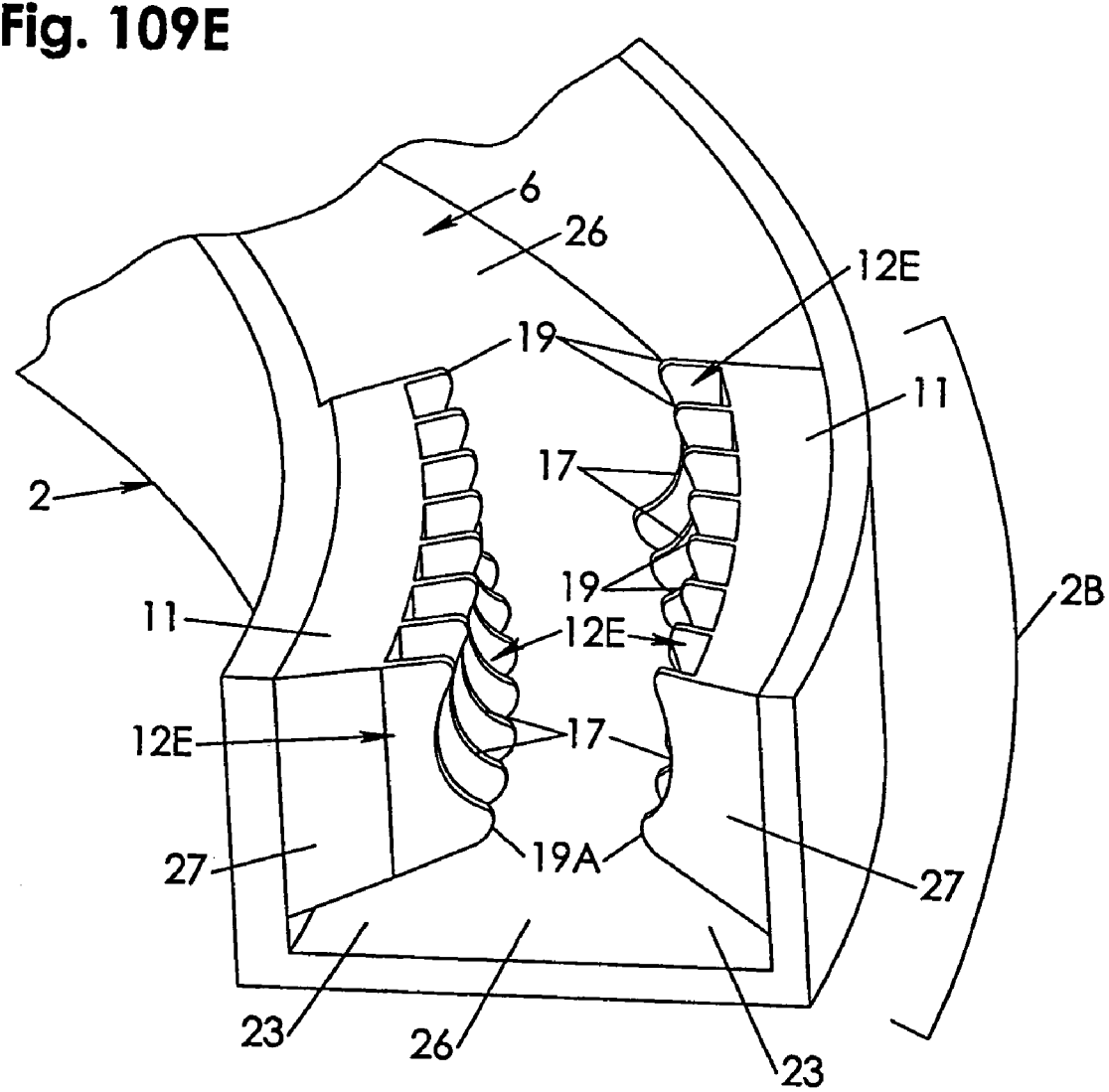

FIG. 109E is a perspective view of the opposite end of the fixed way/case from the end illustrated in FIG. 109D, further illustrating an array of the fixed way blades.

FIG. 109F is a perspective view of a reciprocal driver element, including the three, spaced-apart driver housing bosses mounted on the connection member and fitted with driver blades and a beveled rack.

FIG. 109G is a bottom perspective view of the reciprocal driver, illustrated in FIG. 109F, more particularly illustrating the beveled rack.

Figure 109H:
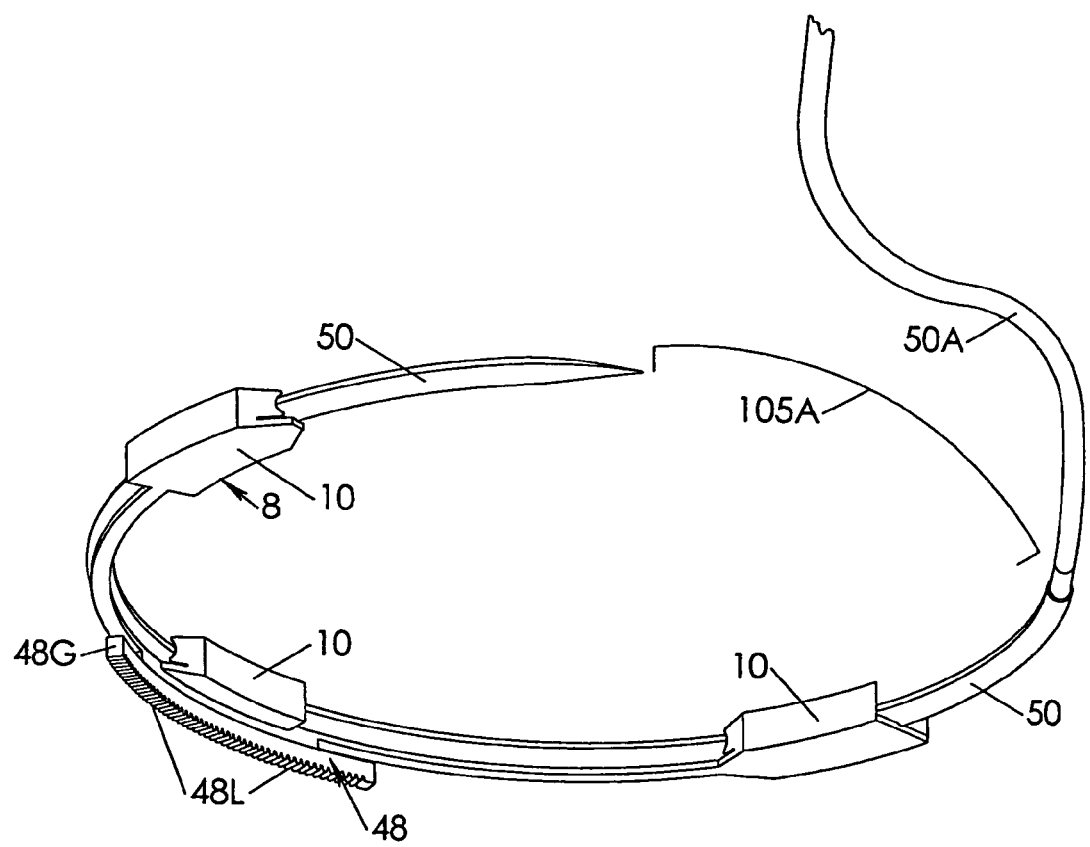

FIG. 109H is a bottom perspective view of the reciprocal driver with the arcuate needle in place.

Figure 109I:
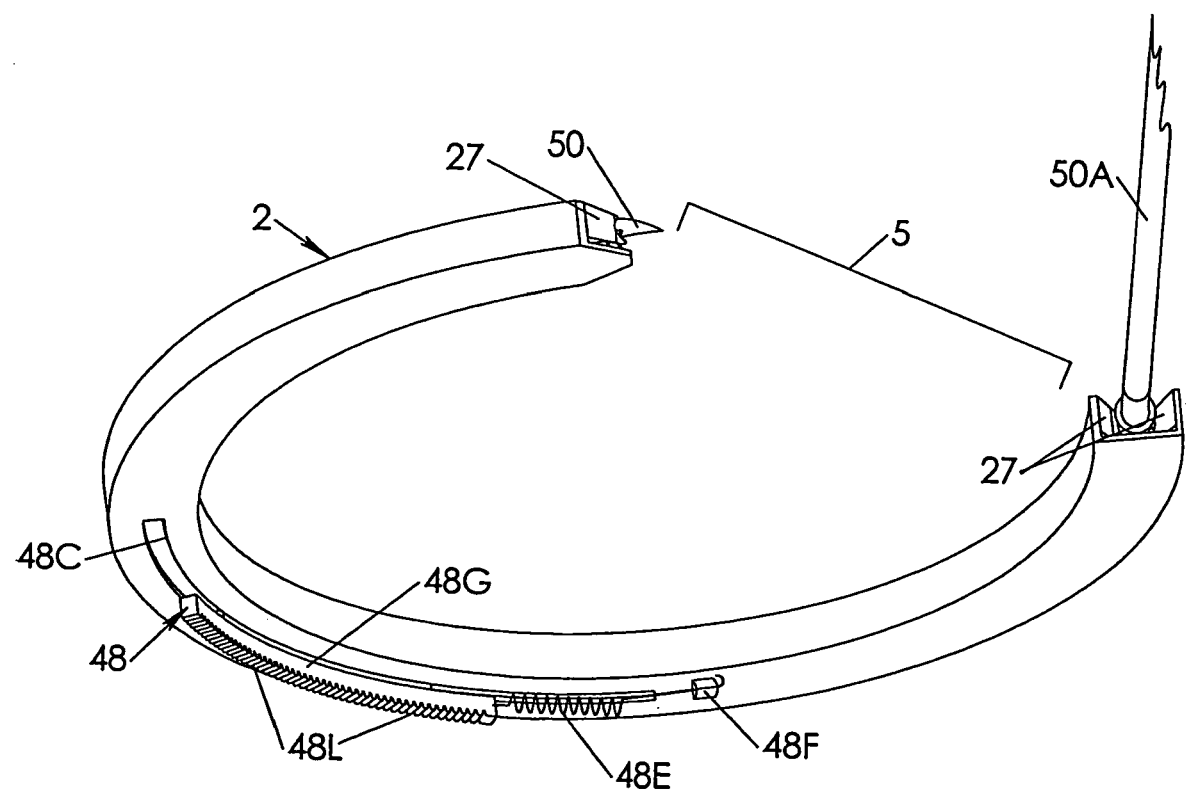

FIG. 109I is a bottom perspective view of the fixed way/case and the reciprocal driver with the beveled rack projecting through a slot in the fixed way/case.

Figure 109J:
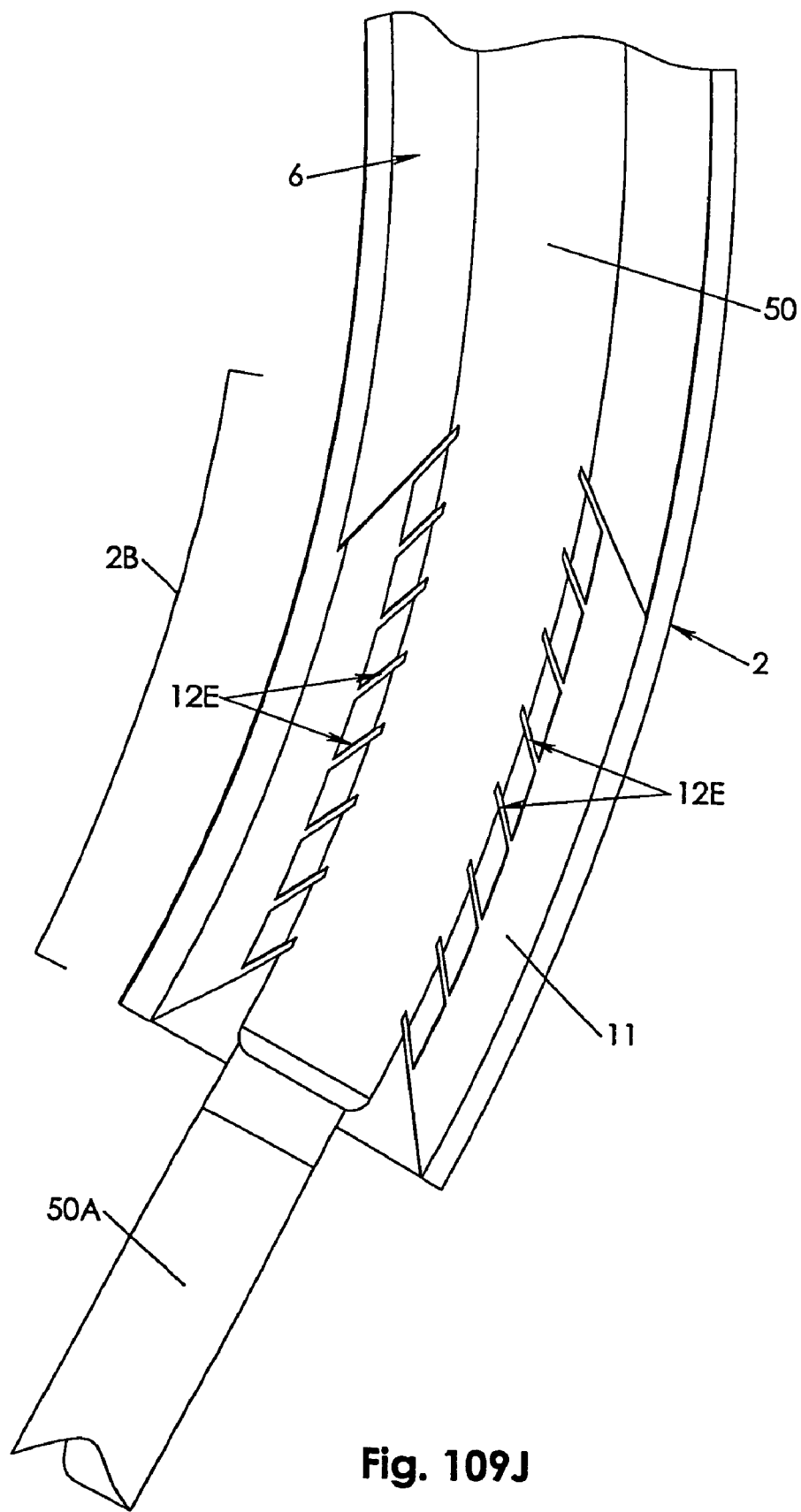

FIG. 109J is a top perspective view of the fixed way/case with the fixed way blades in place engaging the needles.

Figure 110:
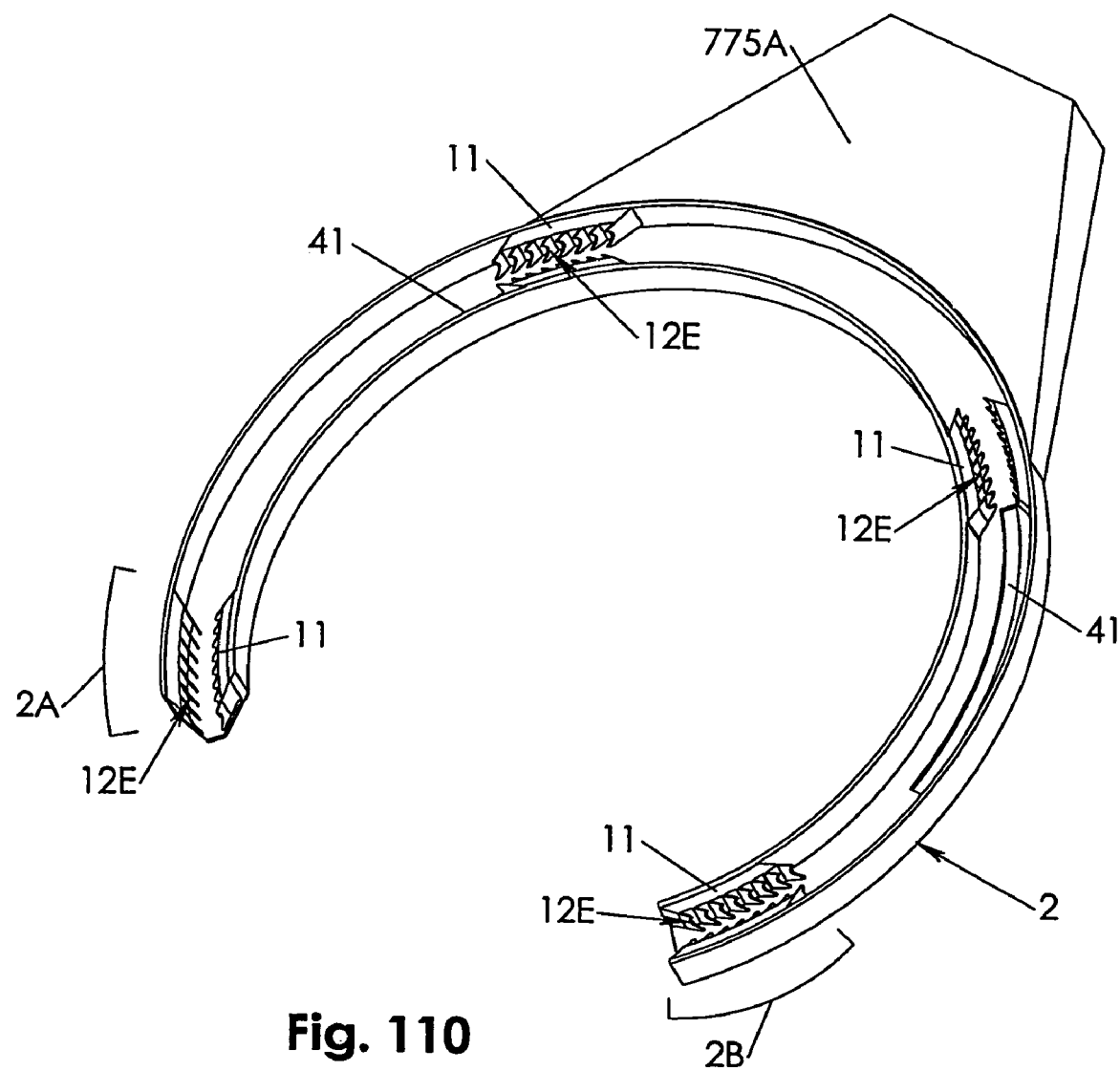

FIG. 110 is a top perspective view of the fixed way/case connected to a socket for attachment to an operator.

Figure 110A:
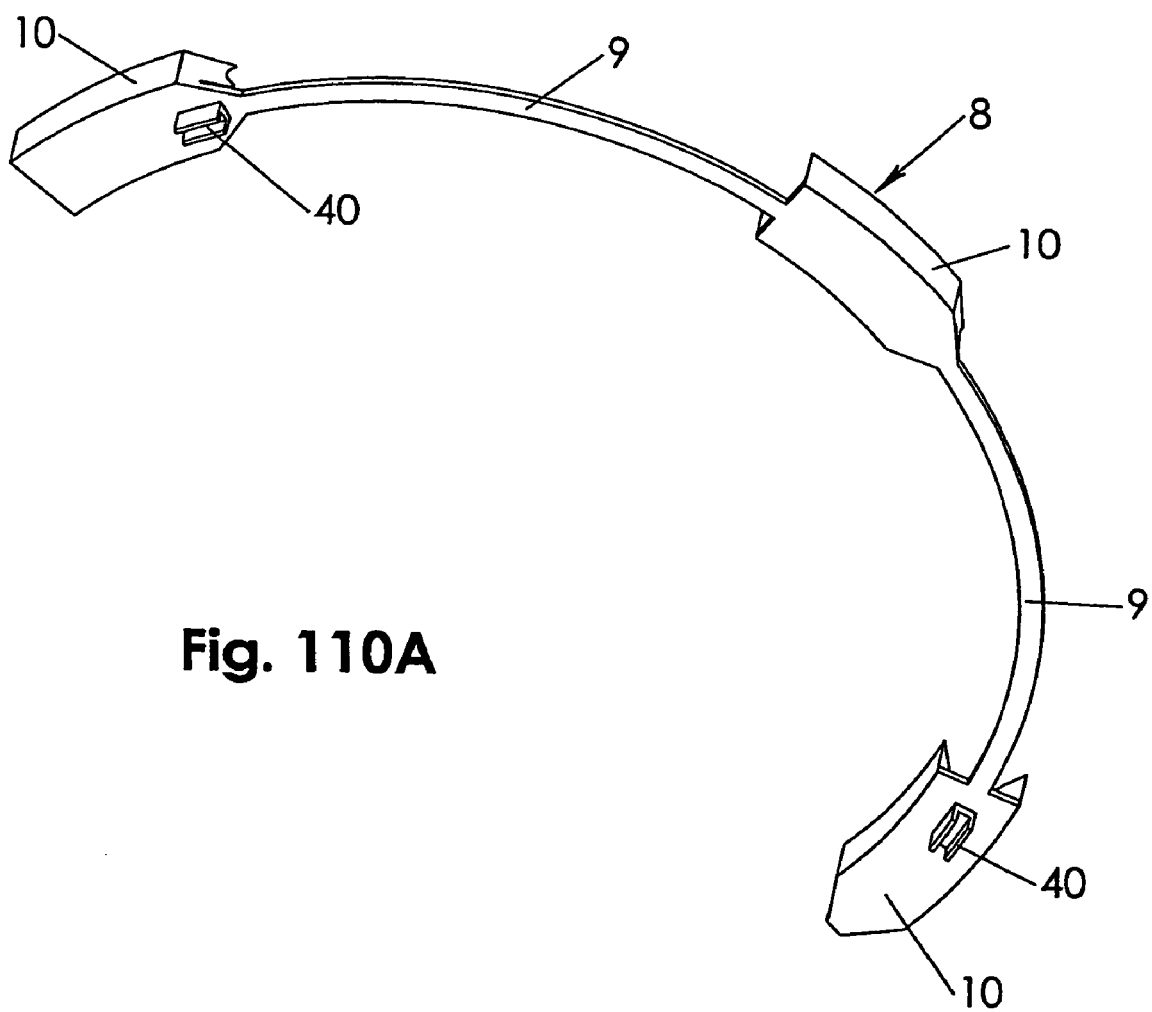

FIG. 110A is a bottom perspective view of the reciprocal driver illustrated in FIG. 109G, fitted with drive cable extensions for receiving drive cables.

Figure 110B:
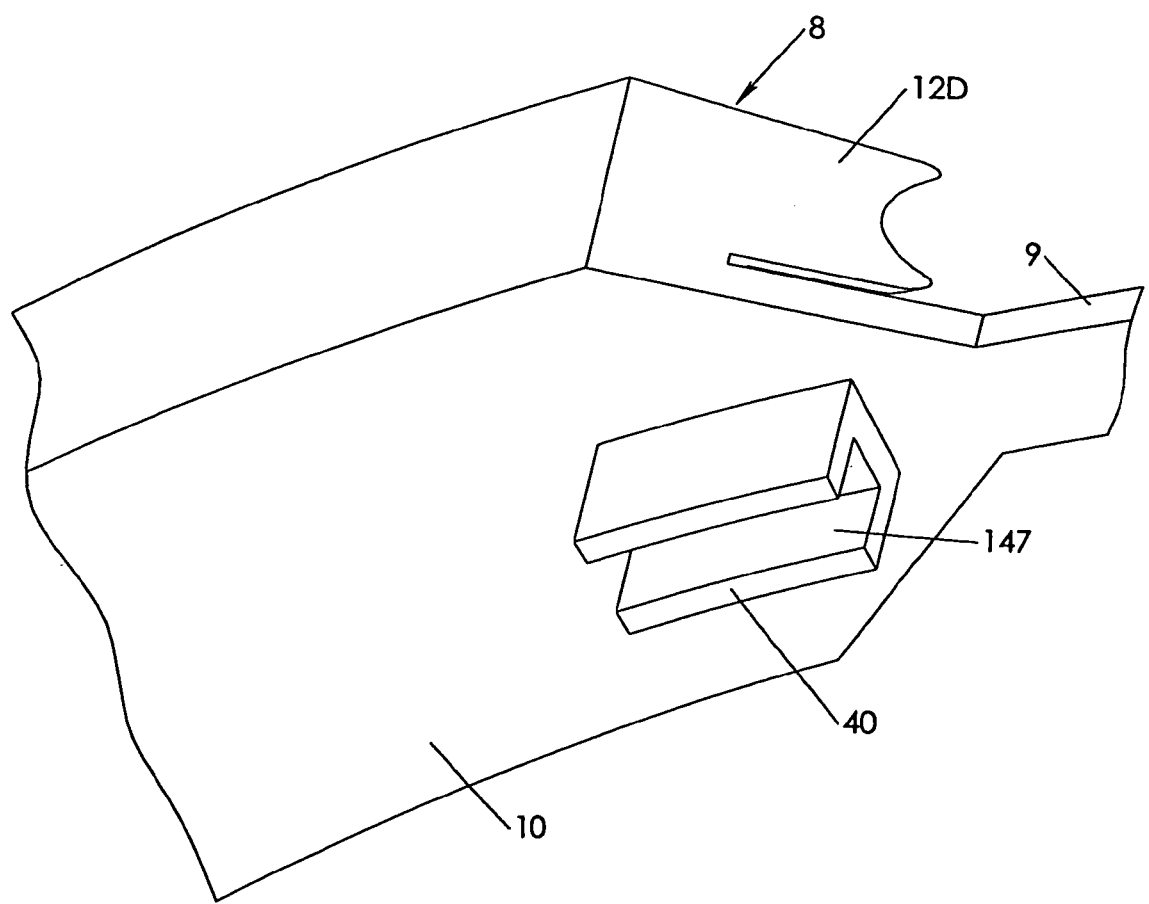

FIG. 110B is a bottom perspective view of an alternative embodiment of the reciprocal driver further detailing a drive cable extension for receiving a drive cable.

Figure 110C:
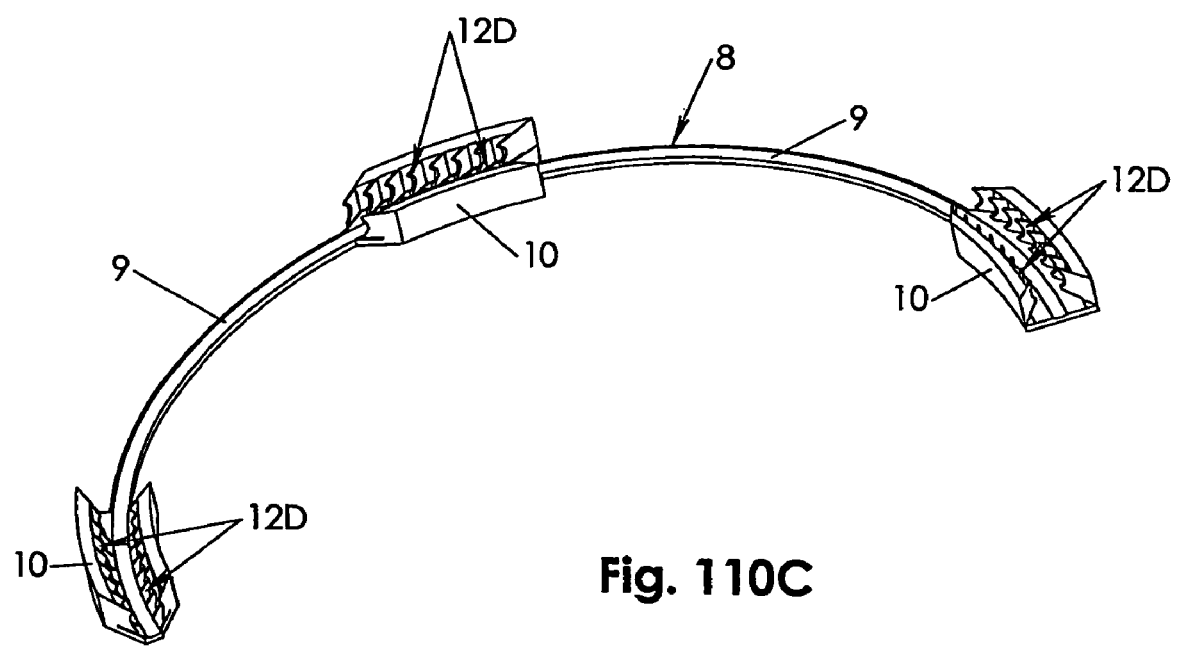

FIG. 110C is a top view of the reciprocal driver, more, particularly illustrating the driver blades in the respective spaced-apart driver housing bosses.

Figure 111:
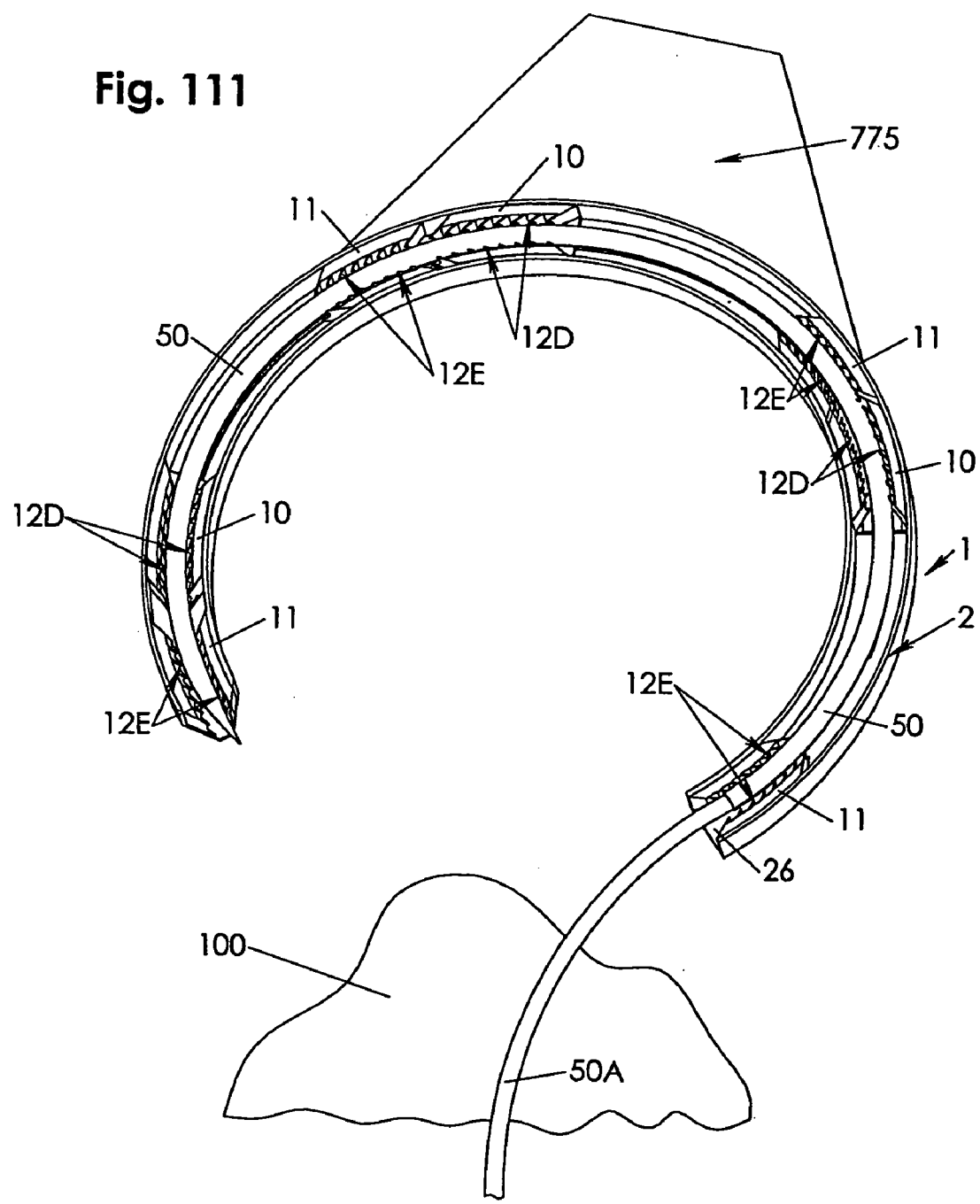

FIG. 111 is a top view of the unidirectional device fitted with the reciprocal driver, more particularly illustrating the proximity of the device to tissue material to be sutured and the positioning of the needle in the device for suturing the tissue.

Figure 111A:
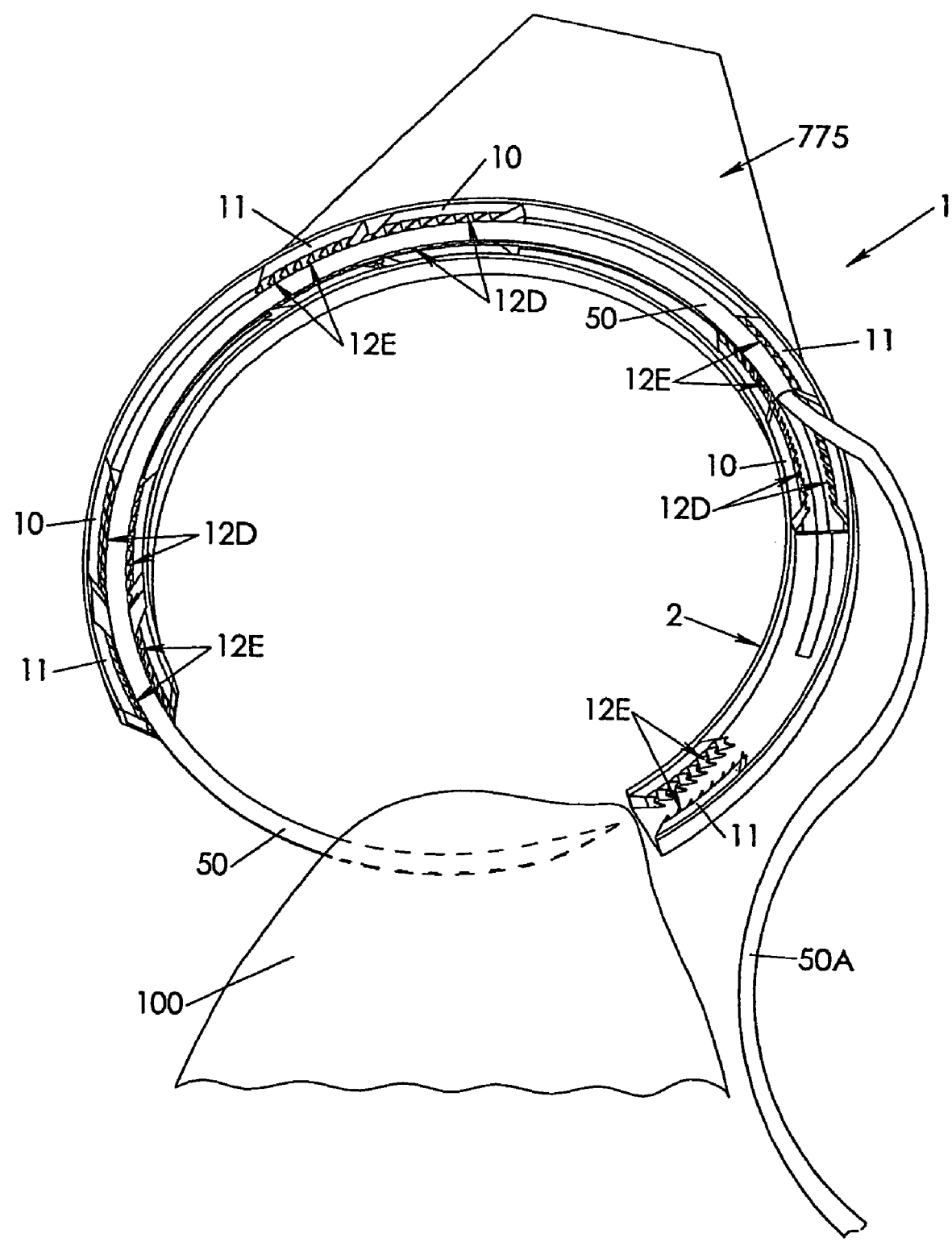

FIG. 111A is a top view of the unidirectional device 1 illustrated in FIG. 111, more particularly illustrating initial incrementation of the needle around the device and entering the material to be sutured.

Figure 111B:
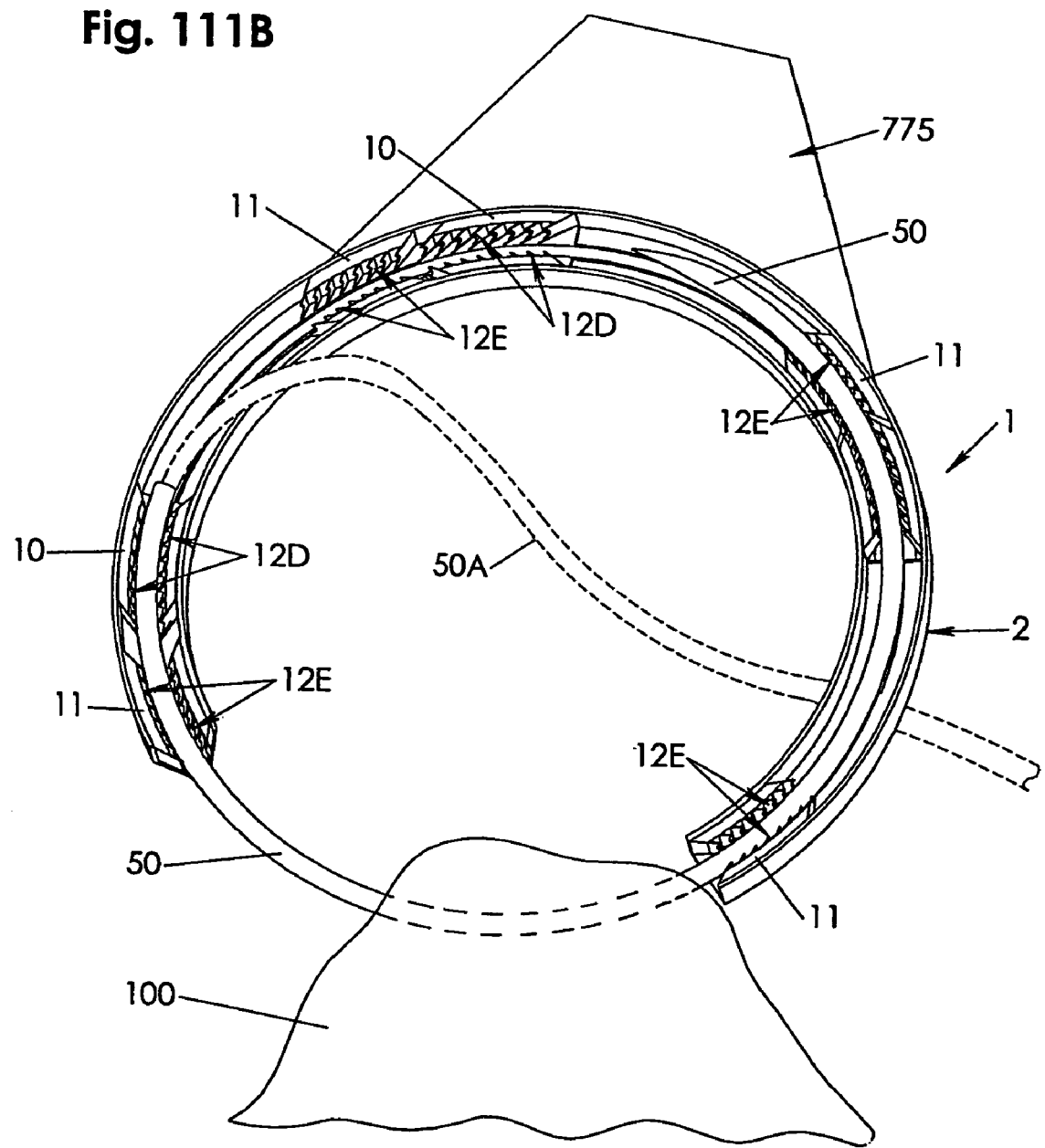

FIG. 111B is a top view of the unidirectional device illustrated in FIGS. 111 and 111A, illustrating further incrementation of the needle through the tissue to be sutured and entering the opposite end of the device.

Figure 111C:
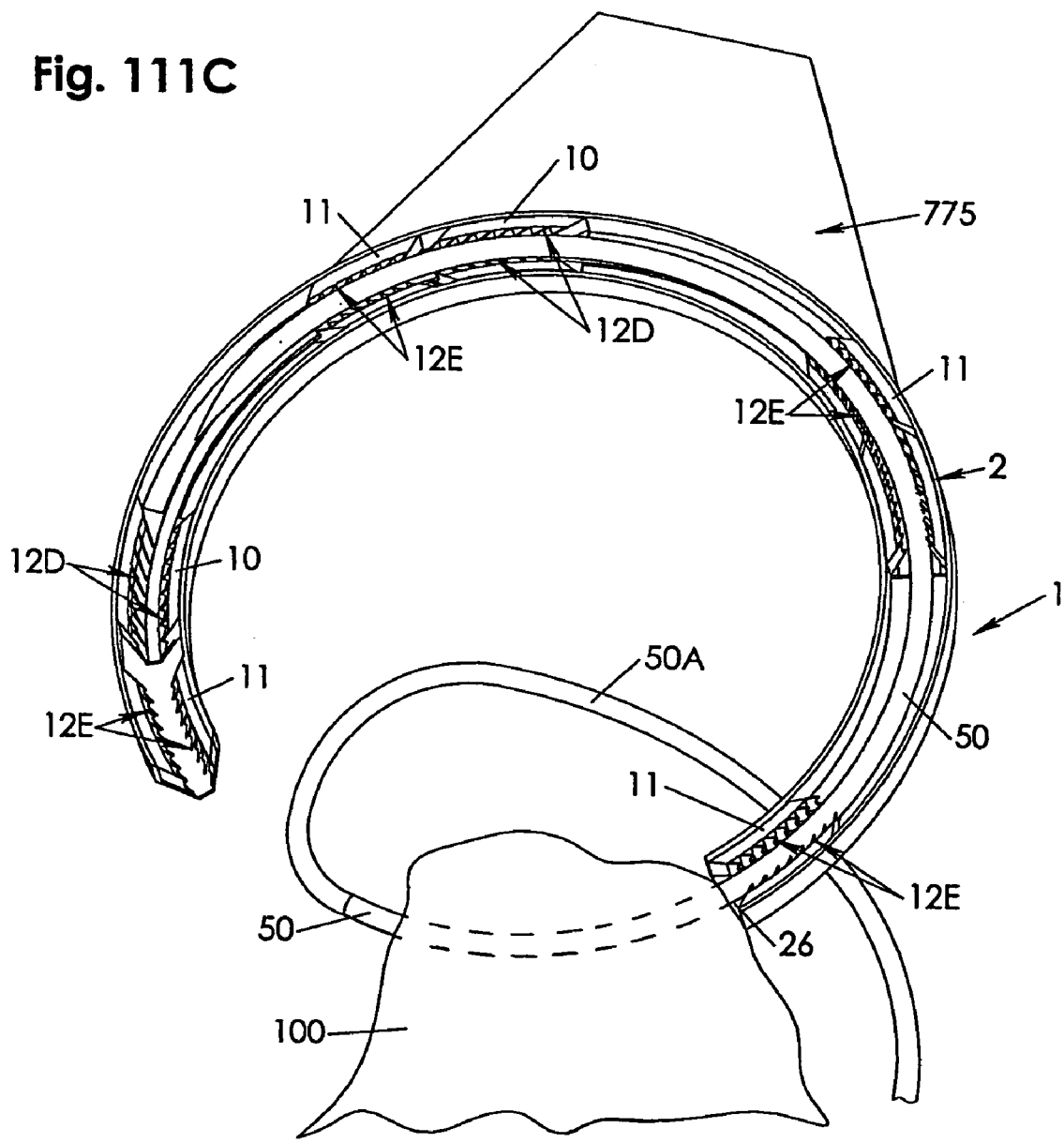

FIG. 111C is a top view of the unidirectional device illustrated in FIGS. 111-111B, more particularly illustrating completion of the needle rotation through the material to be sutured.

Figure 112:
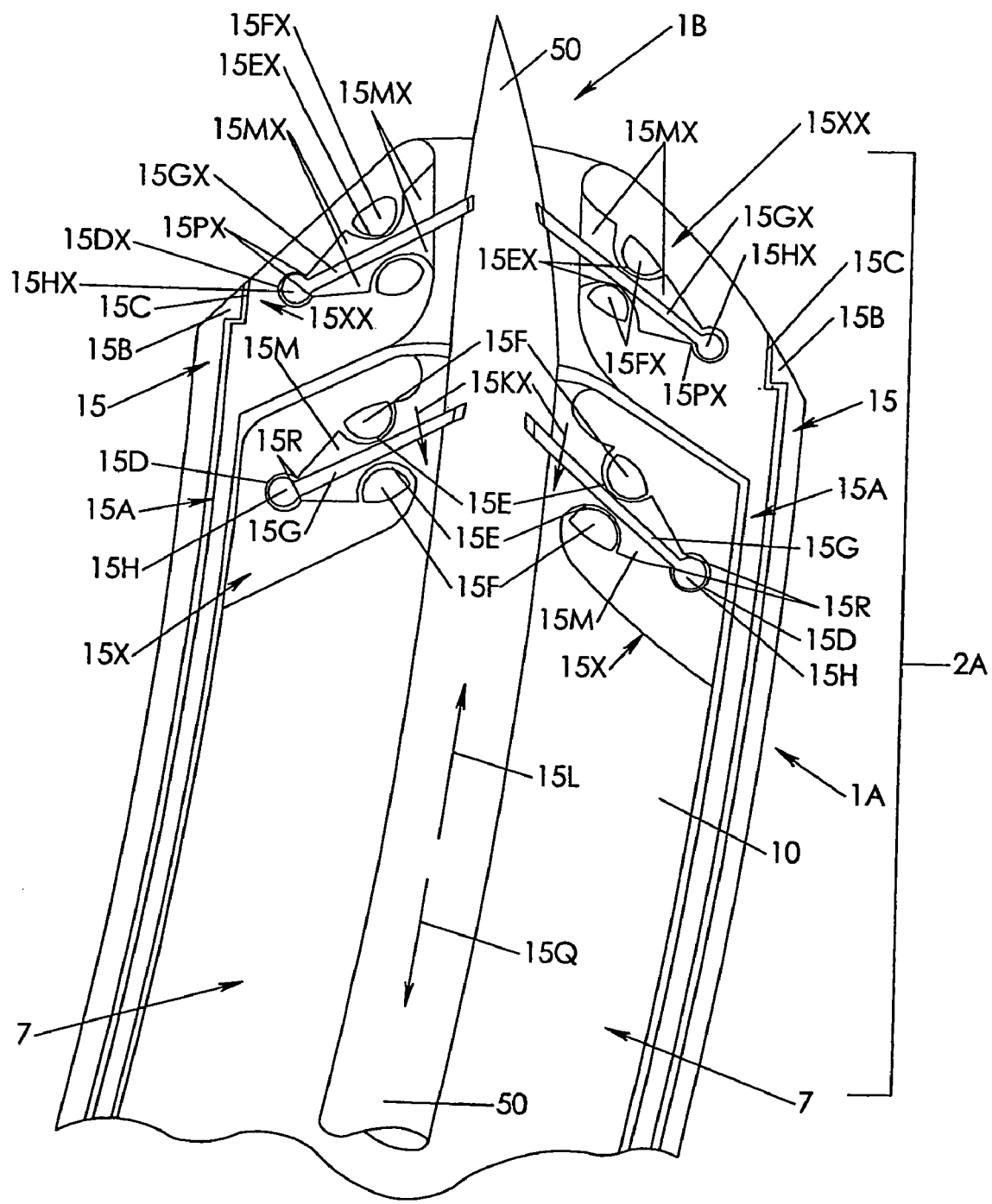

FIG. 112 is a top view of one end of an alternate unidirectional device, more particularly illustrating an alternate driver inserted in an alternate fixed way.

Figure 112A:
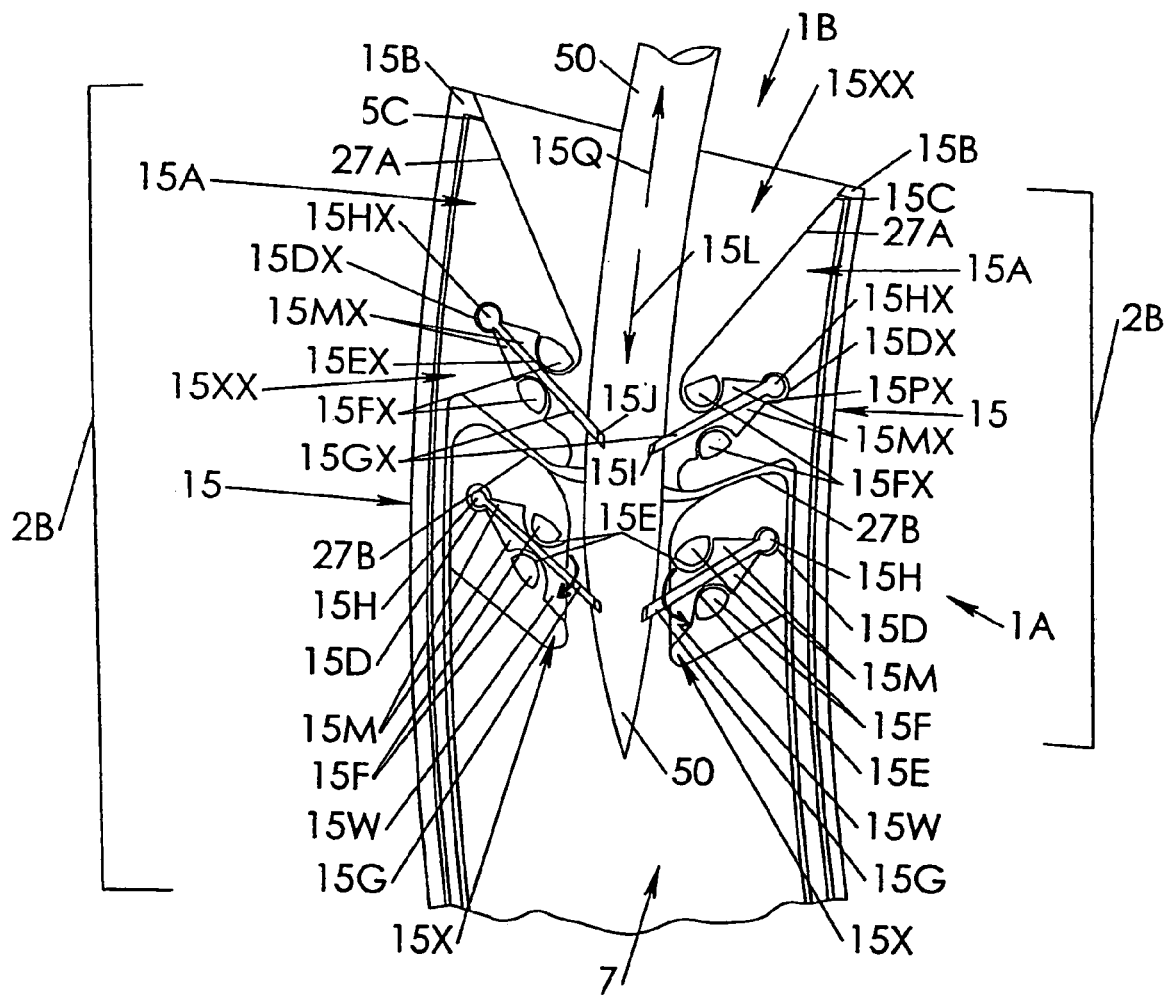

FIG. 112A is a top view of the opposite end of the alternate unidirectional device illustrated in FIG. 112, further illustrating the alternate driver fitted in the alternate fixed way.

Figure 112B:
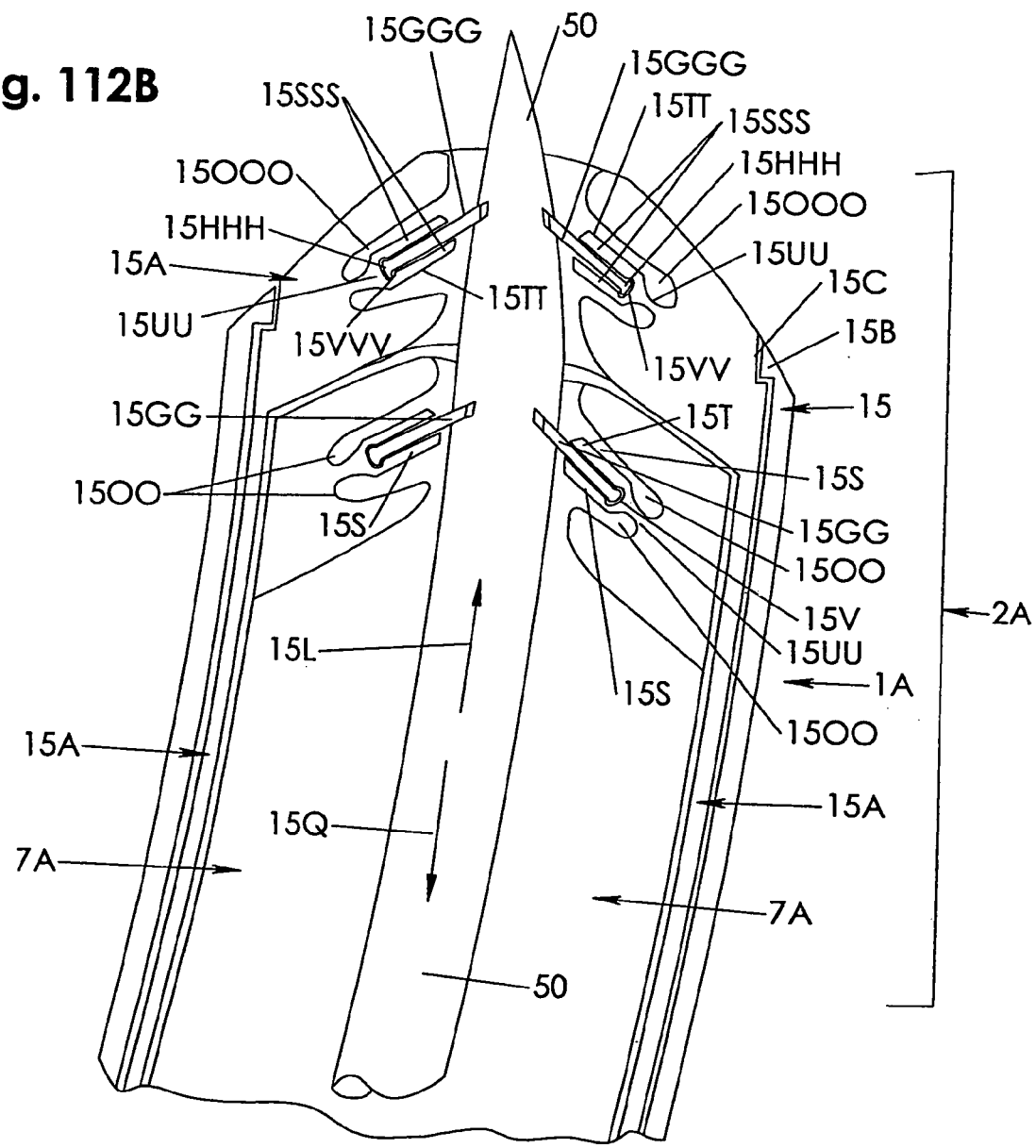

FIG. 112B is a top view of another embodiment of the alternate unidirectional device, wherein a second alternate driver is fitted in the alternate fixed way.

Figure 112C:
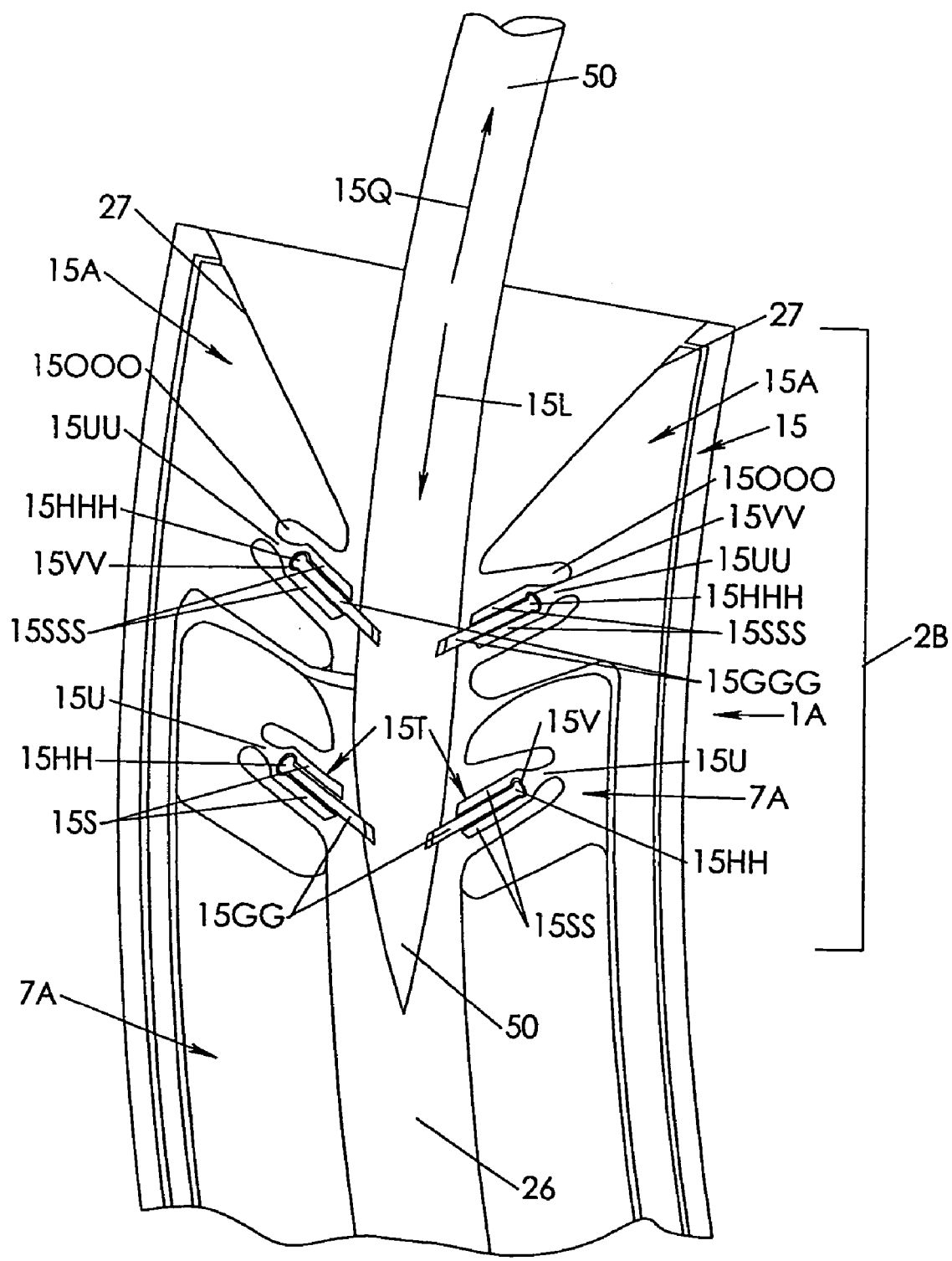

FIG. 112C is a top view of the opposite end of the alternate unidirectional device illustrated in FIG. 112B, with the second alternate driver in the alternate fixed way.

Figure 112D:
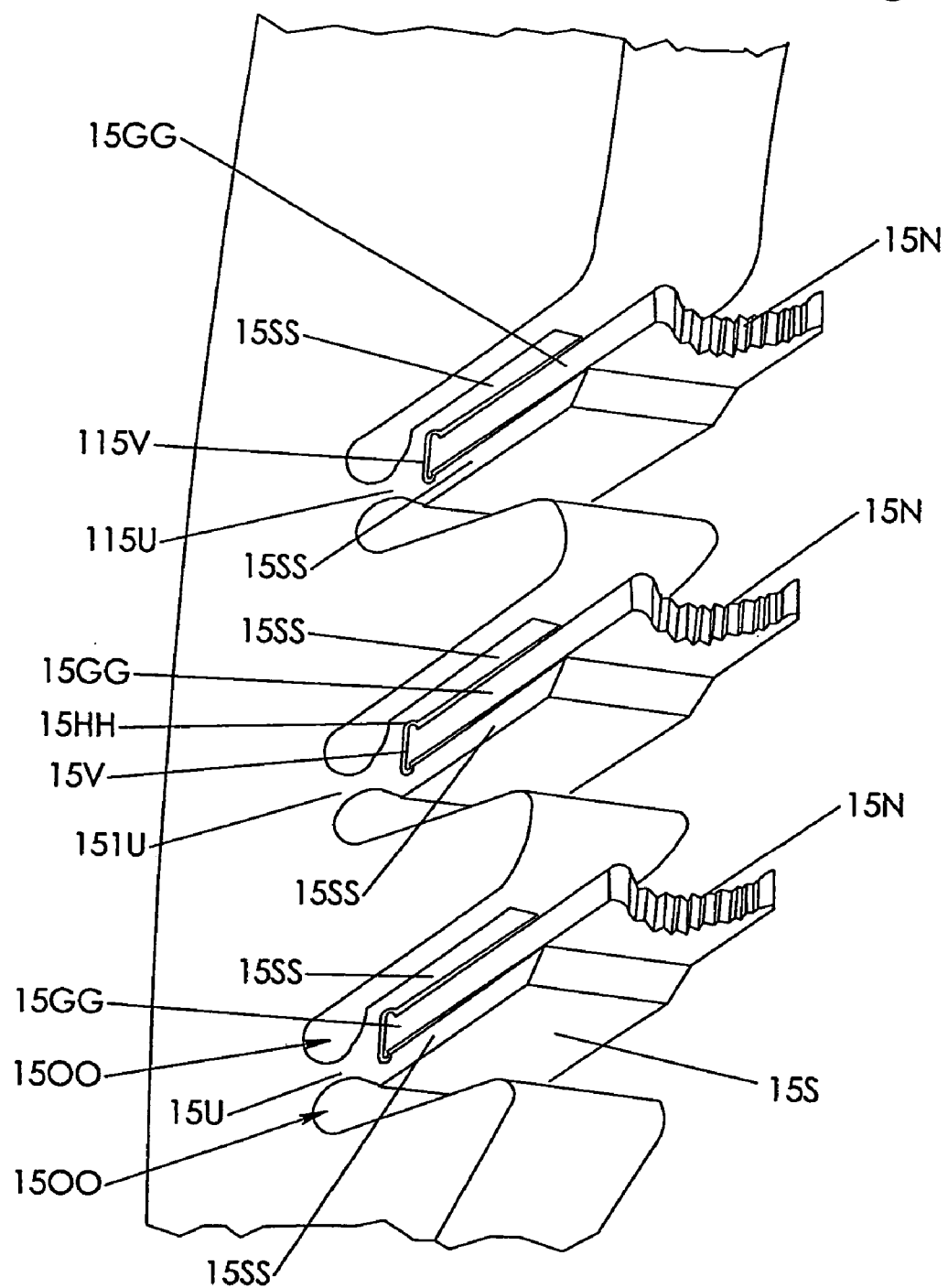

FIG. 112D is a perspective view, partially in section, of alternate fixed way blades, each fitted with a serrated needle contact area.

Figure 113:
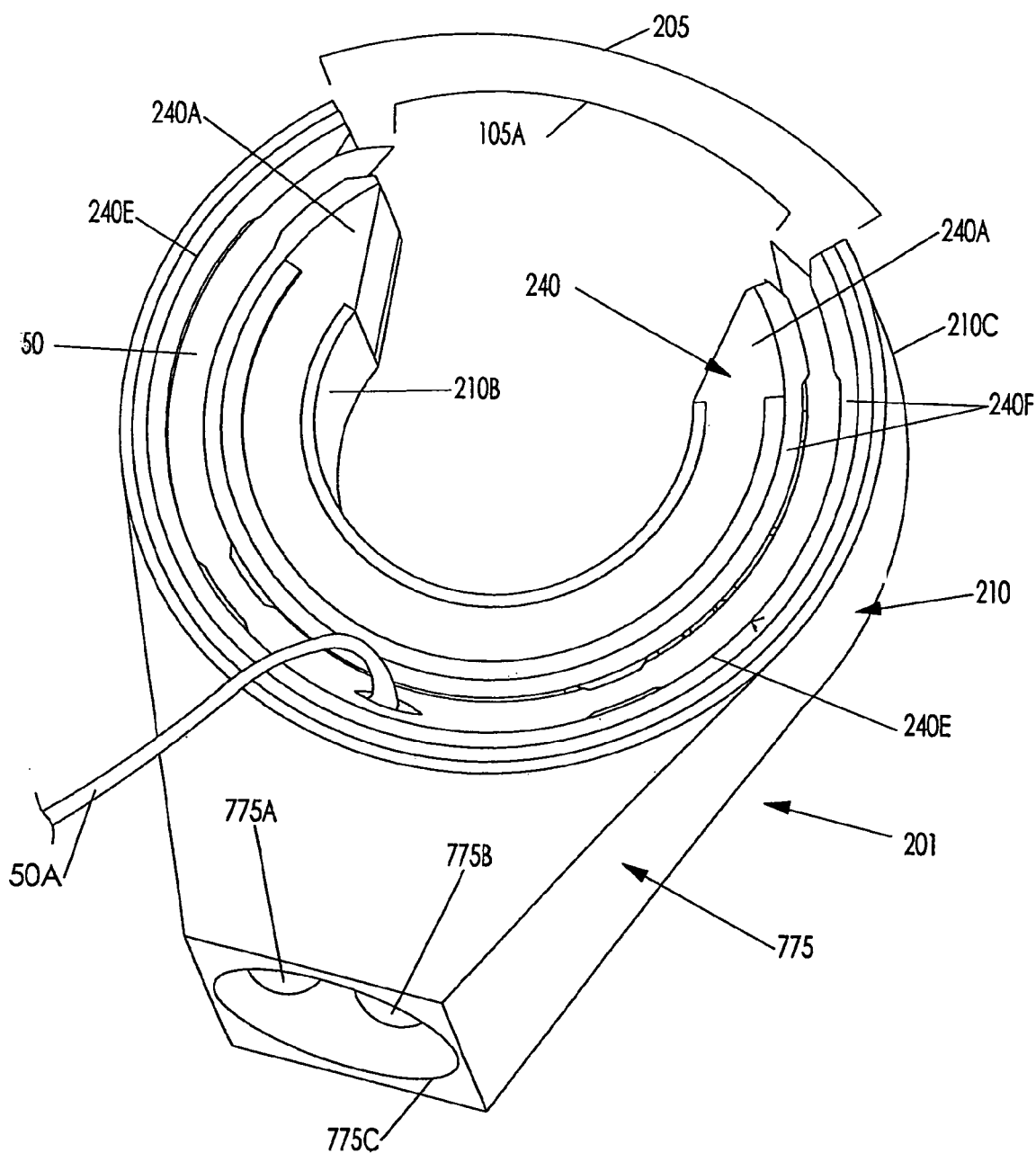

FIG. 113 is a rear perspective view of a forked blade device embodiment of the cycling suturing and knot-tying device, in assembled configuration for attachment to a suitable operator.

Figure 114:
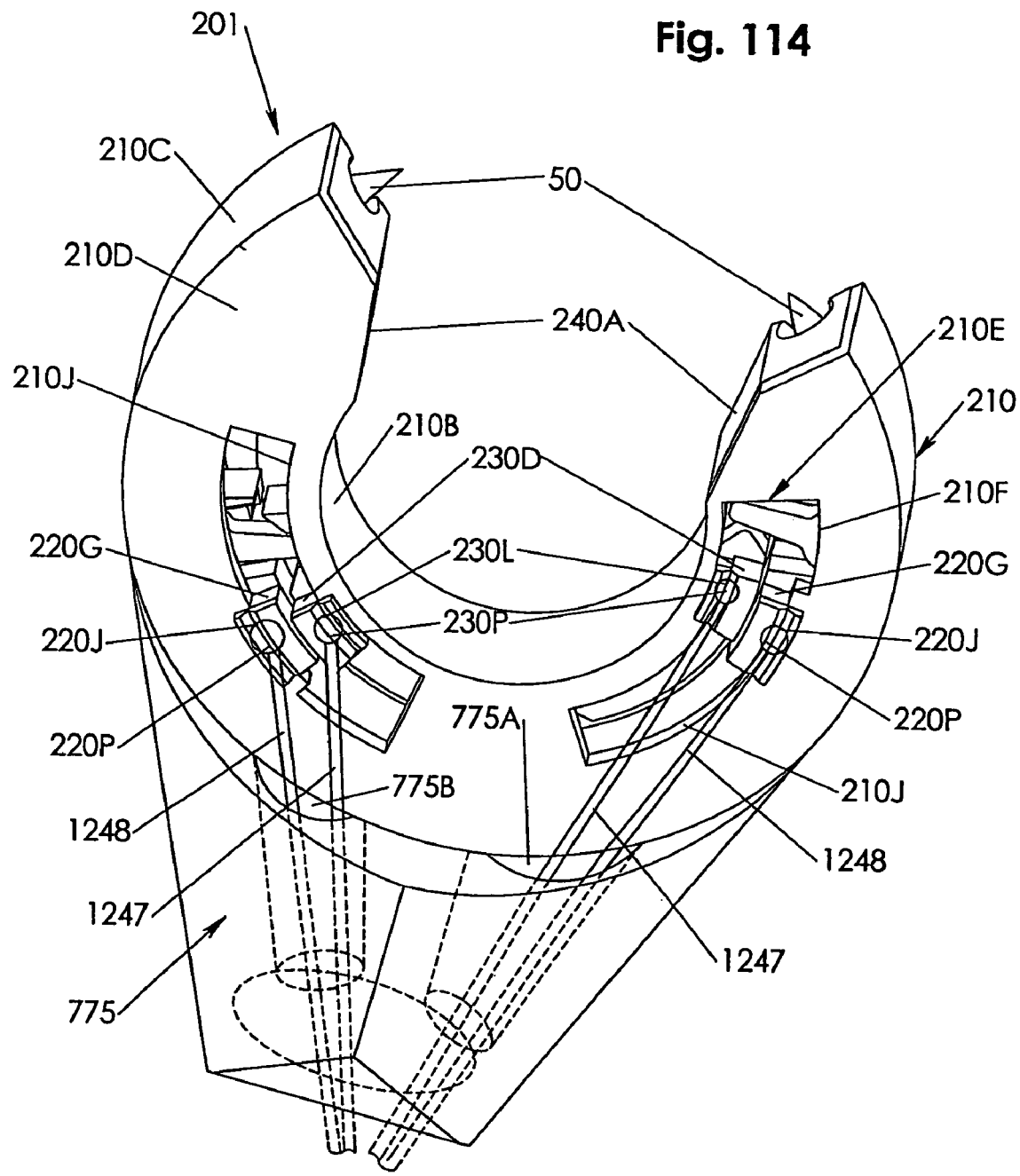

FIG. 114 is a bottom perspective view of the forked blade device illustrated in FIG. 113.

Figure 115:
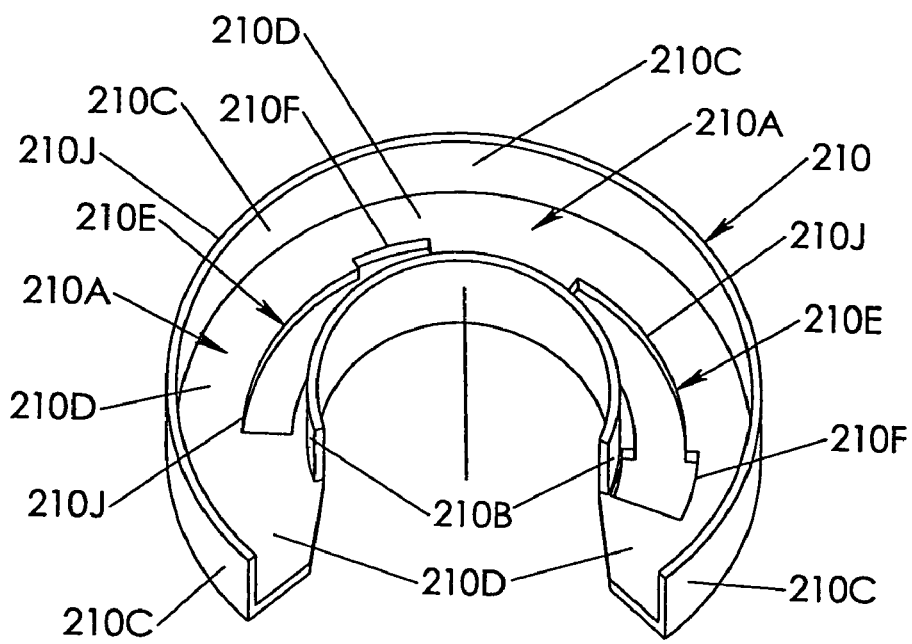

FIG. 115 is a perspective view of the bottom-slotted case element of the forked blade device illustrated in FIGS. 113 and 114.

Figure 116:
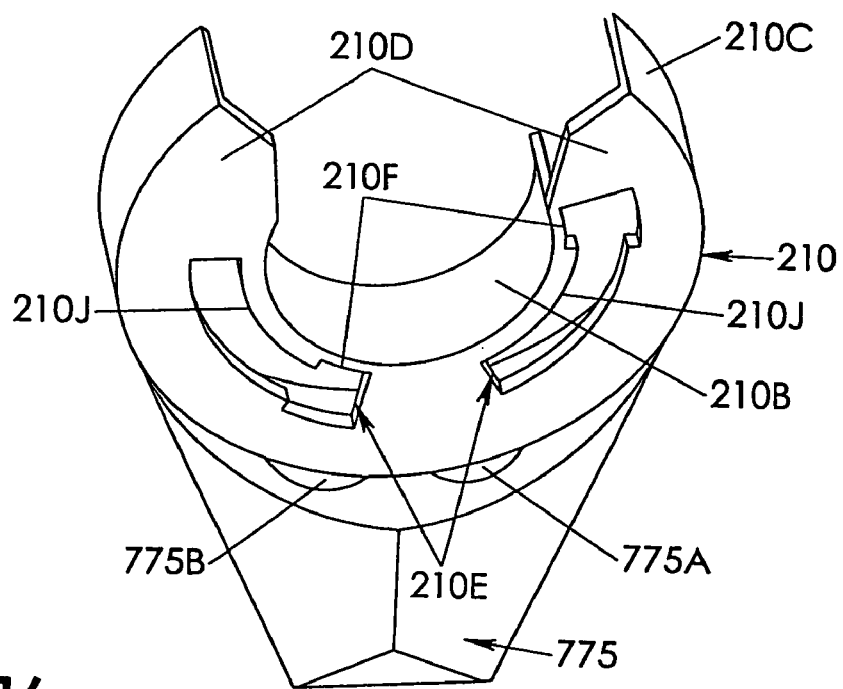

FIG. 116 is a bottom view of the slotted case illustrated in FIG. 115, more particularly illustrating the bottom slots.

Figure 117:
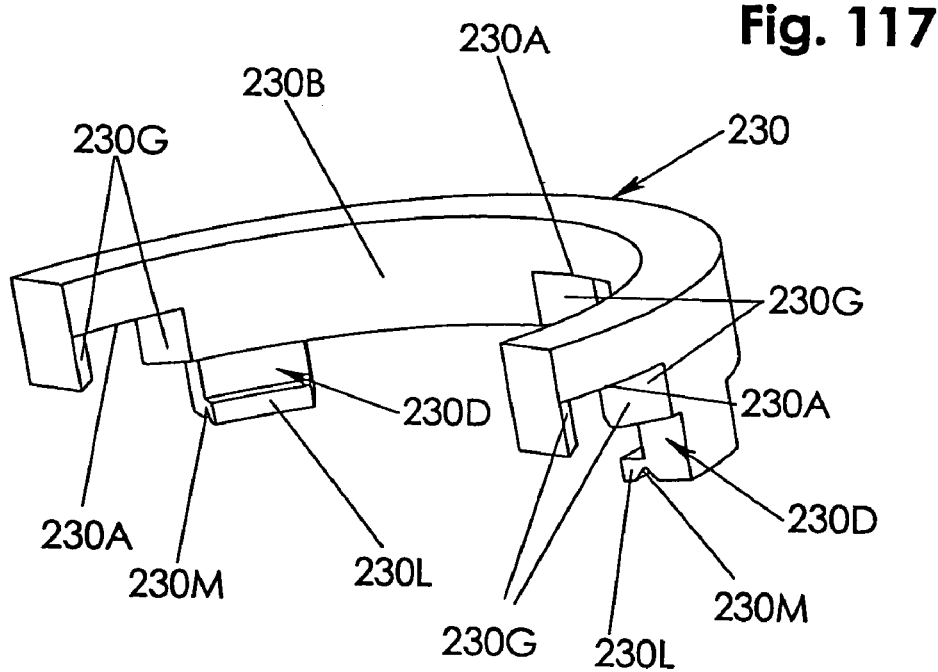

FIG. 117 is a perspective view of the driver element of the forked blade device illustrated in FIG. 113.

Figure 117A:
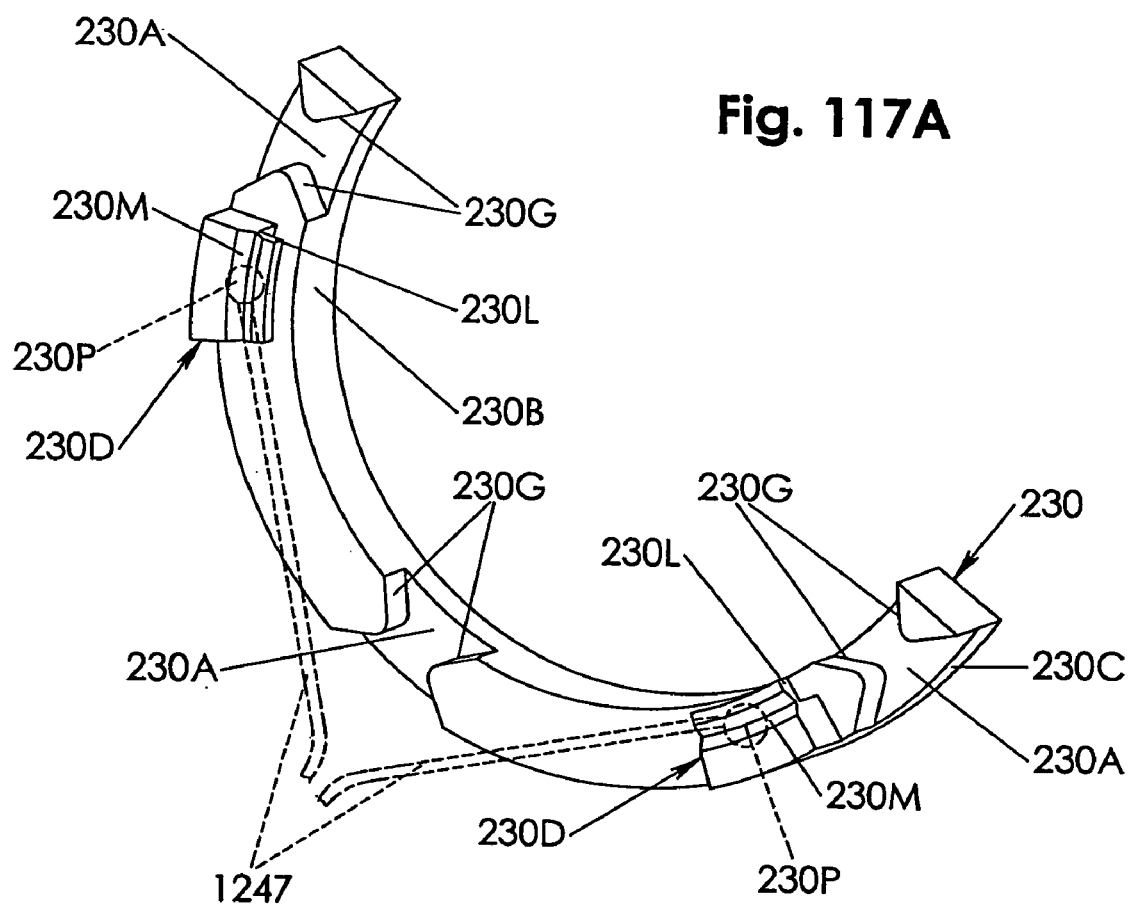

FIG. 117A is a bottom perspective view of the driver element illustrated in FIG. 116, more particularly illustrating a preferred attachment of drive cables to the driver.

Figure 118:
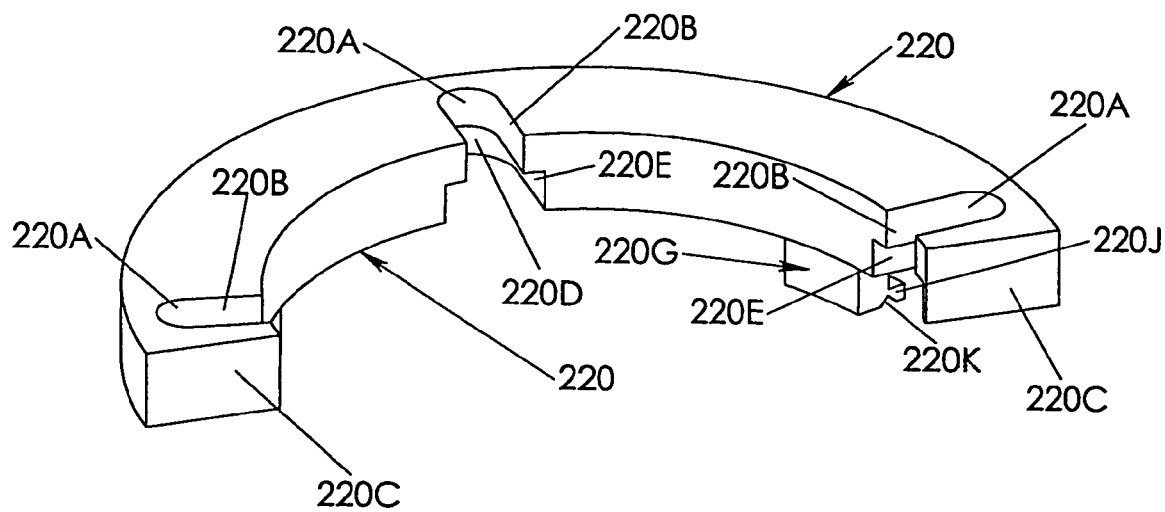

FIG. 118 is a perspective view of the housing element of the forked blade device illustrated in FIG. 113.

Figure 118A:
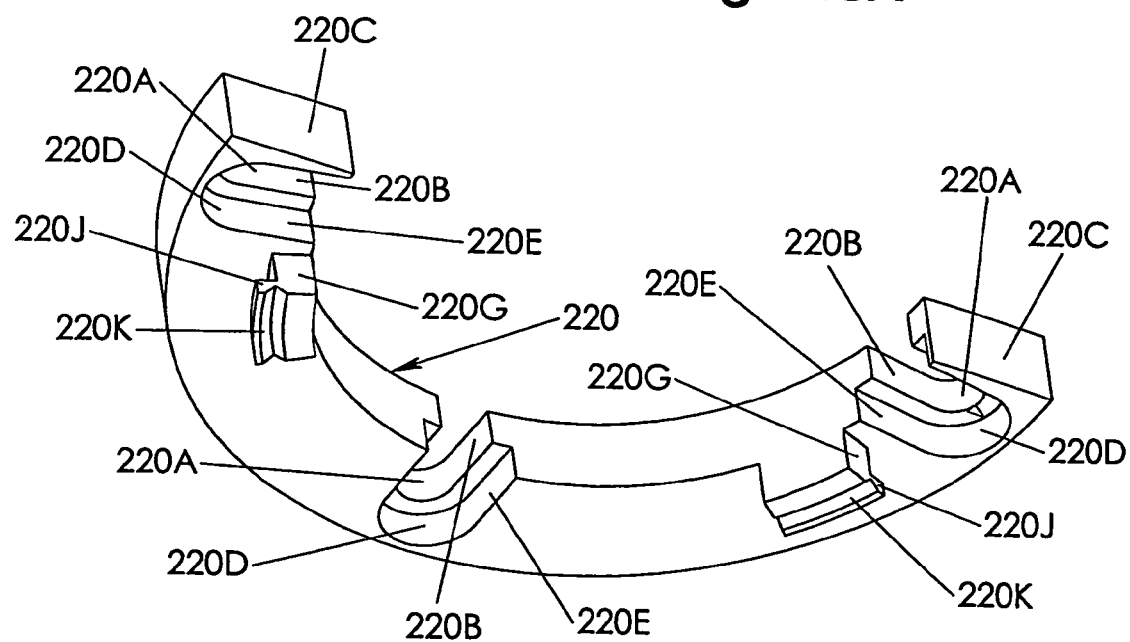

FIG. 118A is a bottom perspective view of the housing element illustrated in FIG. 118, more particularly illustrating downwardly-extending tab extensions and weld attachment grooves for attaching operating cables to the housing.

Figure 119:
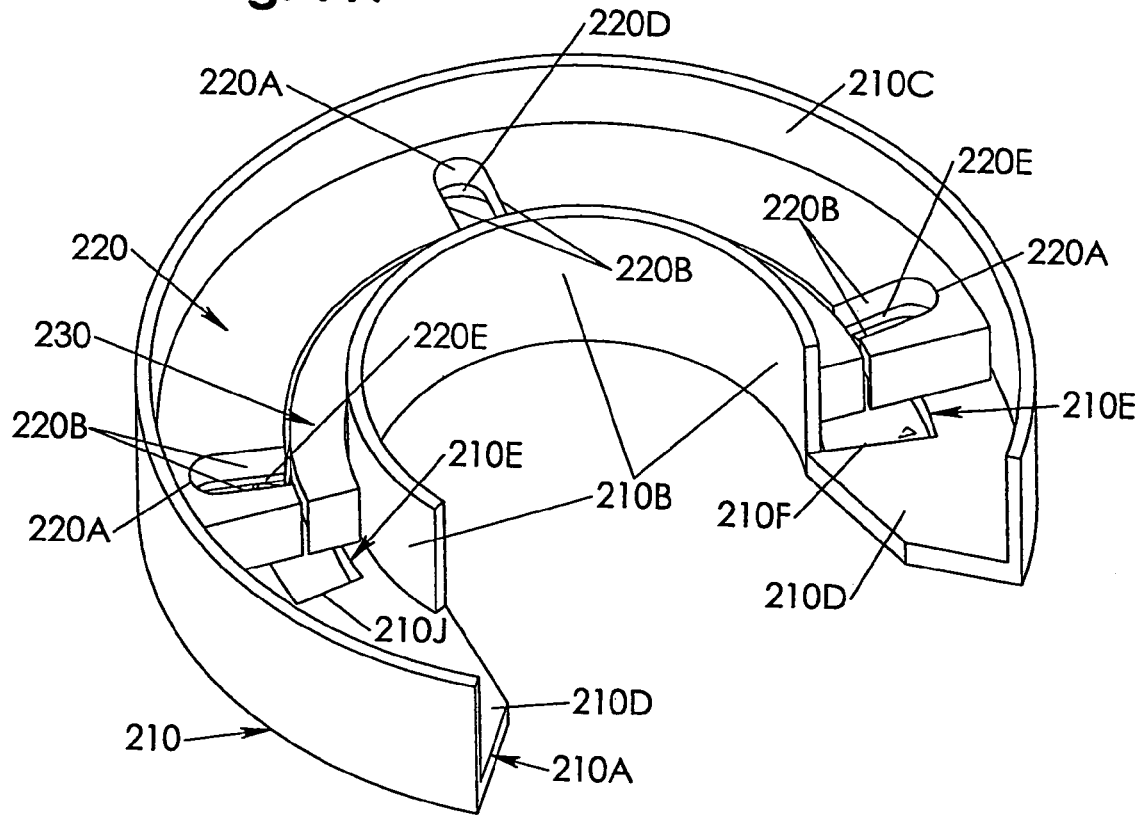

FIG. 119 is a perspective view of the case and housing elements of the forked blade device in assembled configuration.

Figure 120:
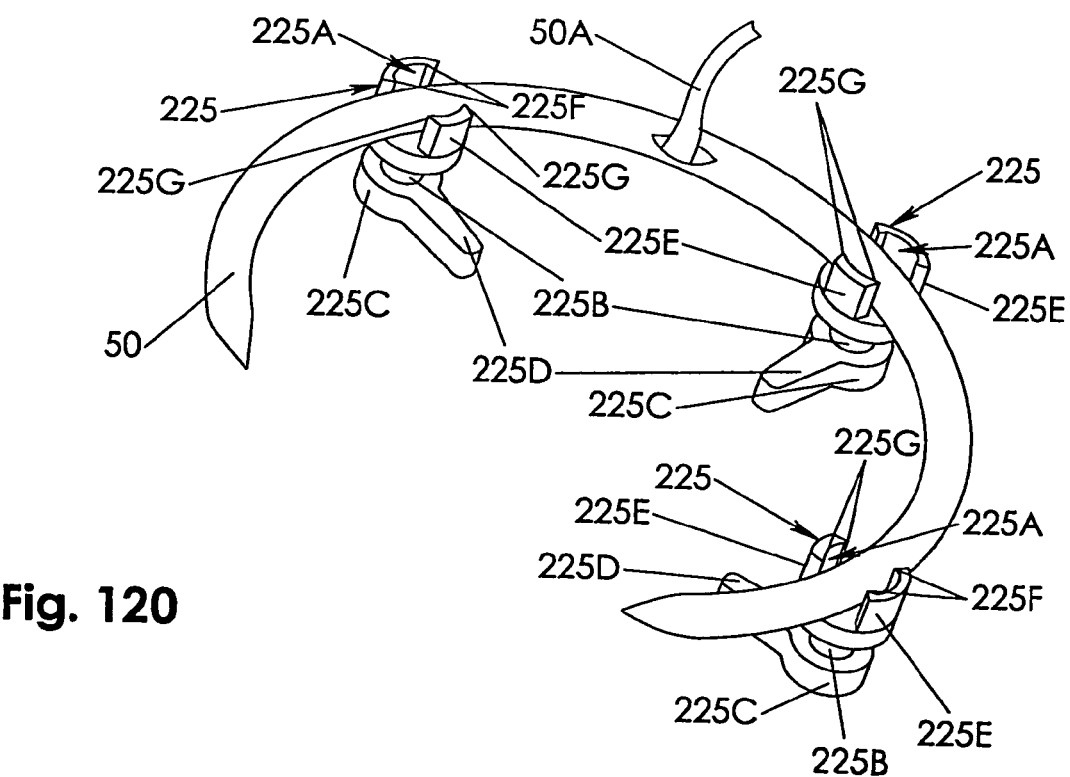

FIG. 120 is a perspective view of the three forked blade assemblies spaced-apart to receive the crescent-shaped needle for driving the needle in either the counterclockwise or clockwise direction in the forked blade device illustrated in FIG. 113.

Figure 121:
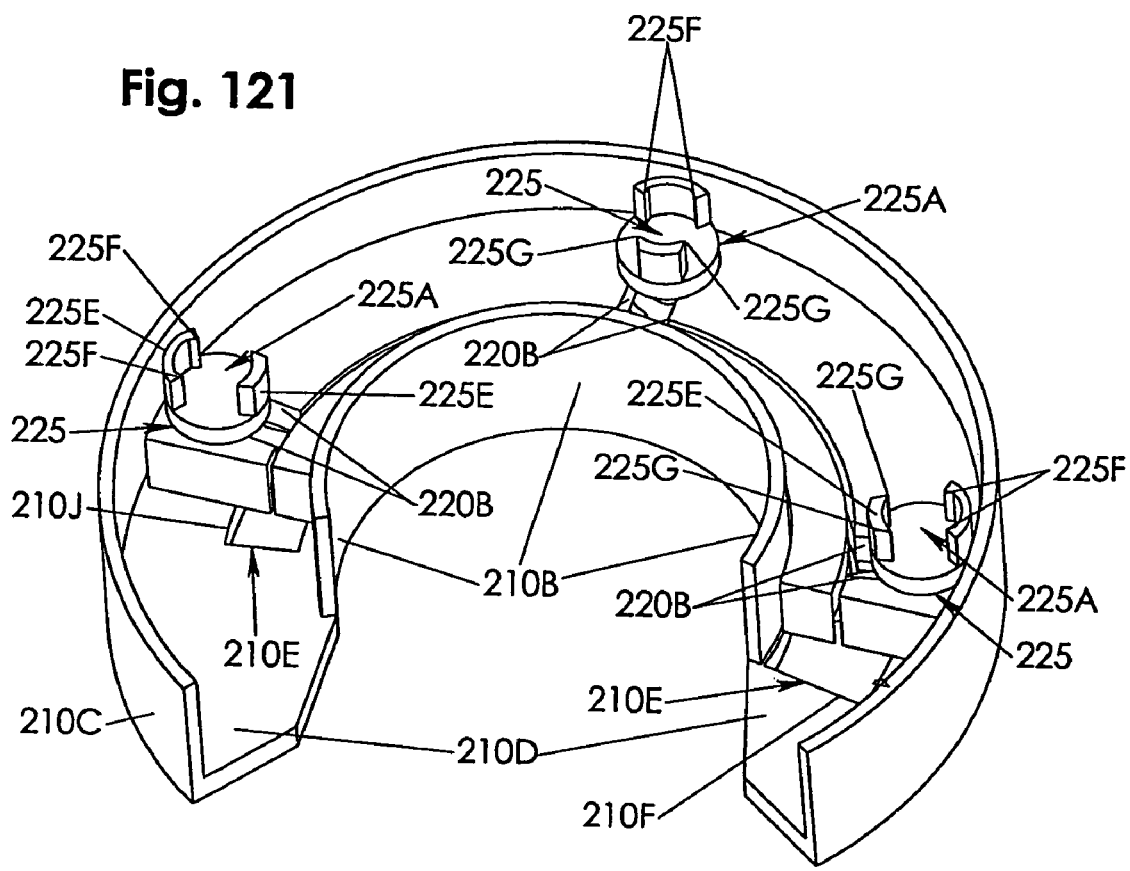

FIG. 121 is a perspective view of the case element with the pivoting forked blades installed therein and with the driver and housing element(s) seated in the case.

Figure 122:
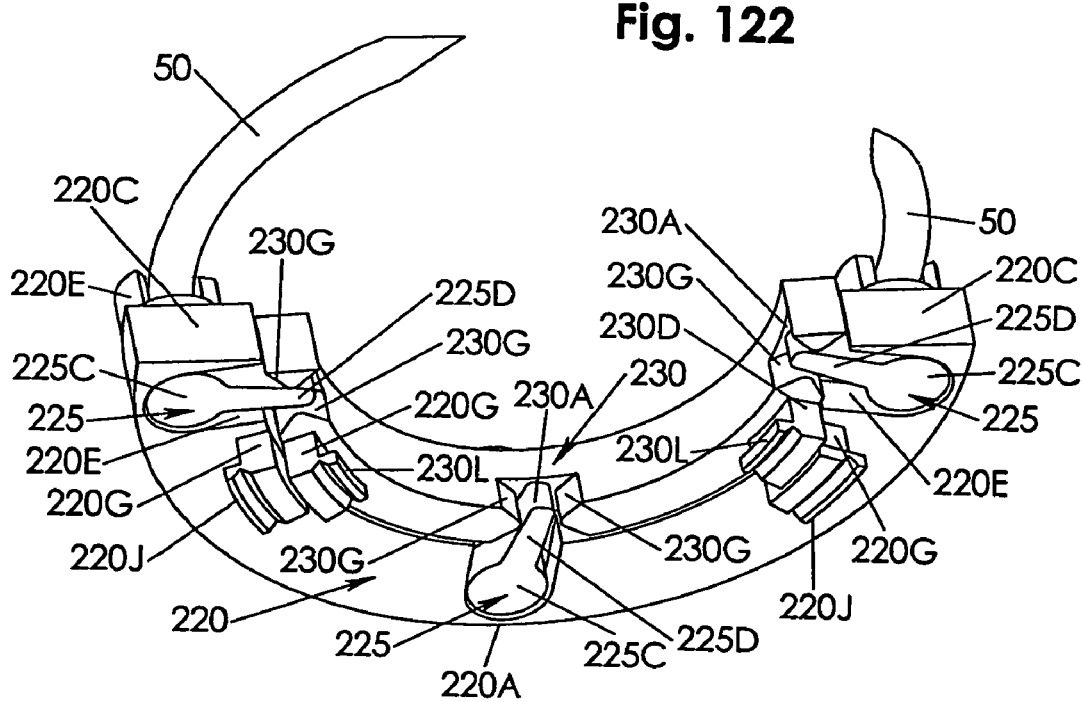

FIG. 122 is a bottom perspective view of the driver and housing in functional configuration with the forked blades in position for incrementing the needle in the forked blade device.

Figure 123:
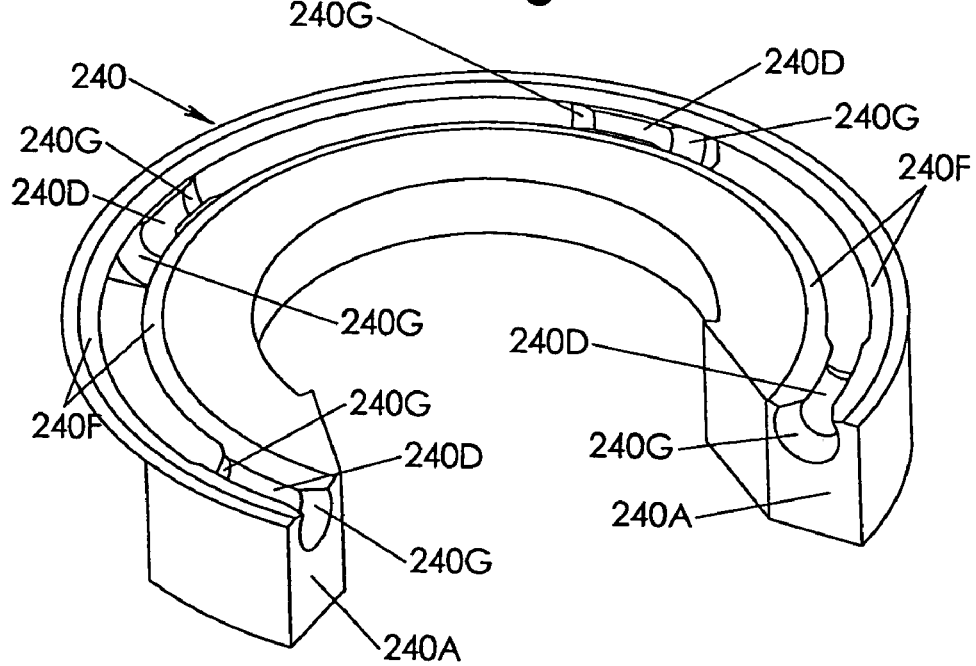

FIG. 123 is a perspective view of the fixed way element of the forked blade device illustrated in 113.

Figure 124:
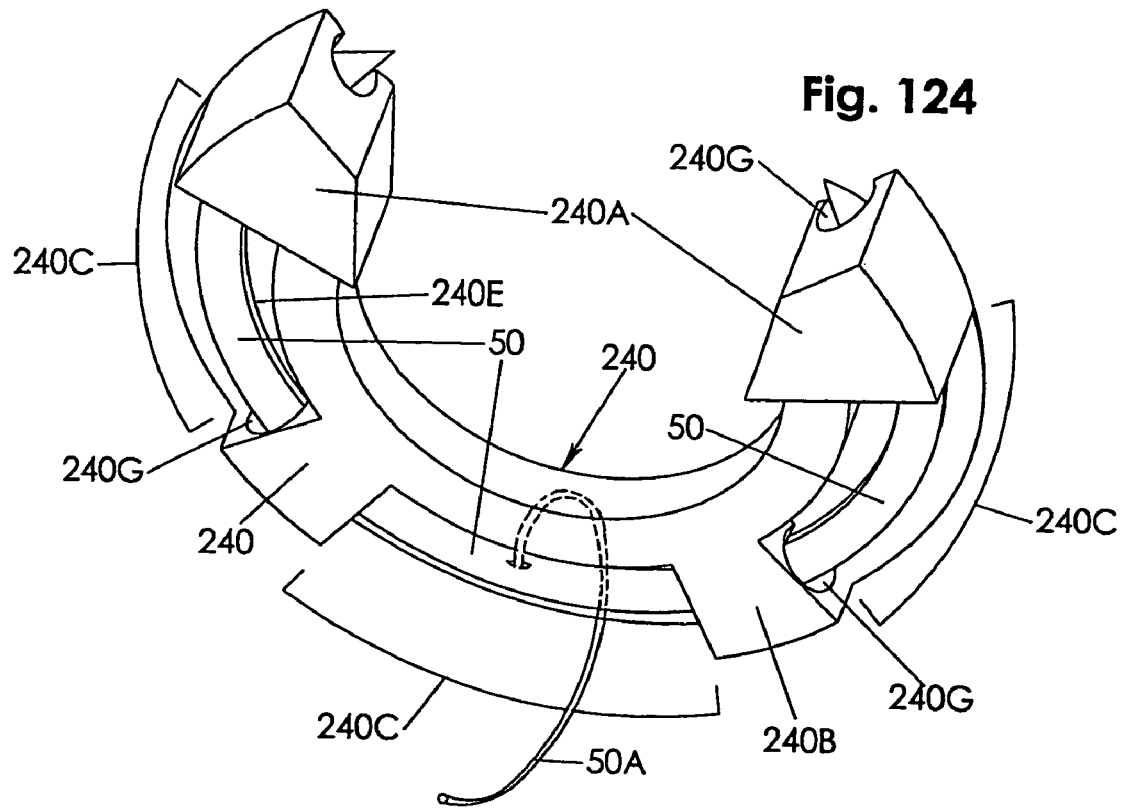

FIG. 124 is a bottom perspective view of the fixed way element illustrated in FIG. 123, with the arcuate needle positioned in functional configuration therein.

Figure 125:
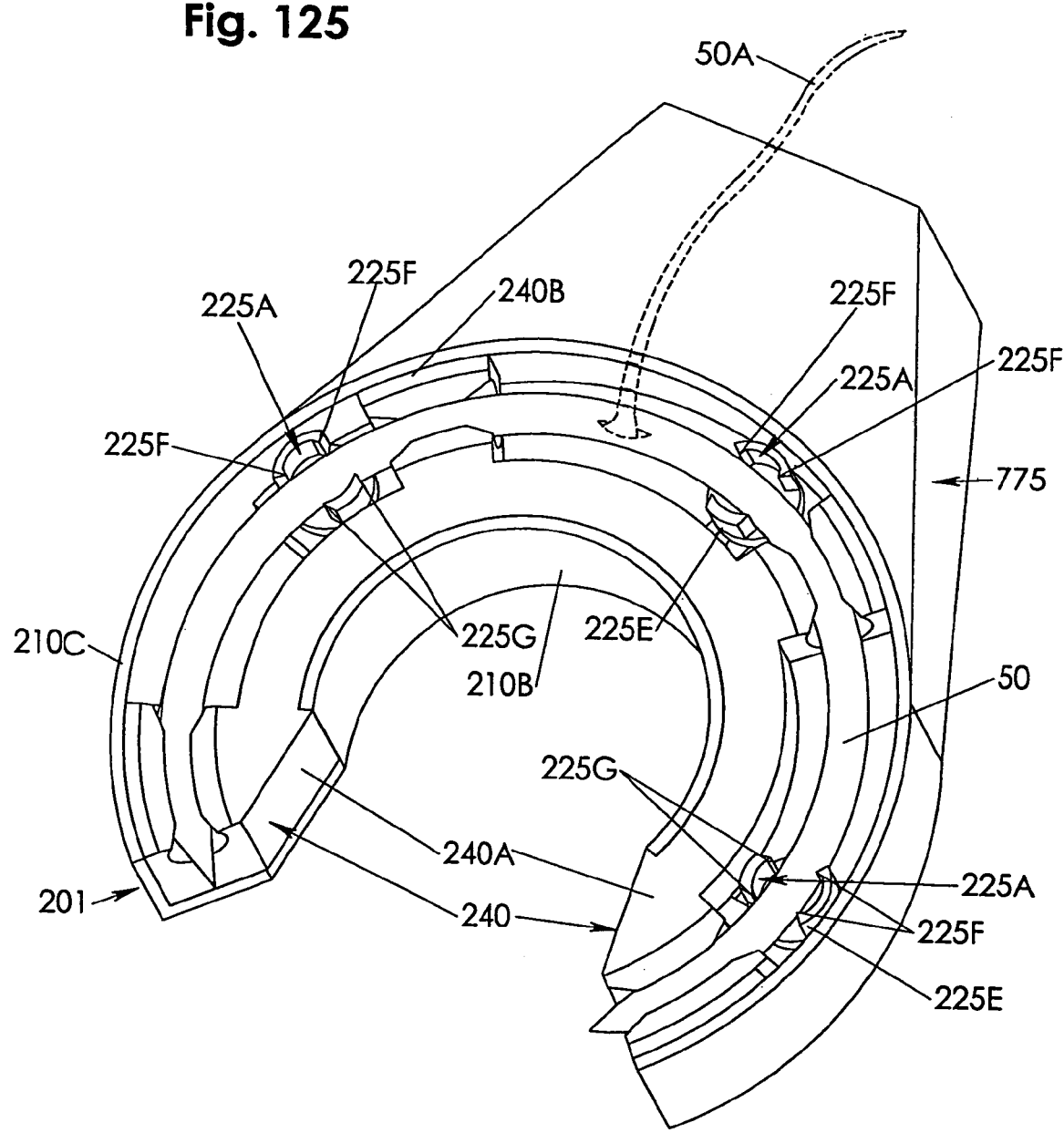

FIG. 125 is a top perspective view of the assembled forked blade device illustrated in FIG. 113, with the way covers removed for brevity, more particularly illustrating the driver housing forked blades and fixed way installed in the case.

Figure 126A:
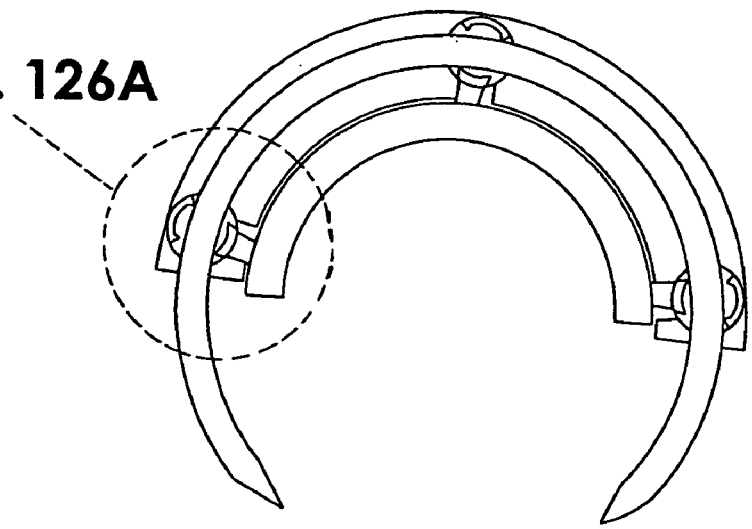
Figure 126A:
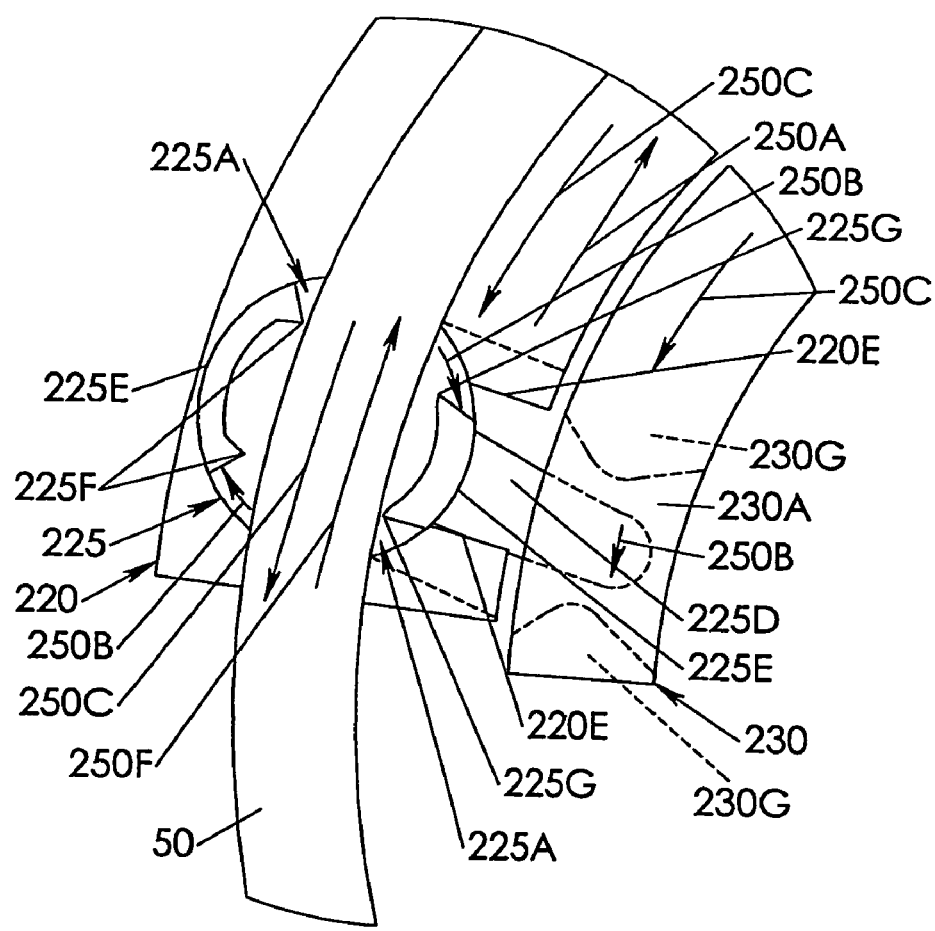

FIG. 126 is an enlarged perspective view of a typical forked blade assembly having a forked blade in close proximity to the arcuate needle, wherein the forked blade assembly is in neutral configuration with respect to the needle.

FIG. 126A is a perspective view of the forked blade assembly illustrated in FIG. 126, wherein the forked blade is rotated or pivoted in the clockwise direction to engage the needle for counterclockwise needle incrementation in the forked blade device.

Figure 127:
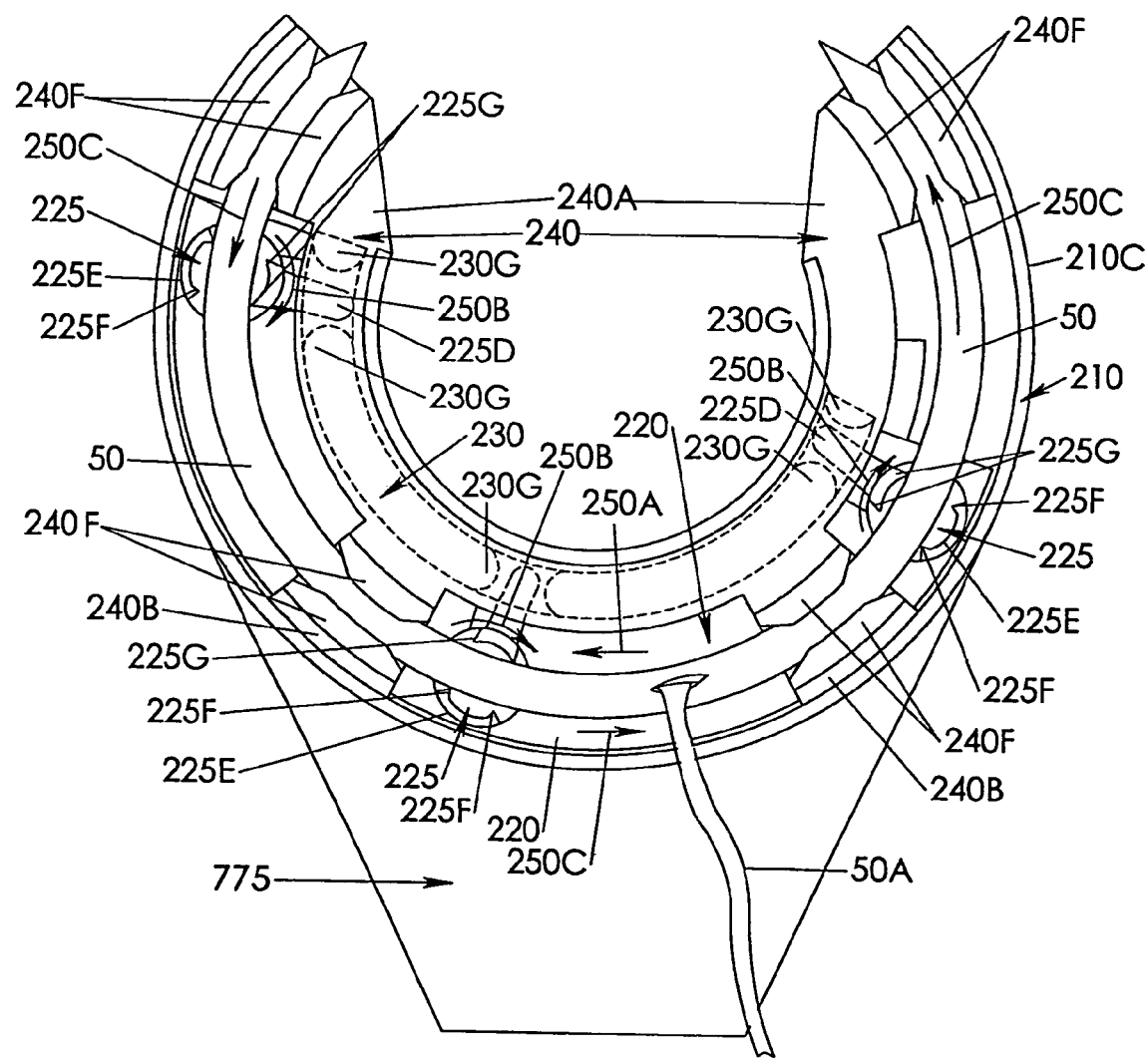

FIG. 127 is a top view of the assembled forked blade device, more particularly illustrating a forked blade needle-engaging configuration to effect counterclockwise rotation of the needle in the forked blade device.

Figure 128:
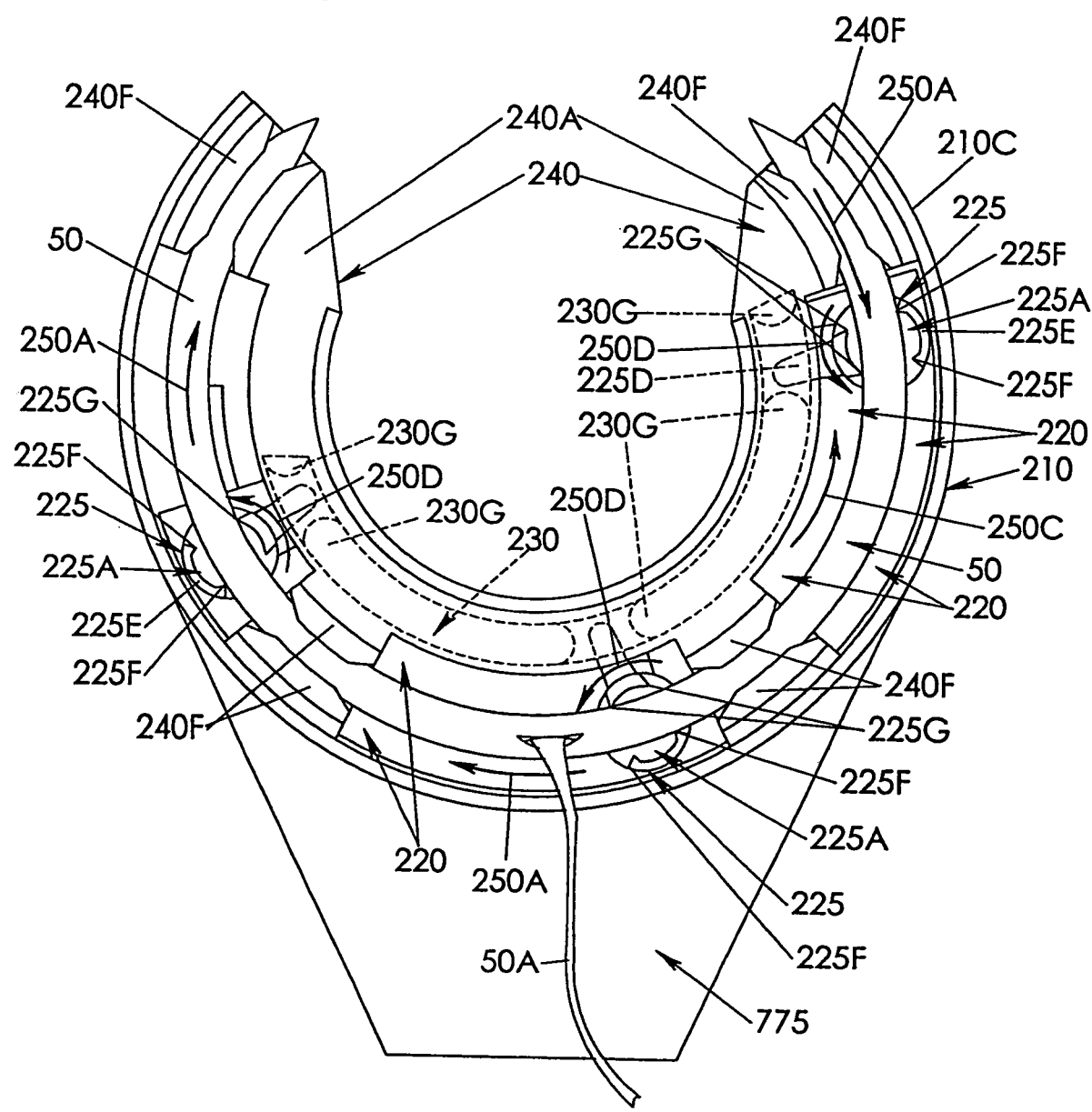

FIG. 128 is a top view of the forked blade device illustrated in FIG. 127, more particularly illustrating a forked blade needle-engaging configuration facilitating clockwise rotation of the needle in the forked blade device.

Figure 128A:
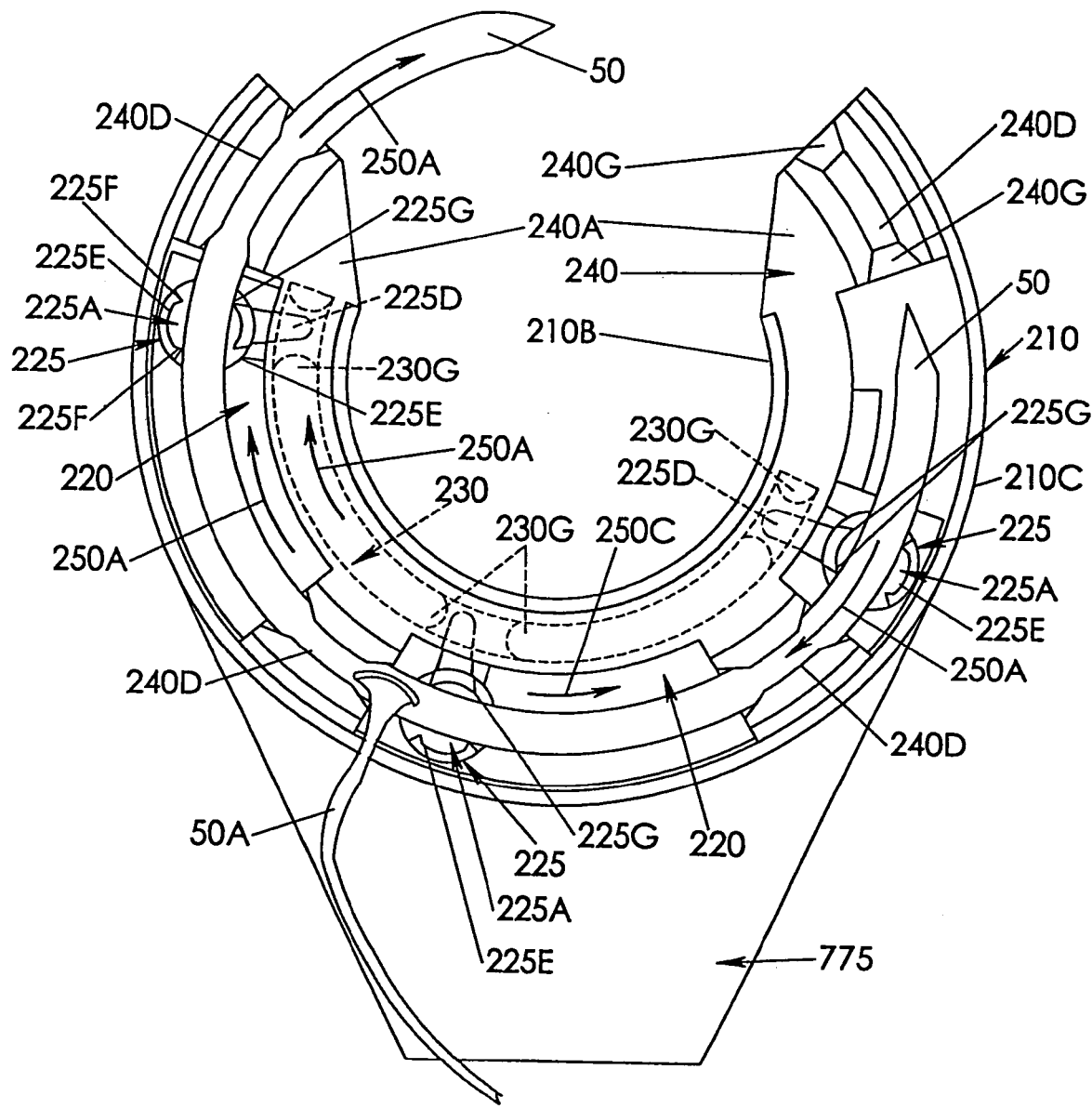

FIG. 128A is a top view of the forked blade device illustrated in FIGS. 127 and 128, more particularly illustrating incrementation of the needle in the clockwise direction by operation of a suitable operator responsive to locking of the forked blades in a counterclockwise configuration.

FIG. 129 is a top view of the forked blade device placed in close proximity to a material to be sutured, more particularly illustrating positioning of the forked blades against the needle to effect counterclockwise rotation of the needle in the forked blade device.

Figure 130:
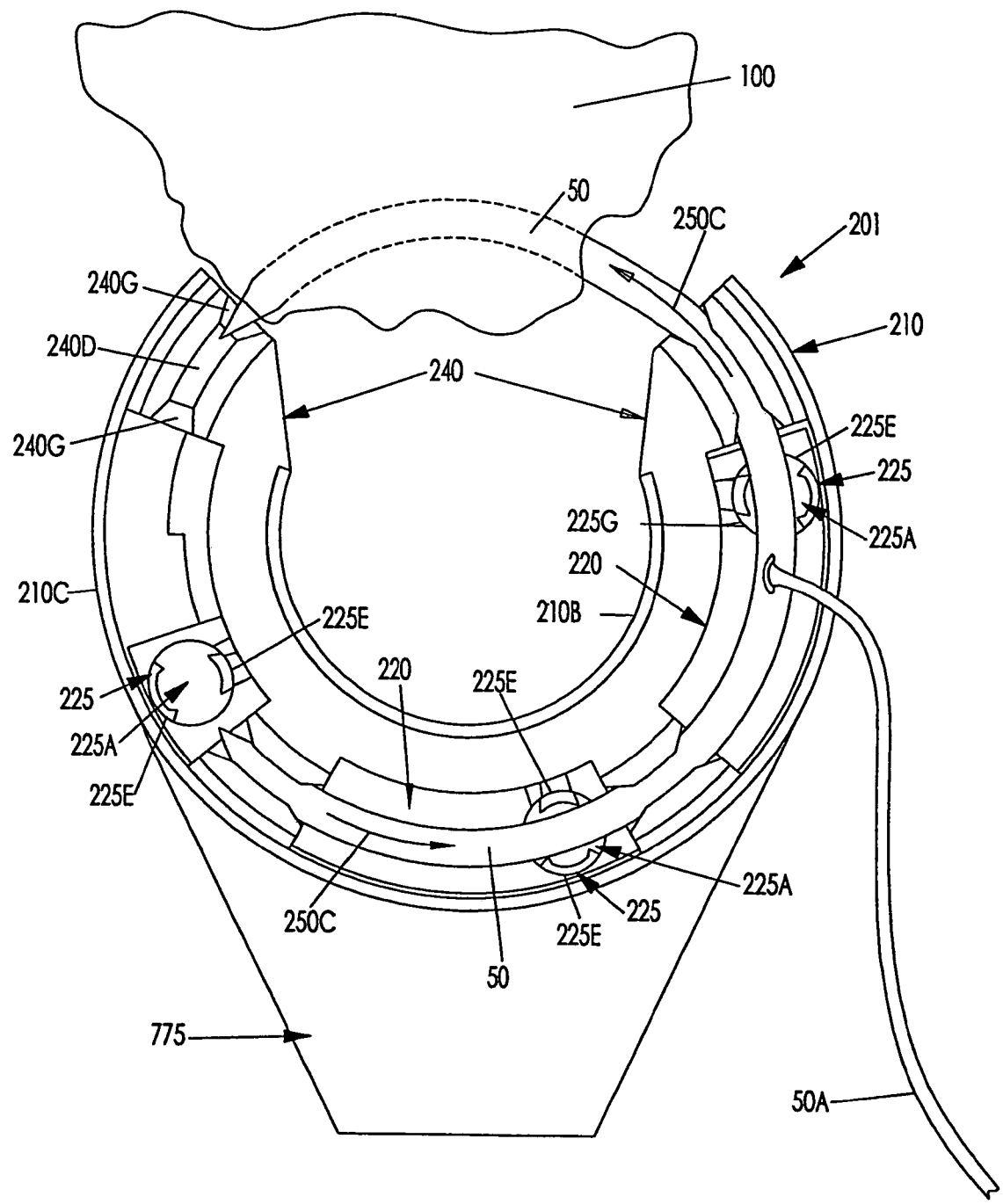

FIG. 130 is a top view of the forked blade device illustrated in FIG. 129, more particularly illustrating incrementation of the needle into the material to be sutured responsive to incrementation of the housing and driver elements of the forked blade device.

Figure 131:
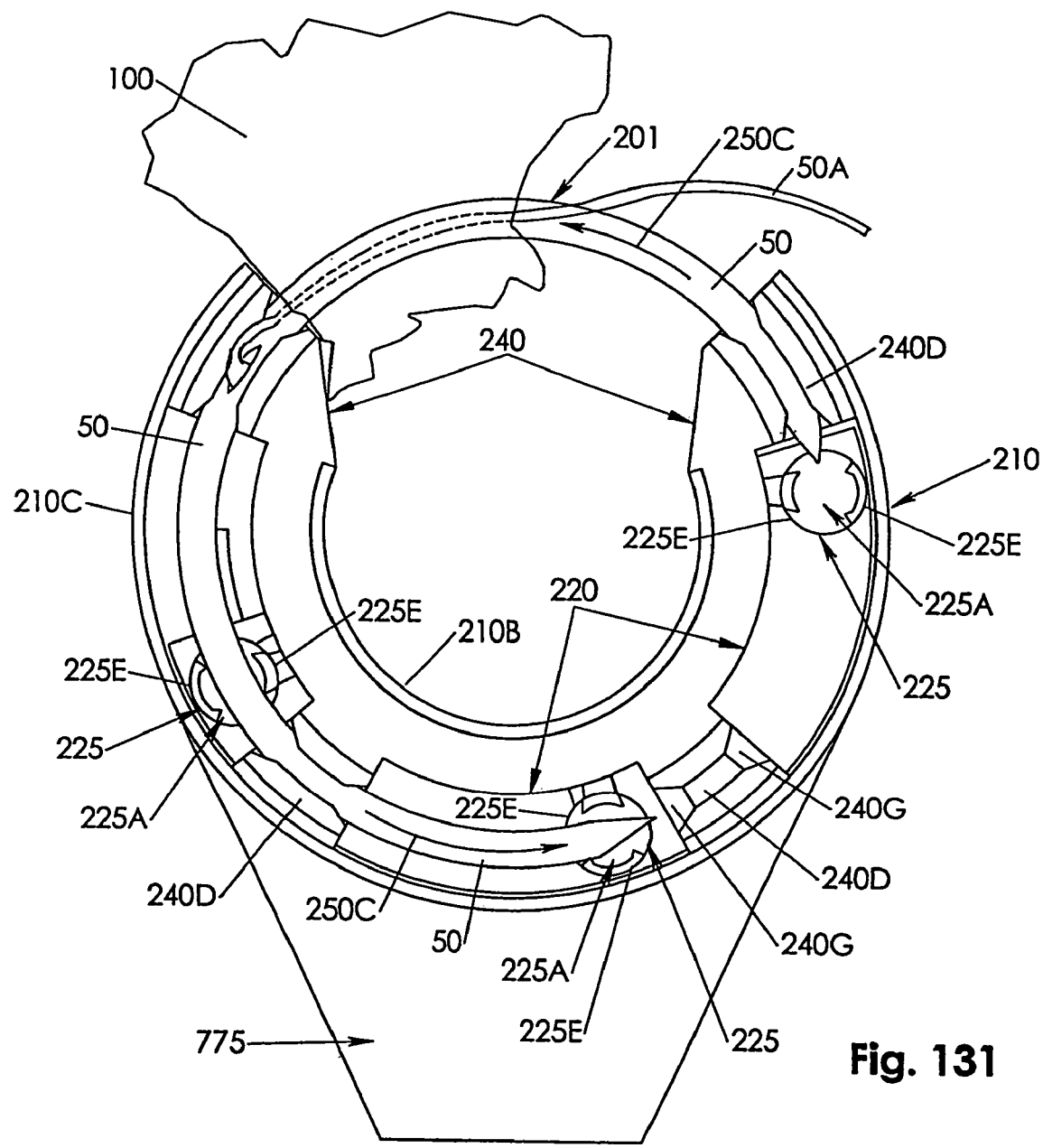

FIG. 131 is a top view of the forked blade device illustrated in FIGS. 129 and 130 and more particularly illustrating further incrementation of the needle through the material to be sutured with the thread carried through the suturing opening, responsive to further incrementation of the driver and housing elements of the forked blade device.

Figure 132:
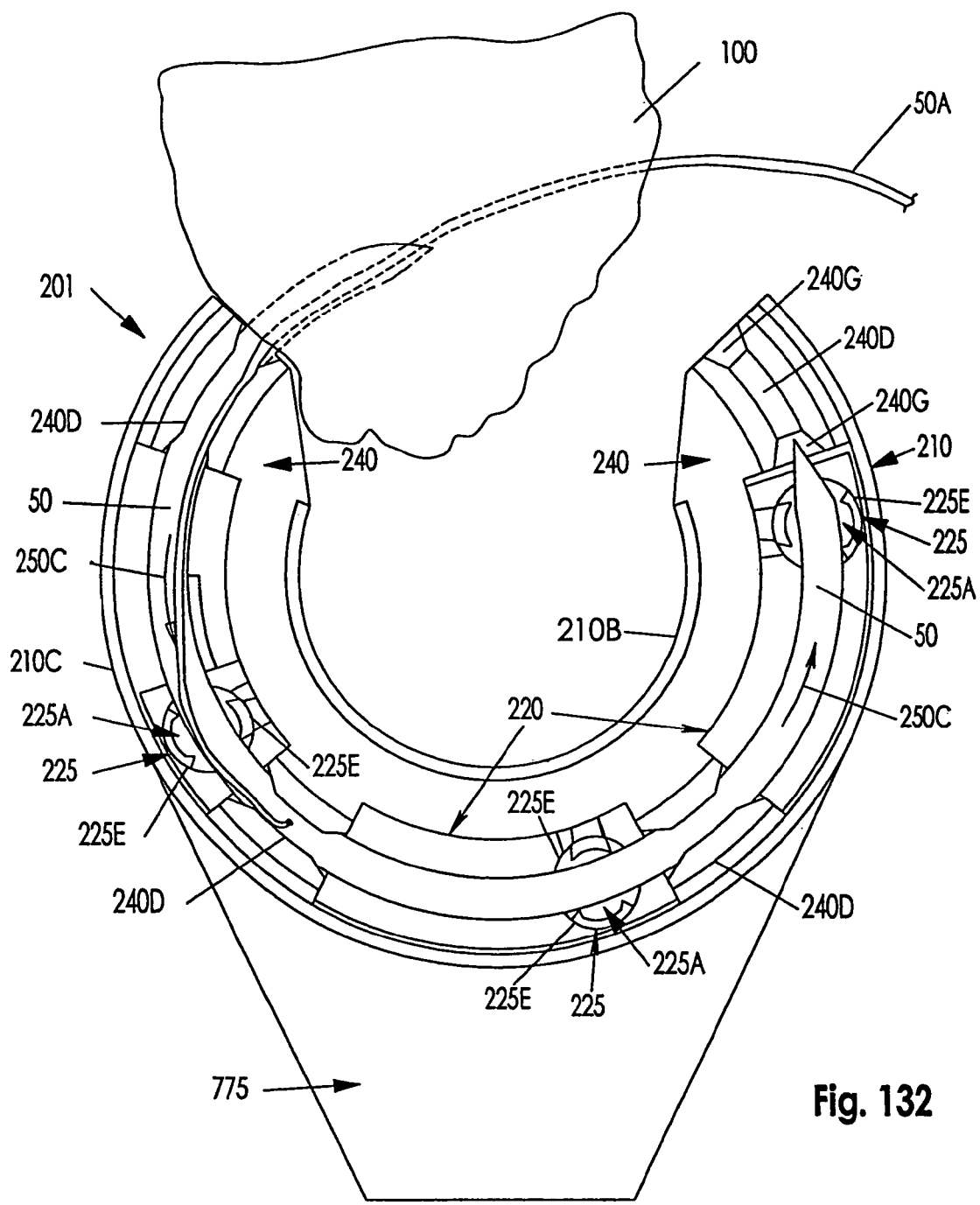

FIG. 132 is a top view of the forked blade device illustrated in FIGS. 129-131, more particularly illustrating the follow-through of the needle as further incremented through the material to be sutured and the thread carried through the needle suture opening, responsive to additional incrementation of the driver and housing elements of the forked blade device.

Figure 133:
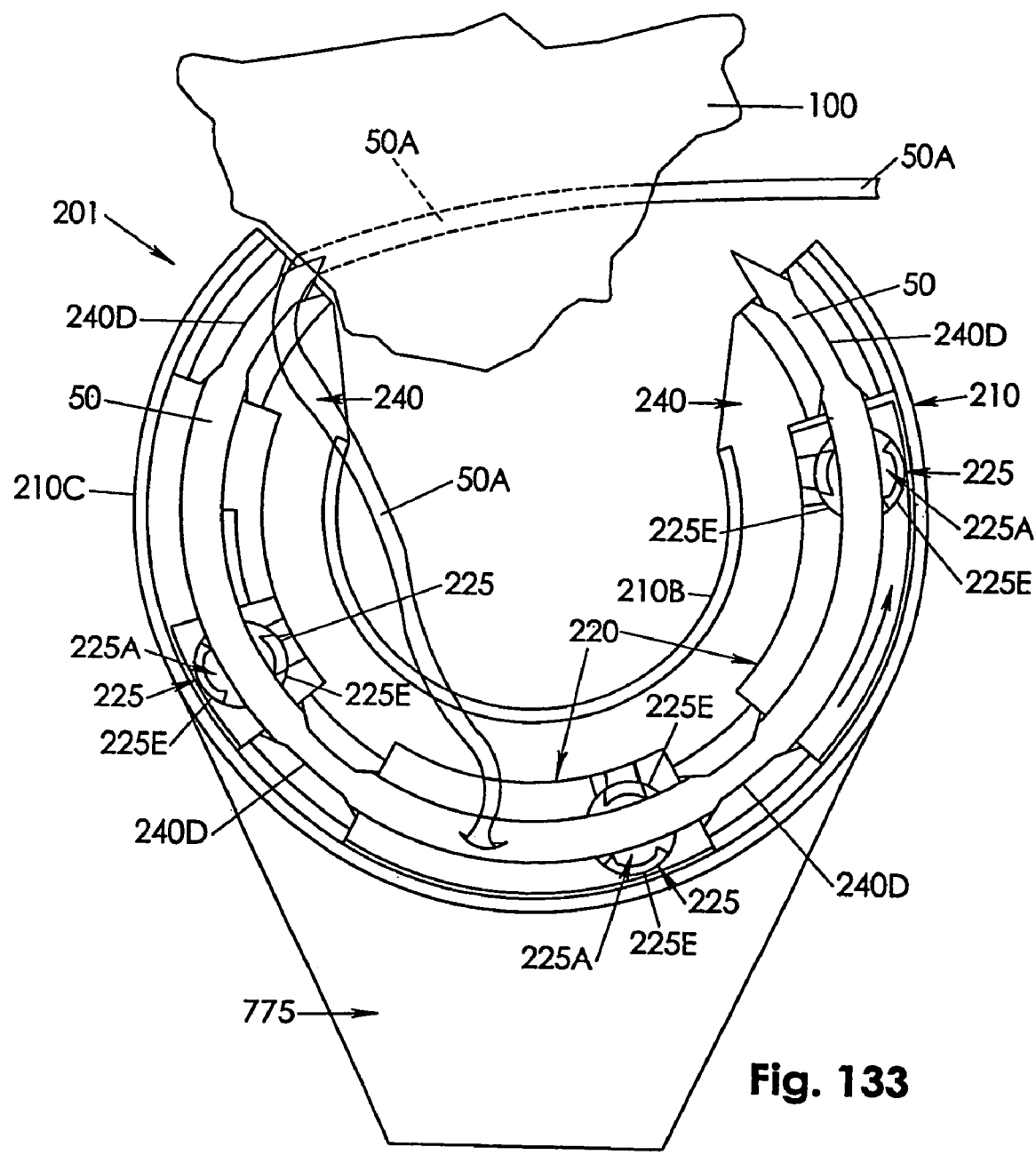

FIG. 133 is a top view of the forked blade device illustrated in FIGS. 129-132, more particularly illustrating still further incrementation of the needle responsive to incrementation of the driver and the housing in the forked blade device.

Figure 134:
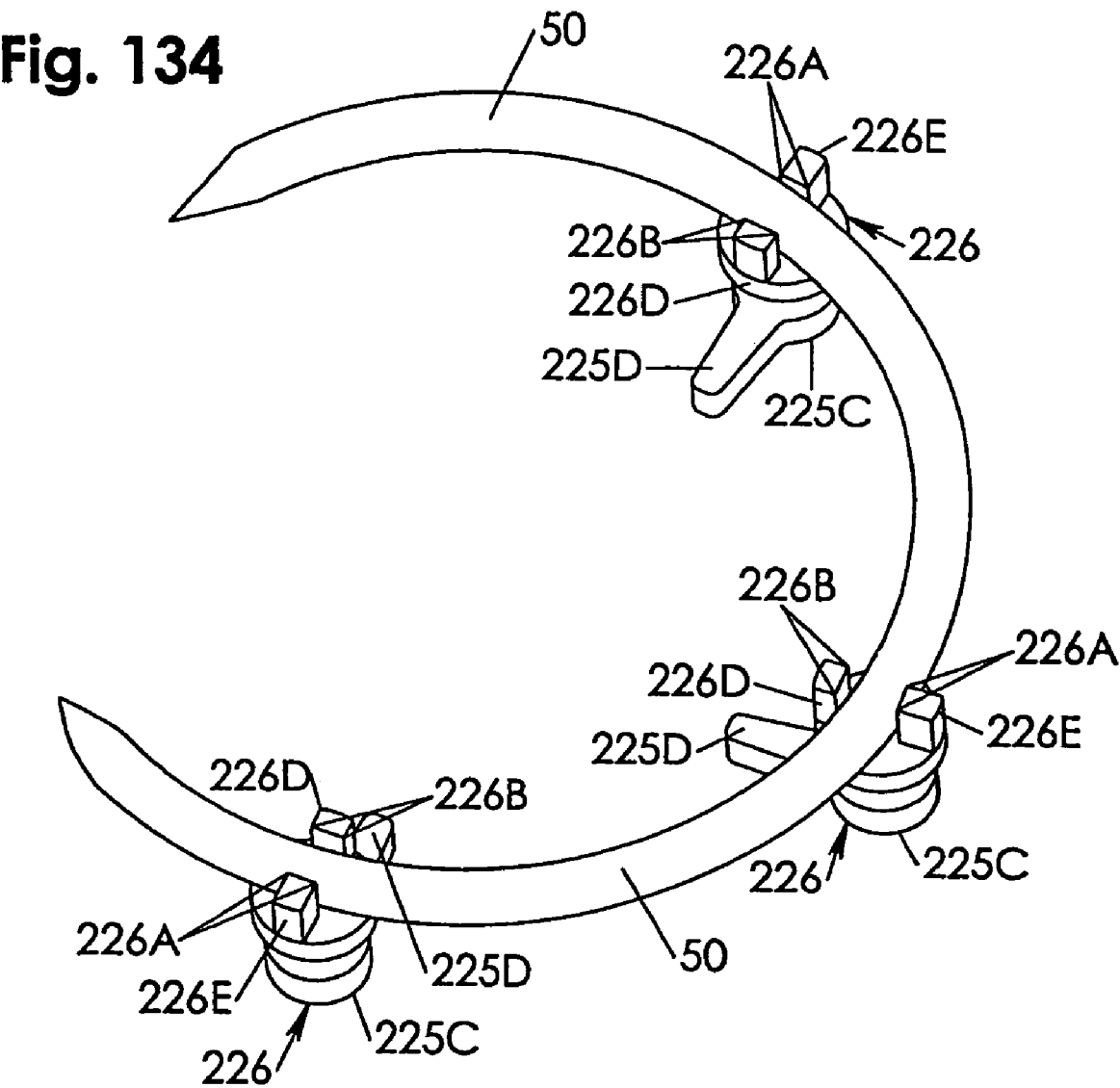

FIG. 134 is a perspective view of an alternative forked blade design for receiving the needle, with the forked blades in neutral configuration.

Figure 135:
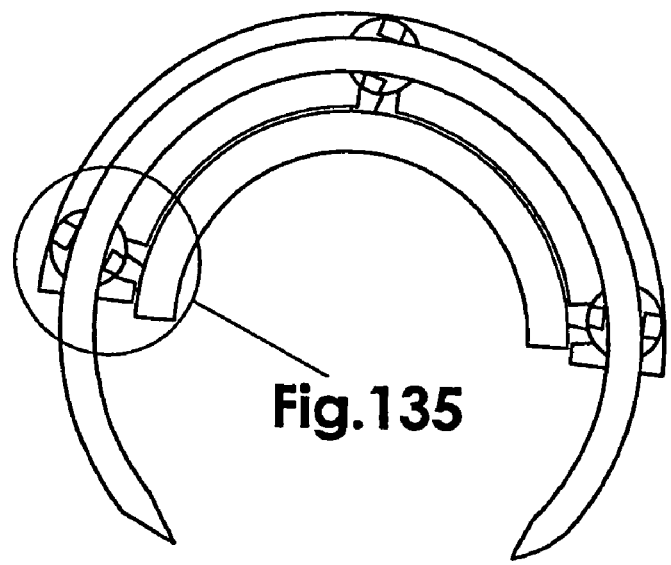
Figure 135:
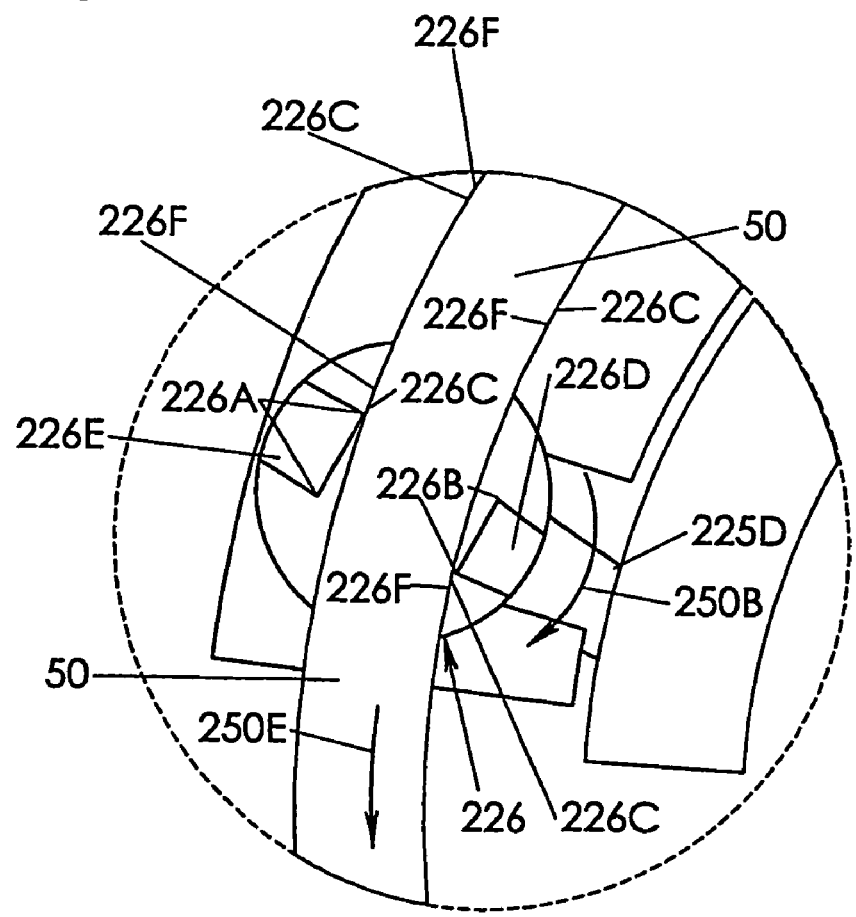

FIG. 135 is an enlarged view of one of the forked blades in the alternative forked blade design illustrated in FIG. 134, more particularly illustrating rotation or pivoting of the forked blade in the clockwise direction to engage the needle in driving configuration and driving the needle in the counterclockwise direction around the forked blade device.

Figure 136:
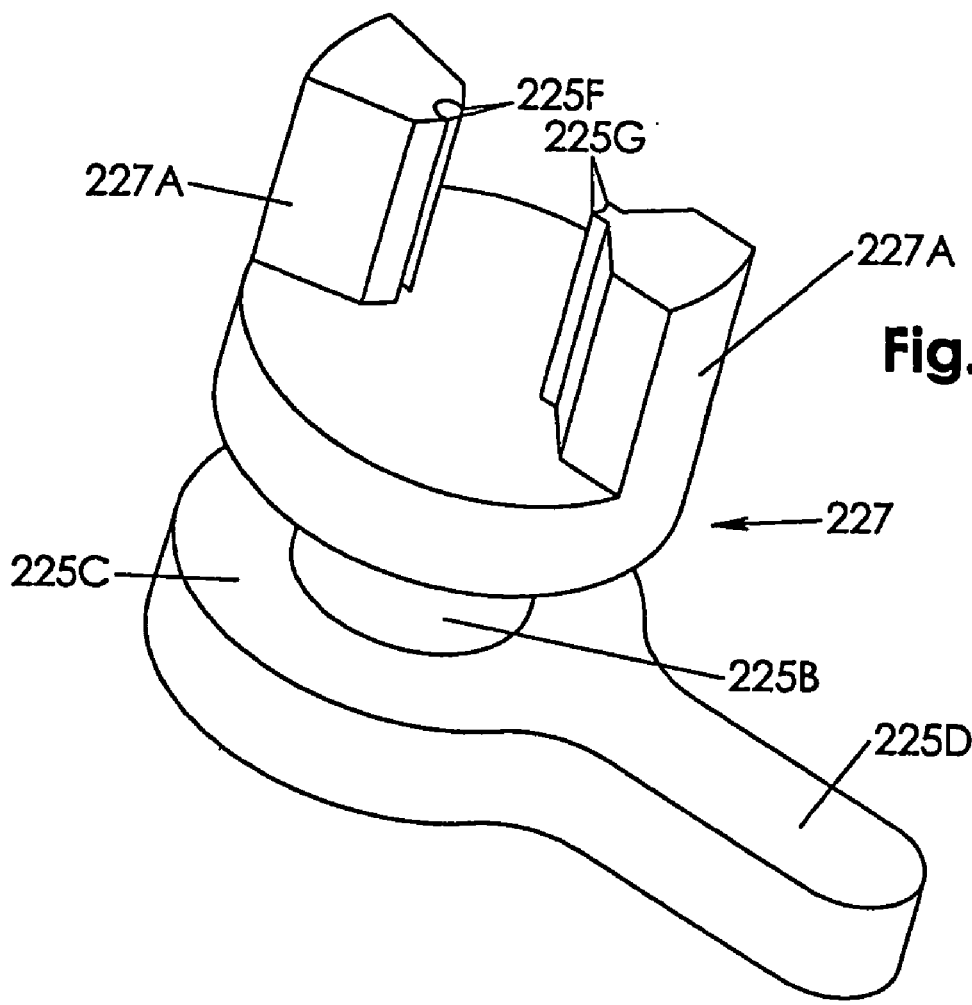

FIG. 136 is a perspective view of another design for the forked blades in the forked blade device.

Figure 137:
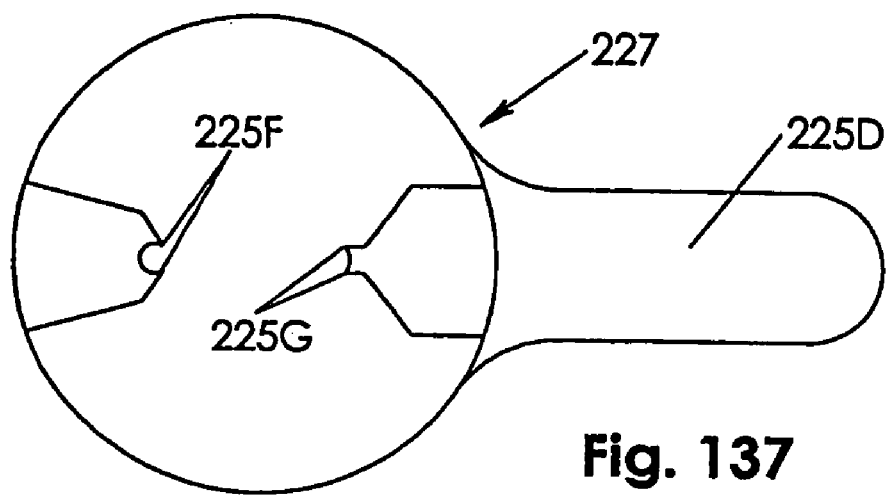

FIG. 137 is a top view of the alternative design of the forked blades illustrated in FIG. 136.

Figure 138:
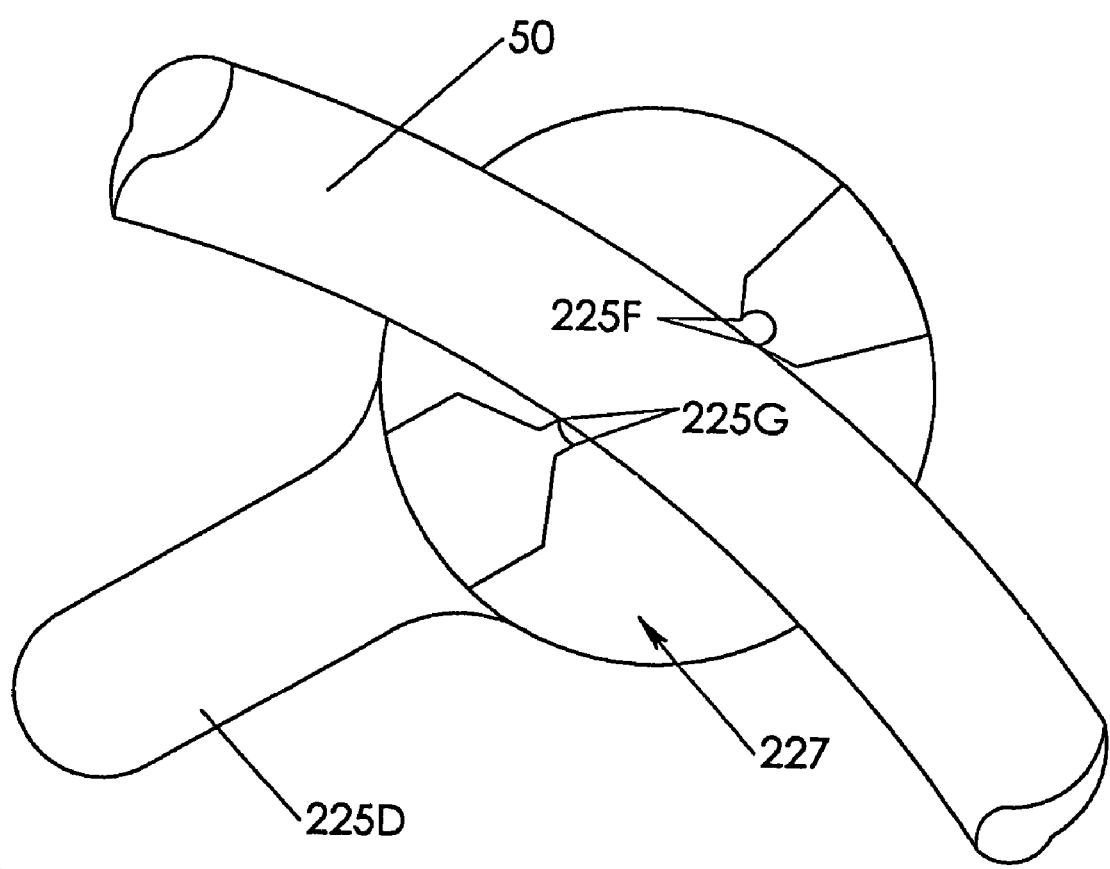

FIG. 138 is a top view of one of the alternative forked blades illustrated in FIGS. 136 and 137, more particularly illustrating engagement of the alternative forked blades with a needle to drive the needle in the forked blade device.

Figure 139:
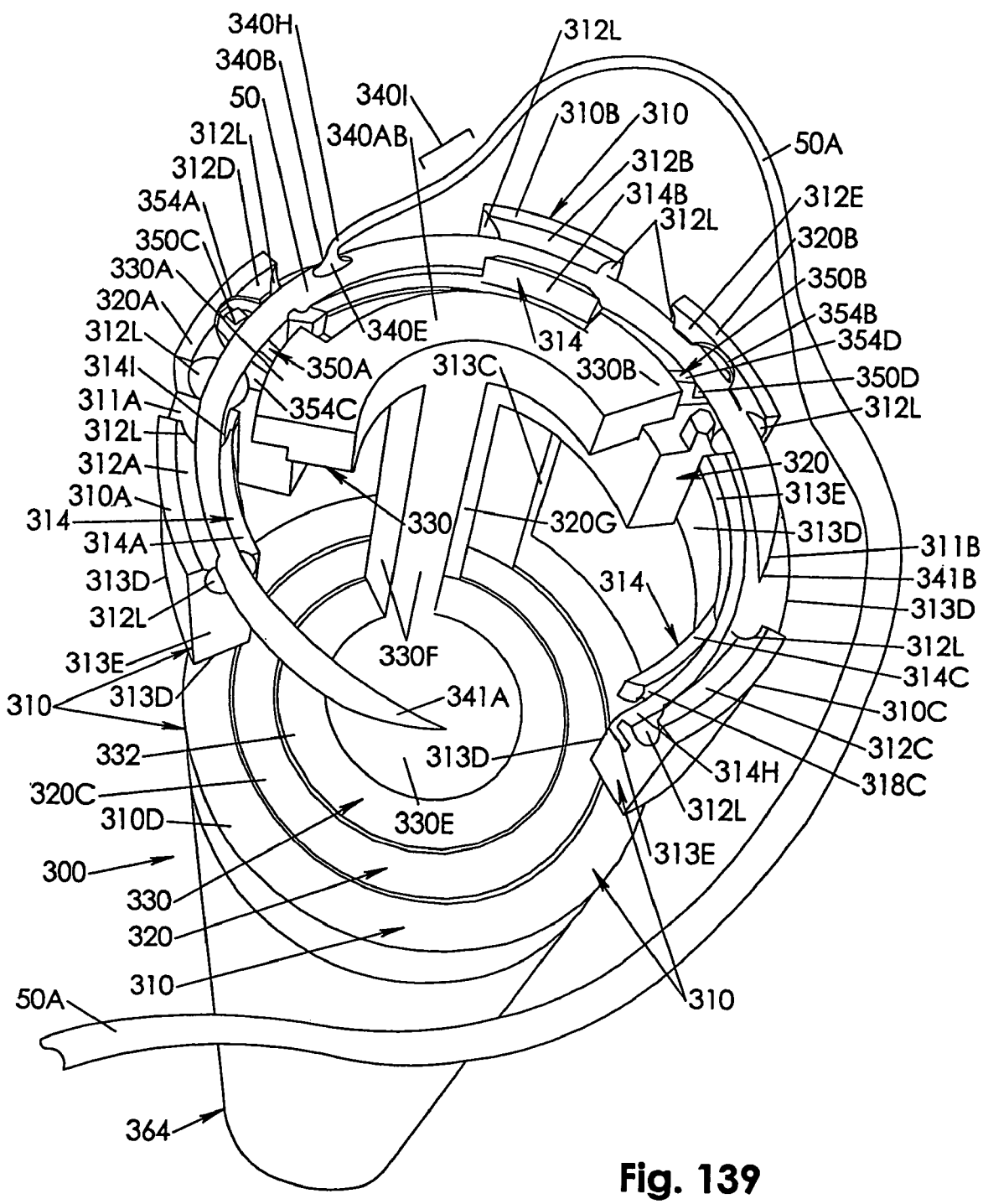

FIG. 139 is a perspective view of a tubular forked blade device of the cycling suturing and knot-tying device in assembled configuration and ready for incrementation of the needle for suturing.

Figure 140:
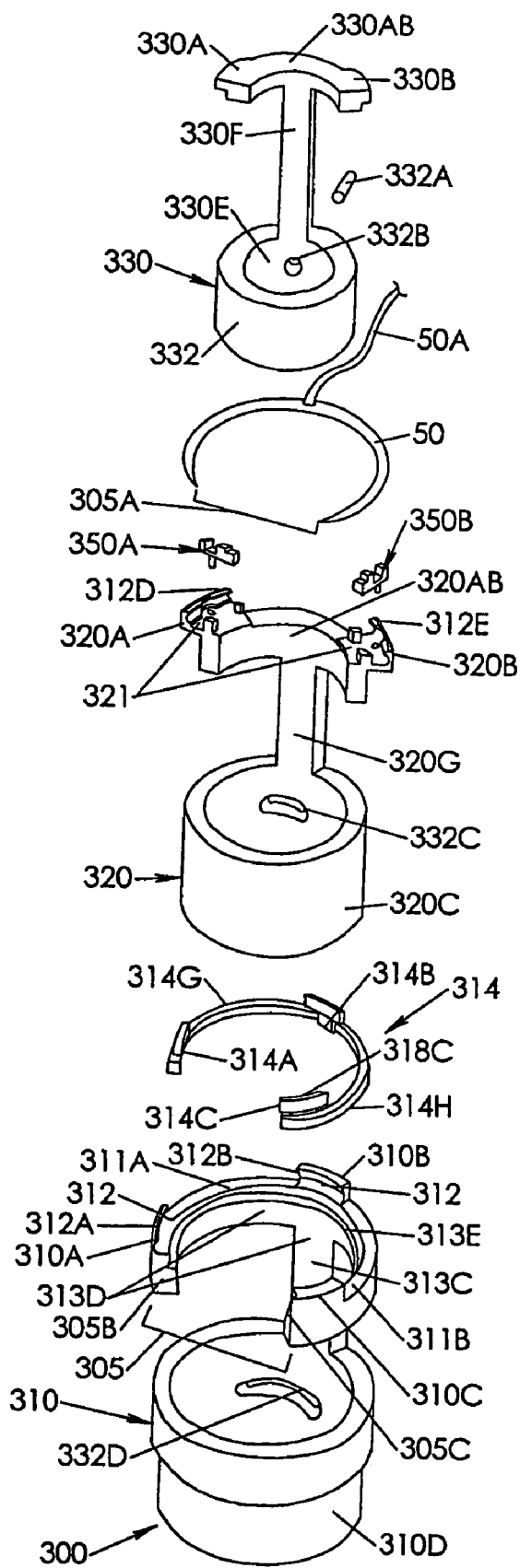

FIG. 140 is an exploded view of the tubular forked blade device illustrated in FIG. 139.

Figure 141:
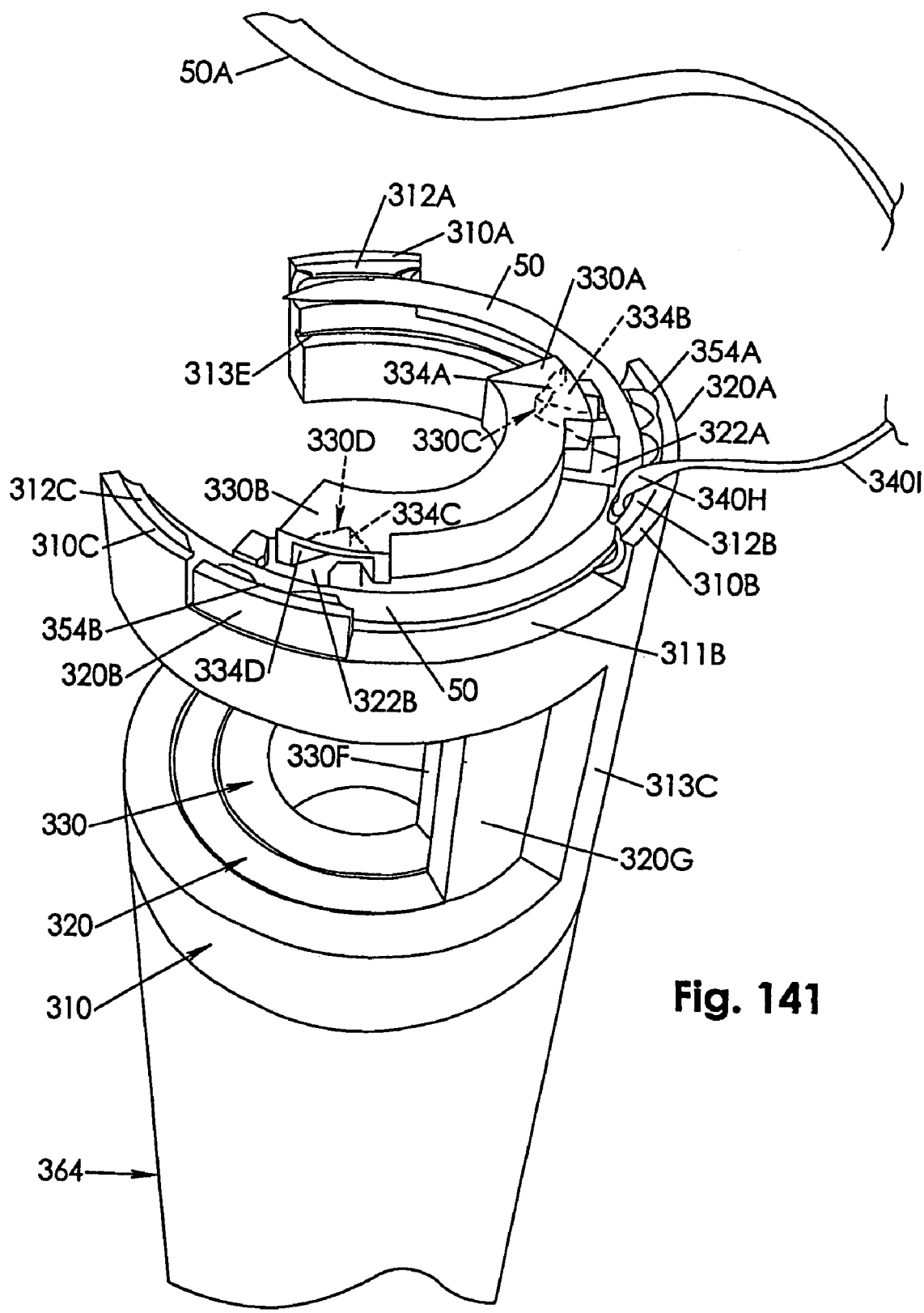

FIG. 141 is a perspective view of the tubular forked blade device illustrated in FIG. 139 with the needle-engaging blades removed for brevity.

Figure 142:
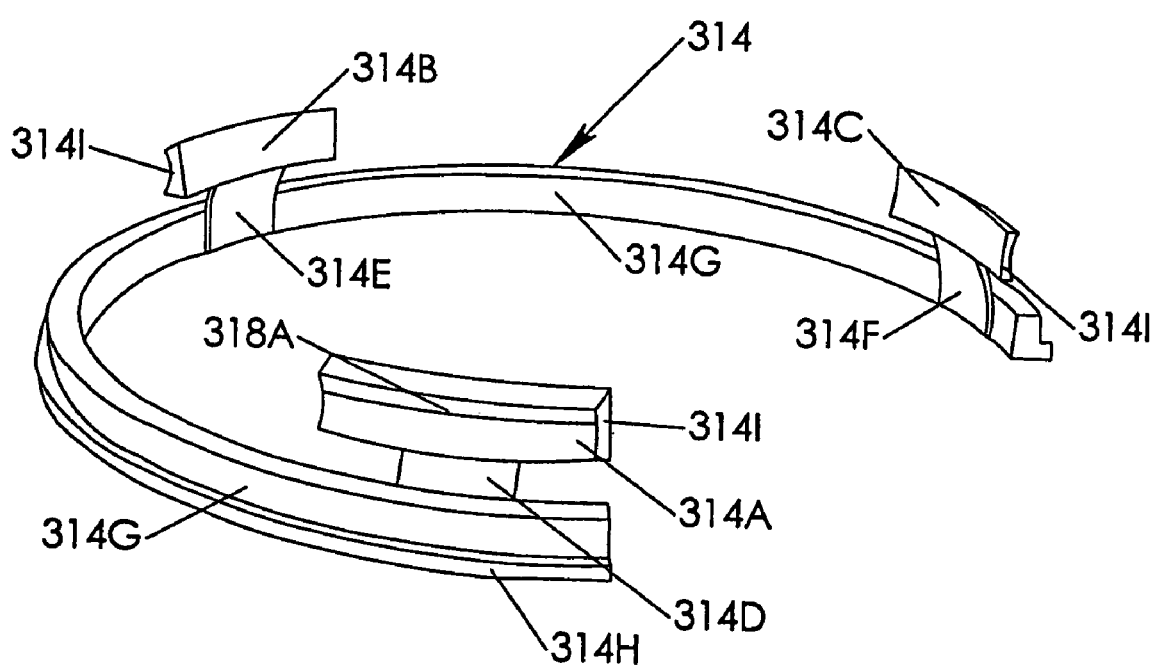

FIG. 142 is a perspective view of a spring pressure pad assembly for use in the tubular forked blade device illustrated in FIG. 139.

Figure 143:
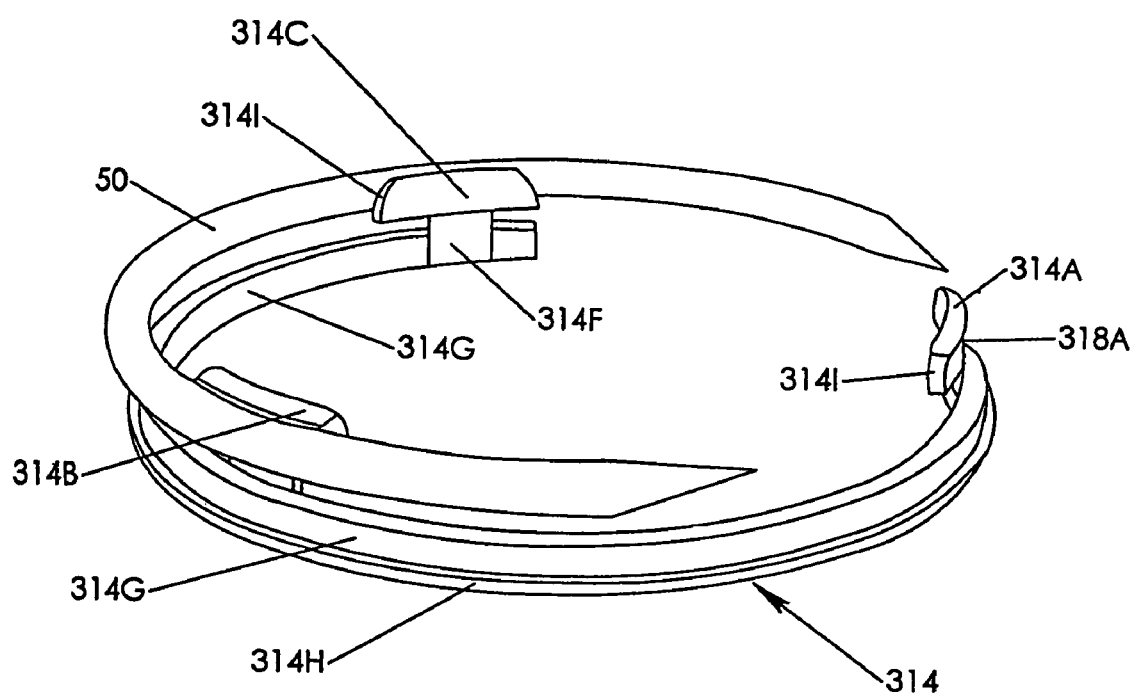

FIG. 143 is a perspective view of the spring pad assembly illustrated in FIG. 142 with the arcuate needle in functional configuration on the respective mounting springs.

Figure 144:
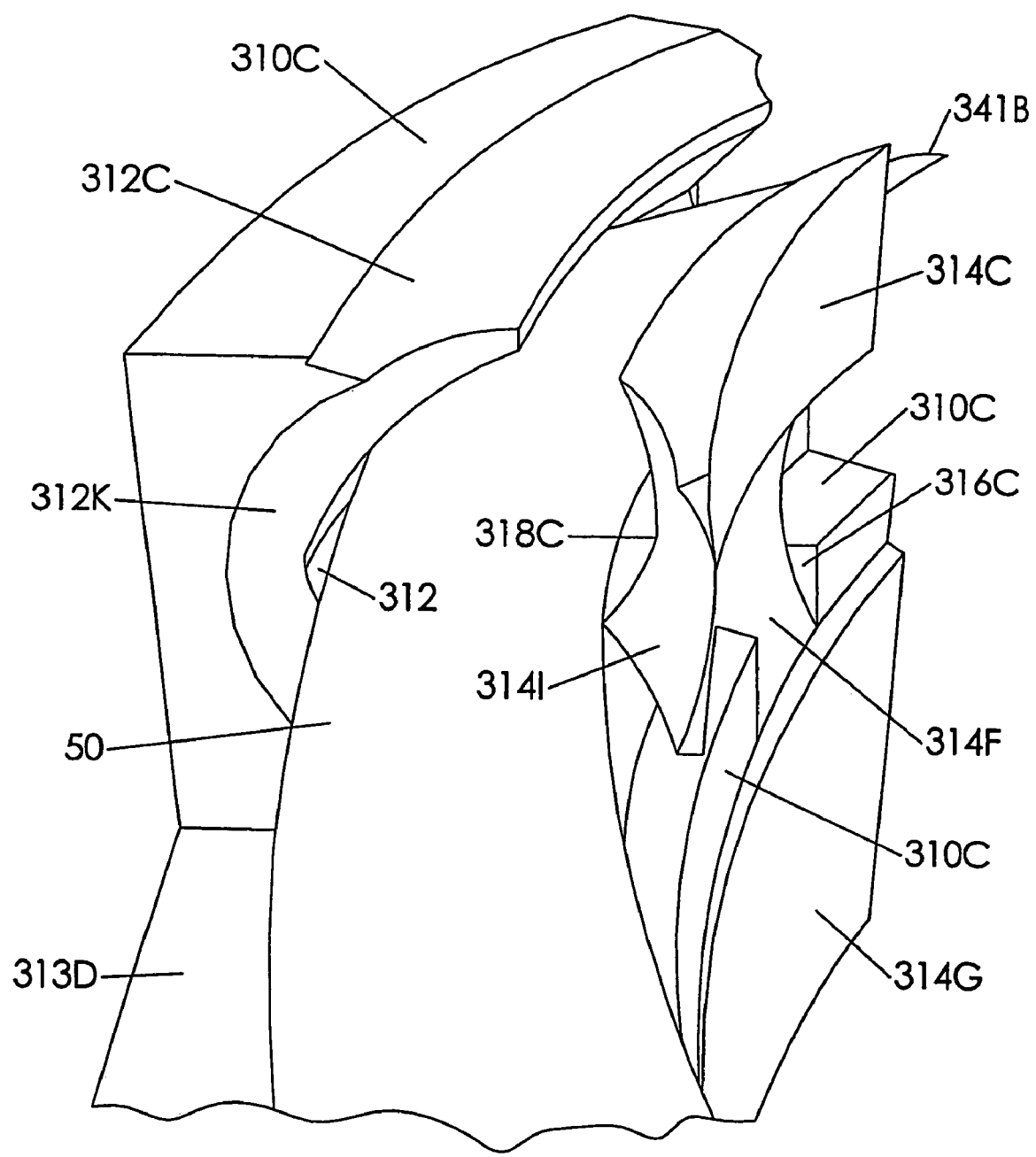

FIG. 144 is an enlarged perspective view of a fixed segment element of the lower fixed support frame tubular member, with one of the spring pressure pad assemblies in place, more particularly illustrating engagement of a retaining pad with the needle.

Figure 145:
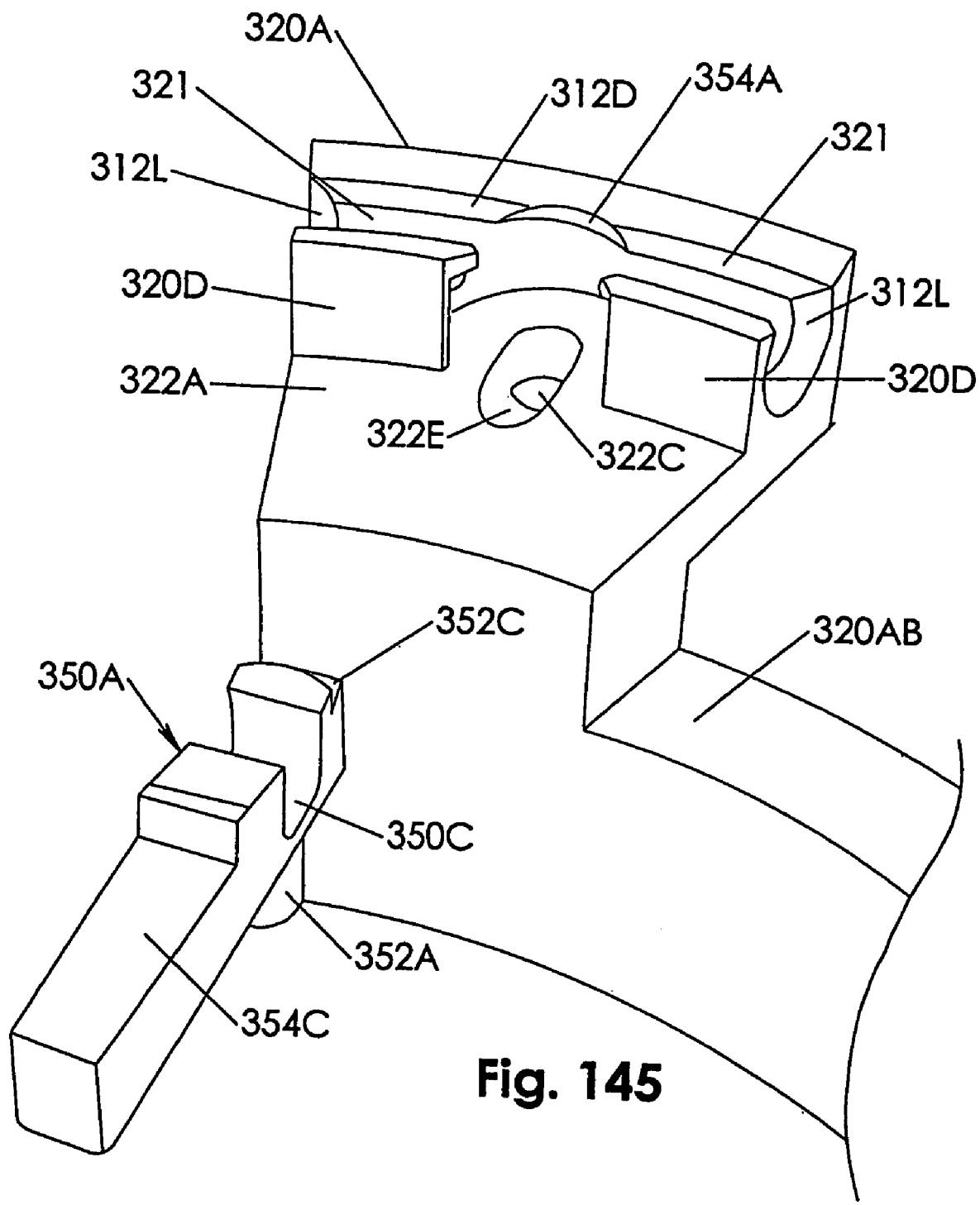

FIG. 145 is an exploded view of a blade housing and blade, more particularly illustrating a first preferred mounting of the blade in the blade housing.

Figure 146:
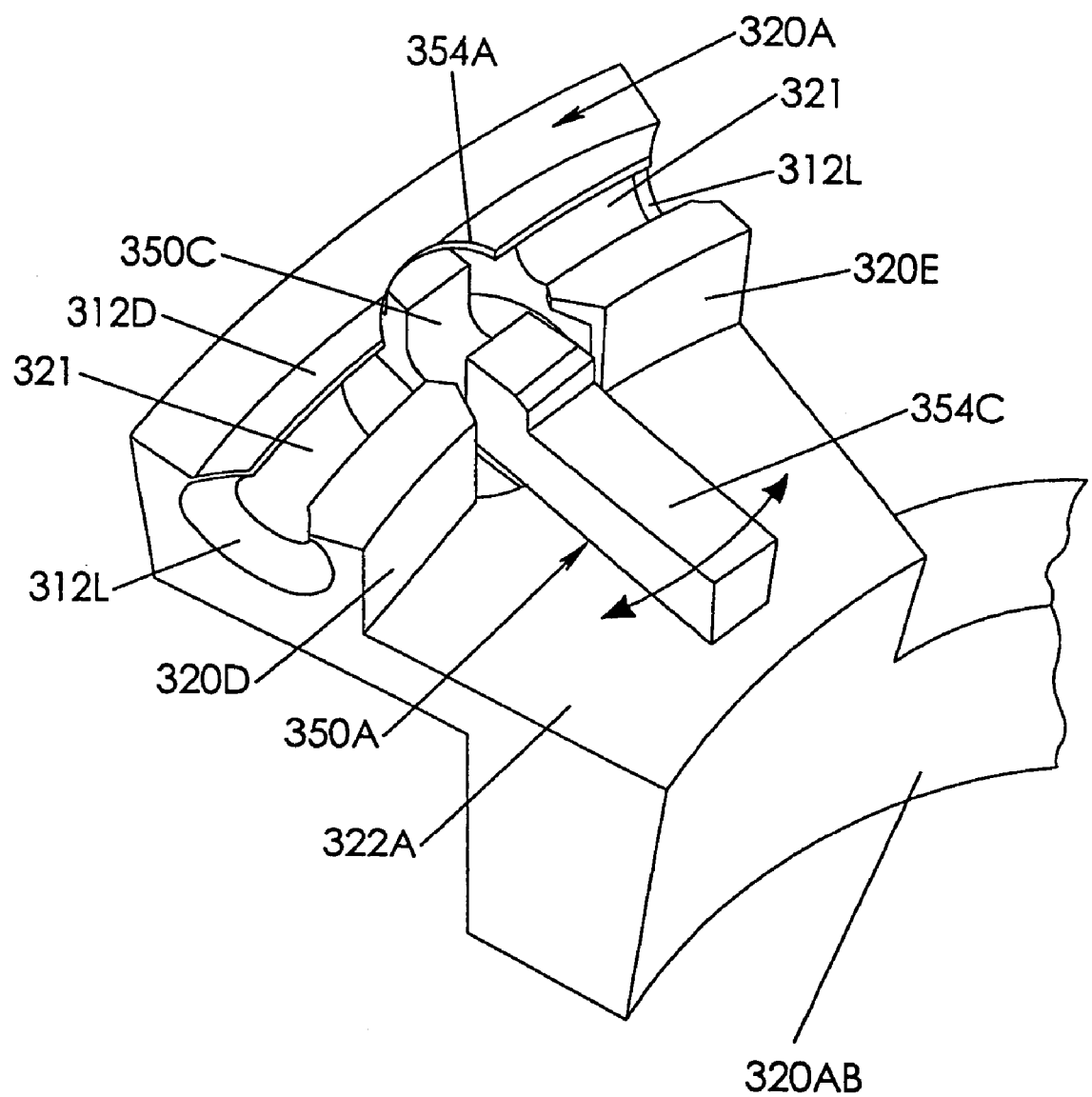

FIG. 146 is a perspective view of the blade housing and blade illustrated in FIG. 145 in assembled configuration, more particularly illustrating the pivoting function of the blade in the blade housing.

Figure 147:
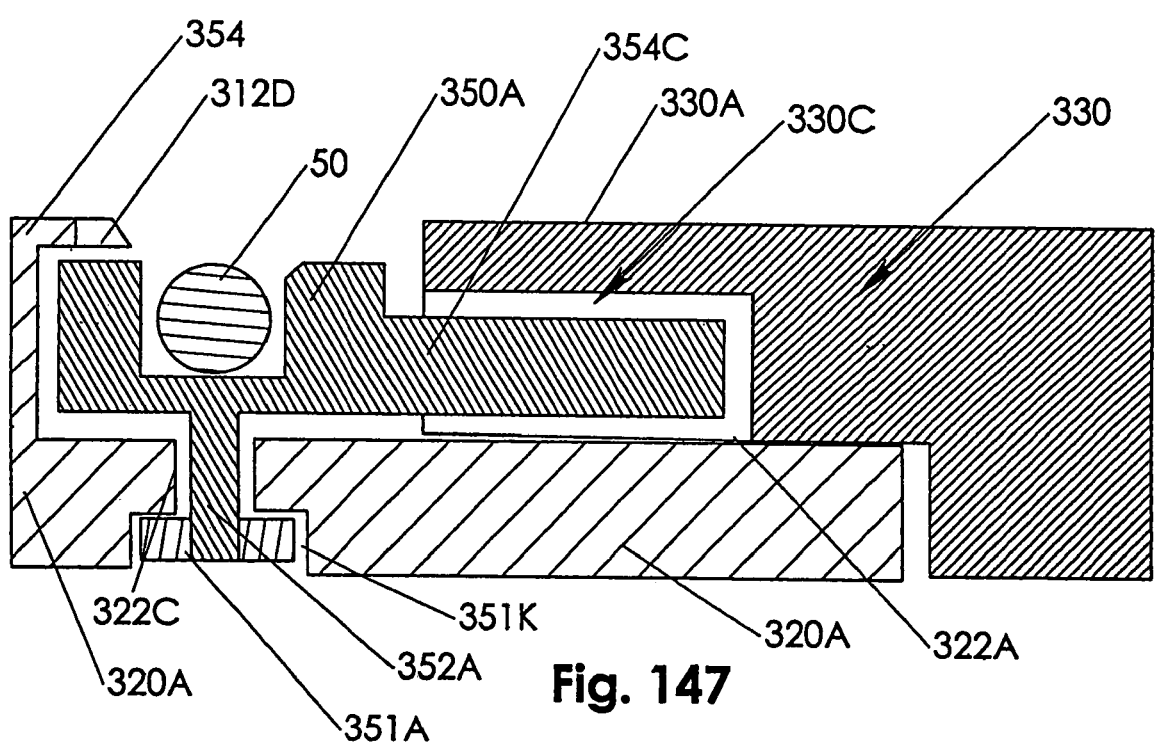

FIG. 147 is a sectional view of an alternative preferred blade and blade housing design.

Figure 148:
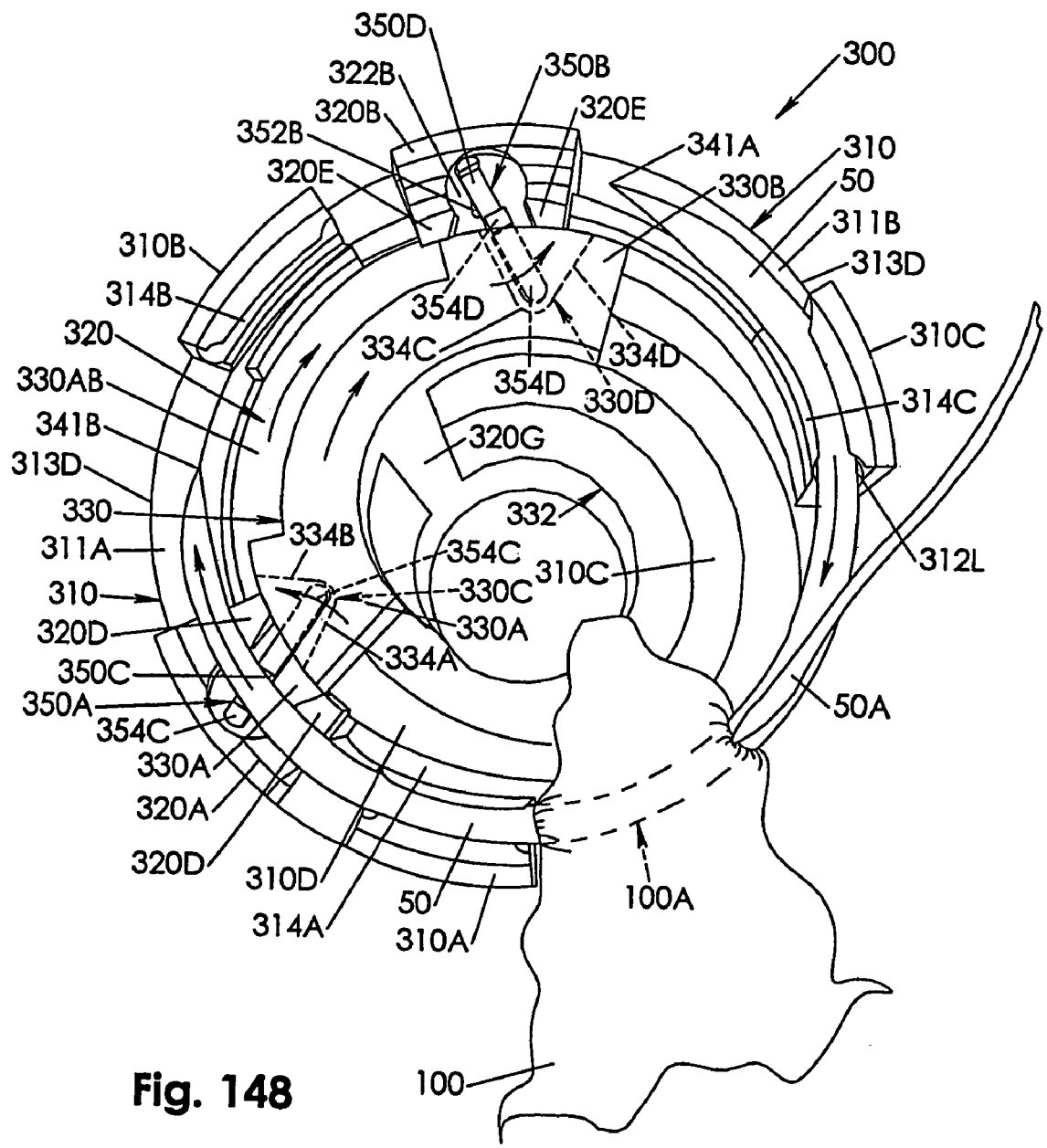

FIG. 148 is a top view of the tubular forked blade device illustrated in FIG. 145, more particularly illustrating typical incrementation of the needle through material to be sutured responsive to incrementation of the middle tube assembly and the drive spur in cooperation with engagement of the blades on the needle.

Figure 149:
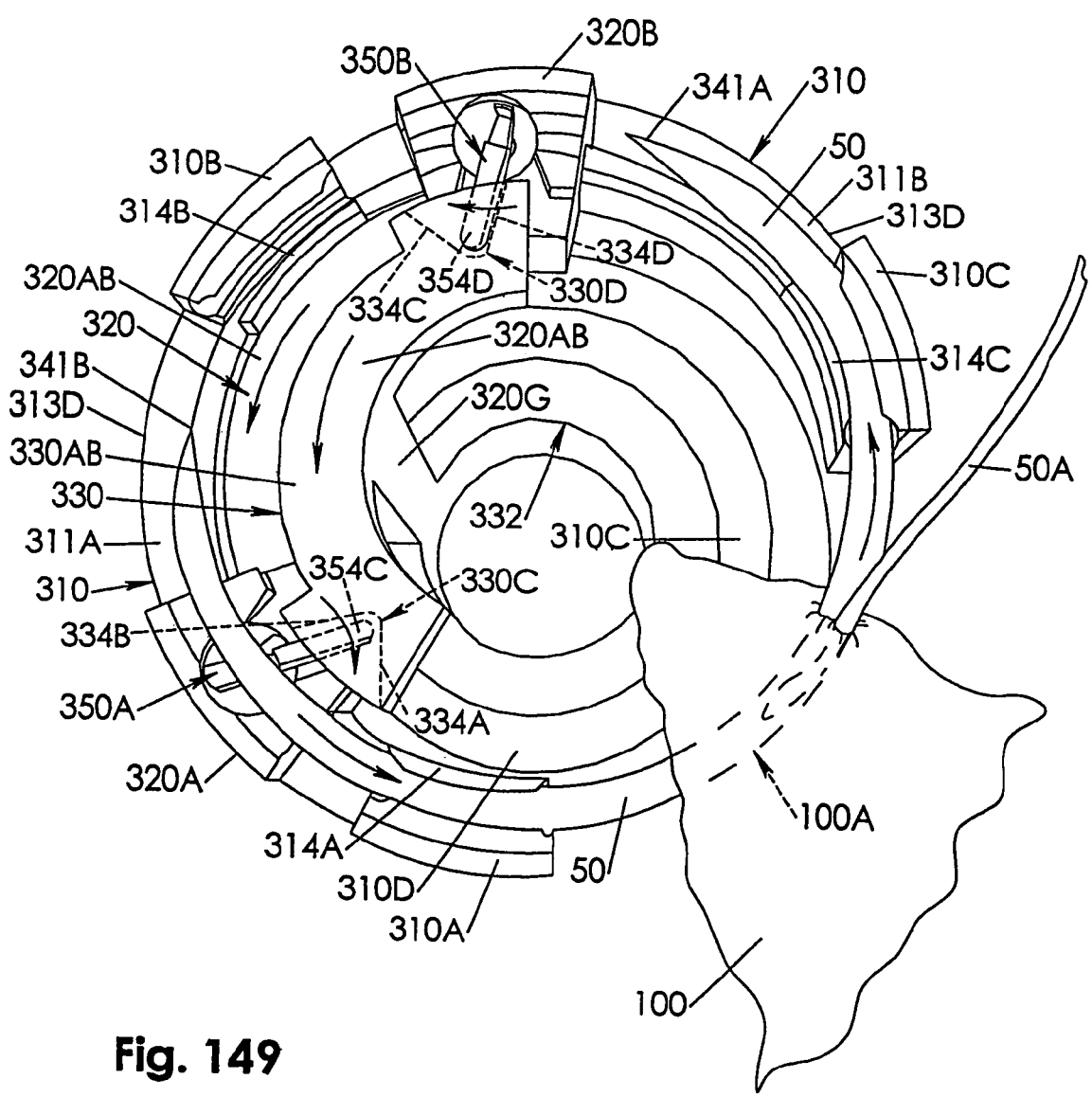

FIG. 149 is a top view of the tubular forked blade device illustrated in FIG. 148, more particularly illustrating opposite incrementation of the needle in the counterclockwise direction responsive to corresponding movement of the middle tube assembly and the drive spur.

Figure 150:
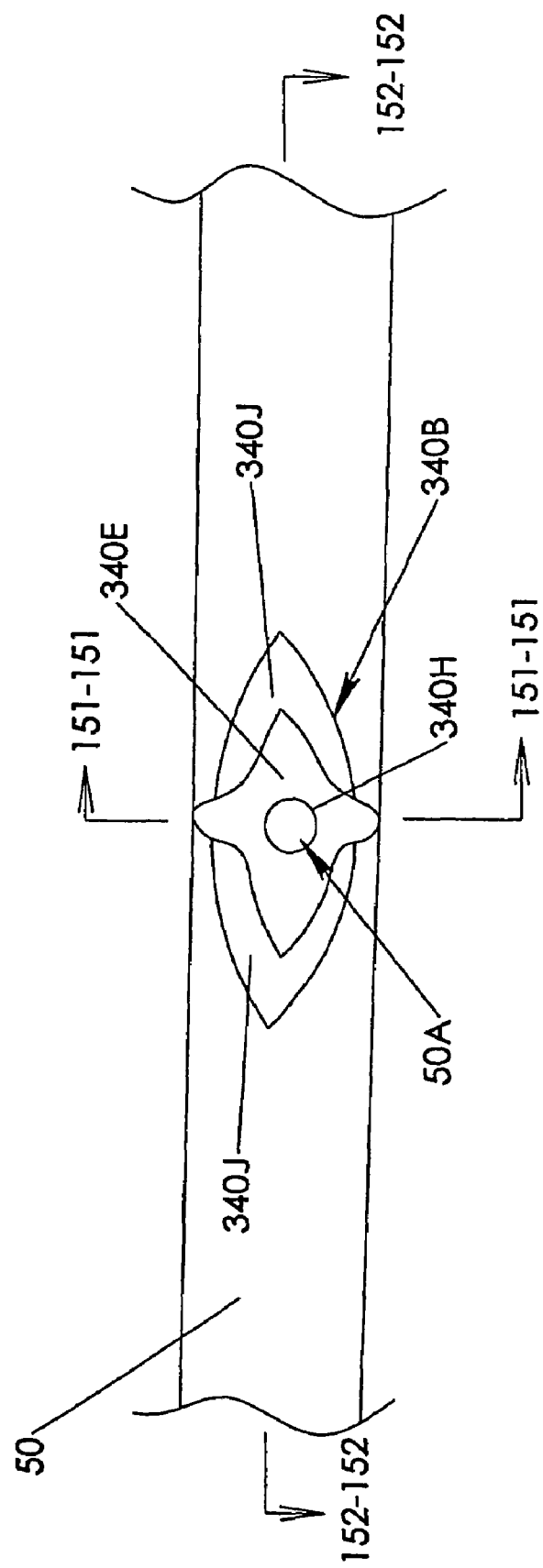

FIG. 150 is a top view of a typical configuration for attaching thread to the center of the arcuate needle illustrated in FIG. 139.

FIG. 151 is a sectional view taken along line 151-151 in FIG. 150, more particularly illustrating a preferred connection between the thread and the needle.

FIG. 152 is a sectional view taken along line 152-152 in FIG. 150, more particularly illustrating the preferred thread-needle attachment.

Figure 153:
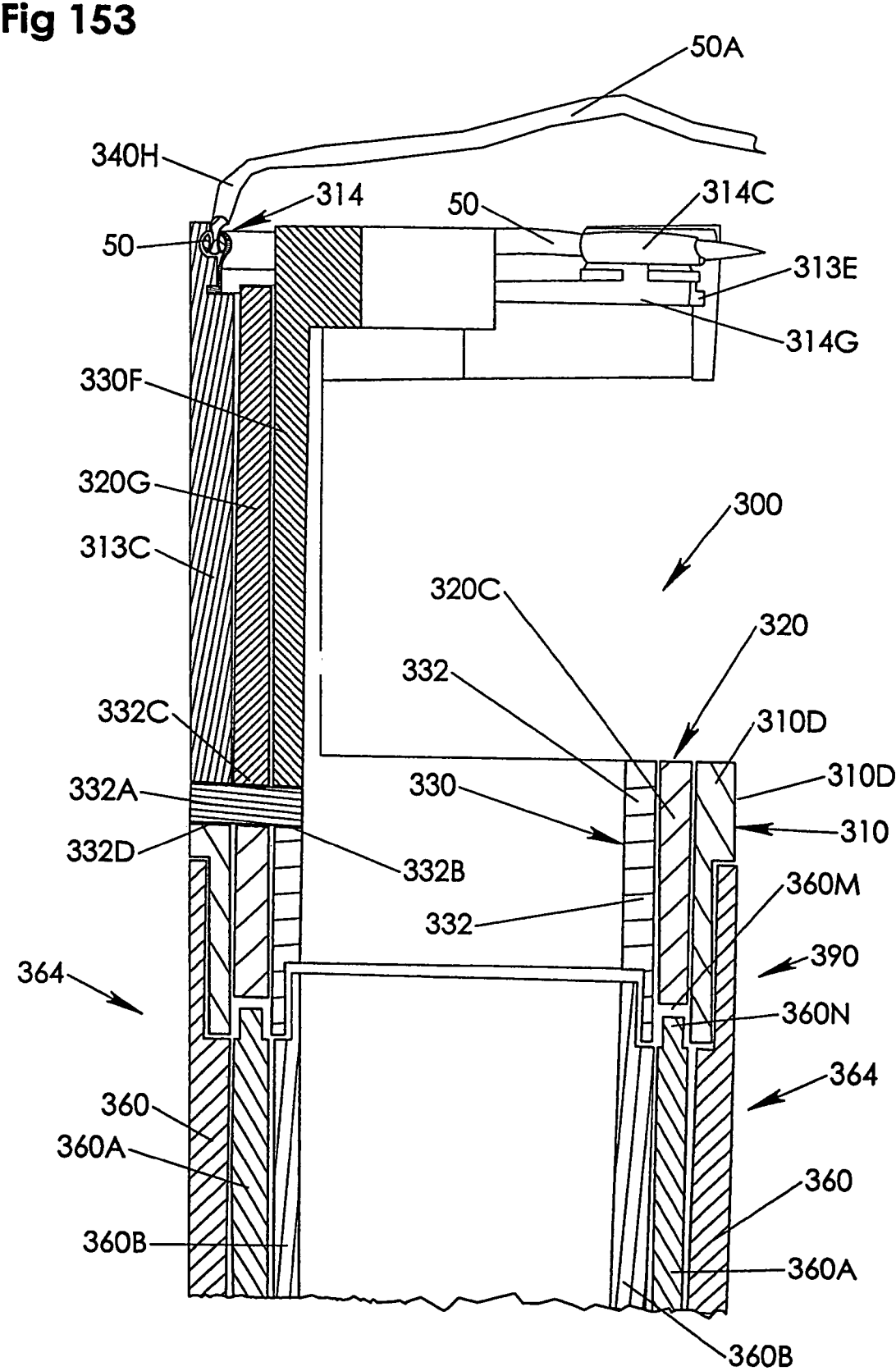

FIG. 153 is a longitudinal sectional view of the tubular forked blade device illustrated in FIG. 139, more particularly illustrating a typical driver or operator attached to the tubular forked blade device for effecting incrementation of the middle tube assembly and the drive spur, to increment the needle in the tubular forked blade device.

FIG. 154 is a side view, partially in section, of the tubular forked blade device, more particularly illustrating a flexible tube connection to the tubular forked blade device for articulation of the forked blade device into a desired configuration in a suturing operation.

FIG. 155 is a sectional view of the main tubular extension attached to the tubular forked blade device for articulating the tubular forked blade device responsive to operation of a cable arrangement extending through the respective tubular extensions.

Figure 156:
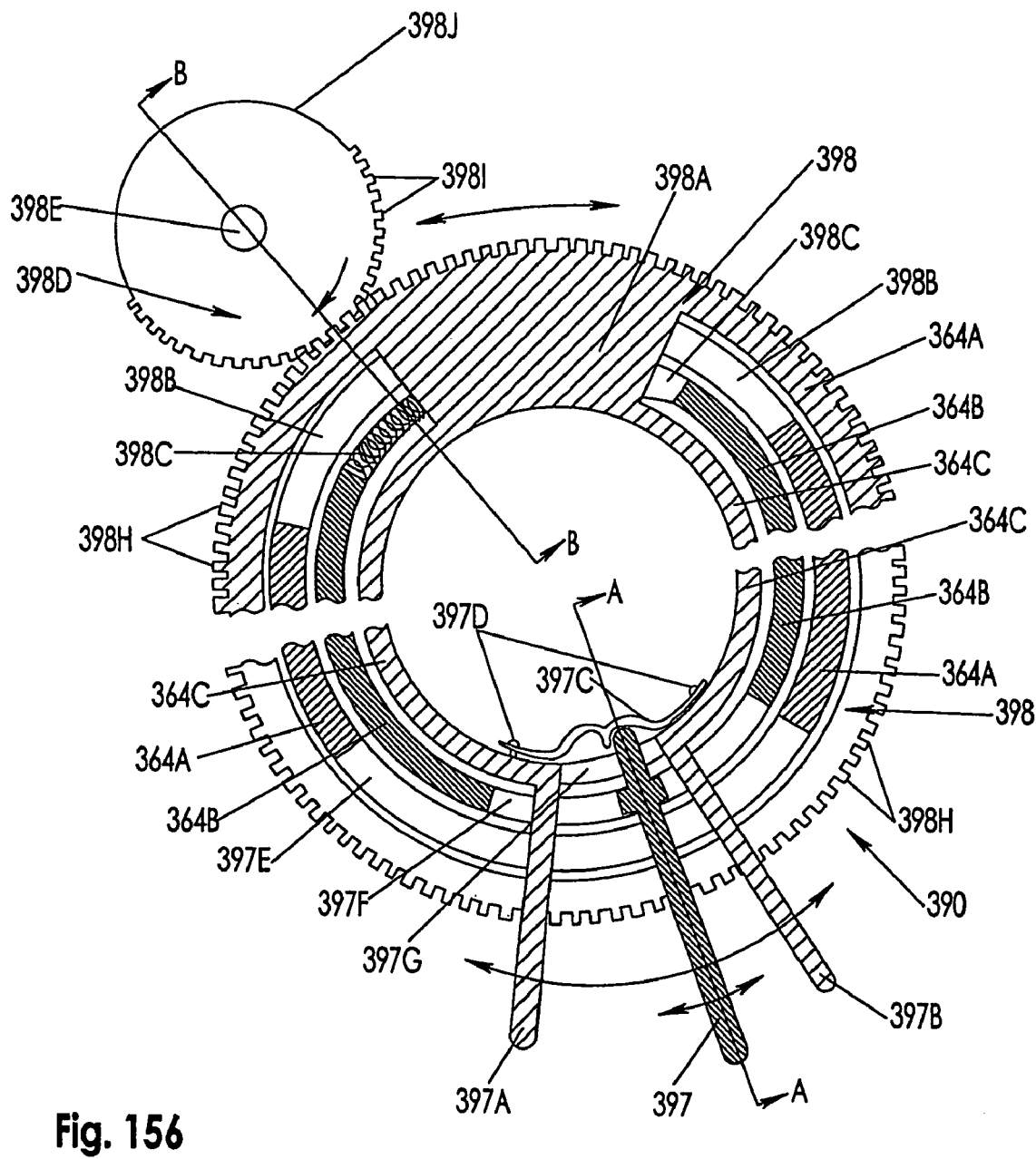

FIG. 156 is a sectional view of an extension structure and drive system for incrementing the drive spur and driving the middle tube assembly to effect incrementation of the needle in the tubular forked blade device.

Figure 157:
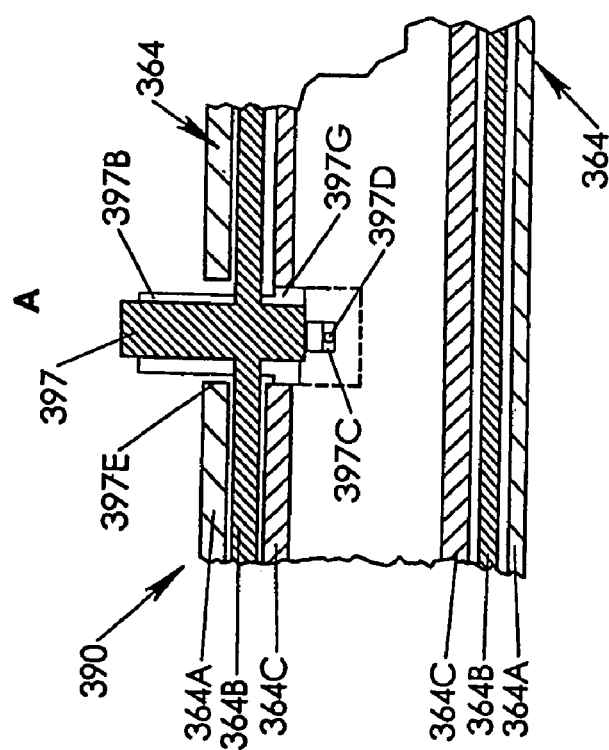

FIG. 157 is a sectional view of the extension structure illustrated in FIG. 156, more particularly illustrating a direction-changing lever element for incrementing the drive spur prior to driving the middle tube assembly and the drive spur in concert and incrementing the needle in the tubular forked blade device.

Figure 158:
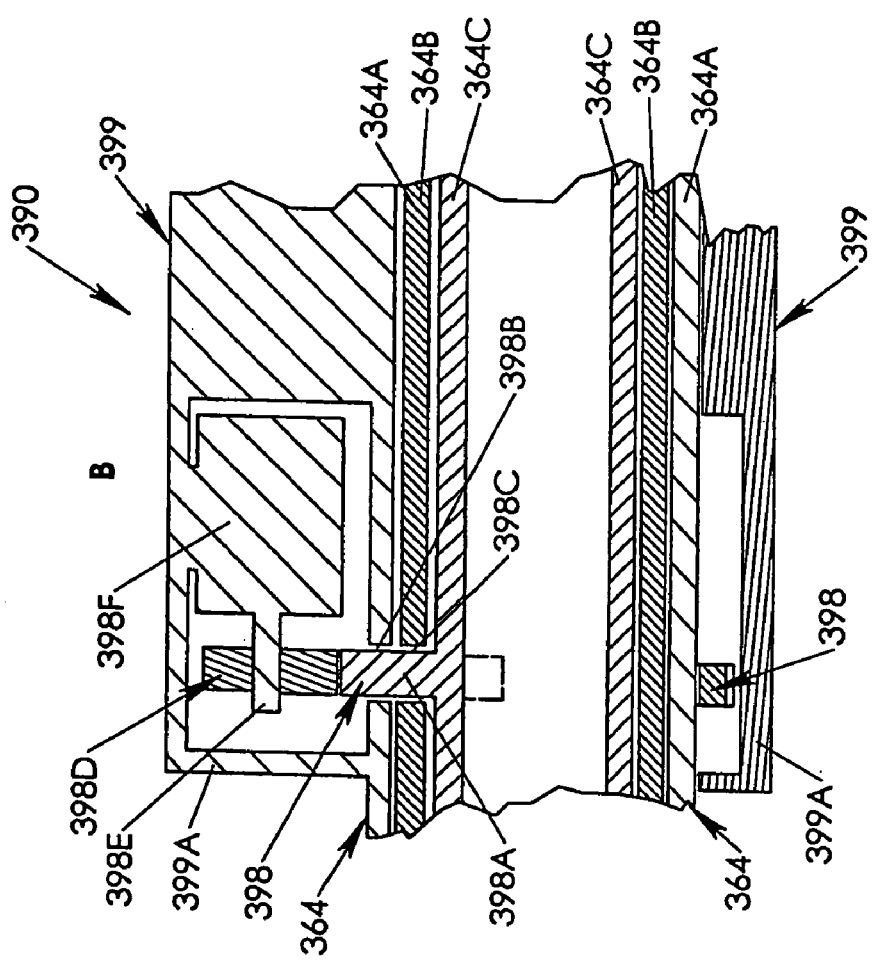

FIG. 158 is a sectional view of the extension structure illustrated in FIG. 157, more particularly illustrating a typical drive motor and drive gear arrangement for driving the middle tube assembly and the drive spur to increment the needle in the tubular forked blade device.

Figure 159:
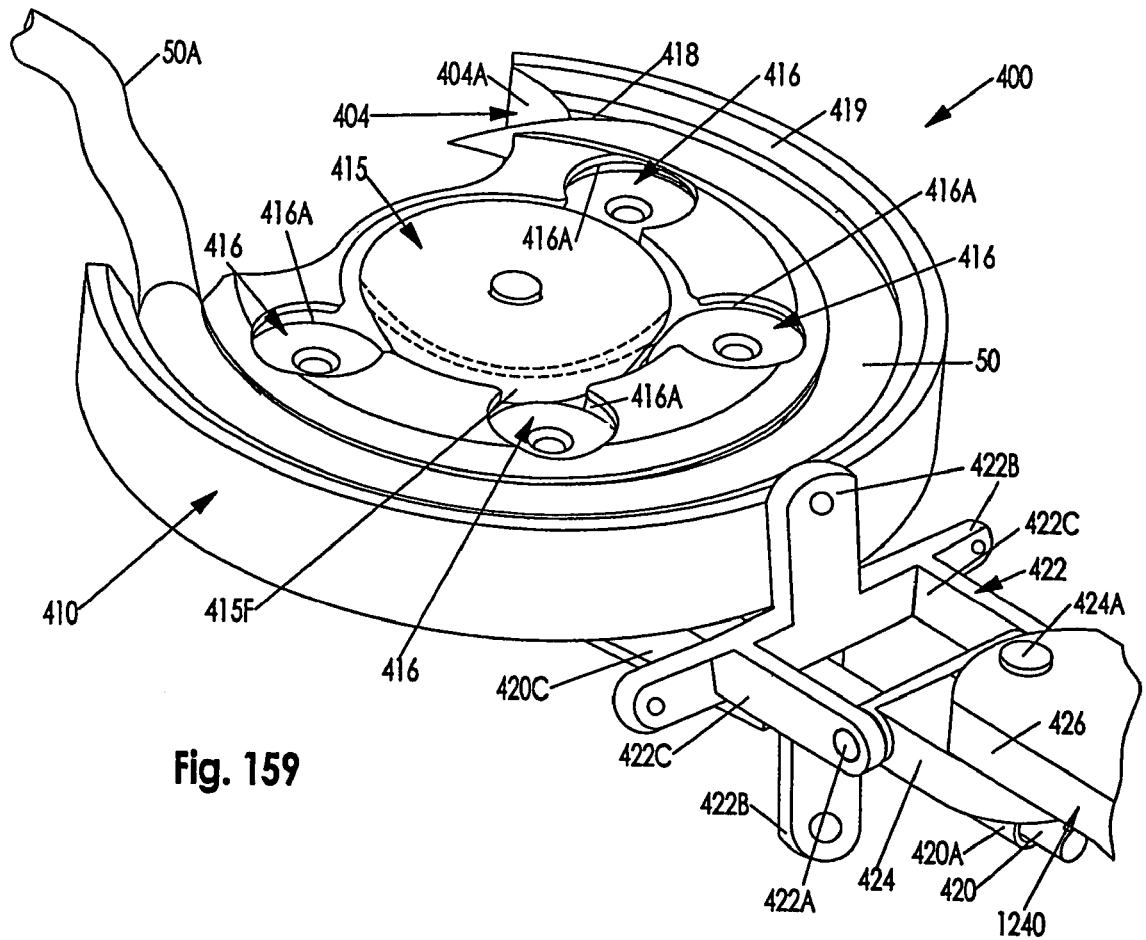

FIG. 159 is a perspective view of the planetary wheel/gear device embodiment of the cycling suturing and knot-tying device, more particularly illustrating a preferred articulating mechanism for positioning the disc body in a variety of positions with respect to a material to be sutured.

Figure 160:
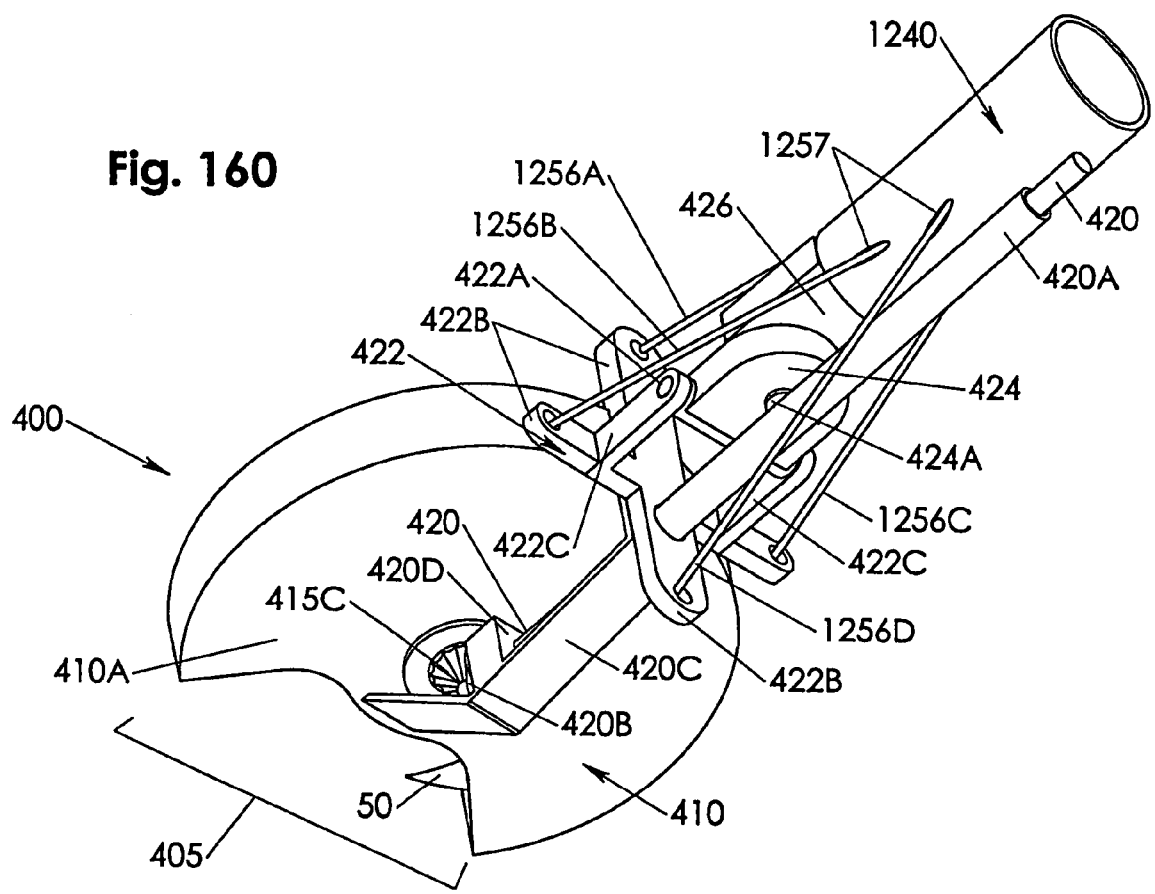

FIG. 160 is a bottom perspective view of the planetary wheel/gear device illustrated in FIG. 159.

Figure 161:
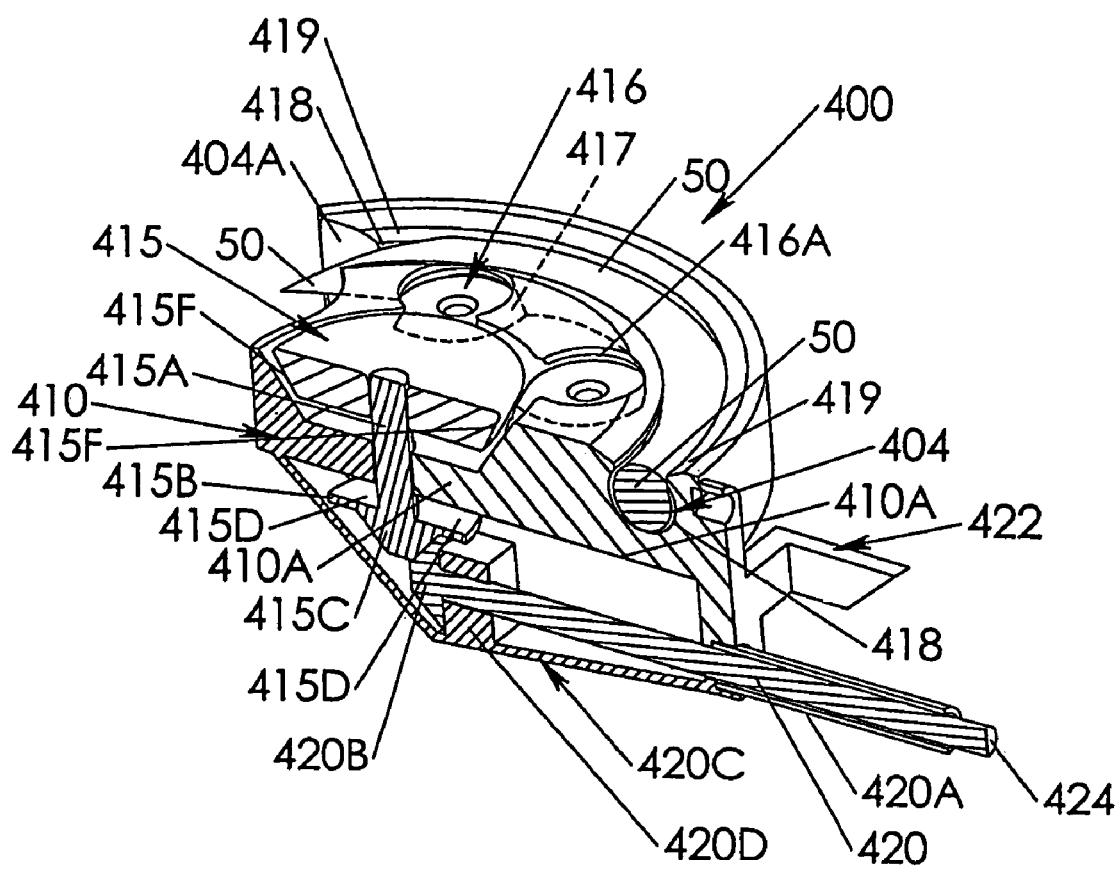

FIG. 161 is a longitudinal sectional view of the planetary wheel/gear device illustrated in FIGS. 159 and 160.

Figure 162:
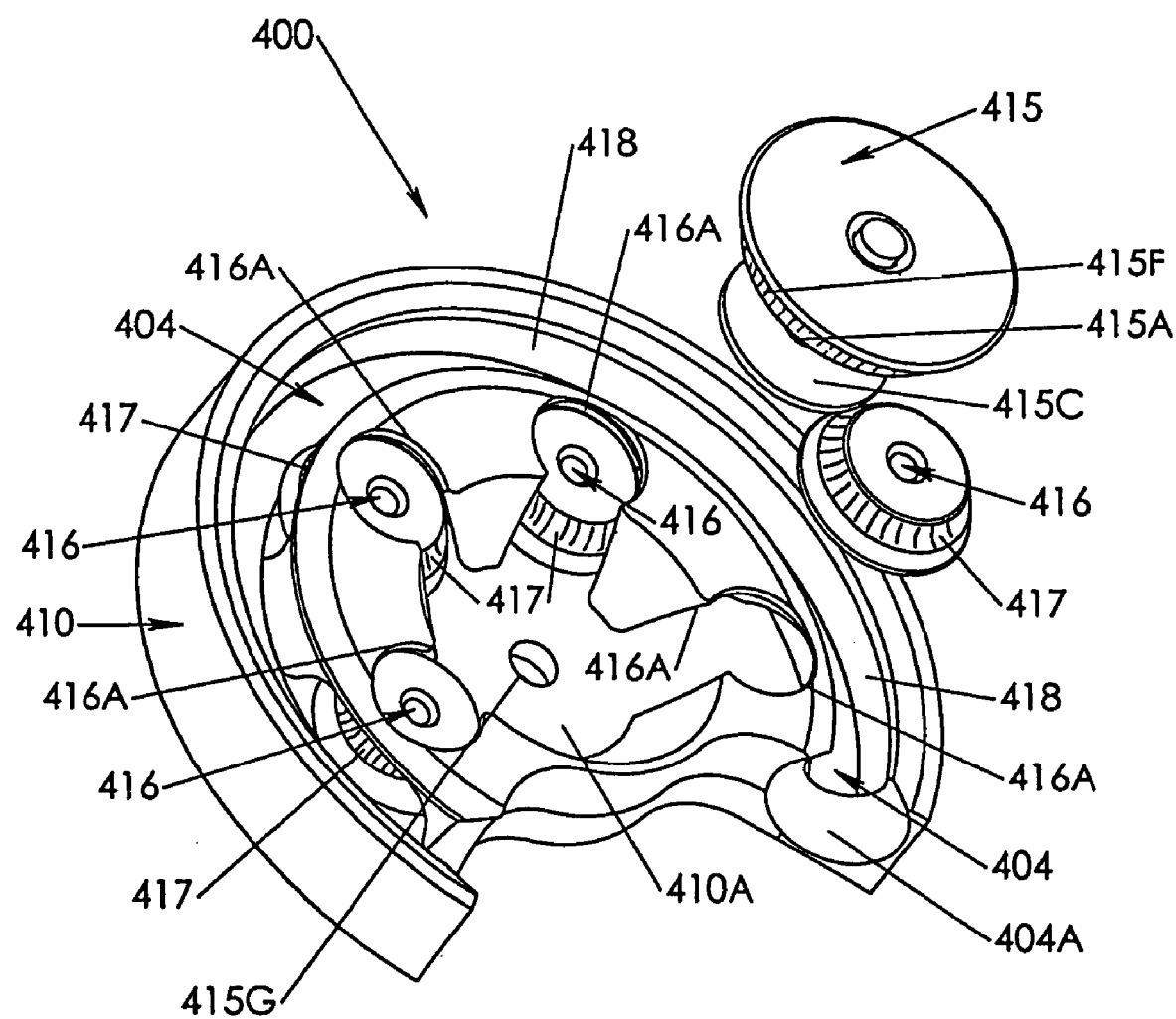

FIG. 162 is an exploded view of the planetary wheel/gear device, more particularly illustrating the conical central gear and toothed rotor driving system.

Figure 163:
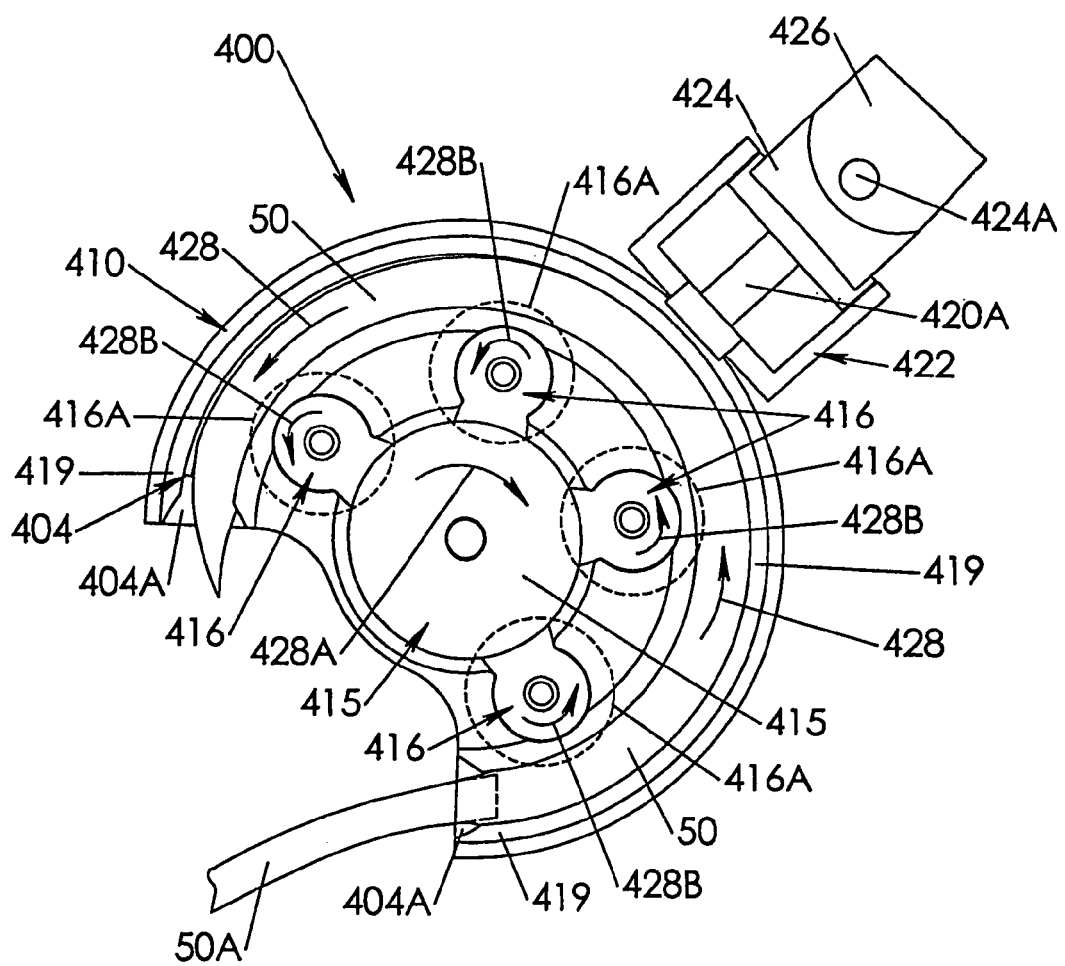

FIG. 163 is a top view of the planetary wheel/gear device, more particularly illustrating directions of rotation of the conical central gear and the respective toothed rotors to effect a counterclockwise incrementation of the needle in the planetary wheel/gear device.

Figure 164:
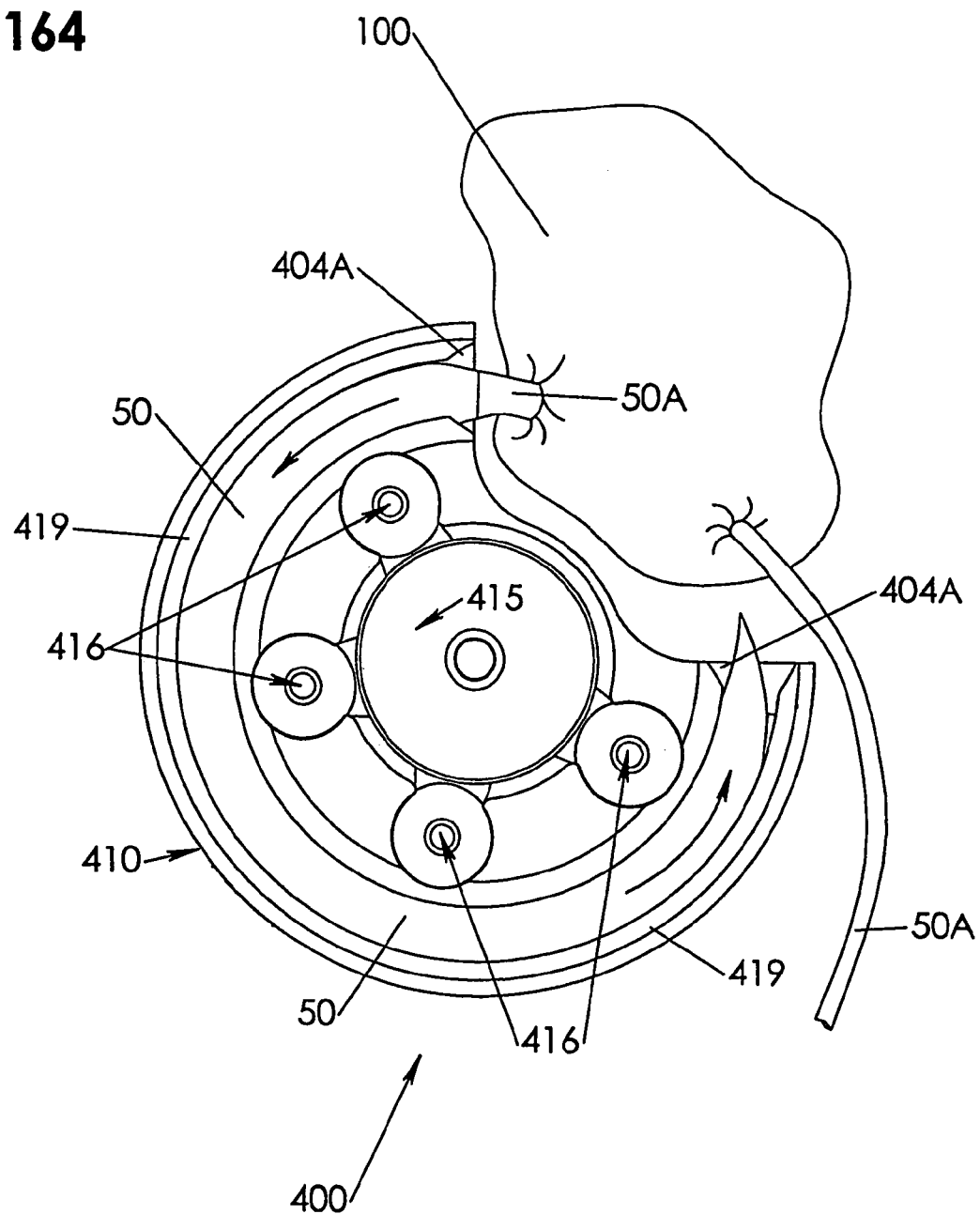

FIG. 164 is a top view of the planetary wheel device illustrated in FIG. 163, more particularly illustrating incrementation of the needle through material to be sutured by operation of the needle drive system, including the conical central gear and the toothed rotors.

FIG. 165 is a sectional view of an alternative preferred embodiment of the conical central gear and concave rotors for incrementing the needle around the planetary wheel/gear device.

FIG. 166 is a sectional view of yet another alternative design for the conical central gear and alternate tooth rotors for incrementing the needle around the planetary wheel/gear device.

Figure 167:
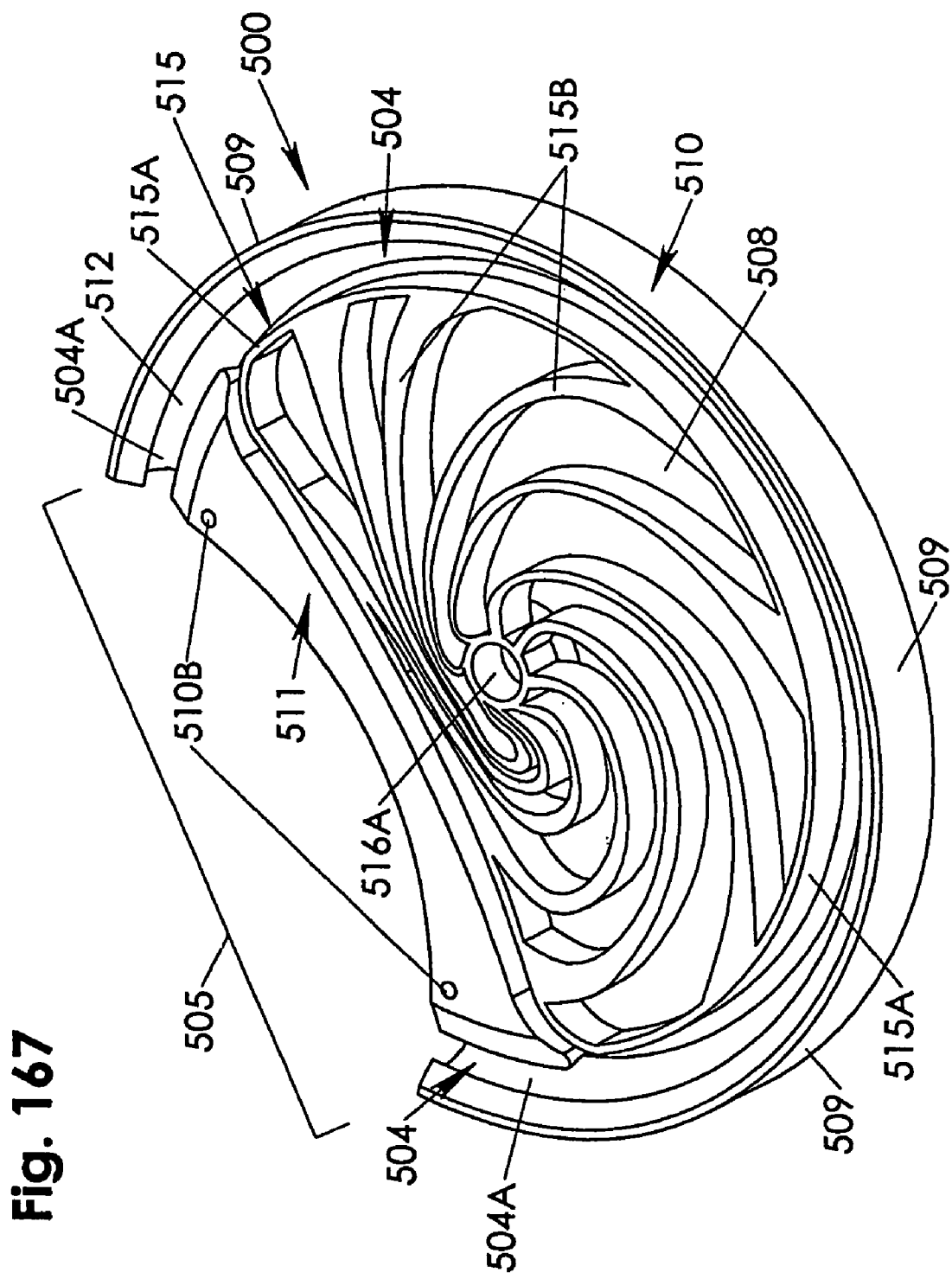

FIG. 167 is a perspective view of a flexible rotor device embodiment of the cycling suturing and knot-tying device, including an arcuate disc and a flexible rotor mounted in the disc for incrementing the needle inside the disc in a suturing operation.

Figure 168:
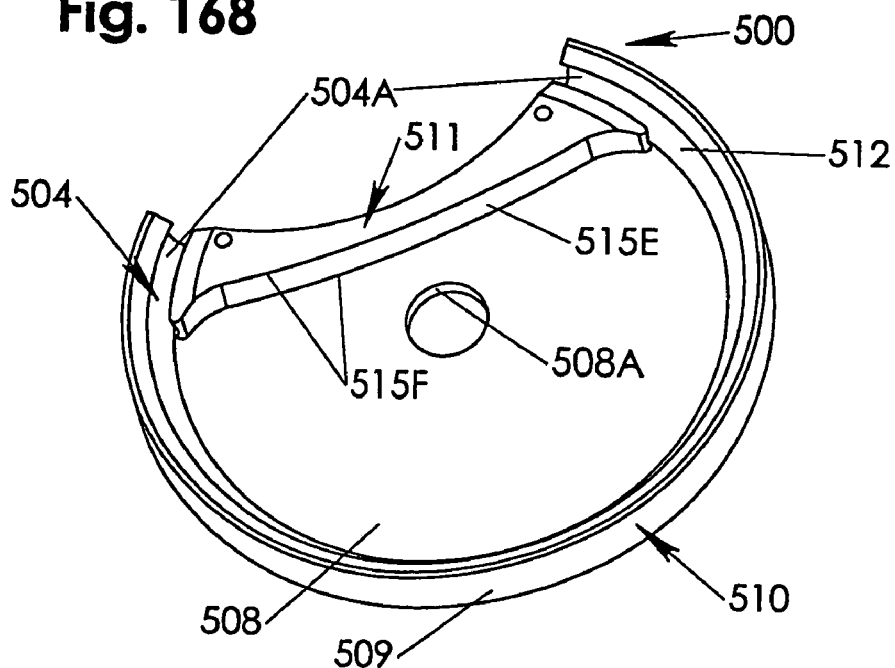

FIG. 168 is a perspective view of the disc element of the flexible rotor device illustrated in FIG. 167.

Figure 169:
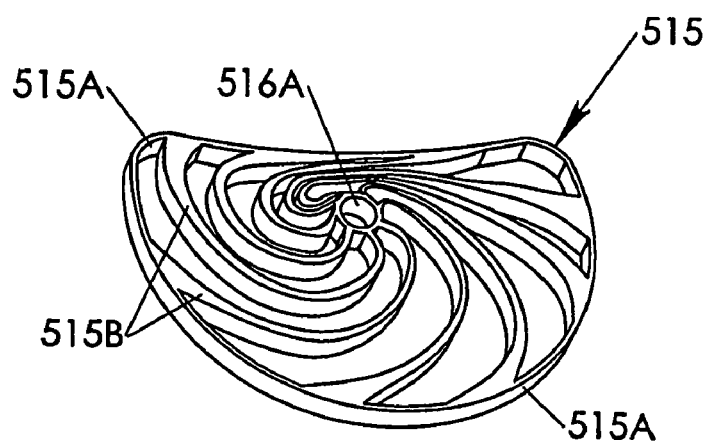

FIG. 169 is a perspective view of the flexible rotor element of the flexible rotor device.

Figure 170:
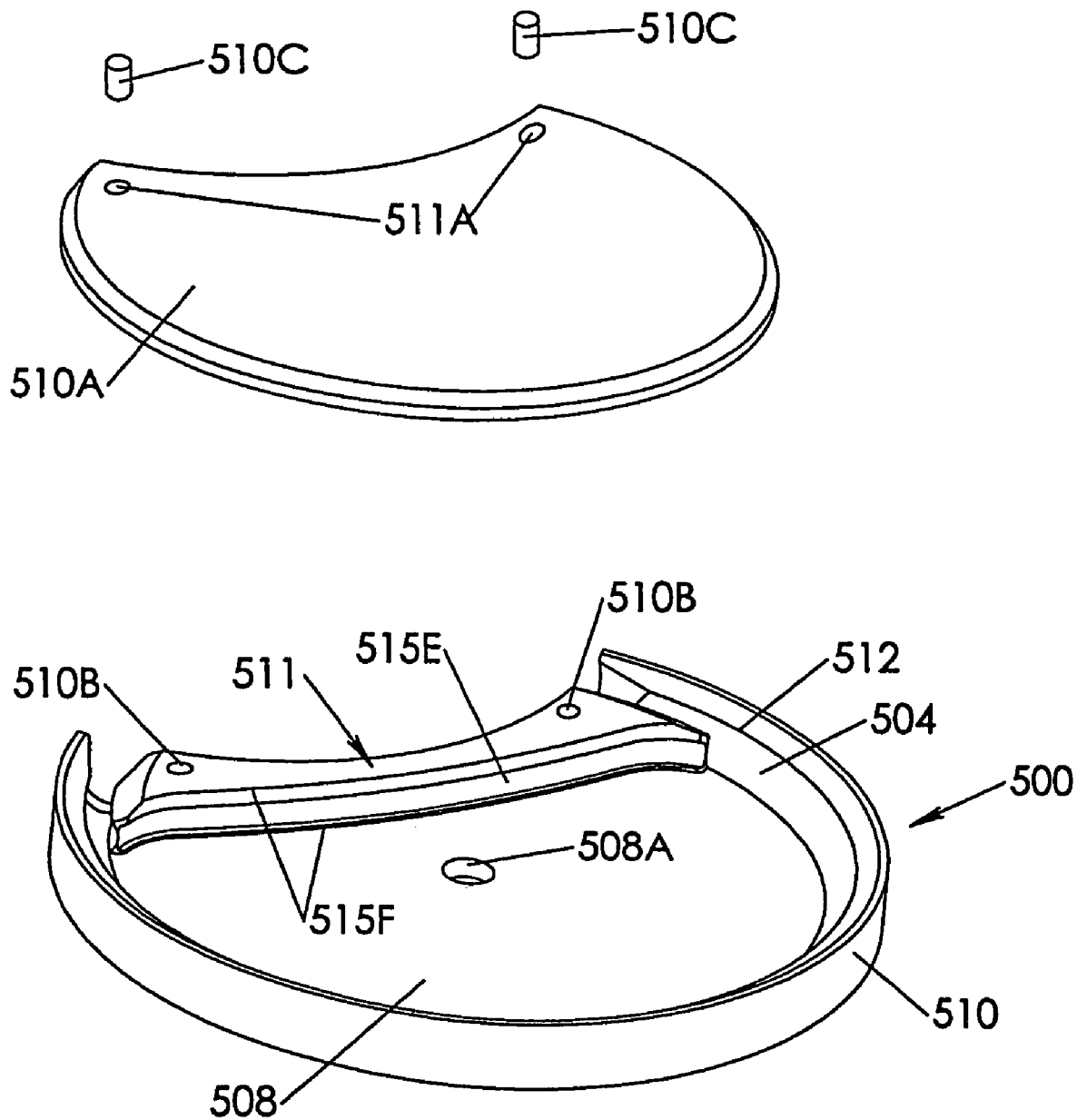

FIG. 170 is an exploded view of the disc element and a protective plate for enclosing the flexible rotor in the disc of the flexible rotor device.

Figure 170A:
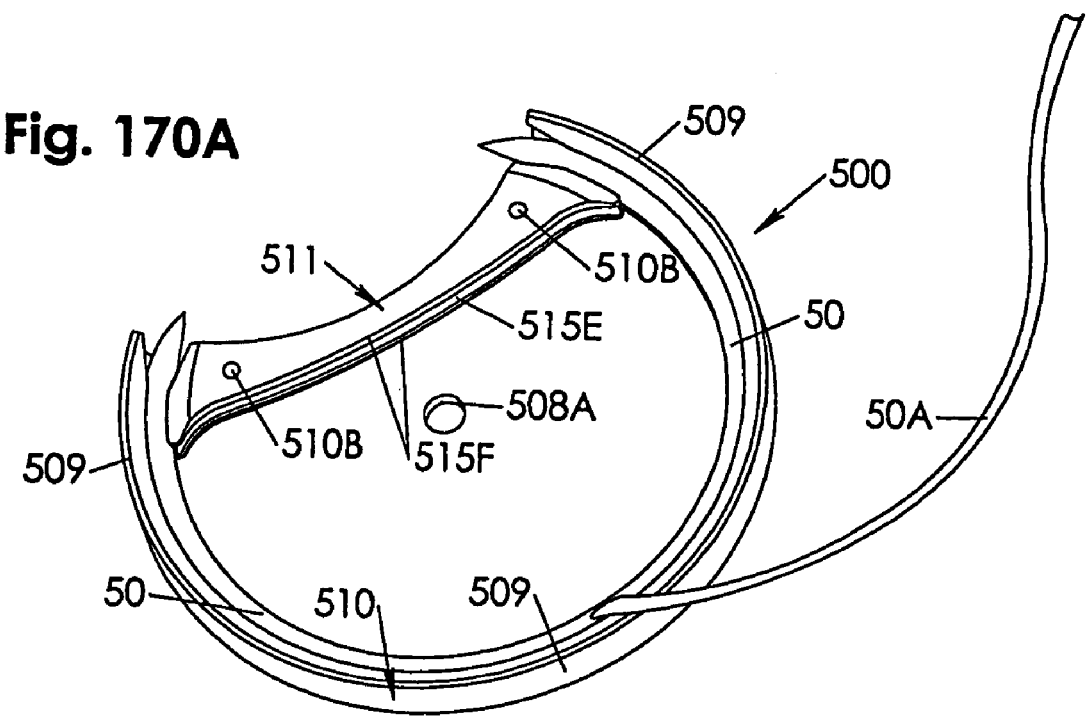

FIG. 170A is a perspective view of the disc element of the flexible rotor device with the arcuate needle in functional configuration in the disc.

Figure 170B:
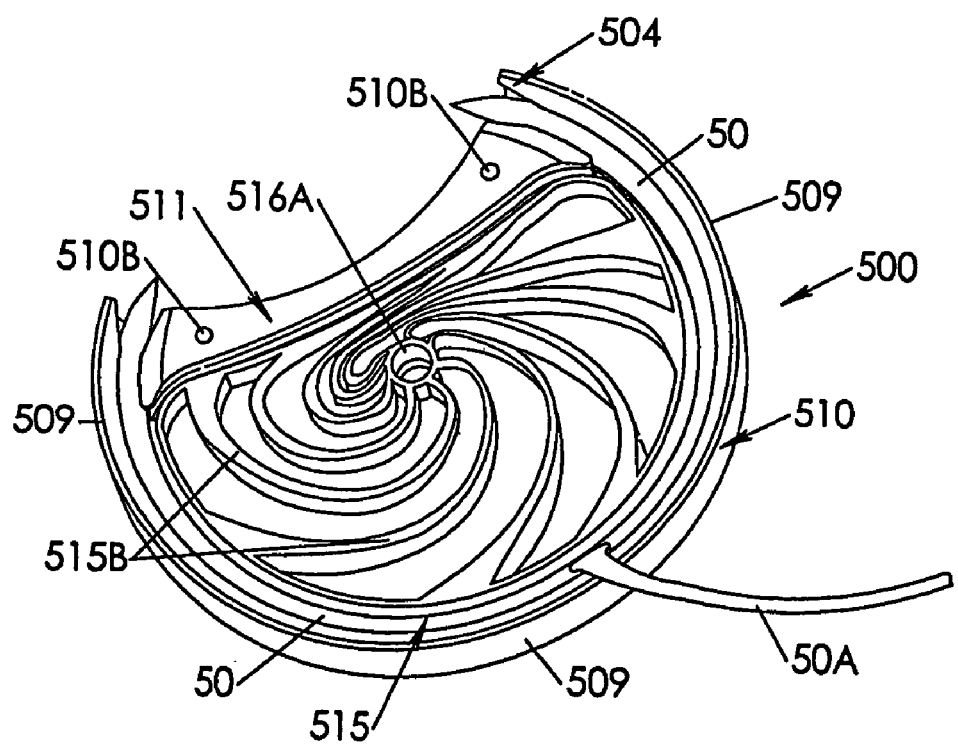

FIG. 170B is a perspective view of the disc and needle illustrated in FIG. 170A, with the flexible rotor installed inside the disc for rotating the flexible rotor in the disc and incrementing the needle responsive to operation of a suitable drive system.

Figure 171:
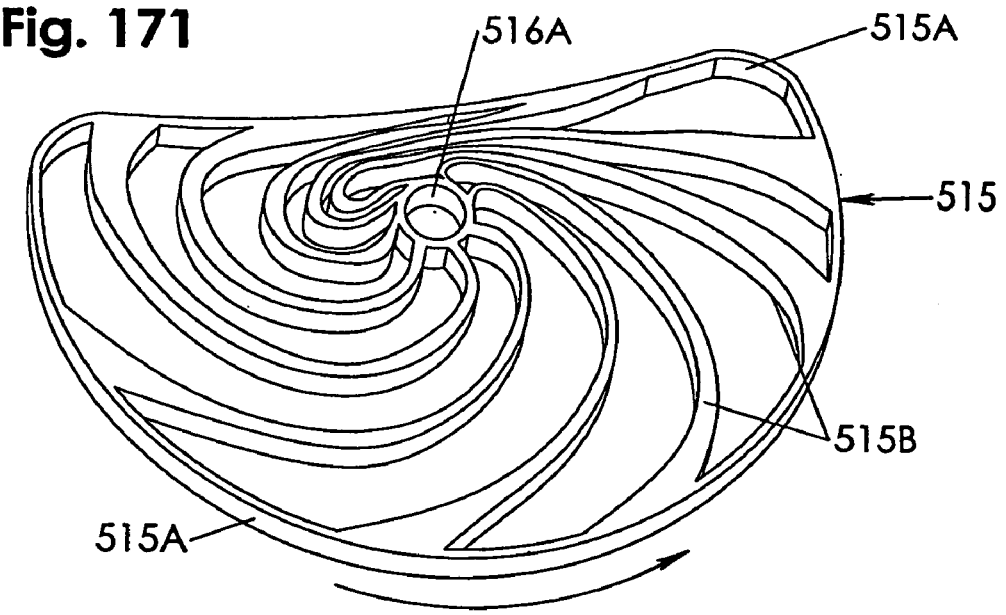

FIG. 171 is a perspective view of the flexible rotor element of the flexible rotor device, more particularly illustrating counterclockwise rotation of the flexible rotor.

Figure 172:
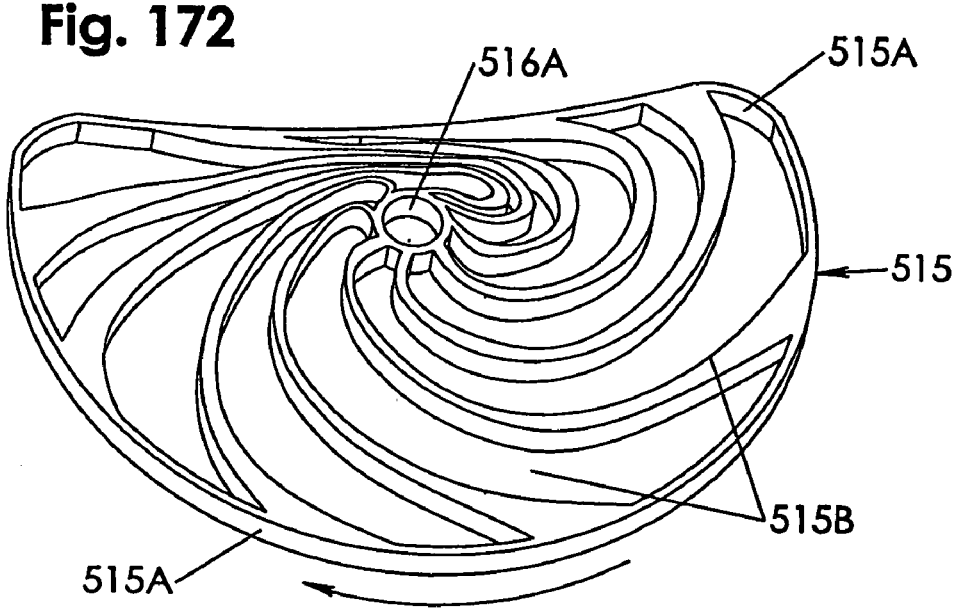

FIG. 172 is a perspective view of the flexible rotor element illustrated in FIG. 171, disposed for clockwise rotation in the flexible rotor device.

FIG. 173 is a sectional view of the disc and flexible rotor, more particularly illustrating engagement of the needle by the flexible rotor.

FIG. 174 is a sectional view of the disc and flexible rotor, more particularly illustrating non-engagement of a flexible rotor with a needle and illustrating a typical drive train for rotating the flexible rotor within the disc.

Figure 175:
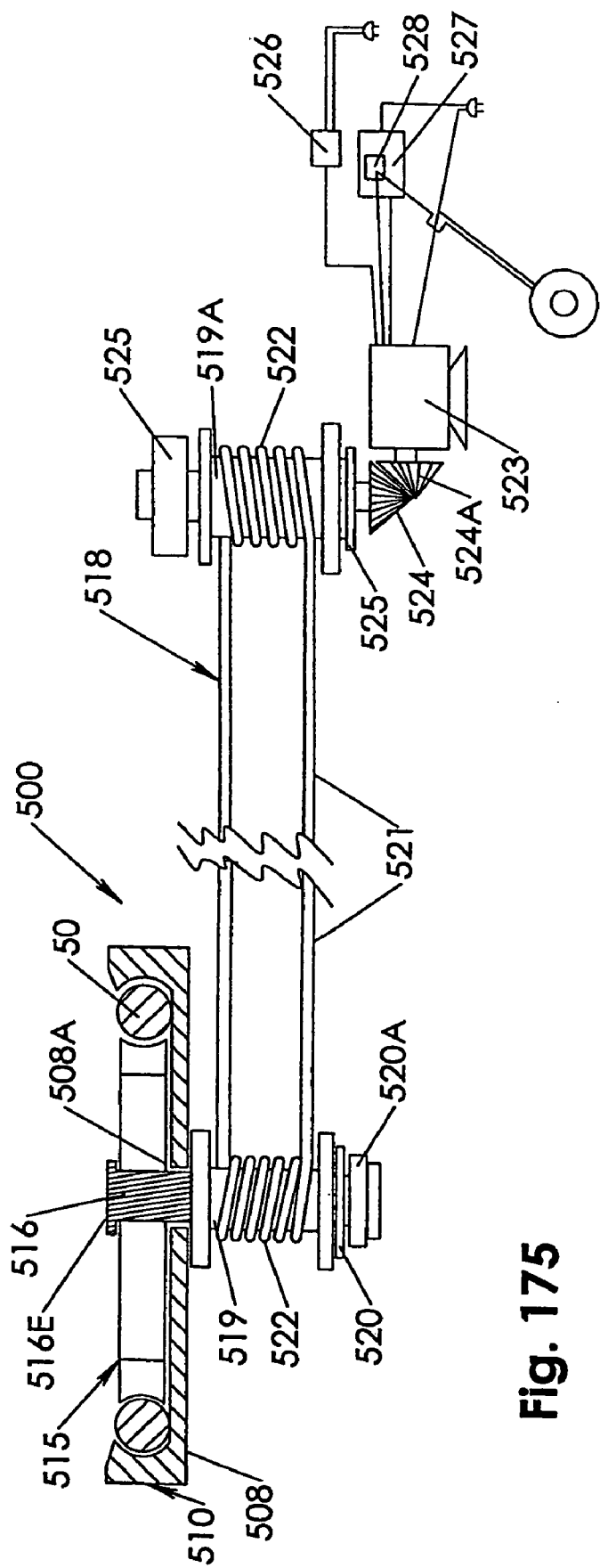

FIG. 175 is a side elevation, partially in section, of an alternative drive system for driving the flexible rotor in the disc and incrementing the needle for suturing.

Figure 176:
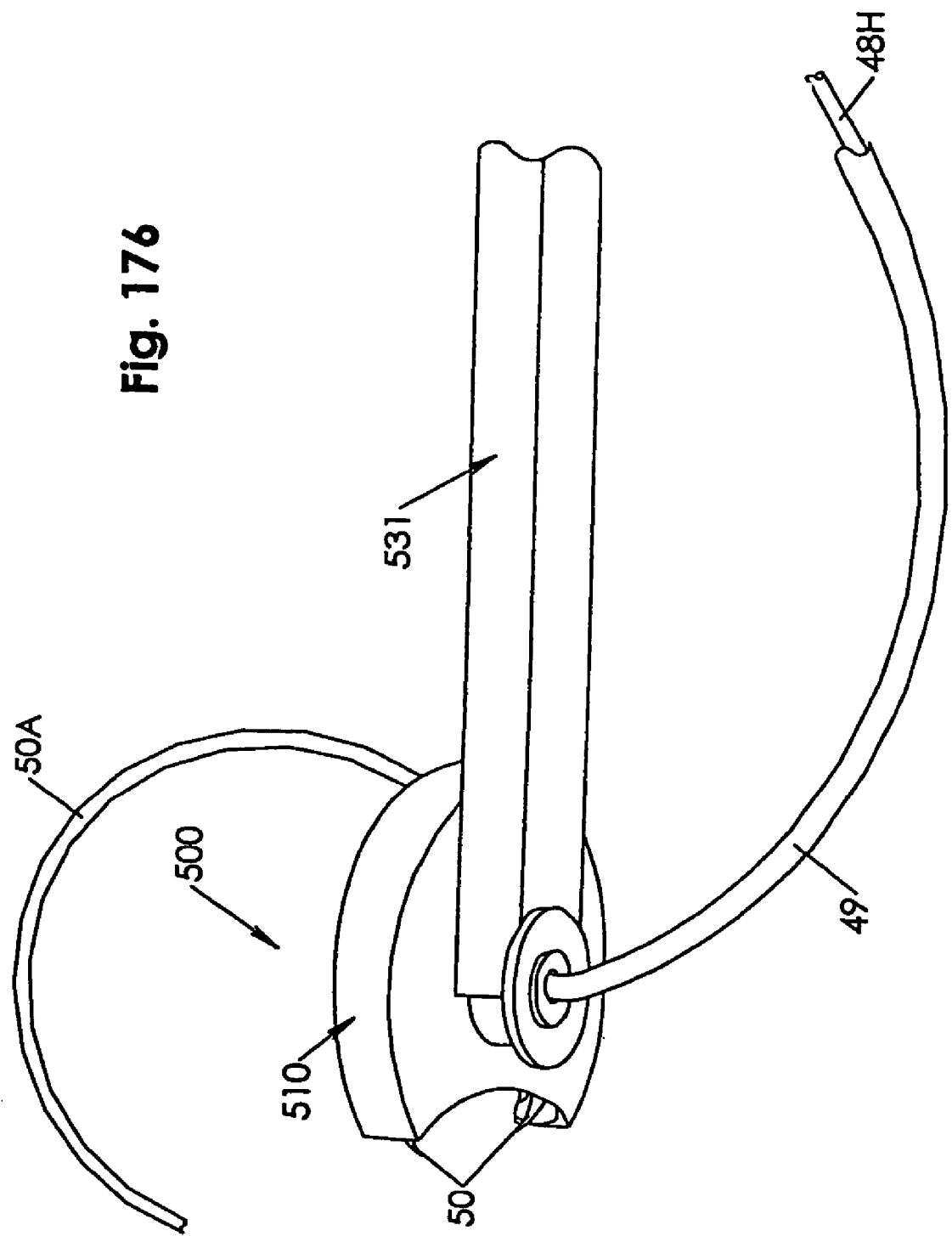

FIG. 176 is a bottom perspective view of another alternative direct drive system for rotating the flexible rotor inside the disc and operating the flexible rotor device.

Figure 177:
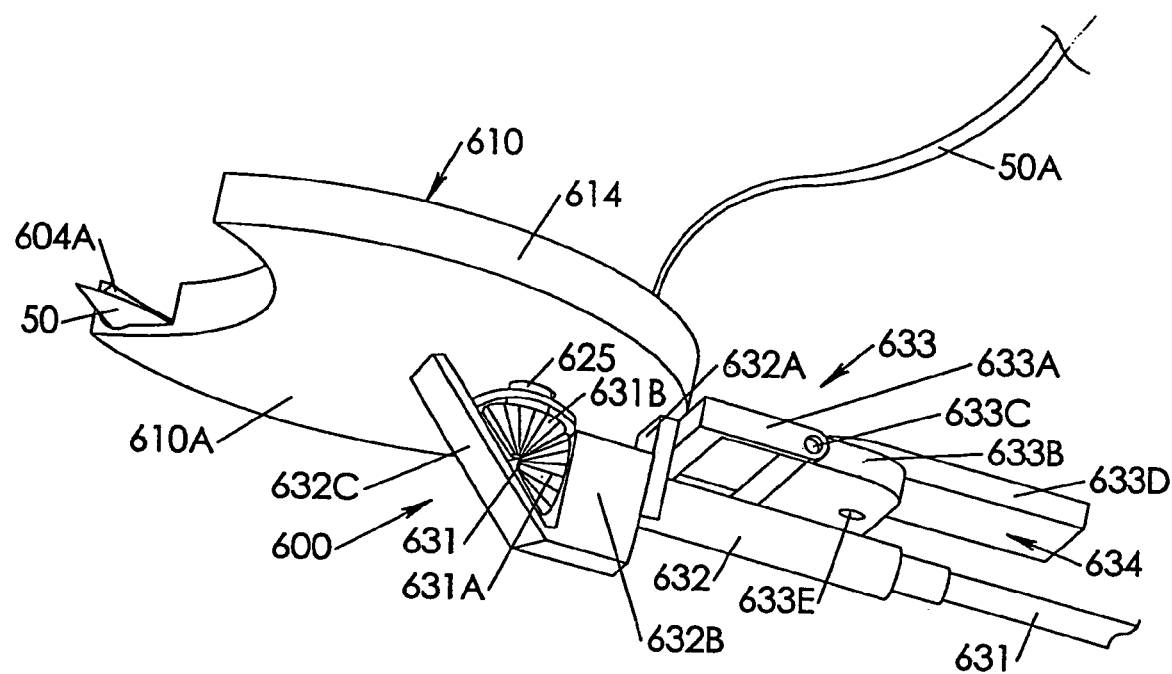

FIG. 177 is a perspective view of a pawl and crank device embodiment of the cycling suturing and knot-tying device, with the pawl and crank device illustrated in articulated attachment to a typical operator.

Figure 177A:
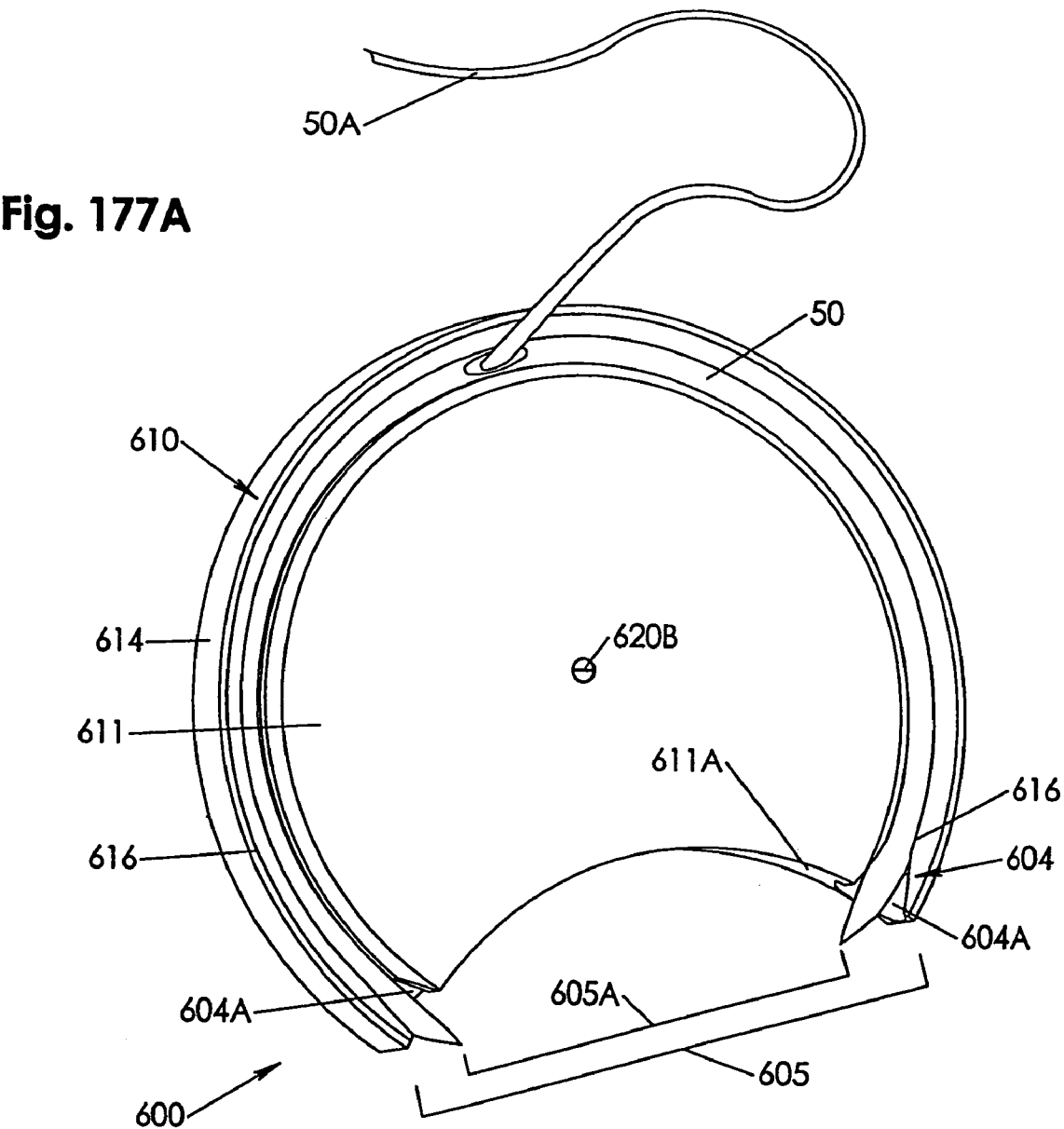

FIG. 177A is a perspective view of the pawl and crank device, more particularly illustrating a disc cover on the disc, with the needle in functional configuration for suturing.

Figure 177B:
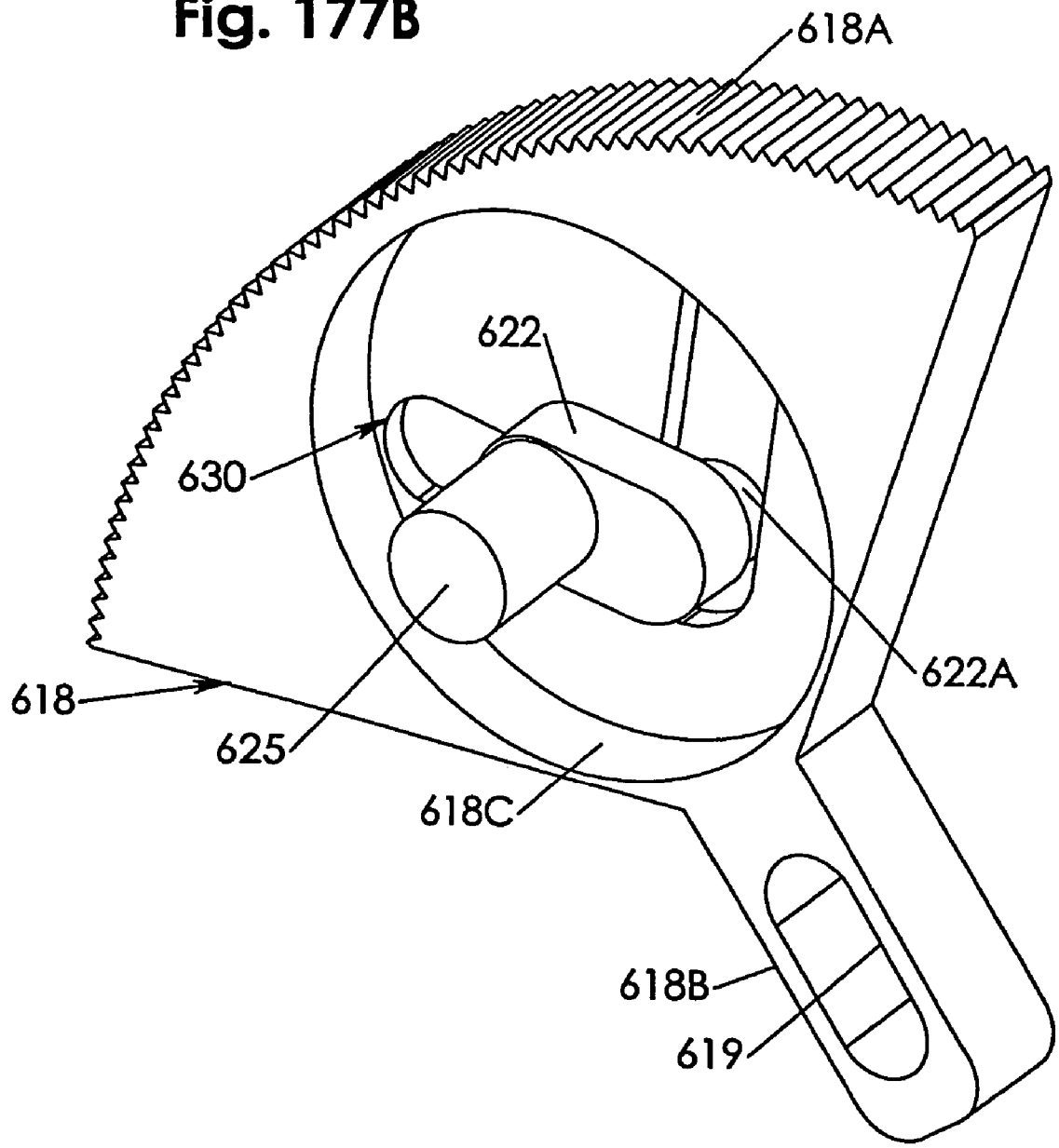

FIG. 177B is a perspective view of a typical pawl with a V-shaped cam slot and crank installed therein for engaging the needle by the pawl teeth and incrementing the needle in the disc illustrated in FIG. 177A.

Figure 177C:
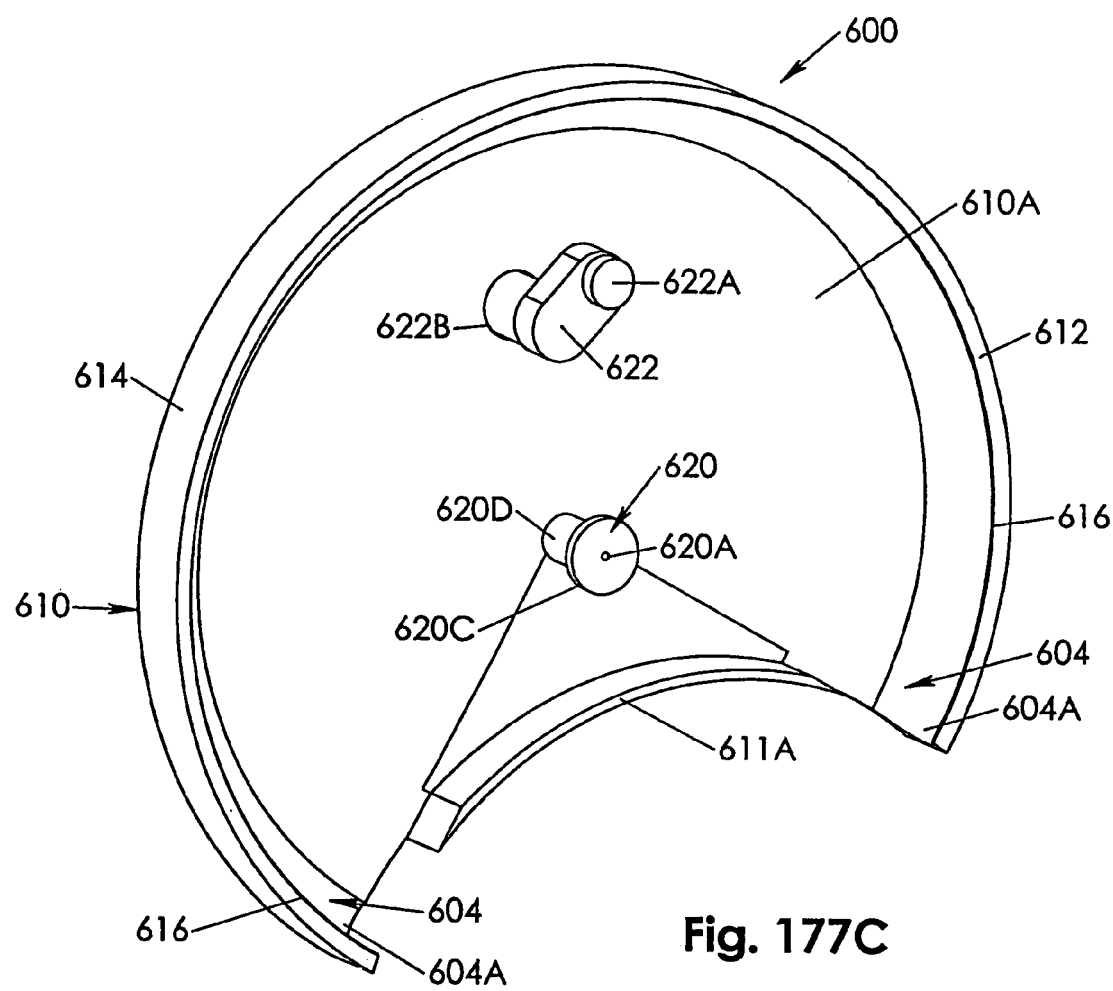

FIG. 177C is a perspective view of the disc element with the crank extending therein.

Figure 177D:
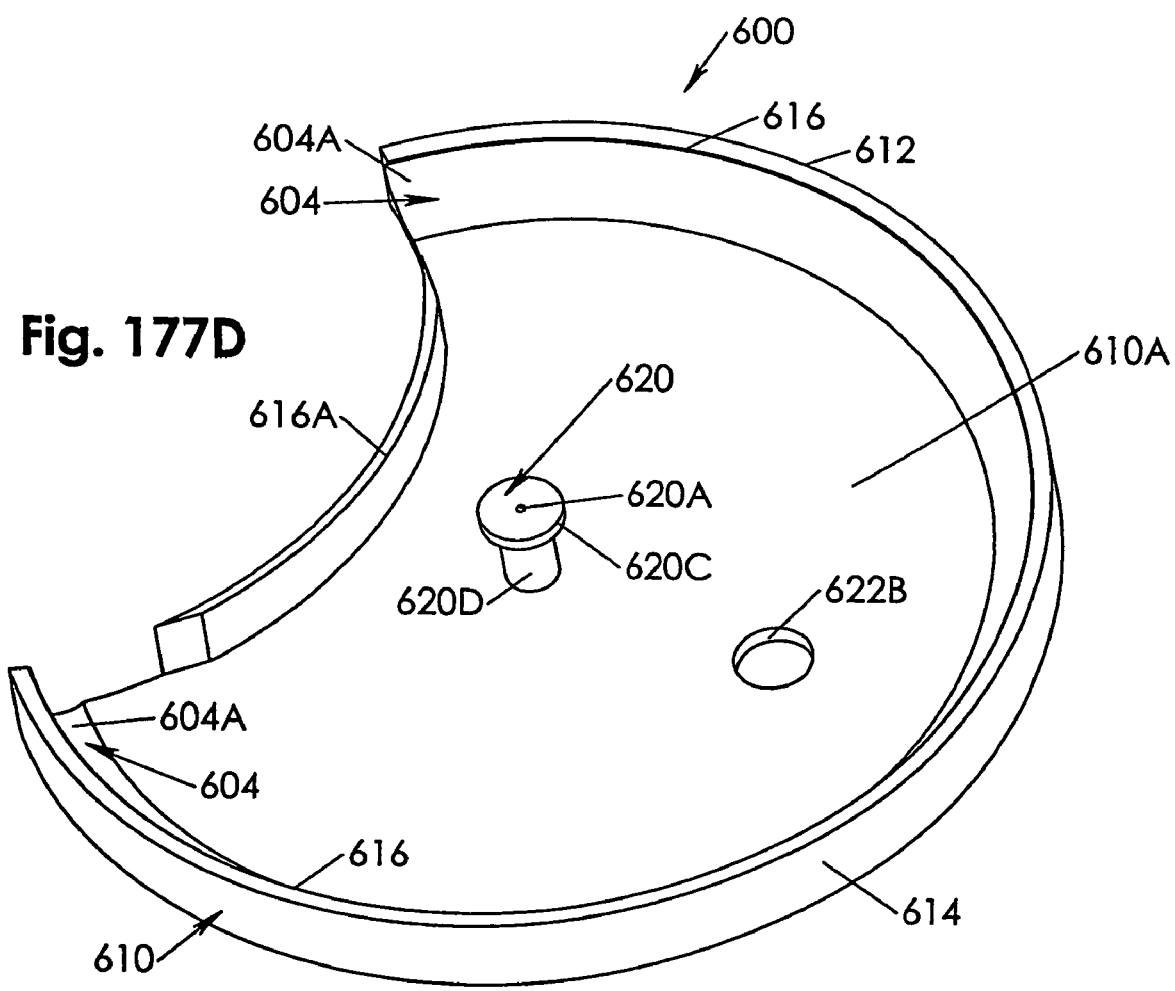

FIG. 177D is a perspective view of the disc illustrated in FIG. 177C, more particularly illustrating an opening for receiving the crank illustrated in FIG. 177C.

Figure 178:
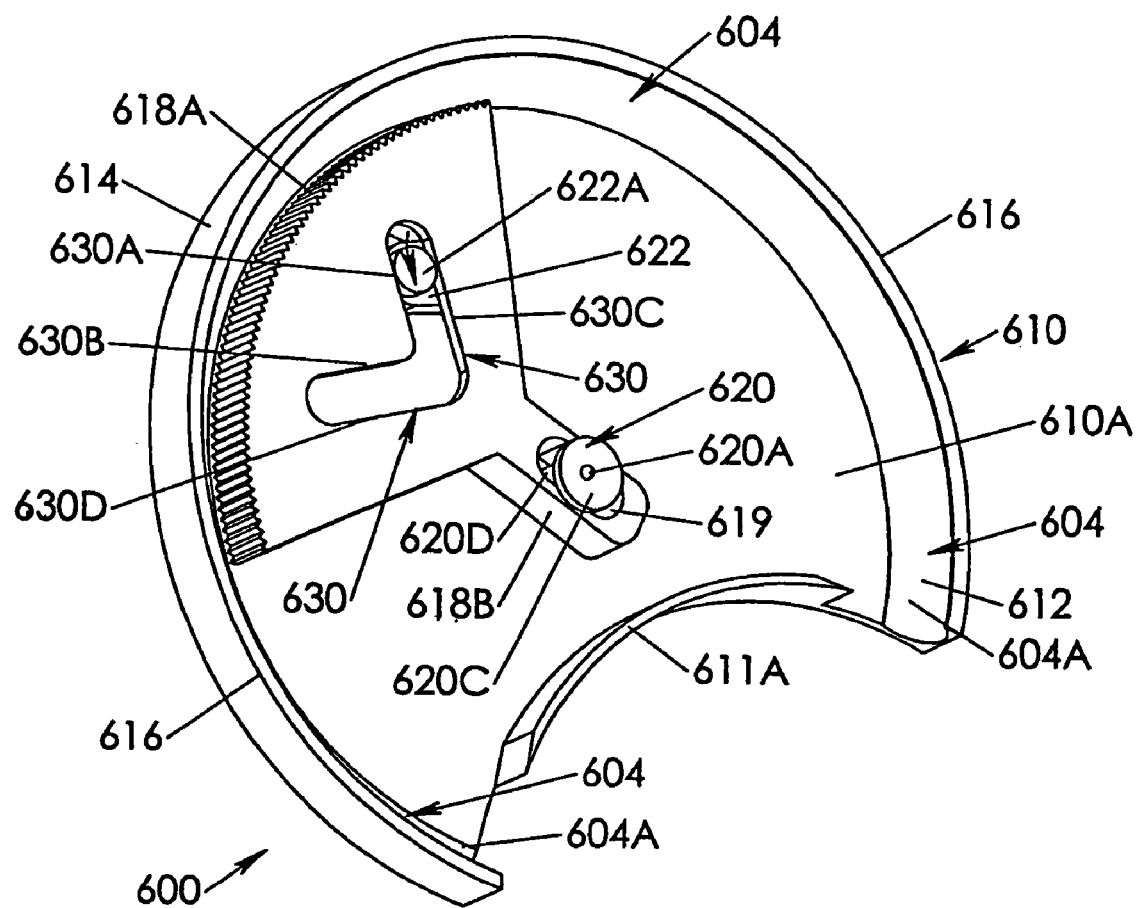

FIG. 178 is a perspective view of the assembled pawl and crank located in the disc, more particularly illustrating the grooved way in the disc for receiving a needle to facilitate incrementing the needle around the way by incrementation of the pawl by rotation of the crank.

Figure 179:
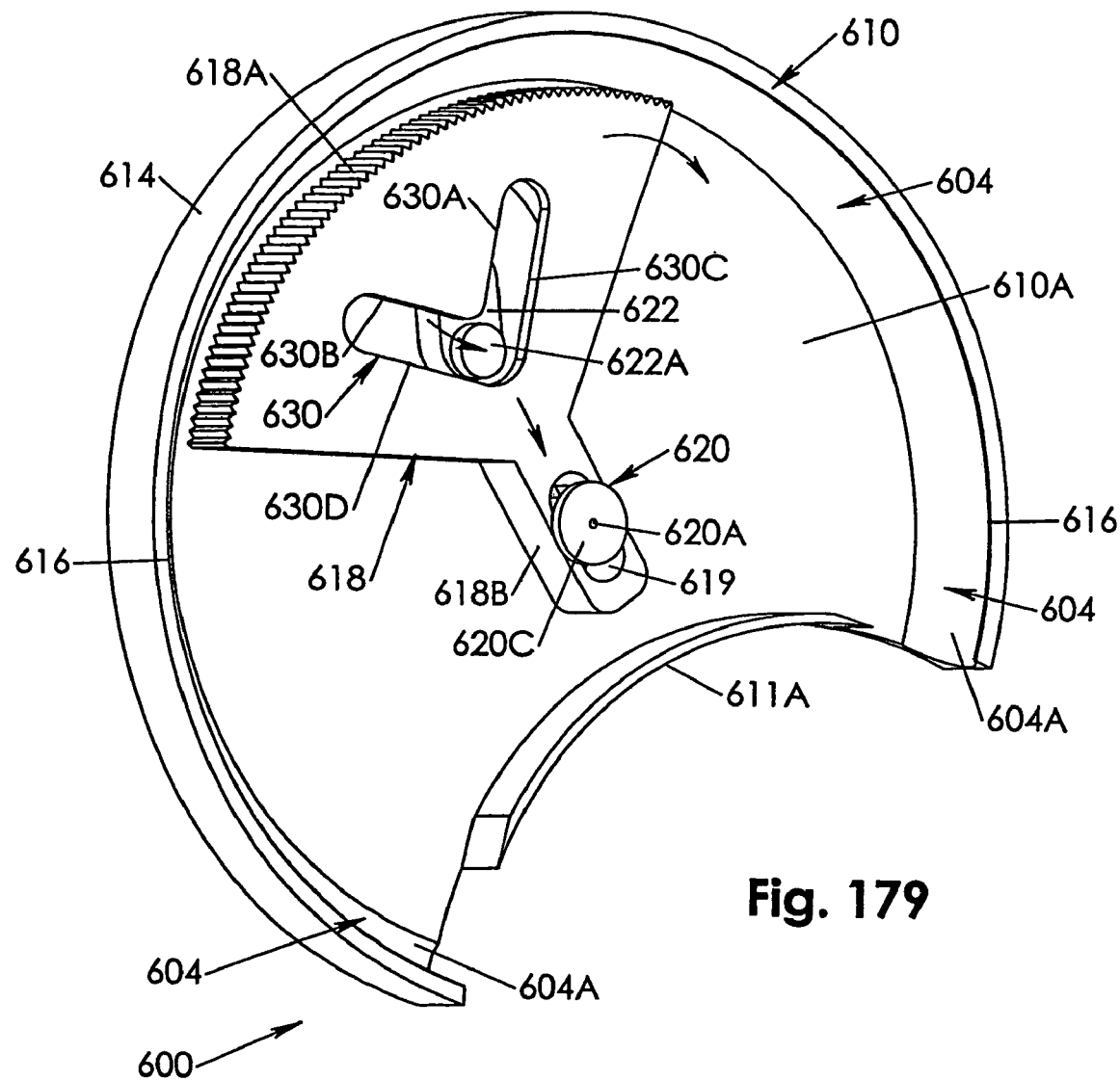

FIG. 179 is a perspective view of the pawl and crank device illustrated in FIG. 178 illustrating rotation of the crank to force the pawl in a clockwise direction disengaged from the needle.

Figure 180:
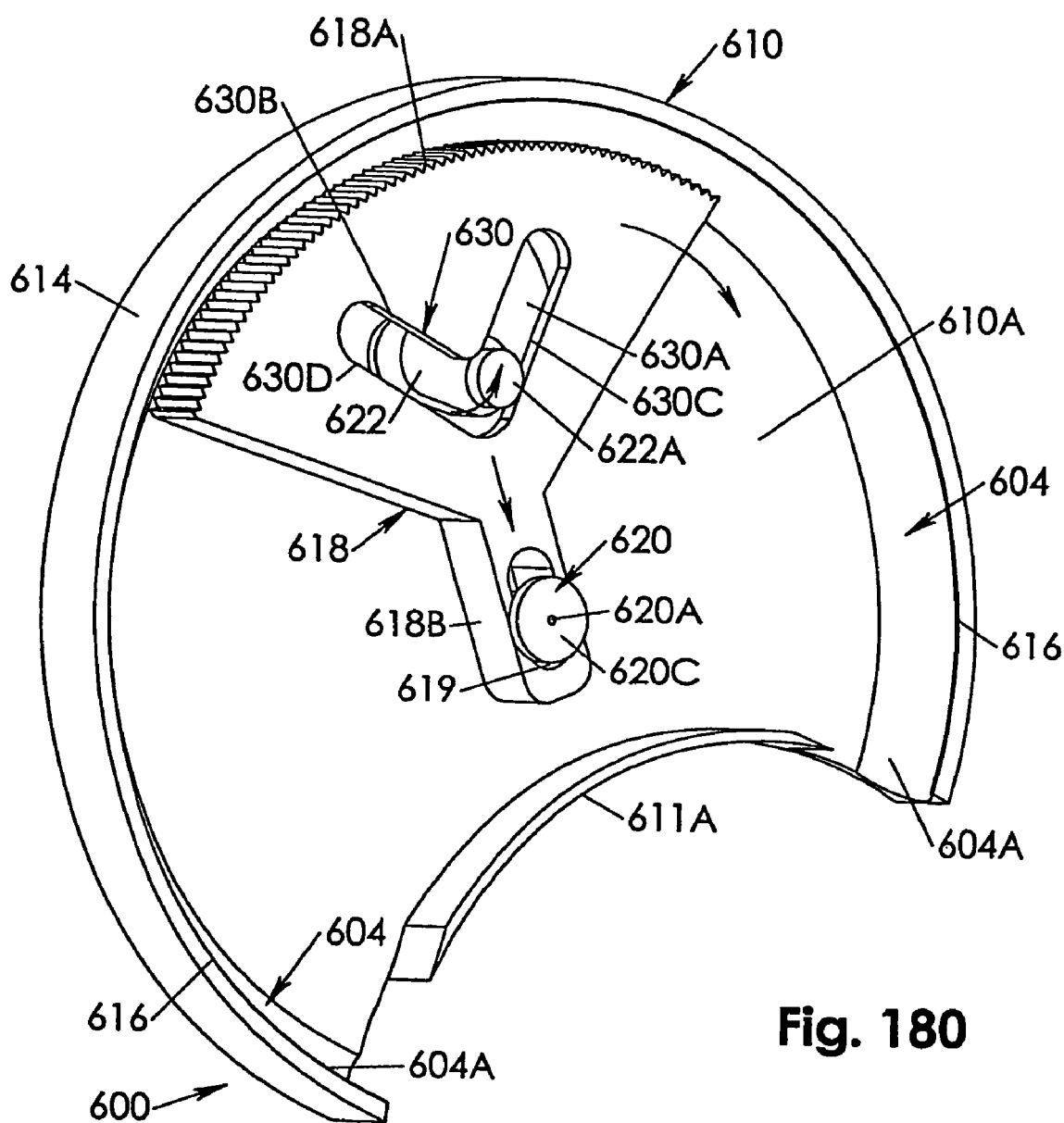

FIG. 180 is a perspective view of the pawl and crank device illustrated in FIGS. 178 and 179, more particularly illustrating further rotation of the crank to effect continued movement of the pawl in the clockwise configuration, disengaged from the needle.

Figure 181:
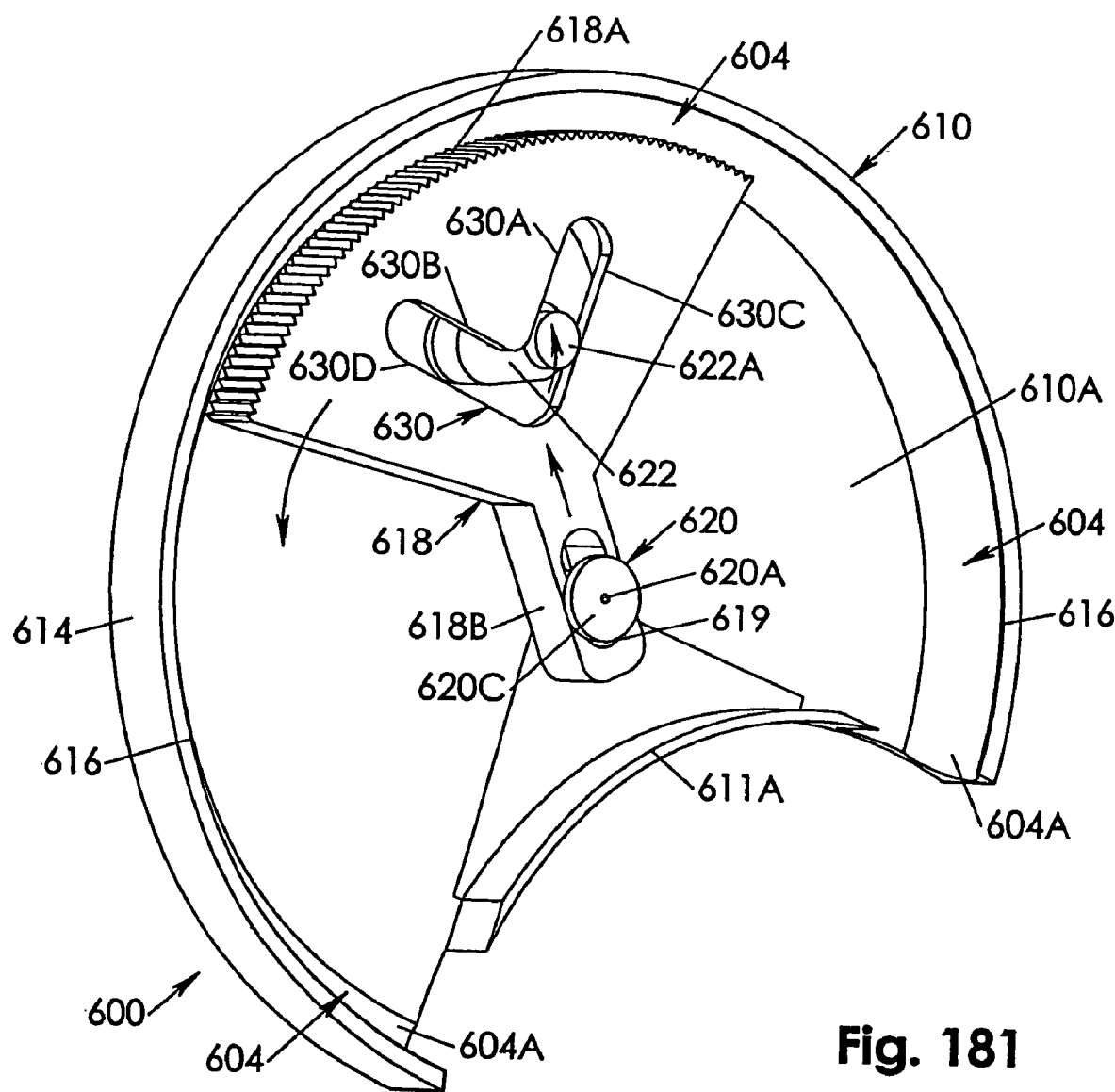

FIG. 181 is a perspective view of the pawl and crank device illustrated in FIGS. 178-180, more particularly illustrating further rotation of the crank for driving the pawl in the opposite or counterclockwise direction around the disc and upwardly against the needle.

Figure 182:
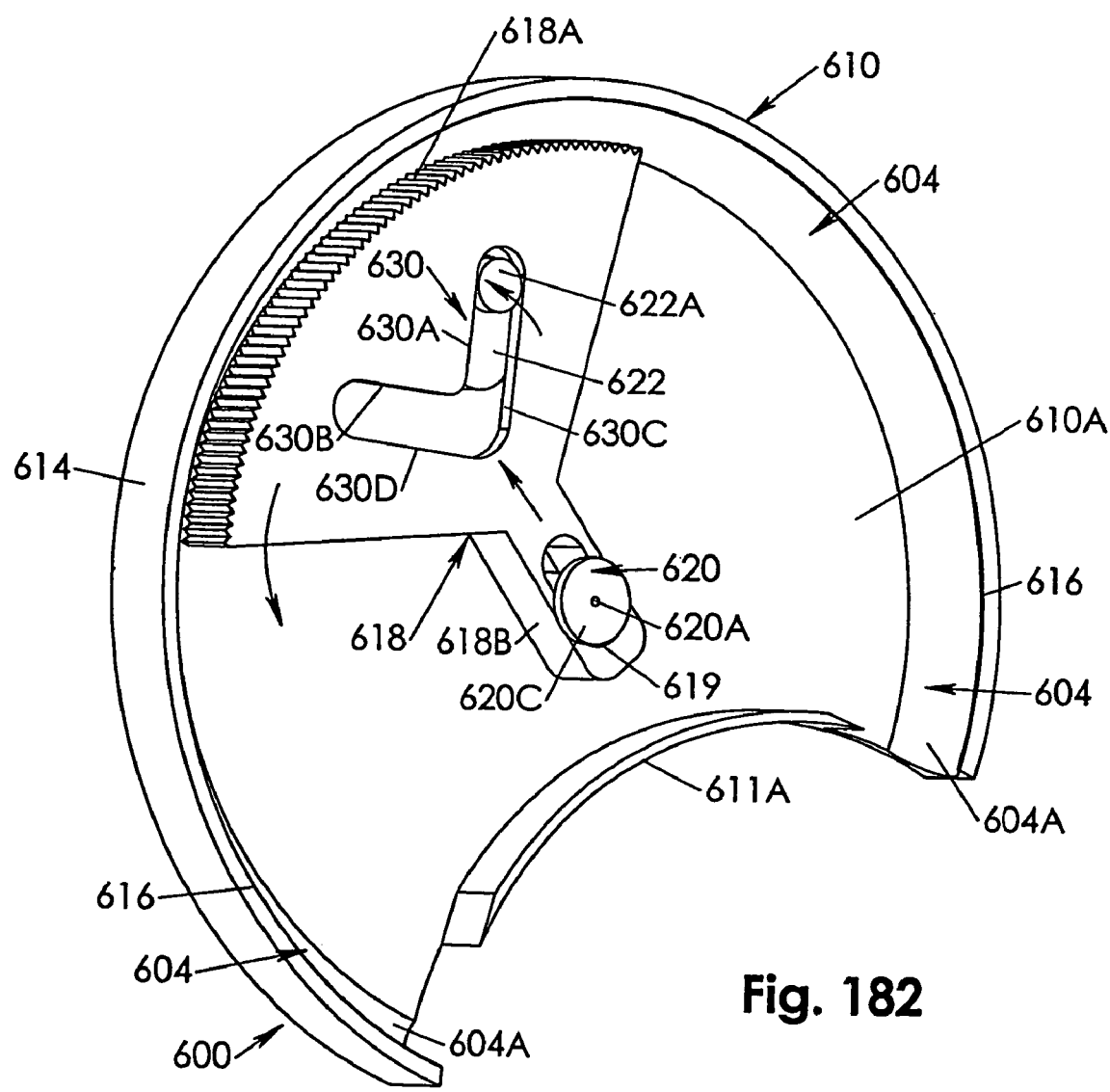

FIG. 182 is a perspective view of the pawl and crank device illustrated in FIGS. 178-181, more particularly illustrating further rotation of the crank for driving the pawl and the needle in the counterclockwise direction.

Figure 183:
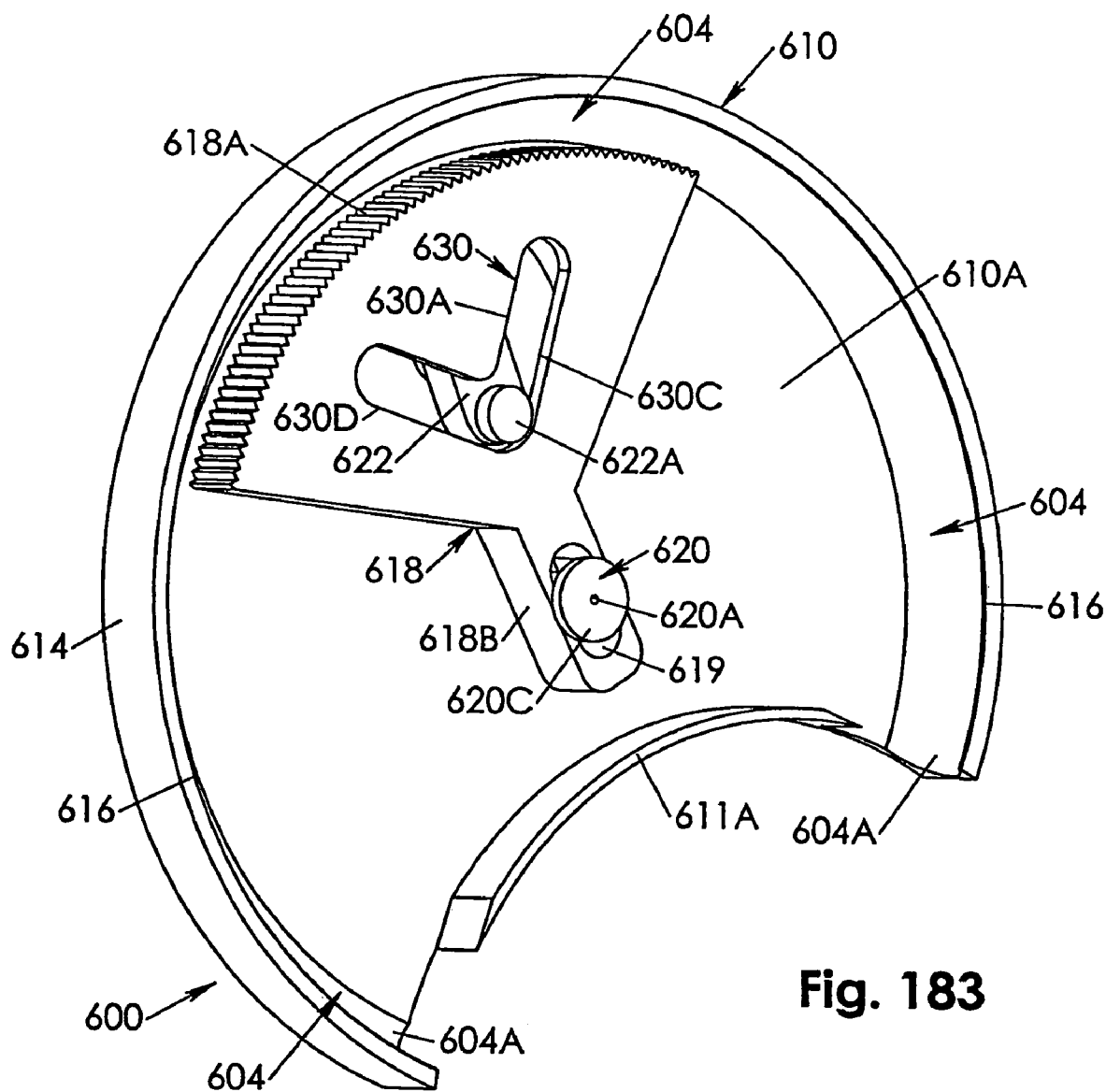

FIG. 183 is a perspective view of the pawl and crank device illustrated in FIGS. 178-182, more particularly illustrating a neutral position of the crank to facilitate terminating movement of the pawl and stopping movement of the needle in the disc.

Figure 184:
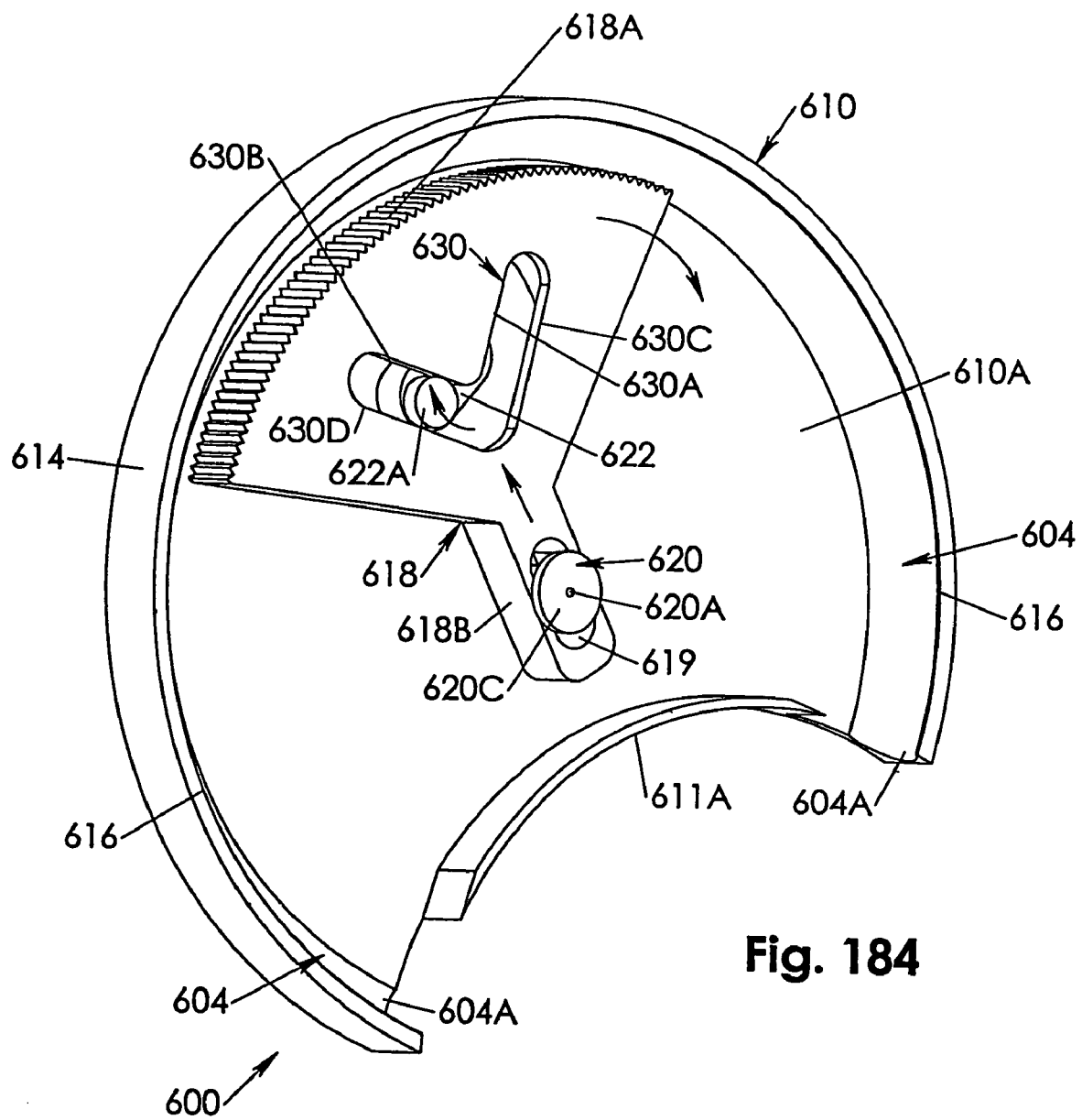

FIG. 184 is a perspective view of the pawl and crank device illustrated in FIG. 183, more particularly illustrating rotation of the crank in the opposite direction to drive the pawl in the clockwise direction and upwardly against the needle, for incrementing the needle in the clockwise direction.

Figure 185:
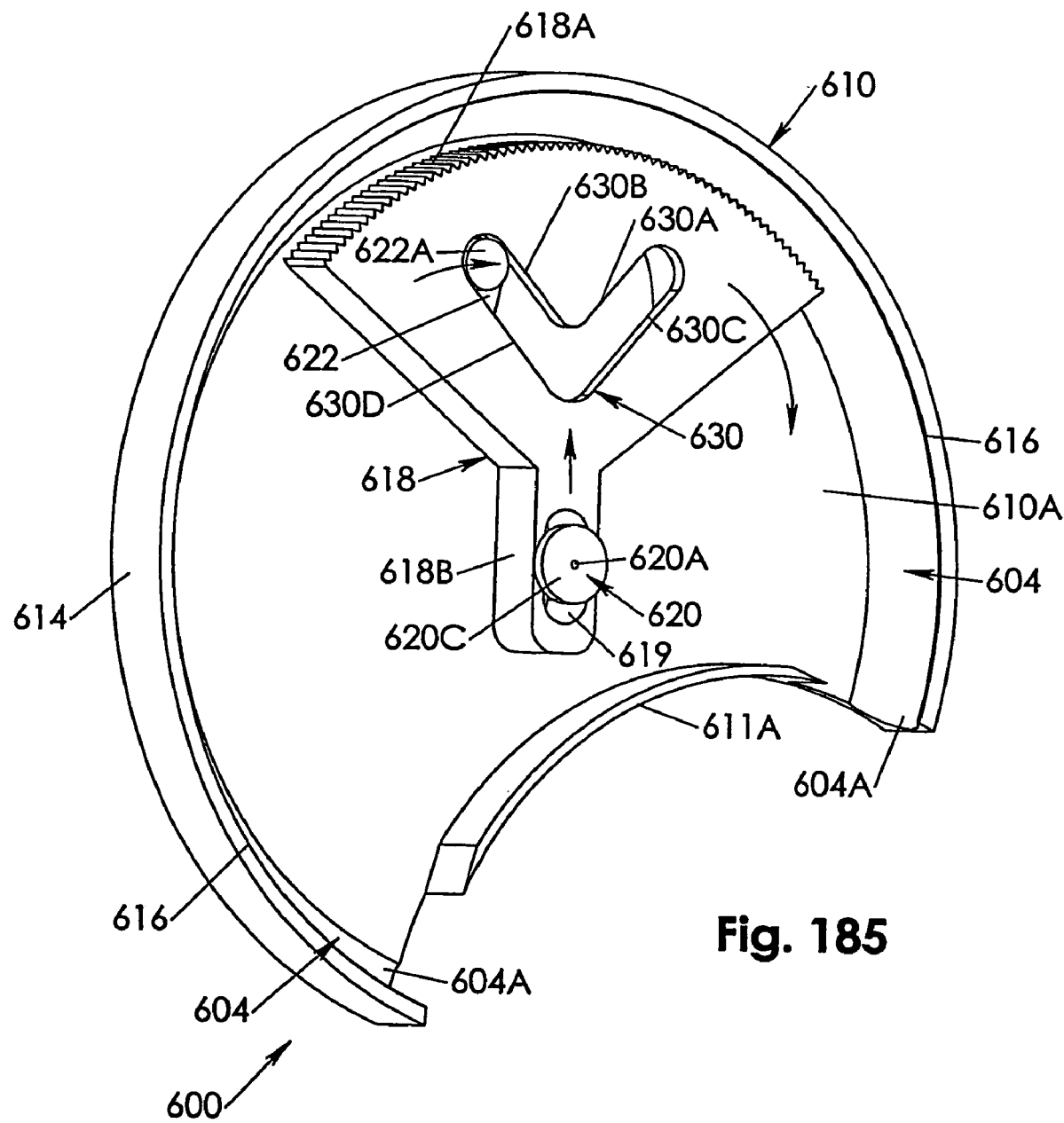

FIG. 185 is a perspective view of the pawl and crank device illustrated in FIGS. 183 and 184, more particularly illustrating additional clockwise rotation of the crank to drive the pawl and needle further in the clockwise direction around the disc.

Figure 186:
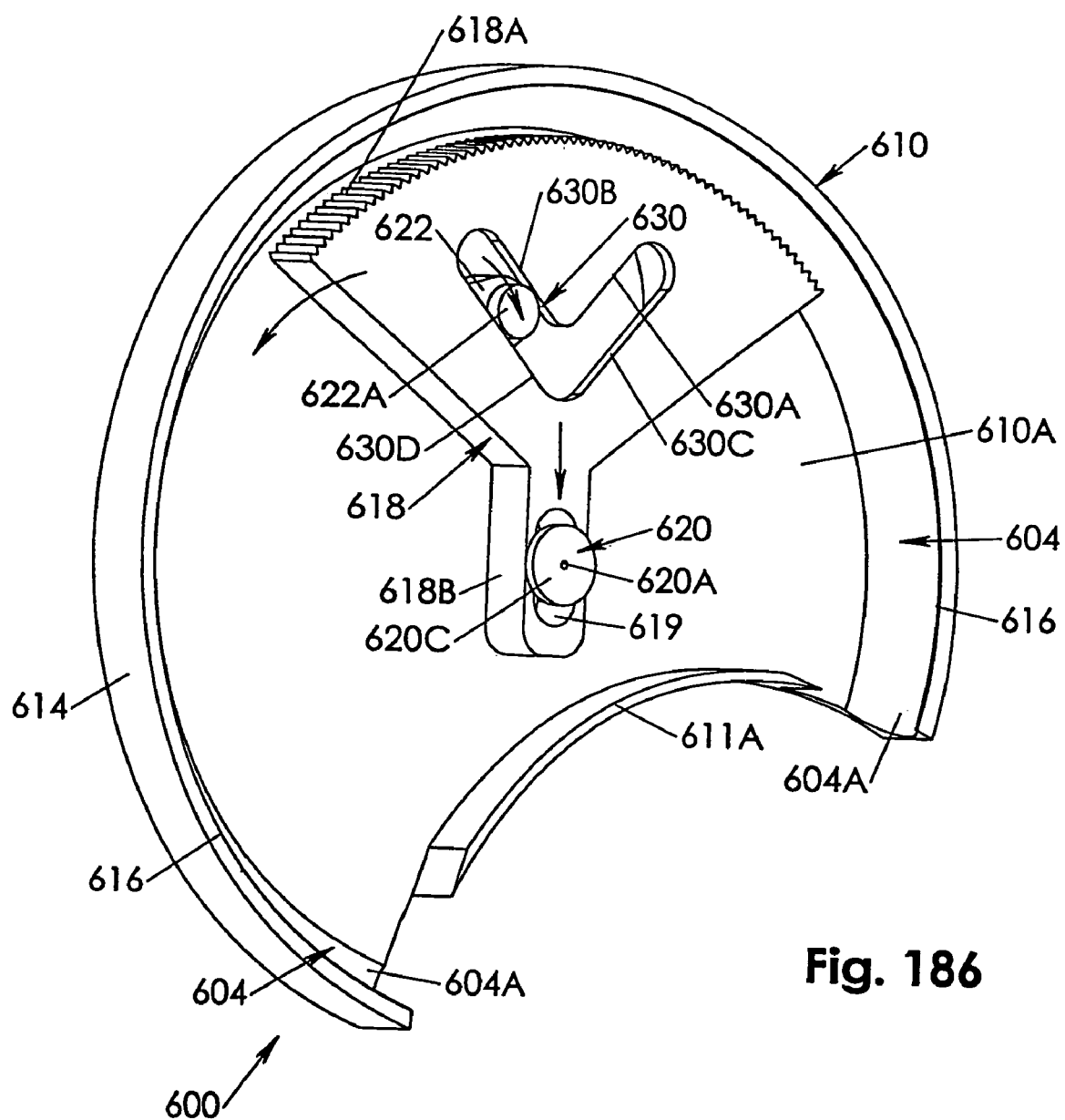

FIG. 186 is a perspective view of the pawl and crank device illustrated in FIGS. 183-185, more particularly illustrating additional clockwise crank rotation to rotate the pawl in the counterclockwise direction away from the needle.

Figure 187:
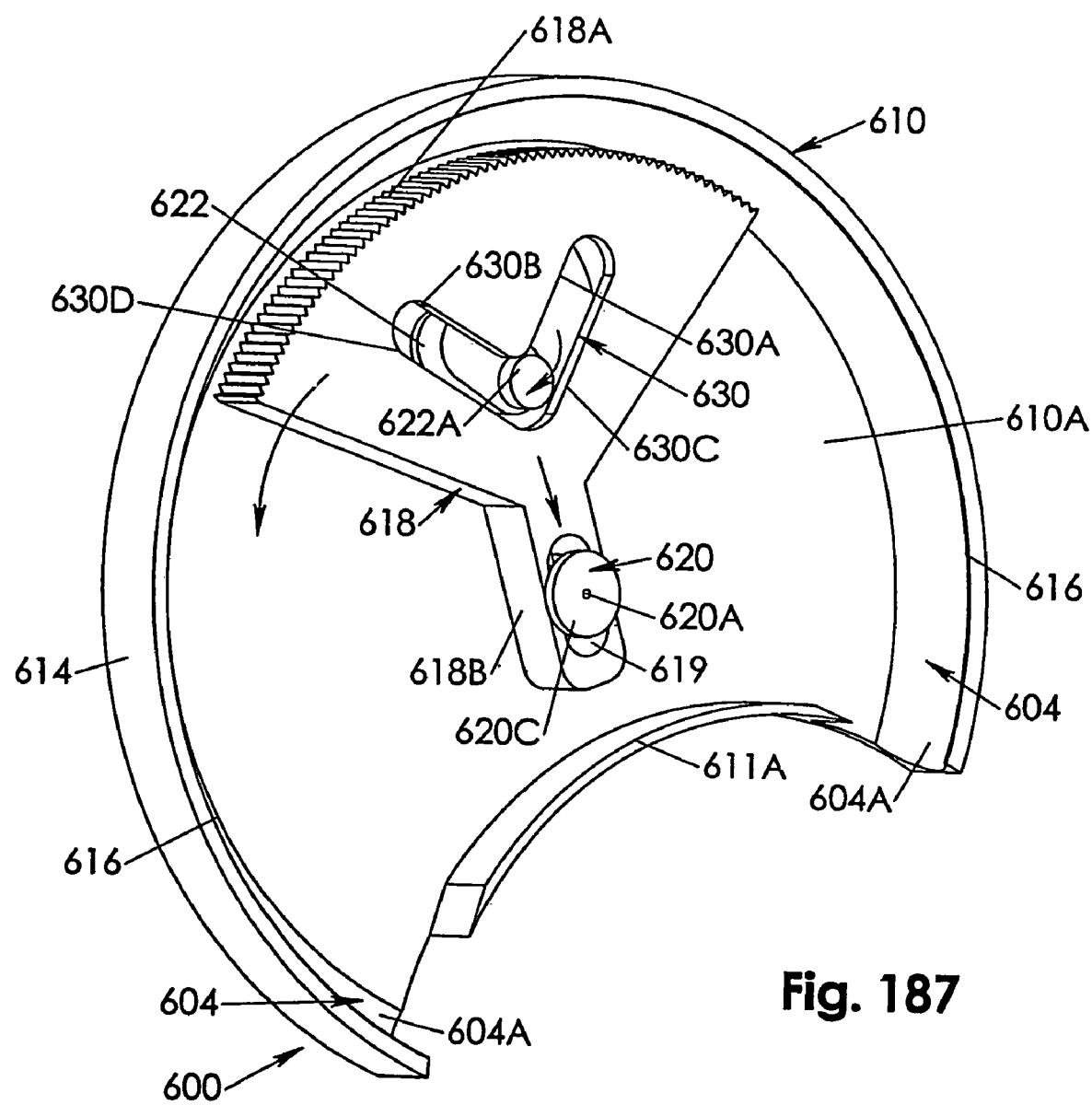

FIG. 187 is a perspective view of the pawl and crank device illustrated in FIGS. 183-186, more particularly illustrating further clockwise crank rotation to drive the pawl further in the counterclockwise direction and away from the needle.

Figure 188:
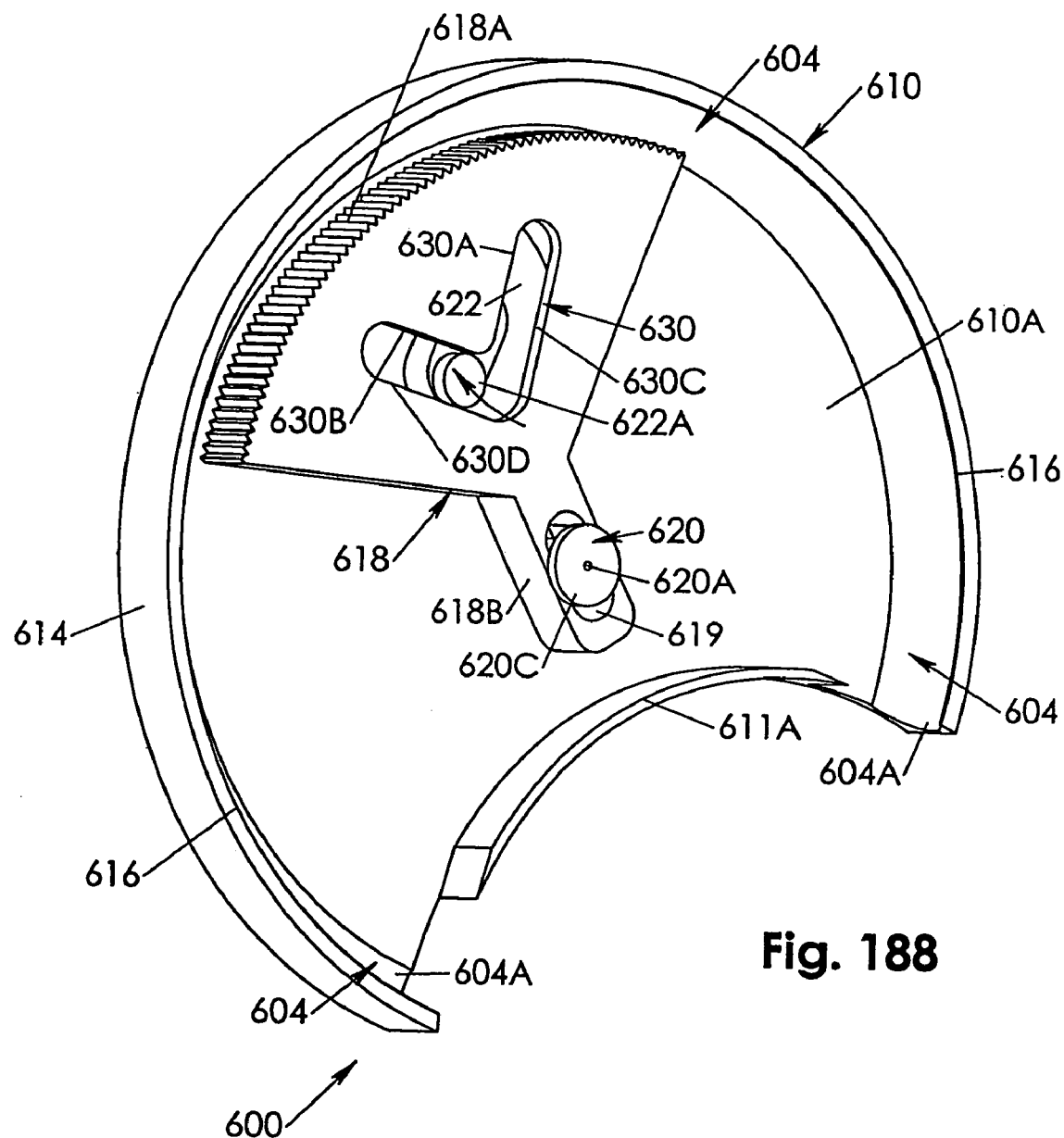

FIG. 188 is a perspective view of the pawl and crank device illustrated in FIGS. 183-187, more particularly illustrating additional clockwise rotation of the crank to effect operation of the pawl and needle in a new clockwise rotational sequence.

Figure 189:
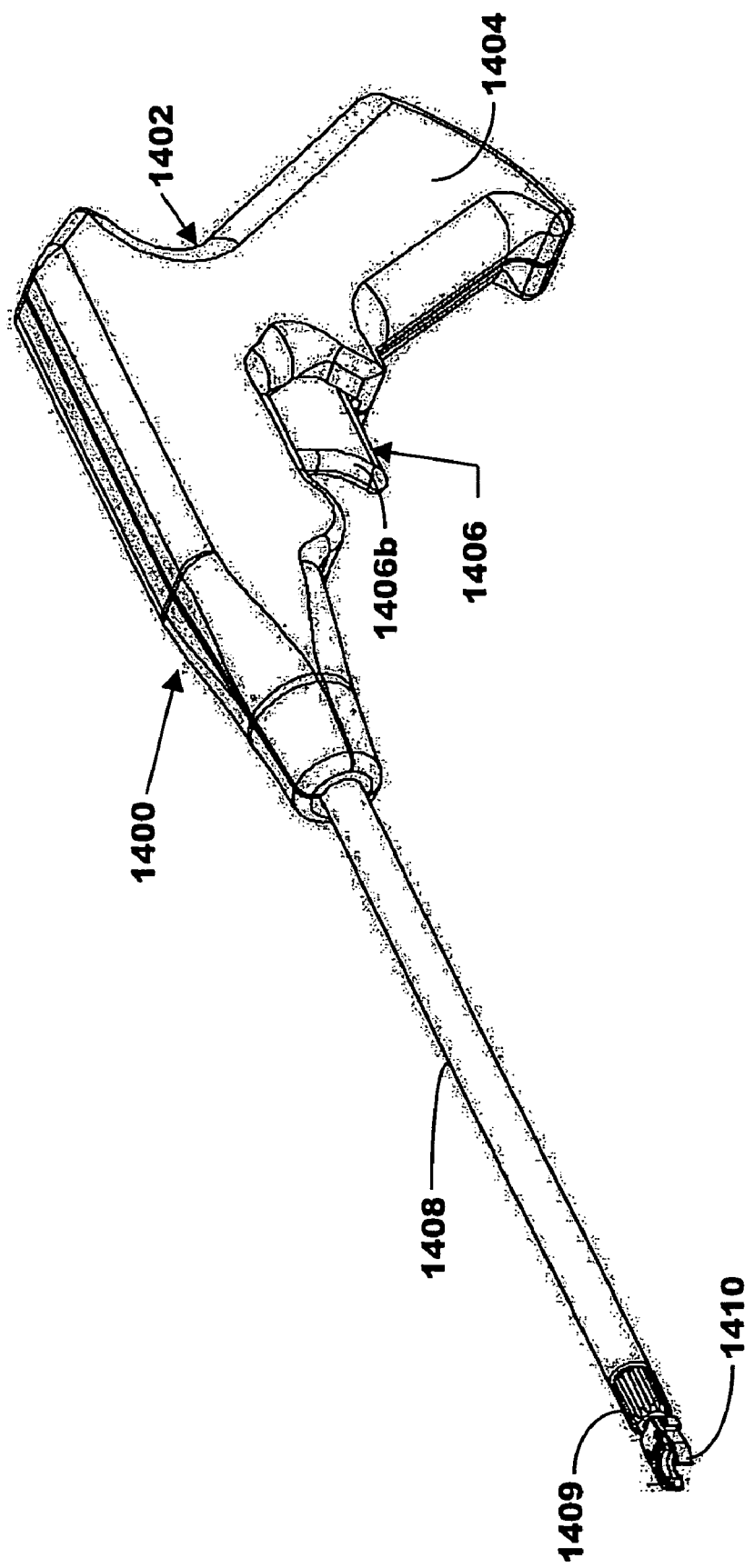

FIG. 189 is a generally perspective view of an alternate form of the suturing device of the present invention.

FIG. 190 is a generally perspective view of the suturing device shown in FIG. 189 as viewed from one side of the device and broken away to show internal construction.

FIG. 190A is a greatly enlarged, generally perspective, fragmentary view of the area designated in FIG. 190 as 190A.

FIG. 190B is a generally perspective view, similar to FIG. 190, but showing the trigger in an actuated position.

FIG. 190C is a greatly enlarged, generally perspective, fragmentary view of the area designated in FIG. 190B as 190C.

FIG. 191 is a generally perspective view of the suturing device shown in FIG. 189 as viewed from the opposite one side of the device and broken away to show internal construction.

FIG. 191A is a greatly enlarged, generally perspective, fragmentary view of the area designated in FIG. 191 as 191A.

Figures 192, 192A:
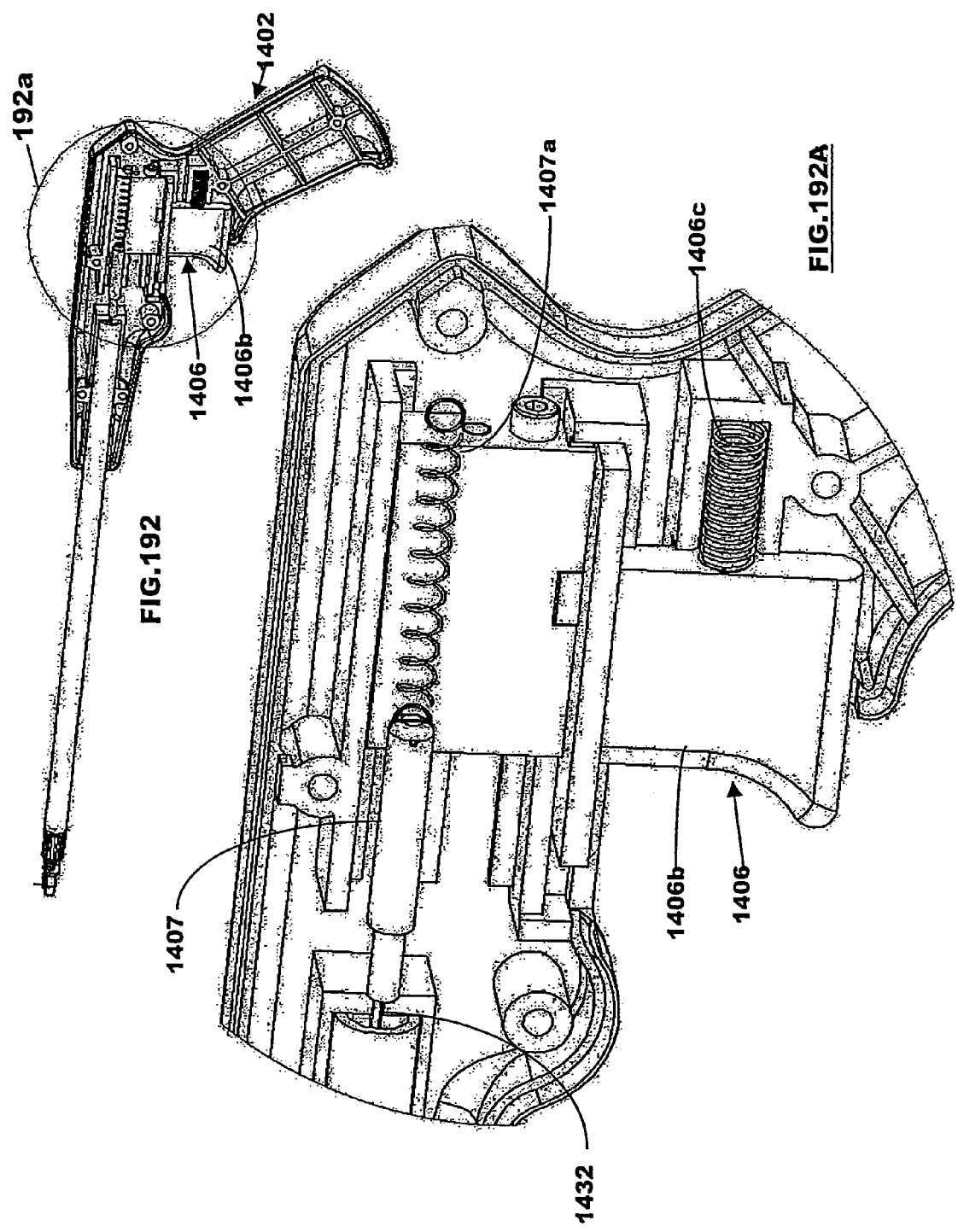

FIG. 192 is a view similar to FIG. 191, but showing the trigger in an actuated position.

FIG. 192A is a greatly enlarged, generally perspective, fragmentary view of the area designated in FIG. 192 as 191C.

Figure 193:
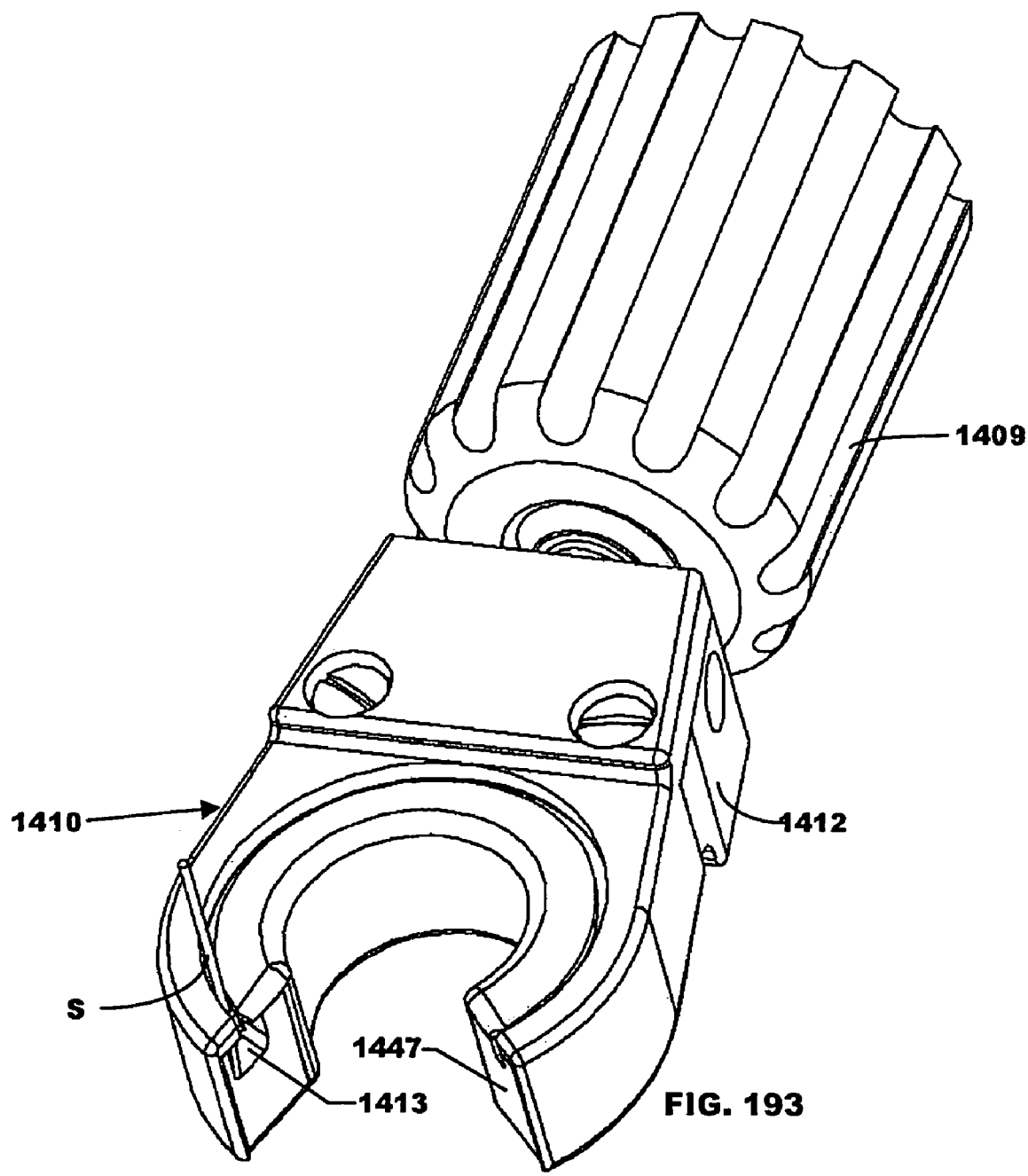

FIG. 193 is a greatly enlarged, generally perspective, fragmentary view of the articuatable head portion of the device and of the coupling subassembly for coupling the head portion to the barrel portion of the device.

Figure 194:
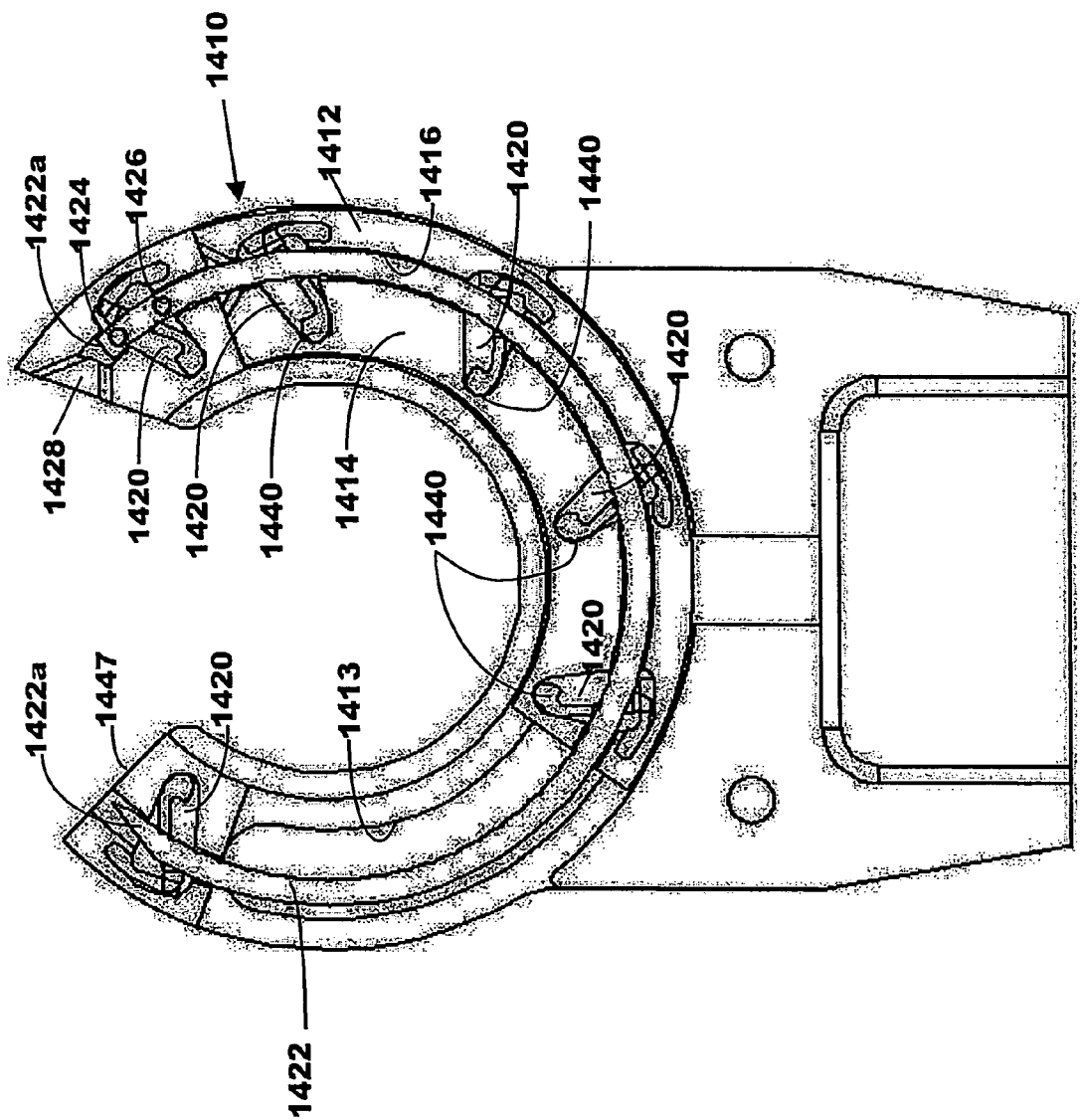

FIG. 194 is a top plan view of the articulatable head portion of the device as it appears after the cover portions have been removed to reveal the internal construction thereof.

Figure 195:
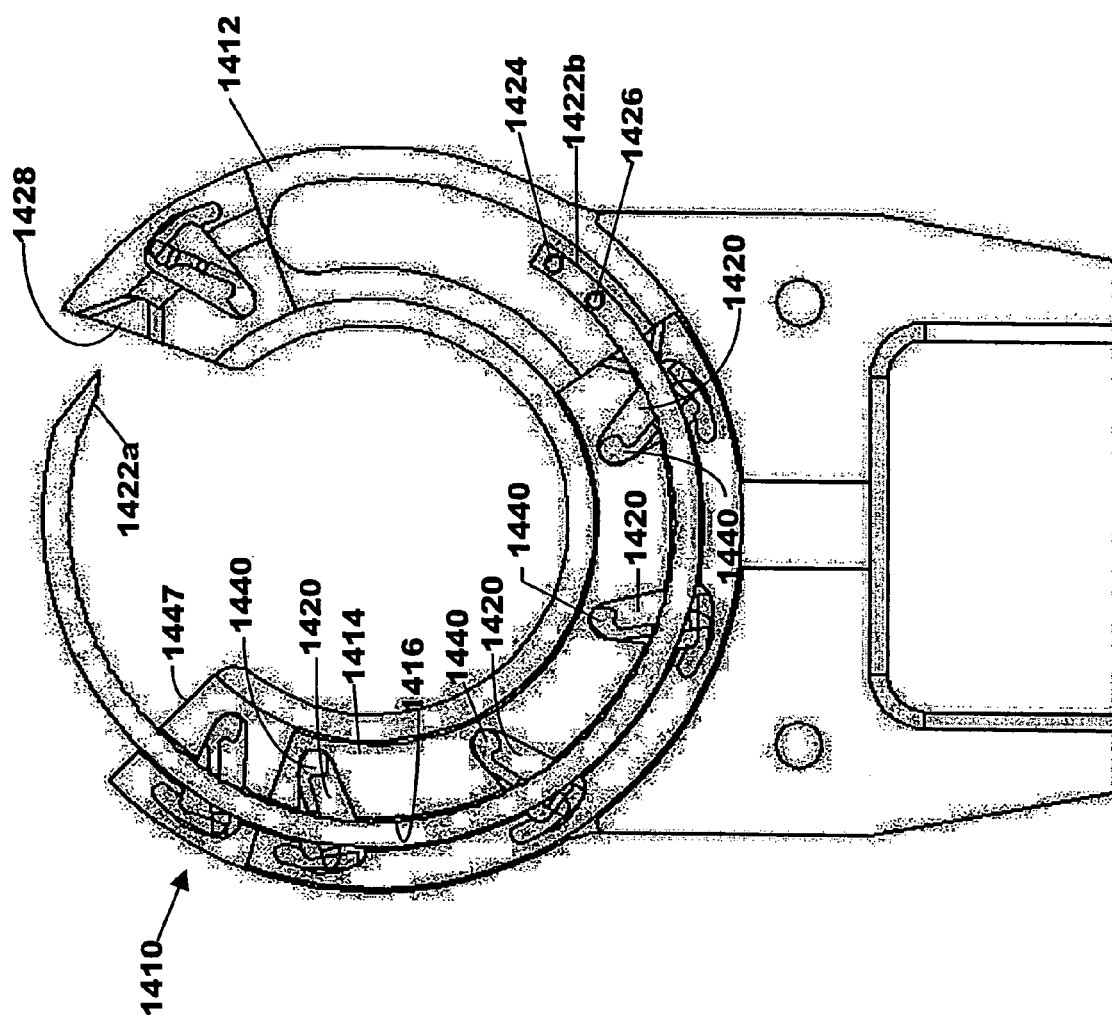

FIG. 195 is a top plan view similar to FIG. 194, but showing the location of the suturing needle of the device after it has been moved from the position illustrated in FIG. 194 to a first advanced position.

Figure 196:
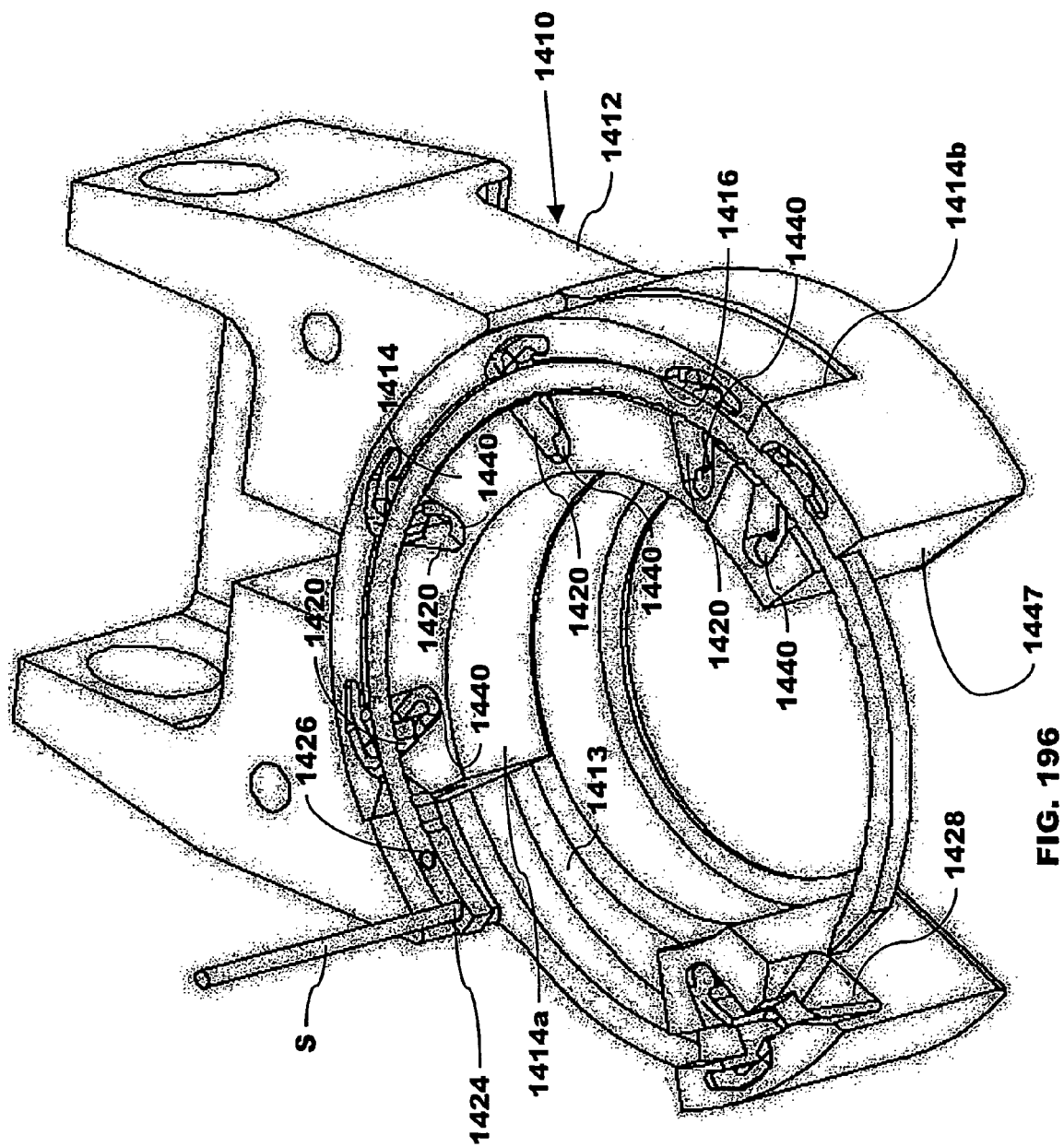

FIG. 196 is a generally perspective, top view similar to FIG. 195 further showing the location of the suturing needle of the device after it has been advanced in a clockwise direction.

Figure 197:
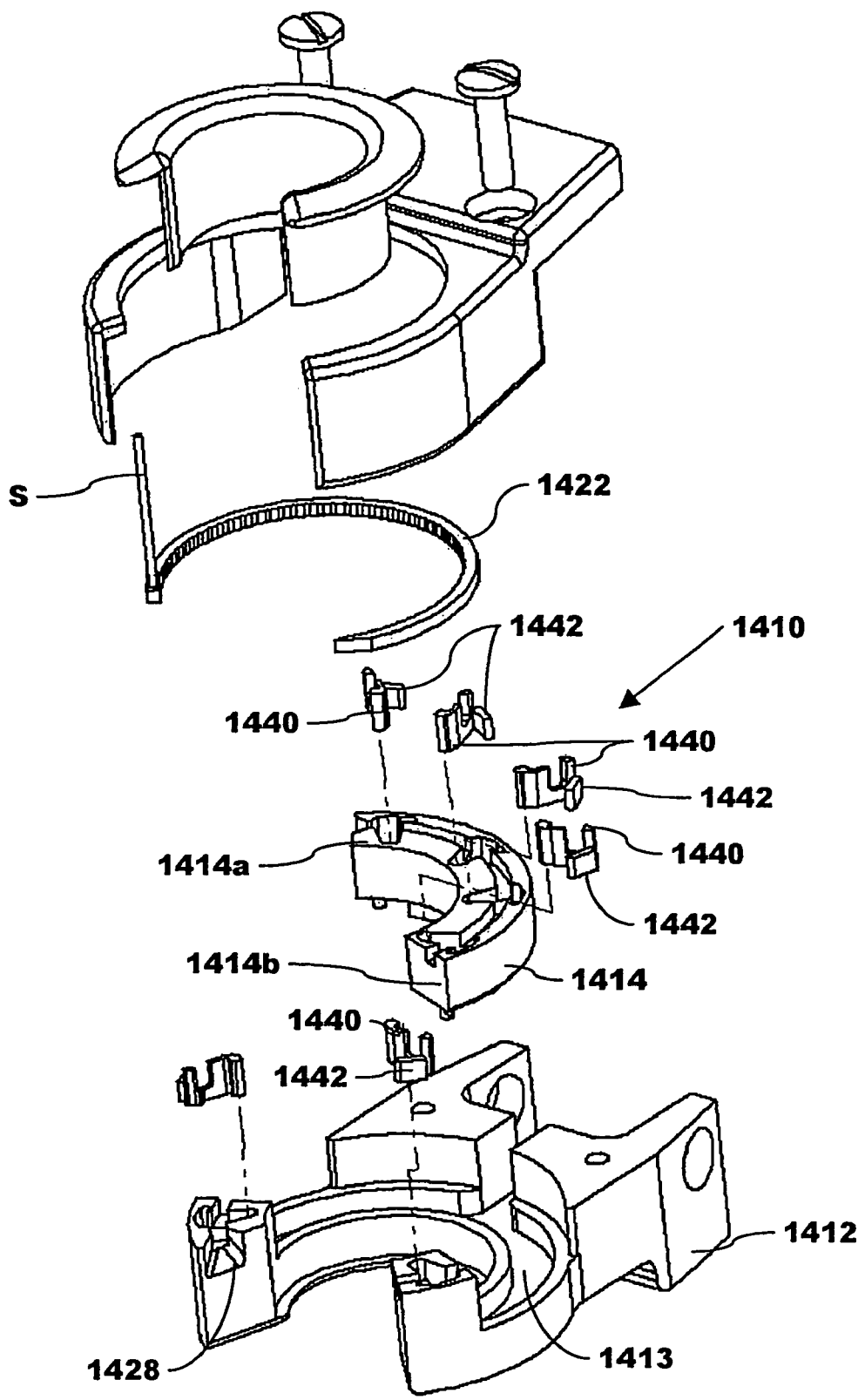

FIG. 197 is a generally perspective, exploded view showing more clearly the various operating components of the head portion of the suturing device.

Figure 198:
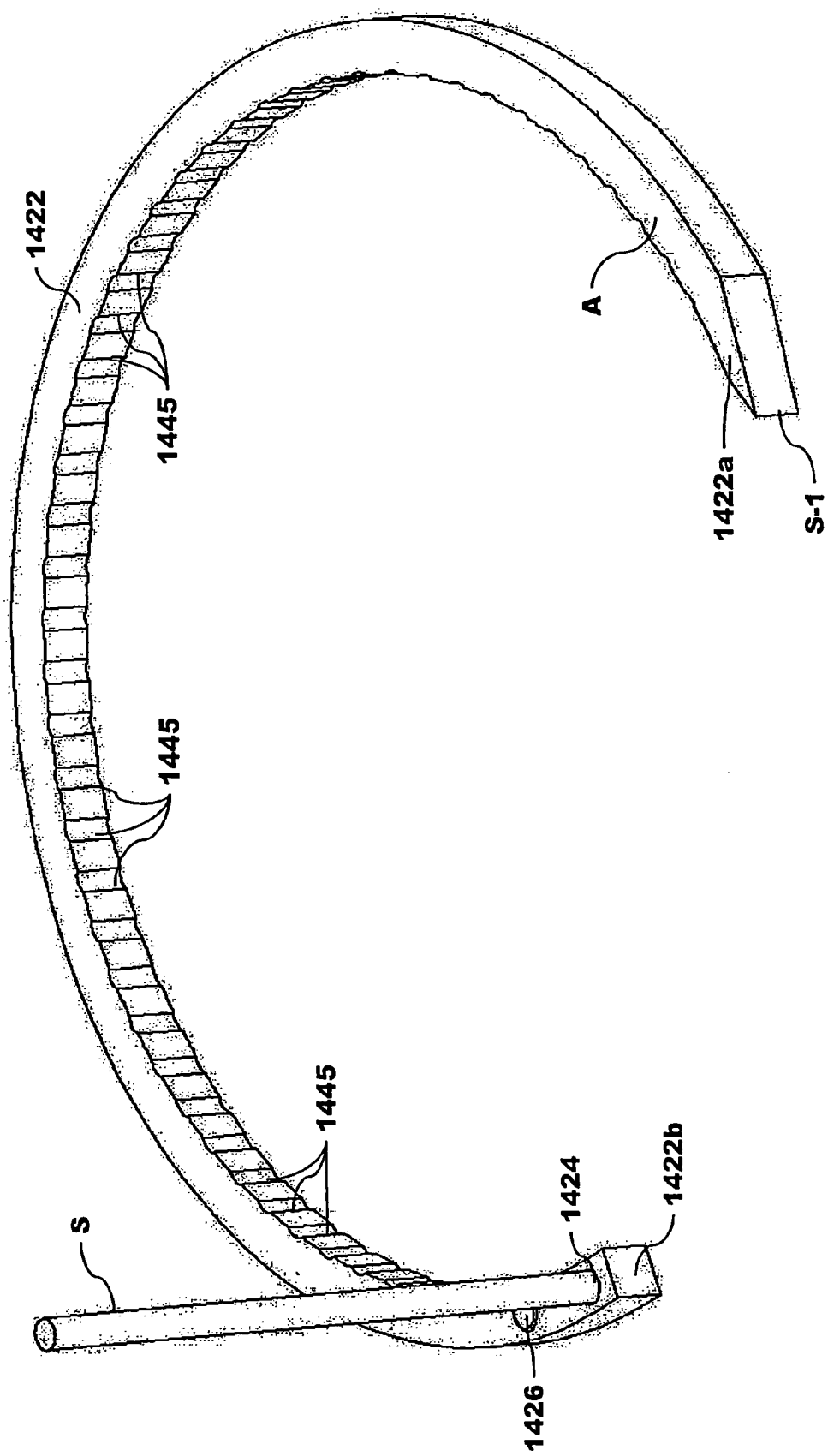

FIG. 198 is a greatly enlarged, generally perspective view of one form of the suturing needle of this latest form of the suturing device.

Figure 199:
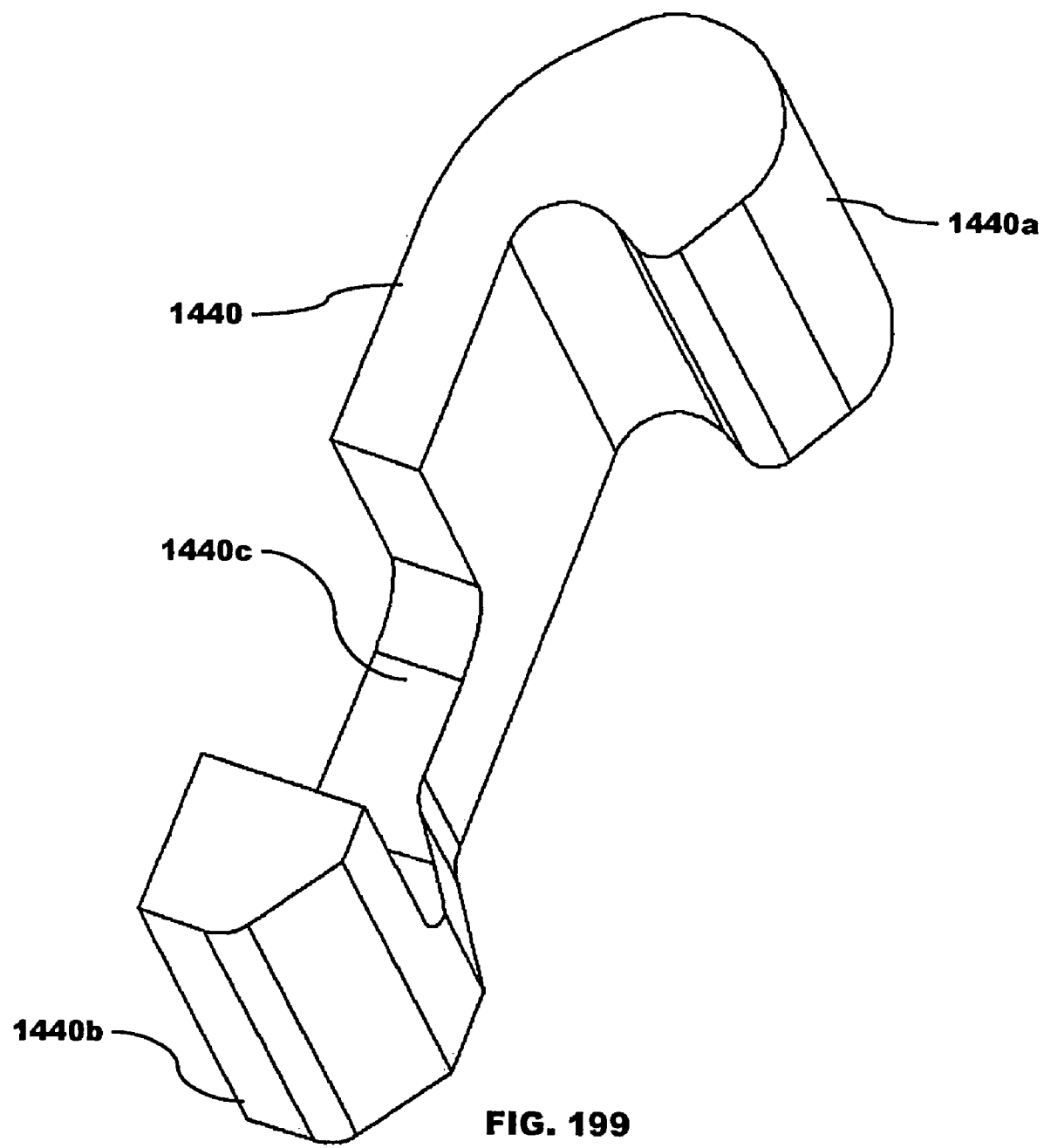

FIG. 199 is a greatly enlarged, generally perspective view of one of the needle engaging members of the invention that, during operation of the device, function to control movement of the suturing needle within a suturing needle guide way formed in the body of the head portion of the device.

Figure 200:
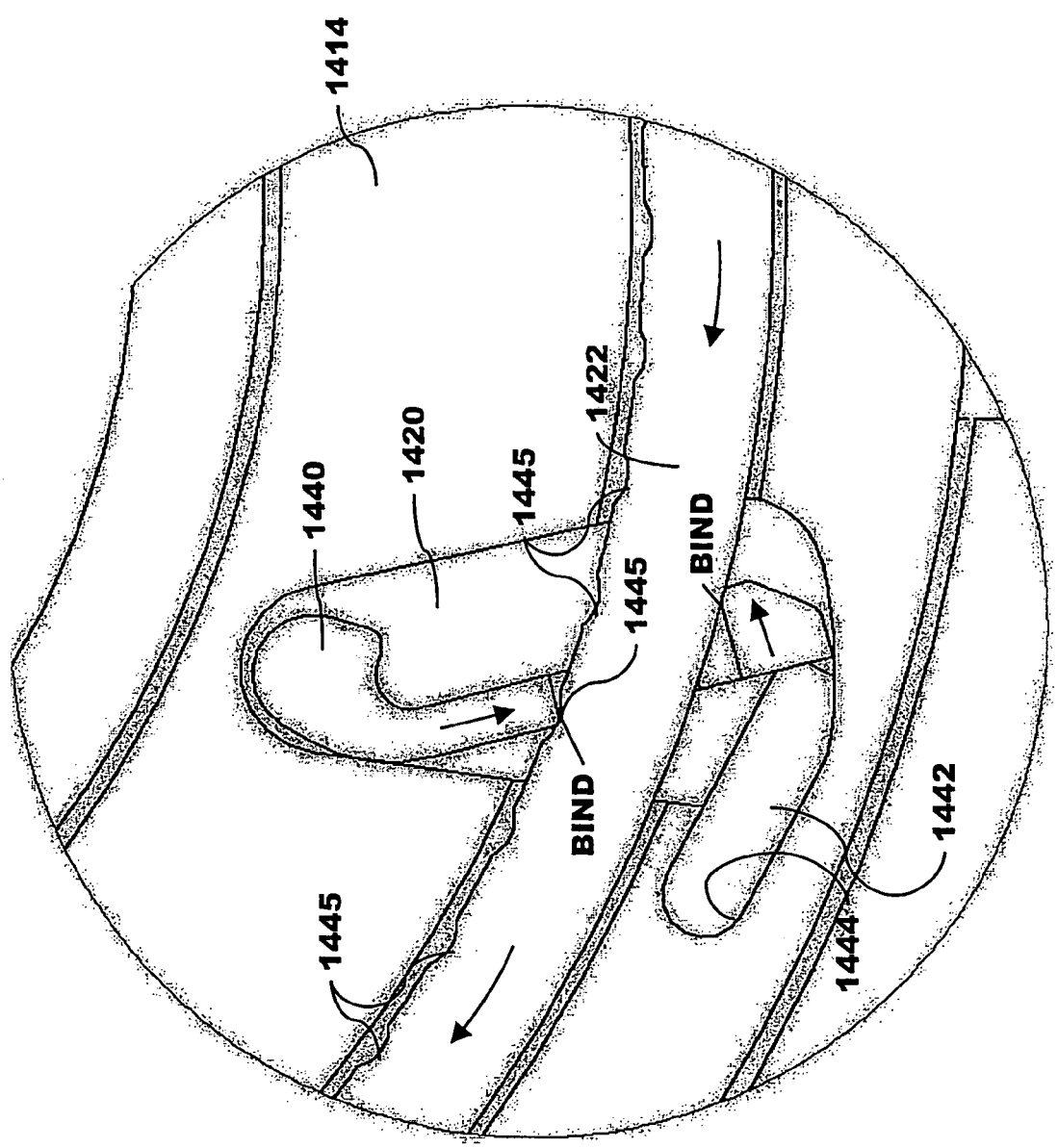

FIG. 200 is a greatly enlarged diagrammatic view of the needle engaging members of the invention illustrating their interaction with the needle during advancement of the shuttle member.

Figure 201:
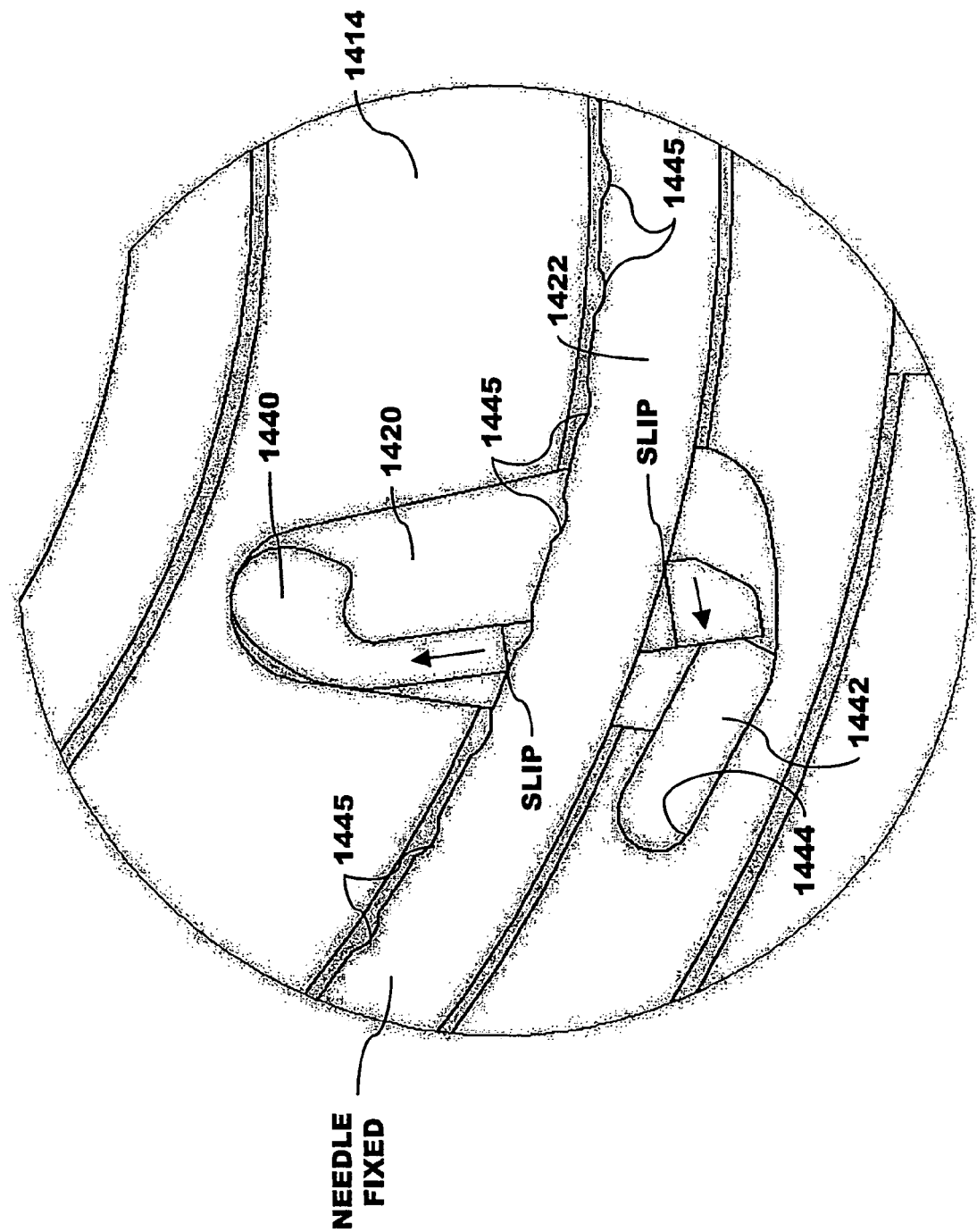

FIG. 201 is a greatly enlarged diagrammatic view of the needle engaging members of the invention illustrating their interaction with the needle during retraction of the shuttle member.

Figure 202:
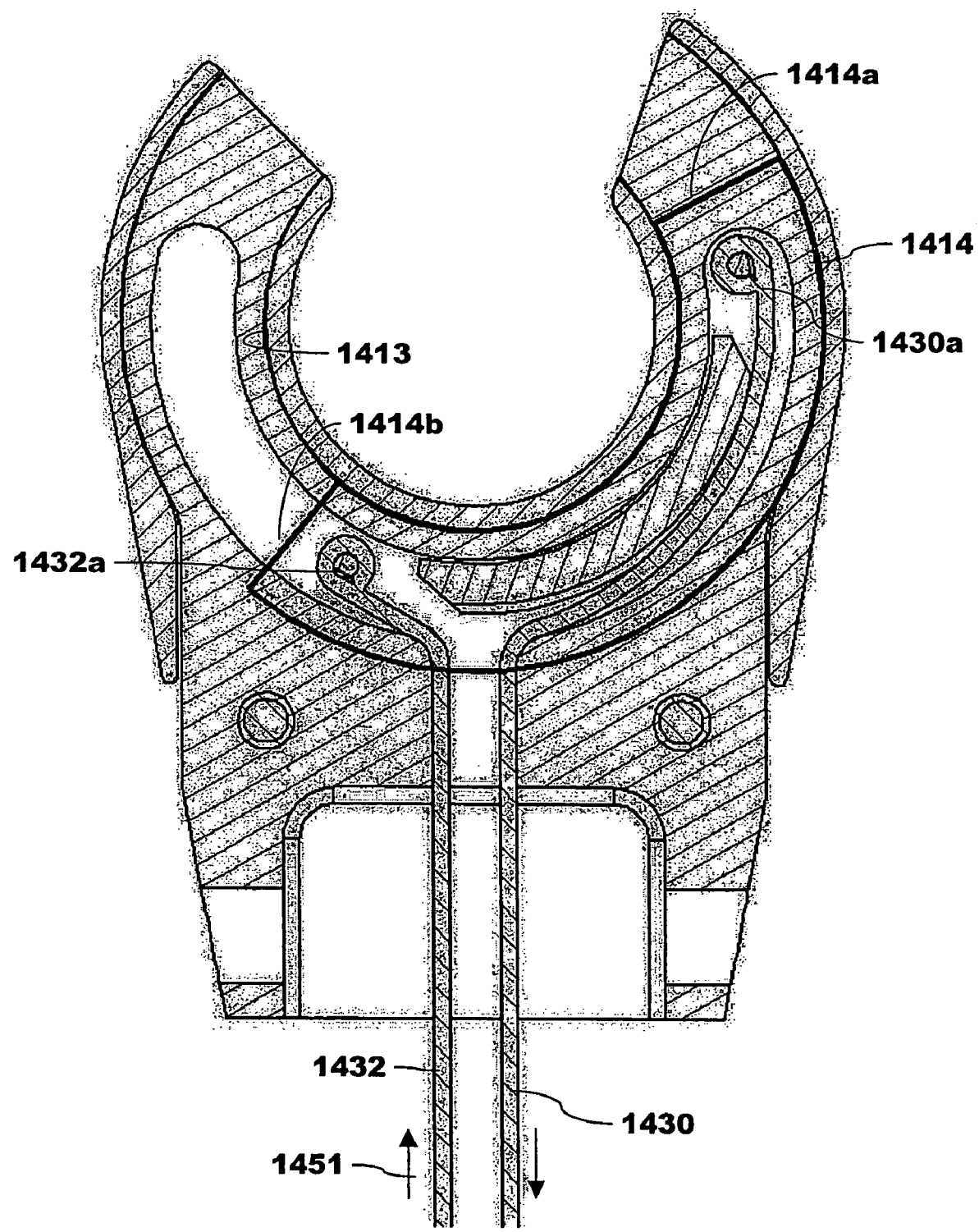

FIG. 202 is a generally enlarged diagrammatic view of the head portion of the apparatus broken away to illustrate the cooperative interaction of the operating cables of the apparatus on the shuttle member.

DESCRIPTION OF THE PREFERRED EMBODIMENTS

Referring initially to FIGS. 1-5 of the drawings one embodiment of the cycling suturing and knot-tying device of this invention is generally illustrated by reference numeral 1. A transmission tube 1200 is characterized by a generally cylindrically-shaped, elongated, hollow tube having a selection bearing socket 1253 on one end, with a lever 1251 pivotally extending therefrom, the transmission tube 1200 tapering inwardly at the opposite end to define a transition cone 1245. An elongated extension tube 1240 projects from the small end of the transition cone 1245 and terminates at a transition guide cone 1238 (FIG. 5), which receives and mounts an arcuate crescent 101, as illustrated. In a preferred embodiment of the invention the transmission tube 1200 is mounted for articulation on a cradle 1276A, seated in a housing 1265. A handle 1260 is attached to the housing 1265 and is fitted with a trigger 1267 for driving a curved suturing needle 50 (illustrated in FIG. 5) in the crescent 101, as hereinafter further described. Intermediate the selection bearing socket 1253 and the transition cone 1245 is provided a drive input section 1200C (FIG. 3) that includes a reciprocation input collar 1216, for interacting with the trigger 1267 and driving the needle 50 in the crescent 101. A direction setting switch section 1200D, including a slide switch mount body 1211, is also provided on the extension tube 1200 forwardly of the reciprocation input collar 1216 and is fitted with a pair of pressure opposing rings 1211A and a direction actuator 1214, slidably positioned on the transmission tube 1200 between the pressure opposing rings 1211A, for changing the direction of rotation of the needle 50 in the crescent 101, as further hereinafter described.

Figure 2:
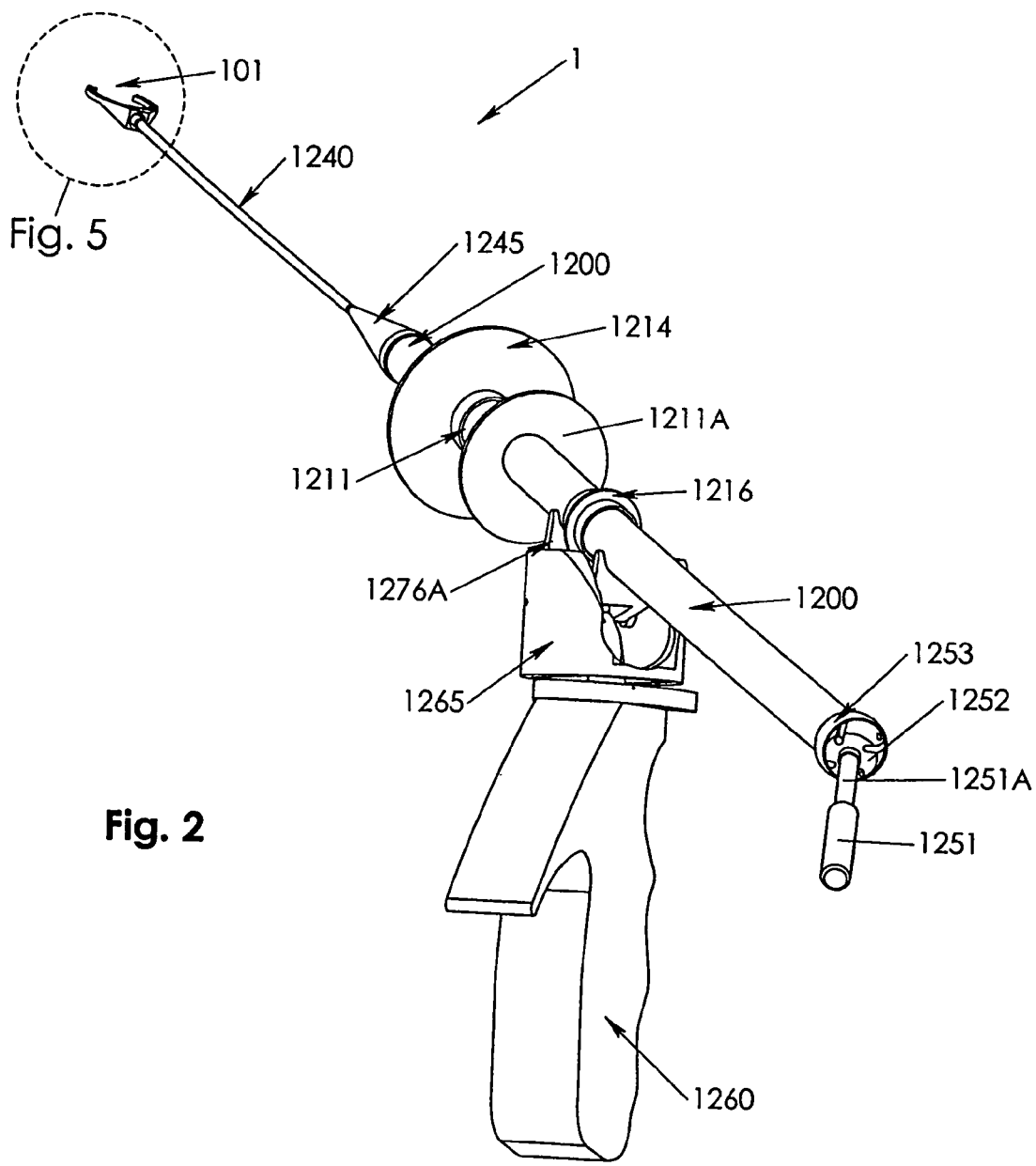
FIG. 2 is a rear perspective view of the operating device illustrated in FIG. 1, more particularly illustrating articulation of the crescent, the extension tube and the housing and housing cradle to the left with respect to the handle.

Referring now to FIG. 2 of the drawings it will be appreciated that the transmission tube 1200 and housing 1265 can be articulated to the left or right with respect to the handle 1260 to precisely position the crescent 101 in a desired location with respect to tissue to be sutured. Accordingly, the extension tube 1240 and crescent 101 on the extending end of the transmission tube 1200 can be articulated to any selected angle from the far left position illustrated in FIG. 2, to a far right position (not illustrated), for the purpose. Similarly, the extension tube 1200 can be pitched downwardly and upwardly throughout a wide angle of pitch by pivoting the cradle 1276A on the handle 1265 and the extension tube 1200 can be rotated 306-degrees along its longitudinal axis within the cradle 1276A, thus further facilitating precise positioning of the crescent 101 in a desired position in close quarters during a suturing operation.

As further illustrated in FIG. 4 of the drawings a second handle 1261, having a second handle trigger 1261B, can be attached to the handle 1260 by means of a flexible connection 1261A and a flexible tube 1141 is projected from the second handle 1261 to a thread incrementing accessory (not illustrated) mounted on the crescent 101, for purposes which will be hereinafter further described.

Referring again to FIG. 5 of the drawings in a preferred embodiment the crescent 101 is attached to the tapered transition guide cone 1238 of the transmission tube 1200 by means of a fixed joint ball 780, provided on the extending end of the transition guide cone 1238. The joint ball 780 is seated in the socket cavity 775C of a socket 775 provided in the crescent 101 and this connection facilitates universal articulation of the crescent 101 with respect to the transition guide cone 1238. Controlled universal articulation of the crescent 101 on the joint ball 780 is facilitated by four crescent angle articulation cables 1256A, 1256B, 1256C and 1256D, respectively, typically extending from within the transition guide cone 1238, through corresponding cable holes 1238A, 1238B, 1238C and 1238D, respectively. As further illustrated in FIG. 5, the extending end of each of the crescent articulation cables 1256A, 1256B, 1256C and 1256D is attached by any suitable method to corresponding base corners 776A, 776B, 776C and 776D, respectively, of the socket 775, while the opposite ends of these cables are attached to the lever 1251, illustrated in FIGS. 1-4, as hereinafter described, such that manipulation of the lever 1251 applies tension in the corresponding one of the crescent angle articulation cables 1256A, 1256B, 1256C and 1256D, to manipulate and articulate the crescent 101 into a desired position with respect to the tissue 100, illustrated in phantom in FIG. 5. Accordingly, in a preferred embodiment of the invention the crescent angle articulation cables 1256A, 1256B, 1256C and 1256D extend from the lever 1251 connection assembly, through the transmission tube 1200, the transition cone 1245, the extension tube 1240 and through the corresponding transition guide cone cable inlet holes 1238A, 1238B, 1238C and 1238D, respectively, in the transition guide cone 1238, to the socket 775 on the crescent 101.

Referring now to FIGS. 1, 5, 6, 6A and 6B of the drawings in a preferred embodiment of the invention the crescent 101 illustrated in FIGS. 1-5 is characterized by a crescent-shaped case 102, which defines a continuous curved groove, except for a gap 105 between the extending ends thereof, which case 102 is mounted on the socket 775 by any suitable means, typically including welding, bolting, bradding or the like, in non-exclusive particular. An arcuate fixed way direction setting plate 136 is seated in the case 102 and is designed to receive a shorter, curved drive direction setting plate 134, the latter of which responds, by means of operating components hereinafter described, to manipulation of the slide switch mount body 1211 on the transmission tube 1200, for determining the direction of rotation of the arcuate needle 50, further illustrated in FIG. 6. The drive direction setting plate 134 is seated on the fixed way direction setting plate 136 and receives a correspondingly-shaped reciprocating driver 108, designed to incrementally drive the crescent-shaped needle 50 in a direction determined by the position of the driver direction setting plate 134, in relation to the reciprocating driver 108. An arcuate fixed way 104 is positioned on the reciprocating driver 108 for accommodating and stabilizing the arcuate needle 50, which is provided with a length of thread 50a, as further illustrated in FIG. 6.

Figure 5:
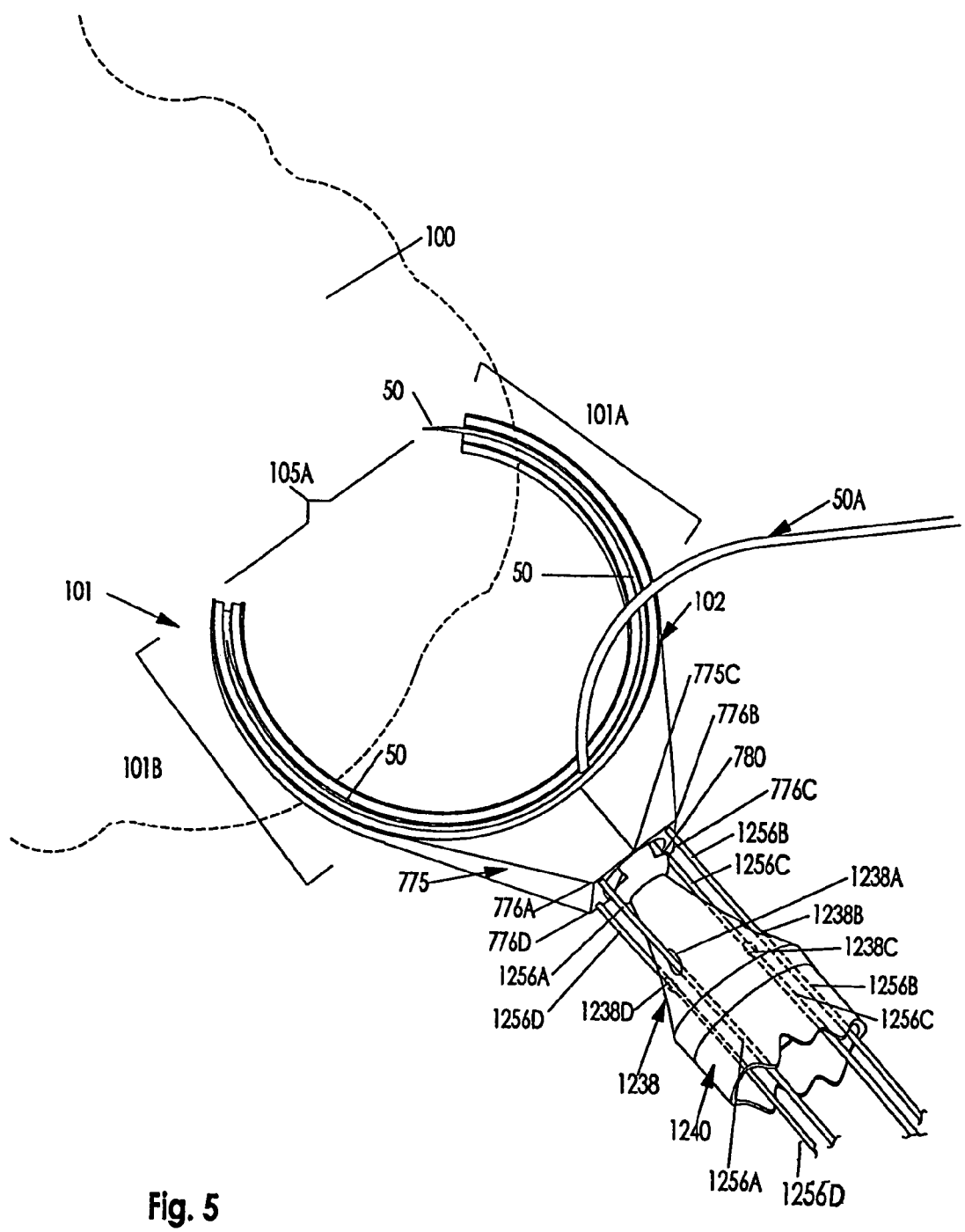
FIG. 5 is an enlarged view of the crescent and the crescent-mount end of the extension tube extending from the transmission tube illustrated in FIGS. 1-4, more particularly illustrating a curved needle rotatably seated in the crescent and a ball which engages a crescent socket and mounts the crescent on the extension tube to facilitate articulation of the crescent responsive to operation of the lever illustrated in FIGS. 1-4.
Figure 6:
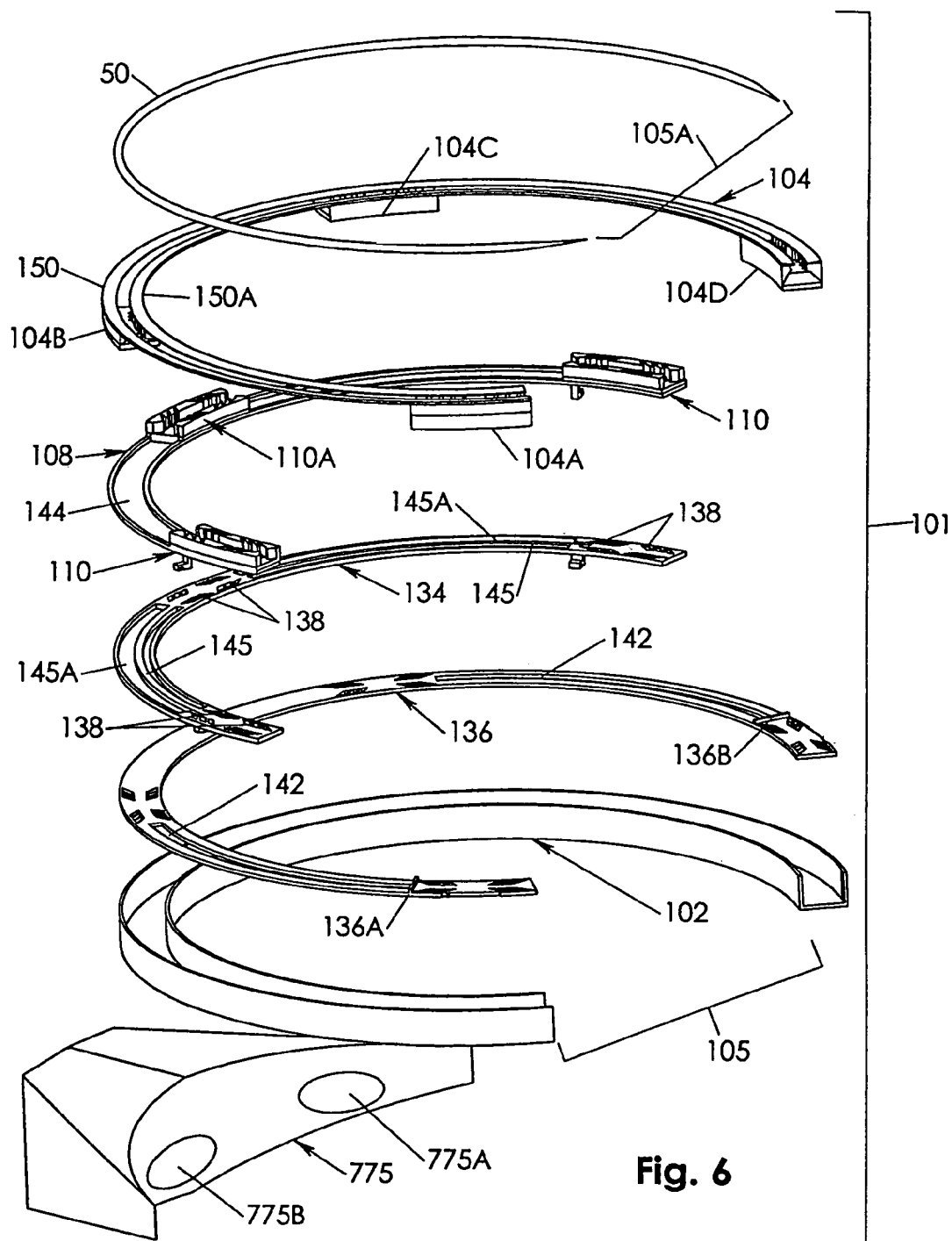
FIG. 6 is an exploded view of the various fixed and rotatable drive components of the crescent for driving the needle in the crescent and determining the direction of needle rotation responsive to operation of corresponding operating components or elements in the operating device.
Figure 6A:
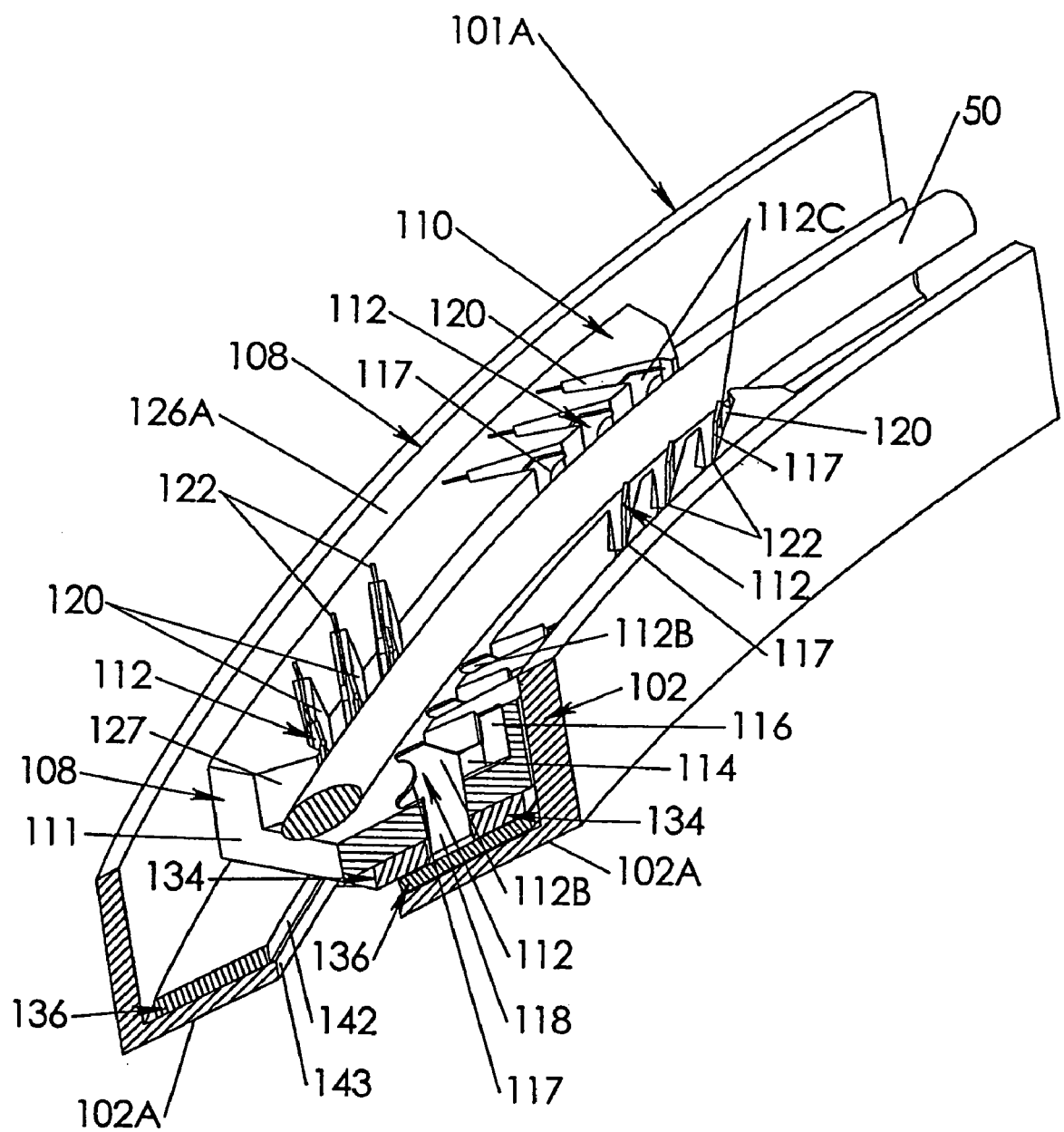
FIG. 6A is a top perspective view, partially in section, of one end of the crescent illustrated in FIG. 6 in assembled configuration with the fixed way removed for brevity, more particularly illustrating the respective needle driver, drive direction setting plate, fixed way direction setting plate and case for suspending and driving the curved needle.
Figure 6B:
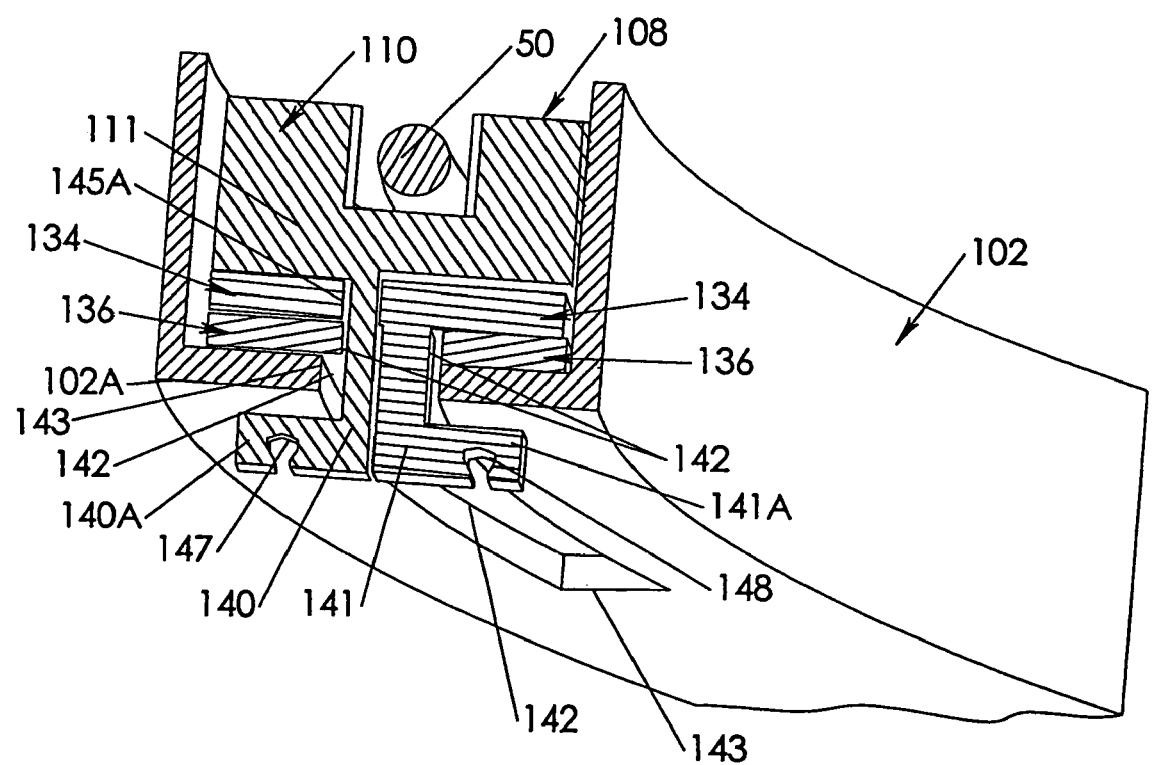
FIG. 6B is a bottom perspective view, partially in section, of the respective blade supporting and driving components illustrated in FIG. 6A, more particularly illustrating cable extension elements for receiving direction and drive cables in the operating device.

Assembly of the respective components of the crescent 101 illustrated in FIG. 6 except the fixed way 104, is illustrated in FIGS. 6A and 6B, wherein a segment of the needle 50 is shown in position on the needle driver 108. The needle driver 108, drive direction setting plate 134 and the fixed way direction setting plate 136 are all stacked and seated in the though-like case 102 and maintained in place by any convenient technique, typically by attaching the fixed way housings 104A-104D to the walls of case 102, e.g., welding or press-fit. As further illustrated in FIG. 6B of the drawings, one of a pair of direction setting access side extensions 141 is illustrated and extends through a case clearance slot 143 in the case base 102A of the case 102 and through an aligned fixed way direction setting plate slot 142 in the fixed way direction setting plate 136, for mounting on the drive direction setting plate 134 and attachment to a cable (not illustrated) that extends to the components of the slide switch 1211 for effecting a change in the direction of rotation of the needle 50 as it traverses the fixed way 104. Similarly, a pair of drive access cable extensions 140 (one of which is illustrated in FIG. 6B) also extends from the spaced-apart blade group housings 110 and 110B in the reciprocating driver 108, through the case clearance slot 143 provided in the case base 102A of the case 102 and through the aligned fixed way direction setting plate slot 142 in the fixed way direction setting plate 136, and the longer tab clearance slot 145A in the drive direction setting plate 134. A second cable (not illustrated) extends from attachment to the drive access cable extension 140 to the reciprocation input collar 1216 on the transmission tube 1200 (FIGS. 1-5) and incrementally drives the needle 50 in the fixed way 104 in a direction determined by operation of the drive direction setting plate 134 and the fixed way direction setting plate 136, by operation of the trigger 1267 in the handle 1260 (FIGS. 1-5) as hereinafter further described.

Figure 7:
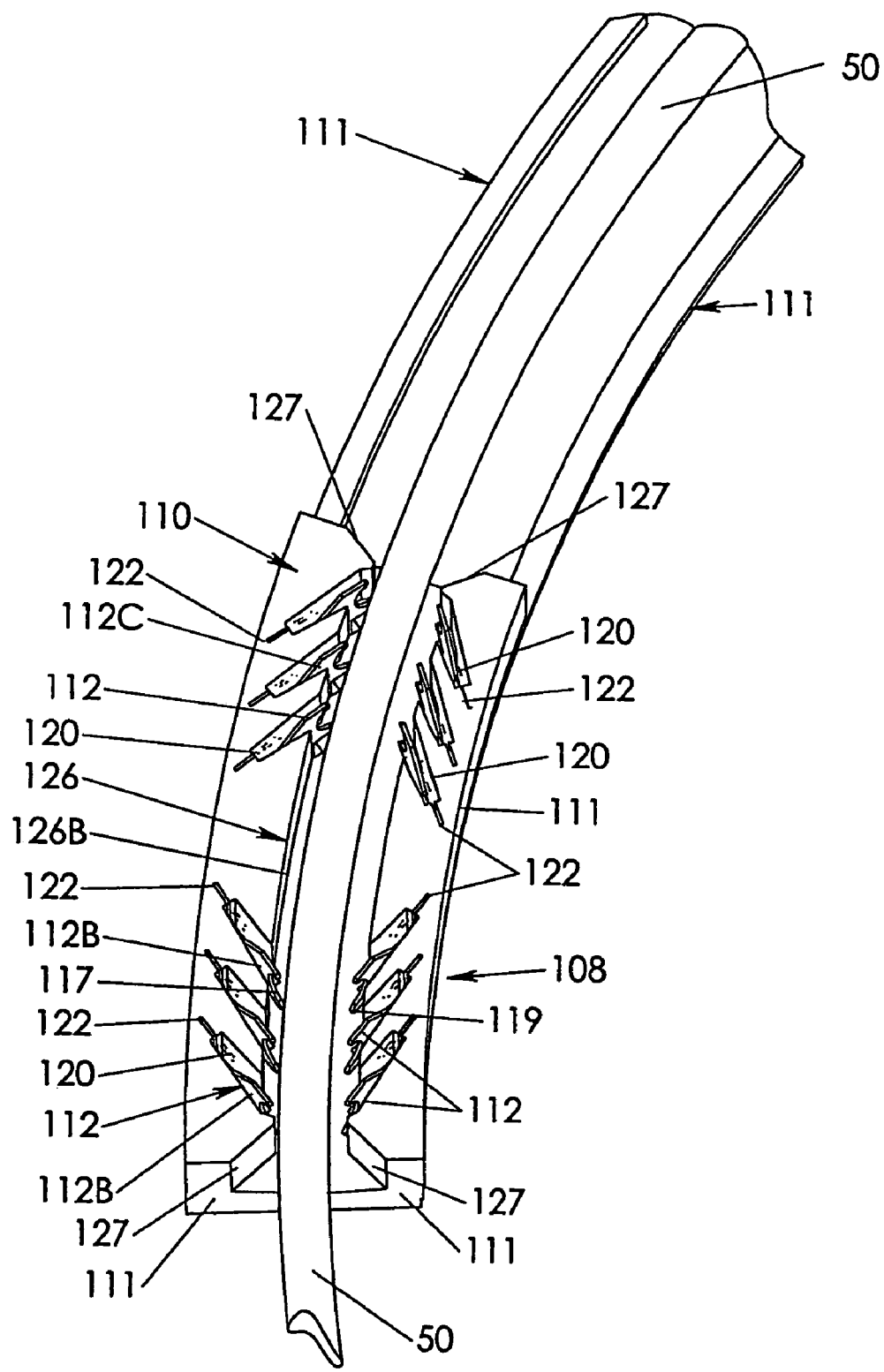
FIG. 7 is a top perspective view of the needle driver element of the crescent, more particularly illustrating a system of two sets of oppositely-disposed needle-engaging blades for selectively engaging and driving a curved needle seated in the arcuate needle driver, responsive to operation of various operating elements in the operating device.
Figure 8A:
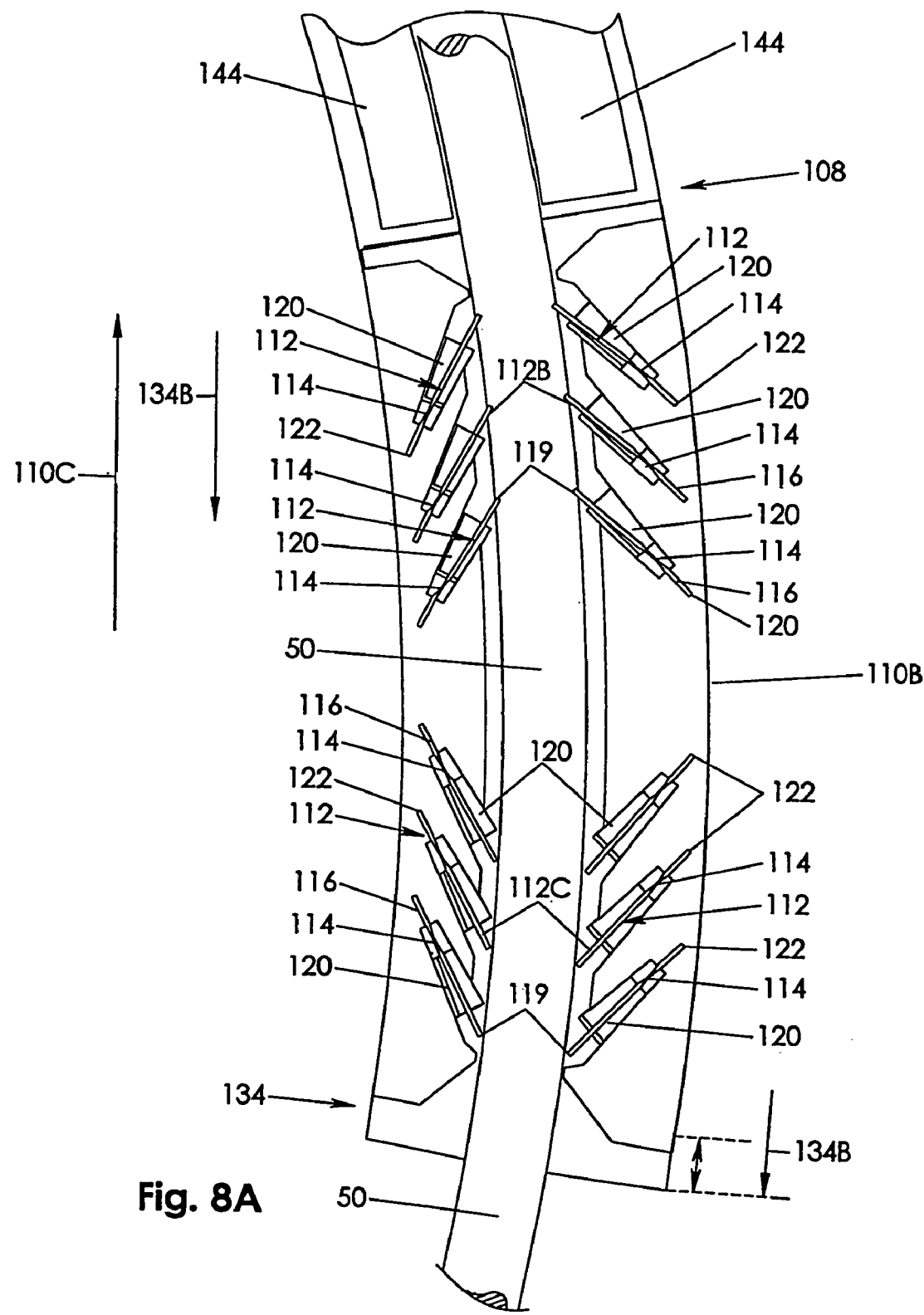
FIG. 8A is an enlarged top view of the needle driver and the underlying drive direction setting plate, more particularly illustrating engagement of one set of oppositely-disposed needle-engaging blades positioned in blade group housing of the needle driver by the drive direction setting plate, for driving the needle in the indicated direction responsive to operation of needle-driving operating components in the operating device.
Figure 8B:
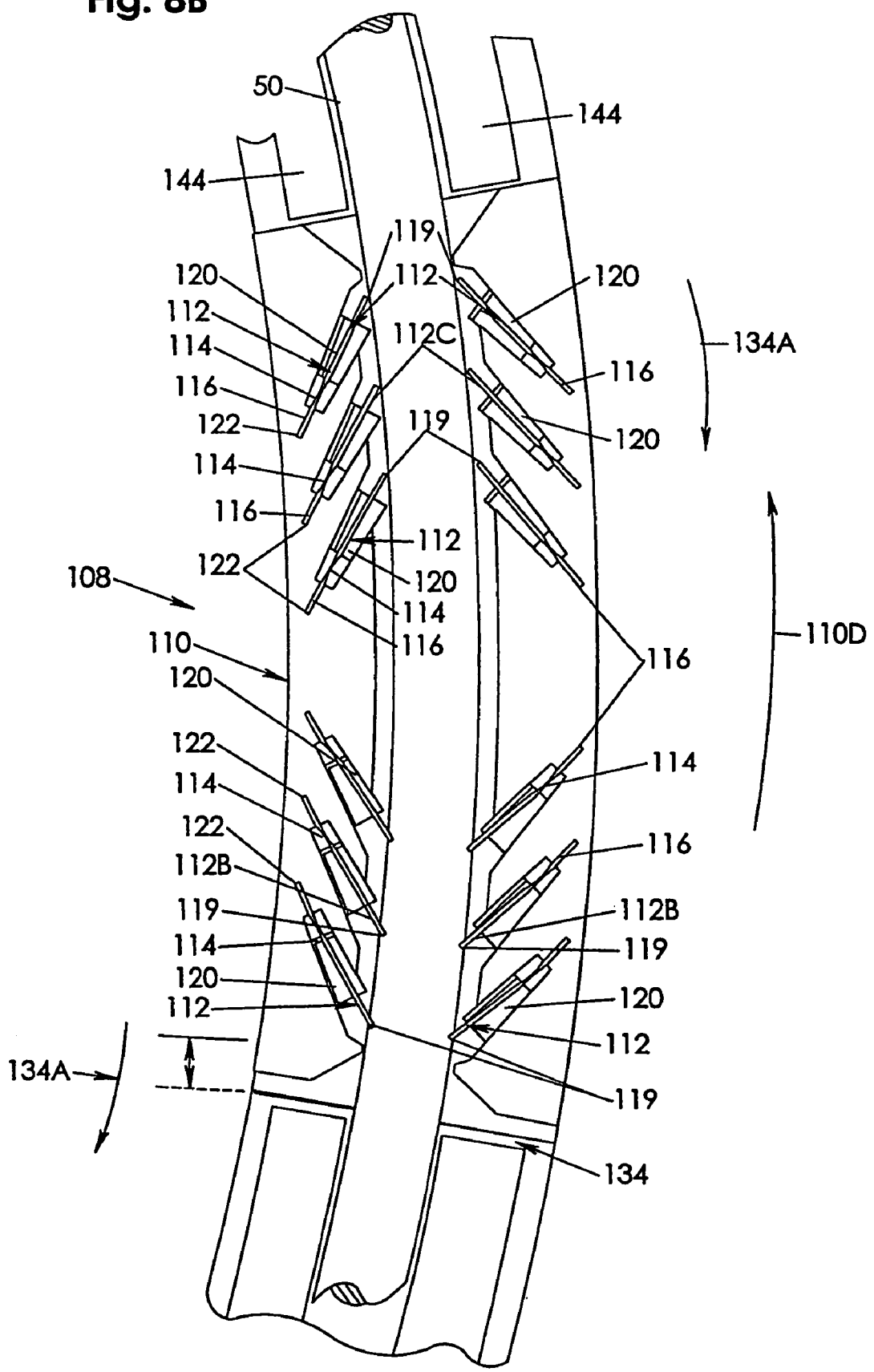
FIG. 8B is a top view of the opposite end of the needle driver and drive direction plate as illustrated in FIG. 8A, more particularly illustrating engagement of the second set of oppositely-disposed blades in the needle driver by the drive direction plate, for driving the needle in the opposite direction as indicated, responsive to operation of the needle-driving operating elements in the operating device.

Referring now to FIGS. 6-13A of the drawings the arcuate reciprocating driver 108 is illustrated and is fitted with three, spaced-apart blade group housings, 110, 110A and 110B, mounted on a group housing base 111, fitted with a pair of curved, parallel driver longer tab clearance slots 144 (FIGS. 8A and 8B). Two of the blade group housings, 110 and 110B, are positioned at the extreme ends of the crescent-shaped reciprocating driver 108 and the third blade group housing 110A is located in the center of the reciprocating driver 108, approximately equally spaced between the blade group housings 110 and 110B (FIGS. 6, 8A and 8B). As further illustrated in FIG. 7, the curved needle 50 extends through a groove or track provided in the group housing base 111 of the blade group housing 110A (as well as in the blade group housings 110 and 110B, (not illustrated). Furthermore, two sets of oppositely-disposed, dual directional blade clearance slots 120 are provided in each group housing base 111 facing the needle 50 in angular relationship, for receiving the driver blades 112, respectively. The driver blades 112 are seated in blade mounting slots 122 provided in the base of the respective blade clearance slots 120, in two sets of six, oppositely-disposed driver blades 112 and the respective sets or groups of driver blades 112 are positioned in opposite directions and identified as forwardly-inclining driver blades 112B and rearwardly-inclining driver blades 112C, in accordance with the opposite directional positioning of the two sets of blade clearance slots 120.

Figure 7A:
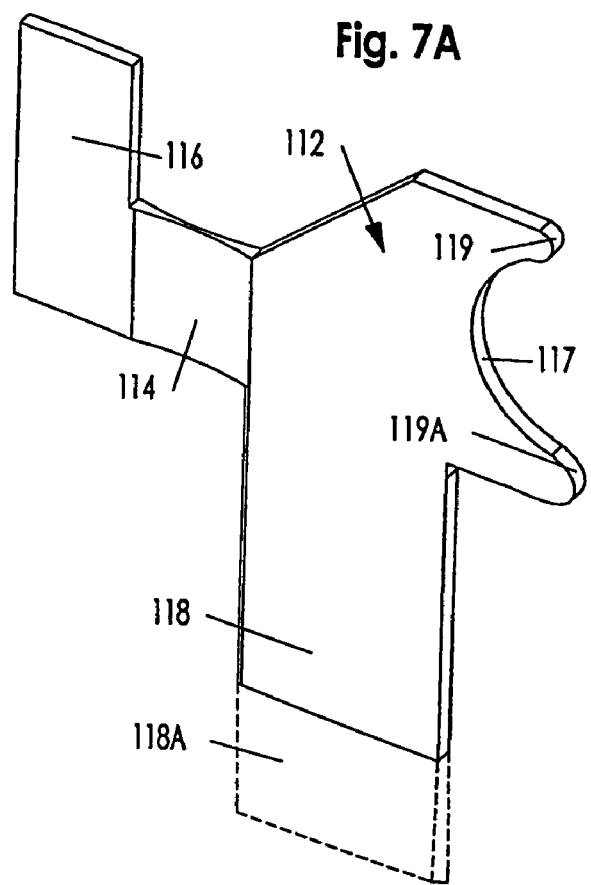
FIG. 7A is a perspective view of a typical needle-engaging blade illustrated in FIG. 7.
Figure 7B:
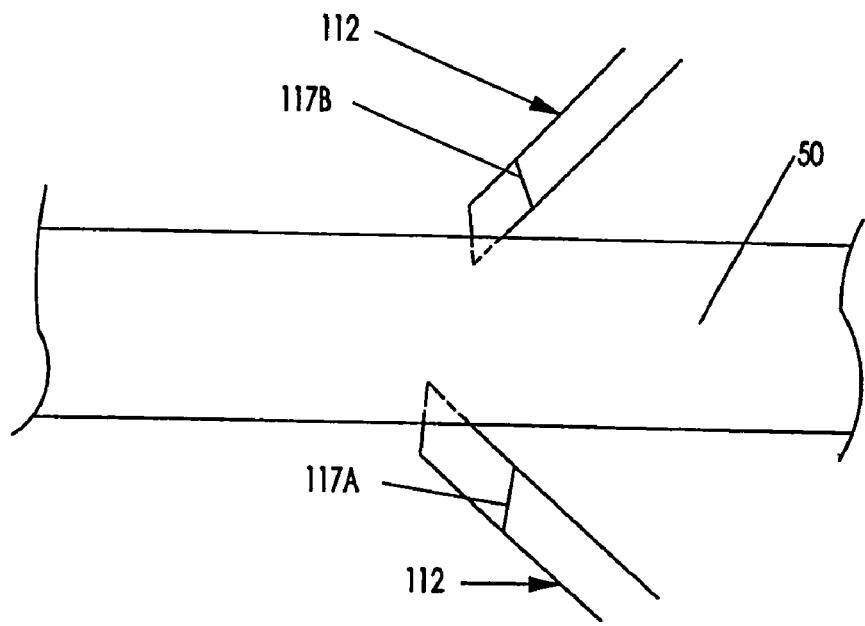
FIG. 7B is a top view, partially in section, of a pair of oppositely-disposed blades illustrated in FIG. 7, more particularly illustrating a blade bevel on each blade designed to efficiently and sequentially engage the needle and selectively drive the needle in the forward or reverse direction.

Referring to FIGS. 7-7B, each of the driver blades 112 typically includes a vertical leaf tensioning tab 118 or a longer tab 118A (illustrated in phantom in FIG. 7A) connected to a vertical fin 116 by means of a narrow, bendable center spring leaf 114. Each of the leaf tensioning tabs 118 is further characterized by a bottom rounded end 119A that curves to define a concave needle contact profile 117, having angle chisels 117A and 117B (FIG. 7B), which concave needle profile 117 terminates in a top rounded end 119. Accordingly, as illustrated in FIG. 7, one set of the driver blades 112 (the forwardly-inclining driver blades 112B) are oppositely-disposed and positioned with the corresponding concave contact profiles 117 (FIG. 7A) positioned for engaging the needle 50 to drive the needle 50 in the counterclockwise direction, while the corresponding second set of driver blades 112 (the rearwardly-inclining driver blades 112C) are positioned in the opposite direction to sequentially engage the needle 50 at the corresponding concave contact profiles 117 when the needle 50 is to be driven in the opposite, or clockwise direction. As further illustrated in FIG. 7, the extreme ends of the blade group housings 110, 110A and 110B in the reciprocating driver 108 are each shaped to define oppositely-disposed angle entry guides 127, to facilitate sure entry of the beveled ends of the needle 50 as the needle 50 incrementally moves in the crescent 101 by operation of the reciprocating driver 108.

Referring again to FIGS. 6-10 of the drawings the drive direction setting plate 134 is positioned beneath and adjacent the reciprocating driver 108 as illustrated in FIGS. 6, 6B, 9 and 10. The drive direction setting plate 134 is fitted with three, spaced-apart groups of two sets each, of oppositely-disposed, dual-directional fixed way direction setting plate parallelogram holes 138 that receive the elongated, downwardly-extending leaf tensioning tab 118 of each of the correspondingly positioned driver blades 112, as illustrated in FIG. 8. The top portions of each of the respective driver blades 112 are seated in the respective driver blade clearance slots 120 in the reciprocating driver 108, as illustrated in FIG. 7 and as heretofore discussed. It is significant that each of the drive direction setting plate parallelogram holes 138 are shaped in the configuration of a parallelogram, the angled walls 139 of which parallelograms are essentially parallel to the respective leaf tensioning tabs 118, and are disposed for contacting the leaf tensioning tabs 118 in sequence responsive to rotation of the drive direction setting plate 134, for purposes described below.

Figure 10:
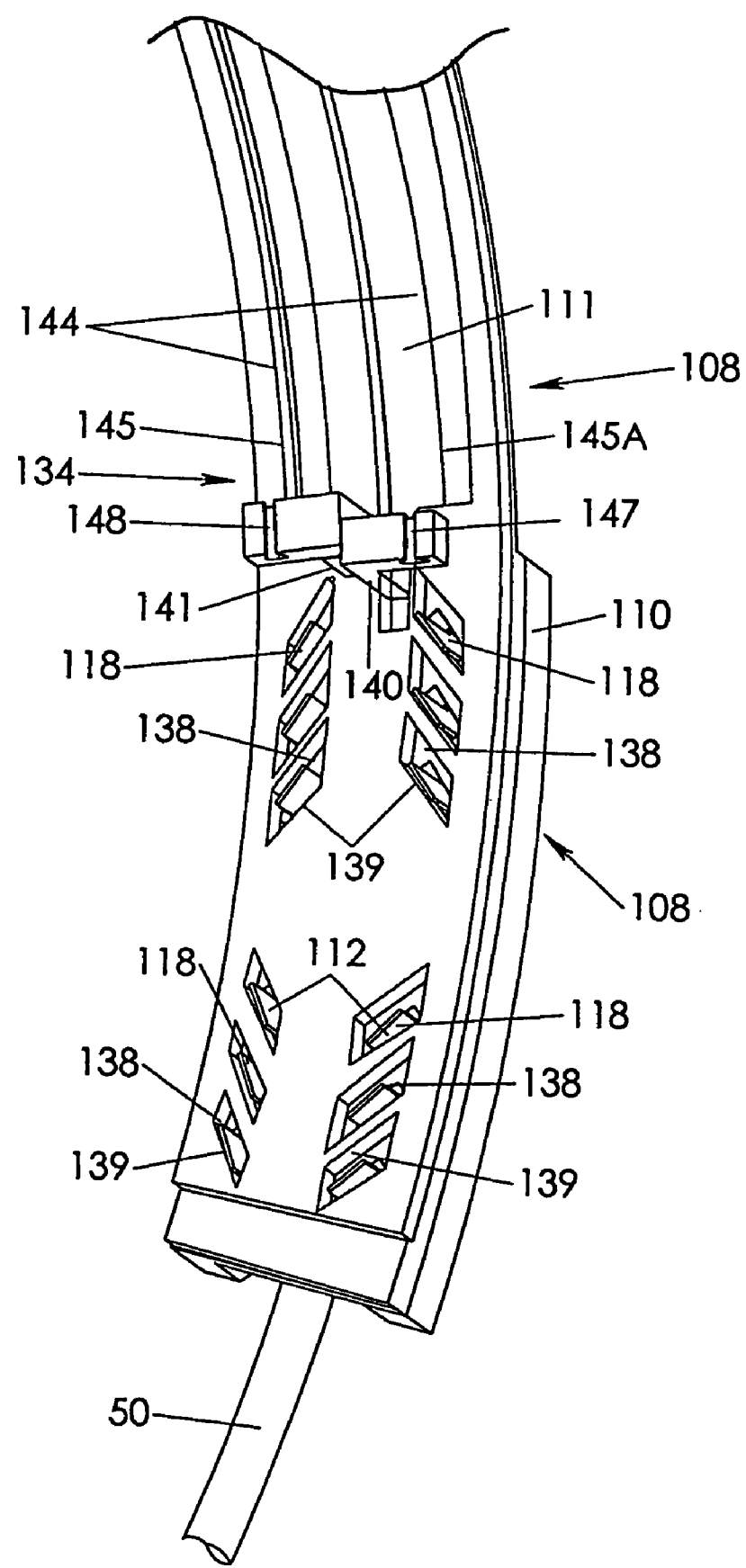
FIG. 10 is an enlarged bottom perspective view of the one end of the needle driver and the drive direction setting plate, more particularly illustrating engagement of the downwardly-extending ends of the blades with the respective walls of parallelogram-shaped slots provided in the drive direction setting plate, for manipulation of the drive direction setting plate by blade direction components or elements in the operating device and determining the direction of rotation of the needle.

As illustrated in FIGS. 8A, 8B and 10 of the drawings and beginning with FIG. 8A, the blade group housing 110B segment of the reciprocating driver 108 is illustrated superimposed on the corresponding section of the drive direction setting plate 134 of the crescent 101. The forward set of oppositely-disposed driver blades 112 (the forwardly-inclining driver blades 112B) engage the curved needle 50 as they are slightly bent at each narrowed center leaf spring leaf 114, respectively, by rearward setting position of the underlying drive direction setting plate 134. Accordingly, the forwardly-inclining driver blades 112B are in needle-driving configuration, such that operation of the reciprocating driver 108 in the counterclockwise direction of the forward arrow 110C advances the needle 50 in that direction responsive to operation of the trigger 1267 in the cycling suturing and knot-tying device 1 illustrated in FIG. 1. The rearward arrow 134B illustrates the direction of setting movement of the drive direction setting plate 134, which rearward movement is required to bend and set the forwardly-inclining driver blades 112B for forward incrementation of the needle 50. This bending of the respective forwardly-inclining driver blades 112B is effected by contact between the angled parallelogram sides 139 of the respective parallelogram holes 138 (FIG. 10) in the drive direction setting plate 134 and the downwardly-extending leaf tensioning tabs 118. The rearwardly-inclining driver blades 1112C are out of contact with the needle 50 during this counterclockwise direction of needle movement, as they are not engaged by the parallelogram sides 139 of the parallelogram holes 138 in the drive direction setting plate 134.

Referring now to FIG. 8B of the drawings, which shows the opposite end of the driver 108 and direction setting plate 134 and blade group housing 110, illustrated is the opposite mode of needle operation from that illustrated in FIG. 8A. Illustrated are the rearwardly-inclining driver blades 112C set in needle-engaging configuration by forward positioning of the drive direction setting plate 134 as shown by the direction of the forward arrow 134A. The parallelogram sides 139 of the corresponding parallelogram holes 138 (FIG. 10) act upon the respective leaf tensioning tabs 118 of the rearwardly-inclining driver blades 112C, bending them into contact with the needle 50 and thus facilitating rotation of the needle 50 in the opposite, or clockwise direction from that illustrated in FIG. 8A. The rearward clockwise arrow 110D, indicates the operation of the reciprocating driver 108 in this direction.

Figure 1:
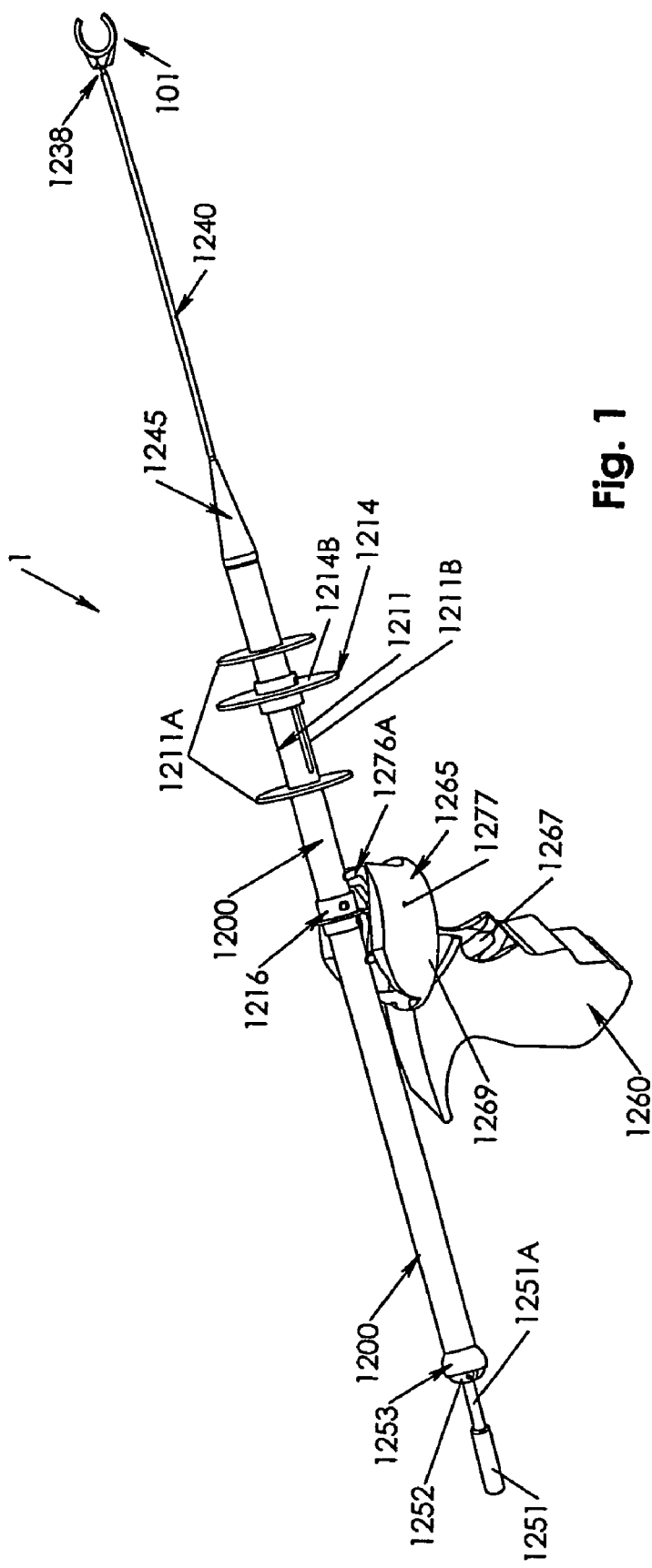
FIG. 1 is a right-side perspective view of a preferred embodiment of a cyclical suturing and knot-tying operating device, generally illustrating a handle; a housing to which the handle is attached; a transmission tube mounted on a cradle pivotally carried by the housing; a cable lever mounted on one end of the transmission tube for manipulating articulation cables extending through the transmission tube and connecting to the arcuate frame. A slide switch is illustrated and a direction actuator mounted on the transmission tube forwardly of the handle, which extends into the tube and attaches to the one of the two cable circuits which sets the direction of the needle movement. An extension tube extending from the opposite end of the transmission tube from the lever further encloses the articulation cables and cable circuits and supports an arcuate needle frame or crescent positioned on the end of the extension tube for receiving the cables, mounting the curved needle and effecting suturing of tissue responsive to operation of the lever and the articulating and needle control elements of the operating device.
Figure 9:
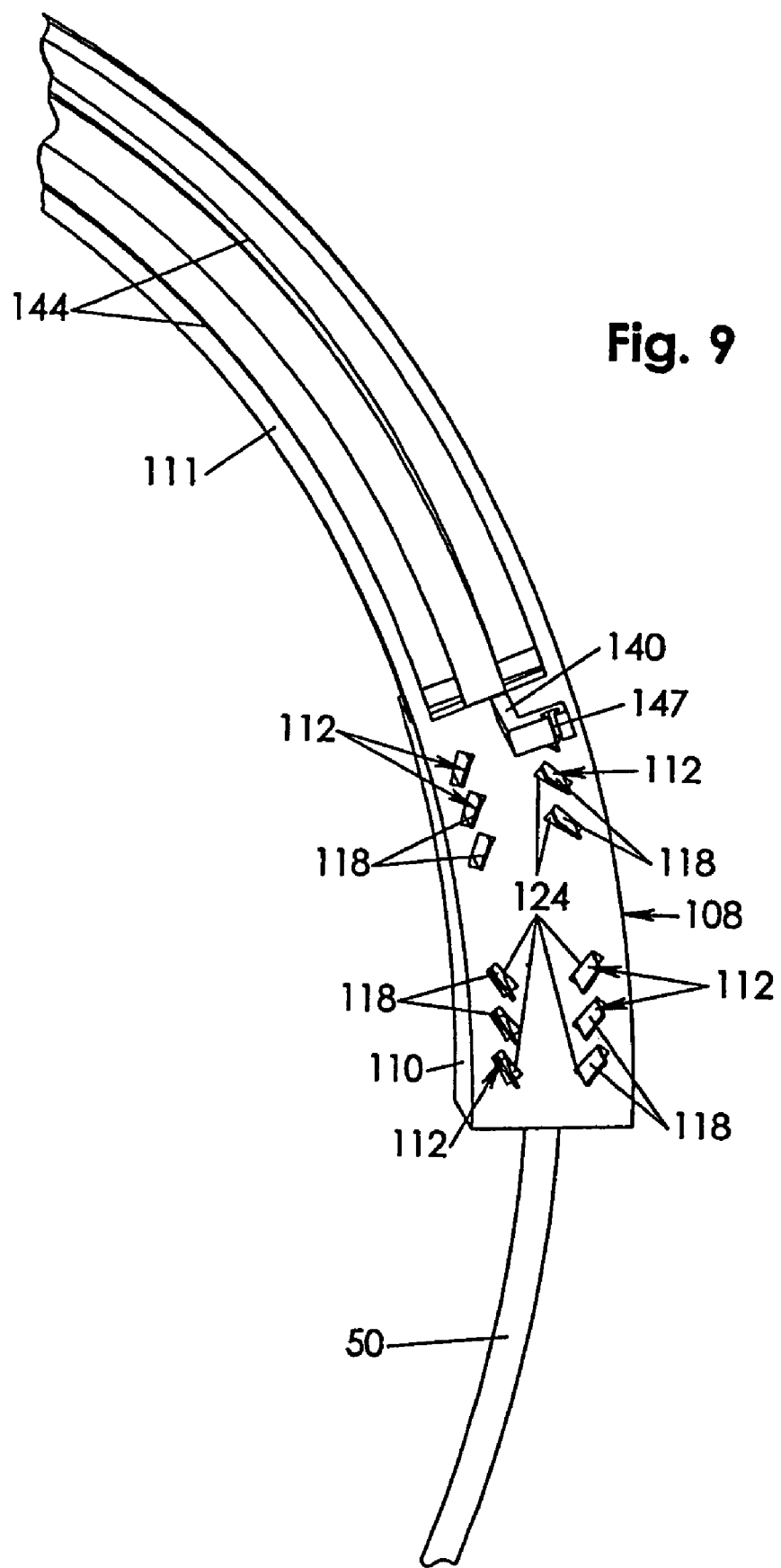
FIG. 9 is an enlarged bottom perspective view of one end of the needle driver, more particularly illustrating extension of the respective needle-engaging blade sets through slots in the needle driver for engagement by corresponding openings in the underlying drive direction setting plate (not illustrated) to determine the direction of rotation of the needle.

As illustrated in FIGS. 9 and 10 of the drawings the group housing base 111 of the reciprocating driver 108 is fitted with two downwardly-extending drive access cable extensions 140 (one illustrated), which include a drive cable crimp trough 147 for receiving a cable (not illustrated) that connects to the reciprocating input collar 1216 mechanism on the transmission tube 1200 to facilitate operation of the reciprocating driver 108 in a specific direction by manipulation of the trigger 1267 on the handle 1260, as illustrated in FIG. 1 and as further hereinafter described. Further illustrated in FIG. 9 are the downwardly-extending leaf tensioning tabs 118 of the respective sets of driver blades 112 which project through the corresponding rectangular drive tab clearance holes 124, for projection into the corresponding drive direction setting plate parallelogram holes 138 in the drive direction setting plate 134, as illustrated in FIG. 10 and as heretofore described.

Referring to FIGS. 1, 10, 11 and 11A of the drawings the reciprocating driver 108 is shown assembled with the drive direction setting plate 134 and the drive access cable extension 140, fixed to the group housing base 111 of the reciprocating driver 108, is illustrated extending through a longer tab clearance slot 145A in the drive direction setting plate 134, to facilitate driving of the needle 50 by operation of the reciprocating driver 108, with the drive direction setting plate 134 in a selected position with respect to the reciprocating driver 108 and traveling with the reciprocating driver 108. Also illustrated in FIG. 10 is the direction access cable extension 141 projecting downwardly from fixed attachment to the drive direction setting plate 134. The direction setting access cable extension 141 includes a direction cable crimp trough 148 for attachment to a cable (not illustrated) which is extended through the transmission tube 1200 to the slide switch 1211 illustrated in FIG. 1. This connection facilitates changing the direction of rotation of the needle 50 in the crescent 101 by manipulation of the drive direction setting plate 134 with respect to the reciprocating driver 108 using the slide switch 1211, as heretofore described and hereinafter detailed. Further described in FIG. 10 are the respective parallelogram holes 138 in the drive direction setting plate 134, each of which parallelogram holes 138 may have an angled parallelogram side angle 139 for engaging the respective parallel leaf tensioning tabs 118 of the driver blades 112 and bending the driver blades 112 at each respective center spring leaf 114, to effect selective engagement of the opposing sets of driver blades 112 with the needle 50, as illustrated in FIGS. 8A and 8B and as heretofore described.

Figure 13:
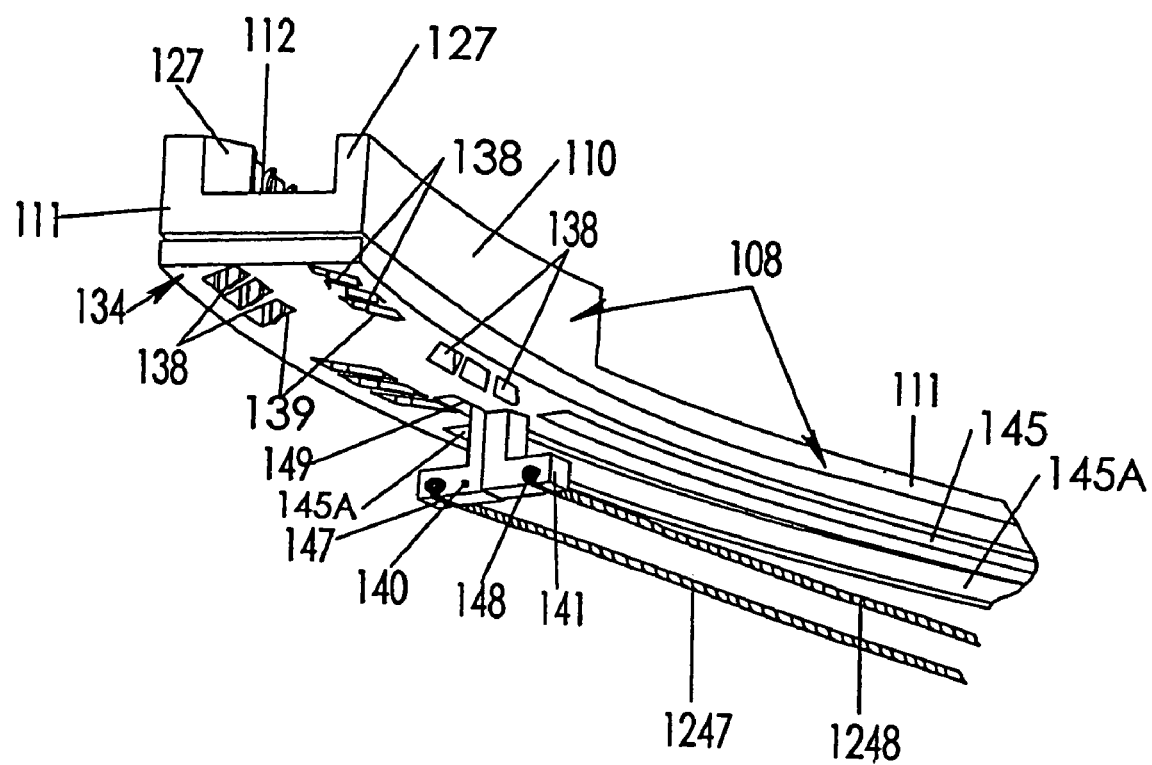
FIG. 13 is a bottom perspective view of one end of the needle drive direction setting plate and the needle driver, more particularly illustrating the parallelogram slots provided in the needle drive direction setting plate for receiving the ends of the downwardly-extending needle-engaging blades from the needle driver (FIG. 12A), and more particularly illustrating downward projection of a drive access cable extension from the needle driver through a first curved slot in the drive direction setting plate for operating the needle driver. Further illustrated is downward extension of a direction setting access cable extension attached to the drive direction setting plate, with cables attached to the drive access cable extension and the direction setting access cable extension for operating both the direction of travel of the needle and needle rotation, responsive to manipulation of the appropriate operating controls in the operating device.
Figure 13A:
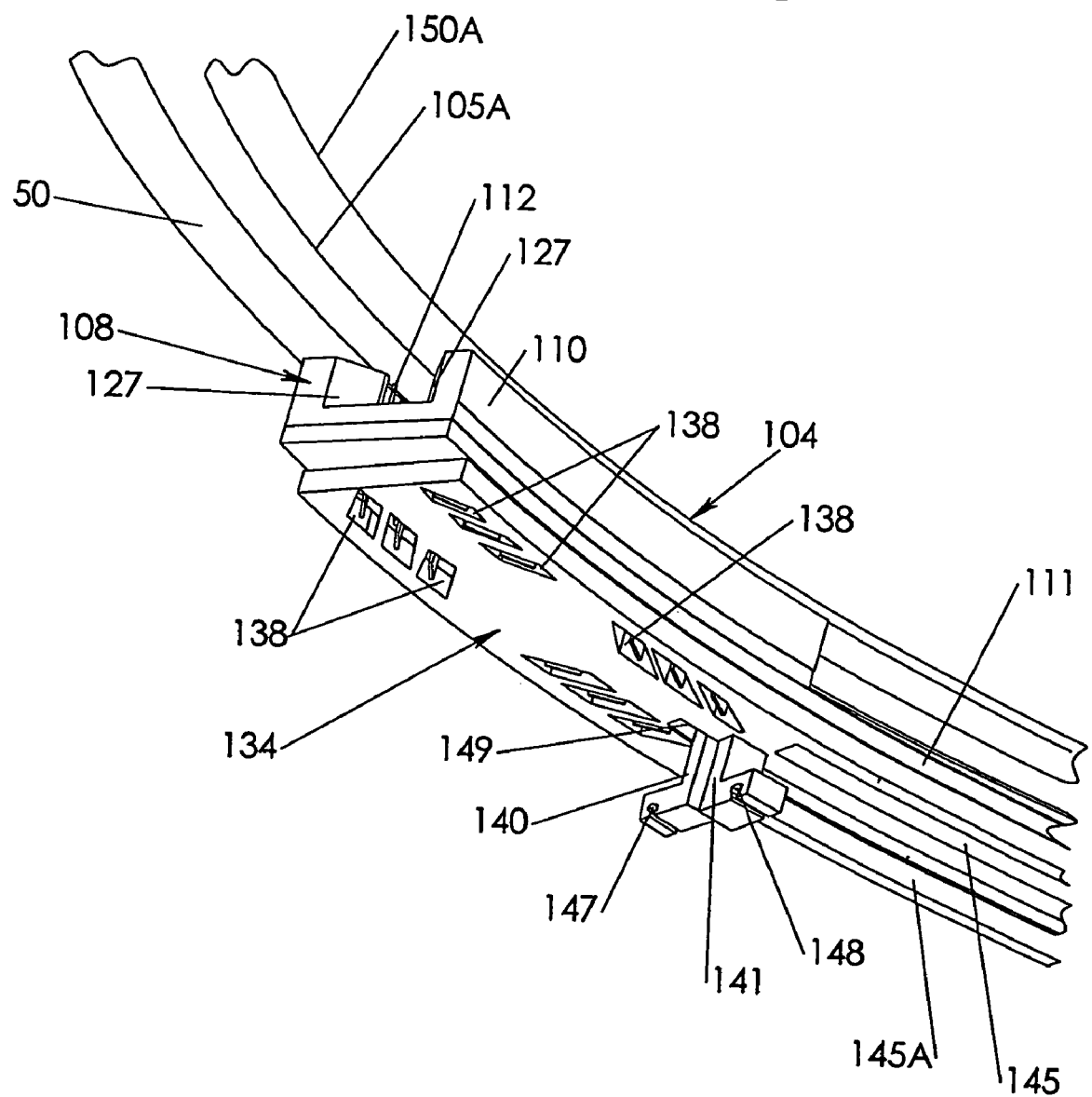
FIG. 13A is a bottom perspective view of one end of the drive direction setting plate mounted below the needle driver and including the fixed way, also mounted above the needle driver, for setting the direction of rotation of the needle and driving the needle by means of cables secured to the underlying drive access cable extension and direction access cable extension, respectively.

As illustrated in FIG. 13A of the drawings the reciprocating driver 108 is again shown assembled on the drive direction setting plate 134 and the longer fixed way 104 is included in the assembly, the combination more particularly illustrating the capacity for bidirectional movement of the former with respect to the latter, and also illustrating downward extension of one set of the respective pairs of drive access cable extension 140 and direction access cable extension 141, for operation of the reciprocating driver 108 and the drive direction setting plate 134 beneath the fixed way 104, respectively.

Figure 12:
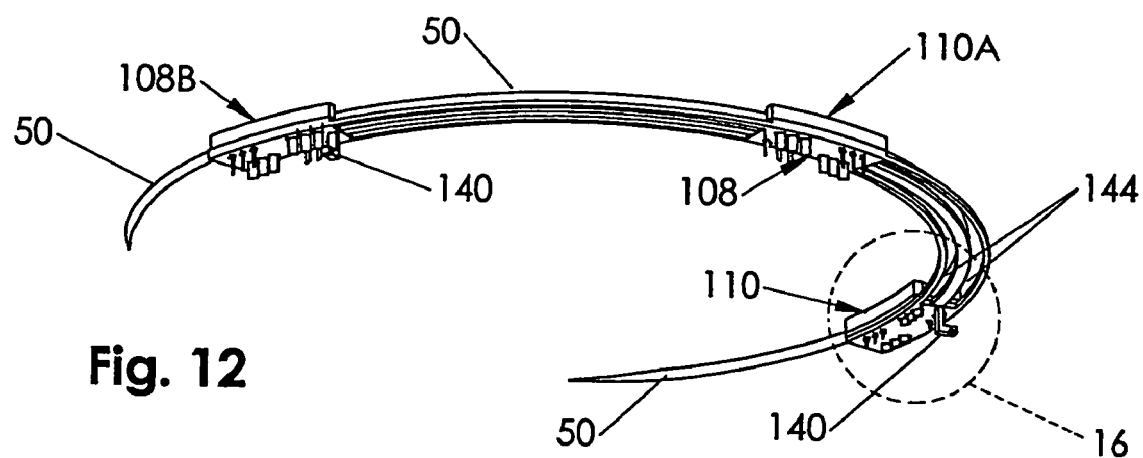
FIG. 12 is a bottom perspective view of the needle driver, more particularly illustrating the two spaced-apart cable mount extensions for attachment to cables (not illustrated) and manipulating the needle driver by operation of the appropriate blade control components in the operating device.

Referring to FIGS. 12-13A of the drawings the reciprocating driver 108 is illustrated assembled on the underlying drive direction setting plate 134 in FIG. 13, such that one of the downwardly-extending drive access cable extensions 140, attached to the group housing base 111 of the reciprocating driver 108 at the blade group housing 110, is illustrated extending through the corresponding slot inlet 149 in the drive direction setting plate 134, that leads to the longer tab clearance slot 145A, illustrated in FIG. 13. One end of a drive cable 1247 is tightly crimped in the drive cable crimp trough 147 of the drive cable extension 140. Further illustrated is one of the downwardly-extending direction access cable extensions 141, fixed to the drive direction setting plate 134 and receiving one end of a direction cable 1248, which is tightly crimped in the direction cable crimp trough 148 of the direction access cable extension 141. The drive cable 1247 and the direction cable 1248 are connected at the opposite ends to the reciprocating input collar 1216 (and the trigger 1267) and to the slide switch 1211, respectively, both illustrated in FIG. 1, as heretofore described.

Figure 14:
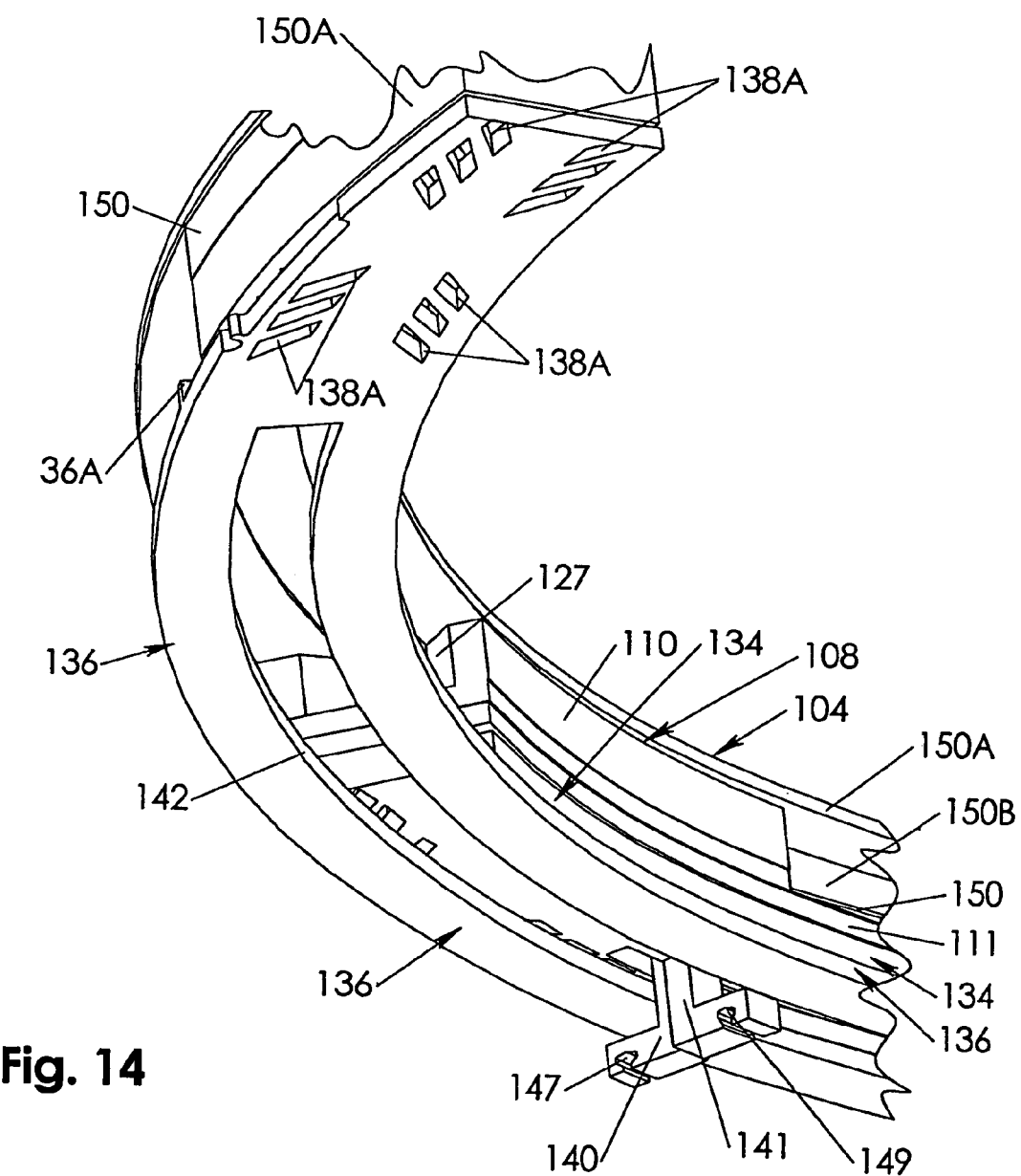
FIG. 14 is a bottom perspective view of one end of the drive direction setting plate, needle driver and fixed way (absent the fixed way housing 104A) combination illustrated in FIG. 13, along with one end of the fixed way direction setting plate element of the crescent.
Figure 15:
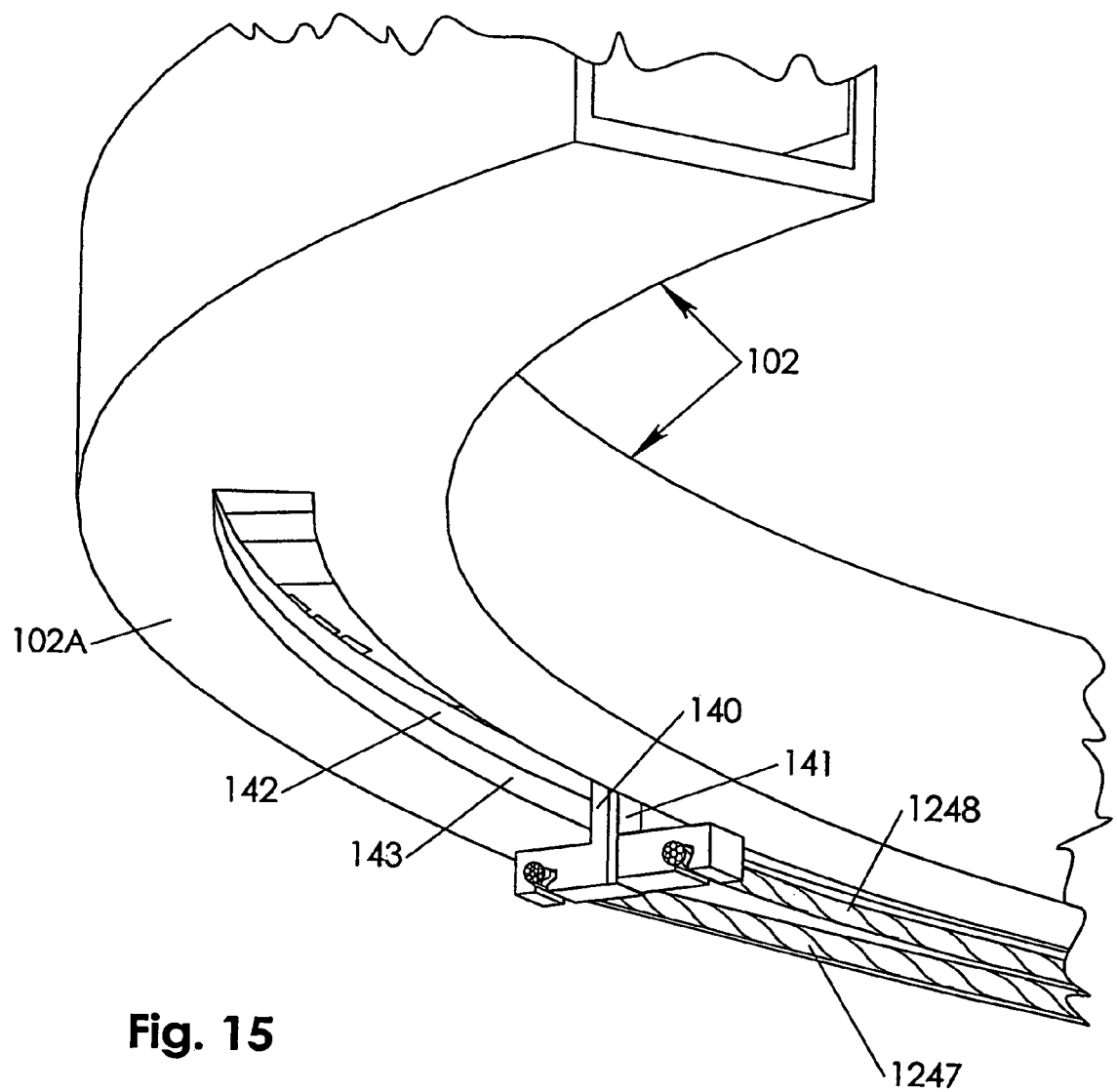
FIG. 15 is a bottom perspective view of the combination illustrated in FIG. 14 along with the case illustrated in FIG. 6, more particularly illustrating the downward extension of the drive access cable extension and the direction setting access cable extension, both projecting through a corresponding curved operating slot in the case and attached to cables for extension to the respective needle direction setting and drive controls provided on the operating device.

Referring now to FIGS. 13A, 14 and 15 of the drawings the reciprocating driver 108 and the drive direction setting plate 134 are illustrated as assembled and placed in assembled position beneath the fixed way 104, to illustrate the top assembly elements of the crescent 101. Furthermore, in FIG. 14 the fixed way direction setting plate 136 is added to the assembly of the drive direction setting plate 134, reciprocating driver 108 and fixed way 104. Moreover, in FIG. 15 of the drawings the case 102 is added to the assembly and one of the two drive access cable extensions 140, attached to the reciprocating driver 108 and one of the two direction access cable extensions 141, connected to the drive direction setting plate 134, project downwardly through a case clearance slot 142 in the case 102, with the drive cable 1247 and direction cable 1248 shown as crimped in place, respectively. The fixed way 104, once placed over the other internal parts, fixed way direction plate 136, drive direction plate 134 and driver 108, can typically be spot welded or otherwise attached to the case 102 for maintaining the assembled components in place.

Figure 16:
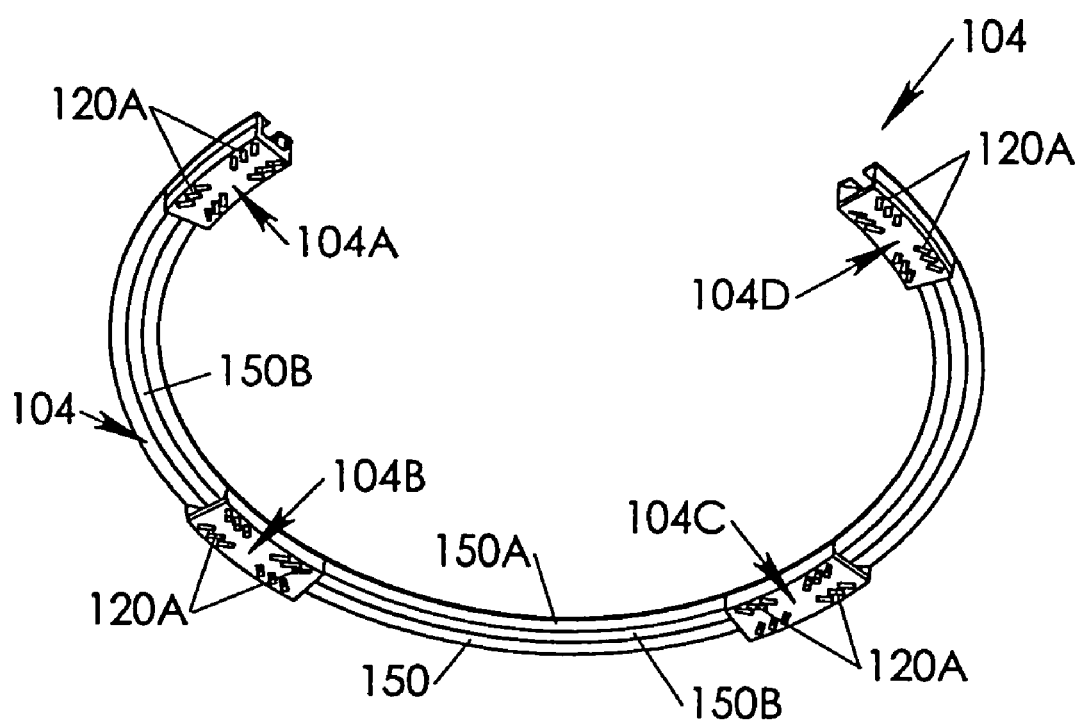
FIG. 16 is a bottom perspective view of the fixed way illustrated in FIG. 6.
Figure 17:
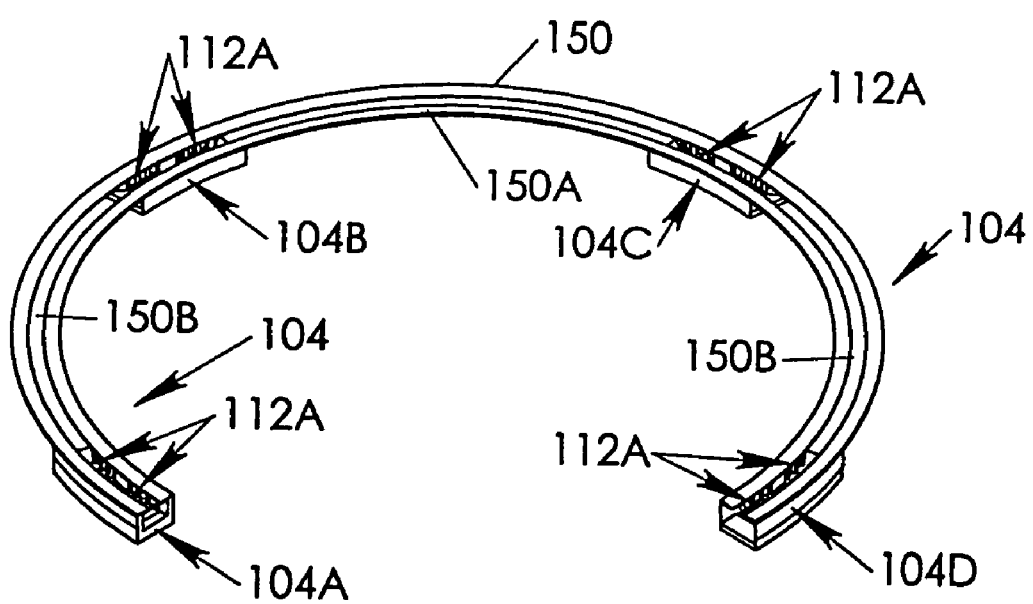
FIG. 17 is a top perspective view of the fixed way illustrated in FIG. 16.
Figure 18:
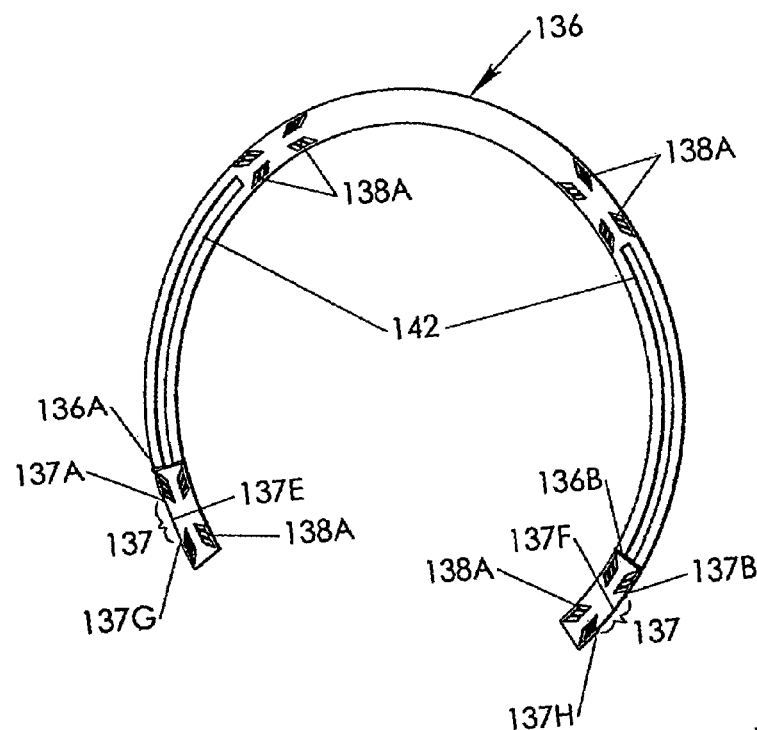
FIG. 18 is a top perspective view of the needle fixed way direction setting plate disposed between the drive direction setting plate and the case illustrated in FIG. 6.
Figure 18A:
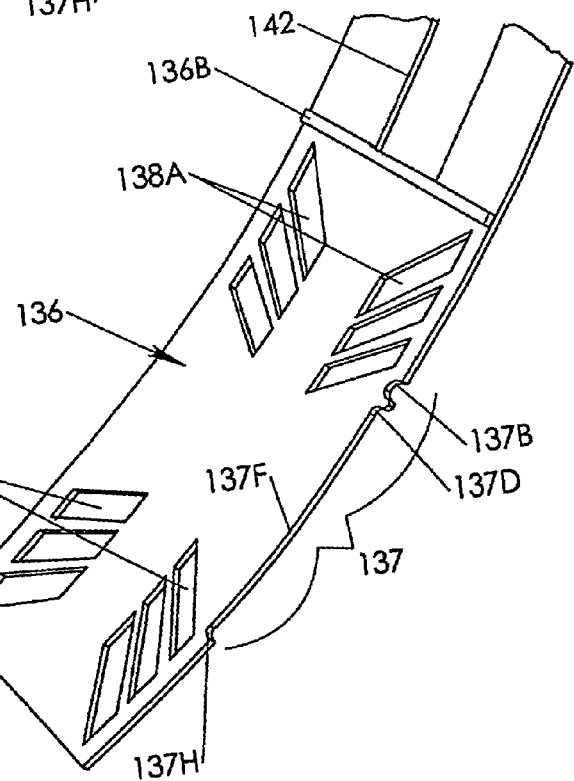
FIG. 18A is a top perspective view of one end of the needle fixed way direction setting plate illustrated in FIG. 18.
Figure 19:
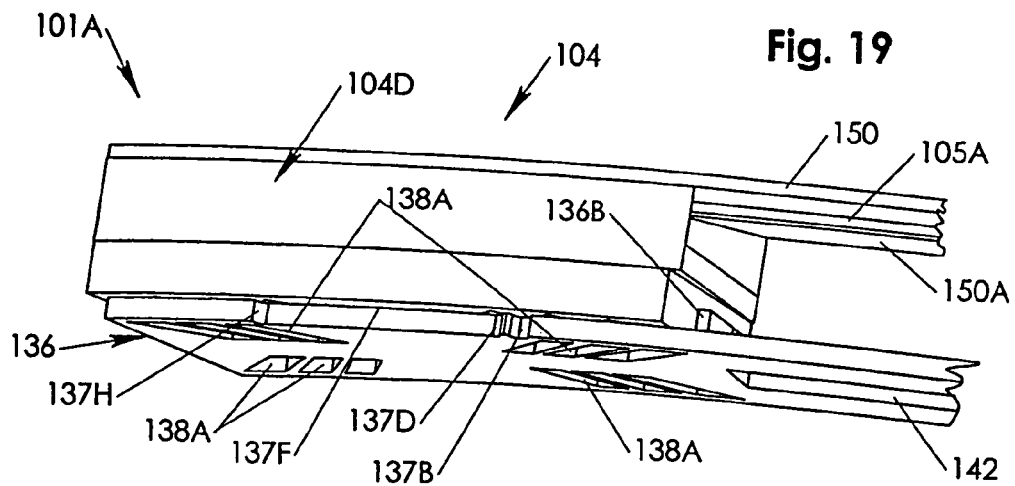
FIG. 19 is a perspective view of one end of the fixed way mounted on the needle fixed way direction setting plate, more particularly illustrating a typical entrance stop and range stop provided on the fixed way drive direction setting plate, for limiting its travel caused by motion of the drive direction setting plate's travel (not illustrated) in determining the direction of rotation of the needle.

Referring to FIGS. 6, 16 and 17 of the drawings the fixed way 104 is illustrated and includes overhead connecting members 150 and 150A, separated by a curved needle access slot 150B, with the fixed way housings 104A, 104B, 104C and 104D provided in spaced-apart relationship on the underside of the overhead connecting members 150 and 150A. Each of the fixed way housings 104A, 104B, 104C and 104D includes two sets of oppositely oriented, parallelogram-shaped fixed way blade mounting slots 122A, for receiving corresponding longer tabbed fixed way blades 112A, as hereinafter further described. As further illustrated in FIG. 6 the fixed way 104 is mounted in any desired manner, directly above the reciprocating driver 108 but not so tightly as to prevent the driver 108 from reciprocating. In this position the fixed way 104 receives the arcuate needle 50 in the needle access slot 150B, provided in the top of the fixed way 104 between the overhead connecting members 150 and 150A, for seating the needle 50 and accommodating the thread 50A without entangling the thread 50A as the needle 50 is incrementally driven around the fixed way 104 by operation of the reciprocating driver 108, as further hereinafter described.

As illustrated in FIGS. 6, 16, 18, 18A and 19 of the drawings the fixed way direction setting plate 136 is illustrated and is provided with oppositely-angled sets of fixed way direction setting plate parallelogram holes 138A, positioned in spaced-apart relationship around the curvature of the crescent-shaped fixed way direction setting plate 136 and vertically matching the fixed way blade clearance holes 124A in the fixed way 104. The sets of fixed way direction setting plate parallelogram holes 138A that are mounted on the extending ends of the fixed way direction setting plate 136 are terminated at the inside ends by upward-standing bosses 136A and 136B, respectively. Furthermore, detent notches 137, detents 137A and 137B, clearance recesses 137E and 137F and entrance stops 137C and 137D are shaped in the outside edges of each end segment of the fixed way direction setting plate 136 adjacent to the fixed way direction setting plate parallelogram holes 138A, respectively, as illustrated. These elements are instrumental in cooperating with the drive direction setting plate 134 and determining the direction of advancement of the needle 50 in the fixed way 104, as further hereinafter described. The fixed way direction setting plate 136 is also provided with a coplanar, curved, discontinuous fixed way direction setting plate slot 142 that extends between respective sets of the fixed way direction setting plate parallelogram holes 138A to accommodate the respective drive access cable extensions 140, extending from the overlying reciprocating driver 108 and the direction access cable extensions 141, projecting from the overlying drive direction setting plate 134, as further illustrated in FIG. 6B.

Figure 20:
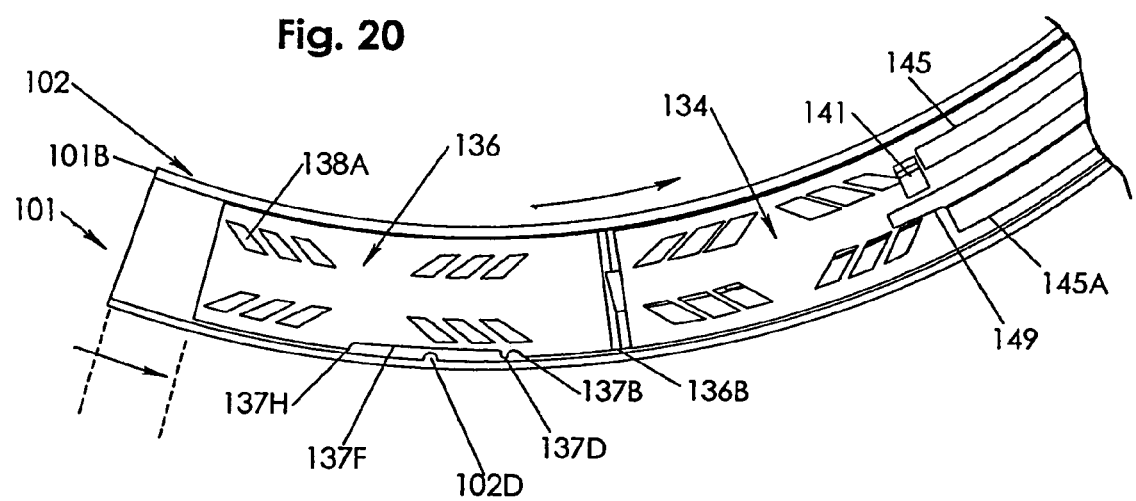
FIG. 20 is a top view of one end of the needle fixed way direction setting plate illustrated in FIG. 19, disposed on the case as illustrated in FIG. 6, more particularly illustrating a clockwise direction of motion of the needle drive direction setting plate with respect to the case for setting the fixed way direction plate in position to allow a counterclockwise direction of rotation of the needle in the crescent.

Referring now to FIGS. 6, 18, 18A, 19, 20, 21 and 38 of the drawings the drive direction setting plate 134 and the fixed way direction setting plate 136 are illustrated superimposed on the case 102, with the reciprocating driver 108 and the fixed way 104 omitted (FIGS. 20 and 21) to more particularly illustrate cooperation between the drive direction setting plate 134 and the fixed way direction setting plate 136 in determining the direction of needle rotation. FIG. 20 details the range stop 137H and the clearance recess 137F that extends from the range stop 137H, both located in a detent notch 137 (FIG. 19A) located on an outside extending edge of one end (typically the receiving arm 101B) of the fixed way direction setting plate 136, with the fixed way housing 104D of the fixed way 104 seated on the fixed way direction setting plate 136. A second range stop 137G and corresponding clearance recess 137E (FIG. 19) are provided in a corresponding detent notch 137 located on the opposite extending end (typically advancing arm 101A) of the fixed way direction setting plate 136 (FIG. 39). The boss 136B is also illustrated in upward-standing configuration on the end of the fixed way direction setting plate 136 illustrated in FIG. 19 and serves to interrupt travel of the fixed way direction setting plate 136 with respect to the fixed way 104, by contact with the fixed way housing 104D (FIG. 19), as hereinafter further described. Furthermore, the two sets of oppositely-oriented fixed way direction setting plate parallelogram holes 138A are also shown in the fixed way direction setting plate 136, along with an entrance stop 137D and corresponding detent 137B, both located at the opposite end of the clearance recess 137F (located in the detent notch 137) from the range stop 137H. As described above corresponding elements, including a second entrance stop 137C and detent 137A, as well as a boss 136A, are provided on the opposite end of the fixed way direction setting plate 136 and some of these elements are illustrated in FIG. 39.

Referring again to FIGS. 1, 8A, 8B, 19, 20, 21 and 30-39 of the drawings, shifting of the drive direction setting plate 134 and the fixed way direction setting plate 136 with respect to the fixed way 104 (not illustrated in FIGS. 20 and 21) to set or determine the direction of traverse of the needle 50 in the fixed way 104, is illustrated. As illustrated in FIGS. 8B, 20, 30-33, 38 and 39, when it is desired to drive the needle 50 in the clockwise direction on the fixed way 104 (illustrated in sequence in FIGS. 30-33) by operation of the reciprocating driver 108 in a suturing operation, the drive direction setting plate 134 is first shifted to contact the boss 136A of the fixed way direction setting plate 136 (FIGS. 32, 33 and 38) by operation of the slide switch mount body 1211 (FIG. 1). This action moves the fixed way direction setting plate 136 in the direction of the arrow 134A in FIG. 8B and the arrows illustrated in FIGS. 20 and 38, and bends the rearwardly-inclining driver blades 112C in each of the blade group housings 110, 110A and 110B of the needle driver 108 into contact with the needle 50 (FIG. 8B) to align the detent 137C and the fixed case boss 102C, located on the lower portion of the outer wall of the underlying case 102 (FIG. 38). As further illustrated in FIG. 38 the fixed case boss 102C rides in the moving clearance recess 137E between the range stop 137G and the detent 137A. Accordingly, the drive direction setting plate 134 is shifted in the direction of the top arrow in FIG. 21, and as indicated by the bottom arrow 134A in FIG. 8B, is moved with respect to the underlying case 102 (FIG. 21), until the case boss 102C (illustrated in FIGS. 38-39 rides over the entrance stop 137C and seats in the detent 137A (FIG. 39) in the fixed way direction setting plate 136. The device is now set for incrementing the needle 50 in the clockwise direction, as hereinafter described.

Figure 21:
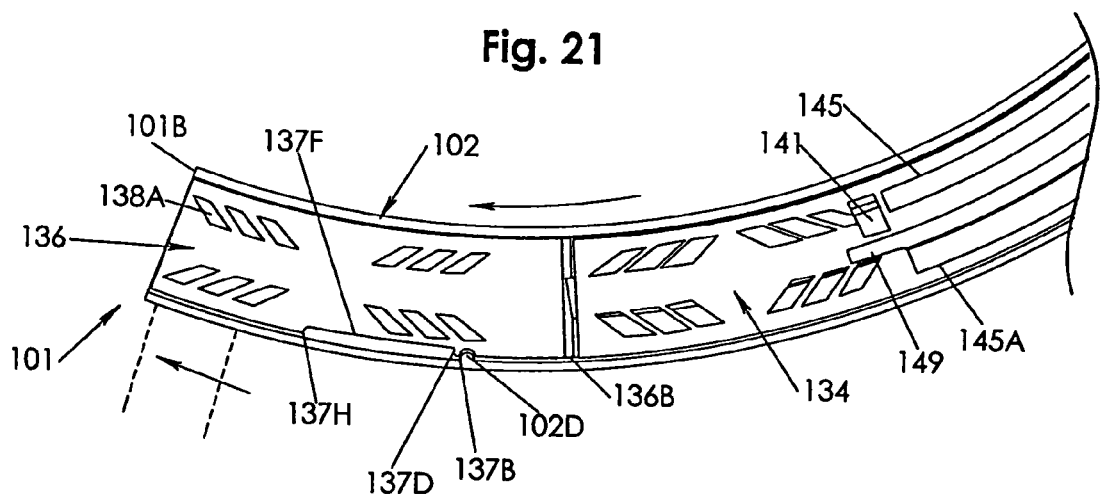
FIG. 21 is a top view of one end of the needle drive direction setting plate illustrated in FIG. 20, more particularly illustrating the fixed way drive direction plate set into a counterclockwise allowing position with respect to the rotation of the needle in the crescent.

Referring now to FIGS. 8A, 21 and 34-37 of the drawings shifting of the drive direction setting plate 134 in the clockwise direction as indicated by the top arrow in FIG. 21 moves the fixed way direction setting plate 136 in the clockwise direction, as the forwardly inclining driver blades 112B in each of the blade group housing 110, 110A and 110B of the needle driver 108 bend to contact the needle 50 (FIG. 8A) and the drive direction setting plate 134 contacts the boss 136B and causes the case boss 102D to engage the moving entrance stop 137D at the opposite end of the clearance recess 137F from the range stop 137H and move over the entrance stop 137D, to seat in the moving detent 137B (FIG. 21). This action terminates movement of the fixed way direction setting plate 136 and facilitates driving of the needle 50 (not illustrated) in the opposite, or counterclockwise direction on the fixed way 104 by operation of the reciprocating driver 108, as hereinafter described.

Figure 22:
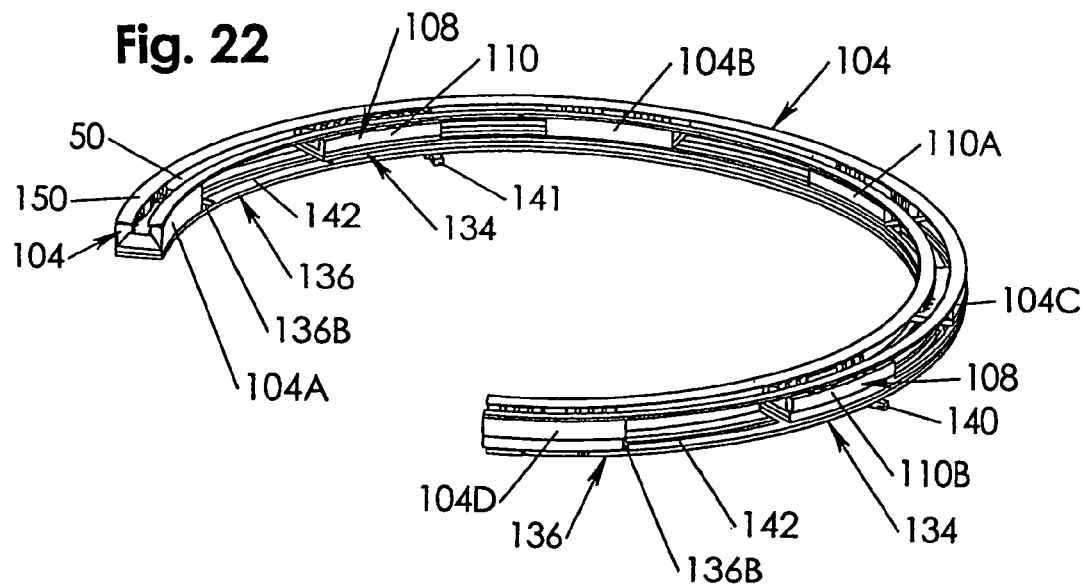
FIG. 22 is a top perspective view of the fixed way, needle driver, needle drive direction setting plate and the fixed way direction setting plate illustrated in FIG. 6, more particularly illustrating assembly of these components.
Figure 22A:
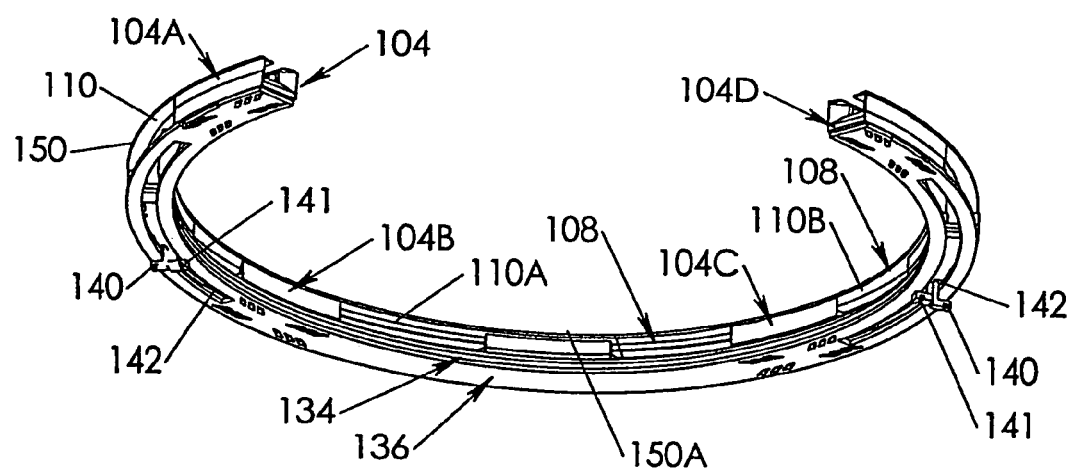
FIG. 22A is a bottom perspective view of the assembled fixed way, needle driver, needle drive direction setting plate and the fixed way direction setting plate assembly illustrated in FIG. 22.

Referring again to FIGS. 22, 22A and 23 of the drawings the fixed way direction setting plate 136, drive direction setting plate 134, reciprocating driver 108 and fixed way 104 are shown in assembled configuration, with the respective pairs of drive access cable extensions 140 and direction setting access cable extensions 141, respectively, illustrated in position extending through the fixed way direction setting plate slot 142 in the fixed way direction setting plate 136 (FIGS. 22A and 23). FIG. 23 further illustrates the proximity of the longer tabs 118A of the longer tabbed fixed way blades 112A, secured in the fixed way housings 104A, 104B, 104C and 104D, respectively, in the same manner as the driver blades 112 in the reciprocating driver 108. The longer tabbed fixed way blades 112A illustrated in FIG. 24 extend through the blade clearance slots 120 in the fixed way housing 104A of the fixed way 104 and into-corresponding fixed way direction setting plate parallelogram holes 138A in the fixed way direction setting plate 136. The needle 50 is also shown in position in the reciprocating driver, 108 and the fixed way 104, and the blade group housing 110 of the reciprocating driver 108 is illustrated in close proximity to the fixed way housing 104A, with one end of the drive direction setting plate 134 resting against the corresponding boss 136A on the underlying fixed way direction setting plate 136. Accordingly, as further illustrated in bottom perspective in FIG. 24, the needle 50 is set for clockwise incrementation as viewed from the bottom. As contact between the drive direction plate 134 and the boss 136A has shifted the fixed way direction setting plate 136 in the opposite, or counterclockwise direction, as described above. The longer tabbed fixed way blades 112A are bent as the corresponding longer tabs 118A are contacted by the slanted or angled parallelogram sides 139 of the respective fixed way direction setting plate parallelogram holes 138A and the blades engage the needle 50 to stabilize the needle 50 and prevent reverse incrementation of the needle 50 during operation of the device.

Figure 26:
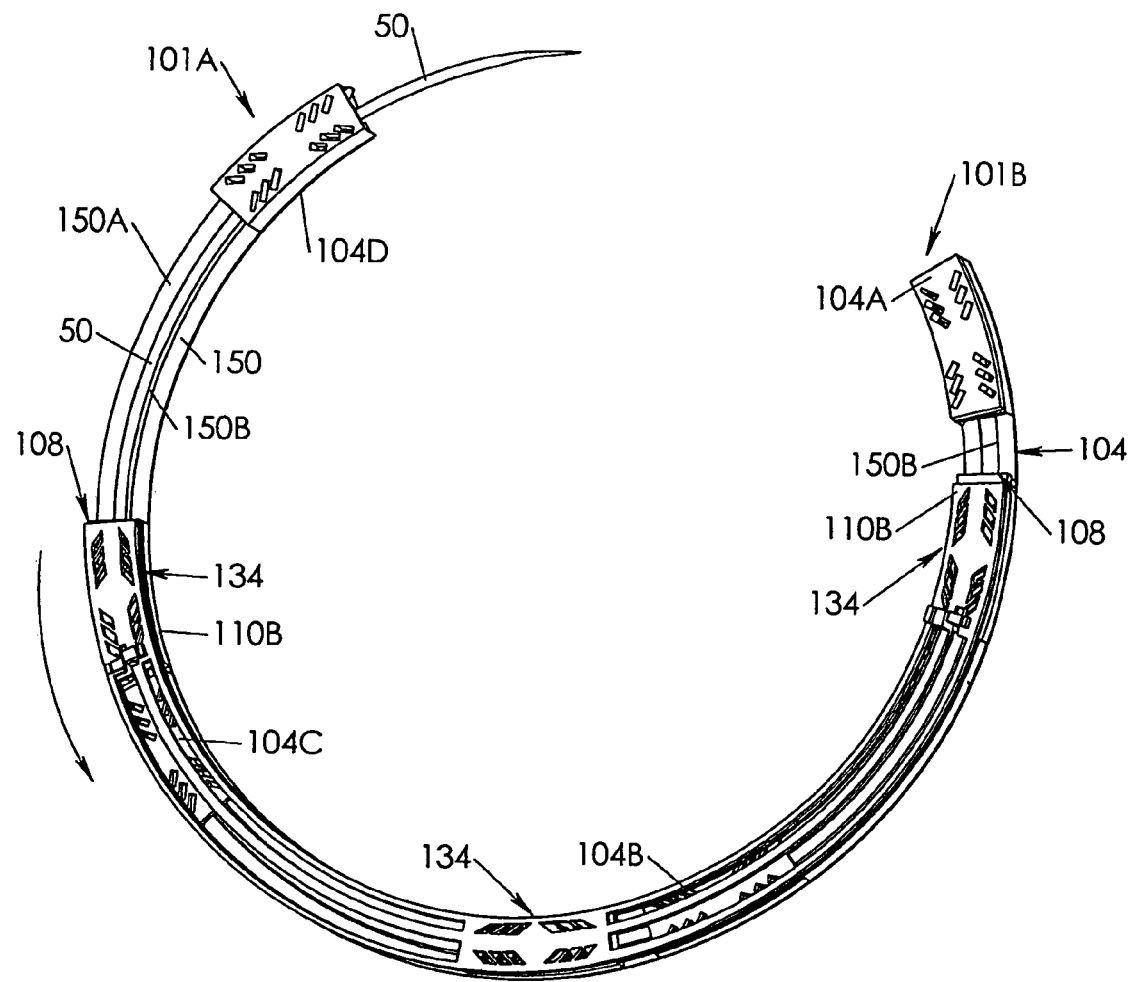
FIG. 26 is a perspective bottom view of the assembled drive direction setting plate, needle driver and fixed way, with the drive direction setting plate and needle driver reversed in direction from that illustrated in FIG. 25 and the needle released by the needle driver, to a position for beginning a second incremental rotation of the needle into the crescent slot.
Figure 27:
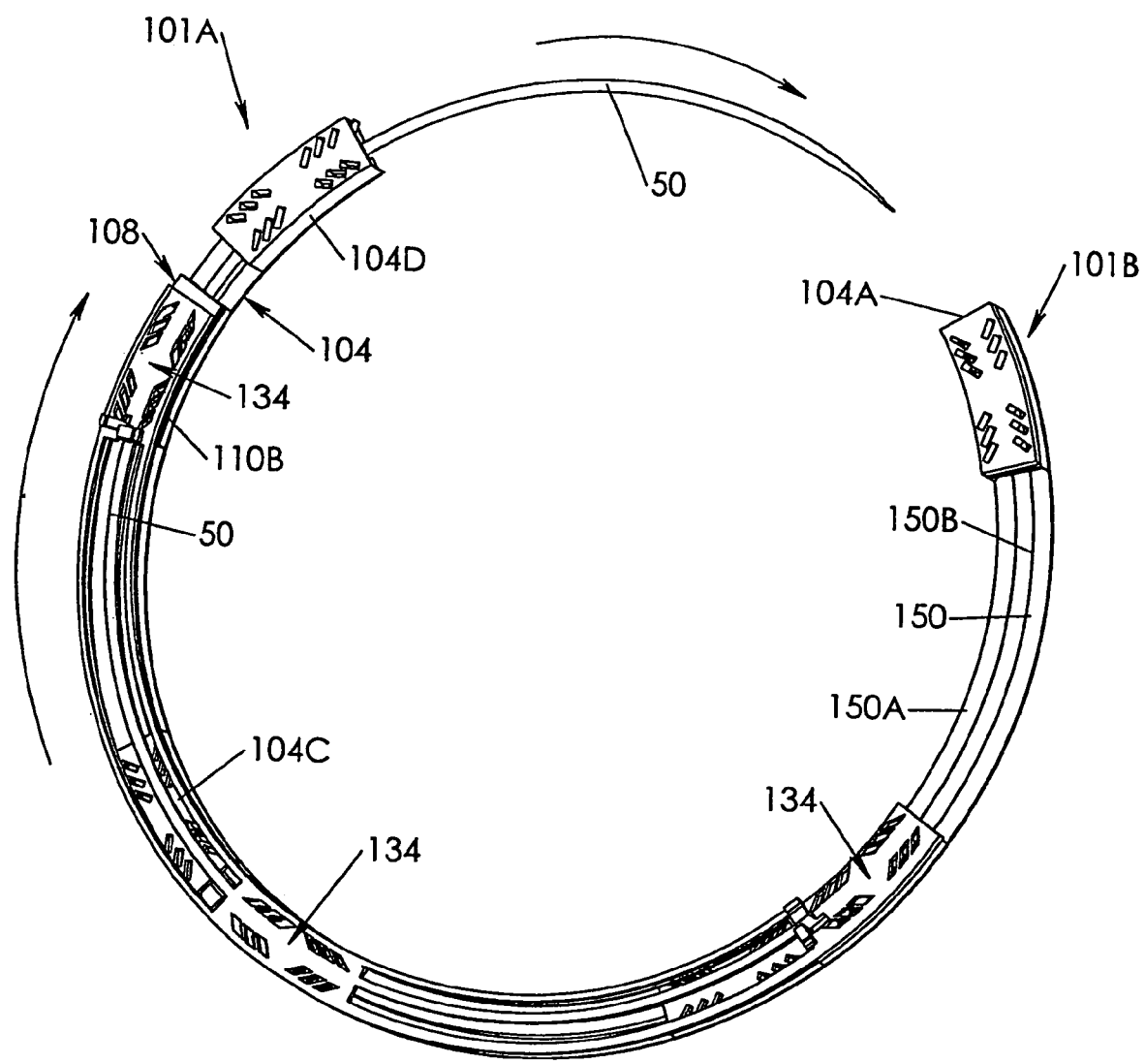
FIG. 27 is a perspective bottom view of the assembled drive direction setting plate, needle driver and fixed way, more particularly illustrating sequential reversal of the direction of rotation of the needle driver and the drive direction setting plate and engagement of the needle by the needle driver, for another incremental rotation of the needle into the crescent slot.
Figure 28:
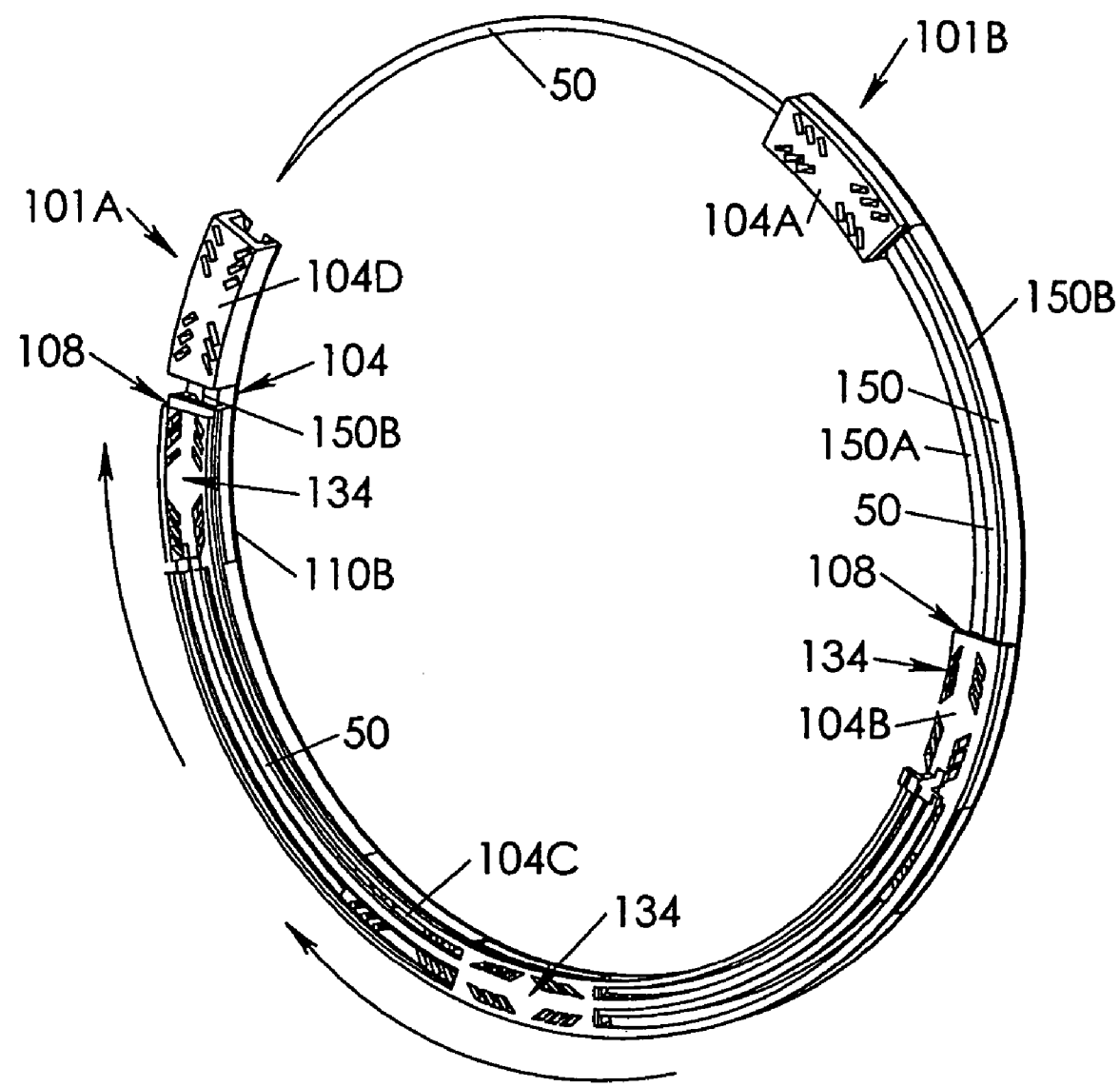
FIG. 28 is a bottom perspective view of the assembled drive direction setting plate, needle driver and fixed way, more particularly illustrating an additional incremental rotation of the drive direction setting plate to extend the needle around the crescent and through the crescent slot.
Figure 29:
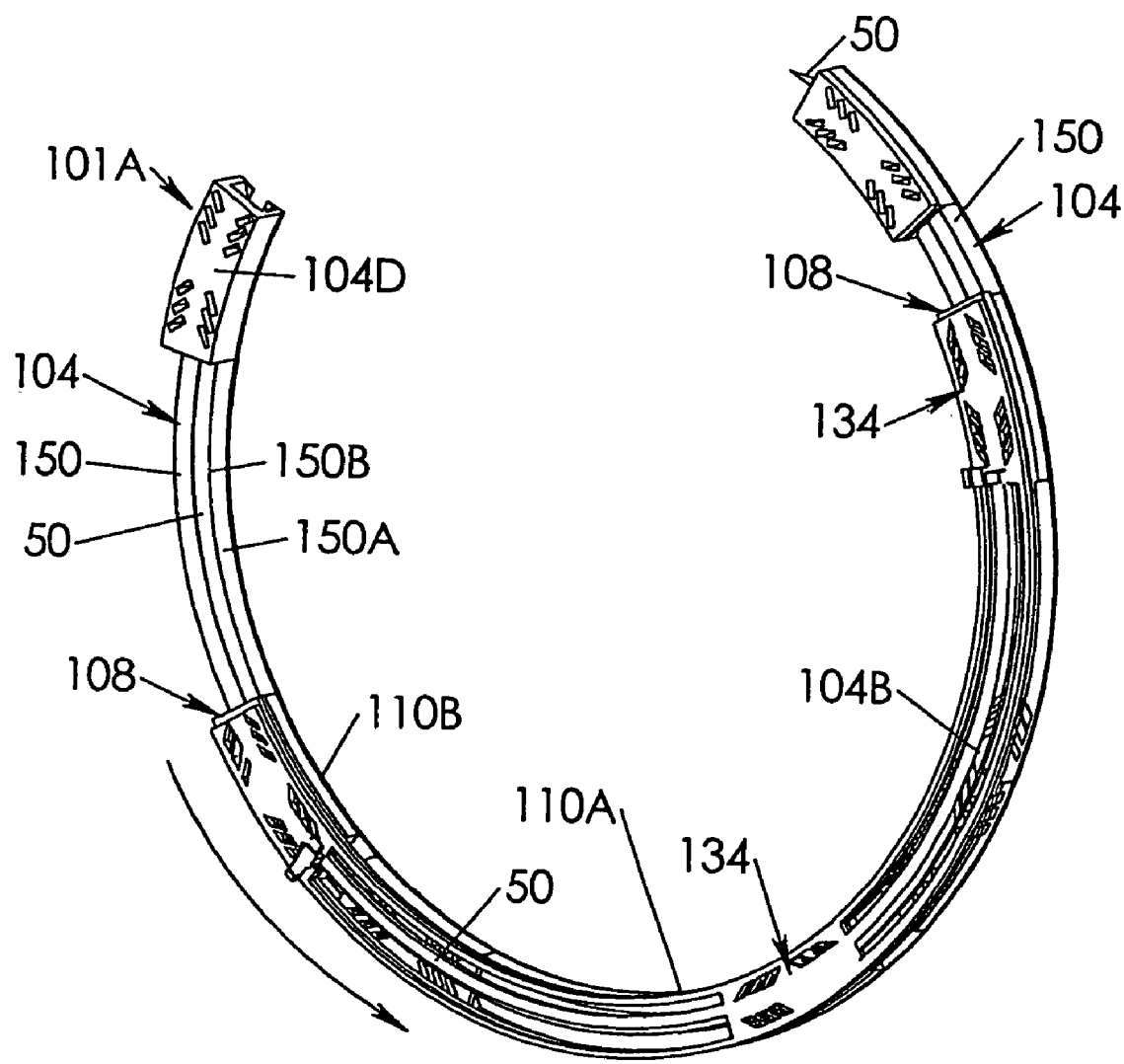
FIG. 29 is a bottom perspective view of the assembled drive direction setting plate, needle driver and fixed way, wherein the drive direction setting plate and the needle driver have been reversed and the needle released for a final incremental driving of the needle back to the position illustrated in FIG. 24.
Figure 32:
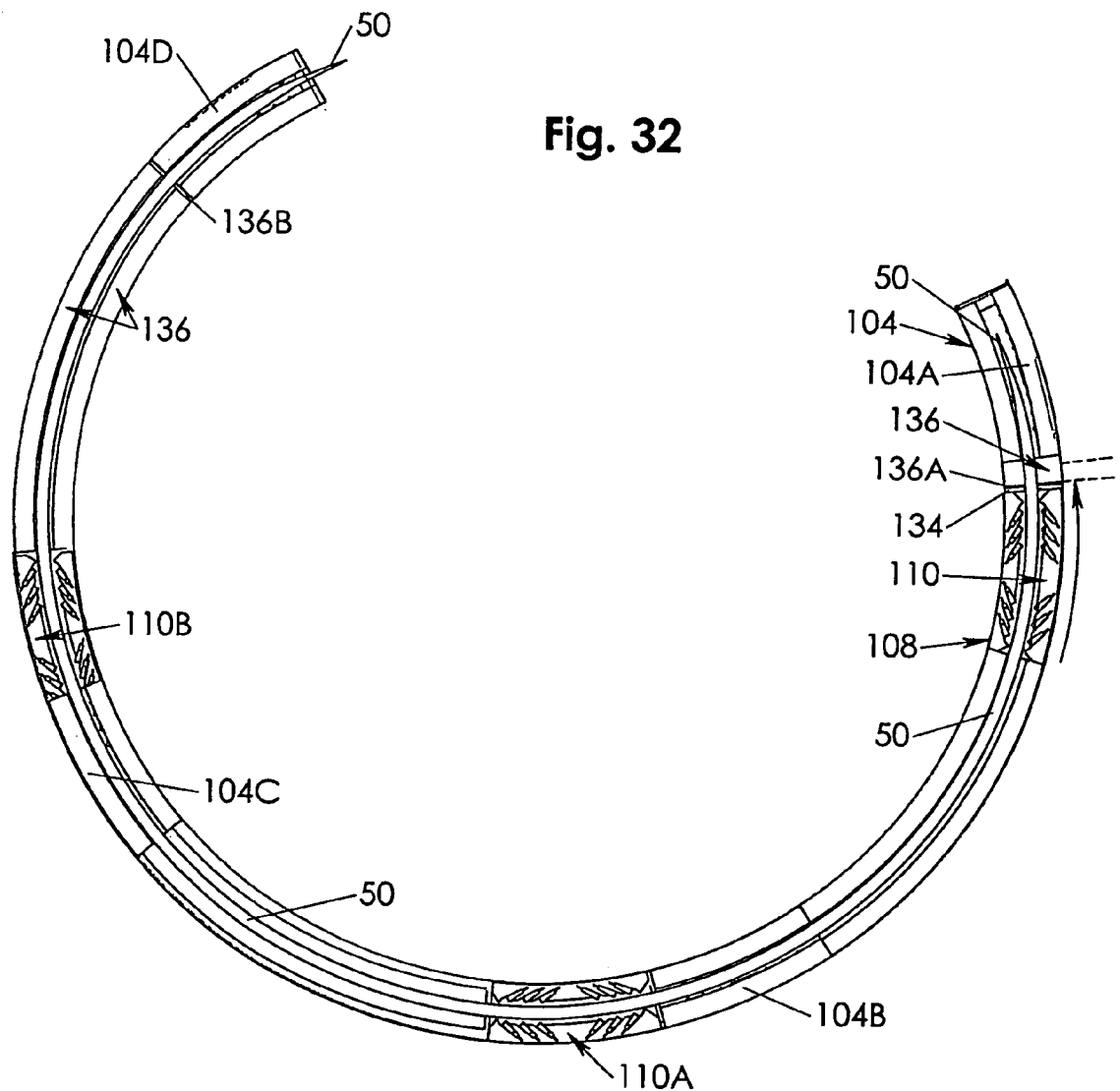
FIG. 32 is a top view of the fixed way direction setting plate and the drive direction setting plate superimposed on the bottom of the needle driver and the fixed way illustrated in FIG. 31, illustrating incremental motion in one direction of the needle driver, the drive direction setting plate and the fixed way direction setting plate with respect to the fixed way.
Figure 33:
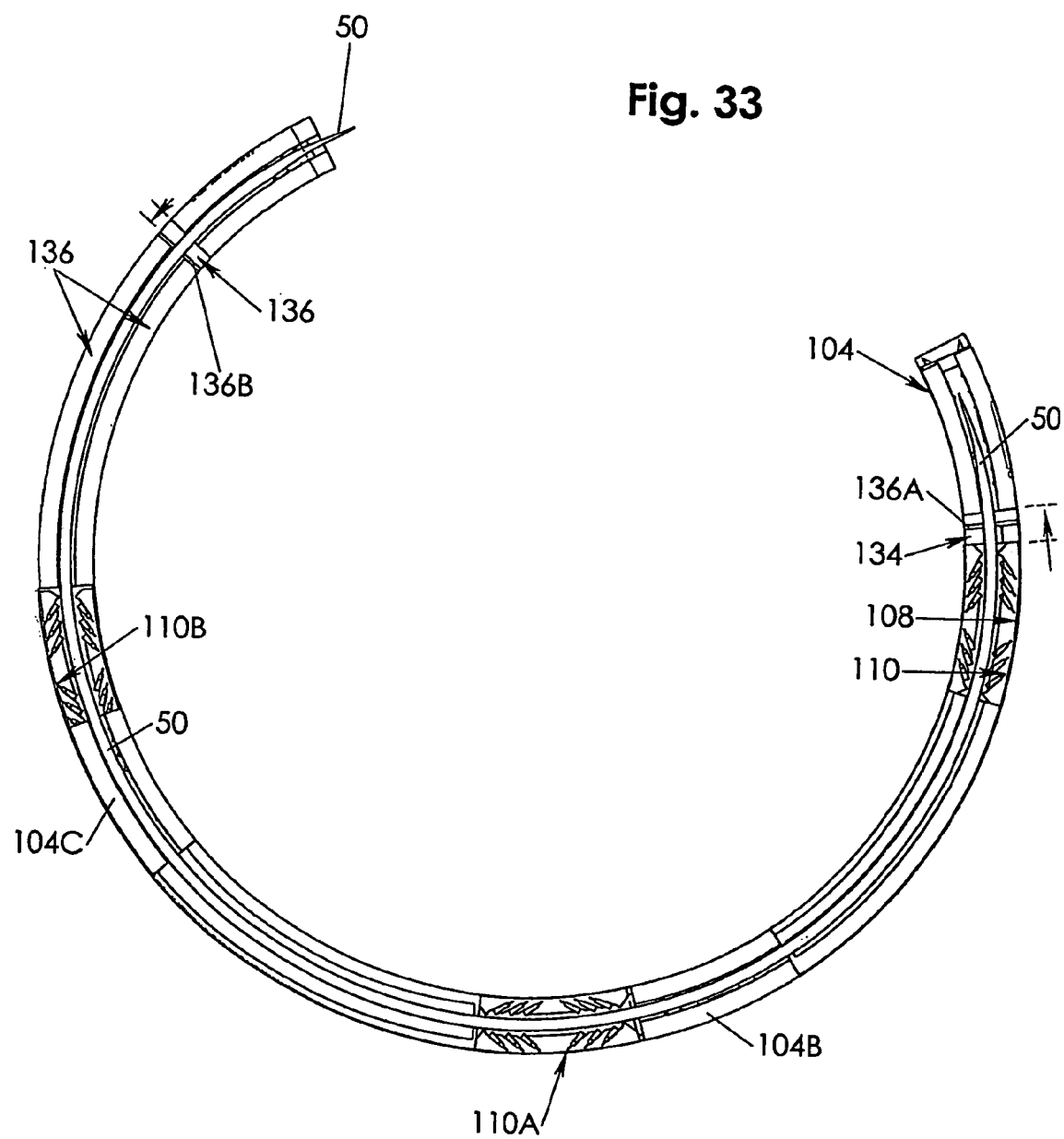
FIG. 33 is a top view of the fixed way direction setting plate and the drive direction setting plate superimposed on the bottom of the needle driver and the fixed way illustrated in FIG. 32, further illustrating the final position of the fixed way direction setting plate with respect to the fixed way for determining the clockwise direction of needle rotation.
Figure 34:
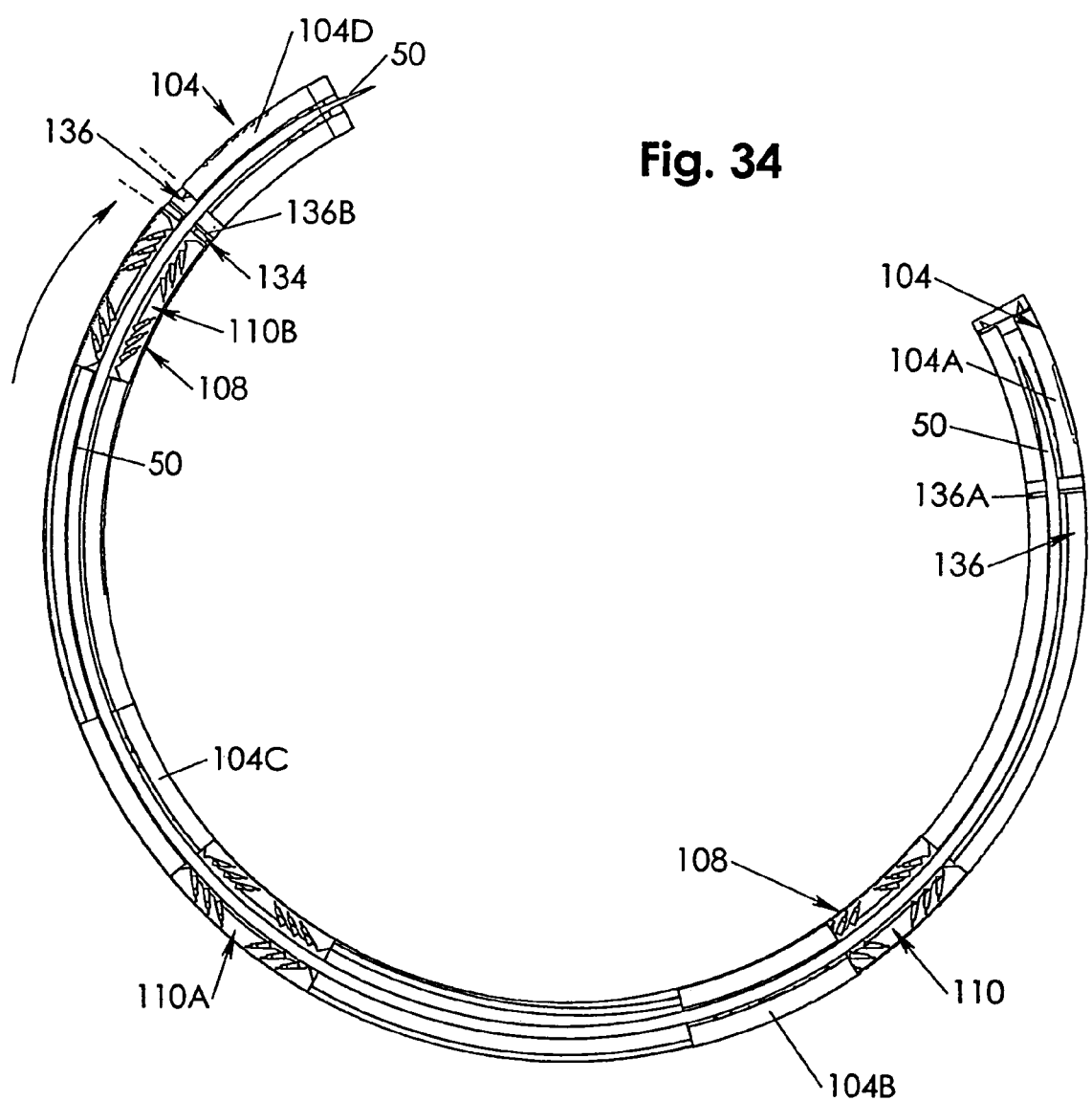
FIG. 34 is a top view of the fixed way direction setting plate and the drive direction setting plate superimposed on the bottom of the needle driver and the fixed way illustrated in FIGS. 30-33, illustrating reverse incremental motion of the drive direction setting plate and the fixed way direction setting plate with respect to the fixed way for reversing rotation of the needle in the crescent.
Figure 35:
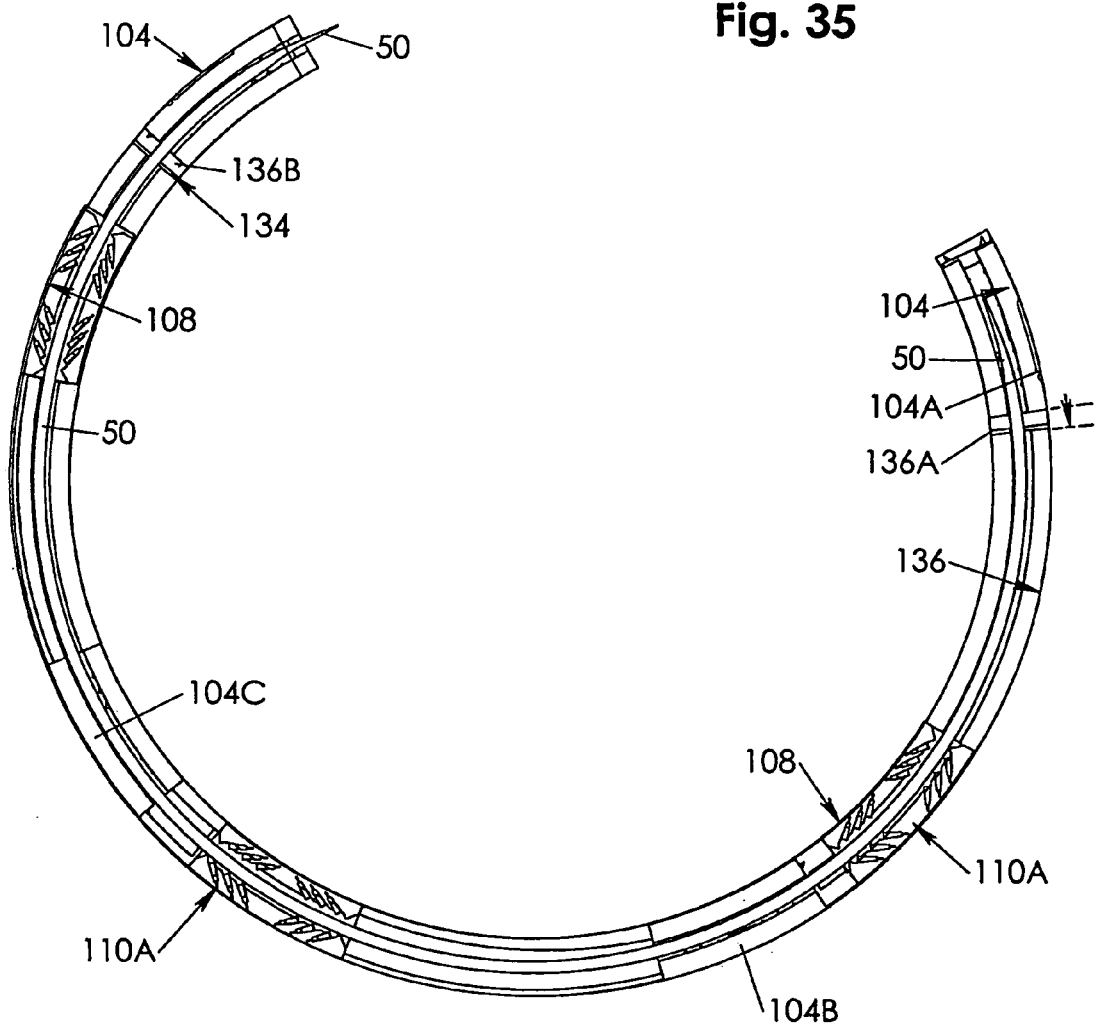
FIG. 35 is a top view of the fixed way direction setting plate and the drive direction setting plate superimposed on the bottom of the needle driver and the fixed way illustrated in FIGS. 30-34, further illustrating the final position of the drive direction setting plate and the fixed way direction setting plate with respect to the fixed way for determining the counterclockwise direction of needle rotation.

FIGS. 20, 21, 24-29 and 39 of the drawings illustrate an operational sequence of the rotation of the needle 50 in the clockwise direction as seen from the bottom (FIGS. 24-29) responsive to operation of the reciprocating driver 108 superimposed on the drive direction setting plate 134, with the needle 50 placed in the reciprocating driver 108 and extending into the needle access slot 150B, defined by the overhead connecting members 150 and 150A. The drive direction setting plate 134 is initially positioned as illustrated in FIGS. 20 and 39, with the blade group housing 110 of the reciprocating driver 108 near the corresponding fixed way housing 104A and the blade group housing 110B in the reciprocating driver 108 spaced from the corresponding fixed way housing 104D in the fixed way 104 (FIG. 24). The drive direction setting plate 134 has previously been manipulated by operation of the two direction setting access cable extensions 141 to the position illustrated in FIGS. 20 and 39 to set the fixed way direction setting plate 136 as illustrated and facilitate rotation of the needle 50 in the clockwise direction responsive to incremented traversal of the reciprocating driver 108 and the drive direction setting plate 134 in concert on the fixed way 104. When the blade group housing 110B approaches the fixed way housing 104D in the fixed way 104 as illustrated in FIG. 25, the needle 50, gripped by the reciprocating driver 108, is driven along the fixed way 104 to project outwardly of the fixed way housing 104D, as further illustrated in FIG. 25. At the point of—maximum traversal of the reciprocating driver 108 with respect to the fixed way 104, the needle 50 is released by reversal of the reciprocating driver 108 and held in place by the rearwardly-inclined fixed way blades 112D in the fixed way 104. As the reciprocating driver 108 is re-incremented in the counterclockwise direction, illustrated in FIG. 26, the needle 50 in the position illustrated in FIGS. 25 and 26 is released. The reciprocating driver 108 is thus returned to the position illustrated in FIGS. 24 and 26 for another sequence of grasping and rotating the needle 50 around the fixed way 104. Continued sequential rotation of the needle 50 is effected by additional incremental forward and backward traversal of the driver 108 on the fixed way 104 to the position illustrated in FIGS. 27 and 28, such that the needle 50 is driven progressively around the periphery of the fixed way 104 and through the gap 105 (FIG. 6) defined by the fixed way housings 104D and 104A, respectively. Accordingly, when the reciprocating driver 108 reaches the position illustrated in FIG. 27, the reciprocating driver 108 again releases the needle 50 and reverses to the position illustrated in FIG. 24, leaving the needle 50 in the advanced position illustrated in FIG. 27. As the reciprocating driver 108 is caused to make another sequential movement around the fixed way 104 as illustrated in FIG. 28, the needle 50 is driven completely across the gap 105 between the fixed way housing 104D and the fixed way housing 104A, such that the trailing end of the needle 50 is illustrated in close proximity to the fixed way housing 104D. The reciprocating driver 108 is then returned again to the position illustrated in FIG. 24 and in FIG. 29 after releasing the needle 50, for another gripping of the needle 50 and driving the needle 50 sequentially around the fixed way 104 in the clockwise direction.

Figure 37:
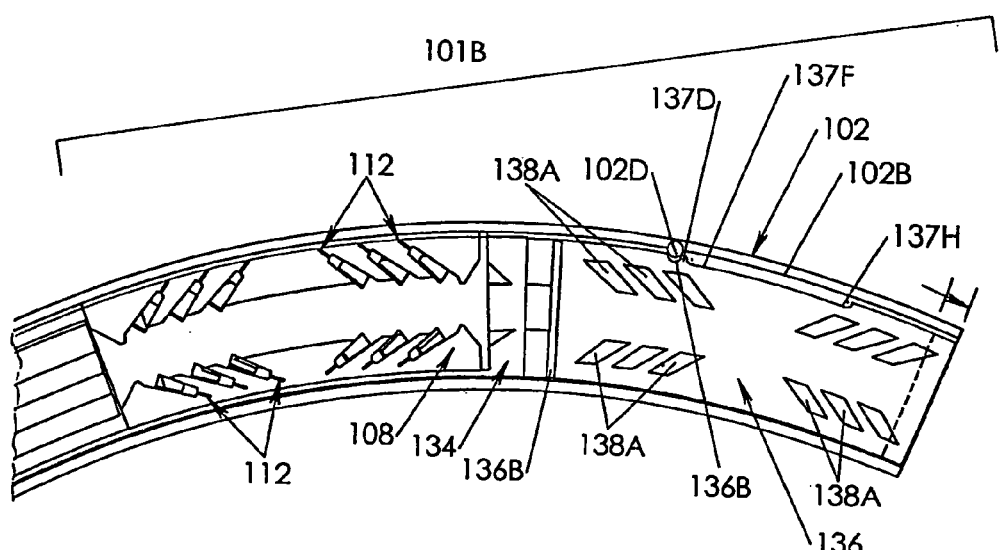
FIG. 37 is a top view of the needle driver, the drive direction setting plate, the fixed way direction setting plate and the case illustrated in FIG. 36, more particularly illustrating engagement of a case boss with a detent in the fixed way direction setting plate for determining counterclockwise travel of the needle with respect to the case.
Figure 38:
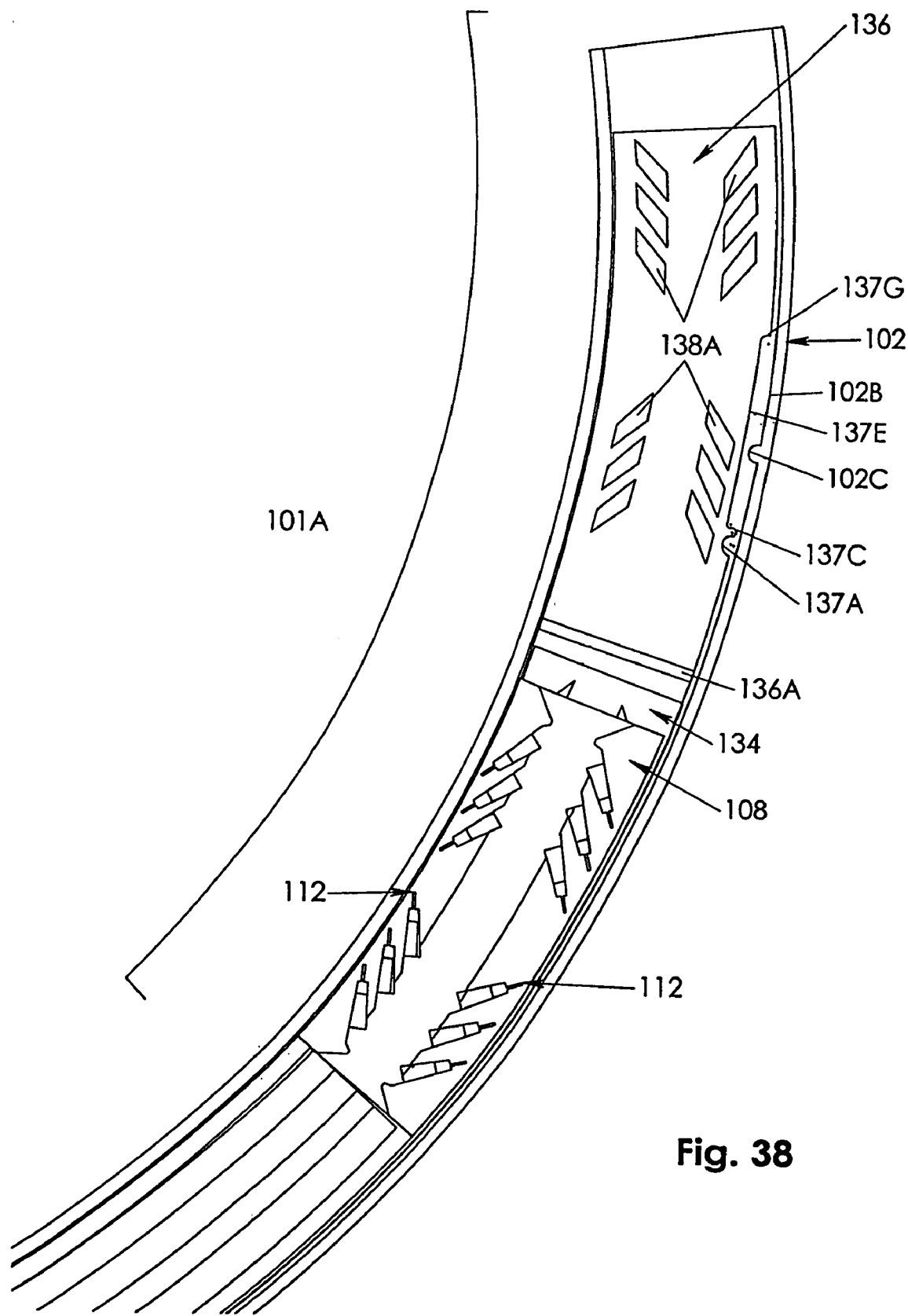
FIG. 38 is a top view of the opposite end of the needle driver, the needle drive direction setting plate, the fixed way direction setting plate and the case, further illustrating the travel relationship between the fixed way direction setting plate with respect to the case to set the needle rotation in the clockwise direction.

Under circumstances where it is desired to drive the needle 50 in the fixed way 104 in the opposite or counterclockwise direction, the drive direction setting plate 134 is positioned as illustrated in FIGS. 21 and 37 and as heretofore described, to set the fixed way direction setting plate 136 in the opposite position on the case 102 by contacting the drive direction setting plate 134 with the boss 136B. This motion causes the case boss 102D to engage the moving entrance stop 137D at the opposite end of the clearance recess 137F from the range stop 137H and move over the entrance stop 137D to seat in the moving detent notch 137B. The action terminates movement of the fixed way direction setting plate 136 in the direction of the arrow (FIG. 21). This reverses the operational sequence described above in FIGS. 24-29 and facilitates driving of the needle 50 in the opposite, counterclockwise direction, as seen from below in the above sequence on the fixed way 104 in reversing the operational sequence described above and illustrated in FIGS. 24-29 of the drawings.

Figure 40A:
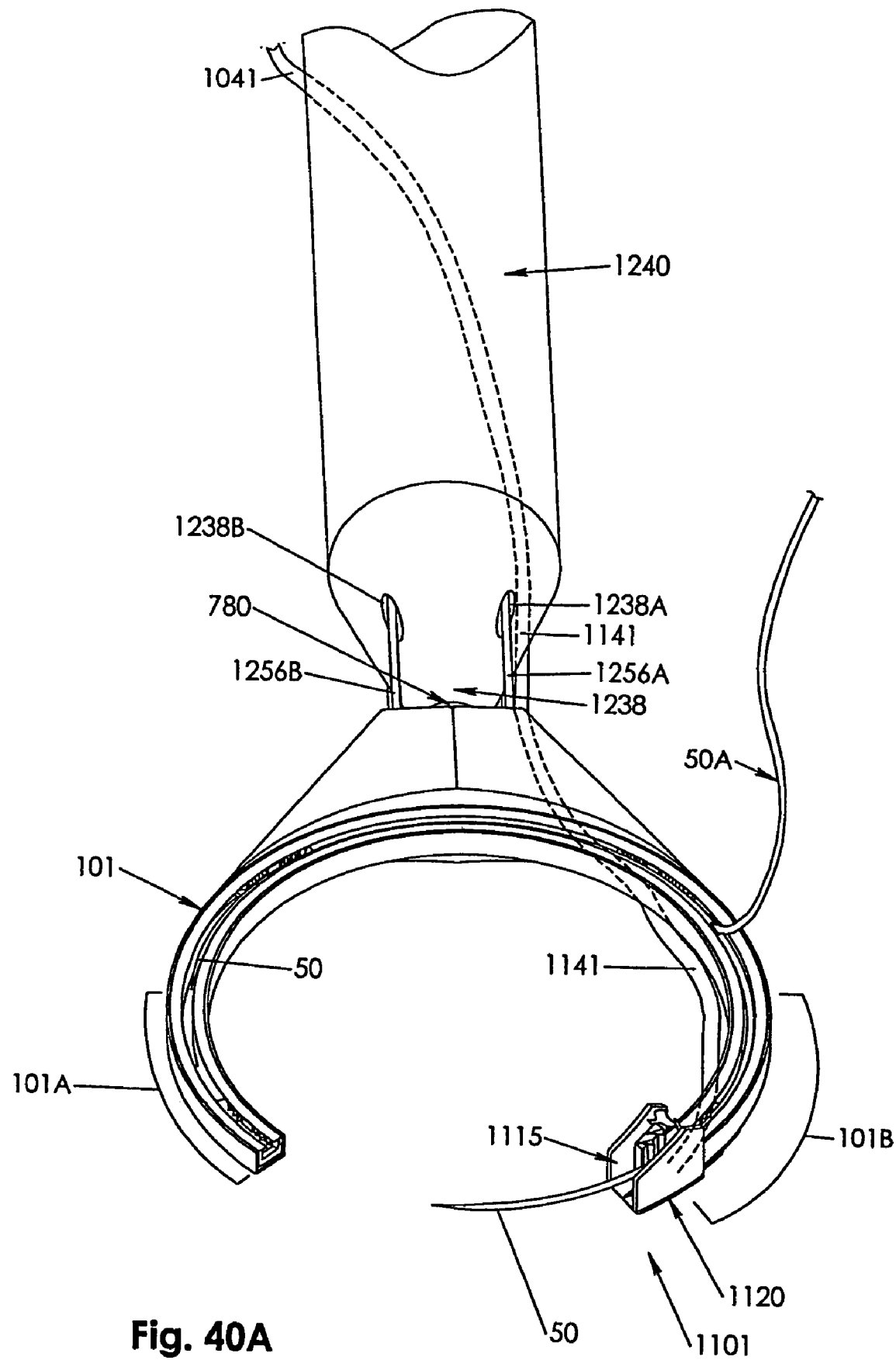
FIG. 40A is a top and front perspective view of the crescent and extension tube mount illustrated in FIG. 40, more particularly illustrating the positioning of a length of thread on the midpoint of the curved needle and a thread incrementing accessory mounted on one end of the crescent to increment and handle the thread.

Referring now to FIGS. 1, 40 and 40A of the drawings the underside of the assembled crescent 101 is illustrated (FIG. 40) with the case 102 fixed to the socket 775 and the joint ball 780 operatively connected to the socket 775 to facilitate universal articulation of the crescent 101 with respect to the joint ball 780 and the transmission tube 1200 by operation of the crescent angle articulation cables 1256A, 1256B, 1256C and 1256D, as illustrated in FIGS. 40 and 40A. As heretofore described, the crescent angle articulation cables 1256A, 1256B, 1256C and 1256D extend from fixed attachment to the socket 775, through transition guide cone openings 1238A, 1238B, 1238C and 1238D, respectively, in the transition guide cone 1238. From that point, the crescent angle articulation cables 1256A, 1256B, 1256C and 1256D extend through the extension tube 1240 and through the transmission tube 1200 to the selection bearing socket 1253 and the lever 1251 (FIG. 1) as hereinafter further described. As further illustrated in FIGS. 40 and 40A, a thread incrementing accessory 1101 is provided on one end of the crescent 101 for the purpose of manipulating and incrementing the thread 50A attached to the needle 50 as the needle 50 traverses the crescent 101, as further hereinafter described.

Figure 41:
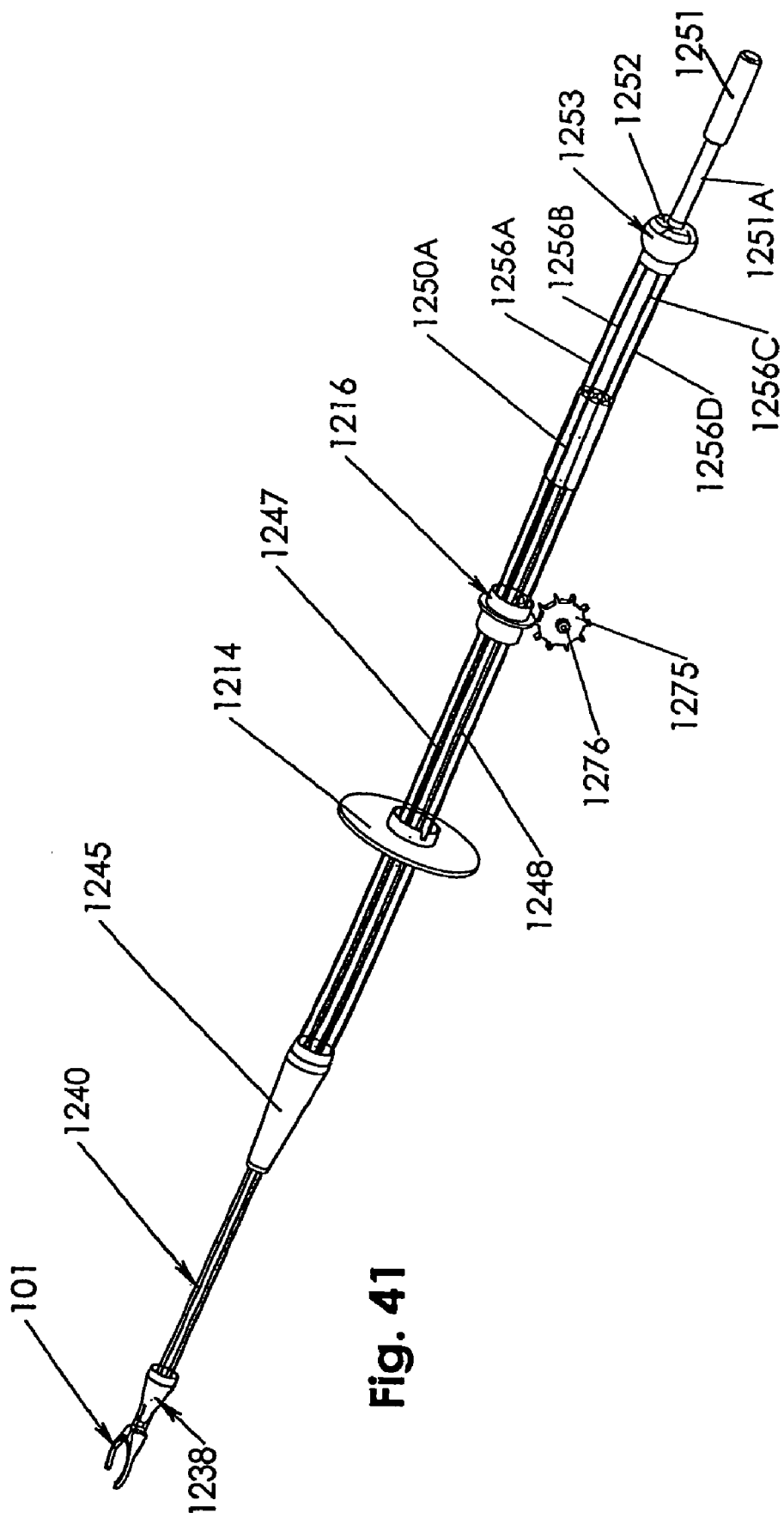
FIG. 41 is a perspective view of the cyclic suturing and knot-tying operating device illustrated in FIGS. 1-4, more particularly illustrating typical cable arrangements extending through the transmission tube, the extension tube and the transition guide cone from the lever to the crescent, for articulating the crescent on the end of the transition guide cone and controlling operation of the needle driver, the needle drive direction setting plate and the fixed way direction setting plate in the crescent.
Figure 42:
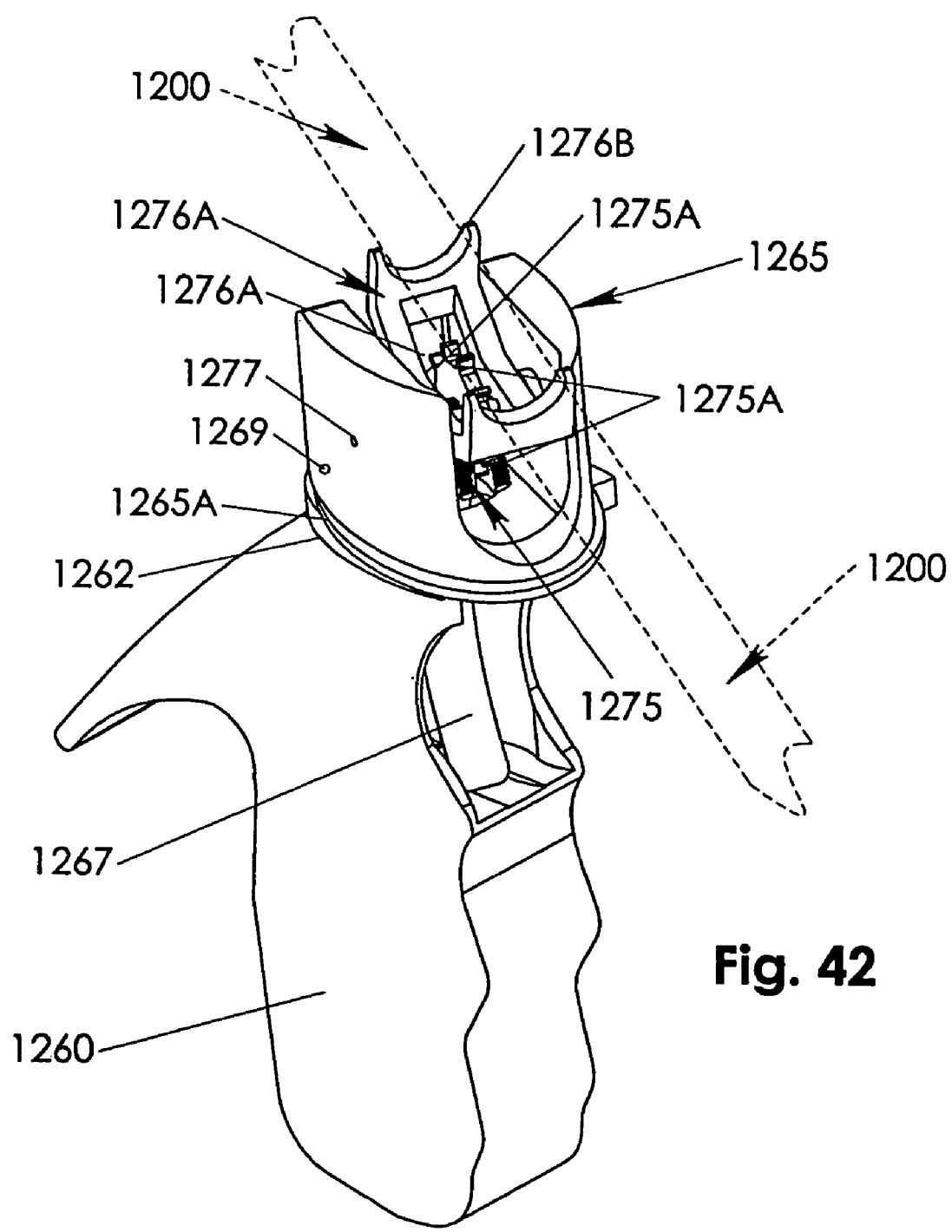
FIG. 42 is a perspective view of the handle element of the operating device illustrated in FIGS. 1-4, more particularly illustrating the handle trigger, housing and cradle elements, the cradle of which receives the transmission tube, illustrated in phantom.
Figure 43:
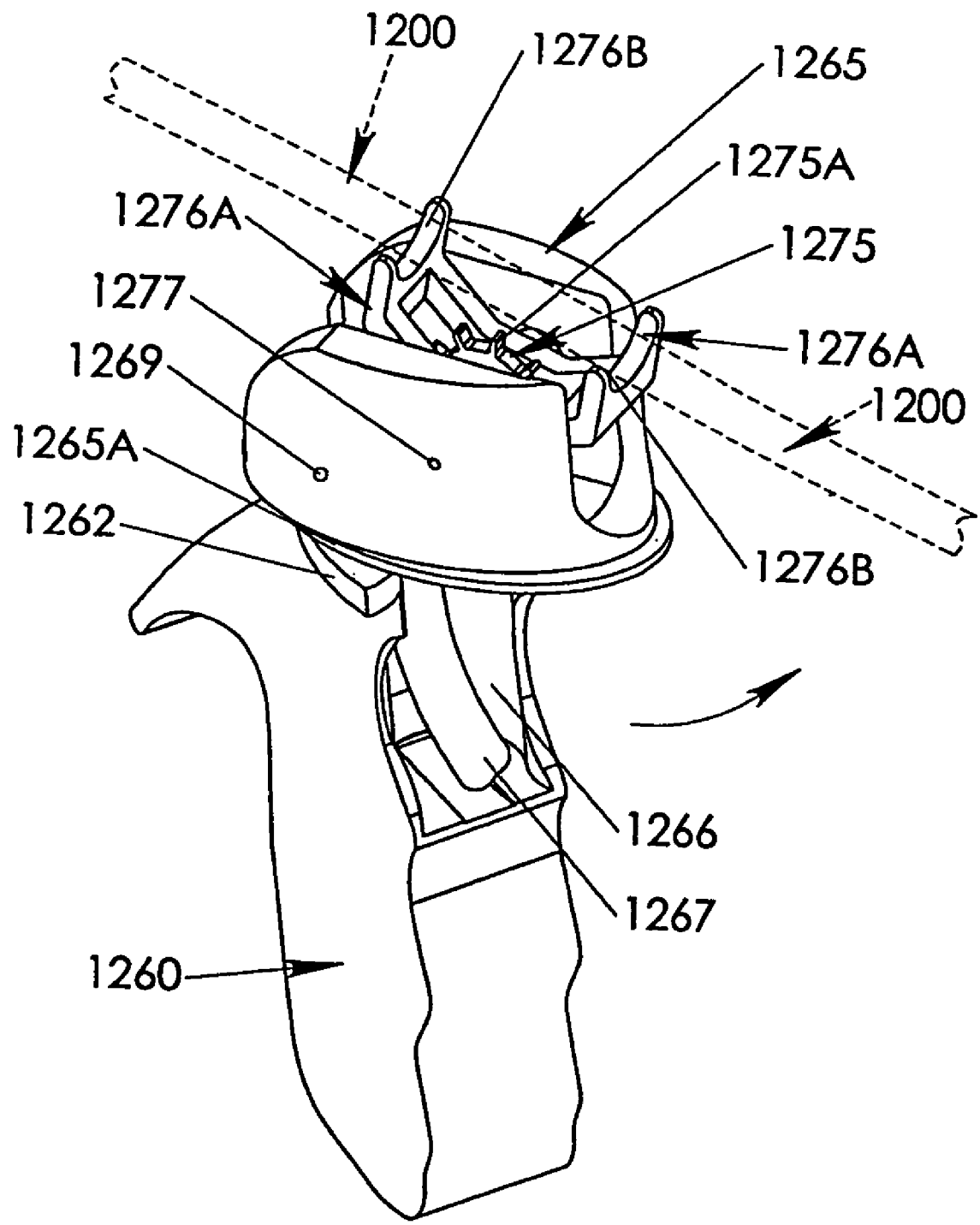
FIG. 43 is a perspective view of the handle illustrated in FIG. 42, with the housing rotated to facilitate multiple positioning of the transmission tube (illustrated in phantom) mounted in the cradle.
Figure 44:
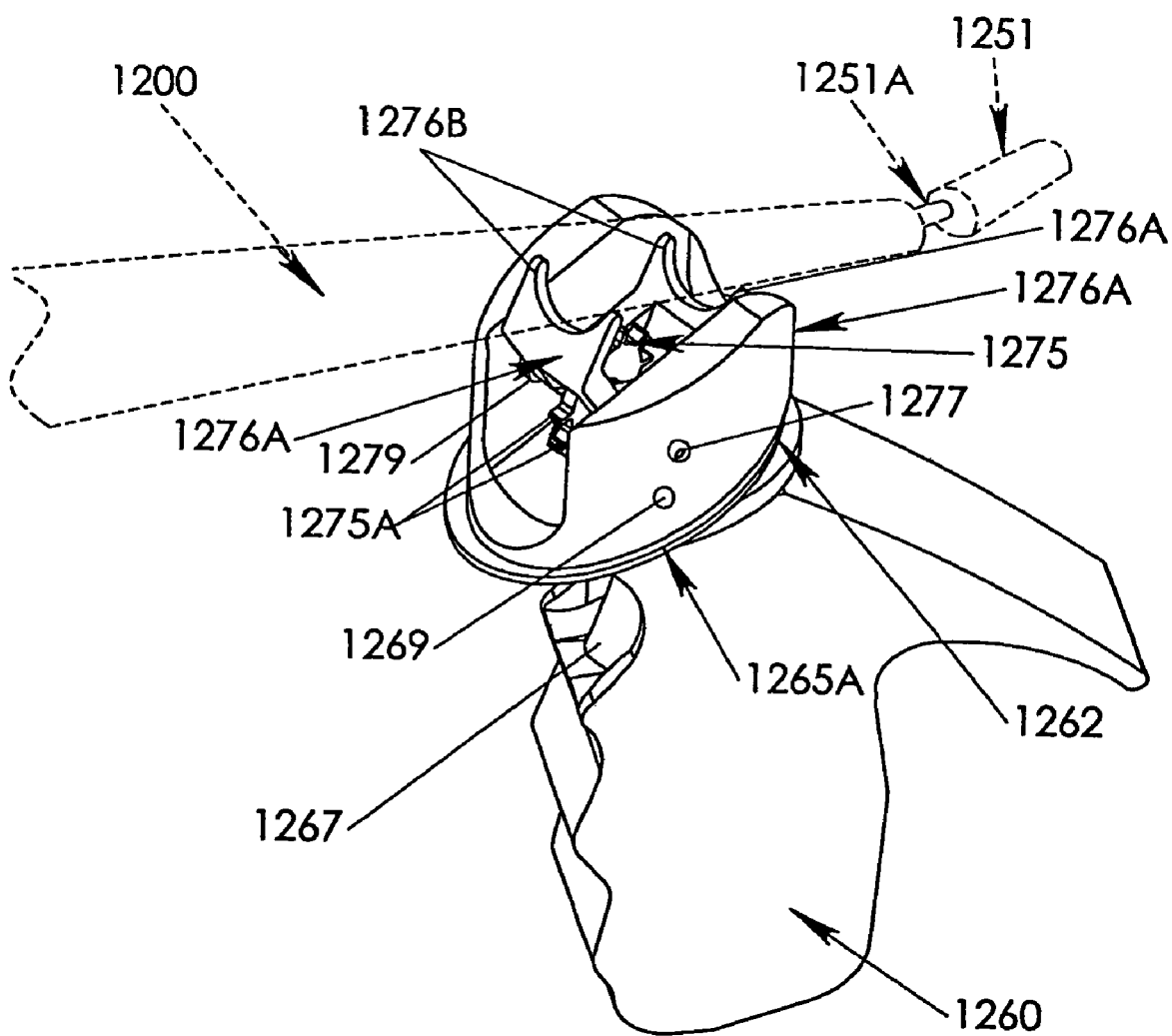
FIG. 44 is a perspective view of the handle, cradle and housing, more particularly illustrating additional rotation of the housing, cradle, and transmission tube with respect to the handle.
Figure 45:
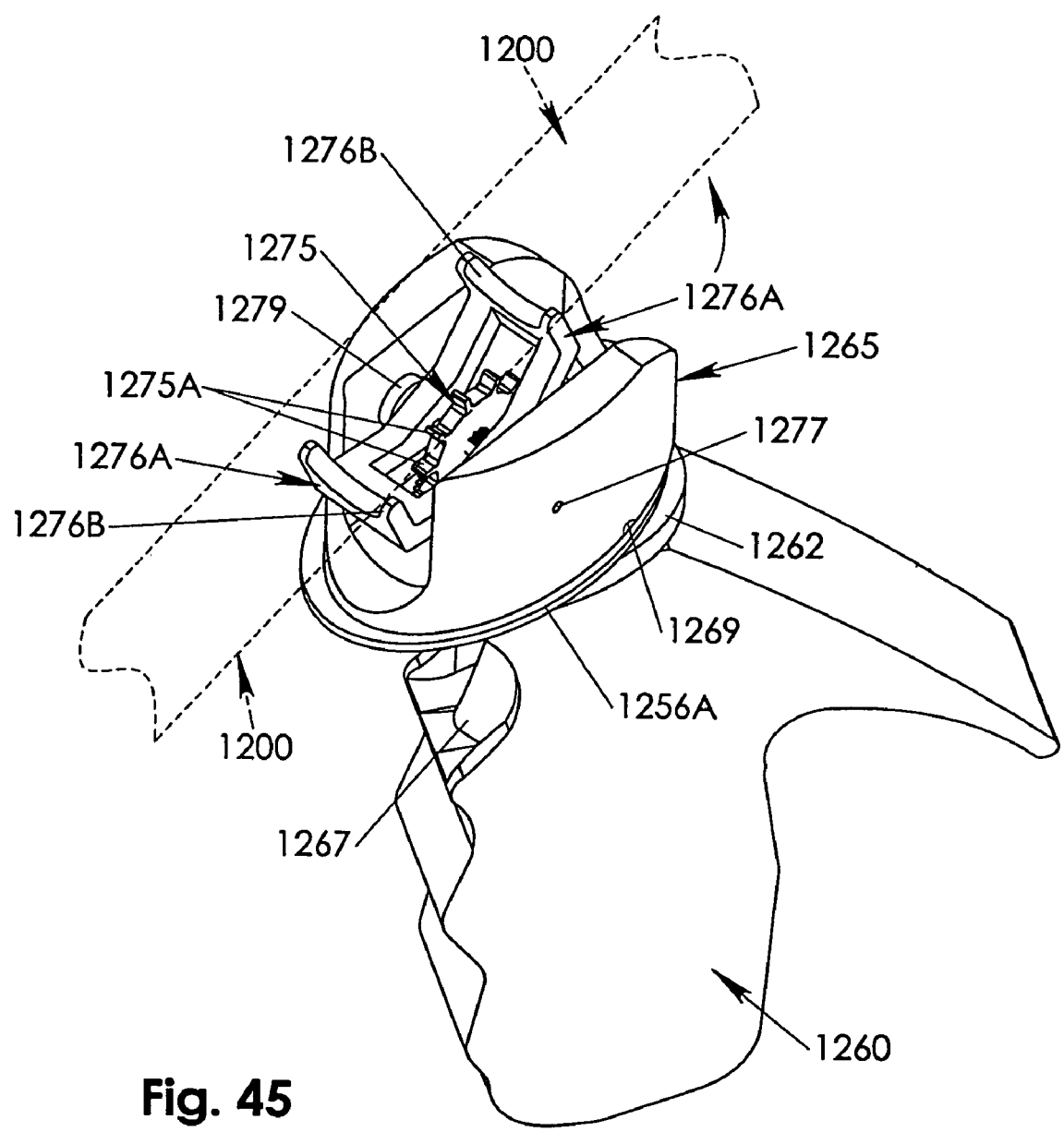
FIG. 45 is a perspective view of the handle, housing and cradle components of the operating device, further illustrating pivoting of the cradle and transmission tube with respect to the housing and handle.

Referring to FIGS. 1 and 41 of the drawings the interior of the transmission tube 1200 is illustrated in FIG. 41 and includes a drive cable 1247, which extends throughout much of the length of the transmission tube 1200 and a direction cable 1248 that parallels the drive cable 1247 inside the transmission tube 1200. Further illustrated in FIG. 41 are the reciprocation input collar 1216, engaged by a sprocket 1275, the direction actuator 1214 and a bottom insert 1205A and a companion top insert 1205B, that adjoin linearly to define essentially a cylindrical member with linear surface slots for receiving the four crescent angle articulation cables 1256A, 1256B, 1256C and 1256D, that terminate at one end at the selection bearing socket 1253, as illustrated. These four cables extend from the selection bearing socket 1253, through the transmission tube 1200, and are directed to the center of the extension tube 1240 at the transition cone 1245 and then through the extension tube 1240, to the transition guide cone 1238 and terminate at the crescent 101, as further hereinafter described.

Referring to FIGS. 42-52 of the drawings a detailed illustration of the handle 1260, housing 1265 and cradle 1276A elements of the device, along with the trigger 1267 and the trigger mechanism for operating the various components in the crescent 101 (not illustrated) is illustrated. The housing 1265 is seated on a base 1265A (FIG. 47), which rests on a platform area 1262, that terminates the top of the handle 1260 and a cylindrical receptacle 1266 (FIG. 47) extends from the housing 1265 into an opening provided in the platform area 1262 to facilitate rotation of the housing 1265 with respect to the handle 1260. The cylindrical housing base insert 1266A defines the top of the cylindrical receptacle 1266 and has sufficient clearance to facilitate operation of the trigger 1267, which is mounted on a trigger pivot pin 1269 located in the housing 1265. Accordingly, referring again to FIGS. 46 and 47, there is sufficient space within the cylindrical housing base insert 1266A and the cylindrical receptacle 1266 to facilitate pivoting of the trigger 1267 on the trigger pivot pin 1269. Furthermore, the housing 1265 may rotate with respect to the handle 1260 as illustrated in FIGS. 42-45 to further facilitate positioning of the crescent 101, illustrated in FIG. 1, in a precise position in an incision or wound (not illustrated) for suturing purposes.

Figure 46:
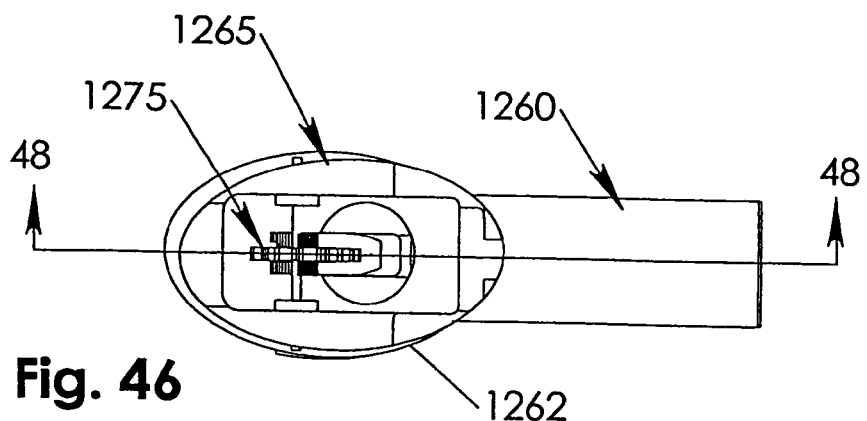
FIG. 46 is a top view of the handle, cradle and housing combination illustrated in FIG. 45, with the transmission tube removed.
Figure 47:
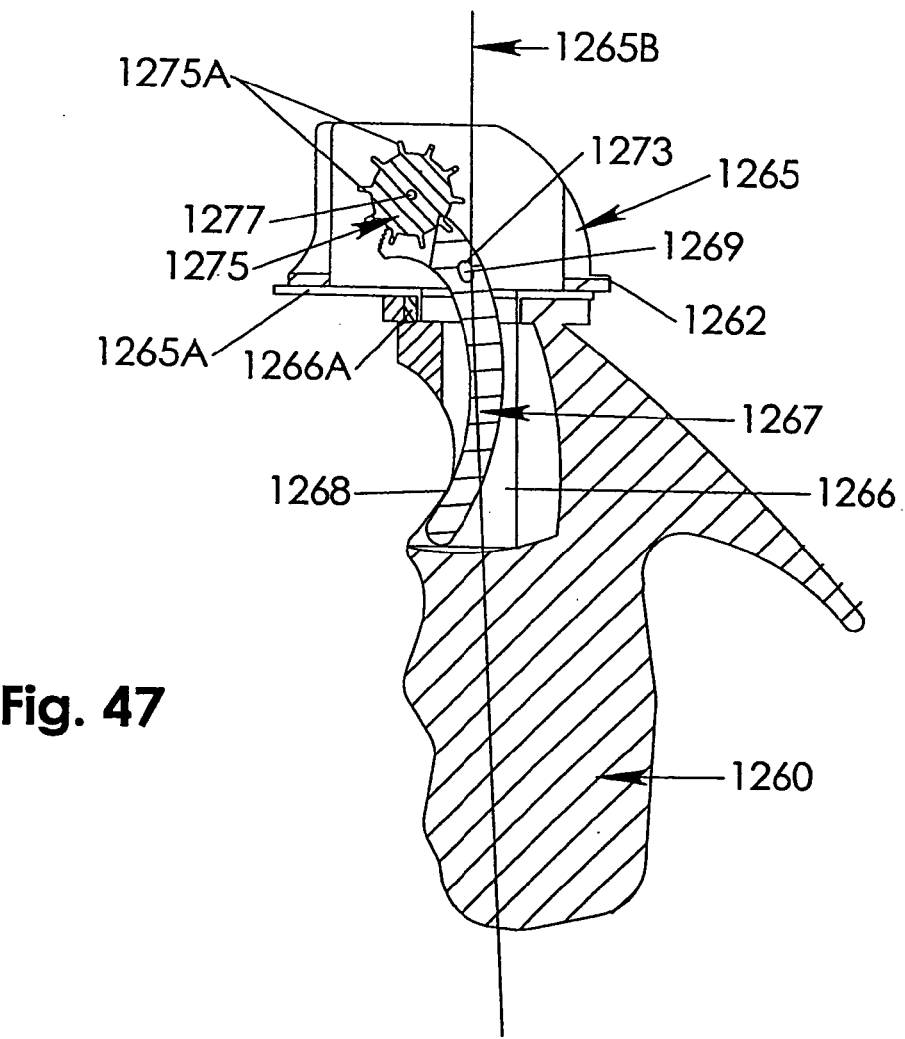
FIG. 47 is a side sectional view, taken along line 48-48 of the handle and housing in FIG. 46, more particularly illustrating a needle-operating trigger and sprocket combination mounted in the handle and housing, respectively.

As further illustrated in FIGS. 1 and 43-47 of the drawings the cradle 1265 is pivotally seated in a friction-fit in a slot or opening in the housing 1265, typically by means of a pair of pivot pin bosses 1279 (FIGS. 44 and 45) that typically receive a sprocket pivot pin 1277, the ends of which sprocket pivot pin 1277 project into the housing 1265 to pivotally mount the cradle 1276A on the housing 1265. The cradle 1276A is further characterized by a pair of U-shaped, oppositely-disposed receptacle nocks 1276B which are spaced-apart in the cradle 1276A in order to receive the extension tube 1200 in a secure friction or "slip fit", such that the extension tube 1200 can be rotated 360-degrees along the longitudinal axis in the U-shape receptacle nocks 1276B with respect to the cradle 1276A to further facilitate a desired spatial orientation of the crescent 101 (FIG. 1) inside an incision or wound for suturing purposes. As illustrated in FIGS. 46 and 47 of the drawings the trigger pivot pin 1269 extends through the housing 1265 and through an elongated pivot pin hole 1273 in the trigger 1267 to facilitate upward and downward, as well as pivotal movement of the trigger 1267 on the trigger pivot pin 1269, responsive to finger pressure applied to the finger pad 1268.

Figure 48:
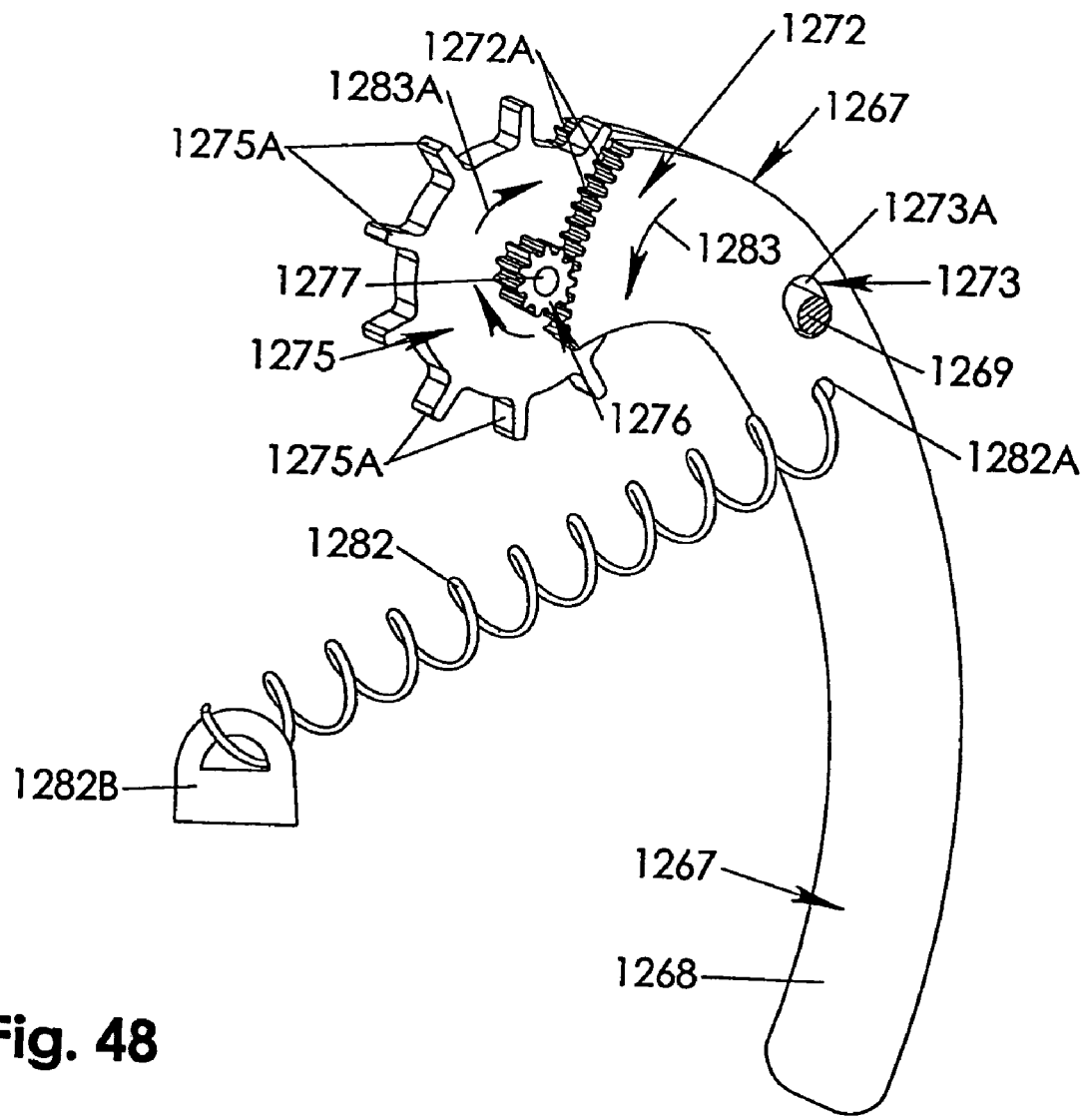
FIG. 48 is an enlarged perspective view of a trigger and sprocket gear engagement to drive a sprocket by manipulation of the trigger in the handle illustrated in FIGS. 42-46.
Figure 49:
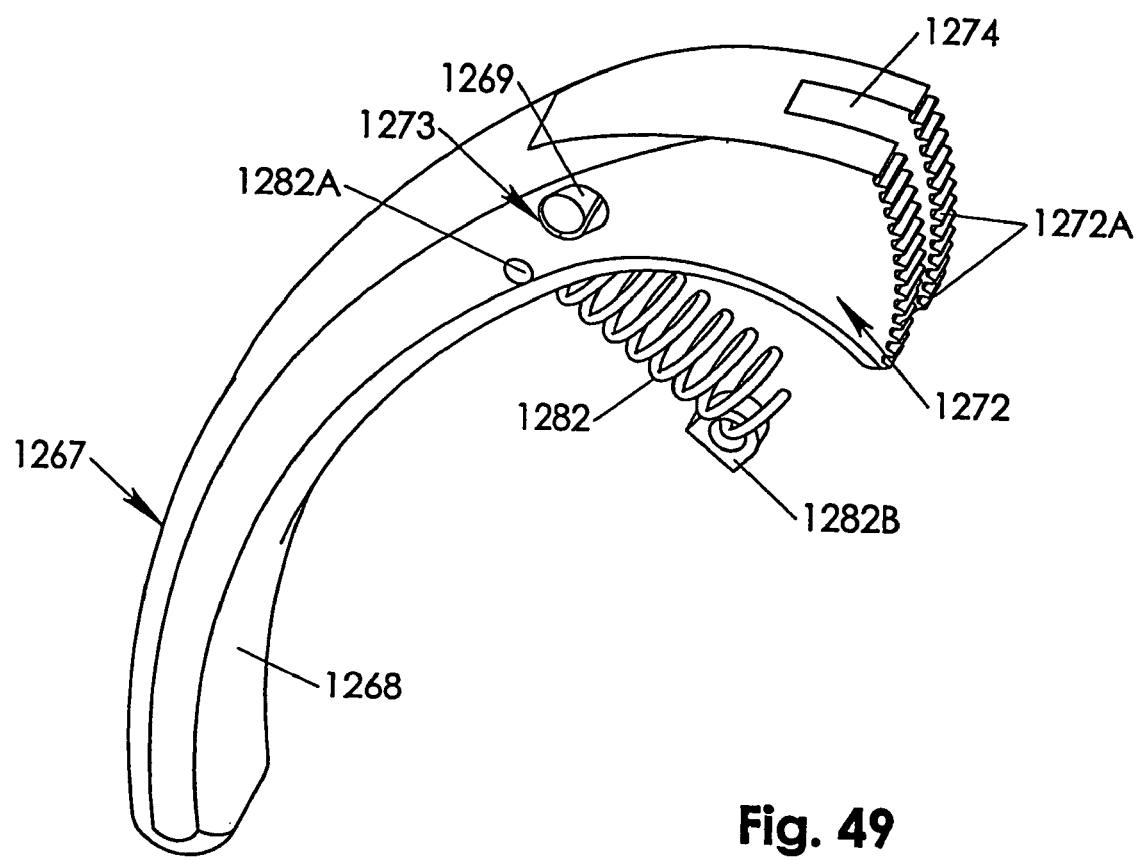
FIG. 49 is a perspective view of the trigger and upper teeth provided on the trigger for engaging the sprocket gear illustrated in FIG. 48 and driving the sprocket responsive to manipulation of the trigger.

Referring now to FIGS. 42-49 of the drawings and to FIGS. 48 and 49 in particular, the bifurcated, geared upper segment 1272 of the trigger 1267 is arcuate and is fitted with teeth 1272A for engaging the teeth of a pair of sprocket gears 1276 when pressure is applied to the finger pad 1268 of the trigger 1267, forcing the trigger 1267 upwardly against the trigger pivot pin 1269 in the elongated pivot pin hole 1273, as illustrated in FIG. 48. Each of the two sprocket gears 1276 is centered on and fixed to a sprocket 1275, having sprocket teeth 1275A, by means of a sprocket pivot pin 1277. The sprocket pivot pin 1277 may also serve to pivotally mount the cradle 1276A in the housing 1265, although the cradle 1276A can be pivotally mounted in the housing 1265 by means of separate pins (not illustrated) extending through the cradle 1276A into the friction-fit pivot pin bosses 1279, illustrated in FIGS. 44 and 45 of the drawings. A trigger spring 1282 has one end attached to the trigger 1267, typically by means of a trigger spring hole 1282A and the opposite end of the trigger spring 1282 is secured to a housing attachment boss 1282B, on the housing 1265, to bias the trigger 1267 into disengagement with the sprocket gears 1276 in the relaxed position illustrated in FIG. 47. As further illustrated in FIGS. 48 and 49 the geared upper segment 1272 of the trigger 1267 is bifurcated to define a trigger gear slot 1274, which accepts the sprocket 1275, as illustrated in FIG. 48. Accordingly, it will be appreciated that the sprocket gears 1276 fixed to each side of the sprocket 1275, engage a separate set of teeth 1272A on the bifurcated geared upper segment 1272 of the trigger 1267 to facilitate a more secure and positive rotation of the sprocket gears 1276 and the sprocket 1275 in concert, responsive to manipulation of the trigger 1267 by an operator, as hereinafter further described.

Figure 50:
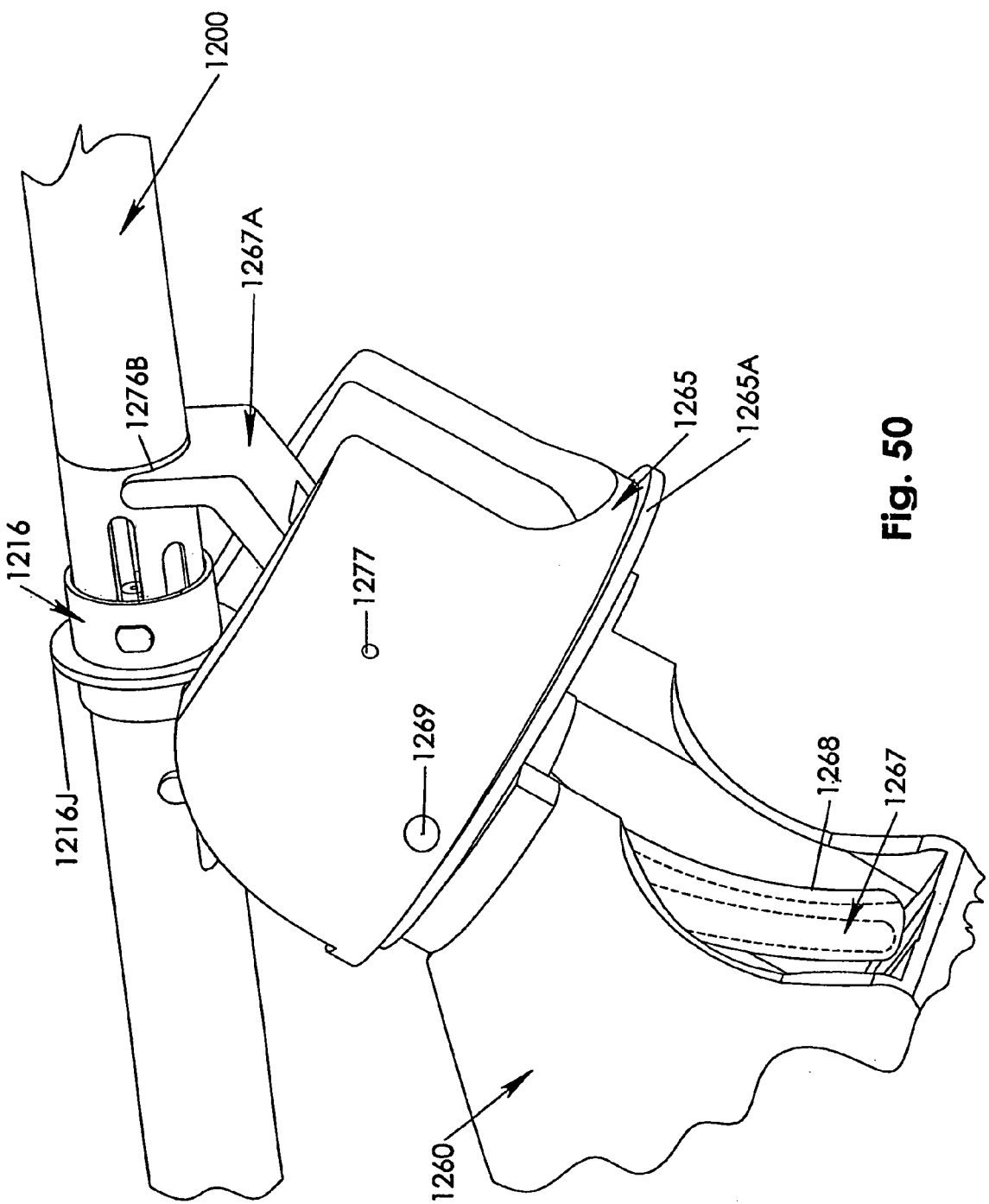
FIG. 50 is an enlarged side perspective view of the handle, trigger, housing, cradle and transmission tube mounted in the cradle.
Figure 51:
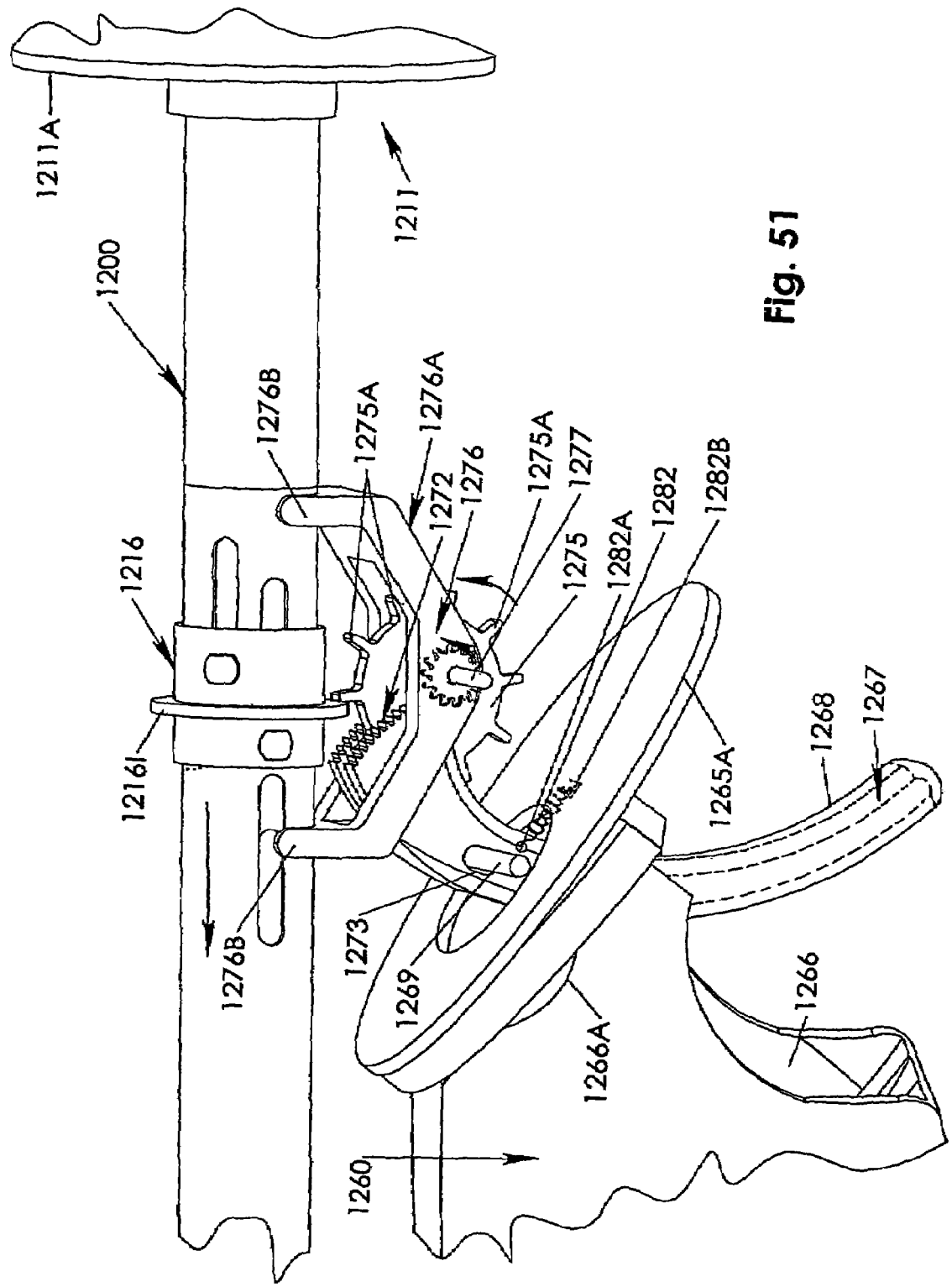
FIG. 51 is an enlarged, side view of the handle, trigger, cradle and transmission tube with the housing removed, more particularly illustrating fitting of the trigger through an opening in a base member of the housing and positioning the sprocket to engage a reciprocation input collar slidably mounted on the transmission tube.
Figure 52:
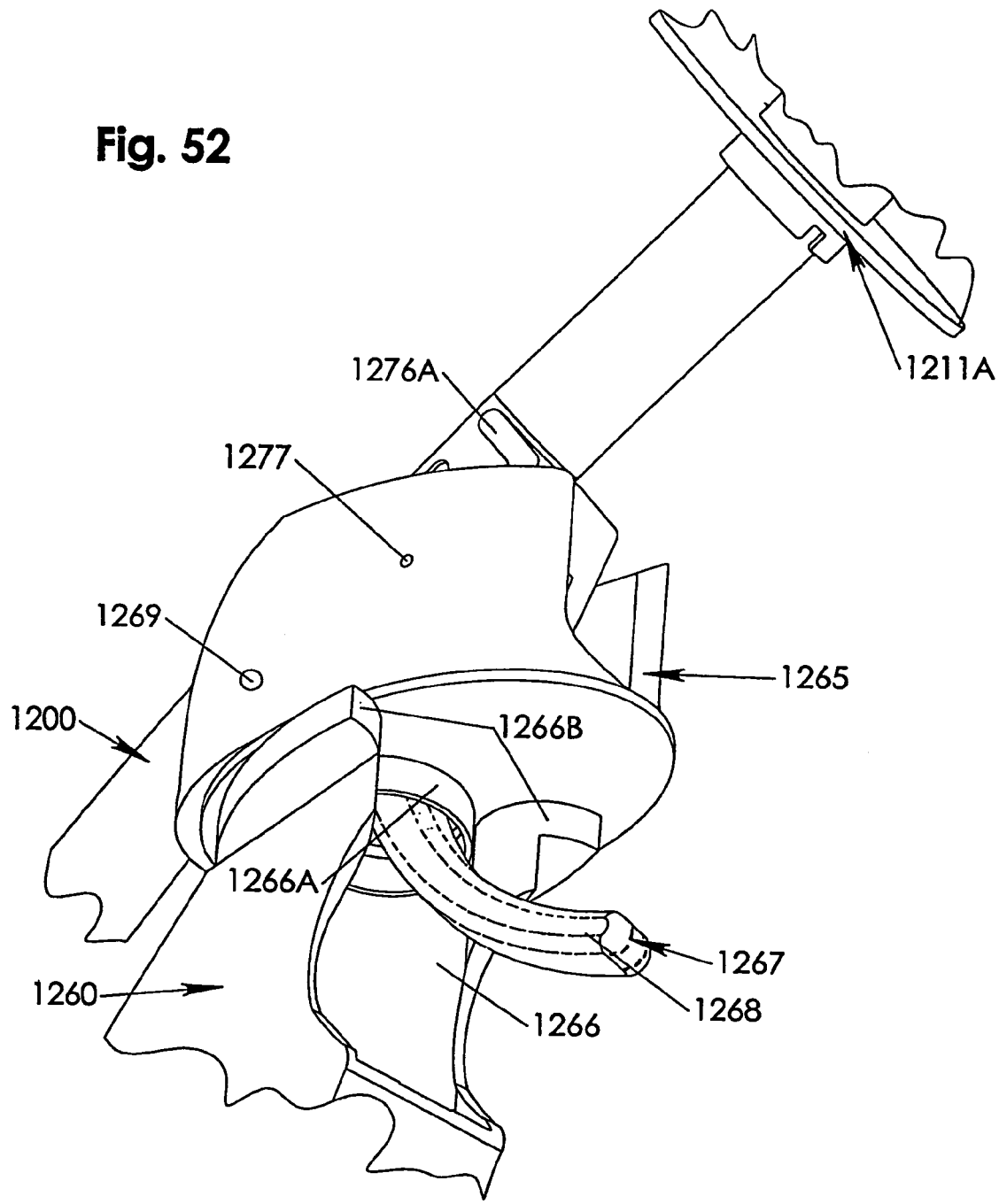
FIG. 52 is a bottom perspective view of the handle, trigger, housing, cradle and transmission tube elements of the device, more particularly illustrating a typical trigger clearance opening in the housing.

Referring to FIGS. 1 and 50-53 of the drawings the transmission tube 1200 is rotatably seated in the pivoting cradle 1276A in a position such that the reciprocating input collar 1216 extends into the slot or opening provided in the housing 1265 immediately above the cradle 1276A, as illustrated in FIG. 50. Furthermore, as further illustrated in FIG. 51, from which the housing 1265 has been removed for brevity, it will be appreciated that the rotating sprocket 1275, mounted on the sprocket pivot pin 1277, engages the reciprocating collar ridge 1216I of the reciprocating input collar 1216 by means of the respective sprocket teeth 1275A, such that rotation of the sprocket 1275 in the counterclockwise direction by trigger action as viewed in FIG. 51, forces the reciprocating input collar 1216 to slide in the direction of the arrow on the extension tube 1200. Since the reciprocating collar ridge 1216 I, fixed to the reciprocating input collar 1216 is round (FIGS. 51 and 53), this configuration facilitates selective rotation of the extension tube 1200 in the cradle 1276A through a 360-degree range along, the longitudinal axis to position the crescent 101 (illustrated in FIG. 1) in a desired orientation inside a wound or incision (not illustrated) without disturbing engagement of the reciprocating collar ridge 1216 I with one of the sprocket teeth 1275A on the sprocket 1275. Referring again to FIG. 51 of the drawings it will be appreciated that the sliding range of motion of the reciprocating input collar 1216 on the extension tube 1200 is limited to a short space between the two U-shaped receptacle nocks 1276B of the cradle 1276A.

Figure 53:
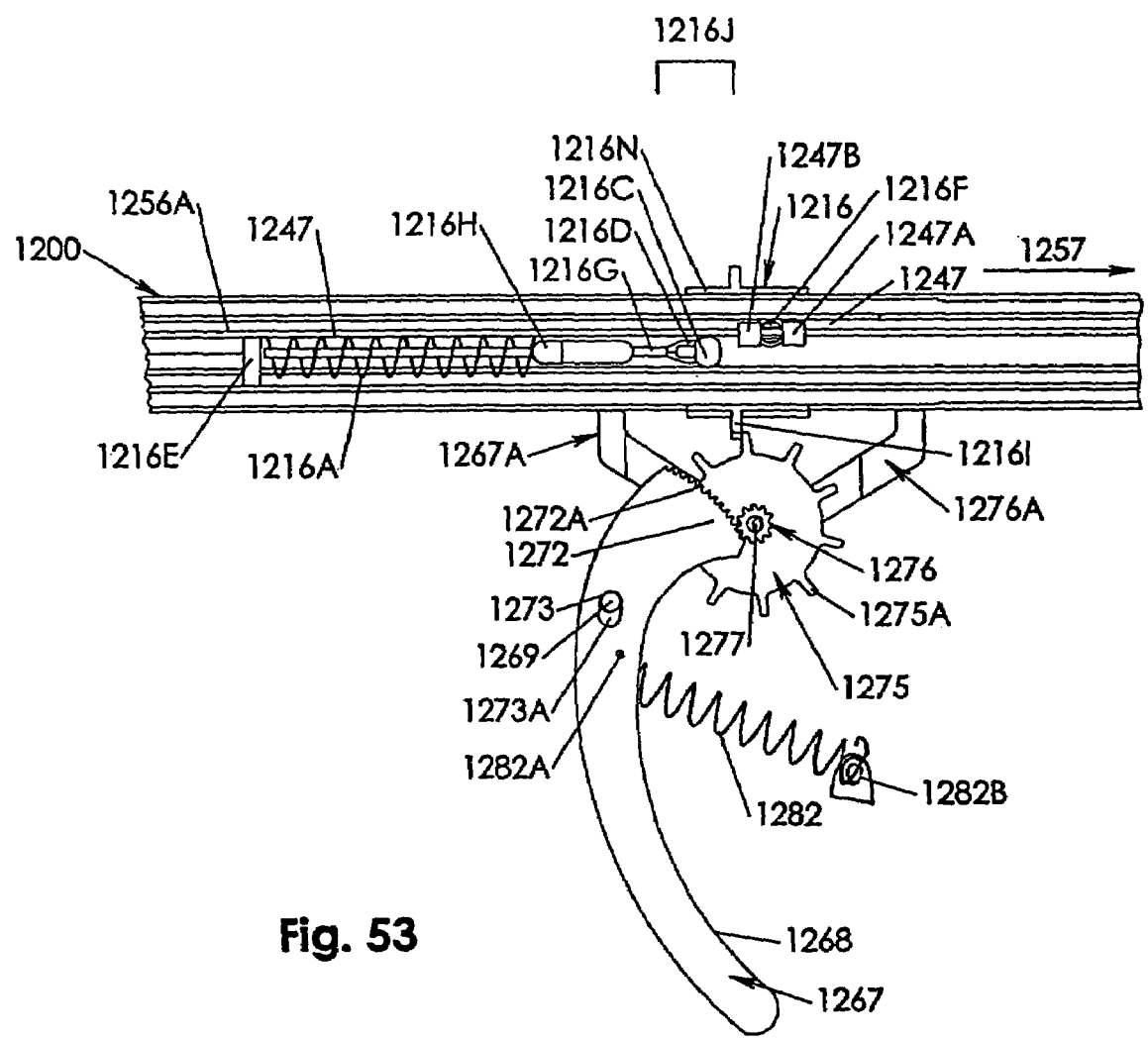
FIG. 53 is a side sectional view of the trigger, cradle, sprocket gear and sprocket combination, interfaced with the respective operating elements of the reciprocating input collar slidably mounted on the transmission tube, and the trigger disengaged from the sprocket gear.
Figure 54:
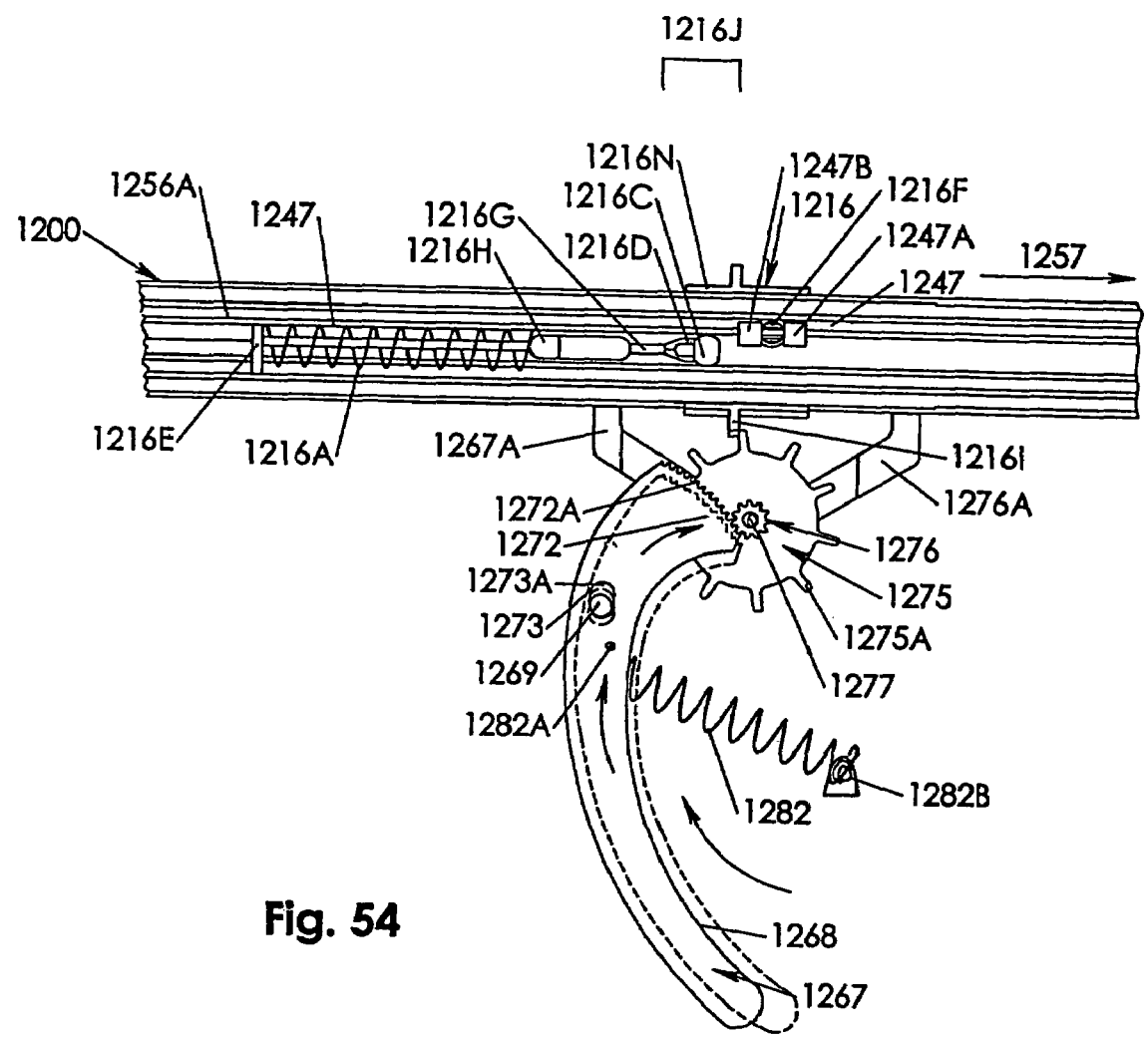
FIG. 54 is a side sectional view of the trigger cradle, sprocket gears and sprocket combination interfaced with the respective operating elements of the reciprocating input collar, slidably mounted on the transmission tube, and the trigger engaged with the sprocket gear.

Referring now to FIGS. 47 and 53 of the drawings the trigger 1267 is illustrated in relaxed configuration with the teeth 1272A on the bifurcated and geared upper segment 1272 slightly spaced from the corresponding teeth on the sprocket gears 1276, by operation of the bias in the trigger spring 1282 and the slack in the elongated pivot pin hole 1273. Furthermore, the sprocket 1275 is so positioned on the sprocket pivot pin 1277, along with the pair of sprocket gears 1276, that one of the sprocket teeth 1275A engages the reciprocating collar ridge 1216 I of the reciprocating input collar 1216. As further illustrated in FIG. 53 the cradle 1276A supports the extension tube 1200 in the horizontal configuration and further illustrated is a spring-eye rod 1216G horizontally situated inside the extension tube 1200 and fitted with a spring-eye 1216D for receiving a projecting spring eye hook 1216C. The elongated spring-eye rod 1216G extends through a fixed spring eye rod guide post 1216H, which is secured to the extension tube 1200 from the inside, and a return spring 1216A is provided on the spring-eye rod 1216G between the spring-eye rod guide post 1216H and a spring-eye rod cap 1216E, terminating the extending end of the spring-eye rod 1216G, opposite the spring-eye 1216D. Accordingly, extension of the spring-eye rod 1216G in the extension tube 1200 stretches the return spring 1216A and biases the spring-eye rod 1216G rearwardly for purposes which will be hereinafter further described.

Figure 55:
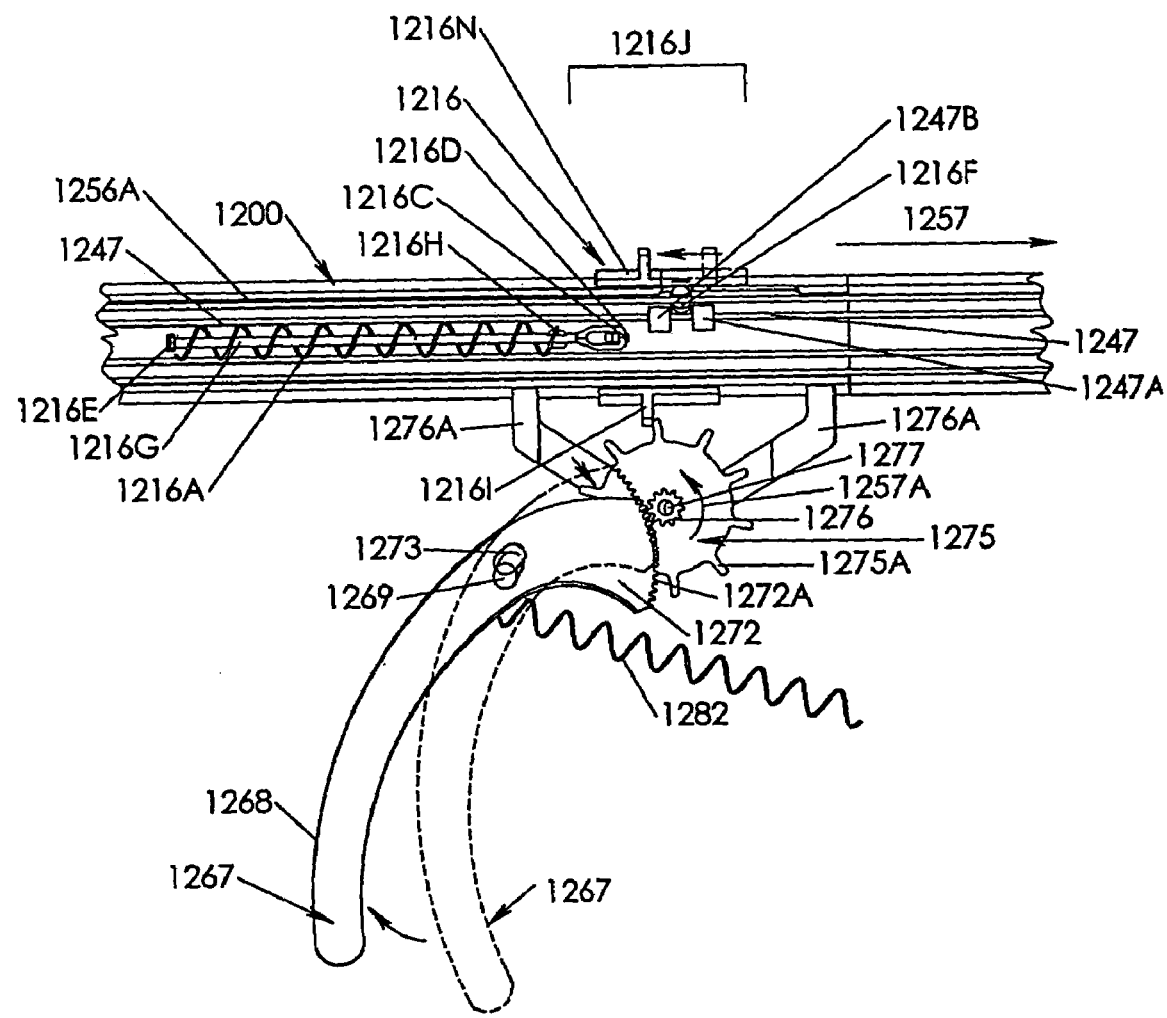
FIG. 55 is a side sectional view of the trigger, cradle, sprocket gear and sprocket combination interfaced with the respective operating elements of the reciprocating input collar slidably mounted on the transmission tube and the trigger fully pulled to rotate the sprocket gear and sprocket and slide the reciprocating input collar on the transmission tube.
Figure 56:
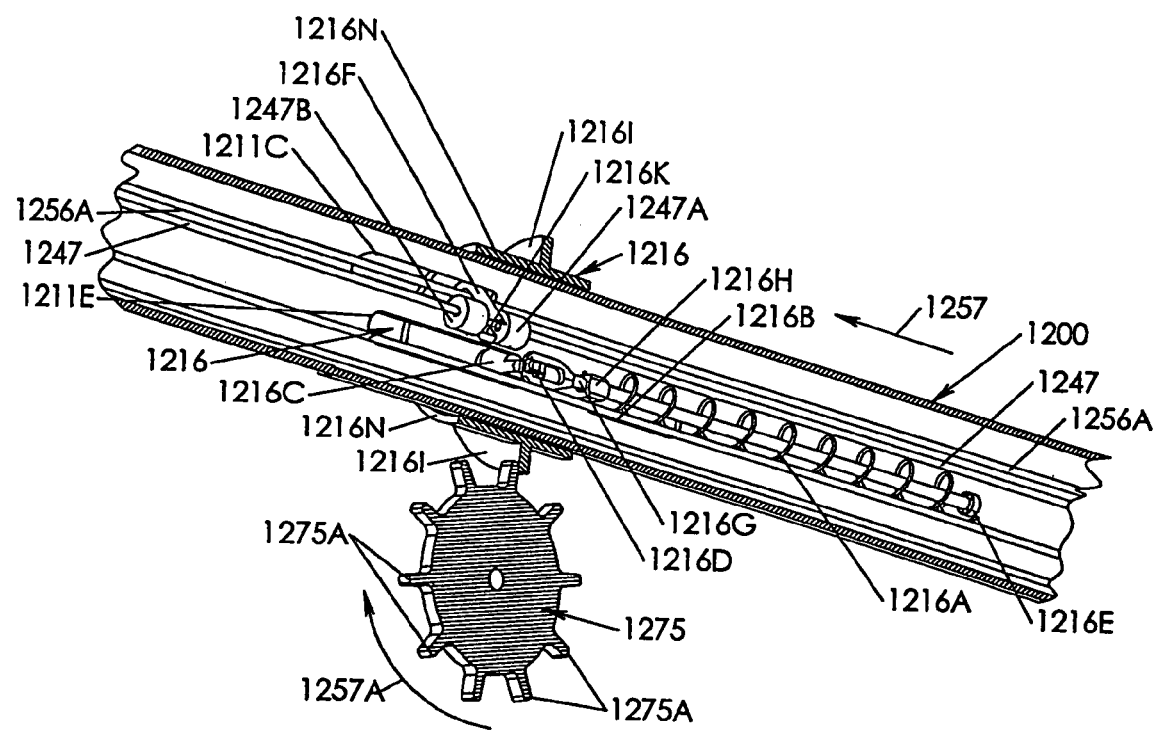
FIG. 56 is an enlarged longitudinal sectional and perspective view of the transmission tube and the internal needle-operating cables and sprocket trigger mechanism operated by the trigger.

Referring now to FIGS. 1, 48, 54, 55 and 56 of the drawings, when pressure is applied to the finger pad 1268 and the trigger 1267 in the direction of the arrow, the respective teeth 1272A on the bifurcated geared upper segment 1272 of the trigger 1267 are forced forwardly into engagement with the corresponding teeth on the pair of sprocket gears 1276 as the trigger 1267 rises in the elliptically-shaped elongated pivot pin hole 1273, until the trigger 1267 engages the trigger pivot pin 1269. Continued finger pressure on the trigger 1267 forces the sprocket 1275 to rotate in the counterclockwise direction as pressure is applied to the two sprocket gears 1276 and the reciprocating collar ridge 1216 I and the reciprocation input collar 1216 are caused to move rearwardly, as illustrated by the collar arrow 1216J in FIG. 55. Rearward movement of the reciprocating input collar 1216 occurs as pressure is maintained on the trigger 1267 and the teeth 1272A traverse the two sprocket gears 1276 until the entire array of teeth 1272A on the bifurcated geared upper segment 1272 of the trigger 1267 traverse the sprocket gears 1276. This continued pressure against the trigger 1267 also maintains bias in the trigger spring 1282 to facilitate return of the trigger 1267 to its original position illustrated in FIG. 53 and in phantom in FIG. 55, when finger pressure is released from the trigger 1267. Accordingly, as further illustrated in FIG. 55 when the respective teeth 1272A on the geared upper segment 1272 fully traverse the corresponding sprocket gears 1276 the reciprocating input collar 1216 has moved to its maximum extended sliding position on the extension tube 1200 from the position illustrated in phantom. This action also forces the spring-eye hook 1216C, the spring-eye 1216D and the spring-eye rod 1216G rearwardly against the extension bias of the return spring 1216A, due to attachment of the spring eye hook 1216C to the input collar tubular base 1216N (FIG. 56). Release of finger pressure from the trigger 1267 immediately disengages the respective teeth 1272A from the sprocket gears 1276 as the trigger 1267 shifts on the trigger pivot pin 1269 by operation of the trigger spring 1282 and the elongated pivot pin hole 1273, to relocate the trigger 1267 back into the position illustrated in phantom in FIG. 55 and in FIGS. 53 and 54. Accordingly, as the trigger 1267 disengages the sprocket gears 1276, the sprocket tooth 1275A that engages the reciprocating collar ridge 1216 I of the reciprocation input collar 1216 also disengages the collar ridge 1261 I at the extreme rearward movement of the reciprocation input collar 1216 responsive to rotation of the sprocket 1275. The reciprocation input collar 1216 then returns to its original position illustrated in FIGS. 53 and 54 and in phantom in FIG. 55, by operation of the return spring 1216A. Additional finger pressure applied to the trigger 1267 thus repeats the operation illustrated in FIGS. 53-55, moving the reciprocating input collar 1216 through another sliding sequence on the transmission tube 1200 and sequentially forcing the spring-eye rod 1216 G rearwardly against the bias of the return spring 1216A to drive the needle (not illustrated) around the crescent 101 (FIG. 1) as hereinafter further described.

Figure 57:
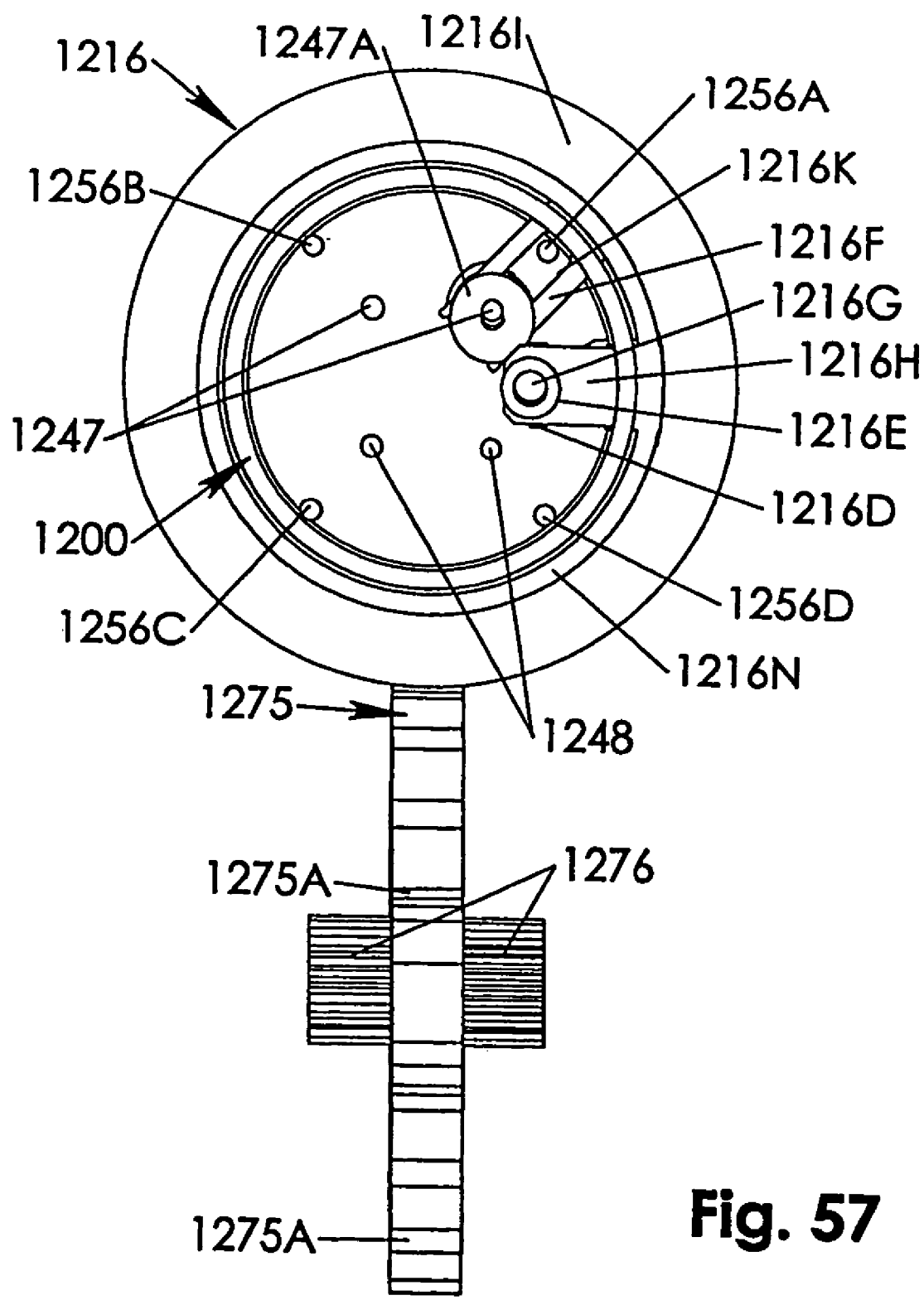
FIG. 57 is a transverse sectional view of the transmission tube and the internal cables and trigger mechanism operated by the trigger at the reciprocating input collar to control needle rotation in the crescent illustrated in FIG. 56.

Referring now to FIGS. 55, 56 and 57 of the drawings in a preferred design of this embodiment of the invention the spring-eye hook 1216C, attached to the spring-eye 1216D of the spring-eye rod 1216G, projects through a spring-eye hook slot 1211E, as particularly illustrated in FIG. 56. Furthermore, the spring-eye rod guide post 1216H is attached to the transmission tube 1200 at a spring plate 1216B, as further illustrated in FIG. 56. Moreover, a pair of drive cable input stops 1247A and 1247B are fitted to the drive cable 1247 and are positioned on either side of a forked transmission rod 1216F, the forked transmission rod slot 1216 K of which receives the drive cable 1247. The forked transmission rod 1216F extends through a reciprocation input forked rod slot 1211C, as further illustrated in FIG. 56. One of the crescent angle articulation cables, 1256A, also extends through the forked transmission rod 1216F and parallels the drive cable 1247. FIG. 57 further illustrates positioning of the direction cable 1248 with respect to the drive cable 1247, as well as the location of the four crescent angle articulation cables 1256A, 1256B, 1256C and 1256D in the transmission tube 1200.

Figure 58:
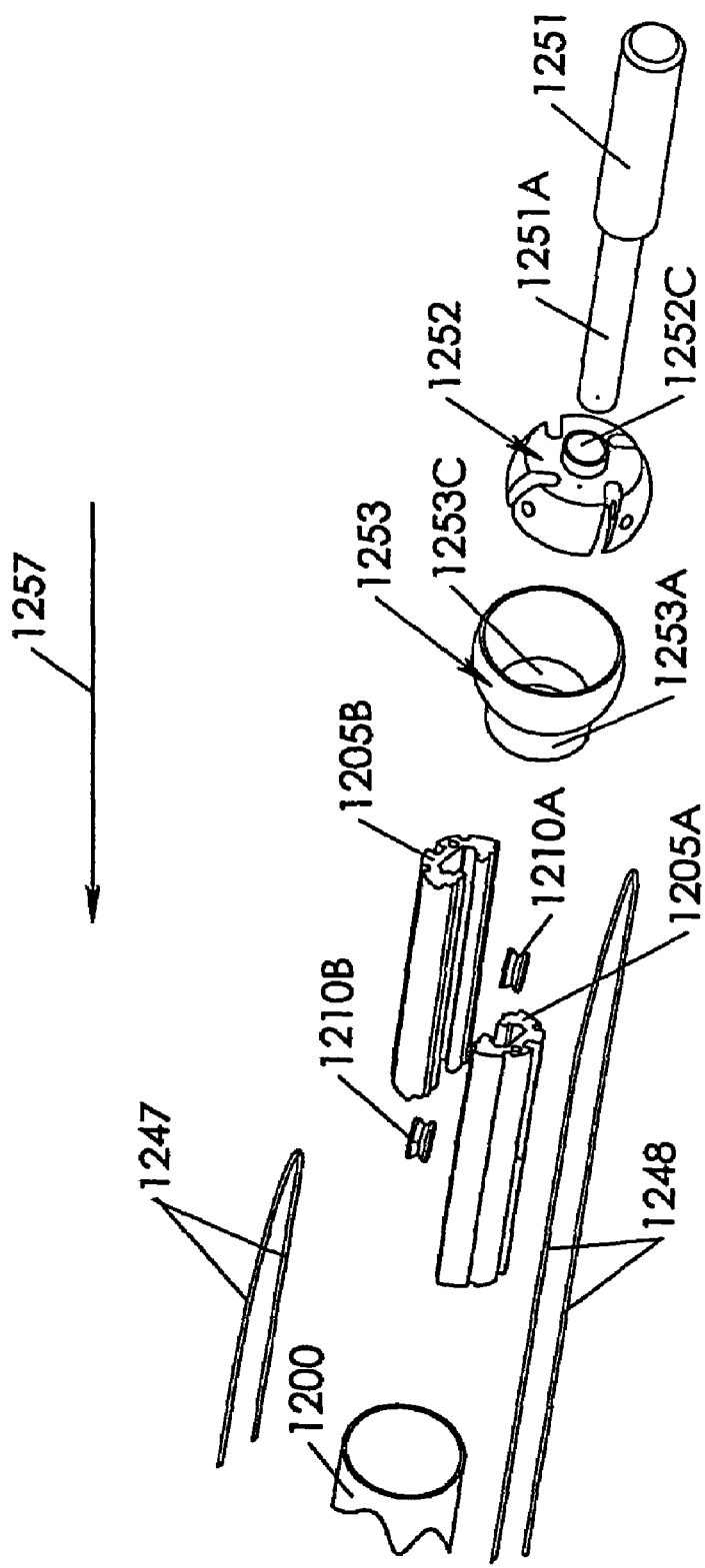
FIG. 58 is an exploded view of the lever and lever cable support and mount assembly for manipulating the crescent on the end of the extension tube.

Referring now to FIGS. 58-64 of the drawings and initially to FIG. 58, the lever 1251 mounted in the selection bearing 1252 at the operating end of the transmission tube 1200 is used to control articulation of the crescent 101 by operation of the crescent angle articulation cables 1256A, 1256B, 1256C and 1256D, as heretofore overviewed. The selection bearing 1252 movably fits in a selection bearing socket 1253C and the mounting post 1251A of the lever 1251 extends through a lever mount hole 1252C in the center of the selection bearing 1252, as illustrated. Accordingly, the lever 1251 is articulated with finger pressure along with the selection bearing 1252 in the selection bearing socket 1253C to control the crescent angle articulation cables 1256A, 1256B, 1256C and 1256D, as hereinafter further detailed. Also illustrated in FIG. 58 are the top insert 1205B, the top pulley 1210B, the bottom insert 1205A and the bottom pulley 1210A, in proximity to the drive cable 1247 and the direction cable 1248 with respect to the operating end of the transmission tube 1200. Connection of these elements and operation of the lever 1251 will be hereinafter further described.

As further illustrated in FIGS. 59-64 the extending end pairs of the looped drive cable 1247 and direction cable 1248 project from the operating end of the transmission tube 1200 forwardly through the transmission tube 1200, the transition cone 1245, the extension tube 1240 and project from the transition guide cone 1238 through the clearance tunnels 775A and 7751A, to the respective drive access cable extensions 140, connected to the reciprocating driver 108 and the direction setting access cable extensions 141, extending from the drive direction setting plate 134, respectively. As illustrated, the end pairs of the drive cable 1247 and direction cable 1248 converge at the joint ball 780 and project through a central opening 780A therein to the respective drive access cable extensions 140 and direction setting access cable extensions 141. Similarly, the crescent angle articulation cables 1256A, 1256B, 1256C and 1256D project through transition guide cone openings 1238A, 1238B, 1238C and 1238D, respectively, provided in the transition guide cone 1238 and extend to spaced-apart, fixed attachment to the four base corners 776A, 776B, 776C and 776D of the socket 775, as illustrated in FIG. 5 and heretofore described. The opposite ends of the crescent angle articulation cables 1256A, 1256B, 1256C and 1256D connect to the selection bearing 1252 as further hereinafter described, to facilitate selective manipulation of the crescent angle articulation cables 1256A, 1256B, 1256C and 1256D by finger and thumb operation of the lever 1251 and corresponding movement of the selection bearing 1252 with respect to the fixed selection bearing socket 1253. This manipulation results in articulation of the crescent 101 to the illustrative positions illustrated in FIGS. 62-64 of the drawings.

Figure 65:
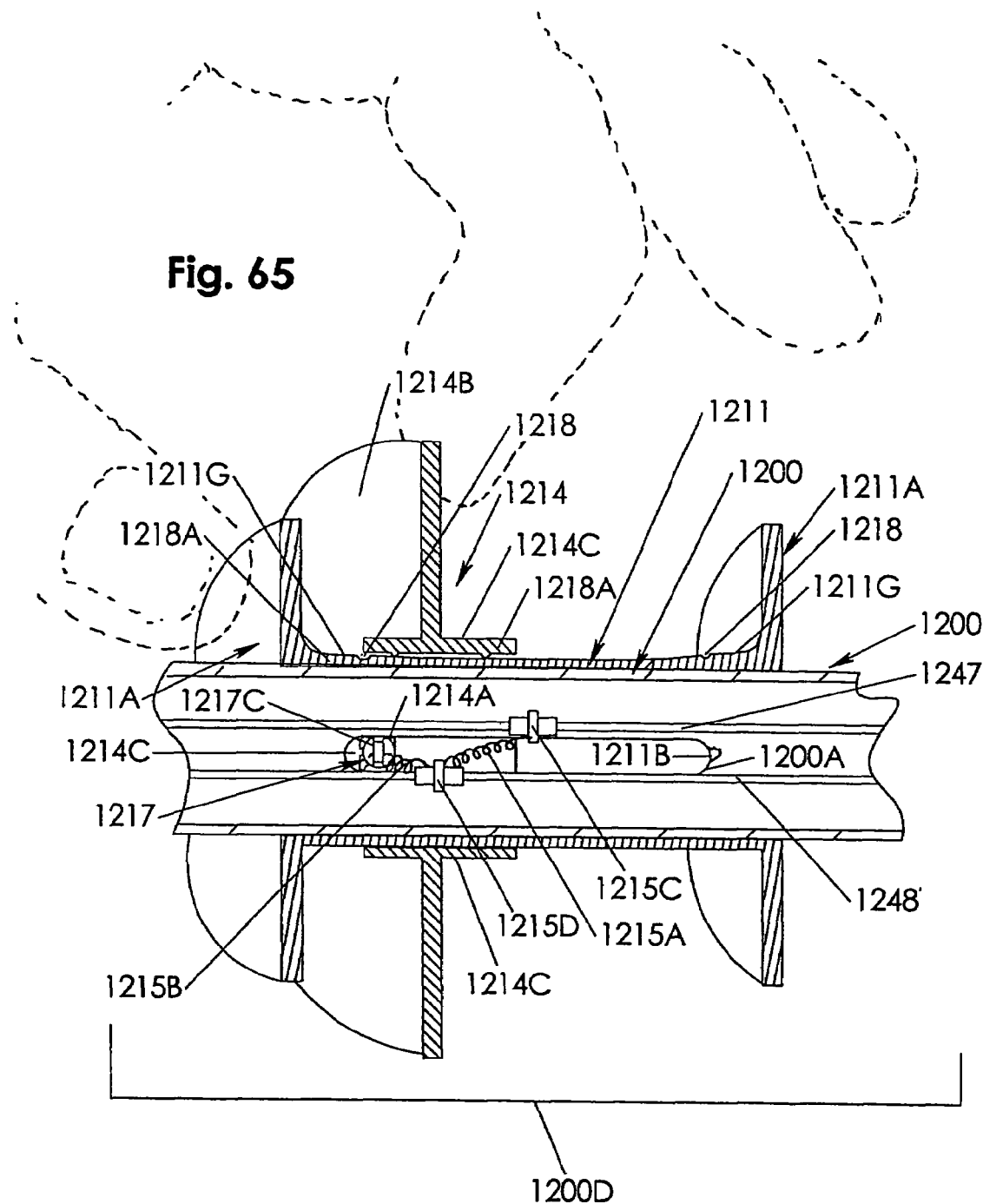
FIG. 65 is an enlarged perspective view, partially in section, of the external and internal components of the needle direction actuator and the slide switch operating components mounted on the transmission tube of the operating device.

Referring now to FIGS. 1 and 65-78 of the drawings, the direction actuator 1214 is illustrated and includes a disc-shaped actuator boss 1214B extending from a tubular base 1214C, that slidably encircles the transmission tube 1200. The direction actuator 1214 is mounted on a tubular slide switch mount body 1211, bounded by a pair of fixed pressure opposing rings 1211A and fitted with a pair of slide switch body detents 1218, that sequentially receive a pair of direction actuator bosses 1218A, located on the underside of the tubular base 1214C of the direction actuator 1214. As further illustrated in FIGS. 65-68 of the drawings, the drive cable 1247 and direction cable 1248 are illustrated extending through the transmission tube 1200 and the drive cable 1247 is fitted with a drive cable spring stop 1215C, while the direction cable 1248 is provided with a similar direction cable spring stop 1215D. The drive cable spring stop 1215C and the direction cable spring stop 1215D are connected by a direction mount—to drive mount spring 1215A and a direction connecting rod 1217 projects through a coextensive transmission tube slide slot 1200A and a mount body slide slot 1211B, located in the transmission tube 1200 and the slide switch mount body 1211, respectively, immediately adjacent to the drive cable spring stop 1215C and the direction cable spring stop 1215D (FIG. 65). A direction connecting rod mounting slot 1214A (FIG. 68) is also provided in the tubular base 1214C of the direction actuator 1214 to receive the direction connecting rod 1217 and a direction connecting rod—to direction mount spring 1215B connects the mounting boss 1217C on the direction connecting rod 1217 to the direction cable spring stop 1215D. Accordingly, referring again to FIGS. 1 and 65-67 of the drawings, sliding manipulation of the direction actuator 1214 on the slide switch mount body 1211 fixed to the transmission tube 1200, positions the direction connecting rod 1217 in a selected position in the coextensive transmission tube slide slot 1200A and mount body slide slot 1211B, extending through the transmission tube 1200 and the slide switch mount body 1211, respectively. This action also moves the drive cable 1247 and the direction cable 1248 in the selected direction inside the transmission tube 1200, as illustrated in FIGS. 66 and 67, for, selectively locking the fixed way direction setting plate 136 (not illustrated) in a selected position on the case 102 (not illustrated) in the crescent 101 (illustrated in FIG. 1) and determining the direction of rotation of the needle 50 (not illustrated) in the crescent 101, as hereinafter further described.

Figure 59:
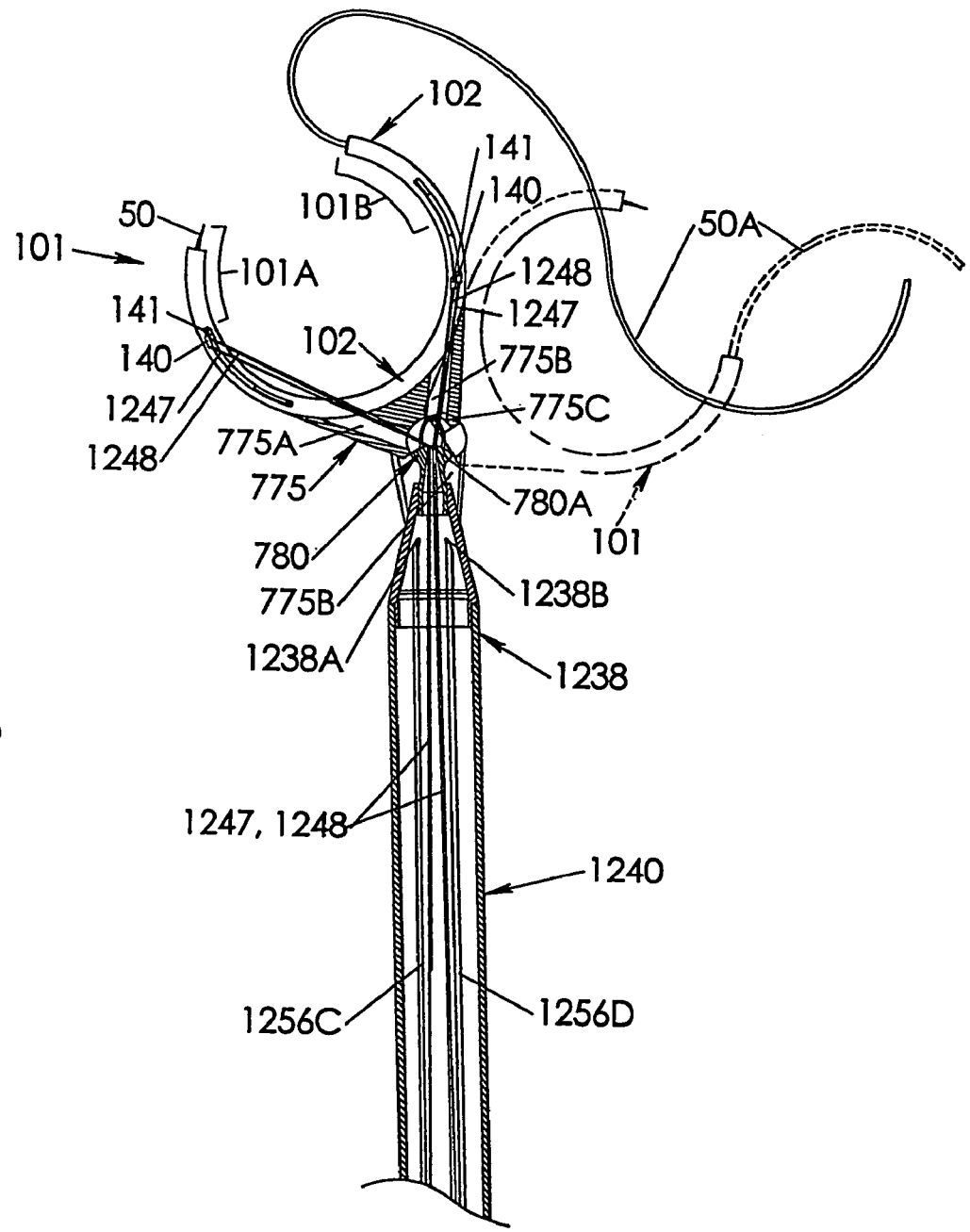
FIG. 59 is a bottom view, partially in section, of the crescent and the crescent ball mounted on the extension tube and seated in the socket in the crescent, and including a preferred cable network extending from the operating elements or components in the transmission tube to articulate the crescent on the end of the extension tube and operate the needle driver, drive direction plate and needle direction plate in the crescent.
Figure 60:
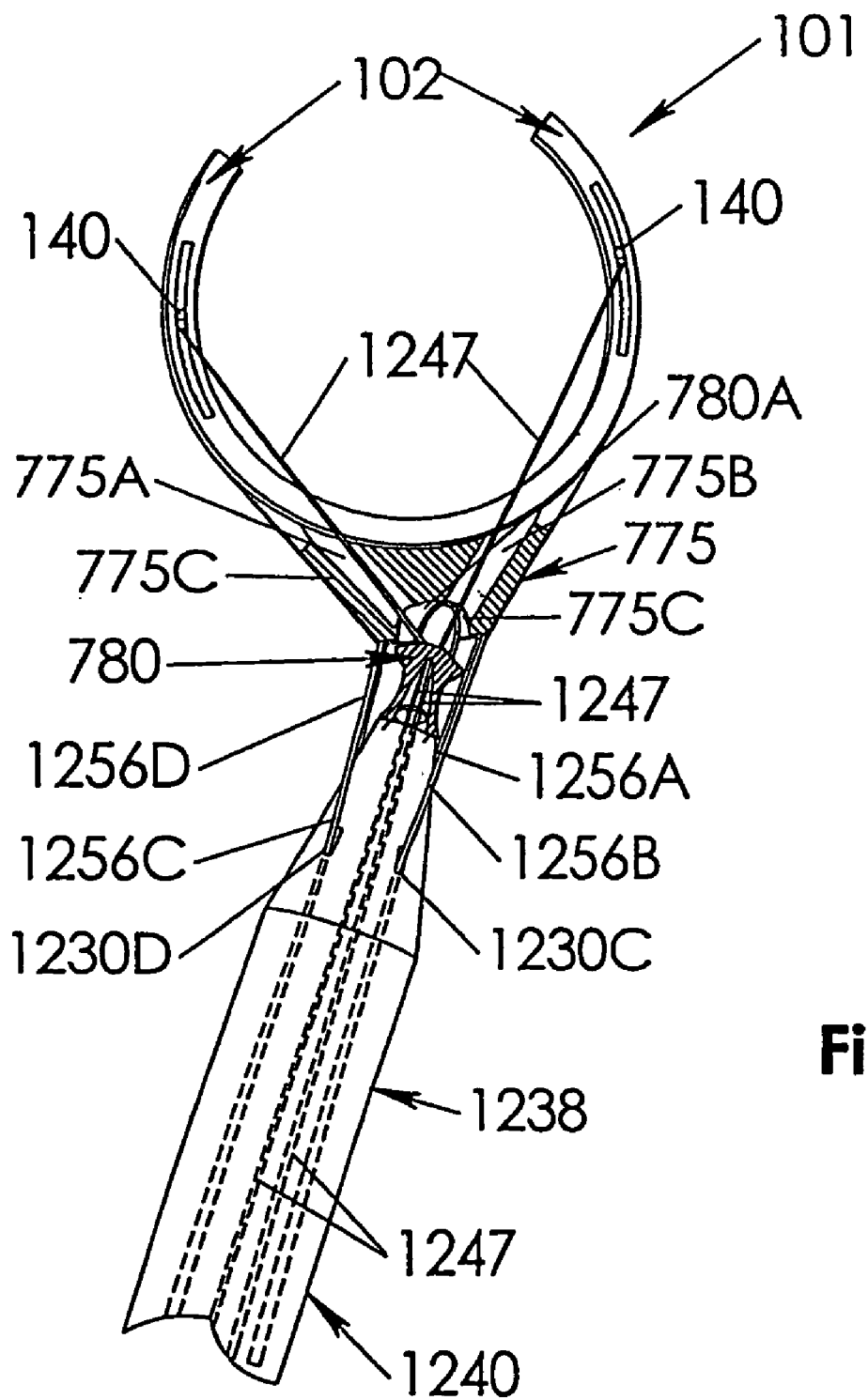
FIG. 60 is a bottom view, partially in section, of the extension tube and the crescent mounted in articulating relationship on the end of the extension tube illustrated in FIG. 59, along with a typical operating cable system for manipulating the crescent with respect to the extension tube and illustrating the drive access cable extensions and clearance tunnels for connection to the operating components of the operating device and operating the needle driver in the crescent.
Figure 61:
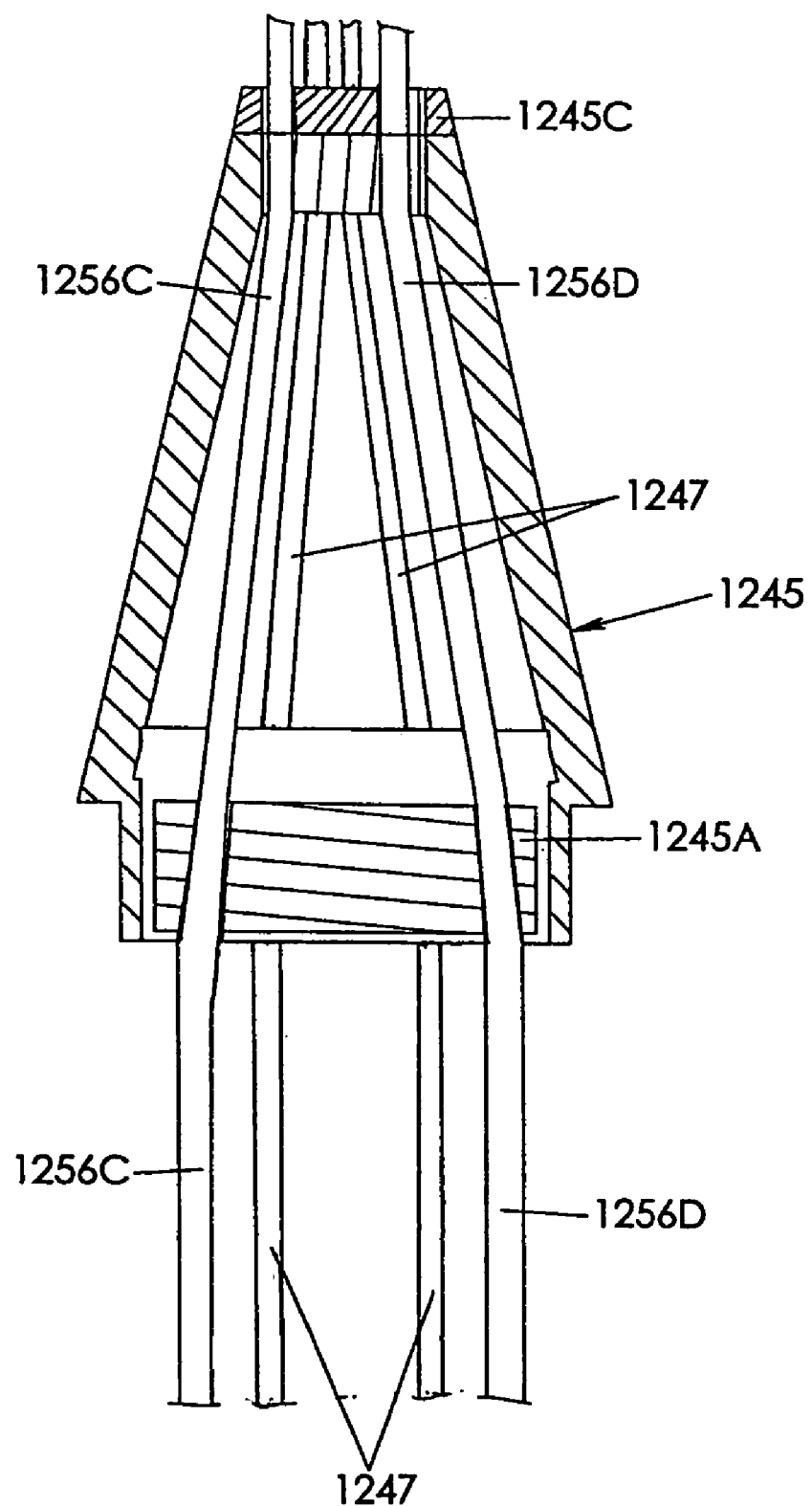
FIG. 61 is a sectional view of the transition cone and spacer ring elements of the device, which transition cone joins the transmission tube to the extension tube and narrows the internal cable run between the transmission tube and the extension tube.
Figure 66:
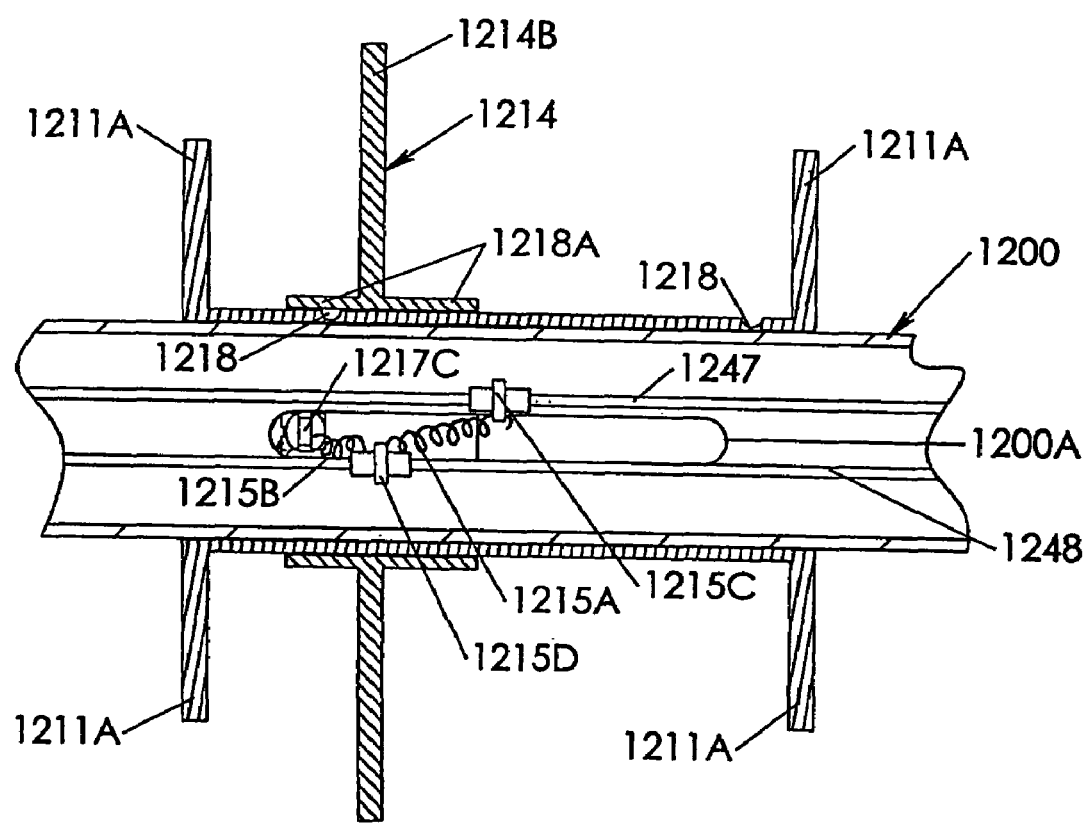
FIG. 66 is an enlarged longitudinal sectional view of the external and internal components of the direction actuator and the slide switch operating components of the operating device illustrated in FIG. 65.
Figure 67:
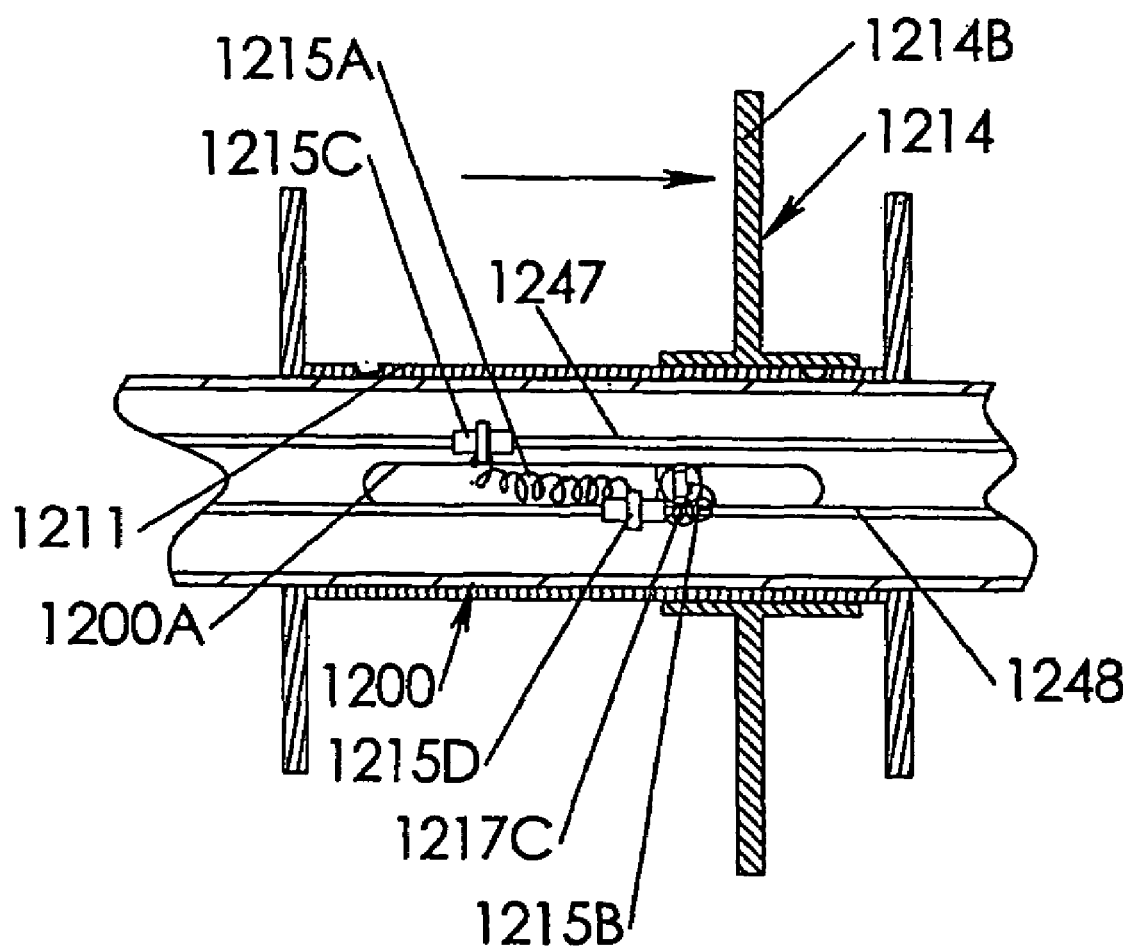
FIG. 67 is an enlarged longitudinal sectional view of the external and internal components of the direction actuator and the slide switch operating components of the operating device illustrated in FIG. 66, with the direction actuator positioned in an alternative functional configuration.
Figure 68:
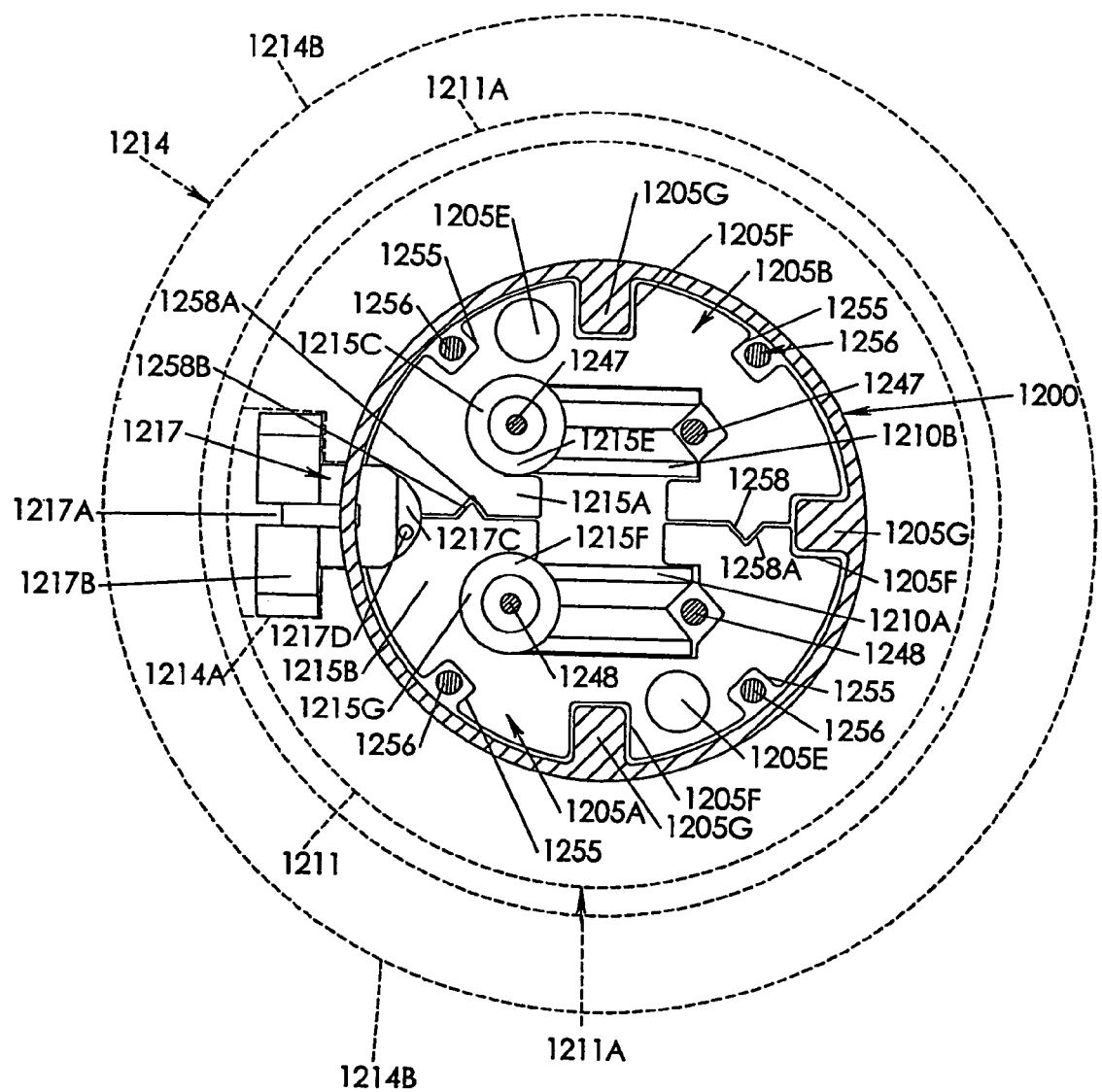
FIG. 68 is a transverse sectional view of the transmission tube, taken at the direction actuator, more particularly illustrating internal elements of the lever mechanism and the direction actuator located inside the transmission tube.
Figure 69:
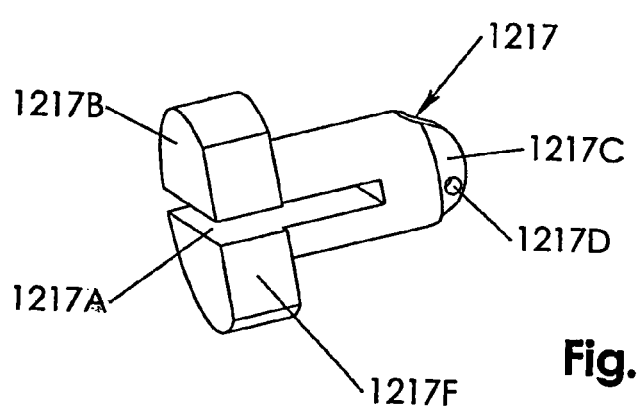
FIG. 69 is a perspective view of an actuator boss element of the direction actuator assembly.
Figure 70:
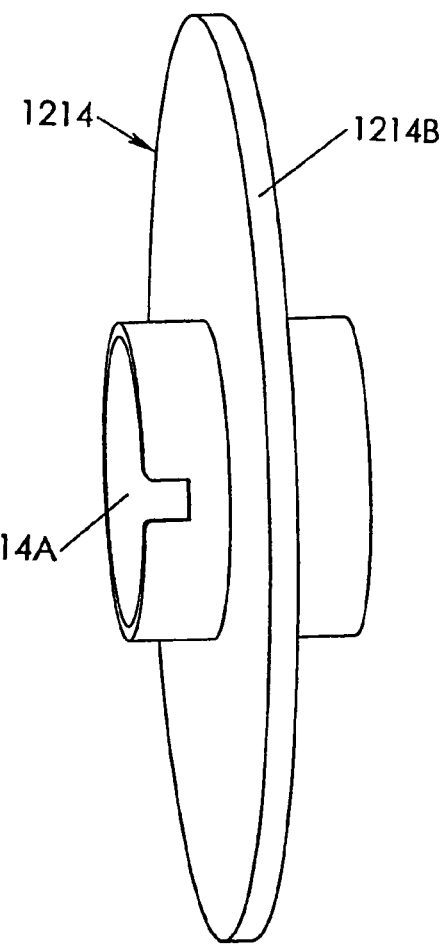
FIG. 70 is a perspective view of a direction connecting rod element of the direction actuator assembly.
Figure 71:
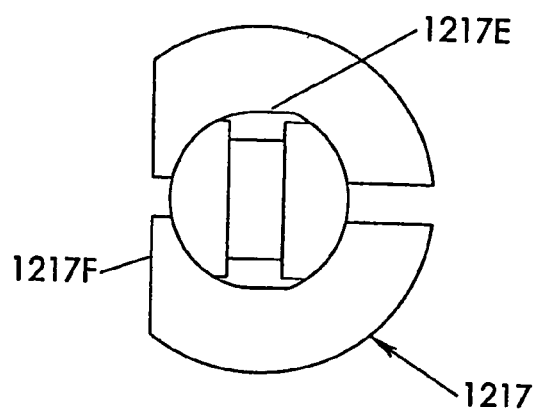
FIG. 71 is a front view of the direction connecting rod element illustrated in FIG. 70.
Figure 72:
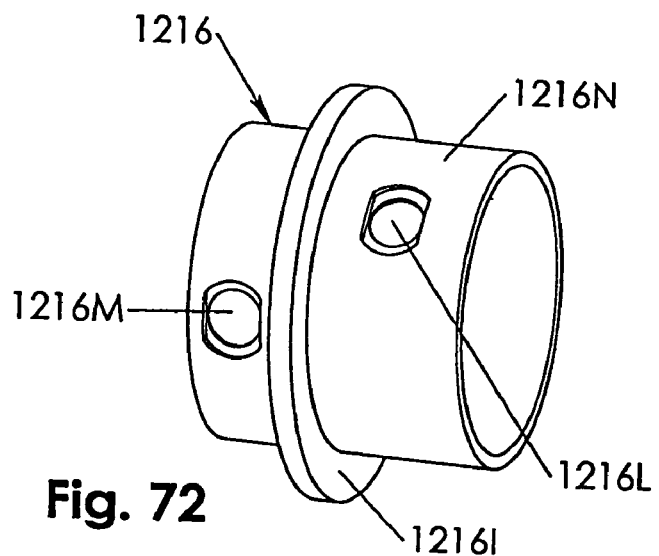
FIG. 72 is a perspective view of a reciprocation input collar element of the direction actuator assembly.
Figure 73:
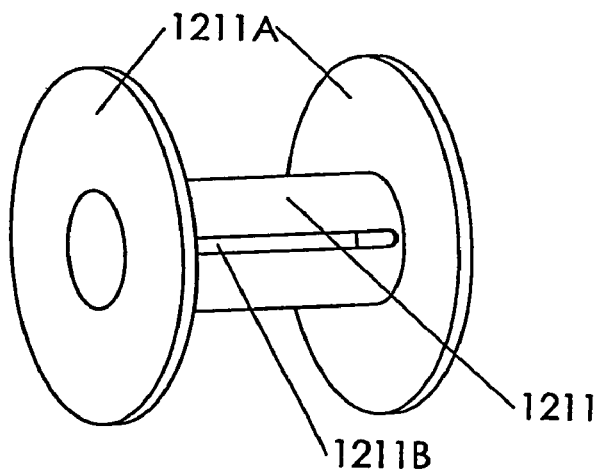
FIG. 73 is a perspective view of a slide switch mount body element of the slide switch element of the operating device.
Figure 74:
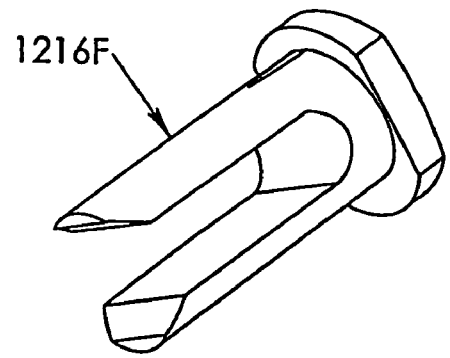
FIG. 74 is a perspective view of a forked transmission rod element of the slide switch.
Figure 76:
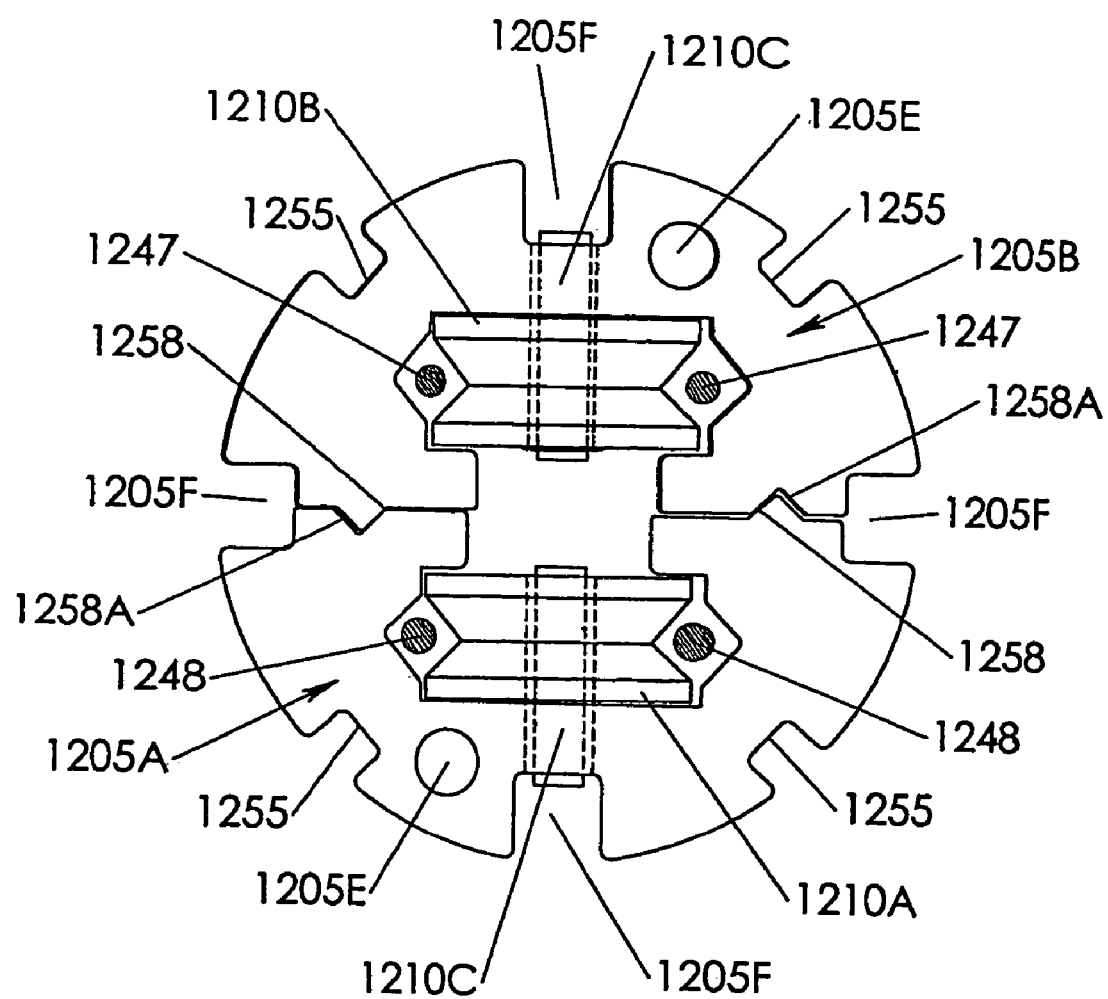
FIG. 76 is a sectional view of the insert and pulley assembly, assembled for mounting in the transmission tube, with the drive cable and direction cable extending around the respective pulleys in the inserts.

Referring now to FIGS. 1, 58, 59, 65-68, 75 and 76 of the drawings locking of the fixed way direction setting plate 136 in a specific position with respect to the case 102 of the device depends upon the positioning of the drive cable 1247 and the direction cable 1248 in the transmission tube 1200. Both the drive cable 1247 and the direction cable 1248 are arranged in a loop at the operating end of the transmission tube 1200, as illustrated in FIGS. 58 and 75 of the drawings. The free ends of the drive cable 1247 are connected to the two drive access cable extensions 140 extending from the reciprocating driver 108 and the free ends of the direction cable 1248 are attached to the pair of direction setting access cable extensions 141, projecting from the drive direction setting plates 134 as illustrated in FIG. 59 and as heretofore described. The opposite loop ends of the drive cable 1247 and the direction cable 1248 are extended around the top pulley 1210B, rotatably positioned in the top insert 1205B and the bottom pulley 1210A, rotatably positioned in the bottom insert 1205A, respectively (FIGS. 75 and 76). This mechanical arrangement facilitates movement of the drive cable 1247 and the direction cable 1248 around the top pulley 12101B and bottom pulley 1210A, respectively, to manipulate both the reciprocating driver 108 and the drive direction setting plate 134 (and set the underlying fixed way direction setting plate 136 in the case 102) responsive to manipulation of the direction actuator 1214, as illustrated in FIGS. 65-67 and as heretofore described. The direction connecting rod—to direction mount spring 1215B and the direction mount—to drive mount spring 121 SA serve to provide a lag in the relative positions of the drive cable 1247 and the direction cable 1248 and thus, rotation of the reciprocating driver 108 and the companion drive direction setting plate 134 (with the fixed direction setting plate 136 in a selected setting), for purposes which will be hereinafter described. This lag is illustrated in the opposite sliding positions of the direction actuator boss 1214B in FIGS. 65-67.

Figure 77:
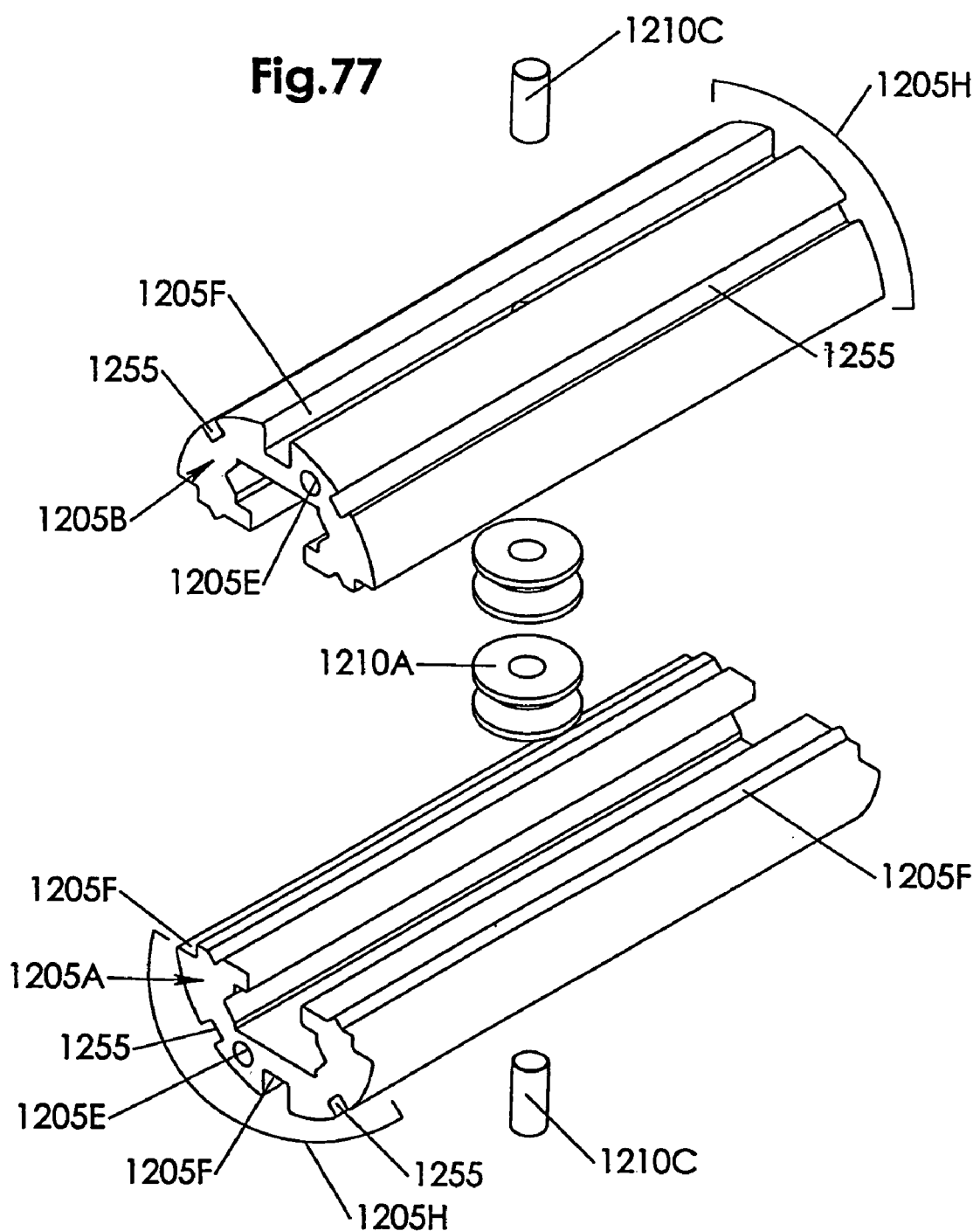
FIG. 77 is a perspective view of the inserts illustrated in FIG. 76, illustrating one of the pulleys mounted internally therein and more particularly illustrating cable slots for receiving the various crescent articulation cables extending through the transmission tube.

Referring to FIGS. 1, 58, 59 and 75-78 of the drawings the top insert 1205B is seated on the bottom insert 1205A in the transmission tube 1200 such that the two inserts may slide longitudinally with respect to each other. The top pulley 1210B is rotatably secured to the top insert 1205B by means of a pulley pin 1210C and in like manner, the bottom pulley 1210A is rotatably attached to the bottom insert 1205A by means of a companion pulley pin 1210C (FIGS. 76 and 77).

Figure 78:
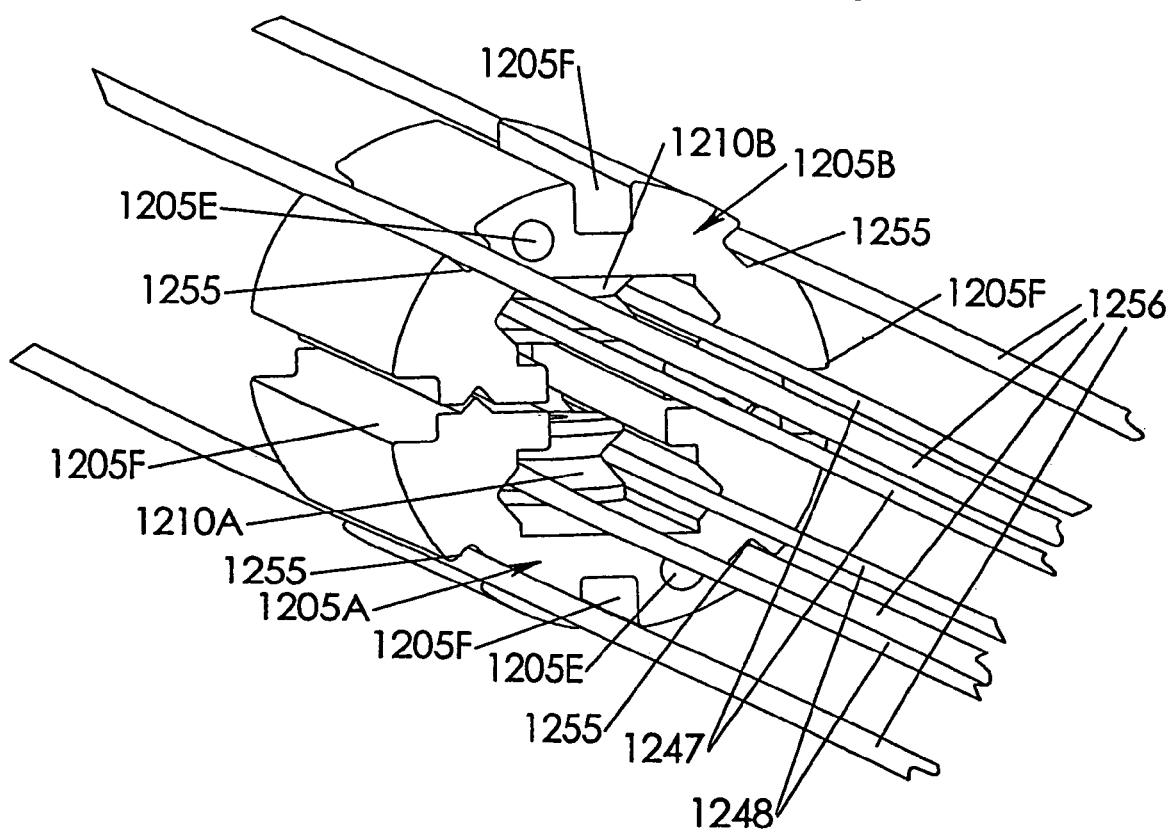
FIG. 78 is a perspective view of the insert, pulley and cable arrangements illustrated in FIGS. 75 and 76, extending around the pulleys and through the insert slots inside the transmission tube.
Figure 79:
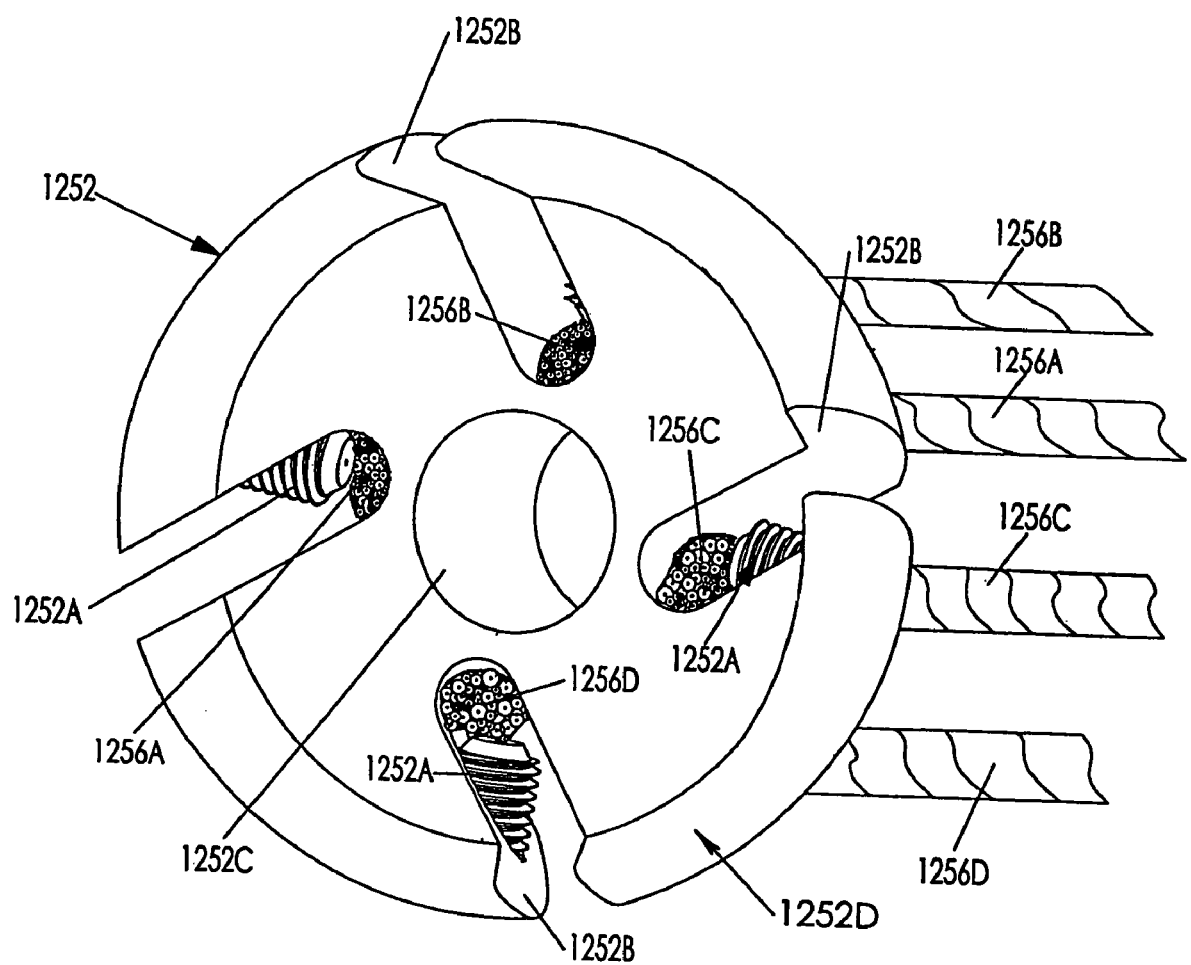
FIG. 79 is a perspective view of a selection bearing that cooperates with the lever illustrated in FIGS. 1-3 and illustrating crescent articulation cables mounted in the selection bearing to facilitate operation of the lever and the cables and articulate the crescent on the extension tube responsive to manipulation of the lever.

As further illustrated in FIGS. 75 and 76 the top pulley 1210B and the bottom pulley 1210A are journalled for rotation on the respective pulley pins 1210C in a cavity or opening provided in the respective top insert 1205B and bottom insert 1205A, such that the looped end (FIG. 58) of the drive cable 47 can be looped around the top pulley 1210B, while the looped end of the direction cable 1248 is looped around the bottom pulley 1210A. As heretofore described, the pairs of extending ends of the drive cable 1247 and the direction cable 1248 project through the transmission tube 1200 to anchor in the respective drive access cable extension 140 and direction setting access cable extension 141. The top insert 1205B and bottom insert 1205A are further provided with four longitudinal, radially spaced-apart cable insert clearance grooves 1255 to accommodate the crescent angle articulation cables 1256A, 1256B, 1256C and 1256D as illustrated in FIGS. 76 and 78. This arrangement facilitates sliding of the respective crescent angle articulation cables 1256A, 1256B, 1256C and 1256D with respect to the top insert 1205B and the bottom insert 1205A, responsive to operation of the lever 1251 and the selection bearing 1252, to which one end of each of the respective crescent angle articulation cables 1256A, 1256B, 1256C and 1256D is connected. This action manipulates the crescent 101, which receives the opposite ends of the crescent angle articulation cables 1256A, 1256B, 1256C and 1256D at the four corners of the socket 775 (FIG. 5), as hereinafter described. Insert tension threaded holes 1205E are provided in the respective ends of the top insert 1205B and the bottom insert 1205A to facilitate insertion of adjusting bolts (not illustrated) for independently adjusting the linear positions of the top insert 1205B and the bottom insert 1205A, respectively, in the transmission tube 1200 for application of tension to the respective drive cable 1247 and direction cable 1248, as deemed necessary while operating the device.

Referring now to FIGS. 1, 58, 59-64, 79 and 80 of the drawings, the respective operating ends of the crescent angle articulation cables 1256A, 1256B, 1256C and 1256D are secured to the selection bearing 1252 (FIG. 79) at the operating end of the transmission tube 1200, typically by means of cable set screws 1252A, seated in corresponding bearing cable slots 1252B provided in the selection bearing 1252. A lever mounting hole 1252C is provided in the center of the selection bearing 1252 to accommodate a mounting post 1251A element of the lever 1251, as illustrated in FIG. 58. Furthermore, the selection bearing 1252 is pivotally seated in the extension clearance hole 1253C of the selection bearing socket 1253, having a socket mounting extension 1253A, for mounting the selection bearing socket 1253 on the operating end of the transmission tube 1200 (FIG. 58). Accordingly, the lever 1251 can be manipulated with a finger and thumb to pivot the selection bearing 1252 in the selection bearing socket 1253 and effect selective tensioning of the respective crescent angle articulation cables 1256A, 1256B, 1256C and 1256D, with a corresponding articulation of the crescent 101, fixed to the respective crescent angle articulation cables 1256A, 1256B, 1256C and 1256D at the respective base corners 776A, 776B, 776C and 776D of the socket cavity base 776 element of the socket 775 (FIG. 80). The joint ball 780 is fixedly mounted to the extending end of the transition guide cone 1238 and receives the socket 775 in rotatable, articulating relationship, as heretofore described. Manipulation of the lever 1251 is therefore effective to facilitate universal movement of the crescent 101 with respect to the transition guide cone 1238, as illustrated in FIGS. 59-64 of the drawings.

Figure 82:
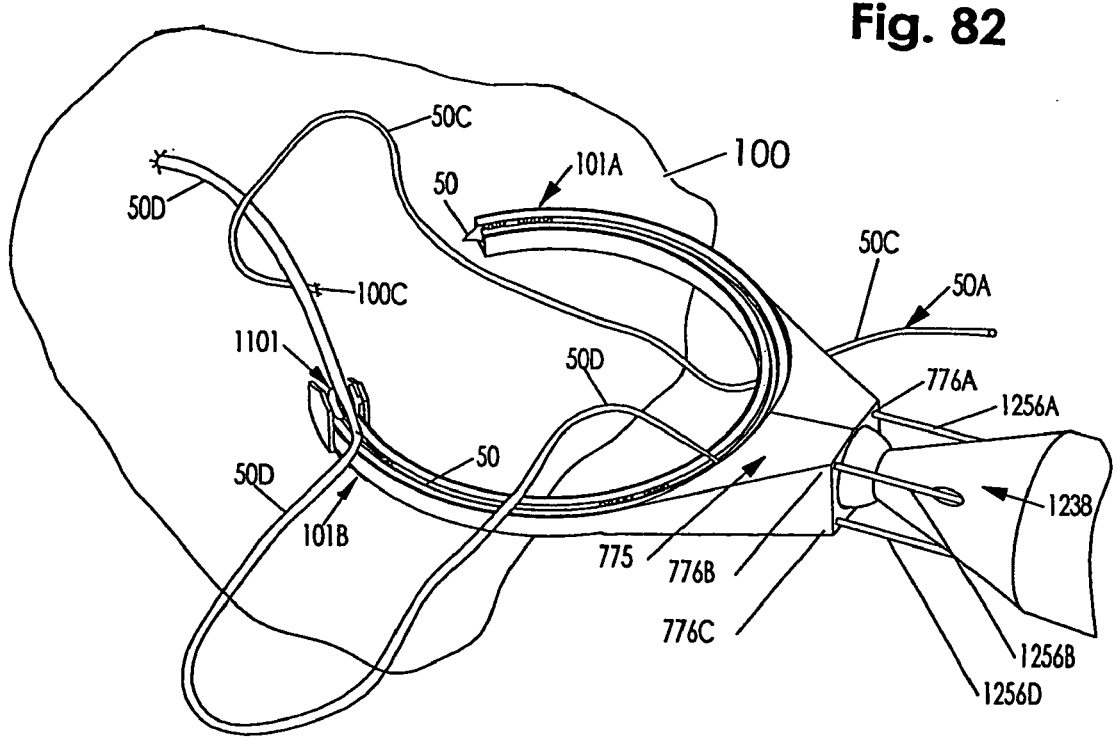
FIG. 82 is a perspective view of the crescent, illustrating a preferred manipulation of the thread illustrated in FIG. 81 in a looping operation to facilitate stitching the tissue while using the operating device and crescent with the thread incrementing device.
Figure 83:
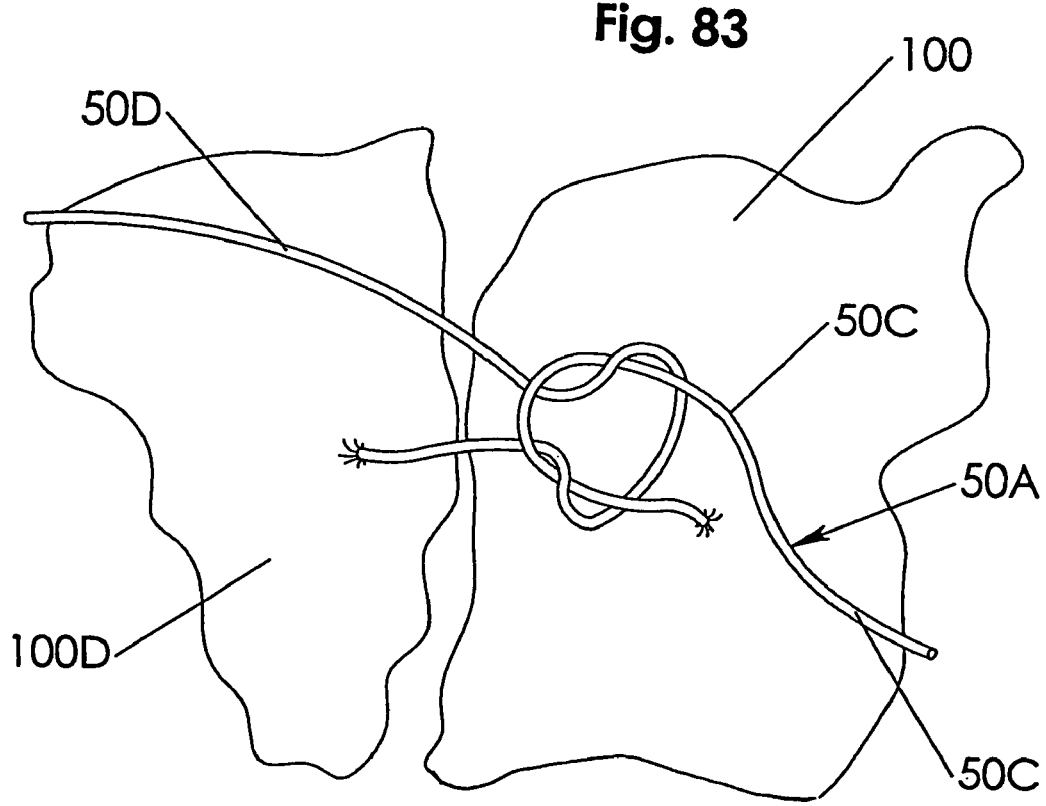
FIG. 83 is a perspective view of a suture knot, illustrating the knotting of two lengths of thread to attach adjacent segments of tissue during the suturing process using the crescent.

Referring now to FIGS. 1, 40A and 80-83 of the drawings a thread incrementing accessory 1101 is illustrated for mounting on one end of the crescent 101 and handling the thread 50A attached to the middle of the crescent-shaped needle 50. Typically, when used alone, the thread incrementing accessory 1101 is mounted on the receiving arm 1011 B opposite the advancing arm 101A of the crescent 101, as illustrated in FIGS. 40A and 80-82 of the drawings. It will be appreciated from a consideration of FIGS. 40A and 80-82 that the crescent-shaped needle 50 is seated in the fixed way 104 element of the crescent 101 such that it can completely traverse the crescent 101 and the gap 105 (FIG. 6) in the crescent 101, between the advancing arm 101A and the receiving arm 101B, as well as the thread incrementing accessory 1101, with the thread 50 following the course of the needle 50. The thread incrementing accessory 1101 is designed to handle and increment the loose thread leading thread head portion 50D of the thread 50A, extending from the needle 50, as the needle 50 traverses a material 100 to be sutured, as illustrated in FIGS. 80-83. Accordingly, referring again to FIG. 80 of the drawings the needle 50 is rotating in the counterclockwise direction as viewed from above and first enters the material 100 at the entrance 100B and exits the material at the exit 100C, to create a continuous tunnel 100A (illustrated in phantom). The thread incrementing accessory 1101 thus picks up the thread 50A as the needle 50 completes its traversal of the tunnel 100A and prevents entanglement of the thread 50A as the crescent 101 is positioned for additional penetration of the material 100. As illustrated in FIG. 81 of the drawings the thread head 50D of the thread 50A may be engaged by a sliding hook 50E to manually take up the slack created by the thread incrementing accessory 1101 out of the thread 50A as the needle 50 rotates and penetrates the material 100. The opposite end or the thread tail 50C projects from the opposite end of the material 100 at the entrance 100B, as illustrated in FIGS. 80 and 81. FIG. 82 illustrates the technique of looping the severed thread tail 50C of the thread 50A around the thread head 50D of the thread 50A as the thread head 50D projects from the exit 100C of the tunnel 100A in the material 100. This maneuver forms the basis for the first knot or suture to be tied in the thread 50A, typically with the help of the thread incrementing accessory 1101. This knot or suture is substantially complete as illustrated in FIG. 83, which illustrates knotting of the thread tail 50C and the thread head 50D of the thread 50A to secure two segments of the material 100 together in a single suture or knot.

Figure 84:
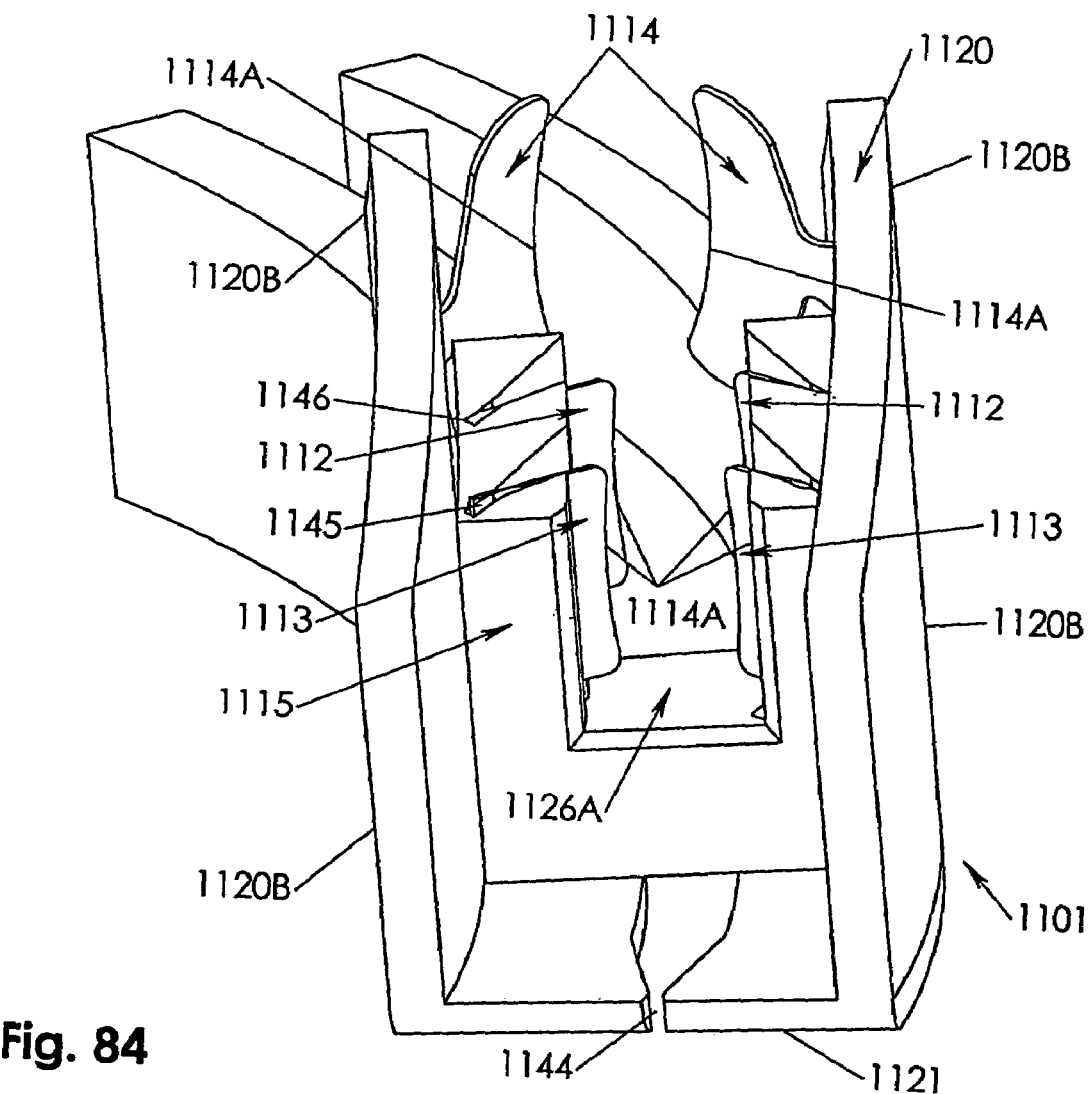
FIG. 84 is a front perspective view of a preferred embodiment of the thread incrementing accessory that handles and increments the thread in the cycling suturing and knot-tying device of this invention.
Figure 85:
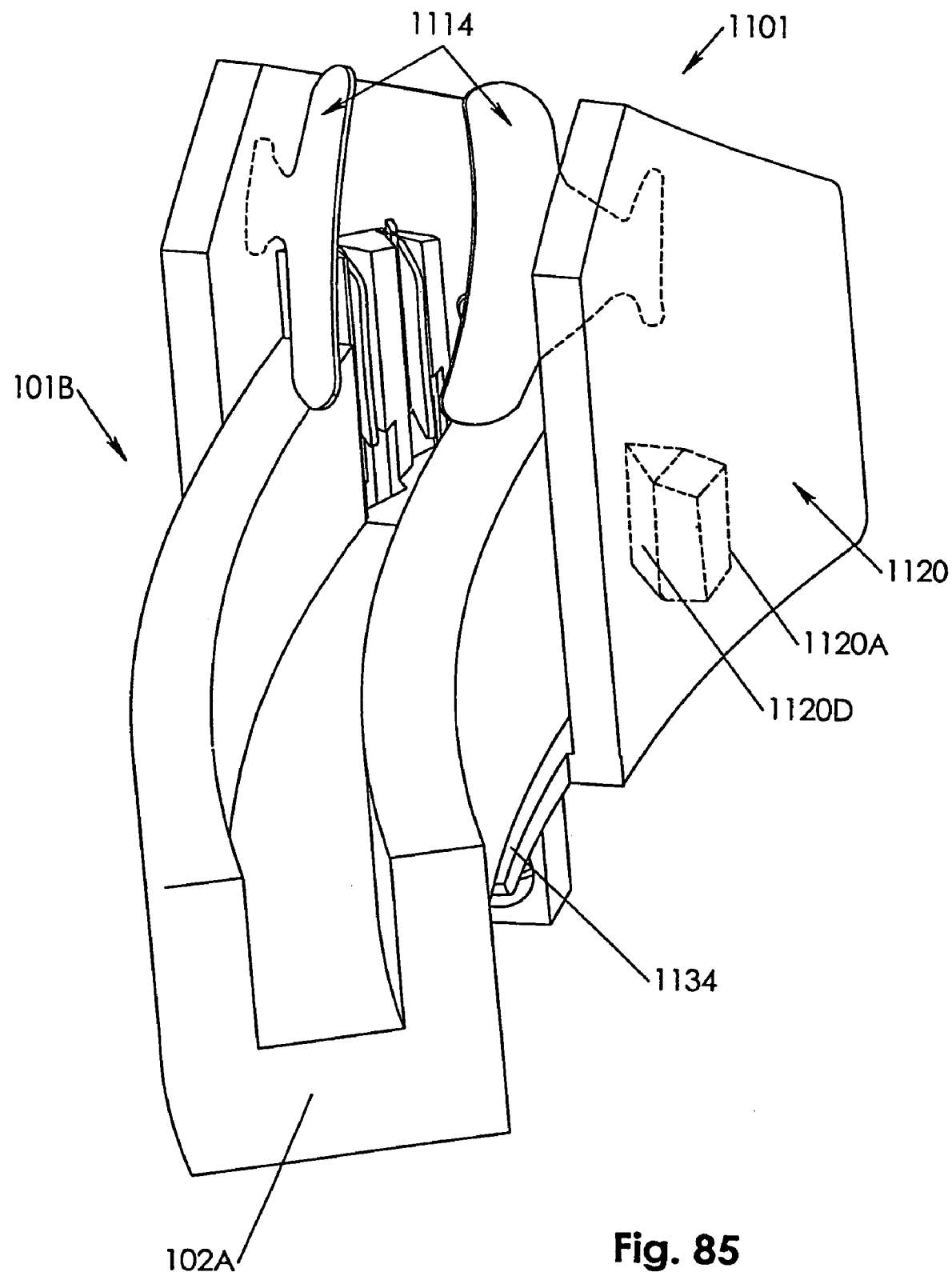
FIG. 85 is a rear perspective view of the thread incrementing accessory illustrated in FIG. 84.
Figure 86:
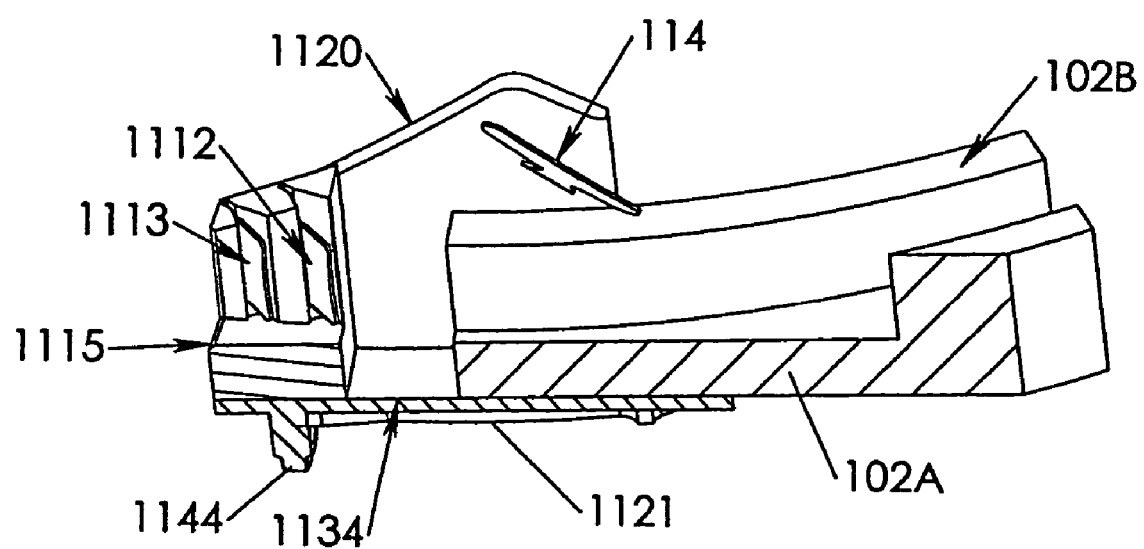
FIG. 86 is a side view, partially in section, of the thread incrementing accessory illustrated in FIGS. 84 and 85.
Figure 87:
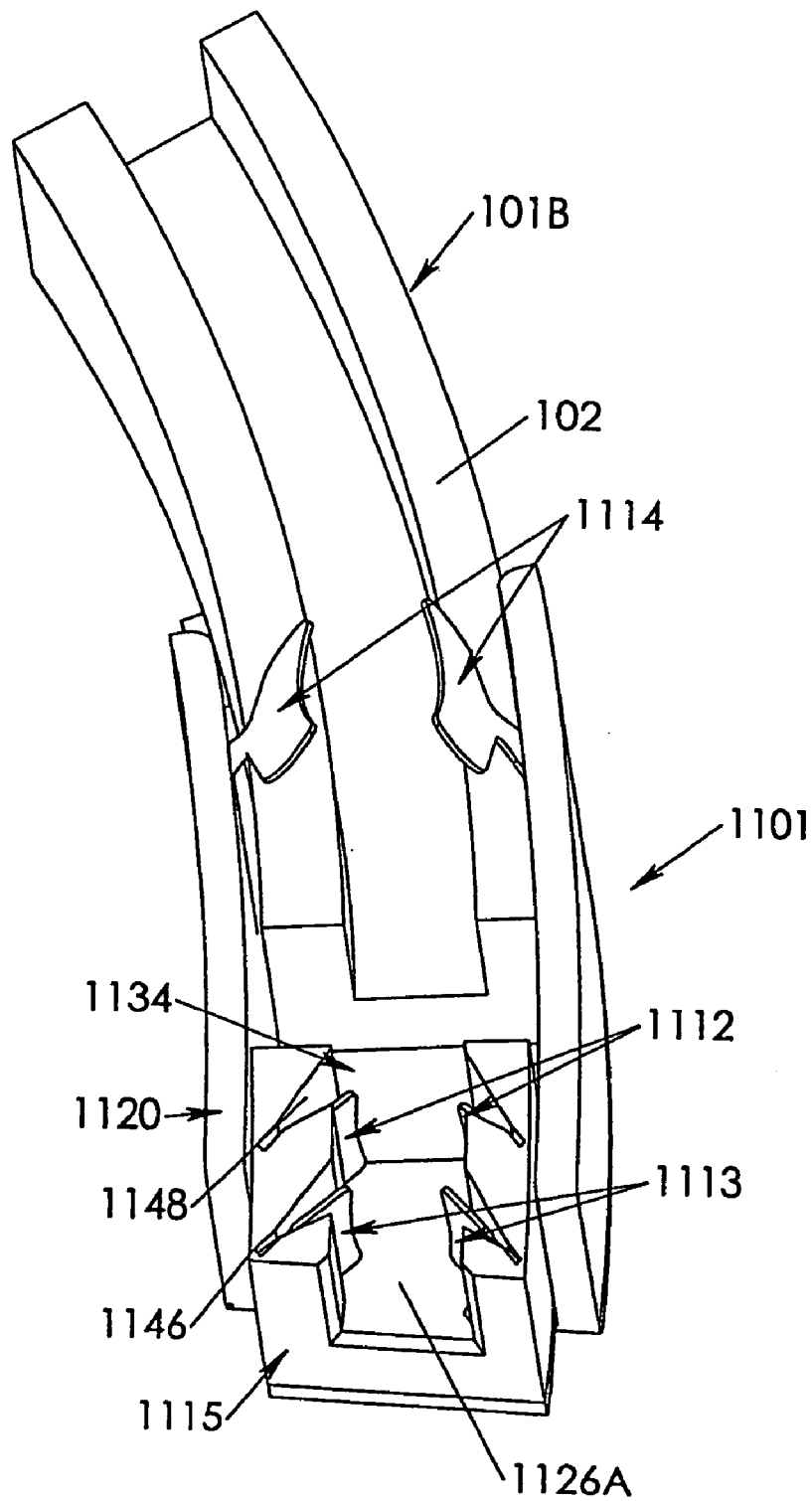
FIG. 87 is a top perspective view of the thread incrementing accessory illustrated in FIGS. 84-86, more particularly illustrating mounting of the thread incrementing accessory on one end of the crescent.
Figure 88:
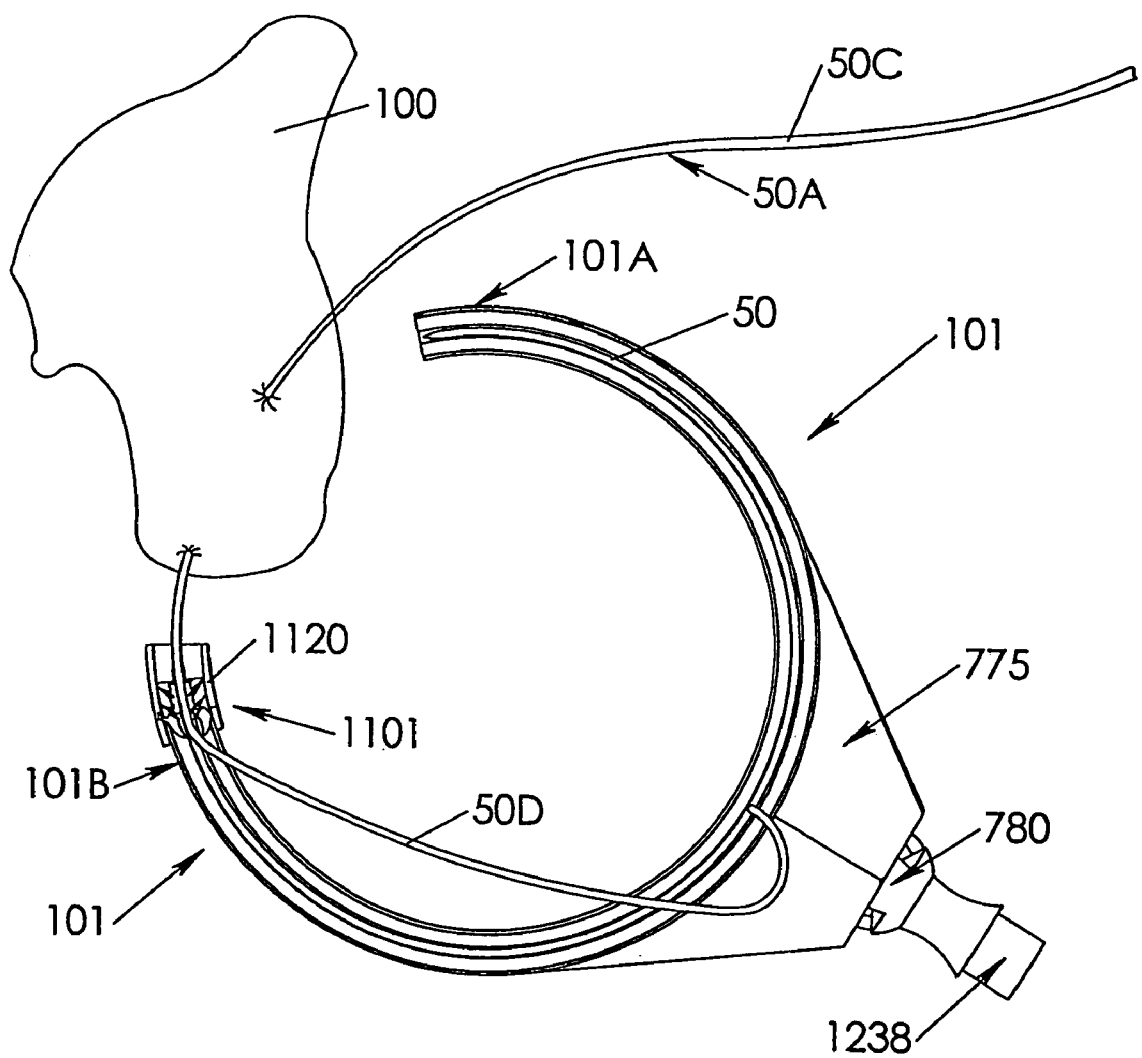
FIG. 88 is a top view of the crescent element of the cycling suturing and knot-tying device, with the thread incrementing accessory mounted on one end thereof, more particularly illustrating positioning of a length of thread extending from the needle in the crescent, through the thread incrementing accessory and through a tissue subjected to suturing, prior to operation of the thread incrementing accessory.

Referring now to FIGS. 1, 40A, 84-88 and 90-93 of the drawings the thread incrementing accessory 1101 is detailed and is characterized by a fixed housing 1120, typically mounted on the advancing arm 101B of the crescent 101 (FIG. 88). The fixed housing 1120 is defined by spaced-apart housing walls 1120B, with fixed blades 1114 extending from the rear portion of the housing walls 1120B, respectively, and higher movable blades 1112 and movable blades 1113, each having concave contact areas 1114A, projecting from corresponding fins 1145, disposed in fin slots 1146, respectively, provided in a movable housing 1115 positioned inside the fixed housing 1120 (FIG. 84). The higher movable blades 1112 and the movable blades 1113 project into a guide slot 1126A provided in the movable housing 1115 to accommodate and selectively engage the thread 50A at the concave contact surfaces 1114A, respectively, as the needle 50 traverses the crescent 101 (FIG. 88). An actuation plate 1134 is slidably disposed above the fixed housing 1120 and beneath the movable housing 1115. A second thread incrementing accessory 1101A may also be designed to seat on the case base 102A on the receiving arm 101B end of the crescent 101, as illustrated in FIG. 89 of the drawings.

Figure 4:
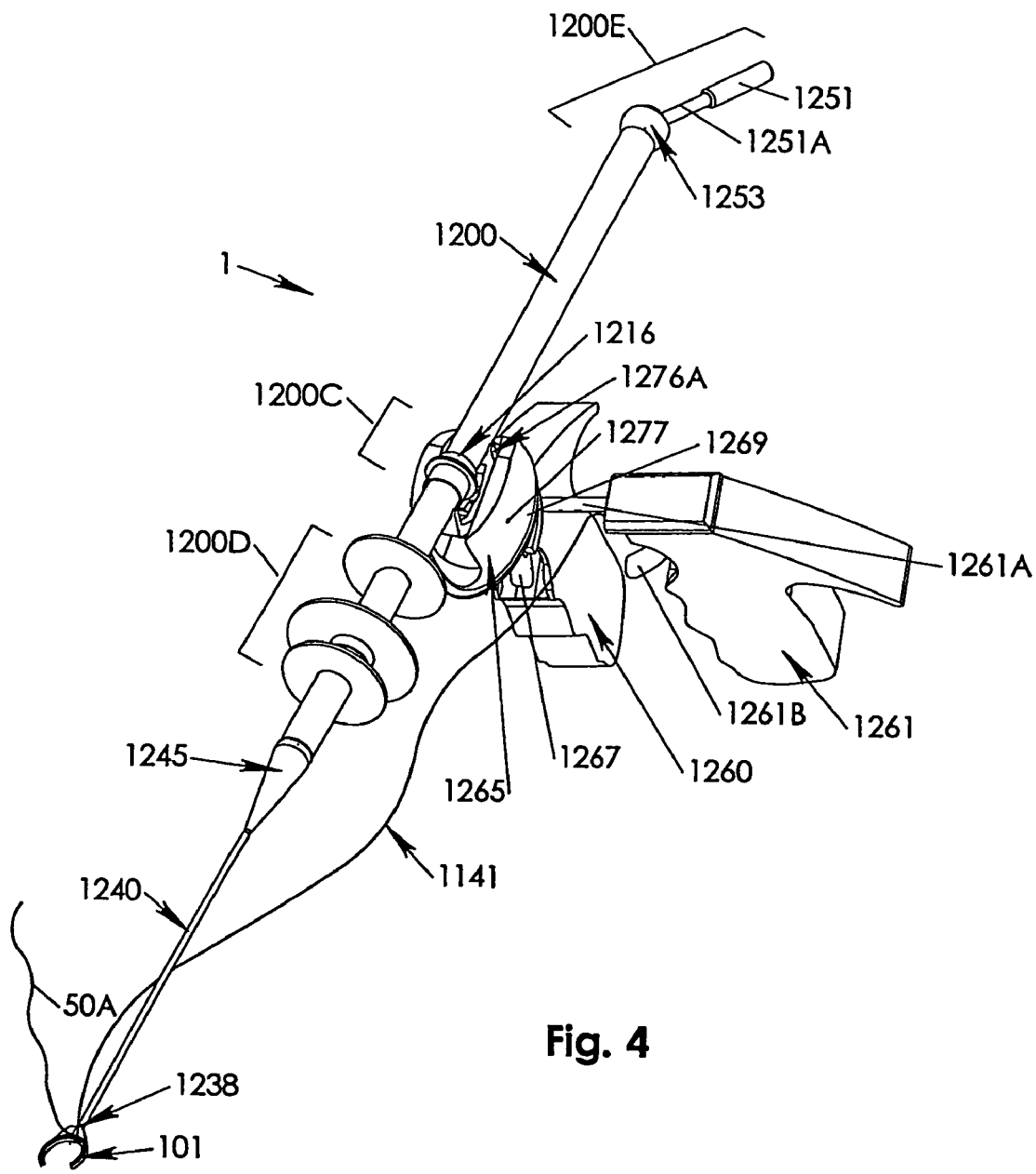
FIG. 4 is a top and left side perspective view of the operating device illustrated in FIGS. 1-3, more particularly illustrating a second handle transversely attached to the first handle and including an auxiliary operating tube extending from the second handle to a thread incrementing accessory attached to the crescent.
Figure 90:
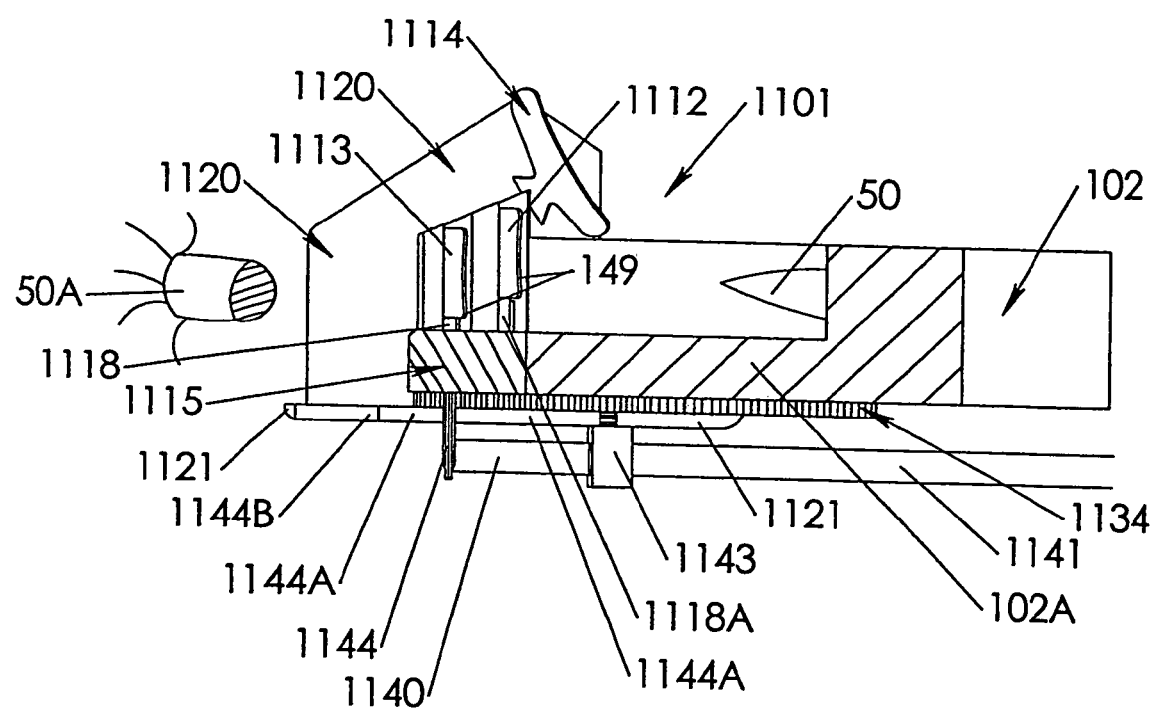
FIG. 90 is a side sectional view of the thread incrementing accessory illustrated in FIG. 87.
Figure 91:
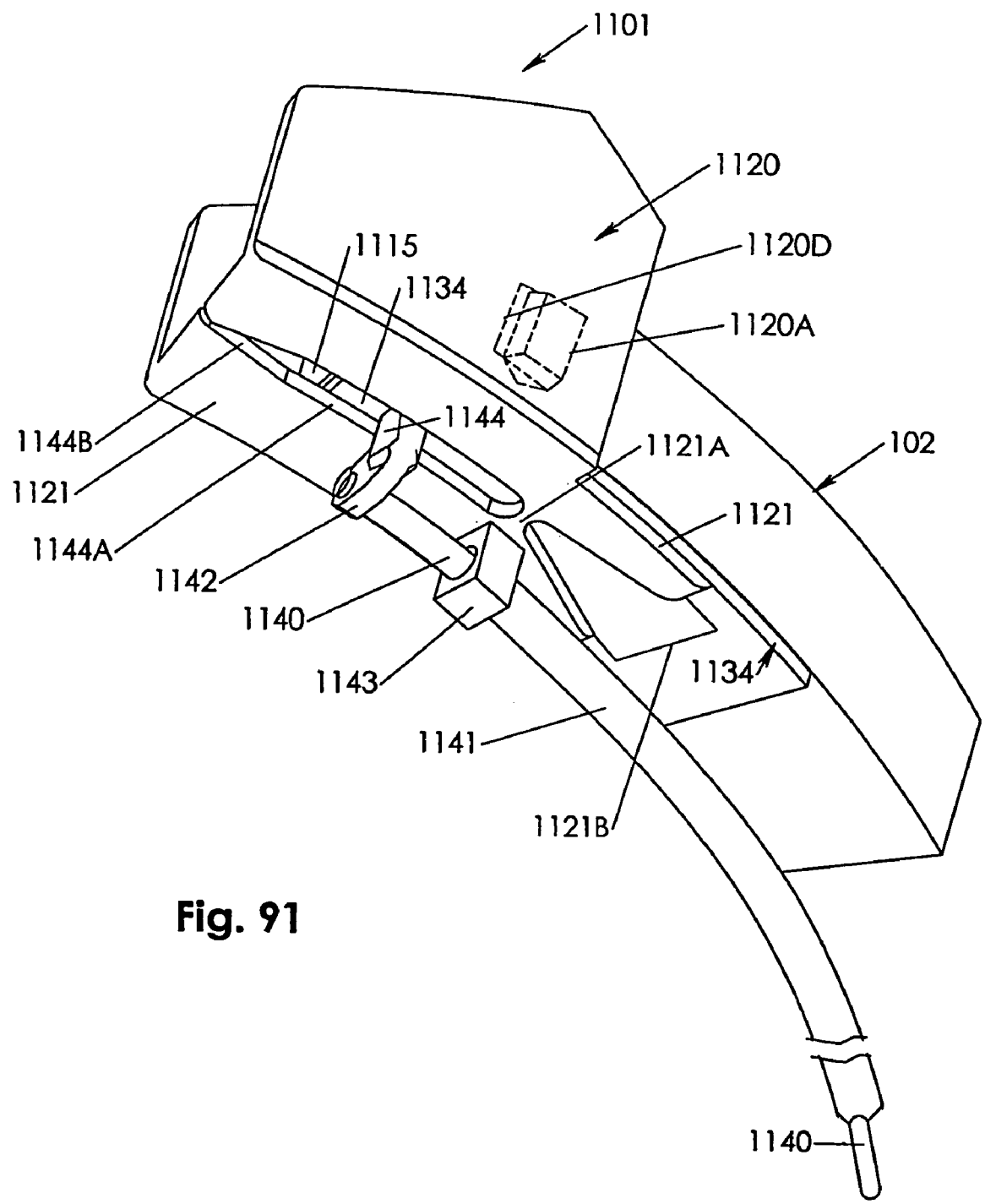
FIG. 91 is a bottom perspective view of the thread incrementing accessory illustrated in FIG. 90, more particularly illustrating an access extension tab and a cable connection in the thread incrementing accessory.
Figure 92:
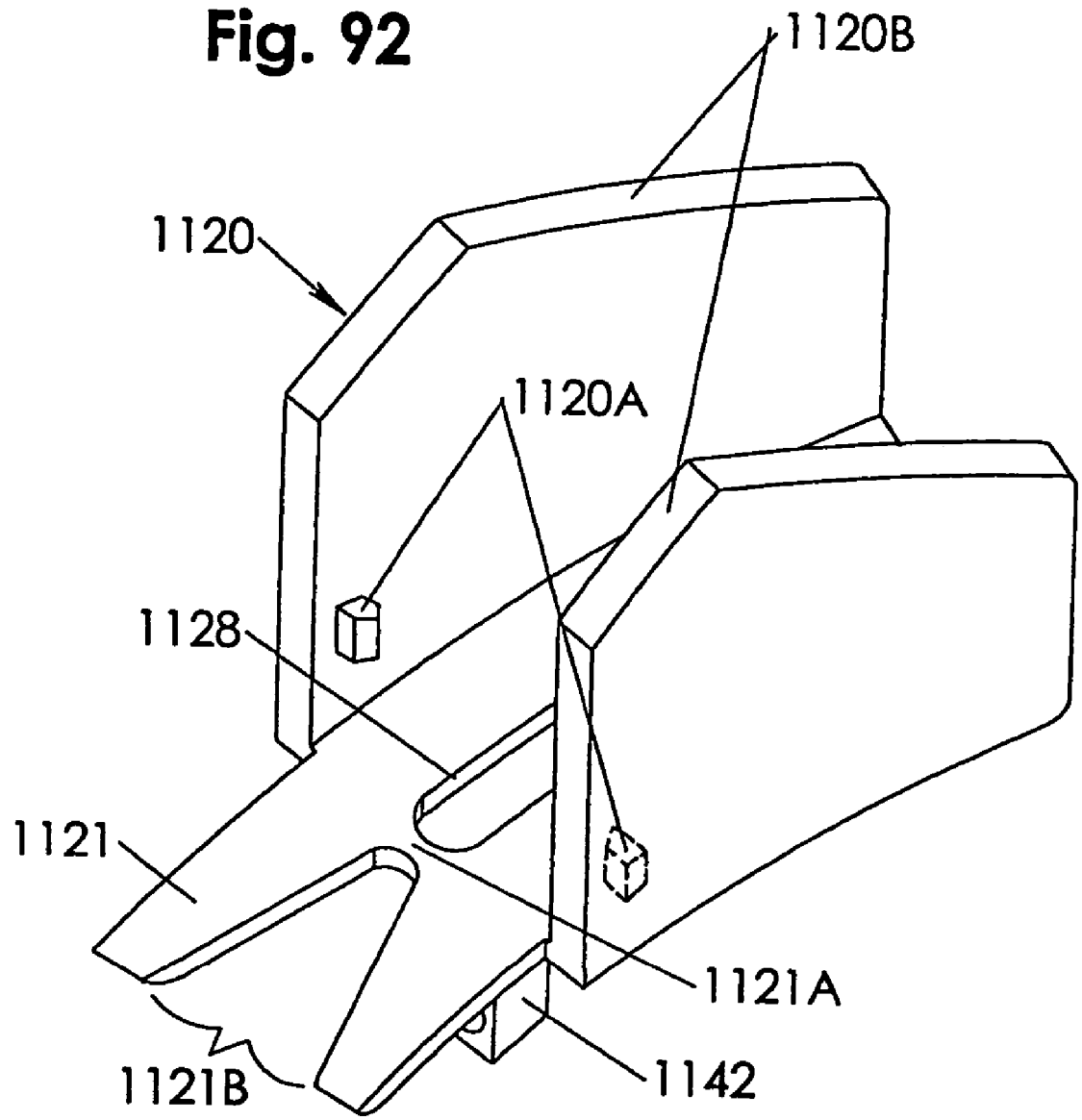
FIG. 92 is a perspective view of the housing and base elements of the thread incrementing accessory illustrated in FIG. 91.
Figure 93:
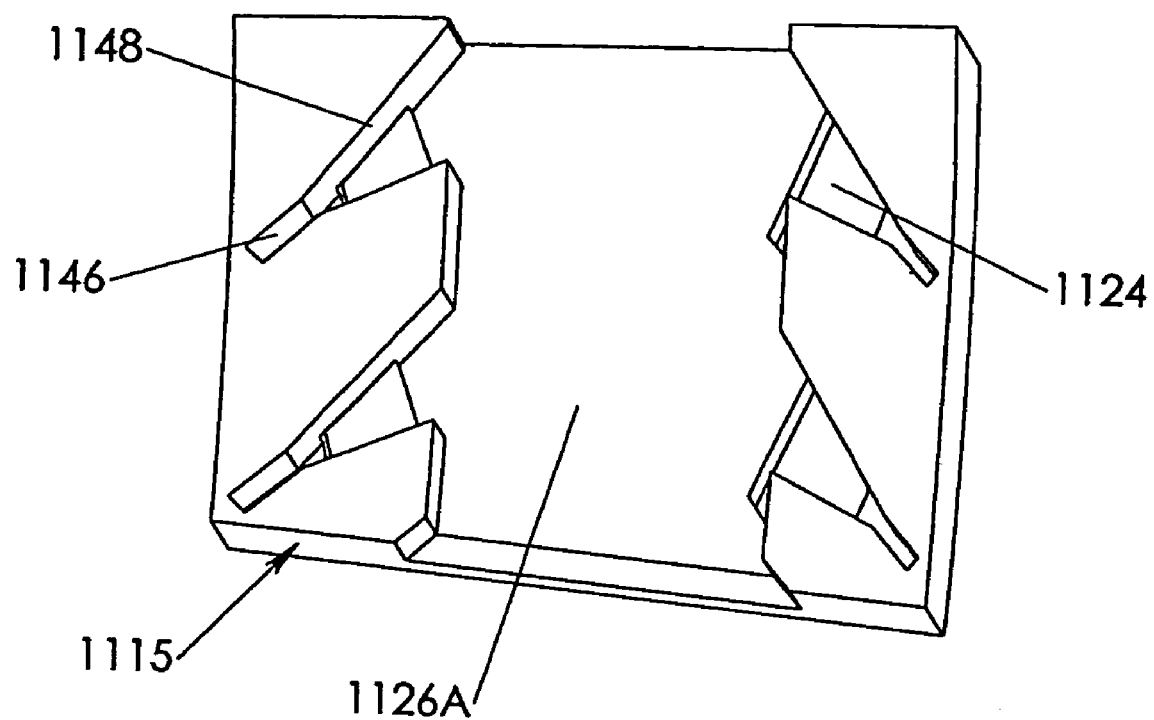
FIG. 93 is a perspective view of the thread incrementing accessory movable housing element illustrated in FIG. 90, more particularly illustrating blade recesses and fin slots in the movable housing.

As further illustrated in FIGS. 4, 84, 90, 91, 92 and 94 of the drawings a base 1121 closes the bottom of the fixed housing 1120 beneath the actuation plate 1134 and an access slot 1144A extends linearly through the base 1121 and tapers at the forward end to define a narrowing slot 1144B at the forward end thereof. An access extension tab 1144 slidably seats in the access slot 1144A and is fixed to the actuation plate 1134 (FIG. 91), and the access extension tab 1144 receives a transmission wire boss 1142 for attachment to one end of a power transmission wire 1140 (FIG. 91). The power transmission wire 1140 extends through an opening in a mounting boss 1143 mounted on the base 1121 and receiving one end of a flexible tube 1141, which is secured to the mounting boss 1143, the opposite end of which flexible tube 1141 terminates in a second handle 1261, having a second handle trigger 1261B, attached to the handle 1260, as illustrated in FIG. 4. A hinge 1121A bridges the gap between the rearward end of the access slot 1144A and a spreading clearance notch 1121B, extending the access slot 1144A. Accordingly, operation of the second handle trigger 1261B in the second handle 1261 (FIG. 4) in the manner hereinafter described facilitates sliding movement of the access extension tab 1144 in the access slot 1144A and in the narrowing slot 1144B of the access slot 1144A to slide the actuation plate 1134 and the attached movable housing 1115 in the fixed housing 1120 and handle the thread 50 during suturing, as hereinafter described. As illustrated in FIGS. 91 and 92 a pair of pivotal bosses 120A extend from the inside surfaces of the respective housing walls 1120B of the fixed housing 1120 for engaging corresponding case boss grooves 1120D in the case 102 and slidably securing the fixed housing 1120 in the case 102.

Figure 94:
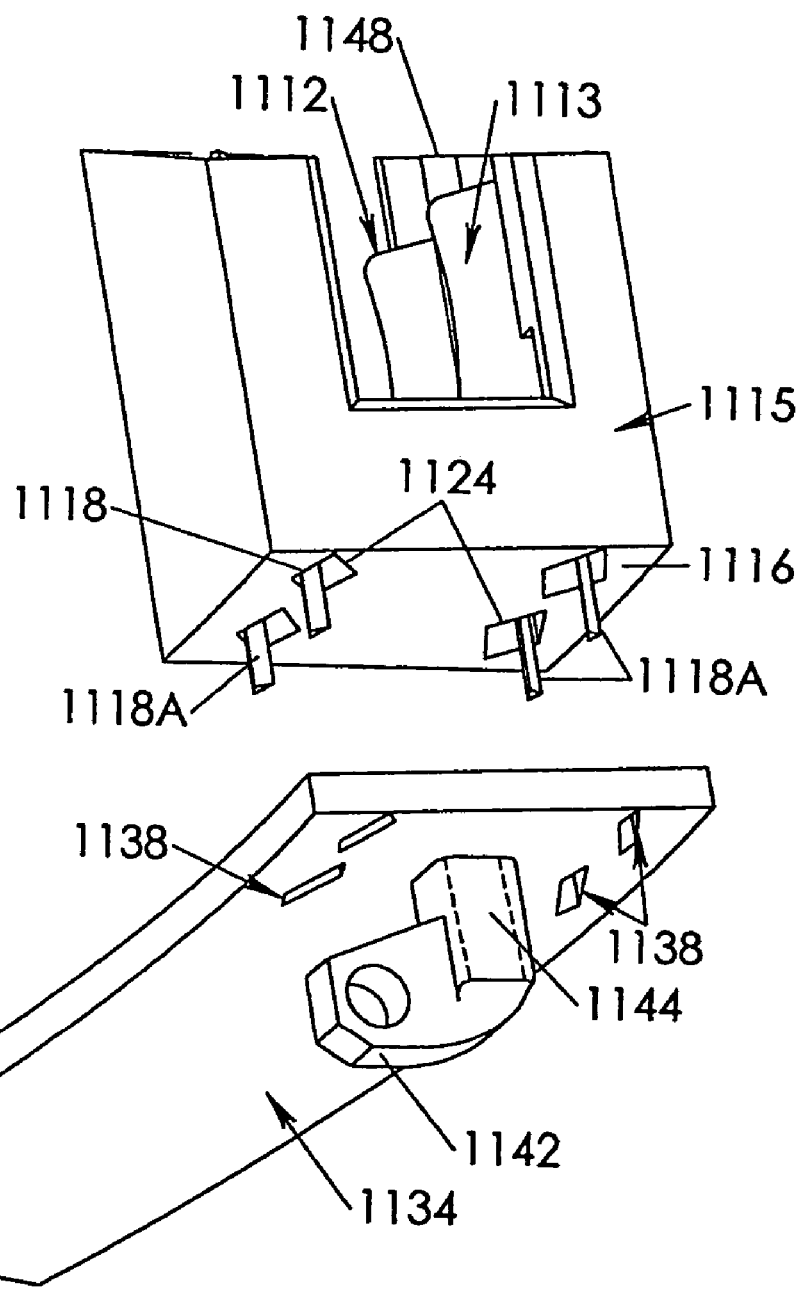
FIG. 94 is an exploded view of the movable housing and actuation plate assembly of the thread incrementing accessory, more particularly illustrating the extension of multiple blade tabs extending through corresponding clearance holes in the movable housing and through the parallelogram holes in the actuation plate.
Figure 95:
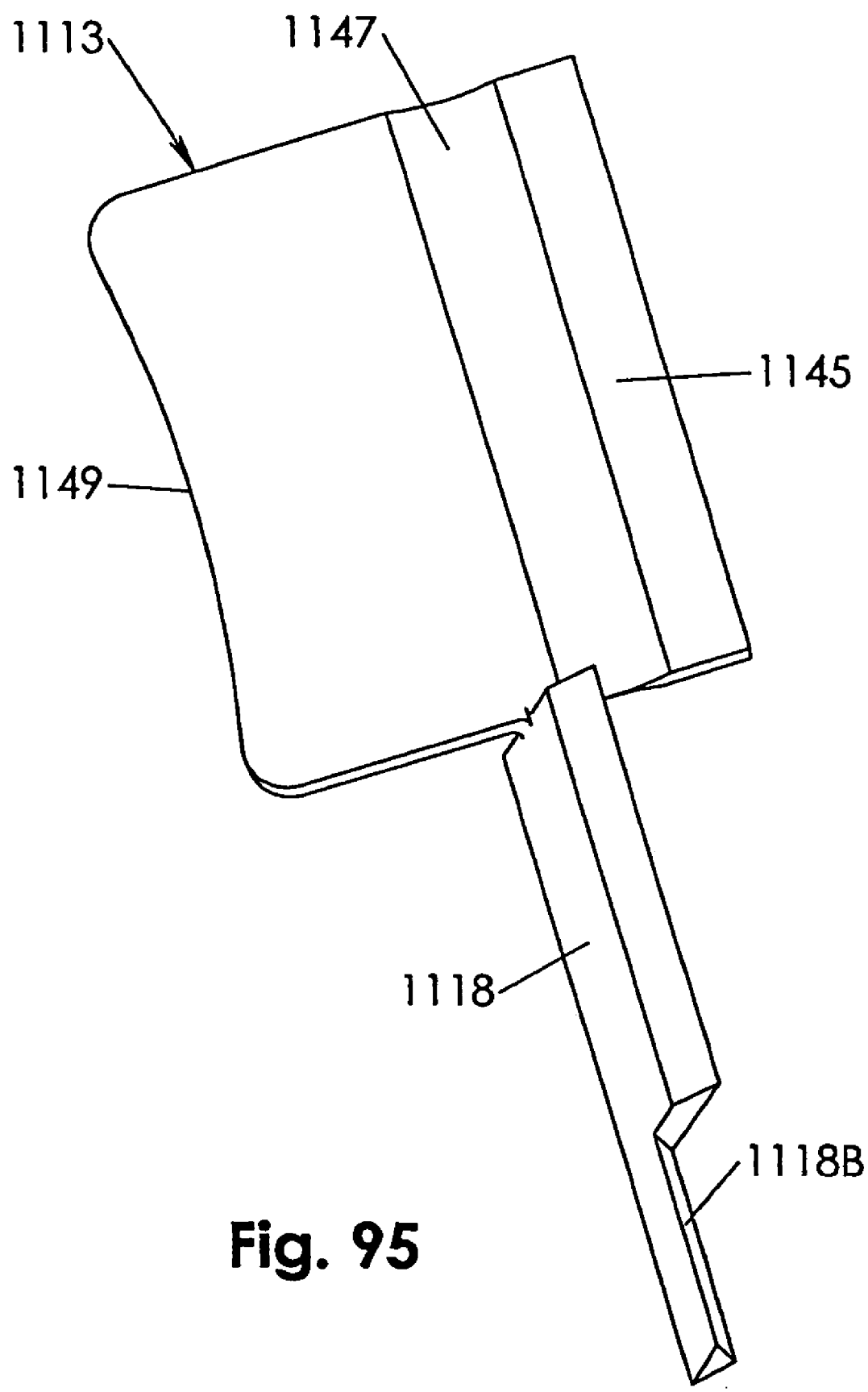
FIG. 95 is a perspective view of a typical thread-engaging movable blade for use in the thread incrementing accessory illustrated in FIG. 84.
Figure 96:
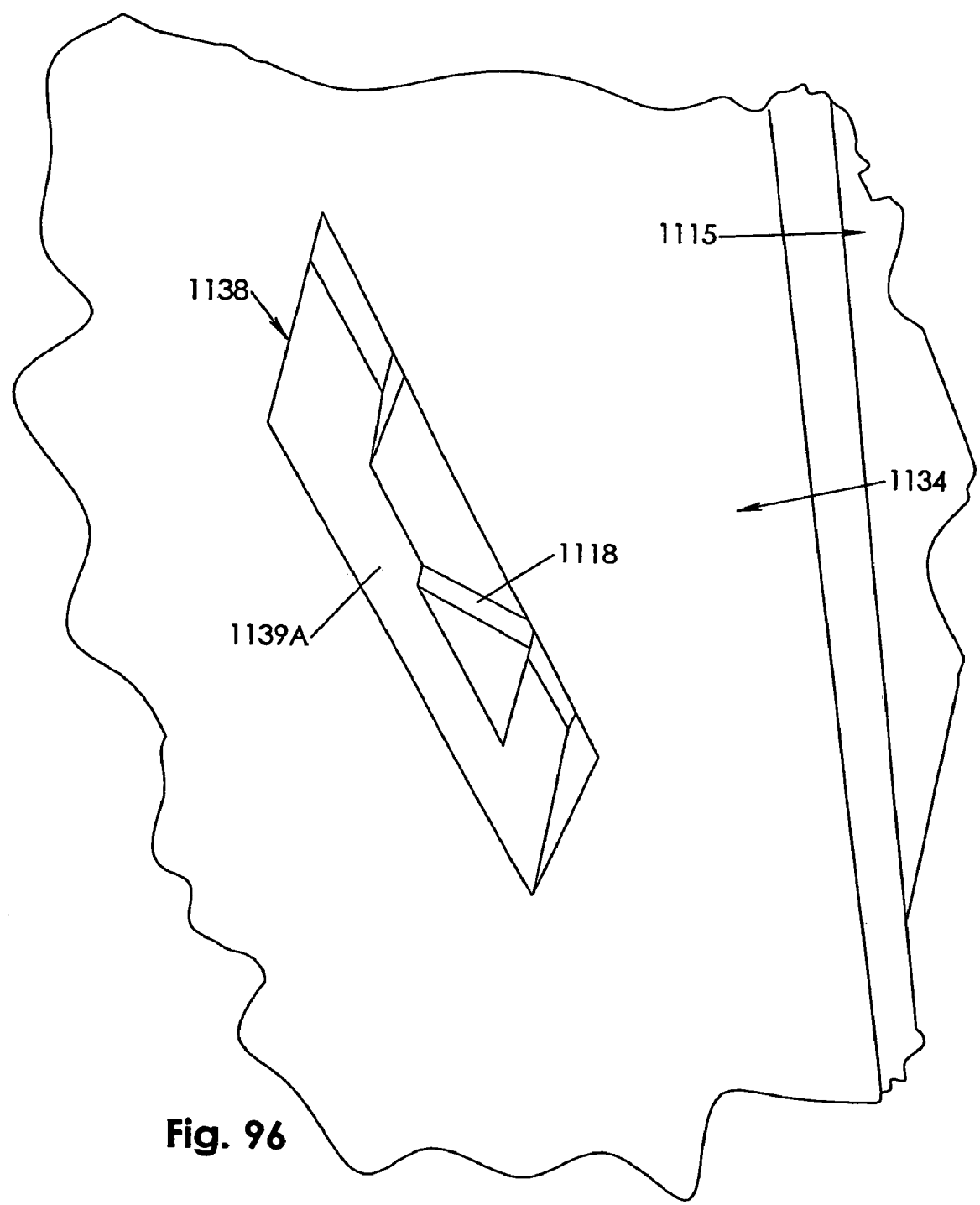
FIG. 96 is a bottom perspective of the actuation plate illustrating the tab of the movable blade in the parallelogram hole, more particularly, the triangular shape of the tab at its lower end where it contacts the angled wall of the parallelogram hole.
Figure 96A:
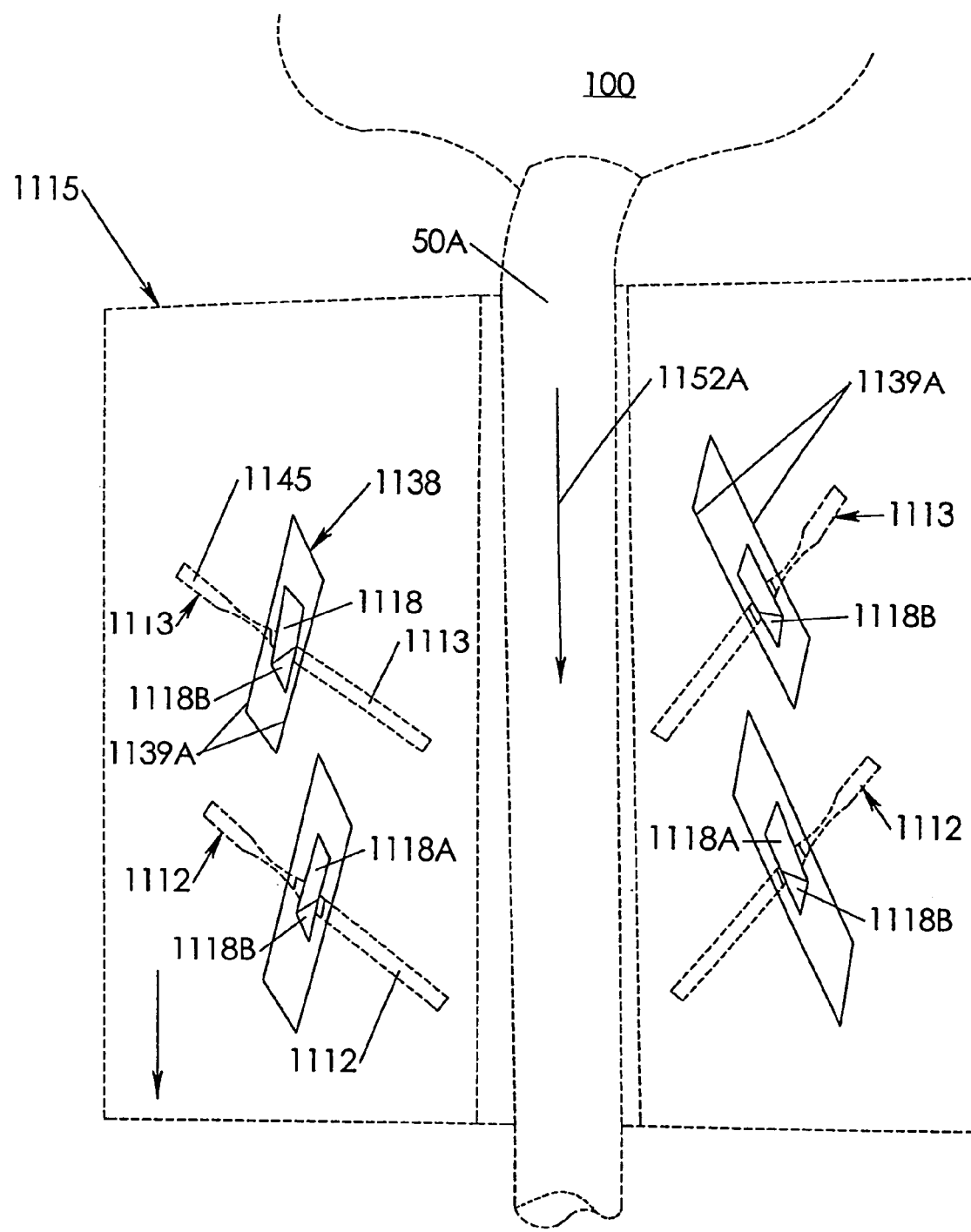
FIG. 96A is a diagram of incrementor blade tabs extending through parallelogram holes in the movable housing in close proximity to the needle thread.
Figure 96B:
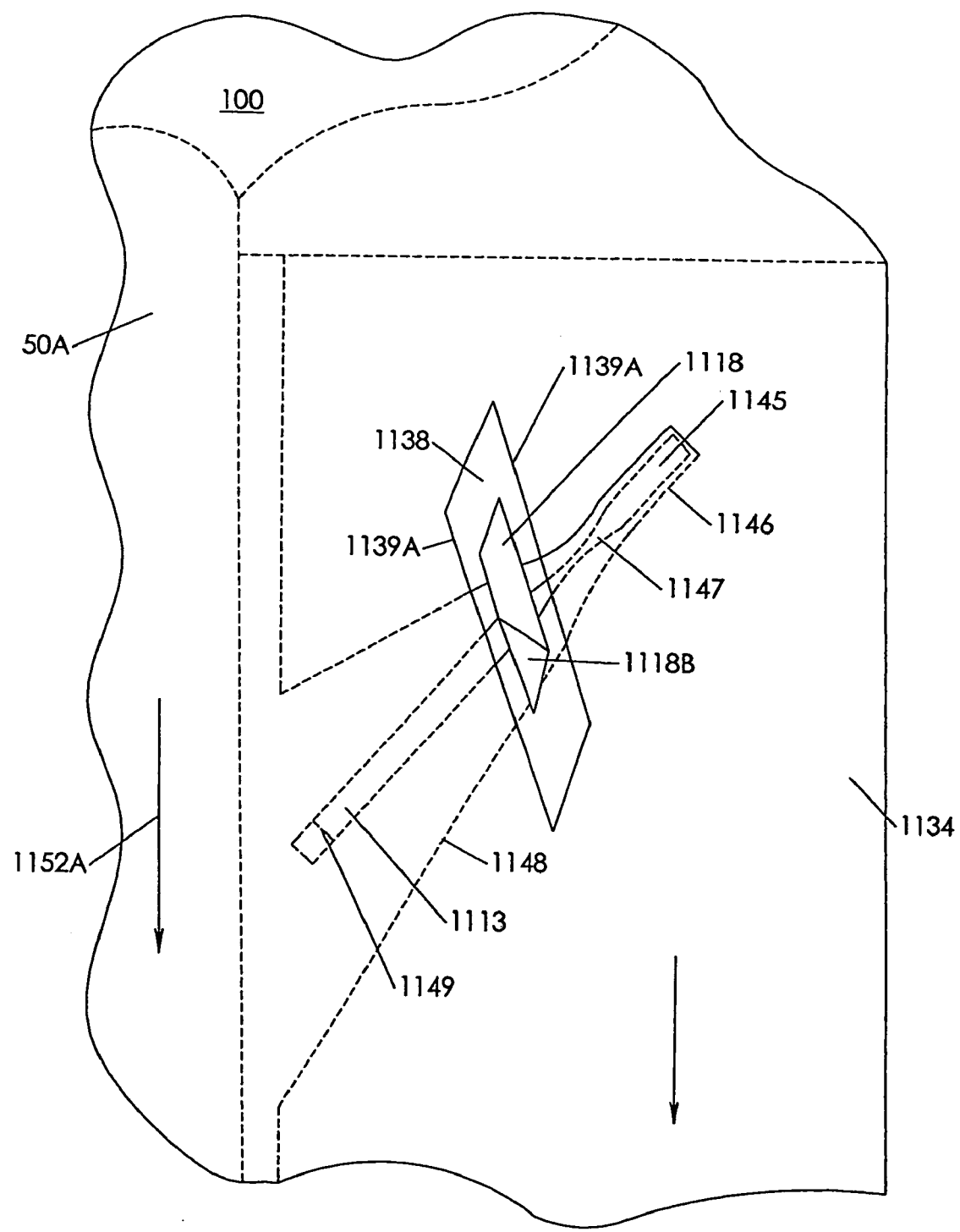
FIG. 96B is an enlarged diagram of a blade tab illustrated in FIG. 96A.
Figure 96C:
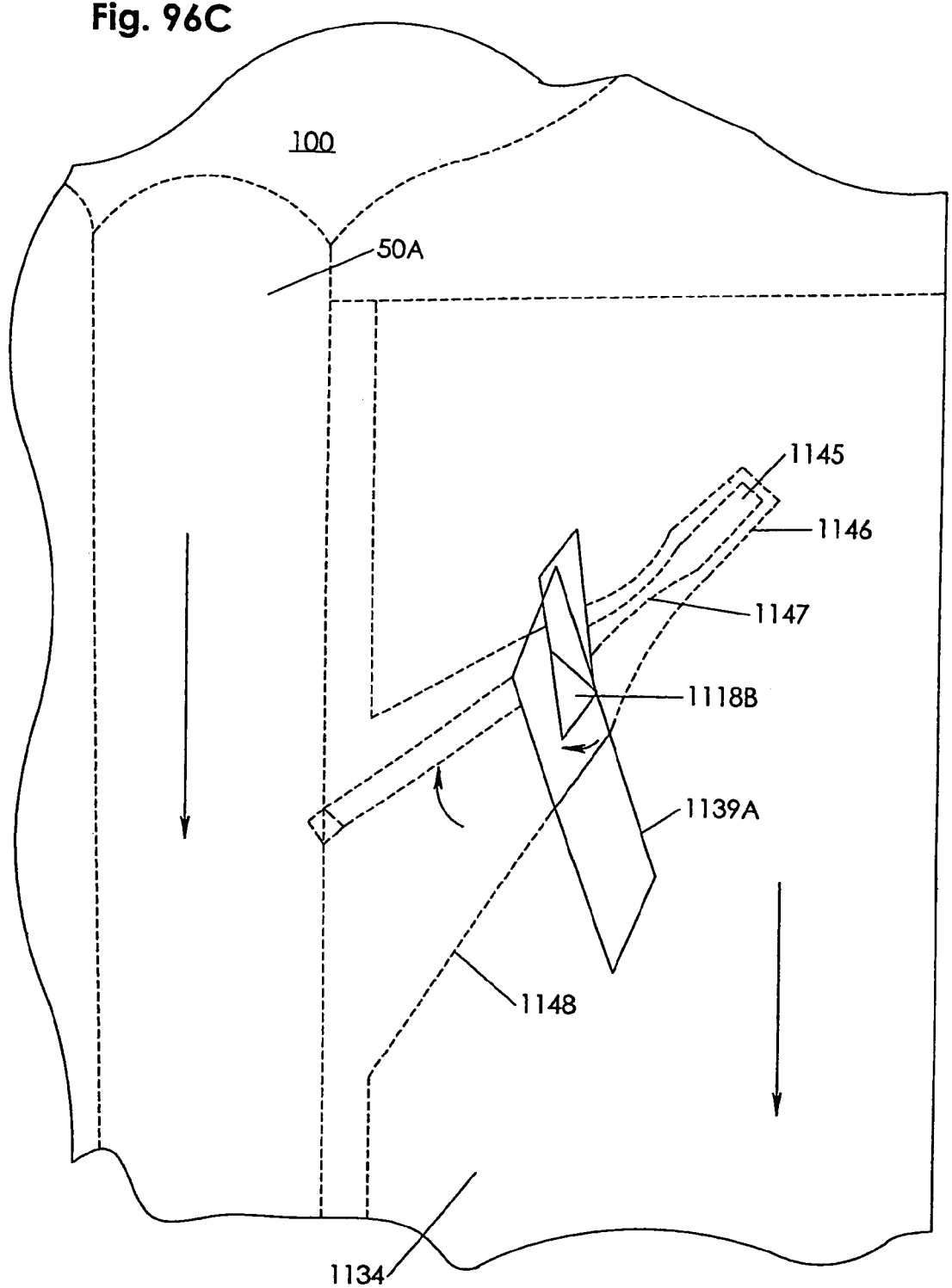
FIG. 96C is a diagram of the blade tab, illustrating the tab and parallelogram holes before contact illustrated in FIG. 96B, and further illustrating contact between the blade tab and the angled walls of parallelogram holes, which caused the blade to bend in toward the thread and contact it.
Figure 97:
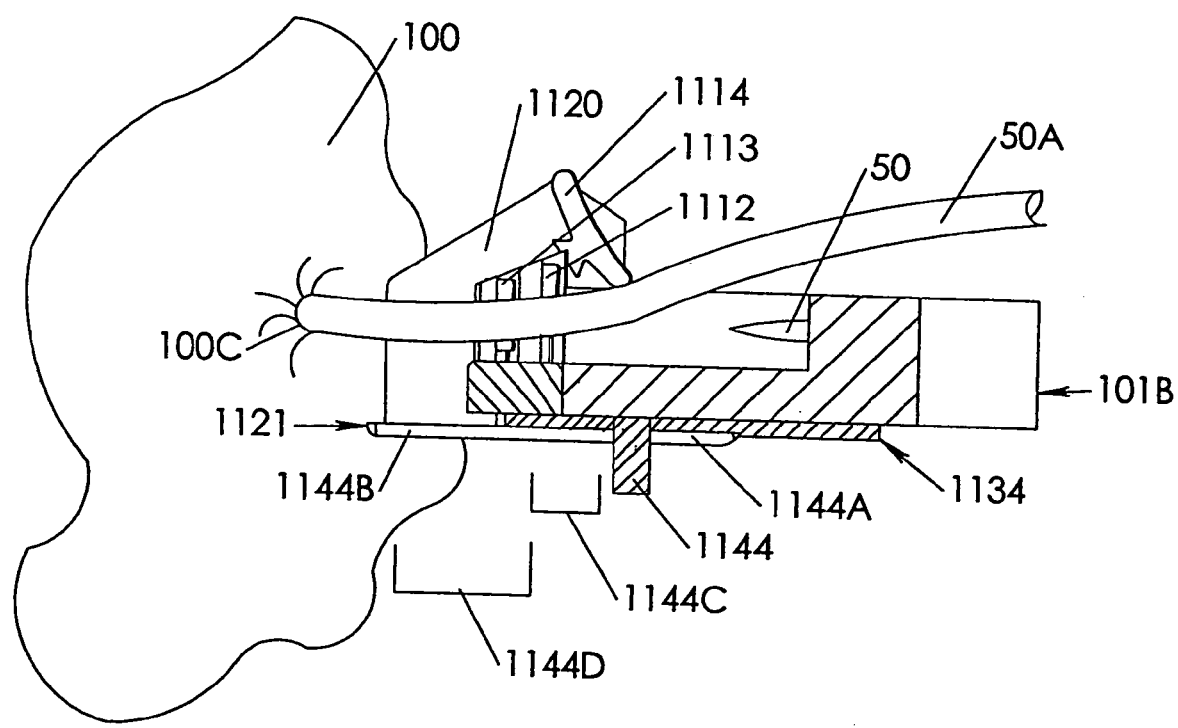
FIG. 97 is a side view, partially in section, of the thread incrementing accessory, more particularly illustrating handling of a length of thread extending from tissue which is sutured and located in close proximity to the thread incrementing accessory.

Referring again to FIGS. 7, 84, 87 and 90C-91, 93, 94, and 95 of the drawings the higher movable blades 1112 and movable blades 1113 are mounted in the movable housing 1115, slidably seated in the fixed housing 1120, when the latter is typically mounted on the case 102 of the advancing arm 101B of the crescent 101 (FIG. 84). The angle of convergence of the higher movable blades 1112 and the movable blades 1113 points rearwardly toward the receiving arm 101B. Furthermore, the pair of higher movable blades 1112 are positioned higher with respect to the base of the movable housing 1115 than the movable blades 1113 (FIG. 84). The rear portions of the respective higher movable blades 1112 and movable blades 1113 define fins 1145 (FIG. 95), which are each pressed into a tight fitting fin slot 1146 (FIGS. 84 and 93), shaped in the back of the blade recesses 1148, respectively, and bending of these blades is restricted to a thin leaf section 1147 joining the fin 1145 to the contact area 1149 of each of the higher movable blades 1112 and movable blades 1113, respectively (FIG. 95). Tabs 1118 and longer tabs 1118A, having triangular tab sections 1118B (FIG. 94), of the movable blades 1113 and the higher movable blades 1112, respectively, extend downwardly through clearance holes 1124, respectively, in the movable base 1116 of the movable housing 1115, as illustrated in FIG. 94. The longer tabs 1118A extend further downwardly from the higher location of the higher movable blades 1112, along with the tabs 1118, to reach aligned parallelogram holes 1138, provided in the actuation plate 1134, as illustrated in FIG. 94. Each of the tabs 1118 and longer tabs 1118A are controlled through these parallelogram holes 1138 by the sliding motion of the actuation plate 1134 with respect to the fixed housing 1120. This control is implemented as the actuation plate 1134 reciprocates by sliding back and forth in the respective normal range of motion 1144C and extended range of motion 1144D, respectively, over the access slot 1144A and the narrowing slot 1144B that extends the access slot 1144A, as heretofore described and as illustrated in FIGS. 90C-91. The actuation plate 1134 slides in the space between the base 1121 of the fixed housing 1120 and the base 102A of the case 102, as further illustrated in FIGS. 86, 90 and 90C-91. This reciprocation and contact with the respective tabs 1118 and 1118A, causes the higher movable blades 1112 and the movable blades 1113 to flex inwardly against the thread 50A (FIG. 90C) when the thread 58 is located in the guide slot 1126A by rotation of the needle 50 in the crescent 101, where contact with the thread 50A then stops the flexing action. Additional movement of the actuation plate 1134 in the normal range of motion 1144C continues to manipulate the respective tabs 1118 and the longer tabs 1118A and by this action, forces the movable housing 1115 in the proximal direction to the rear extent of the range of its movement in the fixed housing 1120.

Figure 89:
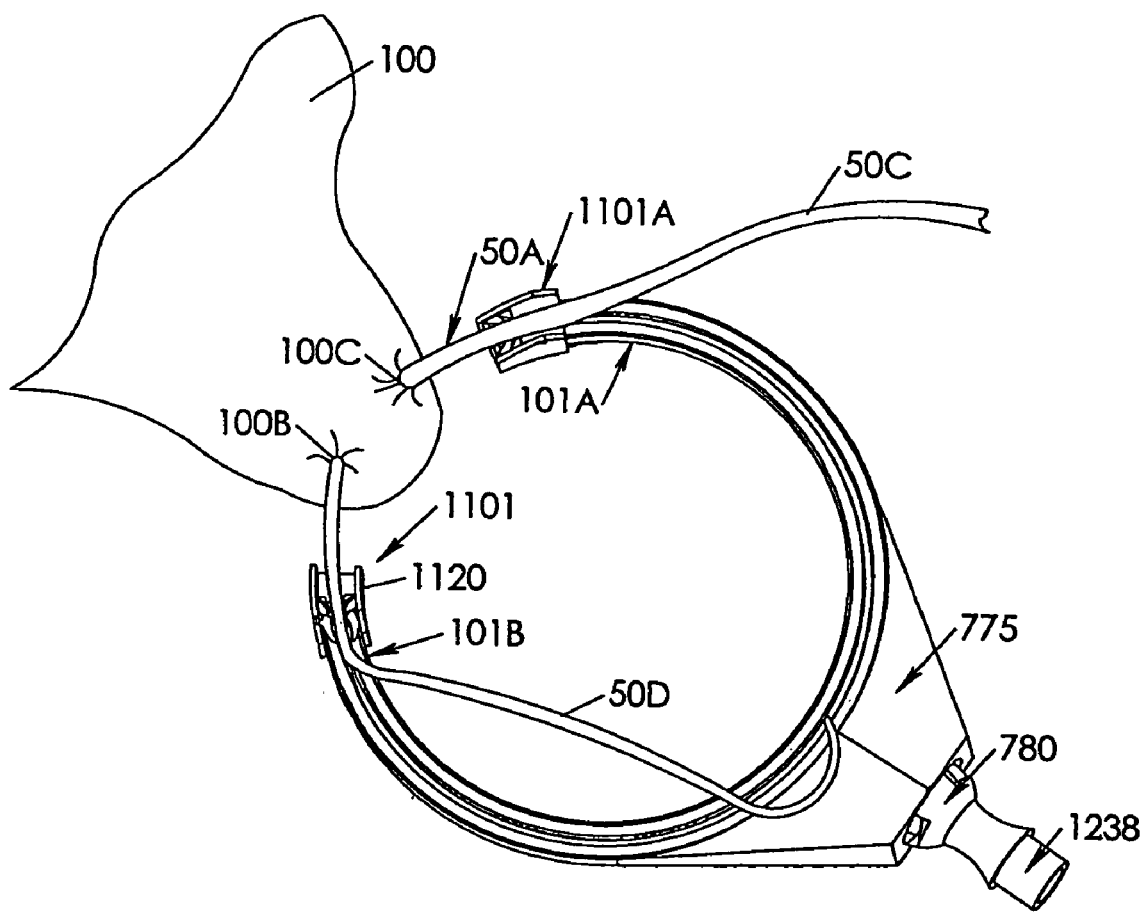
FIG. 89 is a top view of the crescent illustrated in FIG. 88, with a thread incrementing accessory located on each end of the crescent and a length of thread extending from the needle through both thread incrementing accessories and through tissue to be sutured.

It is sometimes necessary to use two thread incrementing accessories 1101 and 1101A, one on the advancing arm 101A and one on the receiving arm 101B of the crescent 101, as illustrated in FIG. 89. Since the number of mechanical actuators must be held to a minimum, the thread incrementing accessories 1101 and 1101A have been designed to operate with a single actuator. In order to accomplish these two functions with one remote actuation input, the angles of the tabs 1118 and the longer tabs 1118A in each thread incrementing accessory 1101 are set in a nearly perpendicular plane with respect to that of the higher movable blades 1112 and movable blades 1113, respectively. This mechanical configuration facilitates reversal of the direction in which the actuation plate 1134 must travel in order to bend the respective higher movable blades 1112 and the movable blades 1113 into contact with the needle 50. This activity facilitates use of the actuation plate 1134 to also serve as a drive plate and pull the movable housing 1115 forwardly, respectively, while the higher movable blades 1112 and movable blades 1113, respectively, are locked on the thread 50A, as hereinafter further described.

Referring now to FIGS. 4, 90 and 91 of the drawings the actuation plate 1134 is driven back and forth by a stiff, but flexible power transmission wire 1140, which is housed within a flexible tube 1141 provided within a main extension tube (not illustrated) that extends to the proximal side of the joint ball 780 on to the second handle 1261. The opposite end of the flexible power transmission wire 1140 is connected to the wire attachment extension boss 1142, provided on the access extension tab 1144 that extends down from fixed attachment to the actuation plate 1134. The access extension tab 1144 passes through the slot 1144 in the base of the fixed housing 1120. The flexible tube 1141 is fixed to the mounting boss 1143 attached to the base 1121 of the fixed housing 1120, near the end of the access slot 1144A.

The simplest technique of pulling and controlling thread when suturing using the cycling suturing and knot-tying device of this invention is use of a sliding hook 50E illustrated in FIG. 81 of the drawings. The hook snags the thread 50A, allowing it to slide across the curved hook section and form a loop as the hook is drawn away from the stitch in the direction of the arrow. Various types of sliding hooks are known in the art and are currently used in suturing operations.

Referring now to FIGS. 98-108 of the drawings in another preferred embodiment of the invention a semi-automatic technique for handling the thread 50A during the suturing operation while using the cycling suturing and knot-tying device includes a thread pulling hook/unhook device 1000 which may be implemented as a double installation version 1000A (FIGS. 98 and 104-106), depending upon the nature of the procedure undertaken. As further illustrated in FIGS. 98-103 and in FIG. 102 in particular, each of the inner housing tubes 1045 includes a retractable hook body 1010, fitted with a curved profile slot defined by spaced-apart, parallel rear hook ejecting slopes 1016 and corresponding parallel forward hook faces 1012 and having a built-in, slidably disposed grip/eject/cut blade 1020, as further illustrated in FIGS. 99 and 100. The grip/eject/cut blade 1020 is further fitted with a rearward gripping/cutting overhang 1026, a preparatory blade slope 1024 at the extending front end thereof and a forward blade ejecting slope 1022, oppositely disposed from and extending outwardly of the gripping/cutting/overhang 26. The grip/eject/cut blade 1020 is slidably disposed in a longitudinal blade slide slot 1010A, shaped in the hook body 1010 (FIG. 102), where the spaced-apart pair of hook faces 1012 terminate forwardly of the corresponding pair of hook ejecting slopes 1016 and spaced-apart, planar preparatory thread lifting slopes 1014 terminate the front end of the hook body 1010. The hook body 1010 and slidably enclosed grip/eject/cut blade 1020 are seated in an inner housing tube 1045, such that the hook body 1010 is fixed to the inner housing tube 1045 and the grip/eject/cut blade 1020 is able to slide with respect to both the inner housing tube 1045 and the hook body 1010. A plunger disc 1065 is provided on the inner housing tube 1045 as further illustrated in FIG. 102 and both the inner housing tube 1045 and the plunger disc 1065 are enclosed within a housing tube enlarged section 1042. In like manner, a second plunger disc 1065A is fixed to the inner housing tube 1045, spaced-apart from the plunger disc 1065 and also enclosed in the housing tube enlarged section 1042. The plunger disc 1065 and second plunger disc 1065A serve to center the inner housing tube 1045 in the housing tube enlarged section 1042. An actuation wire 1050 is slidably disposed inside the inner housing tube 1045 as further illustrated in FIG. 102 and is secured at one end to the grip/eject/cut blade 1020 for slidably manipulating the grip/eject/cut blade 1020 in the blade slide slot 1010A in the hook body 1010, by operation of the actuation wire 1050, as hereinafter further described.

As further illustrated in FIGS. 102 and 102A of the drawings the hook body 1010 is further characterized by a hook open profile 1018 (FIG. 102A) that defines 1a hook containment slot 1070 extending from the parallel hook ejecting slopes 1016 to the parallel hook faces 1012, to accommodate a length of the thread 50A for manipulating and cutting the thread 50A, as hereinafter further described.

Figure 102:
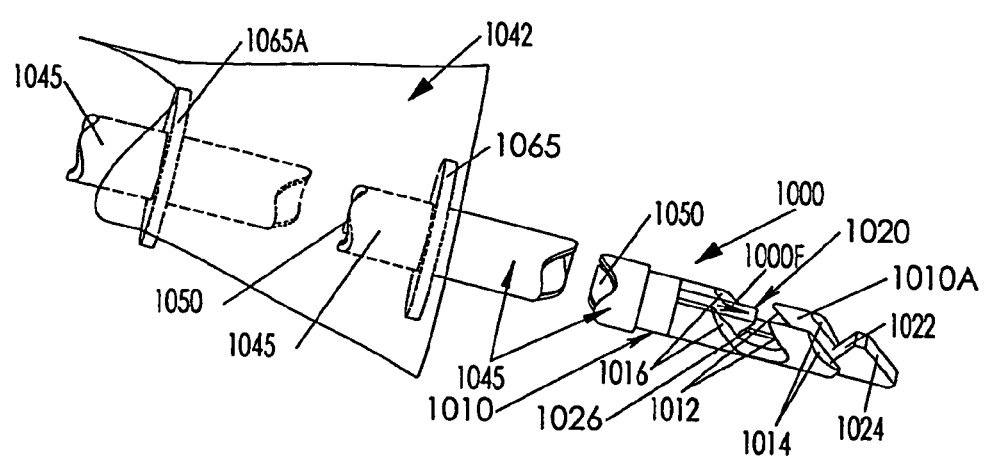
Figure 103:
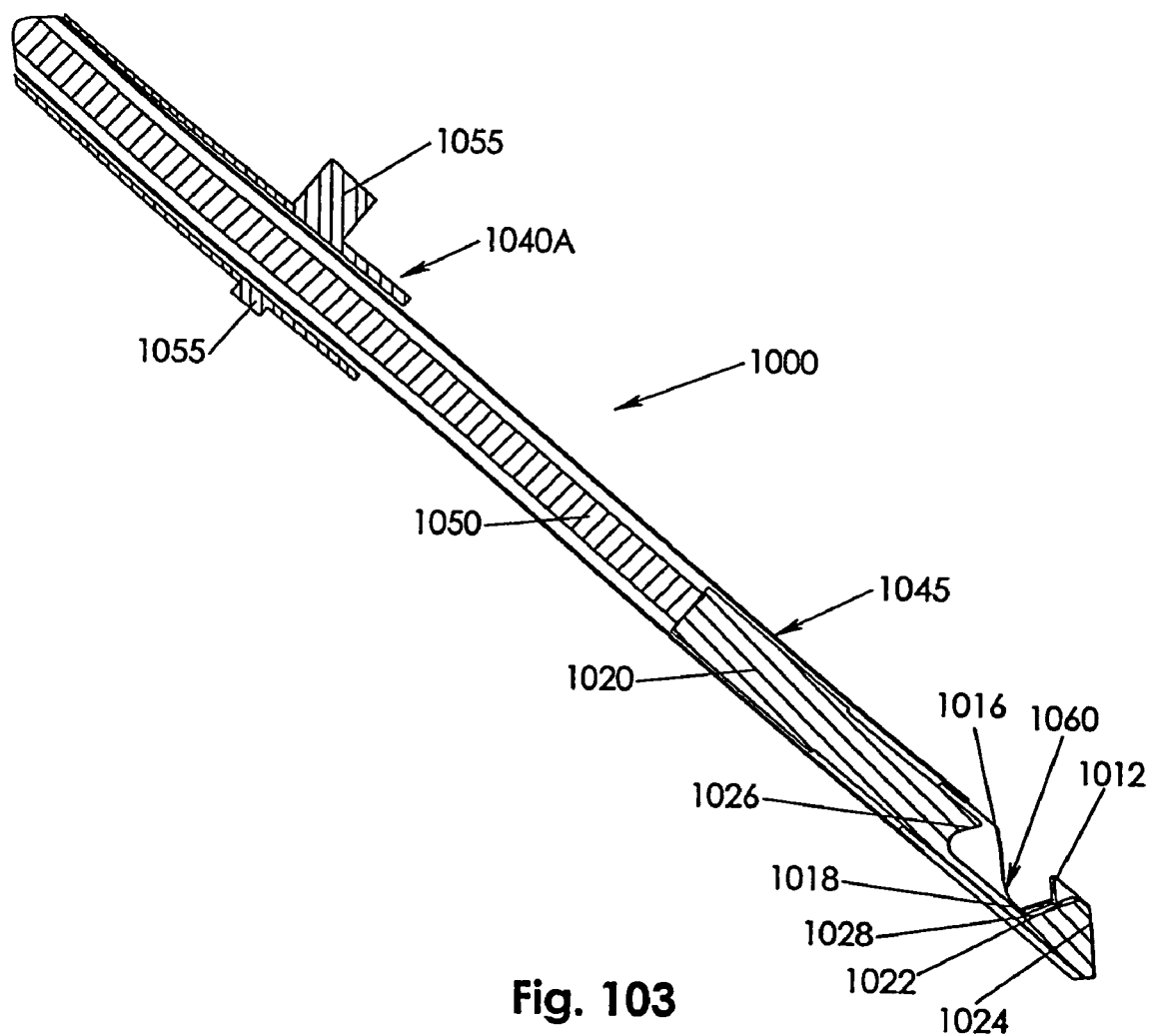

Referring now to FIGS. 102 and 103 of the drawings the grip/eject/cut blade 1020 is illustrated fixed to the extending end of the actuation wire 1050 and is provided with a blade open profile 1028, that extends from the blade ejecting slope 1022 to the grip/cutting overhang 1026. Further illustrated is the preparatory blade slope 1024 provided on the extending end of the grip/eject/cut blade 1020.

Figure 99:
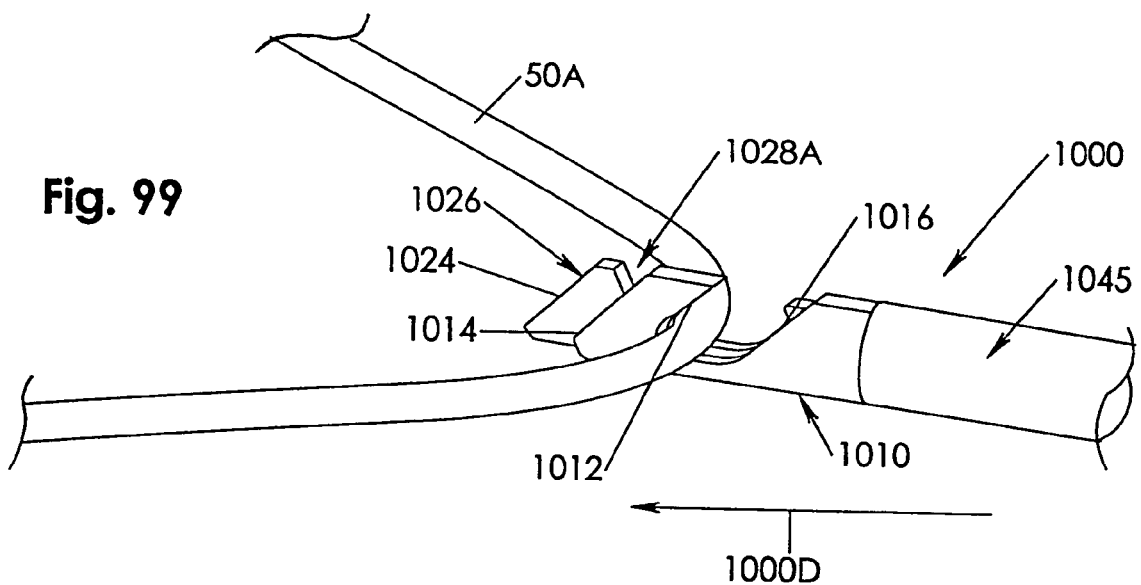
FIG. 99 is a perspective view of a receiving arm illustrated in FIG. 98, more particularly illustrating engagement of the thread by the open thread access slot in the receiving arm.
Figure 100:
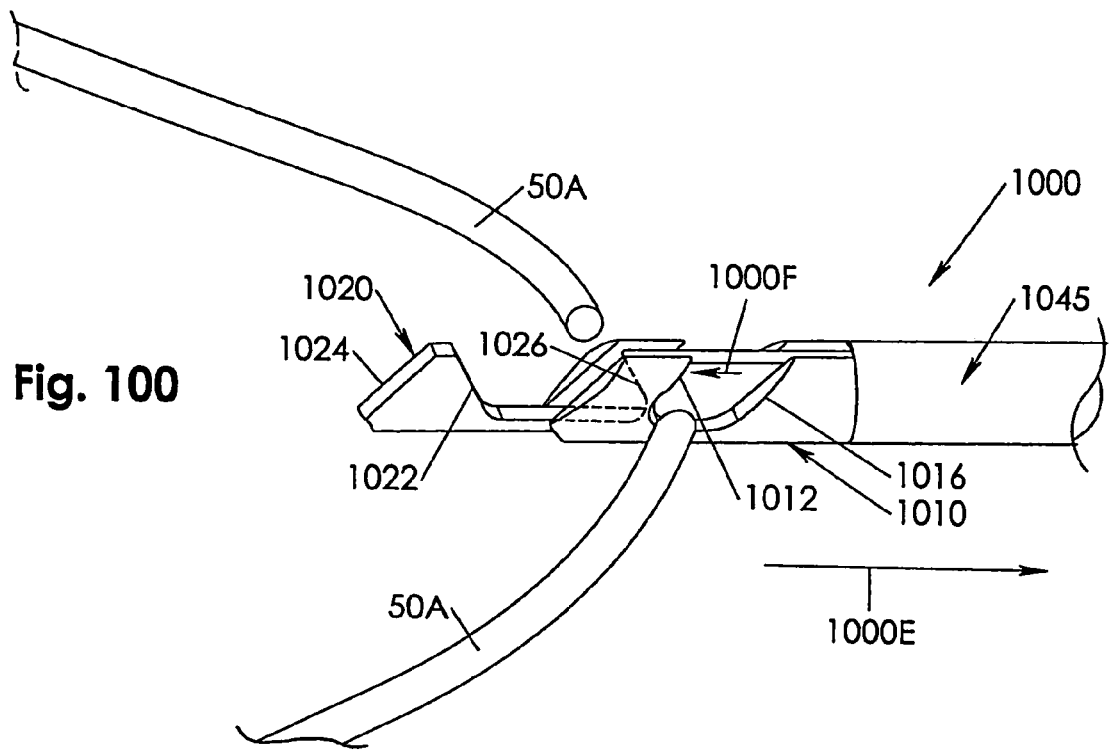
FIG. 100 is a perspective view of a receiving arm, more particularly illustrating severing of the thread by forward movement of the grip/cut/eject blade through the access slot that holds the thread in place, as illustrated in FIG. 99.

Referring to FIGS. 99-103 of the drawings the actuation wire 1050, enclosed within the inner housing tube 1045, the latter of which may be alternatively telescoped inside the smaller auxiliary housing tube 1040A (FIG. 103), can be manipulated as hereinafter further described to cause the grip/eject/cut blade 1020 to extend or retract in the blade slide slot 1010A of the hook body 1010, as desired. For example, as further illustrated in FIG. 102 the actuation wire 1050 can be pushed forwardly to slidably displace the grip/eject/cut blade 1020 forwardly in the blade slide slot 1010A in the direction of the blade extension arrow 1000F, to mismatch the gripping/cutting overhang 1026 in the grip/eject/cut blade 1020, with the hook ejecting slopes 1016 and hook faces 1012 in the hook body 1010. Alternatively, the grip/eject/cut blade 1020 can be reversed by reverse operation of the actuation wire 1050 to slidably displace the grip/eject/cut blade 1020 in the opposite direction with respect to the hook body 1010 and align the gripping/cutting overhang 1026 with the hook ejecting slopes 1016 to facilitate a corresponding blade open profile 1028 and hook open profile 1018 of the hook/unhook device 1000 as illustrated in FIGS. 99 and 103 of the drawings. Under these circumstances, as further illustrated in FIGS. 99 and 100, a loop of the thread 50A can be inserted in the blade open profile 1028 (FIG. 99) and the grip/eject/cut blade 1020 then moved in the forward direction by forward manipulation of the actuation wire 1050 in the direction of the blade extension arrow 1000F, as illustrated in FIG. 102, to sever the loop of thread 50A (FIG. 100). Still further in the alternative, and referring again to FIGS. 99 and 101 of the drawings, the thread 50A can be placed in the blade open profile 1028 and manipulated as illustrated by the device retraction arrow 1000E to a desired position during suturing. Under circumstances where it is desired to eject the uncut loop of thread 50A from the blade open profile 1028 after so manipulating the segment of thread 50A, the grip/eject/cut blade 1020 can be manipulated in the opposite direction illustrated by the blade retraction arrow 1000G (FIG. 101), causing the blade ejecting slope 1022 to contact the loop of thread 50A and force the thread loop from the blade open profile 1028. This operation is effected by reverse movement of the actuation wire 1050 fixed to the grip/eject/cut blade 1020, as hereinafter further described. Accordingly, the hook/unhook device 1000 can be used to handle thread as follows: the device can grip the thread as necessary; it can move the thread without gripping it; the device can grip and cut the thread; and it can grip and then cut the thread, all as described above.

Referring now to FIGS. 98, 102 and 104-108 of the drawings, it will be appreciated that one or more of the hook/unhook devices 1000 can be used, as in the double installation version 1000A illustrated in FIGS. 98 and 104-106. The double installation version 1000A is characterized by a double installation advancing arm side hook 1000B and a double installation receiving arm side hook 1000C, which are identical in design. Each of the double installation advancing arm side hook 1000B and double installation receiving arm side hook 1000C is typically characterized by an inner housing tube 1045 (FIG. 102) that extends into a corresponding and separate housing tube enlarged section 1042 or an auxiliary housing tube 1040A (FIG. 103). Furthermore, each of the double installation advancing arm side hook 1000B and double installation receiving arm side hook 1000C have a hook/unhook device 1000, including a hook body 1010 and a slidably operating grip/eject/cut blade 1020 slidably disposed in the blade slide slot 1010A of the hook body 1010 as further illustrated in FIG. 102. Accordingly, the design and operation of the double installation version 1000A, including the double installation receiving arm side hook 100C and the double installation advancing arm side hook 1000B, is substantially the same as that described above with respect to the hook/unhook device 1000 illustrated in FIGS. 98-103.

Figure 105:
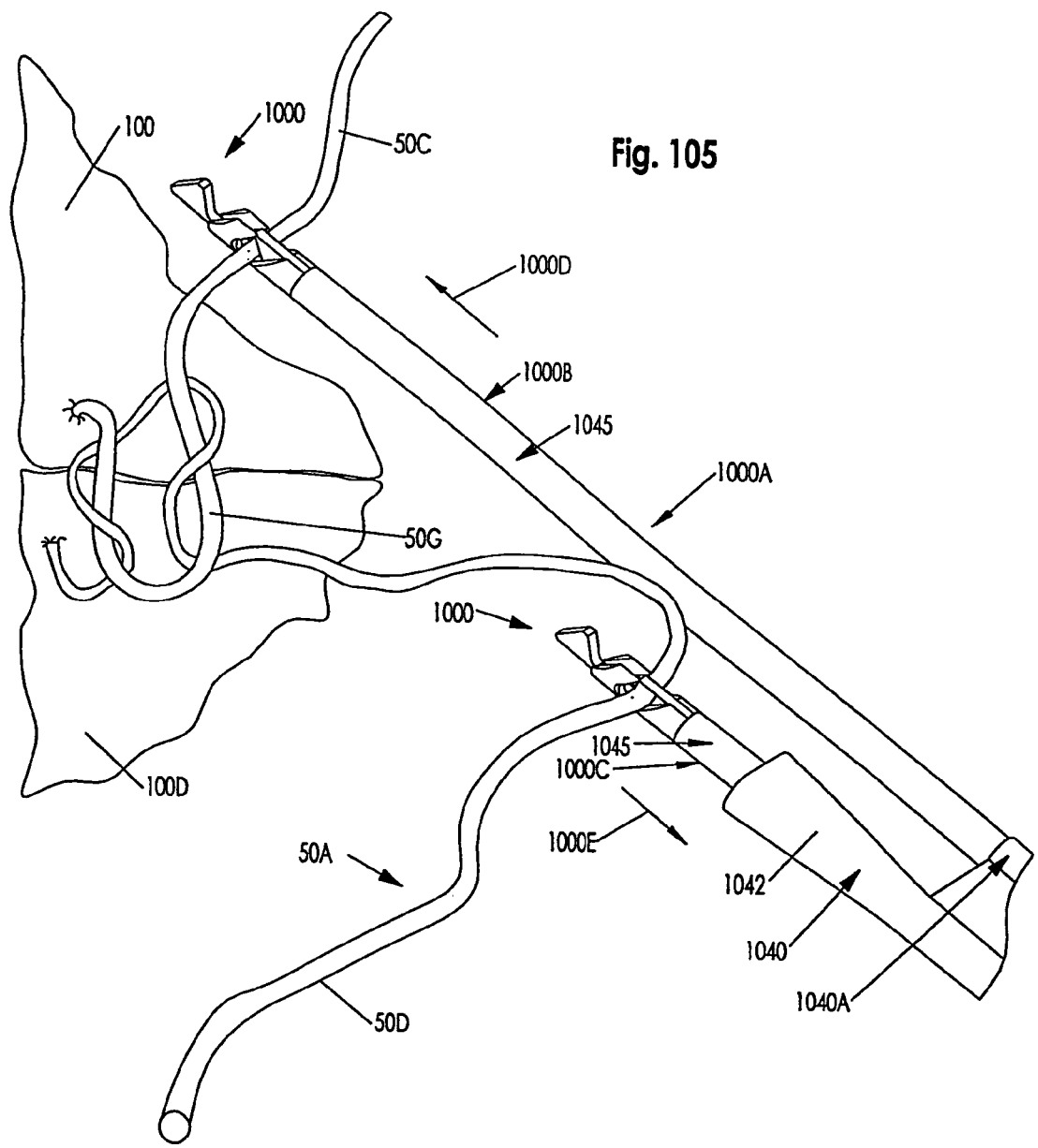
Figure 106:
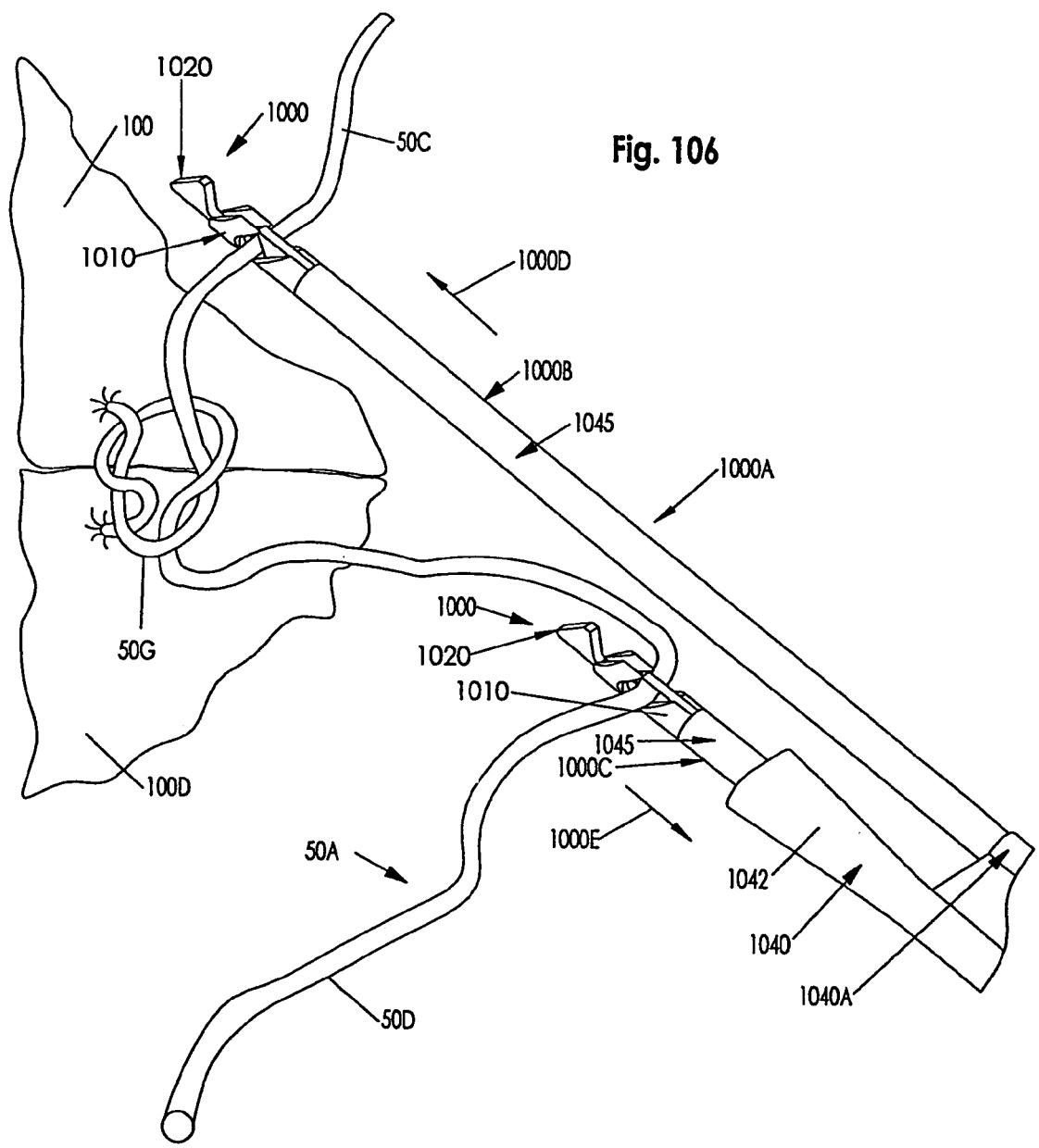

Referring now to FIGS. 105 and 106 of the drawings in a preferred suturing embodiment, knots or sutures may be tied in close quarters inside a wound or incision using the double installation version 1000A of the hook/unhook device 1000 by manipulating the respective double installation advancing arm side hook 1000B and double installation receiving arm side hook 1000C to engage the thread tail 50C and thread head 50D, respectively, as illustrated. This engagement is effected as heretofore described with respect to FIGS. 98-103, and while the inner housing tube 1045 of the double installation advancing arm side hook 1000B is extended from the auxiliary housing tube 1040A in the direction of the device extension arrow 1000D, the corresponding inner housing tube 1045 of the double installation receiving arm side hook 1000C is retracted inside the housing tube 1040 in the direction of the device retraction arrow 1000E, to tighten the entwinements 50G, as further illustrated in FIG. 105. Continued sequential extension and retraction of the respective double installation advancing arm side hook 1000B and double installation receiving arm side hook 1000C in this manner effects a tight knot or suture joining the material 100 to the additional material 1000D as further illustrated in FIG. 106.

Figure 101:
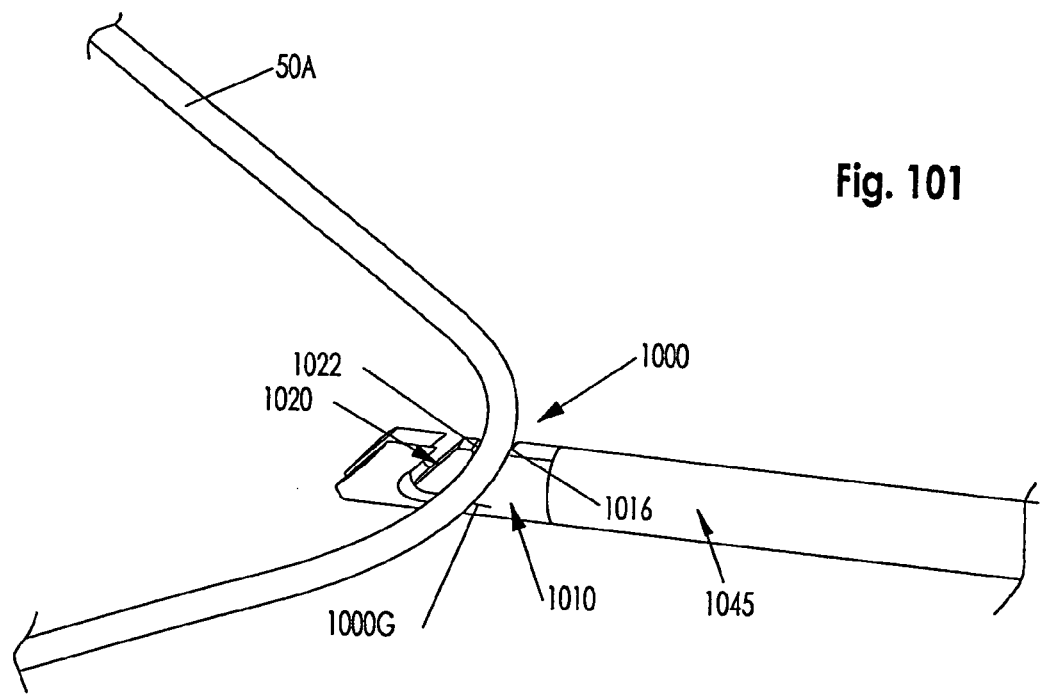
FIG. 101 is a perspective view of a receiving arm, illustrating retraction of the grip/cut/eject blade and preparatory blade slope into the receiving arm and into the thread access slot to alternatively eject the thread from the slot, in lieu of cutting the thread as illustrated in FIG. 100.
Figure 104:
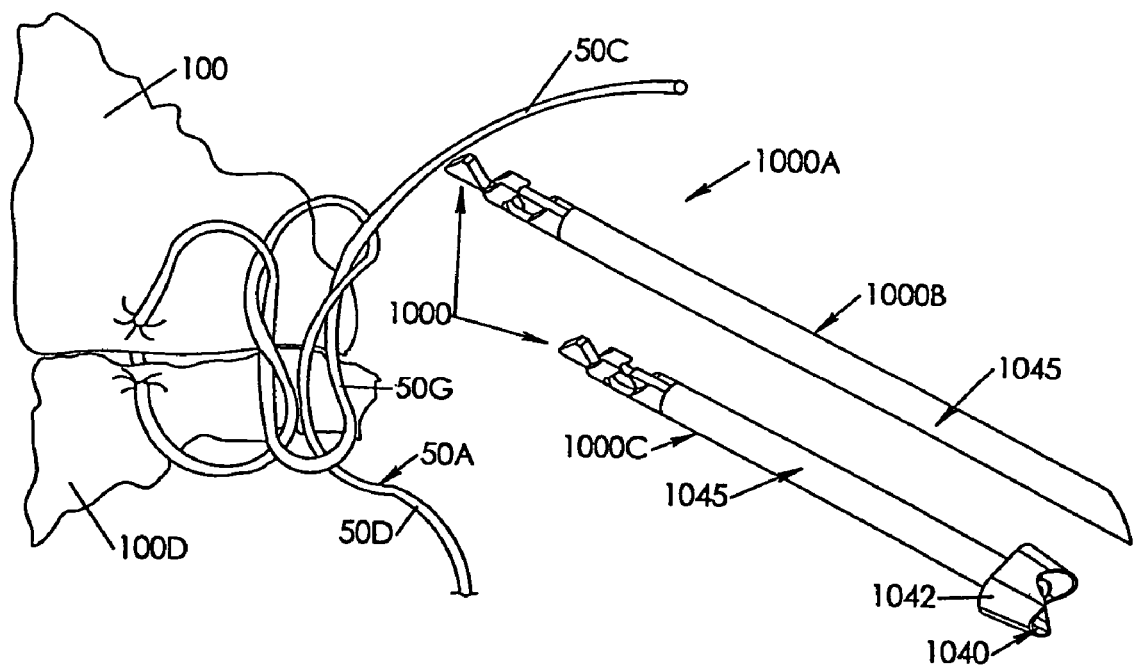
Figure 107:
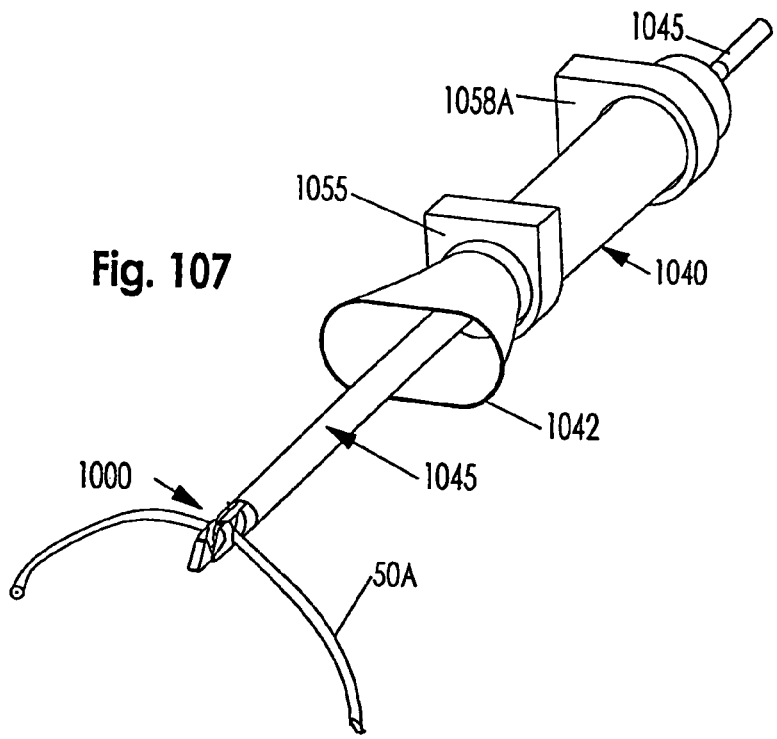
Figure 108:
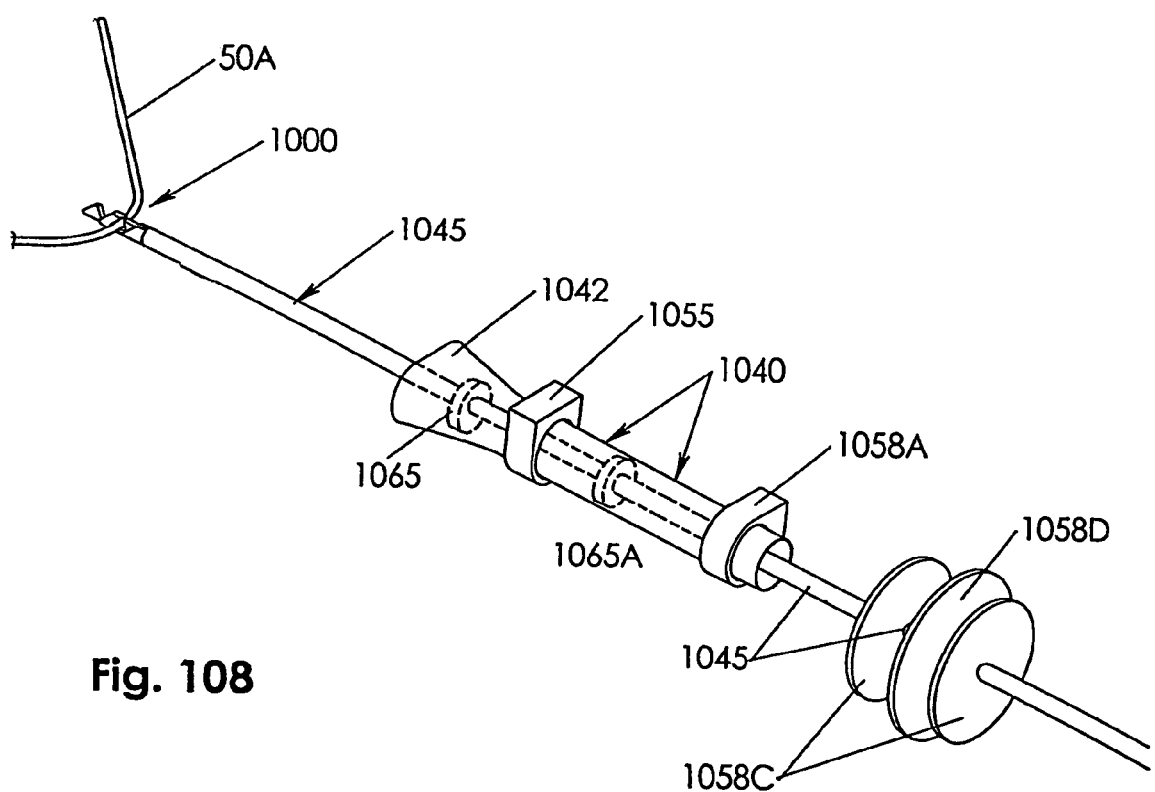

Referring now to FIGS. 102, 107 and 108 of the drawings the operational components of the hook/unhook device 1000, as well as the double installation version 1000A illustrated in FIGS. 104-106, are illustrated. As heretofore described, the hook/unhook device 1000, longitudinally and in the double installation version 1000A, each include an inner housing tube 1045, connected to a hook body 1010 receiving a sliding grip/eject/cut blade 1020, which inner housing tube 1045 is typically encased at a housing tube enlarged section 1042 in a housing tube 1040, as illustrated in FIGS. 107 and 108. It will be appreciated from a consideration in FIGS. 104-106 of the drawings that each of the double installation advancing arm side hooks 1000B and double installation receiving arm side hooks 1000C have a typically identical separate housing tube 1040 and auxiliary housing tube 1040A, respectively each with a corresponding housing tube enlarged section 1042, for receiving and allowing bending of the respective corresponding inner housing tube 1045. As further illustrated in FIGS. 107 and 108 the housing tube 1040 is further typically equipped with a crescent mount 1055 and a tubular handle attachment mount point 1058A, which are similar in design and are spaced-apart on the length of the housing tube 1040, as illustrated. As further illustrated in FIG. 108 the plunger disc 1065 and second plunger disc 1065A are fixed to the corresponding inner housing tube 1045 that projects through the housing tube 1040 and the rear end of the inner housing tube 1045 receives a three-position switch body 1058C, between which is sandwiched a three-position switch actuator 1058D, as illustrated in FIG. 108. It will be appreciated from a consideration of FIG. 108 that the inner housing tube 1045 slides within the housing tube 1040 and is aided and centered in that sliding action by the plunger disc 1065 and second plunger disc 1065A, that act together as spacers. Furthermore, referring again to FIG. 102 of the drawings the actuation wire 1050 slides within the inner housing tube 1045 as heretofore described. Moreover, as illustrated in FIG. 108, both of the three position switch bodies 1058C are fixed to the inner housing tube 1045, while the larger three position actuator 1058D is attached to the actuation wire 1050. Accordingly, manipulation of the three position actuator 1058D between the two fixed three position switch body 1058C elements facilitates sliding operation of the grip/eject/cut blade 1020 in the hook body 1010, to either cut segments of the thread 50A (FIG. 100) or manipulate segments of the thread 50A and then eject those segments from the blade open profile 1028 as illustrated in FIG. 101.

Manipulation of the switch bodies 1058C in concert extends and retracts the inner housing tube 1045 with respect to the housing tube 1040.

Referring again to FIGS. 98 and 108 of the drawings, in a preferred embodiment of the invention the flexible outer housing tube 1040 is typically attached to the underside of the crescent 101 by means of the crescent mount 1055 and, in the case of the double installation advancing arm side hook 1000B and double installation receiving arm side hook 100C illustrated in FIGS. 104-106 of the drawings, both can be attached to the crescent 101 by means of the respective crescent mounts 1055. The respective flexible housing outer tubes 1040, or either of them in case of solo use, are typically secured to the second handle 1261 by means of the tubular handle attachment points 1058A. The respective inner housing tubes 1045 are secured to the second handle trigger 1261B for actuation of the grip/eject/cut blade 1020, as heretofore described.

Figure 3:
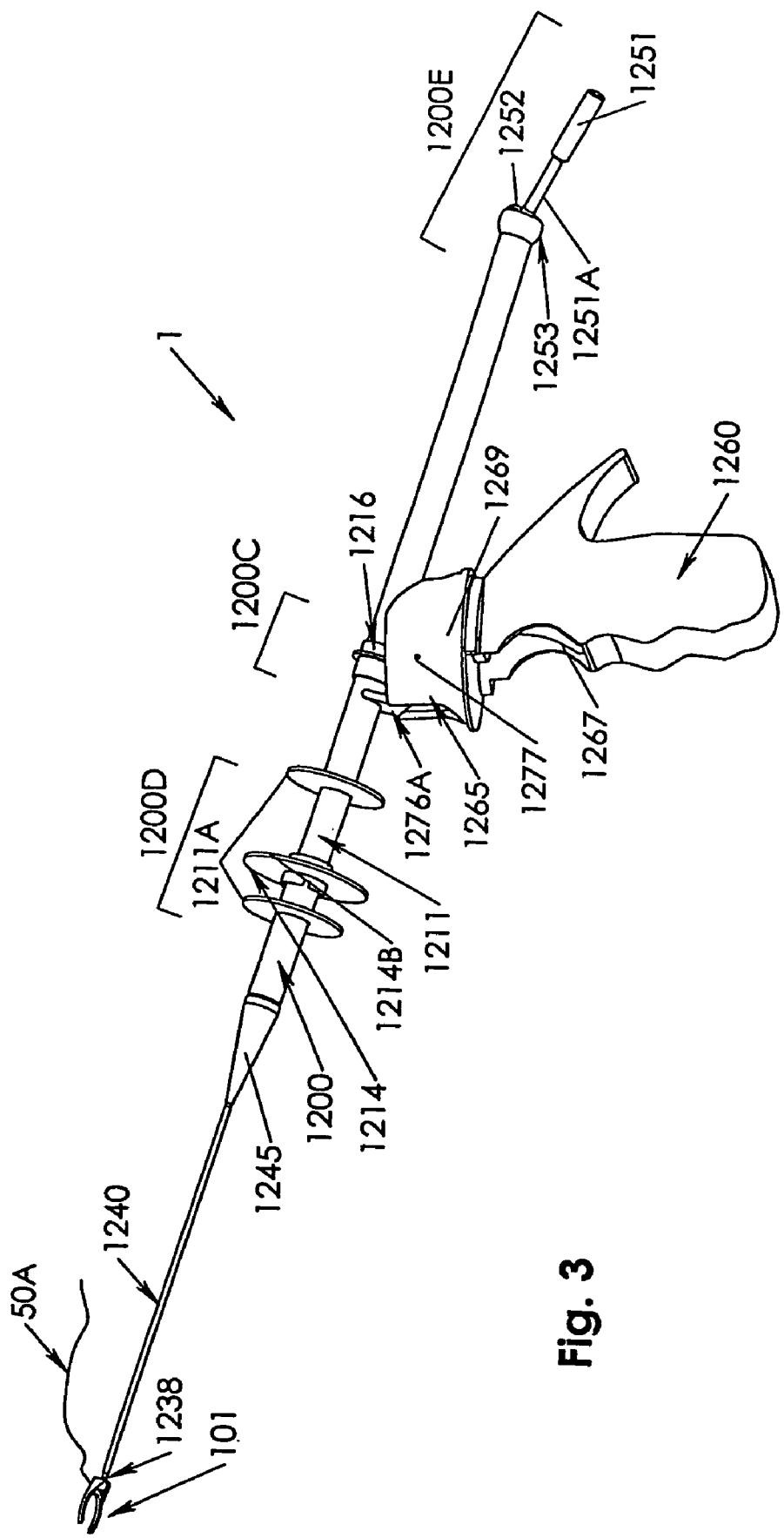
FIG. 3 is a left side perspective view of the operating device illustrated in FIGS. 1 and 2.
Figure 62:
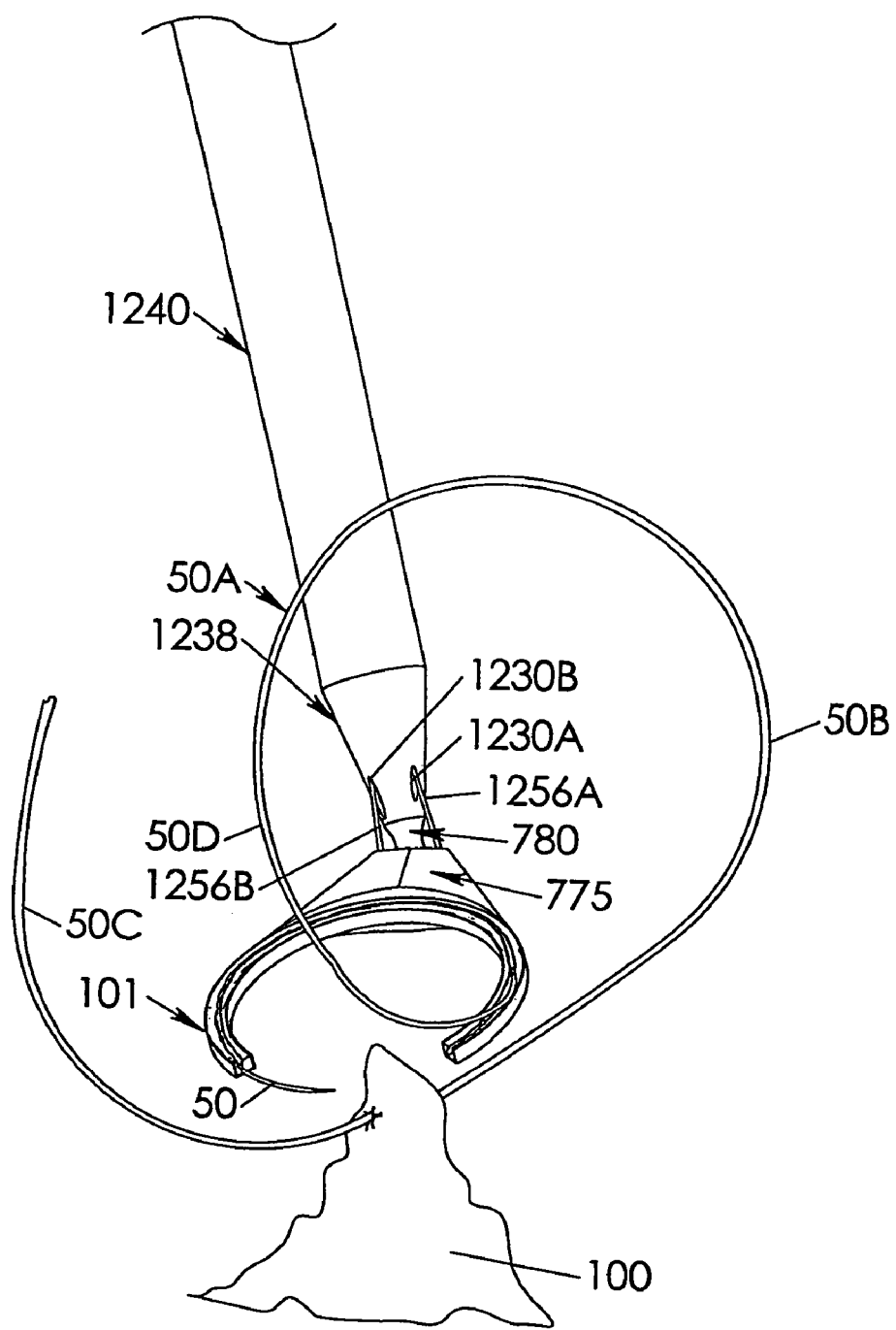
FIG. 62 is a perspective view of the extending end of a short extension tube and the crescent mounted in articulating relationship on the transition guide cone on the extension tube, by means of a ball and socket arrangement and more particularly illustrating articulation of the crescent with respect to the extension tube by operation of a pair of cables extending from the crescent to the lever illustrated in FIGS. 1-3.
Figure 63:
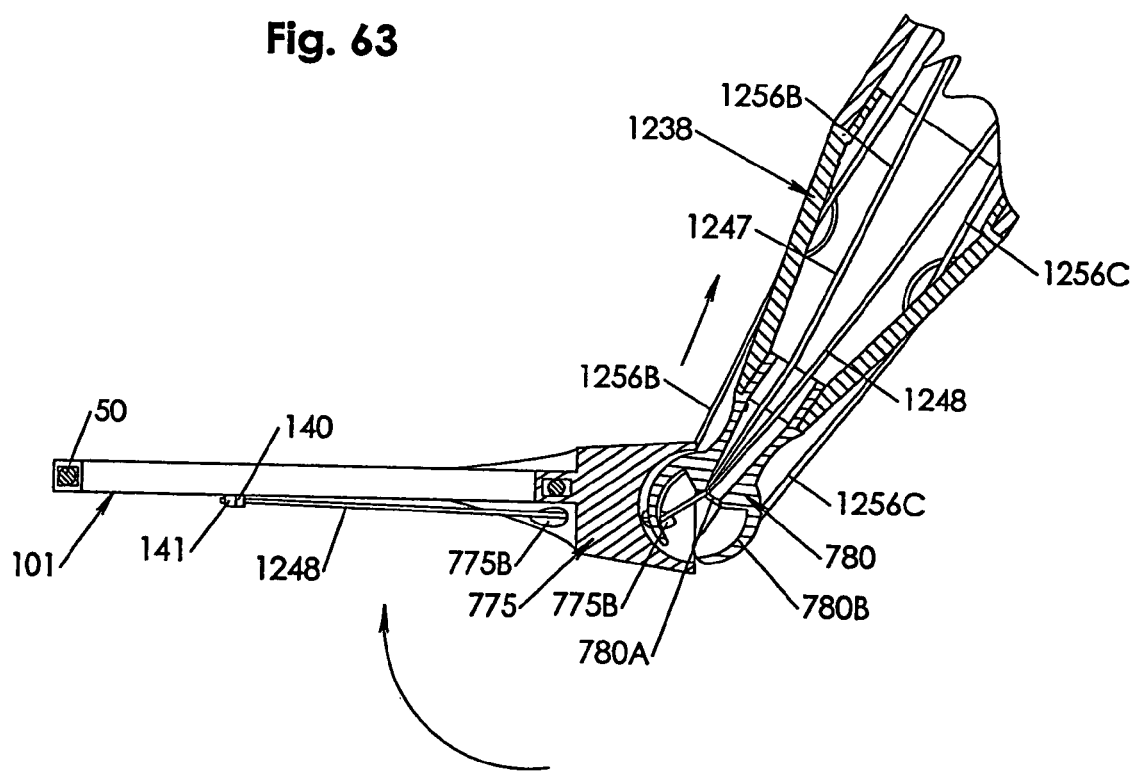
FIG. 63 is a side view, partially in section, of the crescent, the crescent socket provided in one end of the crescent and the cooperating ball provided on the transition guide cone on the extending end of the extension tube and seated in the crescent socket, more particularly illustrating a typical cable arrangement extending through the transition guide cone to the crescent for articulating the crescent to a first position.
Figure 64:
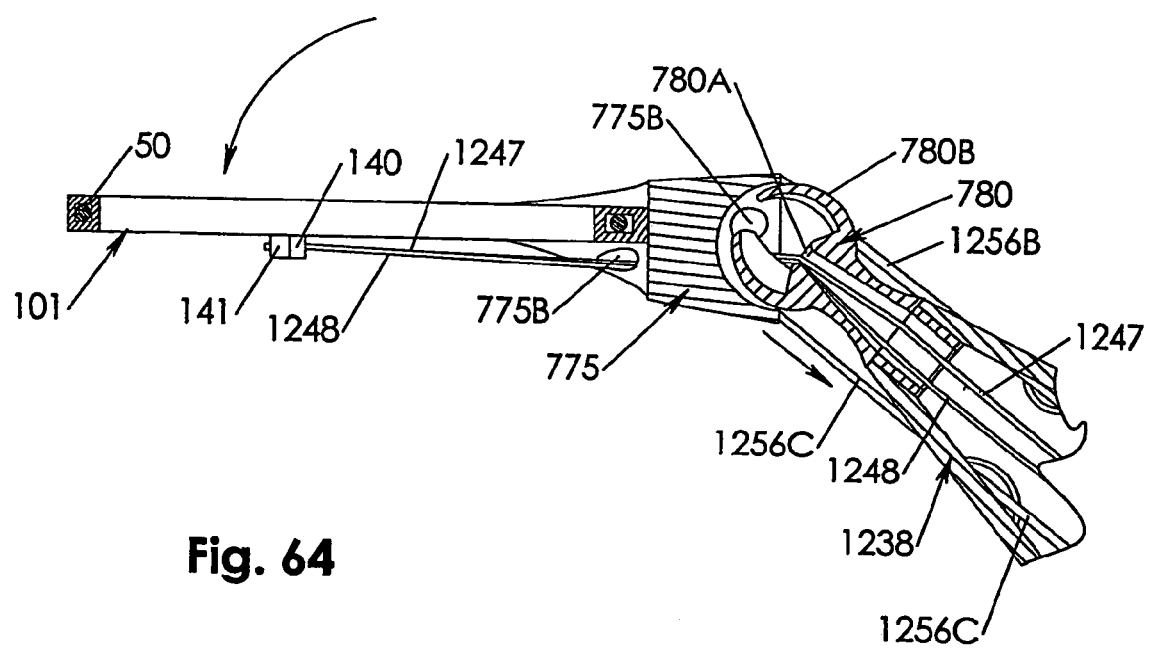
FIG. 64 is a side view, partially in section, of the crescent, the crescent socket provided in one end of the crescent and the cooperating ball provided on the extending end of the transition guide cone on the extension tube and seated in the crescent socket illustrated in FIG. 63, more particularly illustrating a second articulated position of the crescent.

In operation, under circumstances where the cycling suturing and knot-tying device of this invention is utilized as illustrated in FIGS. 1-3 of the drawings without the thread incrementing accessory or the hook/unhook device, the cycling suturing and knot-tying device is used as follows. The device is initially grasped by the handle 1260 with one finger on the trigger 1267 and the transmission tube 1200 is selectively axially rotatably oriented in the cradle 1276A and tilted with the cradle 1276 with respect to the handle 1260, to comfortably position the crescent 101 in an incision or wound adjacent to a material 100 to be sutured (FIG. 62). As further illustrated in FIGS. 62-64 of the drawings the crescent 101 itself may be manipulated by operation of the joint ball 780, seated in the socket 775, into any one of the three illustrative positions and any other necessary position or positions with respect to the material 100, by manipulation of the lever 1251 illustrated in FIGS. 1-4. Finger and thumb manipulation of the lever 1251 selectively tensions the four crescent angle articulation cables 1256A, 1256B, 1256C and 1256D, illustrated in FIG. 41 of the drawings, to achieve the desired orientation of the crescent 101 with respect to the material 100 to be sutured, typically in a configuration and position such as that illustrated in FIG. 62. The arcuate needle 50, provided with a length of thread 50A, typically attached to the center thereof, is caused to rotate either in the clockwise or the counterclockwise direction to extend a length of thread 50A through the material 100 following the needle 50, as further illustrated in FIG. 62. Traversal of the needle 50 around the crescent 101 is effected by squeezing the trigger 1267 while gripping the handle 1260 on the device. This action rotates the sprocket 1275 (FIGS. 55 and 56) in the direction indicated by the arrow 1257A to slidably displace the reciprocation input collar 1216 on the transmission tube 1200 and apply tension to the looped drive cable 1247 in the direction of the arrow 1257 at the drive cable input stops 1247A and 1247B, since the forked transmission rod 1216F is attached to the reciprocation input collar 1216 (FIG. 56). The two free ends of the looped drive cable 1247 are, in turn, connected to the two spaced-apart drive access cable extensions 140 attached to the reciprocating driver 108 (FIG. 6). In a preferred embodiment of the invention depression of the trigger 1267 exerts a force on the drive access cable extensions 140 and causes the reciprocating driver 108 and the drive direction setting plate 134 to traverse the case 102. Typically one full depression of the trigger 1267 results in a complete incrementation of the needle 50 in the crescent 101 in a direction determined by manipulation of the direction actuator 1214 illustrated in FIG. 65, as hereinafter further described. Accordingly, when an exact positioning of the crescent 101 with respect to the material 100 to be sutured is effected in the wound or incision, continued, repetitive finger pressure on the trigger 1267, biased for return by the trigger spring 1282, effects multiple incremental passages of the needle 50 through the material 100 at intervals determined by the operator, with the thread 50A following the needle 50 through the needle opening in each repetition. Large or small adjustments can be made during the suturing operation to position the crescent 101 in a more optimum and comfortable position by selectively and incrementally axially rotating the transmission tube 1200 in the cradle 1276A, manipulating the lever 1251 to change the angle of articulation of the crescent 101 with respect to the transmission tube 1200 and rocking or tilting the cradle 1267A and the seated transmission tube 1200 with respect to the handle 1260, in large or small increments. Accordingly, it will be appreciated from a consideration of the design of the device that the crescent 101 can be placed and maintained in a precise position or positions comfortable to the operator for optimum stitching of the material 100 in both large and very small incision and wound openings in a fast and efficient manner.

Figure 36:
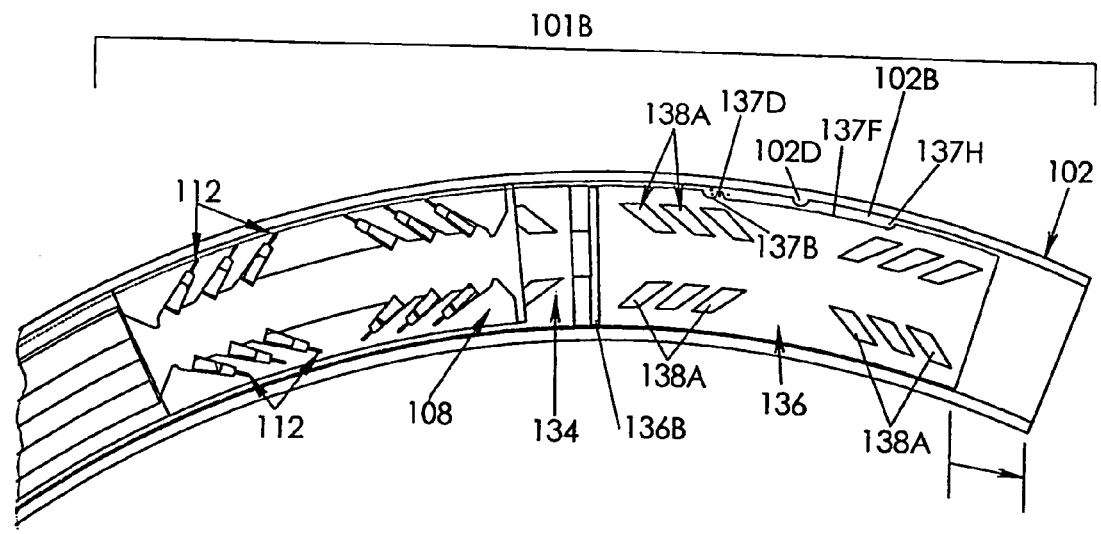
FIG. 36 is an enlarged top view of one end of the needle driver, the drive direction setting plate, the fixed way direction setting plate and the case, more particularly illustrating the case bosses and detents provided in the case and the fixed way needle direction setting plate, for determining the range of motion of the fixed way direction setting plate with respect to the case and counterclockwise rotation of the needle in the crescent.

As heretofore described, the direction of rotation of the arcuate needle 50 in the crescent 101 is selected by operation of the direction actuator 1214, as further illustrated in FIG. 65. Sliding of the actuator boss 1214B and the corresponding tubular base 1214C on the underlying slide switch mount body 1211 between the spaced-apart pressure opposing rings 1211A, effects corresponding tensioning, first of the direction cable 1248 and then the drive cable 1247. Since the two ends of the drive cable 1247 are attached to the spaced-apart pair of drive access cable extensions 140 extending from the reciprocating driver 108 and the two ends of the direction cable 1248 are attached to a pair of spaced-apart direction setting access cable extensions 141 extending from the drive direction setting plate 134, manipulation of the actuator boss 1214B effects rotation of first, the drive direction setting plate 134 and then the reciprocating driver 108, along with the underlying fixed way direction setting plate 136, on the case 102 in the crescent 101 (FIG. 6). Accordingly, as the actuator boss 1214B is slidably manipulated as illustrated in FIG. 65 and is adjusted such that the direction actuator boss 1218A on the tubular base 1214C engages the slide switch body detent 1218 in the slide switch mount body 1211, the needle 50 is typically set for rotation in the counterclockwise direction. This needle rotation setting is effected as the direction cable 1248 is initially tensioned by operation of the direction connection rod-to-direction mount spring 1215B, attached to the mounting boss 1217C and carried by the sliding direction actuator boss 1218A (FIG. 66). This action rotates the drive direction setting plate 134 and the fixed way direction setting plate 136 together with respect to the case 102 and the crescent 101, in the clockwise direction as illustrated in FIGS. 36 and 37 of the drawings. As further illustrated in FIGS. 36 and 37 and as heretofore described, the fixed way direction setting plate 136 is fitted with a detent 137B and an adjacent entrance stop 137D, as well as a clearance recess 137F and a range stop 137H, the latter terminating the forward end of the clearance recess 137F, typically on the receiving arm 101B of the crescent 101. As heretofore described, like components are provided on the opposite or typically, the advancing arm 101A of the crescent 101. Reverse, or clockwise rotation of the needle 50 simply reverses the respective advancing and receiving arm functions. Accordingly, as illustrated in FIGS. 38 and 39 of the drawings, responsive to adjustment of the direction actuator 1214, the drive direction setting plate 134 is caused to first traverse the fixed case 102 in the counterclockwise direction by pressure applied to the spaced-apart direction setting access cable extensions 141, illustrated in FIG. 22A. This action also moves the underlying fixed way direction setting plate 136 from the position illustrated in FIG. 38 to the position illustrated in FIG. 39, where the case boss 102C, provided on the underlying case 102, extends over the entrance stop 137C in the fixed way direction setting plate 136 and registers with the adjacent corresponding detent 137A. This movement of the fixed way direction setting plate 136 is effected by contact between the end of the shorter drive direction setting plate 134 and the corresponding boss 136A, located on the fixed way direction setting plate 136. This contact forces the fixed way direction setting plate 136 in the direction of the arrow illustrated in FIGS. 37 and 38 to effect registration of the case boss 102D on the case 102 in the detent 137A located in the fixed way direction setting plate 136. Accordingly, when the crescent 101 is in this position, the needle 50 is constrained to increment in the clockwise direction responsive to pressing of the trigger 1267 and operation of the reciprocation input collar 1216, as described above, with respect to FIG. 55, since the reciprocating driver 108 is now in the drive position on the drive direction setting plate 134. This drive position is effected by the bias in the direction mount-to-drive mount spring 1215A (FIG. 65) which pulls the drive cable 1247, along with the direction cable 1248 and seats the reciprocating driver 108 in drive configuration in the case 102 when the drive direction setting plate 134 and the fixed way direction setting plate 136 are in position as described above, for counterclockwise rotation of the needle 50.

In one mode, the needle 50 is constrained to move in the counterclockwise direction around the crescent 101, since movable locking of the fixed way direction setting plate 136 on the case 102 as illustrated in FIG. 21 bends the respective leaf tensioning tabs 118 and longer tabs 118A of the driver blades 112 in the driver 108, such that the forwardly-inclining driver blades 112B engage the needle 50, as illustrated in FIG. 8A of the drawings. Furthermore, since the respective sets of the driver blades 112 all extend downwardly through the parallelogram-shaped openings in the reciprocating driver 108 into the drive direction setting plate 134, subsequent rotation of the reciprocating driver 108 responsive to trigger tensioning of the looped drive cable 1247 effects rotation of the reciprocating driver 108, the needle 50 and the drive direction setting plate 134 in concert with respect to the overlying fixed way 104 and underlying fixed way direction setting plate 136 and the case 102, the latter three of which remain immobile. This advancement of the needle 50 in the counterclockwise direction around the crescent 101 continues with forward and reverse incrementation of the reciprocating driver 108 and the drive direction setting plate 134 until the needle direction setting mechanism is changed by again manipulating the direction actuator 1214 opposite to the position illustrated in FIG. 65, as illustrated in FIG. 67. This action causes a shift in the fixed way direction setting plate 136 in the opposite direction on the case 102, along with the reciprocating driver 108, by operation of the drive direction setting plate 134, as heretofore described. This shift causes a different set of driver blades 112 (rearwardly-inclining driver blades 112C) to engage the needle 50 and force the needle 50 in the opposite (clockwise) direction responsive to traversal of the reciprocating driver 108 and the drive direction setting plate 134 around the case 102, as illustrated in FIGS. 8B and 24-29.

Figure 98:
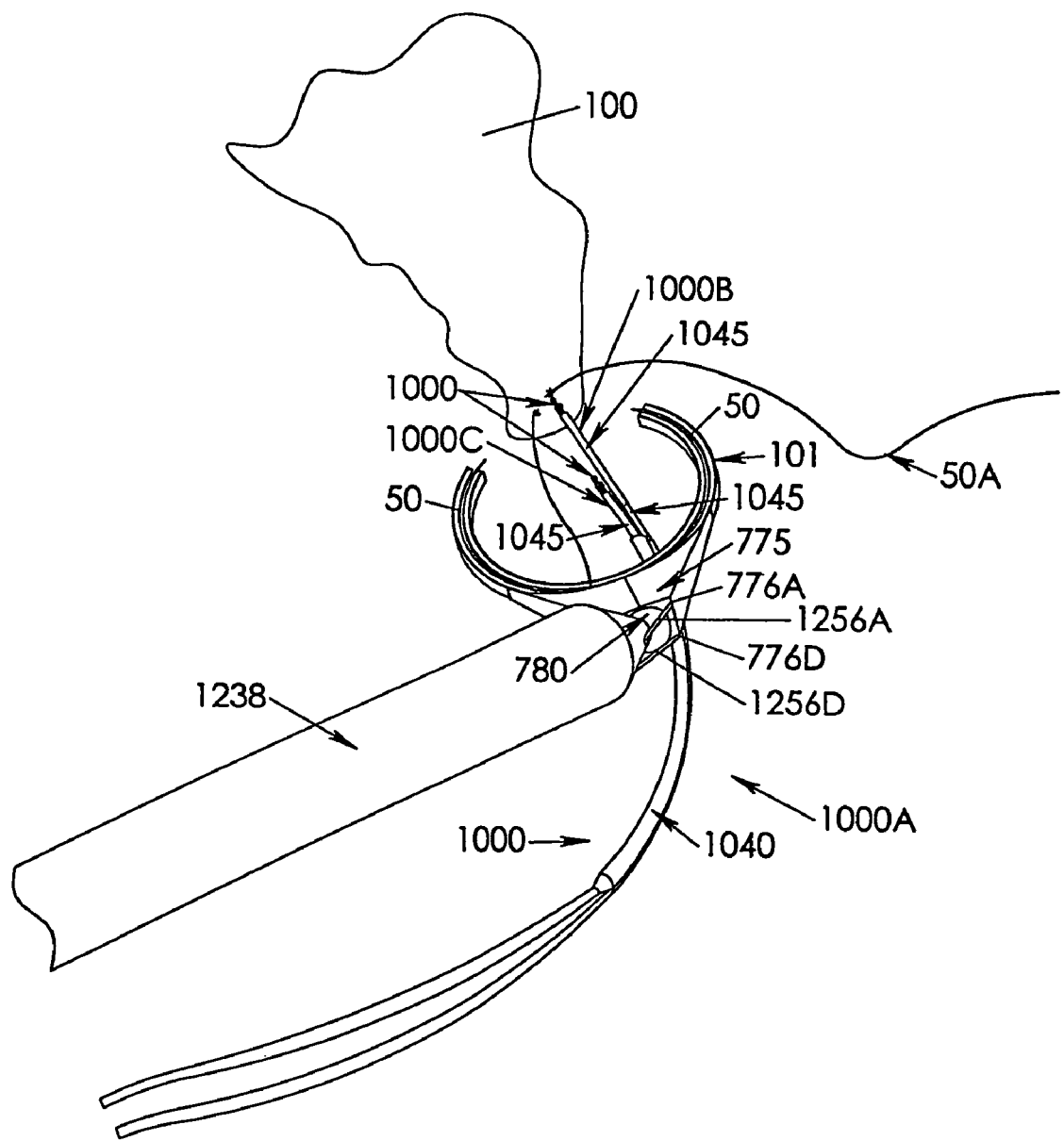
FIG. 98 is a perspective view of the crescent end of the cycling suturing and knot-tying device, with the receiving arms of a hook/unhook device positioned in close proximity to the crescent and to a segment of tissue being sutured, for manipulating the suturing thread.

Referring now to FIG. 81 of the drawings as the needle 50 traverses the crescent 101 in the counterclockwise direction the thread 50 is pulled through the tunnel 100A from the entrance 100B to the exit 100C, as illustrated. In a preferred embodiment of the invention it is desirable to mount a thread incrementing accessory 1101 on at least one end of the crescent 101, typically on the receiving arm 101B, to create a loop in the thread head 50D of the thread 50A during the suturing operation, and provide additional slack for another rotation of the needle 50 through the material 100. Furthermore, a sliding hook 50E, also illustrated in FIG. 81, may be used to manually position the thread head 50D loop and in the alternative, a hook/unhook device 1000 can be utilized for the same purpose, as illustrated in FIG. 98 and as hereinafter further described. Accordingly, with the thread incrementing accessory 1101 mounted on the receiving arm 101B of the crescent 101, the size of the thread head 50D loop in the thread 50A is controlled by operation of the thread incrementing accessory 1101 as hereinafter described.

Referring now to FIGS. 80, 81, 84, 87, 88 and 97 of the drawings after the needle 50 has made an initial traversal through the material 100 of tissue to be sutured as illustrated, the fixed blades 1114 of the thread incrementing accessory 1101 initially engage the thread 50A as the needle 50 pulls the thread around the crescent 101. The thread incrementing accessory 1101 is then operated as hereinafter described to move the movable housing 1115 rearwardly away from the material 100 with respect to the fixed housing 1120 and bend the tabs 1118 and longer tabs 1118A of the corresponding higher movable blades 1112 and movable blades 1113 to engage the higher movable blades 1112 and movable blades 1113 with the thread 50A extending through the guide slot 1126A of the movable housing 1115, as illustrated in FIG. 84. Continued rearward movement of the movable housing 1115 with respect to the fixed housing 1120 on the advancing arm 101B of the crescent 101 pulls the thread 50A through the tunnel 100A and from the exit 100C from the position illustrated in FIGS. 80 and 88 and incrementally, to the position illustrated in FIG. 81, thus forming a loop of desired size in the thread head 50D of the thread 50A. Control of this loop is typically effected by the action of the sliding hook 50E in FIG. 81 or of a hook/unhook device 1000 (illustrated in FIG. 98 of the drawings), as heretofore described. Additional rotations of the needle 50 to create additional tunnels 100A in the material 100 can be effected due to this slack in the thread head 50D of the thread 50A and in each case the thread incrementing accessory 1101 can be operated as described above to create this slack.

Referring now to FIGS. 81-83 of the drawings when the thread head 50D of the thread 50A is formed into a loop as illustrated in FIGS. 81 and 82 using the thread incrementing accessory 1101, a suture loop can be shaped in the thread 50A to begin a suture by extending the free end of the thread tail 50C around the thread head 50D forwardly of the thread incrementing accessory 1101, as illustrated in FIG. 82. Furthermore, as illustrated in FIG. 83, two segments of the material 100 can be joined together with a suture by entwining the thread 50A, which extends through adjacent segments of the material 100, as illustrated. This entwinement 50G is effected by first tightening the first loop illustrated in FIG. 82 and effecting a second loop to define a square knot or entwinement 50G in the thread 50A by again looping the thread tail 50C around the thread head 50D.

As further illustrated in FIG. 89 an additional thread incrementing accessory 110A can be utilized in the crescent 101 by mounting the additional thread incrementing accessory 1101A on the advancing arm 101A, as illustrated. Both the thread incrementing accessory 1101 and the additional thread incrementing accessory 1101A can then be operated as described above to create loops in the thread 50A between the material 100 and the thread incrementing accessory 1101 and the additional thread incrementing accessory 1101A, respectively, to facilitate tying of knots or entwinements 50G to create the desired sutures as illustrated in FIGS. 80-83 of the drawings.

Figure 90A:
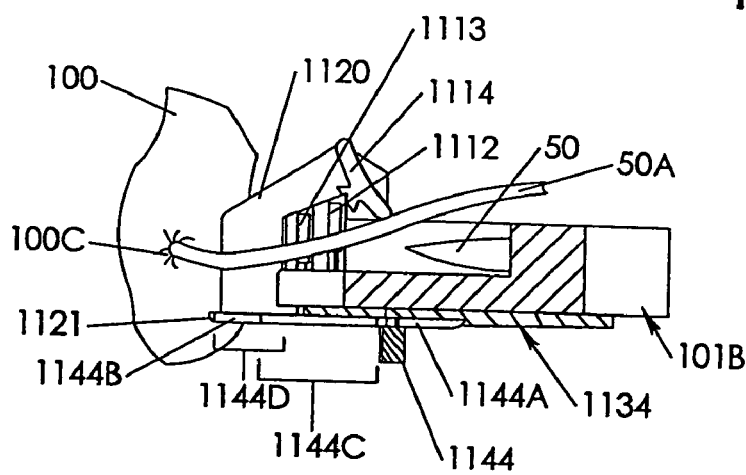
FIG. 90A is a side sectional view of the thread incrementing accessory illustrated in FIG. 90 illustrating the thread incrementing accessory in neutral configuration.
Figure 90B:
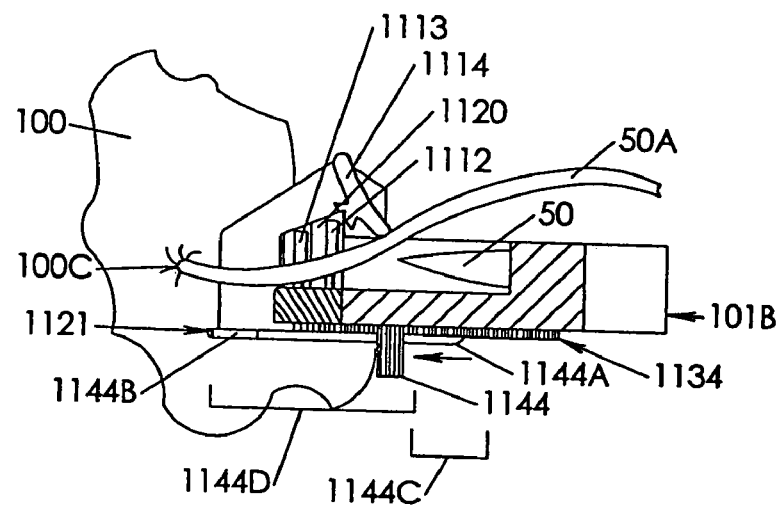
FIG. 90B is a side sectional view of the thread incrementing accessory illustrated in FIG. 90A, with the actuation plate incremented forwardly with no gripping of the thread.
Figure 90C:
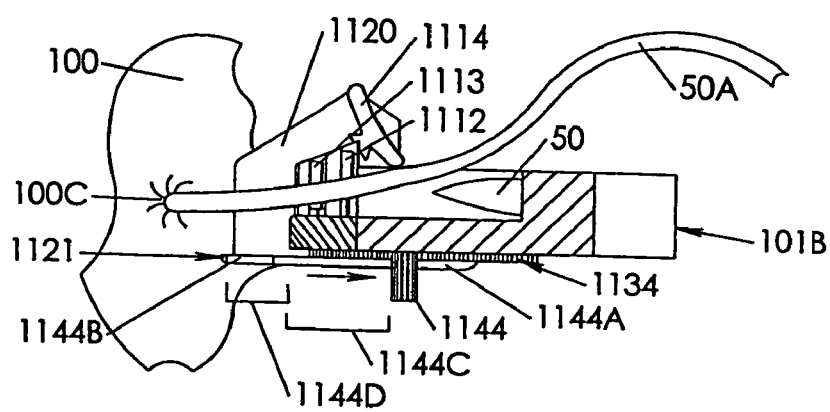
FIG. 90C is a side sectional view of the thread incrementing accessory illustrated in FIGS. 90A and 90B, with the actuation plate incremented rearwardly, with gripping of the thread.

Referring now to FIGS. 4, 84, 87, 90 and 90C-91 of the drawings the thread incrementing accessory 1101 is typically operated by depressing the trigger 1261B on the second handle 1261 as illustrated in FIG. 4 to effect incremental extension and retraction of the power transmission wire 1140 extending through the flexible tube 1141, and move the actuation plate 1134 and the movable housing 1115 back and forth on the case 102 with respect to the fixed housing 1120, on the receiving arm 101B as illustrated in FIGS. 90A-90C. The forward movement opens the higher movable blades 1112 and the movable blades 1113 by releasing pressure on these blades due to release of contact between the actuation plate 1134 and the tabs 1118, the longer tabs 1118A of the higher movable blades 1112 and the movable blades 1113, respectively. This occurs by sliding operation of the actuation plate 1134 from the neutral position illustrated in FIG. 90A, into the normal range of motion 1144C and then into the extended range of motion 1144D (FIG. 90B). Since the actuation plate 1134 is fitted with four parallelogram holes 1138 for receiving the extending ends of the tabs 1118 and longer tabs 1118A of the higher movable blades 1112 and the movable blades 1113, and since these tabs 1118 and longer tabs 118A extend from the movable housing 1115 through corresponding and aligned clearance holes 1124 in the movable housing 1115, pressure is brought to bear on the extending ends of the tabs 1118 and the longer tabs 1118A responsive to rearward sliding movement of the actuation plate 1134 (FIG. 90C). And, as heretofore described, this sliding movement of the actuation plate 1134 and the movable housing 1115 on the case 102 in both directions in the normal range of motion 1144C is accomplished by selectively extending and retracting the power transmission wire 1140 in the flexible tube 1141 responsive to depression of the trigger 1261B on the second handle 1261, as illustrated in FIG. 4. Accordingly, opening of the respective movable blades 1113 and fixed blades 1114 and removing these blades from contact with that portion of the thread 50A which lies within the guide slot 1126A of the movable housing 1115 is effected by forcing the actuation plate 1134 forwardly to move the movable housing 1115 forwardly in the fixed housing 1120 (FIG. 90B), as the power transmission wire 1140 is extended in the flexible tube 1141. This action allows the movable housing 1115 to extend to its farthest distal extension into the extended range of motion 1144D the fixed housing 1120, such that the movable blades 1113 and the fixed blades 1114 are not contacting the thread 50A. The movable blades 1113 and fixed blades 1114 are then caused to engage the thread 50A by reversing movement of the power transmission wire 1140 and moving the movable housing 1115 back to the proximal position rearwardly in the fixed housing 1120 (FIG. 90C), which action bends the corresponding tabs 1118 and the longer tabs 1118A rearwardly and causes opposite rows of these blades to extend inwardly toward each other, engage the thread 50A and pull the thread 50A from the material 100, as illustrated in FIG. 82. Additional incremental movements of the movable housing 1115 in the sequence of first disengaging the movable blades 1113 and the fixed blades 1114 from the thread 50A and then engaging the thread 50A with the movable blades 1113 and fixed blades 1114 responsive to forward and rearward movement of the actuation plate 1134 and the movable housing 1115, respectively, (FIGS. 90B and 90C), facilitates extension of the thread head 50D of the thread 50A as illustrated in FIG. 82 into a sufficiently large loop to allow additional rotation of the needle 50 through the material 100, as well as defining and tightening the sutures in the thread 50A, as illustrated in FIG. 83. The fixed blades 1114 remain in place on the fixed housing 1120 to maintain the thread 50A in the guide slot 1126A of the thread incrementing accessory 1101 during this sliding action of the movable housing 1115. When it is desired to remove the thread 50A from the thread incrementing accessory 1101 without cutting the thread 50A, the actuation plate 1134 is pushed forward (distally) in the access slot 1144A and the narrowing slot 1144B, illustrated in FIG. 91, to open the higher movable blades 1112 and movable blades 1113 and remove these blades from contact with the thread 50A. Further forcing of the actuation plate 1134 forwardly by pressure on the power transmission wire 1140 forces the housing walls 1120D of the fixed housing 1120 apart at the hinge 1121 A (FIGS. 84, 90B and 91), as the access extension tab 1144, attached to the activation plate 1134, is forced into the narrowing slot 1144B (FIG. 91), which action also forces the fixed blades 1114 apart to release the thread 50A from the thread incrementing accessory 1101.

Under circumstances where an additional thread incrementing accessory 1101A is attached to the crescent arm 101A of the crescent 101 as illustrated in FIG. 89, the additional thread incrementing accessory 1101A can be attached to the trigger 1261B and the second handle 1261 by an additional flexible tube 1141 and power transmission wire 1140 (not illustrated) to operate both the thread incrementing accessory 1101 and the additional thread incrementing accessory 110A simultaneously.

Referring again to FIGS. 98-108 of the drawings the hook/unhook device 1000 and the double installation version 1000A of the hook/unhook device 1000 are used to manipulate the thread 50A and facilitate tying of knots or sutures, as follows. As illustrated in FIG. 108 the hook/unhook device 1000, when used alone and in the double installation version 1000A, is characterized by a housing tube 1040 and an auxiliary housing tube 1040A (FIG. 106), each of which encloses an inner housing tube 1045, which extends from the front end of the housing tube 1040 and the auxiliary housing tube 1040A at a housing tube enlarged section 1042, respectively. Each inner housing tube 1045 also extends rearwardly from the corresponding housing tube 1040 and the auxiliary housing tube 1040A, respectively, to receive a pair of three-position switch bodies 1058C, attached to the respective inner housing tubes 1045, as well as a center-located, three-position switch actuator 1058D, secured to the actuation wire 1050 extending through the housing tube 1040 and the auxiliary housing tube 1040A, respectively, as heretofore described. Accordingly, sliding manipulation of the three-position actuator 1058D to reciprocate the actuation wire 1050 and thus, the grip/eject/cut blade 1020 inside the inner housing tube 1045, is illustrated in FIG. 102. As further heretofore described, the crescent attachment mount point 1058 is attached to the crescent 101 by any convenient means, such as screws or welding, in non-exclusive particular, while the tubular attachment mount point 1058A is secured to the second handle 1261, illustrated in FIG. 4 of the drawings.

Figure 102A:
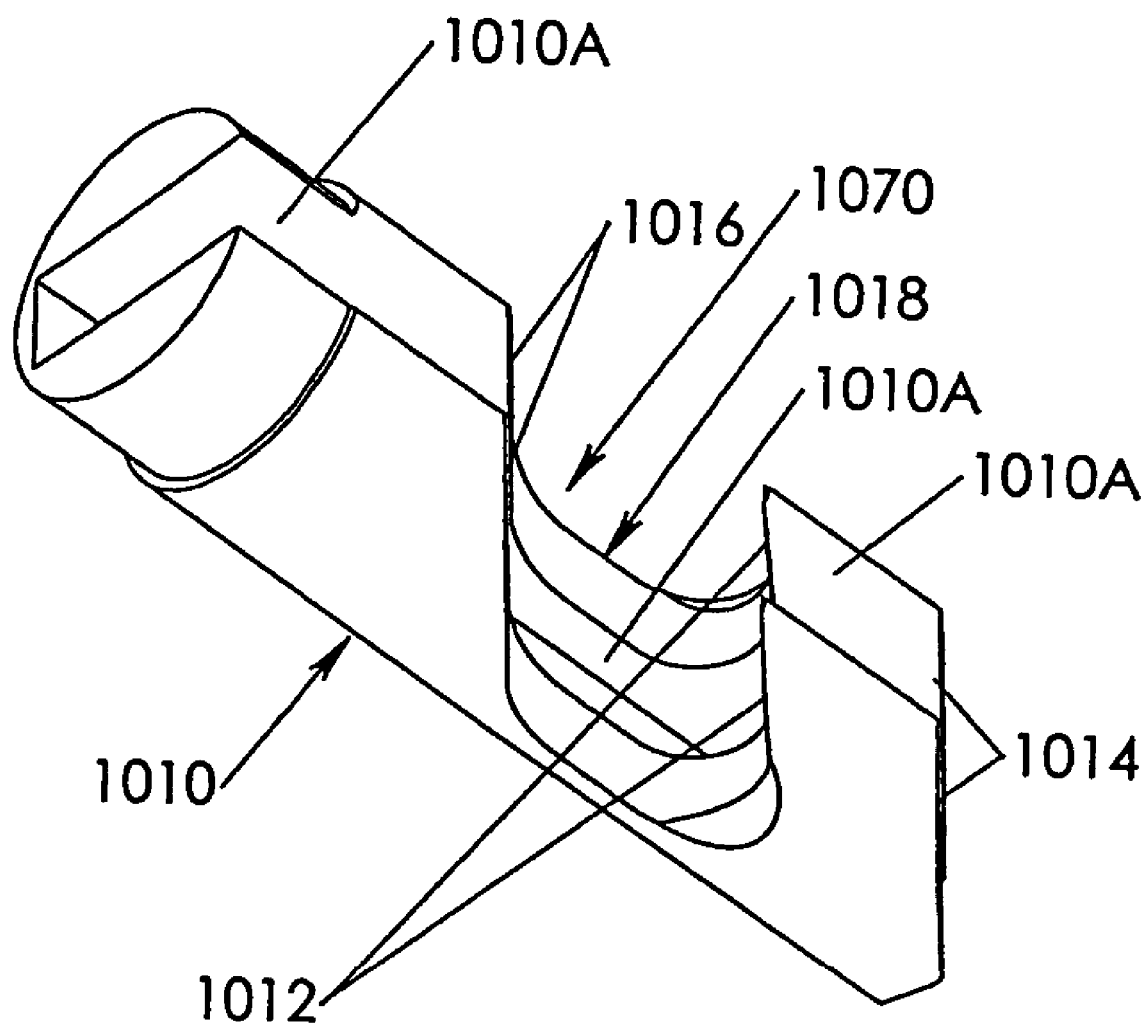

Referring now to FIGS. 98 and 104-106 of the drawings the respective inner housing tube 1045 of the hook/unhook device 1000 individually, and in the double installation version 1000A, is manipulated to receive the thread tail 50C of the thread 50A in the hook open profile 1018, as illustrated in FIG. 102A, responsive to extension of the actuation wire 1050 and the attached grip/eject/cut blade 1020 in the inner housing tube 1045, respectively. This action creates the hook open profile 1018 to accommodate a segment of the thread tail 50C, as illustrated in FIGS. 102A and 105. In like manner, the second hook/unhook device 1000 can be manipulated such that second grip/eject/cut blade 1020 also defines a hook open profile 1018 for receiving a segment of the thread head 50D. Manipulation of the thread 50A into the loosely knotted position illustrated in FIG. 104 is then typically effected by forward and reverse operation of the respective hook/unhook devices 1000 in the double installation version 1000A to tighten the knot or sutures or entwinements 50G, as illustrated in FIG. 105. The knot or entwinement 50G can be further tightened by further extension of one of the hook/unhook devices 1000 in the double installation version 1000A and reverse operation of the companion hook/unhook device 1000, as further illustrated in FIG. 106. Referring to FIGS. 102, 107 and 108 the pulling of the thread 50A through the material 100 to produce a relief loop 50B requires hooking the thread head 50D in first, a sliding hook action using hook faces 1012 then pulling the thread 50A into housing tube's enlarged section 1042 until a large enough loop has been drawn through the material 100. When this has been done the inner housing tube 1045 and hook 1010 are pushed back out of tube section 1042. Plunger disk 1065 ejects the loop 50B from the tube section 1042 allowing it to expand away from the device 101.

Accordingly, it will be appreciated from a consideration of FIGS. 98 and 104-108 that the hook/unhook device 1000 and particularly, the double installation version 1000A, which incorporates two of the hook/unhook devices 1000, can be utilized to manipulate various segments, including the thread tail 50C and the relief loop 50B, as well as the head portion 50D of the thread 50A, both outwardly and inwardly, into the housing tube 1040 to remove the thread loop from the area of operation and create the sutures or entwinements 50G illustrated in FIGS. 105 and 106. The thread loop can then be pushed from the housing tube 1040 by the plunger disc 1065 (FIG. 108). This manipulation is effected by separate slidable movement of the respective three-position switch actuator 1058D located between the corresponding pair of parallel three-position switch bodies 1058C, either by itself or in concert with the three-position switch bodies 1050C, as illustrated in FIG. 108.

It will be appreciated from a consideration of the drawings and the above description that the dual-direction embodiment of the cycling suturing and knot-tying device of this invention is characterized by great flexibility, utility and ease of operation, in that it can be quickly and easily positioned by an operator for rapid, accurate and convenient suturing of incisions and wounds, as well as suturing of organs and other tissue located inside these incisions. The elongated transmission tube 1200 is tapered at the arcuate crescent end to define an extension tube that terminates in a ball and socket-mounted, universally rotatable, arcuate crescent of selected size, fitted with an arcuate needle that traverses the crescent in either direction, depending upon the setting of a slide switch positioned on the transmission tube. The transmission tube is also mounted on a cradle, pivoted on a handle, for both rotatable and pivotal manipulation of the transmission tube to further position the crescent in a precisely determined location. The crescent itself can be easily manipulated on the end of the extension tube into a variety of positions by operation of a lever located at the handle, or operating end of the transmission tube. The curved needle is driven selectively in either the clockwise or counterclockwise direction in the crescent using a system of various numbers of blade housings and blades that are harder than the needle, by depression of a trigger located in the handle for easy control of sutures placed in the tissue. Furthermore, one or more thread incrementing accessory can be placed on one or both ends of the crescent to optimize creation of a loop in the thread for additional needle rotation and to further facilitate knotting or tying or suturing the thread, typically with the help of one or more hook/unhook devices which may be separately manipulated by the operator to articulate the thread into entwinements, knots and sutures in the tissue.

Referring to FIGS. 109-112D of the drawings in a preferred embodiment of the cycling suturing and knot-tying device of this invention a unidirectional device is generally illustrated by reference numeral 1A. As illustrated in FIGS. 109 and 109A the unidirectional device 1A is characterized by an arcuate fixed way/case 2, mounted on a socket 775AA and characterized by four, equally-spaced way/case blade housing bosses 11, provided in the walls of the fixed way/case 2 and fitted with several sets of fixed way blades 12E. The fixed way blades 12E are arranged in an oppositely-disposed configuration defining a chevron pattern pointing in the direction of travel of an arcuate needle 50, which seats in the fixed way/case 2 as further illustrated in FIG. 109. Four sets of 16 flexible fixed way blades 12E, arranged in oppositely-disposed sets of 8, are typically provided in each of the weigh/case blade housing bosses 11. Each of the fixed way blades 12E is preferably characterized by an arcuate concave contact profile 17 for securely engaging the cross-sectionally round needle 50, which concave contact profile 17 extends upwardly to define a top rounded end 19 and downwardly to define a bottom rounded end 19A, as illustrated in FIGS. 109D and 109E. A blade floor clearance 23 is provided between the bottom edges of each of the fixed way blades 12E and the floor of the needle guide slot 26 of the fixed way/case 2, for purposes which will be hereinafter described. The distances between the respective way/case blade housing bosses 11 in the fixed way/case 2 define respective open notches 6 in the needle guide slot 26 to facilitate movement of the respective driver housing bosses 10, spaced-apart on an arcuate connection member 9, to define a reciprocal driver 8 that seats in the fixed way/case 2, as further illustrated in FIGS. 109 and 109A. Each of the driver housing bosses 10 is further characterized by a set of chevron-shaped driver blades 12D which are harder than the needle 50 and are oriented in the direction of travel of the needle 50 and designed to engage the needle 50 for driving the needle 50 forwardly through the fixed way/case 2 by driving mechanisms hereinafter further described. In a preferred embodiment of the invention each of the driver housing bosses 10 contains 16, spaced-apart driver blades 12D, arranged in oppositely-disposed sets of 8, each provided with the same chevron shape and contour pattern as the fixed way blades 12E illustrated in FIGS. 109D and 109E of the drawings. Accordingly, it will be appreciated from a consideration of FIG. 109 that the needle 50 is designed to seat simultaneously in all three of the driver housing bosses 10 and in all four of the way/case blade housing bosses 11 when the needle 50 is inserted in the position illustrated in FIG. 109. A length of thread 50A extends from one end of the needle 50 and the needle gap 105A, measured between the sharpened needle tip and the point where the thread is attached to the opposite end of the needle 50, and essentially corresponds to the gap 5 measured between the respective ends of the curved advancing arm 2A and receiving arm 2B of the fixed way/case 2. Both the fixed way blades 12E and the driver blades 12D can be secured in the fixed way/case 2 by means of slots (not illustrated) or the fixed way blades 12E and the driver blades 12D may be molded or otherwise constructed from a single piece of material that defines each of the way/case blade housing bosses 11 and the driver housing bosses 10, respectively, as illustrated in FIGS. 109D and 109E. Furthermore, the material of construction used in the driver housing bosses 10 and the way/case blade housing bosses 11 may vary, depending upon the needle mount desired and may include a stiff plastic, metal, fiberglass or the like, which is sufficiently strong to ensure the integrity of the blades and which offers sufficient blade resiliency to facilitate easy passage of the needle 50 through the respective blades and retarding of reverse movement of the needle during incrementation of the driving mechanism.

Referring again to FIGS. 109 and 109A of the drawings it will be appreciated that the reciprocal driver 8 is seated in the fixed way/case 2 in the manner illustrated in FIG. 109 such that each of the driver housing bosses 10 is free to increment in the clockwise and counterclockwise direction with respect to the fixed way/case 2 throughout the length of the corresponding notches 6. Accordingly, it will be further appreciated by those skilled in the art that the number of driver housing bosses 10 can be varied on the connection member 9 and additional or fewer way/case blade housing bosses 11 can be provided, to facilitate a longer or shorter reciprocating incrementation between the respective driver housing bosses 10 and the corresponding way/case blade housing bosses 11 in the respective notches 6 of the fixed way/case 2. Various numbers of the driver housing bosses 10 and the way/case blade housing bosses 11 may be necessary to facilitate suturing thin, less dense tissue on the one hand, and also thick, sinewy, dense tissue which requires more pressure on the needle 50 and therefore better gripping of the needle 50 by the respective driver blades 12D in the driver housing bosses 10, respectively. It will be further appreciated from a consideration of FIGS. 109, 109D and 109E of the drawings that the respective driver blades 12D and fixed way blades 12E are angled in the needle guide slot 26 such that the blades are slightly bent when the needle 50 is installed, yet forward movement of the needle 50 between the respective driver blades 12D and fixed way blades 12E meets with little resistance, whereas rearward movement of the needle 50 meets with significant resistance that increases with the applied force in the rearward direction.

Referring now to FIGS. 109A-109C, 109F-109H and 109I of the drawings in a preferred aspect of this embodiment of the invention the driving mechanism for the reciprocal driver 8—is characterized by a curved, beveled rack 48, having a rack access rib 48G fixed to the connection member 9, typically located beneath the center one of the driver housing bosses 10. When the unidirectional device 1 is assembled as illustrated in FIG. 109 the rack access rib 48G of the beveled rack 48 is designed to extend through a curved rack slot 48C, provided in the needle guide slot 26 of the fixed way/case 2, as illustrated in FIGS. 109A and 109D. This facility allows the rack teeth 48L provided on the beveled rack 48 to engage corresponding gear teeth 48K provided on a beveled pinion gear 48A, as illustrated in FIG. 109C. In a first preferred embodiment of this aspect of the drive mechanism the beveled pinion gear 48A is characterized by a continuous set of gear teeth 48K extending around the entire beveled surface area of the beveled pinion gear 48A, to receive power applied to a flexible pinion gear shaft 48H, which extends through a corresponding flexible housing tube 49 to a conventional drive, such as a conventional micromotor 48B, illustrated in FIG. 109A. Operation of the conventional micromotor 48B effects incrementation of the beveled rack 48 and thus, the driver housing bosses 10 of the reciprocal driver 8, in the corresponding notches 6 of the fixed way/case 2. Since the conventional micromotor 48B is reversible, this incrementation of the reciprocal driver 8 can be implemented in both directions, such that the respective driver housing bosses 10 may be selectively manipulated in the clockwise and the counterclockwise direction in the notches 6, by forward or reverse operation of the conventional micromotor 48B. This action facilitates movement of the needle 50 in the forward, typically counterclockwise direction as illustrated in FIG. 109, responsive to driving of the beveled pinion gear 48 in the counterclockwise direction as viewed in FIG. 109C, to force the beveled rack 48A in the same direction. Reverse incrementation of the reciprocal driver 8 occurs when the conventional micromotor 48B is reversed, to change the direction of rotation of the beveled pinion gear 48A and thus, the direction of travel of the beveled rack 48, to return the reciprocal driver 8, but not the needle 50, to the original driving position, as hereinafter further described.

In another embodiment of this aspect of the invention the gear teeth 48K arranged on the beveled portion of the beveled pinion gear 48A are discontinuous at a flattened rack return segment 48D, as illustrated in FIG. 109B to facilitate automatic return of the reciprocal driver 8 to an original incrementing position as the flattened rack return segment 48D rotates into facing relationship with respect to the rack teeth 48L on the beveled rack 48. This action occurs in the mechanical arrangement illustrated in FIG. 109 I, wherein a return spring 48E extends between the rack access rib 48G of the bevel rack 48 and a fixed return spring mount 48F attached to the bottom of the fixed way/case 2. Accordingly, when the flattened rack return segment 48D approaches the rack teeth 48L of the beveled rack 48 and the gear teeth 48K disengage the rack teeth 48L, the beveled rack 48 is caused to return to its original position in the rack slot 48C by operation of the bias in the return spring 48E and automatically re-increment the reciprocal driver 8 back into its original driving position.

In still another embodiment of this aspect of the invention a pair of curved access extension slots 41 may be provided in the bottom of the needle guide slot 26 between opposite respective pairs of the way/case blade housing bosses 11, as illustrated in FIG. 110 and a drive cable extension 40 is provided on each end of the reciprocal driver 8 beneath a corresponding driver housing boss 10, as illustrated in FIGS. 110, 110A, and 110B. Each drive cable extension 40 is extended through a corresponding one of the access extension slots 41 (FIG. 110) to project beneath the fixed way/case 2 for sliding disposition in the respective access extension slots 41 and receiving one end of a pair of drive cables (typically drive cables 1247 illustrated in FIGS. 56 and 57 of the drawings). The opposite ends of these control cables are typically connected to a driving apparatus such as the reciprocation input collar 1216 in input section 1200C and the transmission tube 1200, as further illustrated in FIGS. 56 and 57 to facilitate selective incrementation of the reciprocal driver 8 in both the clockwise and counterclockwise directions and incrementally drive the needle 50 around the fixed way/case 2 in a direction determined by the orientation of the needle 50 in the fixed way/case 2, by manipulation of the cables responsive to operation of the drive mechanism in the transmission tube 1200 or alternative operator.

In another embodiment of the cycling, suturing and knot-tying device of this invention the advancing arm 2A of an alternate unidirectional device 1B is illustrated in FIGS. 112 and 112A, wherein an alternate fixed way 15A insert is provided in place of the way/case blade housing bosses 11, and is constructed of a resilient material such as plastic of suitable composition, designed to receive a pair of oppositely-disposed, forwardly-angled fixed way blades 15GX, as illustrated. The alternate fixed way 15A is inserted or seated in an alternate fixed way case 15 such that the locking bosses 15B in each end of the alternate fixed way case 15 engage corresponding lock notches 15C in the alternate fixed way 15A, to prevent sliding of the alternate fixed way 15A in the alternate fixed way case 15. In a preferred aspect of this embodiment each of the fixed way blades 15GX is seated in a resilient fixed way blade holder 15XX in the alternate fixed way 15A and is provided with an enlarged fixed way blade bearing boss 15HX on one end, which seats in a corresponding fixed way bearing hole 15DX, that curves to define a narrow bearing hole opening or neck 15PX. Accordingly, each fixed way blade 15GX is allowed to pivot with the respective driver bearing boss 15HX in the bearing hole opening or neck 15PX as the opposite end of the fixed way blade 15GX contacts the needle 50. The angle of orientation of each of the fixed way blades 15GX in the alternate fixed way 15A is such that the needle 50 is able to move forwardly in the alternate fixed way case 15 in the direction of the forward direction arrow 15L as illustrated in FIGS. 112 and 112A, but cannot move rearwardly in the direction of the resistance force arrow 15Q, as further illustrated in FIGS. 112 and 112A. Each of the fixed way driver blades 15GX extends from the bearing hole opening or neck 15PX, through a shaped spring expansion relief void 15MX before contacting the needle 50, as further illustrated in FIGS. 112 and 112A. Furthermore, positioned along the length of the spring expansion relief voids 15MX on each side of the fixed way blades 15GX, are fixed way spring membranes 15EX, each of which borders a fixed way spring cavity 15FX. Each of the fixed way spring membranes 15EX are constructed of a resilient material such as a thin wall of plastic, to facilitate flattening of the fixed way spring membranes 15EX into the respective adjacent fixed way spring cavities 15FX, as pressure is brought to bear on the corresponding fixed way blades 15GX by movement of the needle 50 in the counterclockwise direction through the alternate fixed way case 15 of the alternate unidirectional device 1A. Accordingly, the oppositely-disposed fixed way spring membranes 15EX serve as shock absorbers and tensioning members, acting on the respective fixed way blades 15GX, to prevent the needle 50 from undesirable rearward movement in the direction of the resistance force arrow 15Q and to facilitate easier forward movement of the arrow 50 in the direction of the forward direction arrow 15L, as further illustrated in FIGS. 112 and 112A.

Figure 12A:
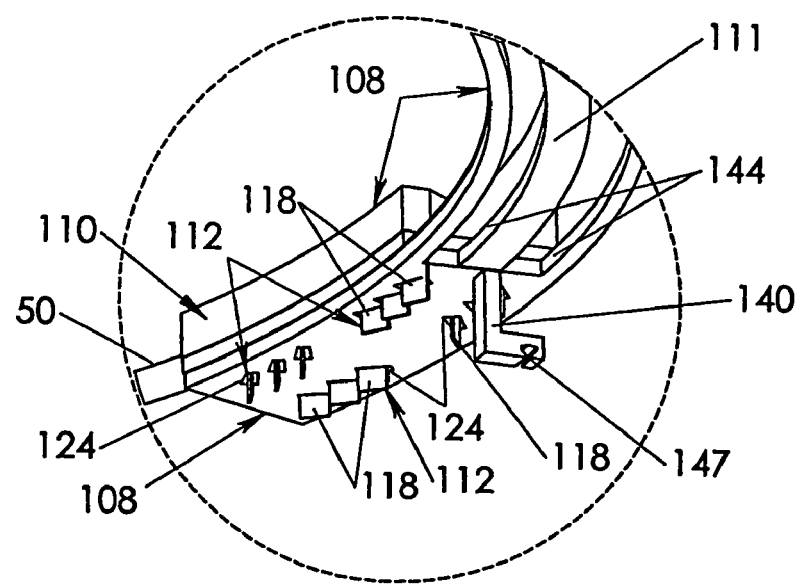
FIG. 12A is an enlarged bottom perspective view of one end of the needle driver, more particularly illustrating downward projection of the needle-engaging blades through corresponding slots in the needle driver and the relative position of one of the cable mount extensions attached to the needle driver for moving the needle driver and the needle and adjusting the blades responsive to operation of the respective control components or elements in the operating device.

In like manner, as further illustrated in FIGS. 112 and 112A, the alternate driver 7 is configured in generally the same shape as the reciprocal driver 8 and is fitted inside the alternate fixed way case 15 and the alternate fixed way 15A in the alternate unidirectional device 1B. The alternate driver 7 includes at least one pair of oppositely-disposed, forwardly-oriented driver blades 15G, each having an enlarged driver bearing boss 15H at the base thereof and seated in a corresponding driver bearing hole 15D in a resilient driver blade holder 15X. Accordingly, a driver blade holder 15X is provided in each of the three driver housing bosses 10, illustrated in FIGS. 109 and 109A. The opposite end of each of the respective driver blades 15G is shaped to engage the needle 50 as indicated in FIGS. 112 and 112A and the driver blades 15G are able to flex forwardly and rearwardly with movement of the needle 50, due to contact with the driver bearing hole opening 15R and the oppositely-disposed driver spring membranes 15E, bordering corresponding driver spring cavities 15F, shaped to extend into each of the corresponding shaped driver relief voids 15M. Accordingly, it will be appreciated from a consideration of FIGS. 112 and 112A that the mechanism for facilitating movement of the driver blades 15G with respect to movement of the needle 50 is the same as the mechanism for effecting movement of the fixed way blades 15GX in the fixed way blade holders 15XX, with corresponding movement of the needle 50. In both cases, the respective driver blades 15G and fixed way blades 15GX facilitate movement of the needle 50 in the direction of the forward direction arrow 15L, but retard reverse movement of the needle in the direction of the blade resistance arrows 15KX and the resistant force arrow 15Q, as illustrated in FIG. 112 and described above. A pair of angled entry guides 27A are also provided on the fixed way blade holders 15XX, respectively, for guiding the end of the needle 50 into the receiving arm 2B of the alternate fixed way case 15, as illustrated in FIG. 12A.

An advantage of the embodiment and means of controlling the swing of the respective fixed way blades 15GX and the driver blades 15G illustrated in FIGS. 112 and 112A is that thicker blade material can be used and it is therefore possible to use fewer blades without lowering the resistance capability of the blades to rearward movement of the needle 50. Furthermore, a precise positioning of each of the fixed way blades 15GX and driver blades 15G, respectively, in relationship to the needle 50, is facilitated.

In yet another embodiment of this aspect of the invention where the alternate unidirectional device 1B and an alternate resilient fixed way 15A is utilized, a pair of alternative fixed way blades 15GGG, each having an alternate fixed way blade retention boss 15HHH are mounted in oppositely-disposed relationship in a pair of resilient alternate fixed way retaining supports 15SS, projecting into the corresponding fixed way structural cavities 15000 (FIG. 112B). The respective alternate fixed way blade retention bosses 15HHH seat the corresponding alternate fixed way blades 15GGG in place in a corresponding alternate fixed way blade retaining cavity 15VVV, all in the alternate fixed way 15A. The alternate fixed way blade mounting structure 15TT tapers rearwardly of the parallel alternate fixed way blade retaining supports 15SSS to define an alternate blade mount flexible connector 15UU that lends additional flexibility and yet resiliency, to the alternate fixed way blade mounting structure 15TT and the fixed way blades 15 GGG themselves. Similarly, the alternate driver blades 15GG in the resilient driver blade mounting structure 15T of the second alternate driver 7A can be mounted in corresponding driver blade retaining supports 15S, that extend into the corresponding driver structural cavities 1500, and taper to define a driver blade mount flexible connector 15U. This mounting structure lends flexibility yet resiliency, to the movement of the alternate fixed way driver blades 15GG, responsive to forward movement of the needle 50 in the direction of the forward direction arrow 15L. The structure also facilitates driver blade resistance to the tendency for rearward movement of the needle 50 in the direction of the resistance force arrow 15Q, as further illustrated in FIG. 112B. A pair of alternate angled entry guides 27 are also provided in the ends of the respective alternate fixed way 15A, for guiding the needle 50 into the receiving arm 2B of the alternate fixed way 15A, as illustrated in FIG. 112C. As further illustrated in FIG. 112 D, in a preferred aspect of this embodiment of the invention the needle-engaging ends of the alternate driver blades 15GG, as well as the alternate fixed way blades 15GGG, the fixed way blades 15GX and the driver blades 15G, are provided with a serrated area 15N to facilitate additional security in the respective blade engagement with the needle 50.

Figure 11:
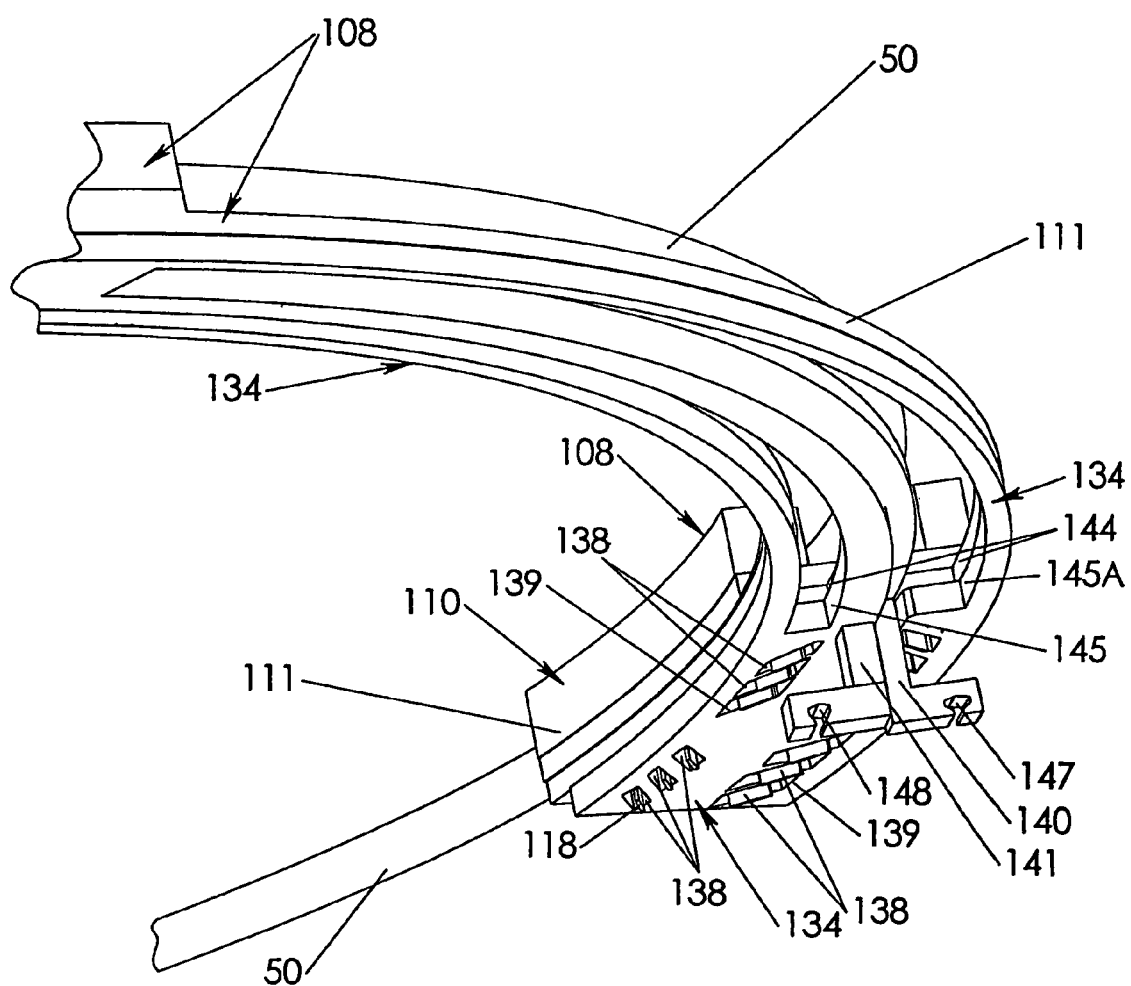
FIG. 11 is a perspective view of the needle driver and the drive direction setting plate in functional connection, more particularly illustrating a pair of cable mount extensions projecting downwardly from the drive direction setting plate and the needle driver, respectively, for operating the needle driver and the drive direction setting plate to both drive the needle and determine the direction of needle rotation, responsive to operation of the respective connecting element control functions of the operating device.
Figure 11A:
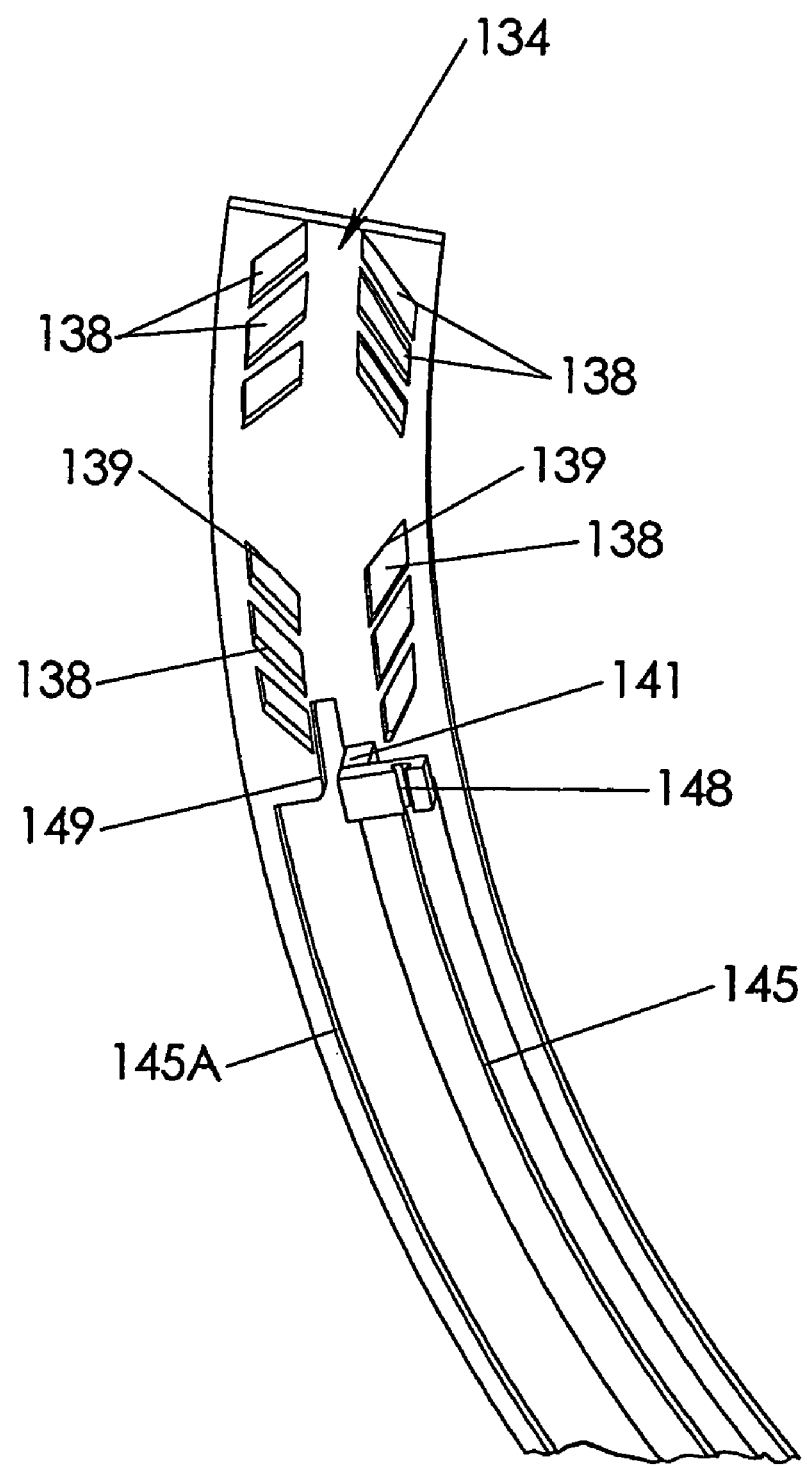
FIG. 11A is a bottom view of one end of the needle drive direction setting plate, more particularly illustrating the respective sets of parallelogram slots for receiving the projecting ends of the corresponding blades from the needle driver and the curved tab clearance slots for accommodating and operating the two cable mount extensions on the needle driver in the crescent.

Referring now to FIGS. 109, 109A, 111-111C of the drawings, under circumstances where any of the driver mechanisms (not illustrated) described above are operated to effect movement of the needle 50 around the fixed way/case 2, (as well as the alternate fixed way case 15) the needle 50 is initially driven in the counterclockwise direction from the position illustrated in FIGS. 109 and 111 to the position illustrated in FIG. 111A and through material to be sutured 100, which is positioned in the opening or gap 5 (FIG. 109) spanning the advancing arm 2A and the receiving arm 2B of the unidirectional device 1A (or the alternate unidirectional device 1B, not illustrated). As the blade 50 enters the material 100 as illustrated in FIG. 111A the reciprocal driver 8 (or the alternate driver 7 or second alternate driver 7A) is incremented inside the needle guide slot 26 with each of the respective driver housing bosses 10 traversing the respective notches 6 lying adjacent to corresponding way/case blade housing bosses 11 (FIG. 109A). The respective driver blades 12D thus engage the needle 50 in driving relationship. At this point, the driving mechanism is reversed to reverse the reciprocal driver 8, or the alternate driver 7, or the second alternate driver 7A, (not illustrated) and re-increment the reciprocal driver 8 or the other drivers from the position illustrated in FIG. 111A back to the position illustrated in FIG. 109. This action leaves the needle 50 in the position as illustrated in FIG. 11A, due to the forward positioning of the respective driver blades 12D and fixed way blades 12E, that prevent reverse-rotation of the needle 50. When the reciprocal driver 8 (or the alternate driver 7 or the second alternate driver 7A) is re-incremented by the driving mechanism into driving mode, illustrated in FIG. 109, those driver blades 12D (or the driver blades 15G or the alternate driver blades 15GGG) contacting the needle 50 again grip the needle 50 and cause the needle 50 to increment forwardly into the position illustrated in FIG. 111B. The reciprocal driver 8, as well as the alternate driver 7 or the second alternate driver 7A are then in the position illustrated in FIG. 111B, but with the needle 50 further incremented through the material 100 and re-entering the receiving arm 2B of the unidirectional device 1. At this point, the reciprocal driver 8 (or the alternative drivers) are then again re-incremented into the position illustrated in FIG. 109, where the driver blades 12D (or the other driver blades described above) contacting the needle 50 again grasp the needle 50 and force it around the needle guide slot 26 in the fixed way/case 2 to the position illustrated in FIG. 111C, where it approaches a complete rotation through the unidirectional device 1, with the thread 50A (illustrated in phantom) also in position for pulling through the material 100 as the needle 50 further increments around the needle guide slot 26 and across the gap 5 (FIG. 109) of the unidirectional device 1.

It will be appreciated by those skilled in the art that the unidirectional devices 1A and 1B embodiment of the invention is characterized by flexibility and simplicity of use since the driving mechanism device can be varied, as heretofore described. In one case, referring again to the drawings, the beveled pinion gear 48A may operate a curved, beveled rack 48 to increment the reciprocal driver 8 in the manner heretofore described and the beveled pinion gear 48A can be selectively operated in forward and reverse mode to effect the desired incrementation. In another embodiment the beveled pinion gear 48A can be provided with a flattened rack return segment 48D where the gear teeth 48K are not continuous, to facilitate automatic reversal of the beveled rack 48 by action of the return spring 48E. In yet another embodiment the reciprocal drive operation can be provided with downwardly-extending drive cable extensions 40 for receiving the ends of cables (not illustrated) that project to an incrementing driving mechanism (not illustrated) for effecting the desired incrementation of the driver, causing the needle 50 to traverse the device. Furthermore, the respective blades, which are in all cases harder than the needle 50, can be mounted in a variety of ways in both the fixed way/case 2 and the respective drivers in the both unidirectional device 1A and alternate unidirectional device 1B to facilitate easy movement of the needle 50 in a chosen direction for suturing, and yet retard rearward movement of the needle 50 responsive to reverse incrementation of the respective drivers.

Referring now to FIGS. 113-138 of the drawings in another embodiment of the cycling suturing and knot-tying device a forked blade device 201 is illustrated for incrementing an arcuate needle 50 in an arcuate fixed way 240 that is typically snapped into an arcuate case 210 over a housing 220 and a driver 230, for manipulating multiple forked blades 225, simpler forked blades 226 or alternative blades 227, seated in the housing 220. The case 210 is provided with a gap 205 that spans the distance between the facing ends of the case 210 and is approximately coextensive with the needle gap 105A extending between the pointed ends of the needle 50, as illustrated in FIG. 113. Referring to FIG. 114 of the drawings the case 210 is fitted with a pair of spaced-apart, curved locking slots 210E, each having a wider section 210F and a narrow section 210J, which wider sections 210F are disposed at opposite ends of the locking slots 210E, for purposes of access, as hereinafter described.

As illustrated in FIG. 115 of the drawings the case 210 is further characterized by an arcuate track 210A, bounded by an inner wall 210B and an outer wall 210C, with the arcuate locking slots 210E extending through the case floor 210D. As further illustrated in FIGS. 114 and 116 a socket 775 is attached to the case 210 opposite the gap 205 and a left clearance tunnel 775A and a right clearance tunnel 775B are provided in the socket 775 to facilitate entry of a pair of device cables 1247 and direction cables 1248 for control purposes, as illustrated in FIG. 114 and as further hereinafter described.

Referring to FIGS. 117 and 117A of the drawings an arcuate driver is generally illustrated by reference numeral 230 and includes a pair of downwardly-extending driver tabs 230D, each having a driver tab extension 230L and a driver tab weld attachment groove 230M, provided on the driver tab extension 230L. The driver tab weld attachment grooves 230M are designed to receive one end of the pair of drive cables 1247, illustrated in FIG. 114 and illustrated in phantom in FIG. 117A, for welding the control cables to the respective driver tab extensions 230L at the weld beads 230P and controlling incrementation of the driver 230 throughout the length of the respective locking slots 210E, as hereinafter further described. Three sets of bearing slots 230A are also provided in the driver 230 and corresponding, oppositely-disposed bearing slot walls 230G project into the bearing slots 230A for pivotally receiving the lever 225D in each of the forked blades 225 (not illustrated), as further hereinafter described.

Referring now to FIGS. 118 and 118A of the drawings an arcuate housing 220 is further illustrated with pivot holes 220A that extend to define pivot hole slots 220B, each of the latter fitted with a counterbore 220D, having a corresponding counterbore slot 220E. The respective sets of pivot holes 220A, pivot hole slots 220B, counterbores 220D and counterbore slots 220F are spaced-apart with respect to each other for receiving the respective levers 225D of the forked blades 225 (not illustrated) in the counterbores 220D, as hereinafter further described. A pair of downwardly-extending housing tabs 220G project from the underside of the housing 220 and are fitted with housing tab extensions 220J and corresponding housing tab weld attachment grooves 220K (FIG. 118A), for receiving and welding a pair of direction cables 1248, as illustrated in FIG. 114 and as hereinafter further described. The housing 220 is further characterized by a curved housing inner wall 220L and is terminated by housing ends 220C, as further illustrated in FIGS. 118 and 118A.

As illustrated in FIGS. 114 and 119 of the drawings the driver 230 and the housing 220 are illustrated inserted in the case 210 in functional relationship, such that the respective pivot holes 220A and extending pivot hole slots 220B provided in the housing 220, face upwardly between the inner wall 210B and the outer wall 210C of the case 210. Due to the presence of the locking slots 210E and the wider sections 210F, it will be appreciated that both the housing 220 and the driver 230 can be inserted in the case 210, with the driver tabs 230D, driver tab extensions 230L, housing tabs 220G and housing tab extensions 220J extending through the wider sections 210F, respectively. Furthermore, the housing 220 and driver 230 can then increment in concert inside the fixed case 210, throughout the length of the two locking slots 210E, as further hereinafter described.

Referring now to FIG. 120 of the drawings the arcuate needle 50 is illustrated seated in the respective top face slots 225A of three, spaced-apart forked blades 225. The needle 50 is fitted with a length of thread 50A, typically attached to the approximate center of the needle 50. The respective top face slots 225A in each of the forked blades 225 are each defined by oppositely-disposed, curved blade extensions 225E that project from a pivot shaft section 225B, fixed to an underlying base section 225C that extends to define an inwardly-extending lever 225D, as illustrated. The inside one of each of the blade extensions 225E is further curved to define a pair of inner lock points 225G and the opposite, or outside ones of the blade extensions 225E are configured to define corresponding outer lock points 225F. Accordingly, it will be appreciated from a consideration of FIG. 120 that the respective forked blades 225 can be rotated in either the clockwise or counterclockwise direction by corresponding pressure applied to the levers 225D, to effect engagement of the respective diametrically-opposed sets of inner lock points 225G and outer lock points 225F with the needle 50, to drive the needle 50 in a clockwise or counterclockwise direction responsive to incrementation of the housing 220 and the driver 230 (not illustrated), as further hereinafter described.

Referring now to FIGS. 120 and 121 of the drawings, the housing 220 and driver 230 are illustrated as installed in the case 210 (FIG. 121), along with the three forked blades 225, (carrying the needle 50 as illustrated in FIG. 120), which are rotatably seated in the corresponding pivot hole slots 220B, extending the pivot holes 220A in the housing 220. Accordingly, the forked blades 225 form a bridge between the housing 220 and the driver 230, allowing only limited movement between these elements and the upper part of each of the forked blades 225 extends above the respective pivot hole slots 220B to expose the respective blade extensions 225E, for receiving the needle 50 in the top face slots 225A. It will be further appreciated from a consideration of FIGS. 120 and 121 that the respective inwardly-extending levers 225D, attached to the corresponding pivot shaft sections 225B, (FIG. 120) are disposed beneath the driver 230 and the housing 220 (FIG. 121) for purposes which will be hereinafter further described.

Referring now to FIGS. 120 and 122 of the drawings the housing 220 is positioned with the adjacent driver 230 in functional relationship and with the needle 50 located in the top face slots 225A of the forked blades 225, as detailed in FIG. 120. Furthermore, the respective levers 225D extend from the corresponding pivot shaft sections 225B and base sections 225C of each forked blade 225, into the respective counterbore slots 220E in the housing 220 and project into the corresponding, adjacent bearing slots 230A of the driver 230. Accordingly, it will be appreciated that shifting of the housing 220 in either the clockwise or counterclockwise direction with respect to the driver 230 by manipulation of a suitable operator (not illustrated) causes the corresponding wall of the counterbore slots 220E and the corresponding bearing slot wall 230G, projecting into the corresponding bearing slot 230A of the driver 230, to contact and pivot each of the levers 225D. This action causes the corresponding diametrically-opposed sets of the outer lock points 225F and inner lock points 225G on the respective curved blade extensions 225E to contact the needle 50 and facilitates a corresponding incrementation of the needle 50 by corresponding incrementation of the housing 220 and the driver 230 in the opposite direction, as hereinafter further described.

As further illustrated in FIGS. 114, 120 and 122 of the drawings the driver tabs 230D, extending downwardly in spaced-apart relationship from the bottom of the driver 230 through the locking slots 210E in the case 210 (FIG. 114) are oriented such that the corresponding driver tab extensions 230L, projecting from the respective driver tabs 230D, are positioned to receive and anchor the drive cables 1247, respectively, for operating the driver 230, as further illustrated in FIG. 114. In a similar manner, the pair of housing tabs 220G extending downwardly from fixed attachment to the underside of the housing 220 are provided with corresponding housing tab extensions 220J for receiving and anchoring a set or pair of direction cables 1248 (FIG. 114). The direction cables 1248 are disposed for incrementing the housing 220 with respect to the case 210 and the driver 230 and pivoting of the respective forked blades 225 to engage a selective diametrically-opposed set of the outer lock points 225F and inner lock points 225G, respectively, (FIG. 120), into contact with the needle 50 and allow either counterclockwise or clockwise rotation of the needle 50, as further hereinafter described.

Referring to FIGS. 113, 123 and 124 of the drawings an arcuate fixed way 240 is illustrated and is terminated by downwardly-extending end segments 240A, with a gap or opening provided between the respective end segments 240A that corresponds substantially to the gap 205 and the needle gap 105A illustrated in FIG. 113. A pair of middle segments 240B (FIG. 124) are also illustrated in the fixed way 240, which middle segments 240B do not extend below the plane of the fixed way 240, as illustrated in FIG. 124. Curved notches 240C are provided between the respective end segments 240A and the middle segments 240B as further indicated in FIG. 124 and guide grooves 240D are also spaced-apart in the fixed way 240, which guide grooves 240D communicate with flared conical entry guides 240G located in the middle segments 240B and the end segments 240A of the fixed way 240. The guide grooves 240D are slightly undersized with respect to the needle 50 to retain the needle 50 in successive incremented positions during return of the respective forked blades 225 to the driving configuration after incrementation with the housing 220 and the driver 230, as hereinafter described. Opposing way covers 240F extend around substantially the entire curvature of the fixed way 240 to define an arcuate thread slot 240E, which is narrower than the diameter of the needle 50 to facilitate retention of the needle 50 in the guide grooves 240D and the fixed way 240 and clearance of the thread 50A as the needle 50 traverses the fixed way 240. The fixed way 240 is typically constructed of plastic and may be permanent or disposable, such that the needle 50 is snapped in and out, as desired.

Illustrated in FIG. 125 of the drawings are the case 210, with the housing 220 (hidden, and the forked blades 225 in place) and the driver 230 (hidden beneath the fixed way 240) and with the way covers 240F of the fixed way 240 removed for brevity. Further illustrated is the underlying needle 50, seated in the top face slots 225A between the blade extensions 225E of the respective forked blades 225. Accordingly, as further illustrated in FIG. 125 the needle 50 is illustrated inserted in the top face slots 225A of the respective forked blades 225 and between the corresponding opposed outer lock points 225F and inner lock points 225G of the facing blade extensions 225E. It will be further appreciated from a consideration of FIG. 125 that the fixed way 240 typically snaps onto the case 210 by a suitable tab and slot combination (not illustrated) and covers both the housing 220 and the driver 230, allowing pivoting action of each of the forked blades 225 responsive to operation of the respective drive cables 1247, as illustrated in FIG. 114 and hereinafter described.

Referring again to FIGS. 1, 64, 65, 66, 77, 78 and 114 of the drawings, the respective drive cables 1247 and direction cables 1248 typically extend from fixed attachment to the corresponding driver tab extensions 230L and housing tab extensions 220J, respectively, through the clearance tunnels 775A and 775B in the socket 775, as illustrated in FIG. 114. From the socket 775, the drive cables 1247 and direction cables 1248 typically extend through the joint ball 780 and the transition guide cone 1238 (FIG. 64) and through the transmission tube 1200 to the reciprocation input collar 1216 and the direction actuator 1214, respectively, illustrated in FIG. 1 of the drawings. At that point the drive cables 1247 are typically connected to the reciprocation input collar 1216 and trigger 1267 mechanism as heretofore described with respect to FIGS. 41-55 of the drawings. The direction cables 1248 are typically connected to the direction actuator 1214 apparatus as described with respect to FIGS. 65, 66, 77 and 78 of the drawings.

In operation, one of the forked blades 225 of the forked blade device 201 (FIG. 113) is illustrated in neutral configuration in FIG. 126. FIG. 126 illustrates a forked blade 225 with the needle 50 extended through the top face slot 225A, defined by the oppositely-disposed blade extensions 225E. Accordingly, the oppositely-disposed sets of outer lock points 225F and inner lock points 225G are not touching the needle 50, since the lever 225D of each forked blade 225 is not yet rotated in the bearing slot 230A of the driver 230 responsive to rotation of the housing 220.

Referring now to FIGS. 126A and 127 of the drawings the forked blades 225 are each rotated in the clockwise direction indicated by the clockwise blade rotation arrows 250B to contact diagonally or diametrically-opposed sets of the outer lock points 225F and the inner lock points 225G with the softer needle 50. This contact is effected along with the clockwise rotation of the forked blade 225 by clockwise rotation of the housing 220 in the direction of the clockwise housing/driver/needle rotation arrow 250A, to facilitate movement of the lever 225D in the direction of the clockwise blade rotation arrow 250B (FIG. 126A), as illustrated. Accordingly, contact between the edge of the counterbore slot 220E in the housing 220 and the lever 225D pivots the lever 225D in the clockwise direction in a camming action, as indicated by the clockwise blade arrow rotation 250B, since the extending end of the lever 225B engages the bearing slot wall 230G in the bearing slot 230A (illustrated in phantom in FIG. 126A) of the drives 230. Consequently, the needle 50 is now in position for counterclockwise rotation in concert with the housing 220 and the driver 230 in the direction of the counterclockwise housing/driver/needle rotation arrow 250C.

Movement of the housing 220 initially in the clockwise direction as indicated by the clockwise housing/driver/needle rotation arrow 250A to seat the forked blades 225 against the needle 50 is effected by tensioning the two direction cables 1248, illustrated in FIG. 114, by operation of suitable direction actuator 1214 apparatus such as that illustrated in FIG. 1 of the drawings, as heretofore described. Furthermore, subsequent rotation of the housing 220 and the driver 230 together in the counterclockwise direction to carry the needle 50 in the same direction as illustrated in the counterclockwise housing/driver/needle rotation arrow 250C, is effected by repetitively tensioning the two drive cables 1247 attached to the driver tab extensions 230L of the driver 230. This action is typically initiated by operation of the reciprocation input collar 1216 and trigger mechanism 1267 also illustrated in FIG. 1, and moves the corresponding driver tabs 230D along the length of the respective locking slots 210E in the case 210, to increment the housing 220, the driver 230 and the needle 50 in the counterclockwise direction around the fixed way 240, as heretofore described. Alternatively, other drive mechanisms may be provided in connection with the housing 220 and/or the driver 230, including bevel gear drives, direct flexible cable drives and rack and pinion drive components, in non-exclusive particular, as illustrated and described in the various embodiments of this invention.

Referring now to FIGS. 128 and 128A of the drawings under circumstances where it is desired to increment and drive the needle 50 in the clockwise direction around the fixed way 240, the procedure for counterclockwise incrementation illustrated in FIGS. 126A and 127 and described above is reversed, as follows. The forked blades 225 are initially caused to rotate in the counterclockwise direction (in the direction of the counterclockwise blade rotation arrow 250D) by corresponding initial counterclockwise rotation of the housing 220, as illustrated by the counterclockwise housing/driver/needle rotation arrow 250C (FIG. 128). This action causes the desired rotation of the forked blades 225 to effect engagement of diagonally or diametrically-opposed sets of the respective outer lock points 225F and inner lock points 225G on the corresponding blade extensions 225E in the forked blades 225, with the softer needle 50, as illustrated. Accordingly, these needle-engaging outer lock points 225F and inner lock points 225G are positioned to effect clockwise rotation of the needle 50 (FIG.

128A) in the guide grooves 240D of the fixed way 240 (FIG. 123) upon corresponding rotation of the housing 220 and the driver 230 in concert in the direction of the clockwise housing/needle rotation arrow 250A. As in the case of the counterclockwise rotation of the needle 50 illustrated in FIGS. 126A and 127, the initial rotation of the housing 220 to effect corresponding the opposite clockwise rotation of the forked blades 225 to the position illustrated in FIG. 128, is typically effected by tensioning of the two direction cables 1248 with finger pressure exerted on the direction actuator 1214 located on the transmission tube 1200, as illustrated in FIG. 1 and as further hereinafter described. Driving of the needle 50 along with the housing 220 and driver 230 in concert in the clockwise direction is effected by tensioning the two drive cables 1247, typically using the trigger mechanism 1267, to increment the reciprocation input collar 1216, as further illustrated in FIG. 1.

Referring now to FIGS. 1, 54-58, 113, 126A, 127 and 129-133 of the drawings under circumstances where the needle 50 is to be incremented in the counterclockwise direction according to the procedure illustrated in FIGS. 126A and 127, the forked blade device 201 is initially positioned with respect to a material 100 to be sutured, such that the material 100 projects into the gap 205 and needle gap 105A (FIG. 113) in the path of the needle 50, as illustrated in FIG. 129. The housing 220 is then incremented in the clockwise direction as illustrated in FIG. 126A, typically by manipulating the direction actuator 1214 in the transmission tube 1200 (FIG. 1), to initially pivot the forked blades 225 in the configuration illustrated in FIG. 129. This positioning of the forked blades 225 engages the respective diametrically-opposed outer lock points 225F and inner lock points 225G with the needle 50 as described with respect to FIG. 126A and facilitates rotation of the housing 220 and the driver 230, along with the needle 50, in the counterclockwise direction along the length of the two locking slots 210E, as illustrated by the counterclockwise/housing/driver/needle rotation arrow 250C in FIG. 130. The housing 220 and driver 230 are then reversed, typically by spring action, as in the trigger 1267 and reciprocation collar 1216 combination described above, (FIGS. 1 and 54-58), back to the position illustrated in FIG. 129, leaving the needle 50 in place, as illustrated. Further rotation of the needle 50 in the fixed way 240 is illustrated in FIG. 131, where the needle 250 continues to penetrate the material 100 with the thread 50A following, as the thread 50A traverses the thread slot 240E defined by the way covers 240F in the fixed way 240. Continued sequential incrementation of the housing 220 and the driver 230 in concert, typically by operation of the trigger 1267 in the transmission tube 1200, effects continued rotation of the needle around the fixed way 240 as illustrated in FIGS. 132 and 133, with the thread 50A following through the opening in the material 100 created by the needle 50, as illustrated. Accordingly, the needle 50 has the capability of encircling its own trailing length of thread 50A to quickly and efficiently suture a wide variety of knots in any type of material 100.

As described above with respect to FIGS. 128 and 128A of the drawings clockwise rotation of the needle 50 in the fixed way 240 is initially effected by corresponding counterclockwise incrementing of the housing 220 and then, clockwise movement of the housing 220 and the driver 230 to facilitate incrementing the needle 50 in the clockwise direction, as illustrated in FIG. 128A of the drawings. Furthermore, in both clockwise and counterclockwise incrementing of the needle 50, as the needle 50 rotates into the position illustrated in FIG. 133, thread-handling devices such as the thread incrementing accessory 1101, illustrated in FIG. 40A of the drawings can be mounted on the case 210 and used to increment the thread 50A as heretofore described with respect to FIG. 40A.

Referring now to FIGS. 134 and 135 of the drawings an alternative configuration of the forked blades 225 illustrated in FIG. 120 is provided in the simple forked blade 226. The simple forked blade 226 includes an inner blade 226D and an outer blade 226E, extending upwardly from a lever 225D and having outer blade lock points 226A on the outer blade 226E and inner blade lock points 226B on the inner blade 226D, as illustrated. Accordingly, pivoting of the lever 225D in the clockwise direction as indicated by the clockwise blade rotation arrow 250B in FIG. 135 as heretofore described, facilitates contact between the respective diagonally-opposed outer blade lock points 226A and inner blade lock points 226B with the needle 50. In a preferred embodiment of the invention the relative hardness of the respective inner blades 226D and the outer blades 226E with respect to the material of construction of the needle 50 is such that contact between the respective outer blade lock points 226A and inner blade lock points 226B with the softer needle 50 causes impressions 226C and burrs 226F to be shaped, formed or cut in the surface of the needle 50. These burrs 226F facilitate a better grip of the respective inner blades 226D and outer blades 226E on the needle 50, as further illustrated in FIG. 135. As in the case of the forked blade 225 embodiment illustrated with respect to FIGS. 127-133 of the drawings, incrementation of the needle 50 is typically effected by operation of the trigger mechanism 1267 and the corresponding reciprocating input collar 1216 in the transmission tube 1200 illustrated in FIG. 1.

In another preferred embodiment of the invention an alternative blade 227 is illustrated in FIGS. 136-138 and is fitted with a lever 225D, to which is attached a pivot shaft section 225B, upon which is mounted oppositely-disposed blade posts 227A, one of which blade posts 227A has a pair of outer lock points 225F and the other of which is fitted with inner lock points 225G. As in the case of the embodiments illustrated above, the outer lock points 225F and inner lock points 225G are designed to engage the needle 50 in diametrically-opposed relationship and effect incrementation of the needle 50 around the fixed way 240 by driving of the housing 220 and the driver 230 in concert in the counterclockwise or clockwise direction, as heretofore described.

Referring again to FIGS. 120, 125 and 126A of the drawings, it will be appreciated that the design of the forked blades 225 (as well as the simple forked blades 226 and the alternative forked blades 227) facilitates firm gripping of the needle 50 in the driving direction, yet, minimal rearward application of force on the needle during return of the housing 220 and driver 230. For example, as illustrated in FIG. 126A the diametrically-opposing outer lock points 225F and inner lock points 225G present to the surface of the needle 50 two different slopes. The slope that faces the direction of needle incrementation is steep in each case, to resist rearward forces and drive the needle 50 onward in the fixed way 240. In control, the opposite slopes of each lock point facing away from needle advancement are disposed at a shallow angle with respect to the surface of the needle 50. This design feature facilitates sliding of the outer lock points 225F (and 226A) and inner lock points 225G (and 226B), respectively, over the surface of the needle 50 without moving the needle 50 rearwardly when the housing 220 and driver 230 reverse direction.

It will be appreciated by those skilled in the art that the forked blade device of this invention facilitates a simple and efficient apparatus for incrementing the needle 50 in either the counterclockwise or clockwise direction responsive to the operation of an operator such as the transmission tube 1200 illustrated in FIG. 1 and as described above. Furthermore, various forked blade designs are possible as described above, for engaging variously designed outer lock points and inner lock points to effect either counterclockwise or clockwise incrementation of the needle in the fixed way of the device.

Referring to FIGS. 139-156 of the drawings a tubular forked blade device is generally illustrated by reference numeral 300 and includes a generally tubular-shaped fixed support frame 310 having a lower fixed support frame tubular portion 310D, fitted with a fixed support frame rotational slot 332D (FIG. 140). A central post 313C is upward standing from the lower fixed support frame tubular portion 310D and terminates in an arcuate top section 313D, that includes three upward-standing fixed segments 310A, 3103B and 310C, spaced-apart by notches 311A and 311B, as further illustrated in FIG. 140. A material gap 305 is provided adjacent the fixed segments 310A and 310C in order to receive and suture material 100 (illustrated in FIGS. 148 and 149), responsive to operation of the tubular forked blade device 300, as hereinafter further described. The gap edges 305B and 305C define the material gap 305 and the material gap 305 corresponds essentially to the width of the needle gap 305A of an arcuate needle 50, as further illustrated in FIG. 140. The needle 50 typically has sharp needle points 341A and 3411B and includes a length of thread 50A, typically extending from the center thereof as illustrated. However, it will be appreciated by those skilled in the art that the needle 50 can be sharp on one end only and the thread attached to the opposite end by techniques known to those skilled in the art under circumstances where it is desired to use a tubular forked way device 300 for suturing in one needle rotational direction only.

As further illustrated in FIG. 139-141 of the drawings and particularly in FIG. 140, a discontinuous fixed guide way 312 is shaped in each of the upward-standing fixed segments 310A, 3101B and 310C for receiving the needle 50 and a fixed segment overhang 312A, 312B and 312C is also provided in each one of the fixed segments 310A, 3101B and 310C, respectively, for maintaining the needle 50 in place in the undercut discontinuous fixed guide way 312. The needle 50 is further maintained in position in the discontinuous fixed guide way 312 by means of a spring pressure pad assembly 314, more particularly illustrated in FIGS. 142-144. The spring pressure pad assembly 314 is further characterized by an arcuate spring base 314G, having a spring base raised rim 314H for seating in a corresponding shallow recess 313E, provided in the arcuate top section 313D of the fixed support frame 310. Mounting springs 314D, 314E and 314F (FIG. 142) extend upwardly in spaced-apart relationship with respect to each other from the spring base 314G and carry spring-mounted friction and retaining pads 314A, 314B and 314C, respectively. Accordingly, it will be appreciated from a consideration of FIGS. 139 and 144 of the drawings that the spring conical entrance guides 314 I and adjacent way segments 318A, 318B and 318C, provided on the spring-mounted friction and retaining pads 314A, 314B and 314C, respectively, are disposed opposite the discontinuous fixed guide way 312 provided in the corresponding fixed segments 310A, 310B and 310C. Since the needle 50 is designed to increment in the discontinuous fixed guide way 312 and the corresponding way segments 318A, 318B and 318C of the spring pressure pad assembly 314, the needle 50 is maintained in position for 360-degree rotation around the upper portion of the fixed support frame 310, as hereinafter described.

Referring again to FIGS. 139-140 of the drawings a middle tube assembly 320 is provided with a tubular shaped lower middle tube portion 320C having an open interior and a middle tube rotational slot 332C, projecting through the wall of the lower middle tube portion 320C in substantial alignment with the fixed support frame rotational slot 332D. A middle tube post 320G extends upwardly from the top edge of the lower middle tube portion 320C and mounts a curved upper middle tube portion 320AB, fitted with a pair of spaced-apart blade housings 320A and 320B, designed to receive corresponding pivoting blades 350A and 350B, respectively. The lower middle tube portion 320C of the middle tube assembly 320 is designed to fit concentrically inside the lower fixed support frame tubular portion 310D and is allowed to rotate to a limited extent therein, as illustrated in FIG. 139.

As further illustrated in FIGS. 139 and 140 of the drawings a drive spur 330 is provided with a lower drive spur tubular portion 332 that fits concentrically inside the lower middle tube portion 320C of the middle tube assembly 320 (FIG. 139). A drive spur hole 332B is provided in the wall of the lower drive spur tubular portion 332 and a locator pin 332A extends through the drive spur hole 332B and into the aligned middle tube rotational slot 332C and the fixed support frame rotational slot 332D, for purposes which will be hereinafter described. An inner tubular post 330F extends upwardly from the lower drive spur tubular portion 332 and terminates in an extension mount 330AB, shaped to define a first leverage extension 330A and a second leverage extension 330B, spaced-apart with respect to each other.

Referring again to FIGS. 139-141 of the drawings under circumstances where the tubular forked blade device 300 is assembled as illustrated in FIGS. 139 and 141 a spring pressure pad assembly 314 is mounted on the arcuate top section 313D, with the corresponding fixed segment 310A, 310B and 310C, respectively, facing the respective spring-mounted friction and retaining pads 314A, 314B and 314C on the fixed support frame 310 (FIG. 139). This arrangement facilitates capturing the needle 50 in the opposing discontinuous fixed guide way 312 in the fixed segments 310A, 3103B and 310C and in the respective way segments 318A, 318B and 318C, shaped in the corresponding spring-mounted friction and retaining pads 314A, 314B and 314C of the spring pressure pad assembly 314, as well as in the discontinuous movable guide way 321, located in the tube blade housings 320A, and 320B on the upper middle tube portion 320AB (FIG. 140). In a preferred embodiment of the invention the needle 50 is slightly oversized with respect to the discontinuous fixed guide way 312 and the discontinuous movable guide way 321 to facilitate application of a slight frictional resistance to rotational movement of the needle 50 during operation of the tubular forked blade device 300, as hereinafter further described. However, the spring pressure pad assembly 314 facilitates acceptance of needles 50 having a variable diameter.

As further illustrated in FIGS. 139, 140, 141 and 145-146 of the drawings the blades 350A and 350B are pivotally mounted in corresponding blade housings 320A and 320B and are each characterized by slots 350C and 350D, respectively, designed to transversely receive the needle 50. Pivot pins 352A and 352B extend downwardly from the levers 354C and 354D, respectively, of the corresponding blades 350A and 350B. In a preferred embodiment the short ends 352C and 352D (not illustrated) project from the slotted ends of the levers 354C and 354D, respectively, for insertion under overhanging undercut ledges 354A and 354B, respectively, provided in the movable segment overhang 312D and 312E, respectively, of the respective blade housings 320A and 320B of the middle tube assembly 320. The pivot bearing holes 322C and 322D (not illustrated) respectively, are provided in the respective floors 322A and 322B of the corresponding blade housings 320A and 320B between the upward-standing shelves 320D and 320E, respectively. In a preferred embodiment the pivot bearing holes 322C and 322D are each provided with ramps 322E and 322F (not illustrated) respectively, to facilitate accommodation of the respective pivot pins 352A and 352B, for inserting the respective blades 350A and 350B into the corresponding pivot bearing holes 322C and 322D, respectively, while assembling the blades in the corresponding blade housings 320A and 320B. Accordingly, when the respective blades 350A and 350B are assembled in the corresponding blade housing 320A and 320B of the middle tube assembly 320 they are constrained to pivot on the corresponding pivot pins 352A and 352B, respectively, as illustrated in FIG. 146 (with respect to the blade 350A), such that the corresponding slot 350C engages the needle 50 and allows rotational movement of the needle 50 in the corresponding discontinuous movable guide way 321 when the blade 350B is positioned perpendicular to the curvature of the needle 50 in a radius of the upper middle tube portion 320AB of the middle tube assembly 320. However, when the blade 350A is pivoted in either direction as indicated by the arrow in FIG. 146, the edges of the blade 350A along the slot 350C engage the needle 50 and facilitate incrementation of the needle 50 in a driving direction and slippage of the needle 50 past the blade 350A in the opposite direction, as hereinafter further described. In another preferred embodiment of the invention the discontinuous movable guide way 321 formed in the shelves 320D and 320E, respectively, as well as in the facing inside wall of the respective blade housings 320A and 320B, respectively, and the discontinuous fixed guide way 312 in the fixed segments 310A, 310B and 310C, are provided with conical entrance guides 312L to guide the needle 50 in its rotation around the respective blade housings 320A and 320B in the upper middle tube portion 320AB and the corresponding fixed segments 310A, 310B and 310C of the arcuate top section 313D.

As further illustrated in FIGS. 141, 148 and 149 of the drawings pivoting of the respective blades 350A and 350B—on the respective pivot pins 352A and 352B in the corresponding blade housing 320A and 320B is facilitated by the provision of angled walls 334A, 334B, 334C and 334D, provided in the respective cavities 330C and 330D, which are undercut in the corresponding first leverage extension 330A and second leverage extension 330B in the extension mount 330AB of the drive spur 330 (FIGS. 148 and 149). These openings allow free movement of the respective levers 354C and 354D of the blades 350A and 350B, respectively, to facilitate selective gripping of the needle 50 by the sides or edges bordering the corresponding slots 350C and 350D of the corresponding blades 350A and 350B.

Referring now to FIG. 147 of the drawings in an alternative blade design, the blades 350A and 350B (not illustrated) are each characterized by levers 354C and 354D (not illustrated) respectively, that terminate at one end in the cavities 330C and 330D in the respective first leverage extension 330A and second leverage extension 330B, respectively, of the drive spur 330, as described above (FIGS. 148 and 149). The opposite ends of the blades 350A and 350B are squared off and, as illustrated, the end of the blade 350A fits beneath the arcuate movable segment overhang 312D of the illustrated blade housing 320A. Furthermore, each of the pivot pins 352A and 352B (not illustrated) respectively, project through a corresponding pivot bearing hole 322C (FIG. 147) and 322D (not illustrated) and one or more discs 351A (FIG. 147) and 351B (not illustrated) are press-fitted or welded on the extending ends of the respective pivot pins 352A and 352B (not illustrated) in the countersinks 351K and 351L (not illustrated), to facilitate mounting of the respective blades 350A and 350B on the corresponding blade housings 320A and 320B, without the necessity of providing corresponding ramps 322E and 322F in the blade housing 320A and 320B, illustrated in FIG. 145.

As illustrated in FIGS. 150, 151 and 152 of the drawings in a preferred embodiment of this and other embodiments of the invention the arcuate needle 50 is fitted with a length of thread 50A at or near the center thereof, by the provision of a needle eye 340B, which is shaped to define a shallow cavity 340F at the bottom end and an upper shallow cavity 340J at the opposite upper end thereof, as illustrated in FIGS. 151 and 152. The thread 50A is fitted with a stop 340D and a secondary stop 340E at the anchored or thread head end 340C, as further illustrated in FIGS. 151 and 152. The area between the stop 340D and secondary stop 340E is concave in configuration to match the internal curvature of the needle eye 340B when the thread 50A is tightened in the lower shallow cavity 340 F and upper shallow cavity 340J of the needle eye 340 B. Accordingly, the thread head end 340C essentially fills the shallow cavity 340F of the needle eye 340B to prevent the thread 50A from being pulled from the needle 50 when tensioned during the suturing operation. In a preferred embodiment of the invention that portion of the thread 50A which extends from the secondary stop 340E upwardly to a predetermined distance is configured to define a flattened hinge 340H to facilitate passage of the needle 50 through tissue (not illustrated) and allow the thread 50A to lie flat against the needle 50 and thus minimize tissue damage due to passage of the thread 50A through the tissue with the needle 50. In another preferred embodiment of the invention the flattened hinge 340H segment of the thread 50A is smaller than that of the thread normal gauge, for a distance slightly greater than half the circular length of the needle. Beyond this distance the diameter of the thread 50A can be larger than the needle 50, to minimize leakage in the tissue, as desired.

Referring now to FIGS. 153-158 of the drawings the tubular forked blade device 300 is illustrated connected to a main tubular extension 364, with an outer flexible tube 360 projecting from the lower fixed support frame tubular portion 310D of the fixed support frame 310. Furthermore, a middle flexible tube 360A is concentric to the outer flexible tube 360 and is connected to the lower middle tube portion 320C of the middle tube assembly 320 by means of a notch 360M, provided in the lower middle tube portion 320C, for receiving a corresponding notch boss 360N on the middle flexible tube 360A, as illustrated. Furthermore, an inner flexible tube 360B is concentric to the middle flexible tube 360A and the outer flexible tube 360 and is connected to the corresponding lower drive spur tubular portion 332 of the drive spur 330. The locator pin 332A is further illustrated extending through the respective drive spur hole 332B in the lower drive spur tubular portion 332, the middle tube rotational slot 332C in the lower middle tube portion 320C and the corresponding fixed support frame rotational slot 322D in the lower fixed support frame tubular portion 310D of the fixed support frame 310. Accordingly, initial manipulation of the inner flexible tube 360B and then the middle flexible tube 360A effects a corresponding incrementation of the drive spur 330 and rotation of the middle tube assembly 320 and the drive spur 330, to first increment the blades 350A and 350B against the needle 50 in the corresponding blade housings 320A and 320B, respectively, and then rotate the needle 50 around the tubular forked blade device 300 for suturing purposes. Incrementation of the inner flexible tube 360B throughout the range of motion allowed by the locator pin 332A facilitates limited incrementation of the drive spur 330 with respect to the middle tube assembly 320. This movement facilitates pivoting of the respective blades 350A and 350B into contact with the needle 50A to determine the direction of rotation of the needle 50, as hereinafter further described.

Referring again to FIGS. 154 and 155 of the drawings under circumstances where it is desired to manipulate the tubular forked blade device 300 into position for suturing in a wound or incision, positioning of the needle 50 to the desired location can be effected by tensioning one of the three cables 396. The cables 396 extend in radially spaced-apart relationship through corresponding cable holes 396A, 396B and 396C, respectively, provided in the outer tubular extension 364A, illustrated in FIG. 155, to a suitable operator (not illustrated). The opposite ends of the cables 396 are attached to the first flexible tube section 360C of a series of flexible tube sections 360C-360L, as illustrated in FIG. 154. Accordingly, tensioning of a selected one of the cables 396 facilitates bending of the outer flexible tube 360, including the outer tubular extension 364A, as well as the middle tubular extension 364B and the inner tubular extension 364C in concert, as illustrated in FIG. 154, typically to the position illustrated in phantom. In a preferred embodiment of the invention the flexible tube sections 360C-360L are constructed such that they typically operate as a "gooseneck" device, such that positioning of the tubular forked blade device 300 in a desired position for suturing by the needle 50 is maintained after adjustment of the respective cables 396, by friction between the respective adjacent flexible tube sections 360C-360L.

As illustrated in FIGS. 154, 155, 156, 157 and 158 of the drawings the tubular forked blade device 300 can typically be operated to drive the needle 50 in the suturing configuration illustrated in FIGS. 148 and 149 using the extension structure 390 (FIG. 157). The extension structure 390 includes the outer tubular extension 364A, middle tubular extension 364B and inner tubular extension 364C illustrated in FIG. 155, wherein the middle tubular extension 364B is fitted with a direction-changing lever 397, as further illustrated in FIGS. 156 and 157. Referring again to FIG. 156 the direction-changing lever 397 is connected to the middle tubular extension 364B and extends radially inward in the main tubular extension 364 to rest against a setting spring 397C, fixed to the inner tubular extension 364C at setting spring attachment points 397D. The setting spring 397C is biased against the extending end of the direction-changing lever 397, such that rotation of the direction-changing lever 397 in the clockwise direction as illustrated in FIG. 156 moves the direction-changing lever 397 from the position illustrated to an alternative adjacent position in the setting spring 397C. This movement also rotates the inner tubular extension 364C in the inner flexible tube 360B, the lower drive spur tubular portion 332 and the first leverage extension 330A and second leverage extension 330B on the drive spur 330. The movement further increments the blades 350A and 350B into the clockwise or counterclockwise rotational configuration for suturing operation of the needle 50, as hereinafter further described.

As further illustrated in FIGS. 156, 157 and 158 a motor 398F is fitted with a motor shaft 398E, to which is attached a gapped gear 398D, having gapped gear teeth 398I provided around a portion of the periphery thereof and fitted with a gear gap 398J in the gapped gear teeth 398I, as illustrated in FIG. 156. As further illustrated in FIG. 156 the gapped gear teeth 398I typically engage corresponding drive gear teeth 398H provided on the drive gear extension 398A of a drive gear 398 and extending around the periphery of the outer tubular extension 364A, for driving the drive gear 398 and the inner tubular extension 364C in the clockwise or counterclockwise direction, responsive to the direction of rotation of the motor shaft 398E and the gapped gear 398D. Referring again to FIG. 158 of the drawings, in a preferred embodiment of the invention an extension tube assembly interface mount 399 is provided on the main tubular extension 364 for mounting the motor 398F and the gapped gear 398D in driving relationship with respect to the drive gear extension 398A of the drive gear 398. Since the drive gear extension 398A projects from fixed attachment to the inner tubular extension 364C, (through the middle tube drive slot 398C in the middle tubular extension 364B and the outer tube drive slot 398B in the outer tubular extension 364A) and engages the gapped gear 398D, the drive gear 398 is able to move in both the counterclockwise and clockwise direction responsive to the driving of the gapped gear 398D. This action rotates the needle 50 around the tubular forked blade device 300. Furthermore, since the gapped gear 398D is fitted with a smooth gear gap 398J in which no gapped gear teeth 398I are provided, upon rotation of the gapped gear 398D to the point of disengagement of the corresponding gapped gear teeth 398I with the drive gear teeth 398H of the drive gear extension 398A, the drive gear 398 and the main tubular extension 364 return to the original position by operation of a tube return spring 398G, illustrated in FIG. 156.

As further illustrated in FIGS. 157 and 158 the main tubular extension 364 can be rotated along its longitudinal axis to properly position the needle 50 in or near a wound or incision (not illustrated) by moving the main tubular extension 364 linearly forwardly or rearwardly to disengage the drive gear extension 398A from the gapped gear 398. This allows rotation—of the main tubular extension 364 and re-engagement of the gears, as necessary.

In operation, referring again to FIGS. 140, 148 and 149 of the drawings, the needle 50 is caused to traverse the respective discontinuous fixed guide way 312 in the fixed segments 310A, 310B and 310C, the way segments 318A, 318B and 318C in the spring pressure pad assembly 314, as well as the corresponding discontinuous movable guide way 321 in the blade housing 320A and 320B of the tubular forked blade device 300. This traverse action is effected typically by operation of the main tubular extension 364, using the drive gear 398 and the gapped gear 398D of the extension structure 390, illustrated in FIGS. 153-158. It will be appreciated that other drive systems can also be utilized as desired, to increment the drive spur 330 and pivot the respective blades 350A and 350B in the blade housing 320A and 320B, respectively, and facilitate a selected directional rotation of the needle 50 in the suturing operation.

Accordingly, referring initially to FIG. 148 of the drawings wherein clockwise advancement of the needle 50 in the direction of the arrow is illustrated, each of the blades 350A and 350B, located in the corresponding blade housing 320A and 320B of the middle tube assembly 320, are pivoted in the counterclockwise direction to engage the softer needle 50, either individually or in concert, and effect the desired rotation of the needle 50, responsive to rotation of the middle tube assembly 320 and the drive spur 330 together. In order to effect clockwise rotation of the needle 50 the drive spur 330 is initially incremented in the clockwise direction as illustrated by the arrow superimposed on the extension mount 330AB of the drive spur 330. This rotational movement of the drive spur 330 (within the span of the middle tube rotational slot 332C with respect to the locator pin 332A) effects contact between the angled wall 334A and the lever 354C in the cavity 330C of the first leverage extension 330A and the corresponding angled wall 334C and the lever 354D in the cavity 330D of the second leveraging extension 330B of the upper middle tube portion 320AB, as further illustrated in FIG. 148. Accordingly, considering the location of the needle 50 in FIG. 148, the sharp edges of the slot 350C in the blade 350A contact the softer needle 50 while the blade 350A is in its pivoted configuration but the blade 350B does not contact the needle 50, as the blade 350B is in the needle gap 305A. Subsequent rotation of the middle tube assembly 320 and the drive spur 330 (in concert in the clockwise direction indicated by the arrow superimposed on the middle tube assembly 320) effects corresponding needle rotation in the clockwise direction, as indicated by the arrow superimposed on the needle 50, through the material 100 with the thread 50A trailing and following the needle 50 through the needle opening material 100, as illustrated. The two blade housings 320A and 320B in the middle tube assembly 320 move with the drive spur 330 in an initial incrementation throughout the length of the respective notches 311A and 311B, provided in the arcuate top section 313D of the fixed support frame 310. When the respective blade housings 320A and 320B reach the end(s) of the respective notches 311A and 311B at the fixed segments 310B and 310C, respectively, the direction of rotation of the middle tube assembly 320 is reversed, typically by the action of the tube return spring 398G (FIG. 156), to facilitate reverse movement of the blade housings 320A and 320B and the middle tube assembly 320, along with the drive spur 330, for re-incrementation. When the middle tube assembly 320 and the drive spur 330 are reversed in this manner, the needle 50 remains in its incremented position because of the slight oversize of the needle diameter with respect to the discontinuous fixed guide way 312 and the way segments 318A, 318B and 318C provided in the respective spring-mounted friction and retaining pads 314A, 314B and 314C, respectively. Furthermore, since the spring pressure pad assembly 314 exerts pressure through the spring-mounted friction and retaining pads 314A, 314B and 314C on the needle 50 as it moves through the corresponding discontinuous fixed guide way 312 and the way segments 318A, 318B and 318C, this pressure serves to hold the needle 50 in place, as the middle tube assembly 320 and the drive spur 330 re-increment for another incrementation of the needle 50 around the tubular forked blade device 300. Furthermore, due to the position of the respective blades 350A and 350B as they engage the needle 50, the needle 50 is allowed to slide in the respective slots 350C and 350D as the blade housings 320A and 320B re-increment in reverse rotation by operation of the tube return spring 398G.

Under circumstances where it is desired to drive the needle 50 in the counterclockwise direction around the tubular forked blade device 300 as illustrated in FIG. 149, the blades 350A and 350B are initially pivoted in the clockwise direction as indicated by the arrow superimposed on the levers 354C and 354D, respectively. This pivoting of the blades 350A and 350B is effected by incrementation of the drive spur 330 in the counterclockwise direction, to effect contact between the respective angled wall 334B and the lever 354C in the cavity 330C of the blade housing 320A and between the angled wall 334D and the lever 354D in the cavity 330D of the blade housing 320B. Locking of the blades 350A and 350B in this pivoted position effects securing of the sharp edges of the slot 350C of the blade 350A on the softer needle 50 and, although the blade 350B is not in contact with the needle 50 as the needle 50 is configured in FIG. 149, the blade 350A is capable of rotating the needle 50 in the counterclockwise direction indicated by the arrow illustrated on the needle 50, by itself. Accordingly, the needle 50 is driven through the material 100 with the thread 50A following as illustrated, as the middle tube assembly 320 and the drive spur 330 are driven in concert in the counterclockwise direction by a suitable operating device such as that illustrated in FIGS. 153-158, as heretofore described.

It will be appreciated from a consideration of FIGS. 139-158 of the drawings that the tubular forked blade device 300 of this invention can be positioned in a desired configuration, typically as illustrated in FIG. 155 utilizing the cables 396, to facilitate suturing of a material 100 in substantially any suturing configuration. Furthermore, although the tubular forked blade device 300 can be operated by means of the main modular extension 364, including the extension structure 390, the drive gear 398 and the gapped gear 398D illustrated in FIGS. 153-158 as noted above, other apparatus and techniques can be utilized to effect incrementation of the drive spur 330 to cause the blades 350A and 350B to contact the needle 50 in driving configuration and facilitate simultaneous driving of the middle tube assembly 320 and the drive spur 330 to effect the desired suturing, as illustrated in FIGS. 148 and 149. Furthermore, it will also be appreciated that although the arc of the needle 50 is fitted with the length of thread 50A at the center thereof, typically as illustrated in FIGS. 150-152 of the drawings, it is understood that the thread 50A may be attached to either end of the needle 50 under circumstances where the needle 50 is to be driven in either the clockwise or counterclockwise direction, depending upon the positioning of the needle 50 in the tubular forked blade device 300. Moreover, insertion of the needle 50 in the respective discontinuous guide way 312 of the fixed segments 310A, 310B and 310C, the way segments 318A, 318B and 318C of the spring pressure pad assembly and the discontinuous movable guide way 321 in the blade housing 320A and 320B, is typically effected by deforming the needle 50 slightly by bending the needle points 341A and 341B toward each other to reduce the diameter of the needle 50 and facilitate installing it beneath the respective fixed segment overhangs 312A, 312B and 312C, located in the corresponding fixed segments 310A, 310B and 310C and the movable segment overhangs 312D and 312E in the blade housings 320A and 320B. When so installed, the needle 50 receives a small amount of frictional resistance from the outside walls of the discontinuous fixed guide way 312 and the discontinuous movable guide way 321 in the movable blade housing 320A and 320B. This resistance is a contributing factor in prevention of the needle from rearward rotation after being incremented in the forward direction responsive to re-incrementation of the middle tube assembly 320 and the drive spur 330 in concert by operation of the tube return spring 398G (FIG. 156) as described above.

Still another embodiment of the cycling suturing and knot-tying device of this invention is illustrated in FIGS. 159-166. Referring initially to FIGS. 159 and 161-163 of the drawings the planetary wheel/gear device 400 is a reversible needle traversing device which receives a curved needle 50 fitted with a length of thread 50A at one end and sharpened at the opposite end. The arcuate needle 50 is designed to seat in a correspondingly-shaped fixed way 404 having a fixed way overhang 419 and a fixed way bevel 404A at both ends thereof for guiding the needle 50 in its circular path and including a fixed way outer wall or groove 418 (FIG. 162) that is curved to accept the curvature of the needle 50. The fixed way 404 is provided in a disc body 410 having a gap 405 (FIG. 160), as further illustrated in FIG. 162 and is typically provided with multiple rotatable, beveled toothed rotors 416, rotatably seated in corresponding conical holes 416A, respectively. In a preferred embodiment of the invention there are four toothed rotors 416 rotatably seated in a corresponding number of the conical holes 416A in spaced-apart relationship around the inner periphery of the fixed way 404. However, it will be appreciated by those skilled in the art that greater or fewer numbers of the toothed rotors 416 may be provided in corresponding conical holes 416A, in the disc body 410, depending upon the size of the planetary wheel/gear device 400 and other design considerations in the device. A conical central gear 415 is rotatably seated in the center of the disc body of the planetary wheel/gear device 400 (FIG. 159) and includes a central bevel gear 415C, mounted on a central gear shaft 415A, extending from the bottom of the conical central gear 415 for engaging a corresponding drive shaft bevel gear 420B, mounted on a flexible drive shaft 420 (FIG. 161). The flexible drive shaft 420 is journalled for rotation in a gear bearing block 420D, attached to the disc bottom 410A of the disc body 410 and engaging the central bevel gear 415C in driving relationship. The conical central gear 415 is also provided with a downwardly-flaring, textured or toothed beveled driving surface 415F that engages corresponding beveled and textured or toothed rotor surfaces 417 on the toothed rotors 416, as further illustrated in FIGS. 161 and 162 of the drawings. Accordingly, rotation of the flexible drive shaft 420 inside the flexible drive shaft housing 420A effects a corresponding rotation of the drive shaft bevel gear 420B and the central bevel gear 415C to rotate the conical central gear 415 and the respective toothed rotors 416 in a desired direction, as hereinafter further described.

Referring again to FIGS. 159 and 160 of the drawings the disc body 410 of the planetary wheel/gear device 400 is attached in articulating relationship to a suitable operator 1240 by means of an extension attachment plate 426 fixed at one end to the operator 1240 and connected to an adjacent swing plate 424 by means of a vertically-oriented swing plate pin 424A. This connection facilitates movement of the disc body 410 from side-to-side responsive to sequential manipulation of four articulation cables 1256A, 1256B, 1256C and 1256D (FIG. 160), as hereinafter further described. The articulation cables 1256A, 1256B, 1256C and 1256D typically extend from the interior of the operator 1240 through four cable openings 1257 to fixed attachment to the respective yoke arms 422B of the universal joint yoke 422, as further illustrated in FIGS. 159 and 160. A pair of spaced-apart, parallel yoke brackets 422C extend from two of the yoke arms 422B of the universal joint yoke 422 and are secured to the swing plate 424 by means of a yoke swivel pin 422A to facilitate up-and-down articulation of the disc body 410 with respect to the operator 1240. Accordingly, referring again to FIG. 160 of the drawings the disc body 410 of the planetary wheel/gear device 400 can be articulated in any desired direction by manipulation of the respective crescent angle articulation cables 1256A, 1256B, 1256C and 1256D and manually rotating the operator 1240 along its longitudinal axis, as hereinafter further described. As further illustrated in FIG. 160 a frame 420C extends from fixed attachment to the universal joint yoke 422 to the disc bottom 410A for securing the universal joint yoke 422 to the disc body 410.

Referring now to FIGS. 161-164 of the drawings and as described above, the conical central gear 415 has a central gear shaft 415A extending downwardly from the bottom thereof through a gear shaft opening 415G provided in the disc body bottom 410A (FIG. 162) and fitted with a central bevel gear 415C that meshes with the corresponding drive shaft bevel gear 420B secured to the flexible drive shaft 420, as illustrated in FIGS. 161 and 162. As further illustrated in FIGS. 161 and 162 a central gear tension spring 415D is interposed between the disc body bottom 410A and the flat top segment of the central bevel gear 415C for exerting a downward force on the conical central gear 415 and engaging its textured or toothed driving surface 415F with the corresponding respective sloping or beveled, textured or toothed rotor surfaces 417 of the toothed rotors 416. This facility insures that rotation of the conical central gear 415 responsive to operation of the flexible drive shaft 420 also causes the respective toothed rotors 416 to rotate and engage the needle 50 and drive the needle 50 around the fixed way 404, as illustrated in FIG. 163 and hereinafter further described. It will be appreciated that the conical central gear 415 can also be biased downwardly against the respective toothed rotors 416 by means of alternative spring configurations such as a spring washer, in non-exclusive particular, as illustrated in FIG. 166 of the drawings, to achieve the same result.

Referring now to FIG. 165 of the drawings in an alternative preferred embodiment of the planetary wheel/gear device 400, an alternative central gear 414 is illustrated, having a doubled beveled edge 414A that contacts multiple alternative concave rotors 416C, having concave surfaces 416CC, shaped to match the double beveled edge 414A of the alternative central gear 414. As in the case of the embodiment illustrated in FIGS. 159-164, a central gear tension spring 415D may be interposed between the central bevel gear 415C, mounted on the central gear shaft 415A, extending through the gear shaft opening 415G in the disc bottom 410A. The disc body bottom 410A of the crescent disc body 410 forces the alternative central gear 414 downwardly as indicated, against the respective alternative concave rollers 416C. Alternatively, as illustrated in FIG. 166, a spring washer 415E can be used to achieve the same result by substituting for the central gear tension spring 415D. Accordingly, as further illustrated in FIG. 165, driving rotation of the alternative central gear 414 in the manner described above with respect to the embodiments illustrated in FIGS. 159-164 also causes rotation of the respective alternate concave rotors 416C. Since the alternate concave rotors 416C also contact the needle 50, the needle 50 is also caused to traverse the fixed way 404 in the crescent disc body 410 in a direction determined by the direction of rotation of the central bevel gear 415C.

In a similar manner, referring again to FIG. 166 of the drawings the conical central gear 415 illustrated in FIGS. 159-166 of the drawings can be rotatably fitted in the crescent disc body 410. Alternate toothed rotors 416B are also rotatably seated in the crescent disc body 410, each of which alternate toothed rotors 416B have a concave, outwardly-flaring bottom surface 416BB and a beveled top surface 416BX, the former of which contact the needle 50 in driving relationship and the latter of which engage the conical central gear 415, to facilitate rotation of each of the alternate toothed rotors 416B. Engagement between the beveled driving surfaces 415F of the conical central gear 415, mounted on the central gear shaft 415A, extending through the gear shaft opening 415G in the disc bottom 410A, and the corresponding beveled top surfaces 416BX of the alternate toothed rotors 416B by downward pressure is insured by operation of an alternate spring washer 415E, interposed between the central bevel gear 415C and the disc body bottom 410A, as illustrated. Alternatively, as heretofore described, the alternate spring washer 415E can be replaced by a central gear tension spring 415D, as illustrated in FIG. 165, to perform the same function.

In operation and referring again to FIGS. 159-165 of the drawings the planetary wheel/gear device 400 is utilized by initially positioning needle 50 in the fixed way 404, and orienting the gap 405 (FIG. 160) such that the needle 50 can traverse the fixed way 404 in a 360-degree rotation, typically in the counterclockwise direction as indicated by the needle direction arrows 428 in FIG. 163, and suture a material 100 as illustrated in FIG. 164. Driving of the needle 50 in the counterclockwise direction as illustrated in FIGS. 163 and 164 is effected by connecting a suitable motor (not illustrated) to the flexible drive shaft 420 (FIG. 161) and rotating the flexible drive shaft 420 in the counterclockwise direction. This action causes the central bevel gear 415C to operate in the clockwise direction and drive the conical central gear 415 in the clockwise direction and the toothed rotors 416 in the counterclockwise direction as indicated by the respective gear arrows 428A and 428B, respectively (FIG. 163), to effect corresponding counterclockwise rotation of the needle 50, which is maintained in place by the fixed way overhang 419. Since the conical central gear 415 is spring-loaded downwardly to engage the respective toothed rotors 416, positive driving of the toothed rotors 416 is effected by engagement between the textured or toothed driving surface 415F of the conical central gear 415 and the corresponding respective beveled or sloping, textured or toothed rotor surfaces 417 of the corresponding toothed rotors 416, as illustrated in FIG. 162. It will be appreciated by those skilled in the art that the respective engaging driving surface 415F and corresponding rotor surfaces 417 can be textured with a friction enhancing material or can be splined or fitted with teeth, as desired, to facilitate the desired frictional or engaging contact therebetween and effect positive driving of the toothed rotors 416 by operation of the conical central gear 415. Since the respective conical holes 416A extend into the fixed way 404, the toothed rotors 416 extend into the inside surface of the fixed way 404 and the corresponding sloping rotor surfaces 417 also engage the needle 50 and cause the needle 50 (oriented in the fixed way 404 for a selected direction of rotation) to traverse the fixed way 404 in the direction of rotation of the toothed rotors 416.

It will be appreciated from a consideration of FIGS. 159 and 160 of the drawings that the crescent disc body 410 can be manipulated into substantially any desired configuration such that the gap 405 (FIG. 164) accommodates the material 100 to be sutured, as further illustrated in FIG. 164, by articulation with respect to the operator 1240 illustrated in FIG. 160. This articulation is effected by manipulation of the respective crescent angle articulation cables 1256A, 1256B, 1256C and 1256D, which project through the corresponding cable openings 1257 and typically connect to a lever mechanism and lever 1251 as described in an earlier embodiment of the invention illustrated in FIGS. 1, 58, 62 and 63. Accordingly, selectively applying tension to the crescent angle articulation cable 1256A using the lever 1251 causes the crescent disc body 410 to rotate to the left on the swing plate pin 424A, while tension in the oppositely-disposed crescent angle articulation cable 1256C causes the opposite movement of the crescent disc body 410. Similarly, tensioning of the crescent angle articulation cable 1256B by manipulating the lever 1251 causes the crescent disc body 410 to move upwardly as it pivots on the yoke swivel pin 422A and tension applied to the crescent angle articulation cable 1256D moves the crescent disc body 410 in the opposite direction or downwardly, to maintain the necessary close positioning between the material 100 to be sutured and the disc body 410 as further illustrated in FIG. 164.

Referring now to FIG. 165 of the drawings, as heretofore described, rotation of the alternative central gear 414 in desired direction determined by the orientation of the needle 50 in the fixed way 404) by driving of the central bevel gear 415C produces a corresponding rotation of the alternate concave rotors 416C in the opposite direction to drive the needle 50 in that opposite direction. In like manner, referring to FIG. 166 of the drawings rotation of the conical central gear 415 in a selected direction imparts rotation of the respective alternate toothed rotors 416B in the opposite direction to drive the needle 50 in that opposite direction in the manner and for the purpose described above.

It will be appreciated by those skilled in the art that the articulation feature of the planetary wheel/gear device 400 illustrated in FIGS. 159-160 is illustrative, it being understood that substantially any articulation operator, including the ball and joint articulation described heretofore with respect to other embodiments of this invention, can be employed to operate the planetary wheel/gear device 400. Other articulation techniques known to those skilled in the art may be employed in the planetary wheel/gear device 400 as desired, to facilitate articulation of the disc body 410 with respect to a material 100 for suturing the material 100 as illustrated in FIG. 164 of the drawings.

A still further embodiment of the cycling suturing and knot-tying device of this invention includes a flexible rotor device 500, illustrated in FIGS. 167-176 of the drawings. Referring initially to FIGS. 167 and 168 of the drawings the flexible rotor device 500 includes an arcuate fixed way 504 having conical entry guides 504A on each open end thereof facing the gap 505 between the open ends of the fixed way 504. The fixed way 504 is provided in a disc 510 having a disc wall 509 and a fixed way outer wall 512, provided in the fixed way 504 to receive the arcuate needle 50, as illustrated in FIGS. 170, 170A and 170B. A protective plate 510A is typically secured on the disc 510 by means of a pair of pins 510C that extend through the corresponding protective plate attachment holes 511A and are seated in the underlying wall holes 5101B of a depression forming wall 511, as illustrated in FIG. 170. As further illustrated in FIGS. 168 and 170 the disc bottom 508 of the disc 510 is provided with a bottom opening 508A. Furthermore, an inwardly-facing wall center section groove 515E is provided on the depression forming wall 511 and the wall center section groove 515E is bounded by a pair of parallel wall shoulders 515F that extend outwardly of the plane of the wall center section groove 515E, as further illustrated in FIGS. 168-170A and 174.

Referring again to FIGS. 167 and 168 of the drawings a flexible rotor 515 includes a flexible outer band 51 SA, with flexible spokes 5151B extending from the flexible outer band 515A inwardly in a spiral pattern to a rotor shaft opening 516A. As further illustrated in FIGS. 173 and 174 the flexible outer band 515A of the flexible rotor 515 includes a curved rotor contact area 515C, bounded by parallel, extending rotor shoulders 515D, which rotor shoulders 515D contact the corresponding wall shoulders 515F of the depression forming wall 511 as the flexible rotor 515 rotates inside the disc 510, as further illustrated in FIG. 174. Accordingly, in a preferred embodiment of this aspect of the invention the rotor shoulders 515D and the corresponding wall shoulders 515F are provided with a smooth surface treatment such as teflon or the like, which is self-lubricating and causes minimum resistance to rotation of the flexible rotor 515 in the disc 510. Furthermore, in another preferred embodiment of the invention the rotor contact area 515C is provided with an abrasive or textured material for securely, yet releasably, engaging the needle 50 and driving the needle 50 around the fixed way 504 responsive to rotation of the flexible rotor 515, as illustrated in FIGS. 173 and 174 of the drawings.

Referring now to FIGS. 170A, 170B, 171 and 172 of the drawings it will be appreciated by those skilled in the art that the flexible rotor 515 can be placed in the disc 510 for either counterclockwise rotation (FIG. 171) or clockwise (FIG. 172) rotation. As illustrated in FIG. 170B the flexible rotor 515 is positioned in the disc 510 for counterclockwise rotation in the direction of the arrow and the needle 50 is in position for counterclockwise rotation in the fixed way 504, with a length of thread 50A typically attached to the center point of the needle 50, as indicated. Accordingly, it will be appreciated from a consideration of FIG. 170B that counterclockwise rotation of the flexible rotor 515 inside the disc 510 by a driving mechanism hereinafter described causes the needle 50 to traverse the fixed way 504, as well as the gap 505 illustrated in FIG. 167, in the same direction. As in the other embodiments of the invention wherein the thread 50A is attached to an approximate center point of the arcuate needle 50, the thread 50A follows the needle rotation for suturing as hereinafter further described. Furthermore, referring now to FIGS. 170 and again to 170B, when the protective plate 510A is secured on the disc 510, typically by means of the pins 510C, sufficient space is provided between the periphery or perimeter of the protective plate 510A and the fixed way outer wall 512 to allow clearance for the thread 50A to traverse the entire curved length of the disc 510.

Driving of the flexible rotor device 500 may be accomplished by any one of several devices and techniques, typically as illustrated in FIG. 173, where the rotor shaft 516 is inserted through the rotor shaft opening 516A of the flexible rotor 515 and through the bottom opening 508A of the disc 510, as illustrated in FIGS. 173 and 174. A cap 516E is typically provided on the top end of the rotor shaft 516 to retain the rotor shaft 516 in place. In one drive embodiment a shaft bevel gear 516B may be attached to or shaped integrally with the opposite end of the rotor shaft 516 from the shaft cap 516E, for engagement with a corresponding drive bevel gear 516C, having a drive bevel gear shaft 516D attached to a source of power, indicated by the letter "P", as illustrated in FIG. 174. This source of power can typically be a drive motor of substantially the same design as the conventional micromotor 48B illustrated in FIG. 109A of the drawings or the like, according to the knowledge of those skilled in the art.

Another drive technique for operating the flexible rotor device 500 includes a direct drive such as that illustrated in FIG. 176, wherein a flexible pinion gear shaft 48H is typically rotatably provided in a flexible housing tube 49 and attached to a drive mechanism such as the conventional micromotor 48B illustrated in FIG. 109A of the drawings. The opposite end of the pinion gear shaft 48H is attached directly to the rotor shaft 516 as illustrated in FIG. 176, to drive the flexible rotor 515 in either the clockwise or counterclockwise direction, as desired, by selective positioning of the flexible rotor 515 in the disk 510 and corresponding operation of the motor.

Referring now to FIG. 175 of the drawings in yet another drive mechanism for operating the flexible rotor device 500, the rotor shaft 516 is connected to a spindle 519 in a rotary cable circuit 518 that connects the spindle 519 to a drive spindle 519A, rotatably mounted between a pair of mount blocks 525. An endless belt or cable 521 is wound on the spindle 519 and the drive spindle 519A and a ratchet 520 and a ratchet pawl 520A are provided on the bottom end of the spindle 519 to facilitate driving of the spindle 519 in one direction and preventing reverse rotation of the spindle 519. A spindle bevel gear 524 is provided on the bottom of the drive spindle 519A and the spindle bevel gear 524 engages a drive bevel gear 524A, connected to the shaft of a motor 523. Accordingly, operation of the motor 523 causes the drive bevel gear 524A and the spindle bevel gear 524 to rotate, thereby rotating the drive spindle 519A and, through operation of the endless cable 521, the spindle 519 also rotates, to effect a corresponding rotation of the flexible rotor 515 and the needle 50 in the disc 510 of the flexible rotor device 500. The motor 23 can be typically equipped with a rotation counter 526 for tracking the number of suturing cycles of the needle 50 and a cutoff switch 527 and a reversal switch 528 may also be provided in a rotary cable circuit 529. It will be understood by those skilled in the art that other operating mechanisms known to those skilled in the art may be used to effect rotation of the flexible rotor 515 and the needle 50 in the flexible rotor device 500, as desired. It will be further appreciated from a consideration of FIG. 175 that the rotary cable circuit 518 can be housed in a suitable operator such as the operator described in other embodiments of this invention, as desired.

Referring again to FIG. 176 of the drawings it will be further appreciated by those skilled in the art that the support or operator 531 can be designed in the manner detailed and described above with respect to other embodiments of this invention and may include a universal coupling, such as the universal joint yoke 422 illustrated in FIGS. 159 and 160 of the drawings and as described with respect to those drawings. Other universal joint features known to those skilled in the art may be utilized to facilitate articulation of the disc 510 with respect to the support or operator 531 illustrated in FIG. 176 of the drawings.

It will be appreciated by those skilled in the art that the flexible rotor device 500 illustrated in FIGS. 167-176 of the drawings and as described above facilitates a simple, yet efficient, technique for effecting rotation of the arcuate needle 50 around the fixed way 504 in either the counterclockwise or clockwise direction, depending upon the orientation of the flexible rotor 515 in the disc 510. Various drive techniques can be utilized as described and illustrated to effect this rotation and a suitable operator can be attached to the disc 510 in any convenient fashion, as heretofore described.

In another embodiment of the cycling suturing and knot-tying device of this invention a pawl and crank device is illustrated in FIGS. 177-188. The pawl and crank device is generally illustrated by reference numeral 600 and as illustrated in FIGS. 177-178, includes an arcuate disc 610, open along one segment to define a disc gap 605 (FIG. 177A) and including a fixed way or groove 604 that flares at each end thereof at a fixed way bevel 604A to accommodate a curved needle 50. The needle 50 is sharpened at both ends which define a needle gap 605A therebetween, which needle gap 605A is slightly more narrow than the disc cap 605 in the disc 610, as further illustrated in FIG. 177A. The disc 610 includes a removable disc cover 611 (FIG. 177A) and a disc bottom 610A which facilitate enclosure of a pawl 618 and a cooperating crank 622 and connecting crank pin 622A, illustrated in FIGS. 177B and 178. As further illustrated in FIGS. 177 and 177A, a length of thread 50A has one end connected to the approximate center point of the curved needle 50 and the needle thread 50A is allowed to traverse the disc gap 605 and the space between the perimeter of the disc cover 611 and the fixed way or groove 604 of the disc 610. This continuous opening in the disc 610 facilitates uninhibited movement of the thread 50A throughout the length of the disc 610 responsive to incrementation of the needle 50 by rotation of the pawl 618, as hereinafter further described.

The disc 610 is typically connected to an articulating joint 633 as further illustrated in FIG. 177 to facilitate articulation of the disc 610 with respect to an operating arm 634, also connected to the articulating joint 633. In a preferred embodiment of the invention the operating arm 634 is attached to a vertical pin bracket 633D, pivotally connected to, a horizontal motion bracket 633B by means of a vertical pin 633E. This connection facilitates horizontal rotation of the horizontal motion bracket 633B and the fixed joint bracket 633A to which it is attached, on the vertical pin 633E, which fixed joint bracket 633A is, in turn, typically connected to the disc 610 by means of shaft support plate 632A. Vertical movement of the disc 610 with respect to the operating arm 634 is effected by means of a horizontal pin 633C that extends through the fixed joint bracket 633A and the horizontal motion bracket 633B. A shaft support bearing 632B is welded or otherwise attached to the shaft support plate 632A and serves to journal one end of a flexible bevel gear shaft 631 for rotation in the shaft support bearing 632B. A drive bevel gear 631A is attached to the extending end of the flexible bevel gear shaft 631, which projects through a bevel gear shaft support 632, the shaft support plate 632A and through the shaft bearing 632B to facilitate rotation of the drive bevel gear 631A, as well as a pivot pin bevel gear 631B, meshed therewith, as further illustrated in FIG. 177. The drive pin bevel gear 631B is fixed to the drive pin 625 for rotating the crank 622 and the crank pin 622A and incrementing the pawl 618, as illustrated in FIG. 177B and hereinafter described. A brace 632C extends from the shaft support bearing 632B to fixed connection to the disc bottom 610A to better support—the disc 610 on the fixed joint bracket 633A. Accordingly, from consideration of FIG. 177 it will be appreciated that manipulation of the disc 610 and thus the disc gap 605, with respect to a material to be sutured (not illustrated) can be effected by movement of the operating arm 634 and implementing the articulating joint 633, since the flexible bevel gear shaft 631 will bend to accommodate the desired movement in the disc 610.

Referring again to FIGS. 177A-177D of the drawings it will be appreciated that the disc cover 611 is typically removably secured to the disc 610 by means of an attachment screw 620B as the disc cover 611 fits on the disc 610 along the inside periphery of the needle 50 and is stabilized in place on the arcuate cover support plate 611A that defines the disc gap 605 illustrated in FIG. 177A. A threaded attachment screw 620B (FIG. 177A) is typically threaded into the internally-threaded hole 620A in the pivot pin cap element 620C of the pivot pin 620, as illustrated in FIGS. 177A and 177C. The pivot pin 620 is fixed to the disc cover 611 by means of a pivot pin shaft 620D that supports the pivot pin cap 620C, as further illustrated in FIGS. 177C and 177D.

Referring again to FIGS. 177C, 177D, and 178 a crank pin opening 622B accommodates the drive pin 625, illustrated in FIGS. 177B and 177C, to facilitate rotation of the crank 622 and the crank pin 622A responsive to operation of the intermeshed drive bevel gear 631A and pivot pin bevel gear 6311B, as hereinafter further described. Accordingly, as further illustrated in FIGS. 177B, 177C, 177D and 178, the pawl 618 is installed in the disc 610 such that the pivot pin shaft 620D, projecting upwardly from fixed attachment to the disc bottom 610A as illustrated in FIGS. 177C and 177D, extends through an elongated pivot pin slot 619 provided in the pawl leg 618B of the pawl 618. The pivot pin cap 620C is positioned such that the attachment screw 620B can be used to secure the disc cover 611 removably on the disc 610 by threadable seating in the threaded hole 620A. Furthermore, as illustrated in FIG. 178 the crank pin 622A, fixed to the crank 622, projects through the chevron cam slot 630 provided in the pawl 618, to facilitate traversal of the crank pin 622A along the periphery of the chevron cam slot 630 and driving of the pawl 618 inside the disc 610 responsive to rotation of the crank 622, as hereinafter described. As further illustrated in FIG. 177B the crank 622 has sufficient 360-degree rotational space to operate, by provision of the crank operating opening 618C, provided in the opposite surface of the pawl 618 from the chevron cam slot 63Q. The curved upper surface of the pawl 618 is provided with pawl teeth 618A, which parallel and match the curvature of the fixed way or groove 604, as further illustrated in FIG. 178. Furthermore, the chevron cam slot 630 provided in the pawl 618 is characterized by a counterclockwise needle side slot wall 630A, a clockwise needle side slot wall 630B, a counterclockwise pivot side slot wall 630C and a clockwise pivot side slot wall 630D. Accordingly, when the crank pin 622A is caused to traverse the chevron cam slot 630 by alternate counterclockwise and clockwise rotation of the crank 622, the crank pin 622A exerts force on each of the counterclockwise needle side slot wall 630A, the clockwise needle side slot wall 630B, the counterclockwise pivot side slot wall 630C and the clockwise pivot side slot wall 630D in the sequences hereinafter described. These actions facilitate sequential clockwise and counterclockwise incrementation of the pawl 618 inside the disc 610 as the pawl teeth 618A sequentially engage and disengage the softer needle 50 to drive the needle 50 in either the clockwise or counterclockwise direction, depending upon the direction of rotation of the crank 622, as further hereinafter described.

In operation and referring now to FIGS. 177A and 178-183 of the drawings and initially to FIGS. 177A and 178, the needle 50 is first positioned in the curved fixed way or groove 604 as illustrated in FIG. 177A and the disc cover 611 is fitted into place and secured by means of the attachment screw 620B. The clearance between the perimeter of the disc cover 611 and the overhang 616 which extends the disc outer wall 614 of the disc 610, allows the needle 50 free rotational movement within the curved fixed way or groove 604, but will not allow the needle 50 to exit the fixed way or groove 604 from the top. As further illustrated in FIG. 178 the pawl 618 is fitted inside the disc 610 such that the pawl teeth 618A are caused to sequentially engage the needle 50 and disengage the needle 50, depending upon pressure exerted by the rotating crank pin 622A, since the elongated pivot pin slot 619 that receives the pivot pin shaft 620D facilitates movement of the pawl 618 to and from the needle 50 resulting from that pressure. Accordingly, as further illustrated in FIG. 178 the crank pin 622A is shown at the end of a power stroke in which the pawl 618 has been in contact with the needle 50 and rotated the needle 50 in the counterclockwise direction. The crank pin 622A is now caused to rotate in the counterclockwise direction as indicated by the arrow superimposed on the crank pin 622A in the chevron cam slot 630, by operation of a power source (not illustrated) that rotates the flexible bevel gear shaft 631 and thus, the drive bevel gear 631A, the drive pin bevel gear 631B and the drive pin 625 to effect corresponding rotation of the crank 622 and the crank pin 622A. This movement of the crank pin 622A in the direction of the arrow illustrated in FIG. 178 causes the crank pin 622A to contact the counterclockwise pivot side slot wall 630C, producing inward movement of the pawl 618 away from contact with the needle 50, as illustrated by the arrow located at the base of the chevron cam slot 630. This action of the crank 622 and the crank pin 622A also effects a clockwise movement of the pawl 618 as further illustrated by the curved arrow below the pawl teeth 618.

As illustrated in FIG. 179 continued rotation of the crank 622 and the crank pin 622A in the counterclockwise direction as indicated by the arrow on the crank pin 622A exerts a continuing force on the counterclockwise pivot side slot wall 630C near the bottom of the chevron cam slot 630, to effect additional clockwise rotation of the pawl 618 in the direction of the curved arrow located beneath the pawl teeth 618A. At this point the crank pin 622A is nearing the distal end of its circular orbit and this movement of the crank pin 622A moves the pawl teeth 618A even further away from the needle 50 in the direction of the arrow at the base of the chevron cam slot 630.

Referring now to FIG. 180 the crank pin 622A is still in contact with the counterclockwise pivot side slot wall 630C as the crank 622 and the crank pin 622A continue to rotate in the counterclockwise direction as illustrated by the arrow superimposed on the crank pin 622A in the chevron cam slot 630. The crank pin 622A is now on the proximal side of its circular orbit and is moving distally as it continues to rotate in the counterclockwise direction to continue movement of the pawl 618 in the clockwise direction, as illustrated by the curved arrow beneath the pawl teeth 618A, while still applying an inward or downward force as illustrated by the arrow located beneath the base of the chevron cam slot 30. In this configuration of the crank pin 622A and the pawl 618, the pawl teeth 618A remain out of contact with the needle 50 due to the downward movement of the pawl 618 facilitated by the pivot pin slot 619.

As illustrated in FIG. 181 of the drawings the crank 622 and the crank pin 622A continue in a counterclockwise rotation as indicated by the arrow superimposed on the crank pin 622A and the crank pin 622A has now contacted the counterclockwise needle side slot wall 630A of the chevron cam slot 630, which action drives the pawl 618 upwardly in the direction of the arrow beneath the base of the chevron cam slot 630, to force the pawl teeth 618A in contact with the needle 50 (not illustrated). Continued pressure exerted on the counterclockwise needle side slot wall 630A of the chevron cam slot 630 by the crank pin 622A also causes the pawl 618 and the needle 50 to move in the counterclockwise direction as indicated by the arrow beneath the pawl teeth 618A and since the pawl teeth 618A are now firmly seated on the needle 50, the needle 50 is also caused to move around the fixed way or groove 604 in the counterclockwise direction.

Referring now to FIG. 182 of the drawings continued rotation of the crank 622 and the crank pin 622A in the counterclockwise direction as indicated, causes additional pressure to be exerted on the counterclockwise needle side slot wall 630A of the chevron cam slot 630 to continue the upward force exerted by the pawl teeth 618A against the needle 50 and counterclockwise rotation of both the pawl 618 and the needle 50 as indicated by the arrows, respectively.

As illustrated in FIG. 183 of the drawings the crank 622 and crank pin 622A have continued to move in the counterclockwise direction and extend the crank pin 622A to the distal end of its circular orbit, thus momentarily bringing the pawl 618 to a stop, as illustrated by the position of the crank pin 622A in the base of the chevron cam slot 630.

Referring to FIGS. 177 and 184, under circumstances where the crank 622 and the crank pin 622A are caused to rotate in the clockwise direction by reverse operation of the respective drive pin 625, the flexible bevel gear shaft 631, the drive bevel gear 631A and the pivot pin bevel gear 631B illustrated in FIG. 177, pressure is initially exerted against the clockwise needle side slot wall 630B of the chevron cam slot 630 by the crank pin 622A in the direction of the arrow superimposed thereon, as illustrated in FIG. 184. This action forces the pawl 618 upwardly as indicated by the arrow at the base of the chevron cam slot 630, into contact with the needle 50 such that the pawl teeth 618 engage the needle 50 in driving relationship. The force supplied by the crank pin 622A against the clockwise needle side slot wall 630B in this mode of operation also forces the pawl 618 and the needle 50 to rotate in the clockwise direction, as indicated by the arrow located beneath the pawl teeth 618A.

As illustrated in FIG. 185 as the crank 622 and crank pin 622A continue to rotate in the clockwise direction as indicated by the arrow superimposed on the crank pin 622A, as continued pressure is exerted against the clockwise needle side slot wall 630B and jointly continue to force the pawl teeth 618A against the needle 50 and cause the pawl 618 and the needle 50 to rotate in the clockwise direction, as indicated by the indicated arrows. Accordingly, the pawl 618 and the needle 50 rotate in concert in the clockwise direction around the inner periphery of the disc 610, with the needle following the fixed way or groove 604.

Referring to FIG. 186, as the crank 622 and the crank pin 622A begin the last quarter of travel in the distal direction in clockwise rotation, the crank pin 622A contacts the clockwise pivot side slot wall 630D of the chevron cam slot 630 and applies pressure to begin moving the pawl 618 inwardly in the direction of the arrow beneath the base of the chevron cam slot 630 and disengage the pawl teeth 618A from the needle 50, causing the pawl 618 to move in the counterclockwise direction, as indicated by the arrow beneath the pawl teeth 618A.

FIG. 187 illustrates continued movement of the crank 622 and the crank pin 622A in the clockwise direction as indicated by the arrow superimposed thereon, to exert pressure on the clockwise pivot side slot wall 630D of the chevron cam slot 630 and move the pawl 618 inwardly and in the counterclockwise direction without contacting the needle 50, as indicated.

As illustrated in FIG. 188 the crank 622 and crank pin 622A continue to rotate in the clockwise direction in the chevron cam slot 630 as indicated by the arrow, to approach contact with the clockwise needle side slot wall 630B, where it will begin another clockwise incrementation of the pawl 618 and drive the needle 50 in the fixed way or groove 604.

It will be appreciated from a consideration of the drawings that selected counterclockwise and clockwise rotation of the crank 622 and the crank pin 622A responsive to corresponding operation of the engaged drive bevel gear 631A and pivot pin bevel gear 631B, effects incrementing of the pawl 618 and driving of the needle 50 in the opposite clockwise or counterclockwise direction in the fixed way or groove 604 of the disc 610. Accordingly, continued rotation of the crank 622 in the same direction releases the pawl 618 from the needle 50 and facilitates reincrementing of the pawl 618 in the opposite direction for additional contact with, and driving of the needle 50 in the first direction. It will be further appreciated from a consideration of FIGS. 178-188 of the drawings that the needle 50 is thusly caused to completely traverse the fixed way or groove 604 of the disc 610 in either direction and to periodically traverse the disc gap 605 to suture tissue extending in the disc gap 605 and the needle gap 605A, as illustrated in FIG. 177A. Furthermore, since the thread 50A has a clear path to rotate throughout the curved length of the disc 610 in the opening defined by the disc cover 611 and the overhang 616 of the disc outer wall 614, it will be carried through the material sutured in the disc gap 605 as the needle 50 penetrates that material in the suturing operation.

The pawl and crank device 600 is characterized by convenience, ease of operation and easy cleaning, in that the cover 611 can be quickly and easily removed from the disc 610 by removing the attachment screw 620B from the underlying pivot pin cap 620C to facilitate access to the pawl 618 and the chevron cam slot 630, as well as the other operating and fixed elements of the device. Furthermore, it will be appreciated by those skilled in the art that the pawl and crank device 600 can be designed to facilitate removal of operating elements such as the pivot pin 620 and thus the pawl 618, from the interior of the disc 610 and disassembly of the drive train, including the drive bevel gear 631A and the pivot pin bevel gear 631B, as well as the other components of the drive system, as desired. Moreover, it will be further appreciated by those skilled in the art that the articulating joint 633 illustrated in FIG. 177 is exemplary, it being possible to provide other articulating designs, such as the operator 1240, illustrated in FIG. 160, which are equally effective in manipulating and articulating the disc 610 with respect to the operating arm 634 of the device.

It will be further appreciated by those skilled in the art that although a single pawl is shown in this embodiment of the invention, a system of pawls can be utilized to enhance certain characteristics of the device. For example, a shorter throw at each of the multiple pawl movements and narrower pawl profiles, together with shorter crank pin offset parameters can make possible multiple pawl arrangements which expand the pawl contact area with the needle. Additional pawls can also serve to facilitate placement of the needle-engaging teeth closer to the ends of the fixed way or groove. Each additional pawl can typically be driven by a separate crank shaft and pin and independent shafts or a central planetary gear arrangement can be utilized to power such mechanical configurations. Alternatively, piezo electrical elements grouped in an appropriate manner, can also be utilized under application of electric current to advance the pawl or pawls by expanding in length with a force sufficient to act upon the pawl or pawls, thus producing a mechanically multiplied force to the outer curvature of the pawl teeth against the needle. It will also be appreciated by those skilled in the art that power transmission to the bevel gears and thus to the pawl or pawls, can be provided by any one of several mechanisms known to those skilled in the art.

It is understood that various materials of construction known to those skilled in the art can be used in the respective components and parts of the above embodiments. Among these are metal and plastic (e.g. various blades, cases, housings, enclosures), silicon-coated parts (e.g., blades and needle tips, cases, housings, enclosures) and the like.

It is also understood that the device of this invention, in any or all of the above described embodiments, can be used in sewing applications other than suturing, including sewing of cloth, canvas, plastic materials, sheet metal and the like, in non-exclusive particular.

Turning to FIGS. 189 through 198 of the drawings an alternate embodiment of the cycling suturing and knot-tying device of this invention is there illustrated and generally identified by the numeral 1400. This embodiment is similar in some respects to the embodiments described in U.S. Ser. No. 10/263,902, but includes several improvements the nature of which will be discussed in the paragraphs which will follow. U.S. Ser. No. 10/263,902 was published on May 1, 2003 as US 2003/0083674 A1. Because of its pertinence Publication 2003/0083674 A1 is hereby incorporated by reference as though fully set forth herein. Referring particularly to FIG. 189 of the drawings, device 1400 can be seen to comprise a gripping portion 1402 comprising a generally pistol shaped handgrip 1404 and a trigger mechanism 1406 connected to the handgrip in the manner shown in FIGS. 190 and 191. Trigger mechanism 1406 comprises a part of the novel operating means of the invention, the character of which will presently be described.

Connected to gripping portion 1402 is an elongated, hollow barrel portion 1408, and connected to the hollow barrel portion by connector means is an articulating, or multipositionable, suturing head portion generally designated by the numeral 1410. Multipositionable head portion 1410, which comprises one of the improved features of this latest form of the invention, is of a novel design that includes a generally semicircular-shaped body 1412 having a generally semicircular-shaped shuttle track 1413 (FIGS. 194 and 195). The connector means, here provided as a knurled, generally cylindrically shaped connector 1409 functions to interconnect the head portion with the barrel portion in the manner shown in FIGS. 189 and 195.

Operably associated with body 1412 is a generally semi-circular-shaped shuttle member 1414 that is slidably movable by the operating means of the invention along the shuttle track between a first position shown in FIG. 194 and a second position shown in FIG. 195. As best seen in FIGS. 196 and 197, shuttle member 1414, which has a first end 1414a and a second end 1414b, is provided with a generally semicircular shaped needle groove, or guide 1416 that extends from the first end of the shuttle member to the second end thereof. Uniquely, shuttle member 1414 is also provided with a plurality of strategically shaped, circumferentially-spaced cavities 1420 the purpose of which will be described in the paragraphs which follow.

Carried within a needle guide 1416 that is formed in shuttle member 1414 is a highly novel, generally semicircular-shaped suturing needle 1422. Needle 1422, which can be constructed from metal or plastic, is incrementally movable along the needle guide from a first position shown in FIG. 194 to a second position shown in FIG. 195 and then to a third and subsequent further advanced positions. As best seen in FIG. 198, needle 1422, which has first and second ends 1422a and 1422b, is of a unique construction. Unlike most prior art suture needles, needle 1422, rather than being circular in cross-section, is generally rectangular in cross-section and has upper and lower surfaces disposed within the generally parallel planes (See FIG. 198). The first end of the suture needle is tapered or chamfered at a precisely selected angle, while the second end thereof is provided with a pair of spaced-apart apertures 1424 and 1426. These apertures, which receive the suture "S" extend generally perpendicular to the plane of the upper and lower surfaces of the needle. To compensate for the tendency of the needle to open up as it penetrates the tissue to be sutured, the point "S-1" of the needle is off-center of the axis "A" of the arc of the needle (see FIG. 198).

As best seen in FIGS. 195 and 196, the first end 1414a of shuttle member 1414 is provided with a generally tapered or conically shaped opening 1428 for receiving the tapered end of the needle as the needle is incrementally advanced. The opening 1428 is strategically configured so as to permit the tapered or chamfered end of the needle to deflect somewhat as it is guided into the groove or guide 1416 formed in the shuttle member.

Considering now in greater detail the previously mentioned operating means of this latest form of the invention, as will be understood from the discussion that follows, this novel operating means functions to controllably advance and retract the shuttle member 1414 along shuttle track 1413 between its first and second positions. This sequential movement of the shuttle member, in turn, uniquely causes the suturing needle 1422 to incrementally move smoothly along the needle guide from its first position to its second position and then onto further advanced positions within the shuttle head. In addition to the previously mentioned trigger mechanism 1406, this important operating means also comprises first and second operating cables 1430 end 1432 which are strategically entrained through hollow barrel portion 1408 in the manner illustrated in FIGS. 190A, 190C, 191A and 192A. As seen in the drawings, operating cable 1430 has a first end 1430a connected proximate the first end 1414a of shuttle 1414 (see FIG. 202) and a second end 1430b connected to a coupling mechanism 1406a or trigger mechanism 1406 (see FIG. 190A). Similarly, second operating cable 1432 has a first end 1432a connected proximate second end 1414b of shuttle 1414 and a second end 1432b connected to a return mechanism 1407 which includes a biasing means or return spring 1407a that is connected to the gripping portion 1402 (See FIG. 191A). The function of this biasing means will presently be discussed in greater detail.

With the construction described in the preceding paragraph, sequential actuation and release of the trigger 1406b of the trigger mechanism, will cause the shuttle to sequentially move along the shuttle track between the first and second positions in the manner illustrated in FIGS. 194 and 195. More particularly, when the trigger 1406b of the trigger mechanism is actuated, the first operating cable 1430 will move the shuttle 1414 in a clockwise direction from the first position shown in FIG. 194 to the second position shown in FIG. 195. As this occurs, the biasing means, or return spring 1407a of the return mechanism 1407, which is connected to the reciprocally movable coupling mechanism 1406b, is extended as illustrated in FIG. 192A. In its extended position the extension spring acts upon the second operating cable 1432 tending to return it to its starting position and, in turn, tending to move the shuttle 1414 in a counterclockwise direction toward its starting position. To return the trigger 1406b to its starting position following trigger actuation a compressible coil spring 1406c is provided. Spring 1406c, which comprises a part of the trigger mechanism 1406, is compressed in the manner shown in FIG. 192A when the trigger is actuated and functions to return the trigger to its default, or starting position shown in FIG. 191A, when pressure on the trigger is released.

In a manner now to be described, movement of the shuttle 1414 along the shuttle track 1413 causes concomitant, controlled movement of the suture needle 1422 along needle guide 1416. As previously mentioned, shuttle member 1414 is provided with a plurality of strategically shaped, circumferentially spaced cavities 1420. Disposed within each of these cavities 1420 is a uniquely configured needle engaging member 1440 (see FIG. 199) that includes first and second, rounded ends 1440a and 1440b and a needle receiving opening 1440c for closely receiving the needle 1422. Members 1440 are adapted for both transverse and pivotal movement within the cavity in response to movement of the 1414 shuttle between its first and second positions. This novel movement of the members 1440 within the cavities 1420 is illustrated in FIGS. 200 and 201 of the drawings. As shown in FIG. 200, also partially disposed within cavities 1420 are biasing means, shown here as compressible and expandable elastomeric springs 1442, which act upon members 1440. Springs 1442, which are of a generally flat configuration are carried within smaller cavities segments 1444 which communicate with larger cavities 1420 in the manner illustrated in FIGS. 197, 200 and 201.

Turning particularly to FIG. 198, it is to be noted that suturing needle 1422 is provided with a plurality of circumferentially spaced-apart notches 1445, which are uniquely constructed and arranged to be engaged by the needle engaging members as the needle engaging members move within cavities 1420. More particularly, as the shuttle member 1414 moves from the first position shown in FIG. 194 toward the second position shown in FIG. 195, the needle engaging members will engage the needle in the manner illustrated in FIG. 200, causing the needle 1422 to move along with the shuttle member and penetrate the tissue disposed within the head opening 1447. Unlike the prior art circular cross section suturing needles, which provide only a point contact with a needle driving member, the novel rectangular cross section needle of the present invention presents a substantially flat, grooved or notched wall that provides a superior line contact with the driving member that advances the needle.

As indicated in FIG. 200, spring 1442 continuously urges the drive members into binding engagement with the needle. However, upon release of the trigger 1406a, which permits the shuttle to return to its starting position due to the urging of the extension spring 1436, the needle engaging members 1440 will compress the elastomeric springs 1442 and will pivot and move transversely within cavities 1420 in the direction of the arrows to engage the needle in the manner shown in FIG. 201. With the needle engaging members in this position, the members will slide relative to the needle permitting the needle to remain in place when the trigger 1406a is released and allowing the shuttle member 1414 to move counterclockwise to the position illustrated in FIG. 194. When the trigger 1406b is once again actuated, the shuttle member 1414 will again move in a clockwise direction as illustrated in FIG. 195 causing the needle engaging members 1440 to once again grip the suturing needle 1422 due to the urging of the elastomeric springs 1442. This gripping of the needle will again cause it to advance in a clockwise direction along the needle guide 1416 toward its third advanced position (not shown). As the process is repeated, the needle will continue to advance in a clockwise direction along the needle guide 1416 so that the suturing can be controllably and efficiently completed.

As illustrated in FIGS. 194 195 and 196, body 1412 of the suturing head is also provided with a pair of strategically shaped, circumferentially spaced cavities 142 within which needle engaging members 1440 are housed. These members cooperate with and function in an identical manner as the needle engaging members housed within the cavities formed in the shuttle 1414 to control the movement of the suturing needle within guide way 1416 as the shuttle moves along the shuttle track 1413. More particularly, as the shuttle member 1414 moves from the first position shown in FIG. 194 toward the second position shown in FIG. 195, these needle engaging members will engage the needle in the manner illustrated in FIG. 200, causing the needle 1422 to move with the shuttle member. However, upon release of the trigger 1406a, which permits the shuttle to return to its starting position due to the urging of the extension spring 1436, these needle engaging drive members will move into the needle slip configuration shown in FIG. 201 permitting the needle to remain in its advanced position.

In using the suturing device of the present invention, with the suturing head components in the position illustrated in FIG. 194 and with the tissue to be sutured disposed within open 1447, the suturing process is begun by actuating the trigger 1406b of the trigger mechanism. When the trigger is actuated, the first operating cable 1430, which is connected proximate the bottom of the first end of the shuttle 1414, (see FIG. 202) will move the shuttle 1414 in a clockwise direction from the first position shown in FIG. 194 to the second position shown in FIG. 195. As the shuttle moves in this clockwise direction, cable 1432 will be foreshortened the direction of the arrow 1451 of FIG. 202 causing the return spring 1407a to be extended in the manner shown in FIG. 192A.

During the clockwise movement of the shuttle, elastomeric springs 1442 will urge spring engaging members 1440 into binding engagement with the needle 1422 in the manner illustrated in FIG. 200 causing the needle, along with the suture "S", to advance to the needle penetrating position shown in FIG. 195. When the needle and the shuttle reaches this advanced position, the shuttle 1414 will be urged to move in a counterclockwise direction toward its starting position due to the urging of return spring 1407a. During this counterclockwise movement of the shuttle members, the needle engaging members 1440 will move within cavities 1420 into the needle slip position illustrated in FIG. 201. This novel pivotal and transverse movement of the needle engaging members within their respective cavities will compress elastomeric springs 1442 and will permit the needle 1422 to slip relative to the shuttle members and remain in the advanced position shown in FIG. 195.

After the shuttle members return to their starting positions, actuation of the trigger member 1406a will once again cause clockwise movement of the shuttles along the shuttle track 1413. As before, during this clockwise movement of the shuttle, elastomeric springs 1442 will urge spring engaging members 1440 into binding engagement with the needle 1422 in the manner illustrated in FIG. 200 causing the needle and the suture "S" to advance to a third, further advanced position (not shown). It is to be appreciated that by the repeated actuation and release of the trigger member 1406a, the suturing needle can be smoothly in controllably incrementally further advanced along the needle guide 1416 to efficiently complete the suturing operation.

While the preferred embodiments of the invention have been described above, it will be recognized and understood that various modifications may be made in the invention and the appended claims are intended to cover all such modifications which may fall within the spirit and scope of the invention.

We claim:

1. A suturing device comprising:
   (a) a gripping portion;
   (b) a head portion operably associated with said gripping portion, said head portion comprising:
      (i) a body having a shuttle track;
      (ii) a shuttle operably associated with said body for movement along said shuttle track between a first position and a second position, said shuttle being provided with a needle guide and at least one cavity;
      (iii) a needle carried by said shuttle for movement along said needle guide between a first position and a second position; and
      (iv) a needle engaging member carried in said at least one cavity for engagement with said needle to control movement of said needle along said needle guide; and
   (c) operating means operably associated with said gripping portion for moving said shuttle between said first and second positions, said operating means comprising:
      (i) an advancing mechanism operably associated with said shuttle for moving said shuttle to said second position;
      (ii) a first operating cable having a first end connected to said shuttle and a second end connected to said advancing mechanism; and
      (iii) a return mechanism connected to said shuttle for automatically moving said shuttle to said first position.

2. The suturing device as defined in claim 1, further including a barrel portion connected to and extending from said gripping portion.

3. The suturing device as defined in claim 2 in which said advancing mechanism includes a trigger mechanism carried by said gripping portion.

4. The suturing device as defined in claim 3 in which said shuttle is provided with a plurality of circumferentially spaced cavities and further includes a needle engaging member carried within each of said circumferentially spaced-apart cavities for transverse and pivotal movement within said cavities in response to movement of said shuttle between said first and second positions.

5. The suturing device as defined in claim 4 in which said needle is semicircular in shape and is provided with a plurality of circumferentially spaced-apart notches that are so constructed and arranged as to be engaged by said needle engaging member as said needle engaging member moves within said cavities.

6. The suturing device as defined in claim 5 in which said needle is generally rectangular in cross-section and has first and second ends, said first end being tapered and said second end being apertured.

7. The suturing device as defined in claim 6 in which said shuttle has first and second ends, said first end being provided with a tapered opening for receiving said first tapered end of said needle.

8. The suturing device as defined in claim 6 further including connector means for connecting said head portion to said barrel portion to permit movement of said head portion relative to said barrel portion into a multiplicity of positions.

9. A suturing device comprising:
   (a) a gripping portion comprising a handgrip and a trigger mechanism connected to said handgrip;

(b) an elongated, hollow barrel portion connected to said gripping portion;

(c) a multipostionable head portion connected to said barrel portion, said head portion comprising:

(i) a generally semicircular-shaped body having a shuttle track;

(ii) a generally semicircular-shaped shuttle operably associated with said generally semicircular-shaped body for movement along said shuttle track from a first position to a second position and from said second position to a third advanced position, said shuttle having first and second ends and being provided with a generally semicircular-shaped needle guide and a plurality of circumferentially spaced cavities;

(iii) a generally semicircular-shaped needle carried by said shuttle for movement along said needle guide between a first position and a second position, said needle having first and second ends said first end being tapered; and (iv) a needle engaging member carried in each of said plurality of circumferentially spaced cavities for engagement with said needle to control movement of said needle along said needle guide; and (d) operating means carried by said gripping portion and said barrel portion for controllably moving said shuttle, said operating means comprising: first and second operating cables carried by said hollow barrel portion, said first operating cable having a first end connected to said first end of said shuttle and a second end connected to said trigger mechanism; a return mechanism connected to said shuttle for automatically moving said shuttle to said first position; and said second operating cable having a first end connected to said second end of said shuttle and a second end connected to said return mechanism.

10. The suturing device as defined in claim 9 in which said needle engaging member is movable both transversely and pivotally within said cavities.

11. The suturing device as defined in claim 9 further including biasing means carried within each of said circumferentially spaced-apart cavities and being operably associated with said needle engaging member for yieldably resisting movement of said needle engaging drive members within said circumferentially spaced-apart cavities.

12. The suturing device as defined in claim 11 in which said needle is provided with a multiplicity of circumferentially spaced-apart notches that are so constructed and arranged as to be engaged by said needle engaging member as said needle engaging member moves within said cavities.

13. The suturing device as defined in claim 12 in which said needle is generally rectangular in cross-section.

14. The suturing device as defined in claim 13 in which said first end of said shuttle is provided with a generally conically shaped opening for receiving said chamfered end of said needle.

15. The suturing device as defined in claim 13 in which said needle has a generally planar surface lying within a plane and in which said second end of said needle is provided with the aperture extending generally perpendicular to said plane to receive a suture.

16. A suturing device comprising:

(a) a gripping portion comprising a handgrip and a trigger mechanism connected to said handgrip;

(b) an elongated, hollow barrel portion connected to said gripping portion;

(c) an articulating head portion connected to said barrel portion, said articulating head portion having:

(i) a generally semicircular-shaped body having a shuttle track;

(ii) a generally semicircular-shaped shuttle operably associated with said generally semicircular-shaped body for movement along said shuttle track from a first position to a second position and from said second position to a third advanced position, said shuttle having first and second ends and being provided with a generally semicircular-shaped needle guide and a plurality of circumferentially spaced cavities;

(iii) a generally semicircular-shaped needle carried by said shuttle for movement along said needle guide between a first position and a second position, said needle having first and second ends said first end being chamfered;

(iv) a needle engaging member carried in each of said plurality of circumferentially spaced cavities for engagement with said needle to control movement of said needle along said needle guide, each said needle engaging member being movable both transversely and pivotally within said cavity; and (v) biasing means carried within each of said circumferentially spaced-apart cavities and being operably associated with said needle engaging member for yieldably resisting movement of said needle engaging members within said circumferentially spaced-apart cavities; and (d) operating means carried by said gripping portion and said barrel portion for controllably moving said shuttle, said operating means comprising: first and second operating cables entrained through said hollow barrel portion, said first operating cable having a first end connected to said first end of said shuttle and a second end connected to said trigger mechanism; a return mechanism connected to said shuttle for moving said shuttle to said first position; and said second operating cable having a first end connected to said second end of said shuttle and a second end connected to said return mechanism.

17. The suturing device as defined in claim 16 in which said biasing means comprises a compressible, expandable elastomeric member.

18. The suturing device as defined in claim 16 in which said needle is provided with a multiplicity of circumferentially spaced-apart notches that are so constructed and arranged as to be engaged by said needle engaging member as said needle engaging member moves within said cavities.

19. The suturing device as defined in claim 18 in which said needle is generally rectangular in cross-section.

20. The suturing device as defined in claim 19 in which said first end of said shuttle is provided with a generally conically shaped opening for receiving said chamfered end of said needle.

21. The suturing device as defined in claim 20 in which said needle has a generally planar surface lying within a plane and in which said second end of said needle is provided with an aperture extending generally perpendicular to said generally planar surface.

22. The suturing device as defined in claim 21 in which said needle is constructed from plastic.

23. The suturing device as defined in claim 21 in which said return mechanism comprises biasing means connected to said second operating cable for urging movement of said shuttle from said second position toward said first position.

24. A suturing device comprising:
(a) a head portion operably associated with said gripping portion, said head portion comprising:
  (i) a body having a shuttle track;
  (ii) a shuffle operably associated with said body for movement along said shuttle track between a first position and a second position, said shuffle being provided with a needle guide and at least one cavity;
  (iii) a needle carried by said shuttle for movement along said needle guide between a first position and a second position; and
  (iv) a needle engaging member carried in said at least one cavity for engagement with said needle to control movement of said needle along said needle guide; and
(b) operating means operably associated with said head portion for moving said shuttle between said first and second positions, said operating means comprising:
  (i) an advancing mechanism operably associated with said shuttle for moving said shuttle to said second position;
  (ii) a first operating cable having a first end connected to said shuttle and a second end connected to said advancing mechanism; and
  (iii) a return mechanism connected to said shuttle for moving said shuttle to said first position.

25. The suturing device as defined in claim 24 in which said operating mechanism further includes a second operating cable having a first end connected to said shuttle and a second end connected to said return mechanism.

26. The suturing device as defined in claim 25 in which said return mechanism comprises biasing means connected to said second operating cable for yieldably resisting movement of said shuttle to said second position.

27. The suturing device as defined in claim 25 in which said shuttle is provided with a plurality of circumferentially spaced cavities and further includes a needle engaging member carried within each of said circumferentially spaced-apart cavities for movement within said cavities in response to movement of said shuttle between said first and second positions.

28. The suturing device as defined in claim 27 in which said needle is semicircular in shape and is provided with a plurality of circumferentially spaced-apart notches that are so constructed and arranged as to be engaged by said needle engaging member as said needle engaging member moves within said cavities.

* * * * *